US012545952B2

(12) United States Patent
Sabeti et al.

(10) Patent No.: US 12,545,952 B2
(45) Date of Patent: Feb. 10, 2026

(54) AMPLICON-BASED SEQUENCING USING DNA SPIKE-INS

(71) Applicants: THE BROAD INSTITUTE, INC., Cambridge, MA (US); PRESIDENT AND FELLOWS OF HARVARD COLLEGE, Cambridge, MA (US)

(72) Inventors: Pardis Sabeti, Cambridge, MA (US); Bronwyn Macinnis, Cambridge, MA (US); Erica Normandin, Cambridge, MA (US); Katie Siddle, Cambridge, MA (US); Steven Reilly, Cambridge, MA (US); Matthew Bauer, Cambridge, MA (US); Kim Lagerborg, Cambridge, MA (US)

(73) Assignees: The Broad Institute, Inc., Cambridge, MA (US); President and Fellows of Harvard College, Cambridge, MA (US)

( * ) Notice: Subject to any disclaimer, the term of this patent is extended or adjusted under 35 U.S.C. 154(b) by 712 days.

(21) Appl. No.: 17/684,328

(22) Filed: Mar. 1, 2022

(65) Prior Publication Data

US 2022/0282321 A1 Sep. 8, 2022

Related U.S. Application Data

(60) Provisional application No. 63/273,117, filed on Oct. 28, 2021, provisional application No. 63/155,258, filed on Mar. 1, 2021.

(51) Int. Cl.

| | |
|---|---|
| ***C12Q 1/686*** | (2018.01) |
| ***C12N 15/10*** | (2006.01) |
| ***C12Q 1/6809*** | (2018.01) |
| ***C12Q 1/6848*** | (2018.01) |
| ***C12Q 1/6855*** | (2018.01) |

(52) U.S. Cl.

CPC ....... *C12Q 1/6855* (2013.01); *C12N 15/1096* (2013.01); *C12Q 1/6809* (2013.01); *C12Q 1/6848* (2013.01); *C12Q 1/686* (2013.01); *C12Q 2527/101* (2013.01); *C12Q 2527/107* (2013.01); *C12Q 2527/146* (2013.01); *C12Q 2545/101* (2013.01); *C12Q 2600/16* (2013.01)

(58) Field of Classification Search

CPC ............ C12Q 1/6848; C12Q 2527/107; C12Q 2527/146; C12Q 2545/101; C12Q 1/686; C12N 15/1096

See application file for complete search history.

(56) References Cited

U.S. PATENT DOCUMENTS

| | | | | |
|---|---|---|---|---|
| 2017/0275691 A1* | 9/2017 | Christians | .............. | G16B 30/10 |
| 2019/0249334 A1* | 8/2019 | Piehl | .................... | C12Q 1/6848 |

OTHER PUBLICATIONS

Lagerborg et al. Synthetic DNA spike-ins (SDSIs) enable sample tracking and detection of inter-sample contamination in SARS-CoV-2 sequencing workflows. Nature Microbiology 2022; 7: 108-119. (Year: 2022).*

Lagerborg et al. DNA spike-ins enable confident interpretation of SARS-COV-2 genomic data from amplicon-based sequencing. bioRxiv [preprint] Mar. 16, 2021; doi:10.1101/2021.03.16.435654 + Supplementary Material. (Year: 2021).*

Chen, et al., "The Overlooked Fact: Fundamental Need for Spike-In Control for Virtually All Genome-Wide Analyses", Molecular and Cellular Biology, vol. 36, No. 5, Mar. 2016, 662-667.

Jiang, et al., "Synthetic Spike-in Standards for RNA-Seq Experiments", Genome Research, vol. 21, 2011, 1543-1551.

Quail, et al., "SASI-Seq: Sample Assurance Spike-ins, and Highly Differentiating 384 Barcoding for Illumina Sequencing", BMC Genomics, vol. 15, No. 110, 2014, 1-12.

* cited by examiner

*Primary Examiner* — Angela M. Bertagna

(74) *Attorney, Agent, or Firm* — F. Brent Nix, Esq.; Johnson, Marcou, Isaacs & Nix, LLC; Drew P. Harding

(57) ABSTRACT

Embodiments disclosed herein provide methods of using synthetic DNA spike-ins (SDSIs) to detect, prevent, and quantify contamination in amplicon sequencing. These embodiments may, but are not limited to, reveal sample swaps, intra-batch contamination, and, on a larger scale, intra-laboratory contamination. Embodiments disclosed herein also provide synthetic DNA spike-ins for use in amplicon-based sequencing methods.

14 Claims, 59 Drawing Sheets

Specification includes a Sequence Listing.

SEQUENCE LISTING

<160> NUMBER OF SEQ ID NOS: 636

<210> SEQ ID NO 1
<211> LENGTH: 140
<212> TYPE: DNA
<213> ORGANISM: Artificial Sequence
<220> FEATURE:
<223> OTHER INFORMATION: Synthetic

<400> SEQUENCE: 1
caattgctcc ctcgtatccc ttgtacatta tctcagctcc gcttaatgat attaattta 60 ccttgagtgt ttttgctaaa gcctttgcca tcatcgtttt acctactcca ggtggcccgt 120
aaagcaacac agctttggca 140

<210> SEQ ID NO 2
<211> LENGTH: 140
<212> TYPE: DNA
<213> ORGANISM: Artificial Sequence
<220> FEATURE:
<223> OTHER INFORMATION: Synthetic

<400> SEQUENCE: 2
ttctccaaaa cctacccagt tctccgagga acctcttagc atctgttaaa tcgttattag 60
tattagcttc caccatctca agttccttta aggcgttact cacactcttc ttacctatct 120
tttagagaac cactcgtcag 140

<210> SEQ ID NO 3
<211> LENGTH: 140
<212> TYPE: DNA
<213> ORGANISM: Artificial Sequence
<220> FEATURE:
<223> OTHER INFORMATION: Synthetic

<400> SEQUENCE: 3
gttatcaaag cccttaaaga gtggtagggg caaaagtctg aagcgtcctt acttaactgg 60
agtatctgag atggccttaa tccgcttagg tctttaattt tatcccttaa tgaacattcc 120
ctgcactcta tgtcttcggg 140

<210> SEQ ID NO 4
<211> LENGTH: 140
<212> TYPE: DNA
<213> ORGANISM: Artificial Sequence
<220> FEATURE:
<223> OTHER INFORMATION: Synthetic

<400> SEQUENCE: 4
gagatgtagc agacgggcta agagtttcaa accctctaag gatcactaca aacaagagag 60
agagacaatc ctctcttttg tcttgtcatt gtgtttcaaa ccctctaagg atcactacaa 120
acatctttaa catagatacc 140

<210> SEQ ID NO 5
<211> LENGTH: 140
<212> TYPE: DNA
<213> ORGANISM: Artificial Sequence
<220> FEATURE:
<223> OTHER INFORMATION: Synthetic

<400> SEQUENCE: 5
gaccggacgt tgtgatcacg ggtaccttga tctggtactc aaaggtttgc ccccgtgaag 60
tctggtacat ggctagacac gtcactccat tcgagggaca ttcgaagtta gagaagggca 120
gagcgataca tcagatatat 140

<210> SEQ ID NO 6
<211> LENGTH: 140
<212> TYPE: DNA
<213> ORGANISM: Artificial Sequence
<220> FEATURE:
<223> OTHER INFORMATION: Synthetic

<400> SEQUENCE: 6
gtcttttctc tactaattct cctcacgaga tctctaaaca ttcttgctga aagaggatcc 60
aaacctaatg taggttcgtc aagcaataaa attggaggat cagttattaa tgctcttgct 120
aaggctagtt tcctctgcat 140

<210> SEQ ID NO 7
<211> LENGTH: 140
<212> TYPE: DNA
<213> ORGANISM: Artificial Sequence
<220> FEATURE:
<223> OTHER INFORMATION: Synthetic

<400> SEQUENCE: 7
gattttgcca tcattaaaaa caacaatttg atcacccata gtcatagctt ctaattgatc 60
gtgagttaca taaatacttg tggtgtttaa catacggtga atatttacaa tttctcttcg 120
catgttttct cttagtttag 140

<210> SEQ ID NO 8
<211> LENGTH: 140
<212> TYPE: DNA
<213> ORGANISM: Artificial Sequence
<220> FEATURE:
<223> OTHER INFORMATION: Synthetic

<400> SEQUENCE: 8
gtatctttca attctcgaaa gaaaaggtta caagtctcat agatttattc ctcttcactg 60
ttgtacgttg gcagctagag agagtttaga ttatgagaaa attaagagaa tatatgagga 120
ttcgttttct tggtttaagt 140

<210> SEQ ID NO 9
<211> LENGTH: 140
<212> TYPE: DNA
<213> ORGANISM: Artificial Sequence
<220> FEATURE:
<223> OTHER INFORMATION: Synthetic

<400> SEQUENCE: 9
ctaattgatt ttcctgtacc atgtggtaaa acaacgctac ctcttaattg ttgatctgct 60
tttctagtat caagatttaa tctaaaagct aaatcaactg aagcatcaaa ttttgtataa 120
gaagtttttt tcactaattc 140

<210> SEQ ID NO 10
<211> LENGTH: 140
<212> TYPE: DNA
<213> ORGANISM: Artificial Sequence
<220> FEATURE:
<223> OTHER INFORMATION: Synthetic

<400> SEQUENCE: 10
tcggttttcc cgtgaactaa taaacaccta ctggagccaa gaacgggtca gaattgatgg 60
aataaacgtt gcggagaatg aaattaattt gtacatcaga gacattgatg acaacggtga 120
ccctatacag tcaactatac 140

<210> SEQ ID NO 11
<211> LENGTH: 140
<212> TYPE: DNA
<213> ORGANISM: Artificial Sequence
<220> FEATURE:
<223> OTHER INFORMATION: Synthetic

<400> SEQUENCE: 11
cttaatggaa agtatgcttt agataccttc tggaacgcta tctcacttgg cgggaattca 60
gatatggaga gtaaattaag ggatctggaa gtaaagttaa tgtcgttaat ctatttaaat 120
gagtcaccat taaaatcacc 140

<210> SEQ ID NO 12
<211> LENGTH: 140
<212> TYPE: DNA
<213> ORGANISM: Artificial Sequence
<220> FEATURE:
<223> OTHER INFORMATION: Synthetic

<400> SEQUENCE: 12
cataatatgt tagaggtaga atttctttgt gatagaatat tattgatgaa tgatggaaga 60
gaattagcat taggaaaacc taaggaactg gtaaaggata cagaatctaa gaatcttgaa 120
gaggttttcc ttaaacttgt 140

<210> SEQ ID NO 13
<211> LENGTH: 140
<212> TYPE: DNA
<213> ORGANISM: Artificial Sequence
<220> FEATURE:
<223> OTHER INFORMATION: Synthetic

<400> SEQUENCE: 13
ccttacttca tctctcaaga taagggtaat aagttcactt caaatatctg gtcttatcgc 60
aagttgattg aggctatagt gtataagctc tatgagtatg gtataaacgt gttcctcgtt 120
gtagagtata acacttcacg 140

<210> SEQ ID NO 14
<211> LENGTH: 140
<212> TYPE: DNA
<213> ORGANISM: Artificial Sequence
<220> FEATURE:
<223> OTHER INFORMATION: Synthetic

<400> SEQUENCE: 14
agtctaggtt ttaattcttc aactgcttca aatactagct tactgtagtt atctgccctc 60
atgttaggat atatatctgg aatataagga ggttgatgag ttataagaag tggatgaaat 120
tgttgtcaca cactccccta 140

<210> SEQ ID NO 15
<211> LENGTH: 140
<212> TYPE: DNA
<213> ORGANISM: Artificial Sequence
<220> FEATURE:
<223> OTHER INFORMATION: Synthetic

<400> SEQUENCE: 15
ctacctcttc ggccttgtac caacgtaccc ctgatacaag ttccaagcag agatggaaaa 60
ctcgaagatg gtatcaccca agatgagata cgatatcaat gaaggcgagc ctaggtacaa 120
gtaaagggat accacgagag 140

<210> SEQ ID NO 16
<211> LENGTH: 140
<212> TYPE: DNA
<213> ORGANISM: Artificial Sequence
<220> FEATURE:
<223> OTHER INFORMATION: Synthetic

<400> SEQUENCE: 16
ctcgtaagcg tttcctaccc tcgagagggc catcctggtg gtgaggaagt cgtcgaagtg 60
ggctaagtaa aaagcgaaga tctcgaccca caattacctc ctcctgtaca ccaggaatac 120
ccctatcagg atagagatac 140

<210> SEQ ID NO 17
<211> LENGTH: 140
<212> TYPE: DNA
<213> ORGANISM: Artificial Sequence
<220> FEATURE:
<223> OTHER INFORMATION: Synthetic

<400> SEQUENCE: 17
gcgcgtccgg gtcgcggccg gggacgaccg tcttgacgaa gtcggtcgac ccctcgtcgg 60
tcgagatggt cgtcacctcg gtgtcgaggc cgtacgtttc gagcgcgtcg cgtaccagtt 120
cgccgtccgc gtcgggacgg 140

<210> SEQ ID NO 18
<211> LENGTH: 140
<212> TYPE: DNA
<213> ORGANISM: Artificial Sequence
<220> FEATURE:
<223> OTHER INFORMATION: Synthetic

<400> SEQUENCE: 18
catgtactcg ttccagaagg tgagttcgct cccctcgatt tcgacctcgc ccacgtcgaa 60
gccgccggtc gtttcgagcg cgaacgactc gacgggaccg acgagcgaaa cttcgccgcc 120
gagcacgtcg gcgacgcgtt 140

<210> SEQ ID NO 19
<211> LENGTH: 140
<212> TYPE: DNA
<213> ORGANISM: Artificial Sequence
<220> FEATURE:
<223> OTHER INFORMATION: Synthetic

<400> SEQUENCE: 19
ctcgatgcgc tcgggcttgt aggactcccc gagggcgtcc ttgttggtga agacgttttg 60
ttttcgctcg aaccggcgca ttagcgtcgg tccgttgtag cgtcccctta tttaaaaccc 120
cgatttcatc tgattcatgt 140

<210> SEQ ID NO 20
<211> LENGTH: 140
<212> TYPE: DNA
<213> ORGANISM: Artificial Sequence
<220> FEATURE:
<223> OTHER INFORMATION: Synthetic

<400> SEQUENCE: 20
tcacggtccg cgacgtgaat cgggcgttcc agtcggcgtt cggctacgac gccgacgacg 60
tggtcggaag cgacctcctc gggcgaatcg tgccccccggt gccggacccg gacccggtgc 120
cggaaccggg ggacgacgag 140

<210> SEQ ID NO 21
<211> LENGTH: 140
<212> TYPE: DNA
<213> ORGANISM: Artificial Sequence
<220> FEATURE:
<223> OTHER INFORMATION: Synthetic

<400> SEQUENCE: 21
gcgtccgcga gttcatcctg aacgtcgtcc cgctgtcgcc cggcgaggag cgcggggcgg 60
gctacgccat ctacaccgac atcacggagc ggaagacccg cgaaagcgag ctagagcgac 120
agaacgagcg attggaggag 140

<210> SEQ ID NO 22
<211> LENGTH: 140
<212> TYPE: DNA
<213> ORGANISM: Artificial Sequence
<220> FEATURE:
<223> OTHER INFORMATION: Synthetic

<400> SEQUENCE: 22
gcgagaccgg cgacgaggtg cgcttcgaca ccgccgagcg ggcgctcgaa cagatggagg 60
aactcatcga cgacctgctg tcgctcgccc gtcgcggcca actggtcgac gagacggagc 120
gcgtcgacct cggggcggtc 140

<210> SEQ ID NO 23
<211> LENGTH: 140
<212> TYPE: DNA
<213> ORGANISM: Artificial Sequence
<220> FEATURE:
<223> OTHER INFORMATION: Synthetic

<400> SEQUENCE: 23
acgaactcgt cggtgaacat ctcgtcttcc ggggagcccg ccgctcatgg cctgcccccg 60
ccgtaagctg ctgcataaac ccgctccaaa atatacggat cattcacccc ttggaatcgc 120
tcaatcagat caatgtacac 140

<210> SEQ ID NO 24
<211> LENGTH: 140
<212> TYPE: DNA
<213> ORGANISM: Artificial Sequence
<220> FEATURE:
<223> OTHER INFORMATION: Synthetic

<400> SEQUENCE: 24
tgcgtacatt ccccctaagc ggctcccaat atacagacgc cggttaacga cagctggcga 60
ccctgtgatc tcagtaccgg tgtcgaatga ccacatcagc ttgcctgtcc gtgcatggag 120
ttcgtatacg tacccgtcgt 140

<210> SEQ ID NO 25
<211> LENGTH: 140
<212> TYPE: DNA
<213> ORGANISM: Artificial Sequence
<220> FEATURE:
<223> OTHER INFORMATION: Synthetic

<400> SEQUENCE: 25
agatagatga gccgatcaga gatcgctggt gagttggtaa ttgtcccgac atagacacgc 60
caacgttctg ttccatctgc tgcgtcgtag gtcgcgagat acggccagcc accaacatac 120
acaatcccat cgacgaggac 140

<210> SEQ ID NO 26
<211> LENGTH: 140
<212> TYPE: DNA
<213> ORGANISM: Artificial Sequence
<220> FEATURE:

<223> OTHER INFORMATION: Synthetic

<400> SEQUENCE: 26
atacaccacc ccatcagcaa caactgaatc atgattaagt atcgcaccag catcgtagcg 60
ccagcgttca ctgccagtgg tgctatcgaa tgcatagaag atatgctcct aatcgccaat 120
atcagtactt cacaaagccg 140

<210> SEQ ID NO 27
<211> LENGTH: 140
<212> TYPE: DNA
<213> ORGANISM: Artificial Sequence
<220> FEATURE:
<223> OTHER INFORMATION: Synthetic

<400> SEQUENCE: 27
tcgacgagga gaggggcgag tacatctgca cgcttacggg agaggtagtt gaggagacgg 60
ttatagatac agggcccgaa tggagggctt acacacctga ggagaggacc cgcagaagcc 120
gcgtgggcag cccgcttacc 140

<210> SEQ ID NO 28
<211> LENGTH: 140
<212> TYPE: DNA
<213> ORGANISM: Artificial Sequence
<220> FEATURE:
<223> OTHER INFORMATION: Synthetic

<400> SEQUENCE: 28
agtcgatggc tgcggcagct gtctatgctg cctgccgtat acgcggcata cccaggagta 60
tagacgacat agcggaggtc gtgaagggtg gccgtaagga ggttgcccgc tgctaccgcc 120
tcatagtccg cgagctgaag 140

<210> SEQ ID NO 29
<211> LENGTH: 140
<212> TYPE: DNA
<213> ORGANISM: Artificial Sequence
<220> FEATURE:
<223> OTHER INFORMATION: Synthetic

<400> SEQUENCE: 29
gtggagtctt ttgtcacacc gcagaggcgt agcgctgcag agcaggagcc caagcctact 60
gccaacatag agaacatagt ggctacagta tccctcgacc agactctaga cctgaacctc 120
atagagagga gcatactgac 140

<210> SEQ ID NO 30
<211> LENGTH: 140
<212> TYPE: DNA
<213> ORGANISM: Artificial Sequence
<220> FEATURE:
<223> OTHER INFORMATION: Synthetic

<400> SEQUENCE: 30
cgtcgcctgg gttaagagga tgttcggcct ctccaaggcg ggtcacggag gcacgctgga 60
cccgaaggtc accggcgtcc tccccgtagc cctggaggaa gcaaccaagg tcataggcct 120
ggtggtgcac acgagcaagg 140

<210> SEQ ID NO 31
<211> LENGTH: 140
<212> TYPE: DNA
<213> ORGANISM: Artificial Sequence
<220> FEATURE:
<223> OTHER INFORMATION: Synthetic

<400> SEQUENCE: 31
cgtgggcgag atctaccaga ggccgccgct ccgcagcagt gttaagagaa gcctccgcgt 60
caagaggata tacgagatag agctgctgga gtacaacggc aggtacgcgc tcatgagggt 120
gctctgcgag gccggcacat 140

<210> SEQ ID NO 32
<211> LENGTH: 140
<212> TYPE: DNA
<213> ORGANISM: Artificial Sequence
<220> FEATURE:
<223> OTHER INFORMATION: Synthetic

<400> SEQUENCE: 32
cgctggaaga acgagggcaa ggaggacctg ctgcggagct acatcaagcc cgtcgagtac 60
gccgtgagcc acctgcccaa gatagttata cgcgataccg cggtggacgc catagcccat 120
ggcgcgaacc tcgcggtgcc 140

<210> SEQ ID NO 33
<211> LENGTH: 140
<212> TYPE: DNA
<213> ORGANISM: Artificial Sequence
<220> FEATURE:
<223> OTHER INFORMATION: Synthetic

<400> SEQUENCE: 33
gggagacccc aaggtgaccg gcgtcctacc agtggggctc gccaacagca ccaaggtcat 60
tggtaatgtt atacatagtg ttaaagaata cgtgatggtt atacagctcc acggcgatgt 120
agccgagcag gatttaagaa 140

<210> SEQ ID NO 34
<211> LENGTH: 140
<212> TYPE: DNA
<213> ORGANISM: Artificial Sequence
<220> FEATURE:
<223> OTHER INFORMATION: Synthetic

<400> SEQUENCE: 34
tagagggaaa gactgtagct ttcattccta ggcacggaaa gagacacaga atacctccac 60
ataagataaa ttatagagct aatatatggg cattaaaaga actaggagtg aaatgggtca 120
tctcagtttc tgccgtagga 140

<210> SEQ ID NO 35
<211> LENGTH: 140
<212> TYPE: DNA
<213> ORGANISM: Artificial Sequence
<220> FEATURE:
<223> OTHER INFORMATION: Synthetic

<400> SEQUENCE: 35
tgagggagct caggaggact cgcacggggc cctacaggga ggatgagaca cttgtaaggc 60
tccaggacgt cagcgaggcc ctgctcctgt ggaggagcaa cggggatgag aggtatctta 120
gacgcatcgt gctacccgtt 140

<210> SEQ ID NO 36
<211> LENGTH: 140
<212> TYPE: DNA

<213> ORGANISM: Artificial Sequence
<220> FEATURE:
<223> OTHER INFORMATION: Synthetic

<400> SEQUENCE: 36
gaaacatcta tcgcccacct cccgaagata atgatcttgg atacagctgt cgacgccata 60
gcacatggtg ccaacctggc tgccccaggc gtcgccaggt taaccaggaa catcgcgaag 120
ggtagtaccg tagcgatcct 140

<210> SEQ ID NO 37
<211> LENGTH: 140
<212> TYPE: DNA
<213> ORGANISM: Artificial Sequence
<220> FEATURE:
<223> OTHER INFORMATION: Synthetic

<400> SEQUENCE: 37
tcgctatccc cgtgtacagc atggtggggg tgccgatgcc cgggtagaac ttggtgacgc 60
tctccagctt ctcgaggacg gtttccttgg ggaggctcgc ggtgtccacg agggttatcg 120
cgtcctcggc gccgtcgccg 140

<210> SEQ ID NO 38
<211> LENGTH: 140
<212> TYPE: DNA
<213> ORGANISM: Artificial Sequence
<220> FEATURE:
<223> OTHER INFORMATION: Synthetic

<400> SEQUENCE: 38
cgaggacgcg aagagcgcgg tggatgtgga cgcgccgccg cacacgtagc cgtcgaggta 60
gcgcggaacc atcggcgaca tcagccccac gacgcgaccc gaggcgttgc cgaggatcac 120
gtcgagcgtc acgcgcggca 140

<210> SEQ ID NO 39
<211> LENGTH: 140
<212> TYPE: DNA
<213> ORGANISM: Artificial Sequence
<220> FEATURE:
<223> OTHER INFORMATION: Synthetic

<400> SEQUENCE: 39
ctcgacaccg tgccgttgcc ctcctctaag tagtcggaaa gcctcatccg cgactccagc 60
ttcgccaccg gctcctcgag caggaggagg acgcggttga tgcggtagga cgcactgccc 120
gcctccagca ccgcgccgtc 140

<210> SEQ ID NO 40
<211> LENGTH: 140
<212> TYPE: DNA
<213> ORGANISM: Artificial Sequence
<220> FEATURE:
<223> OTHER INFORMATION: Synthetic

<400> SEQUENCE: 40
tctatggtgt agaacgggtc gttgcggagc cagcctggcg gcacgtaccg gtcgtccgct 60
atcgccagcg atctctcgaa gaggtcgagg taggcggacg cgttggcgaa cgccccgtgt 120
atcacgacgt ctatcccgcc 140

<210> SEQ ID NO 41
<211> LENGTH: 140

<212> TYPE: DNA
<213> ORGANISM: Artificial Sequence
<220> FEATURE:
<223> OTHER INFORMATION: Synthetic

<400> SEQUENCE: 41
gtataggttt caggtattga taatgcatag gaggttttta aaaccttgag ccgcatagtc 60
ttctggatgg gcgagagaca tggttaagta taagtgcggc aggtgcggat acgtcttcga 120
cgacgaggag atgaagagga 140

<210> SEQ ID NO 42
<211> LENGTH: 140
<212> TYPE: DNA
<213> ORGANISM: Artificial Sequence
<220> FEATURE:
<223> OTHER INFORMATION: Synthetic

<400> SEQUENCE: 42
cctacgccgg gtgcgtagga gggctcgagt acatccatgt ctatactgat gtatgtttta 60
cccaggtcgc ctagtgccag gggtcccttt aacgcttcca ggatagagta cacggtgacg 120
tctctagtct tcttcaagaa 140

<210> SEQ ID NO 43
<211> LENGTH: 140
<212> TYPE: DNA
<213> ORGANISM: Artificial Sequence
<220> FEATURE:
<223> OTHER INFORMATION: Synthetic

<400> SEQUENCE: 43
ctactagcgt gtcaacggag ctcttcaacg cctttactat tggataggtt ataaggtgct 60
cgcctccgag gaatcccagg agcatgccgg gatactcgtc tacaacgcct ttcaccacgt 120
cacctatgat tcttaaagag 140

<210> SEQ ID NO 44
<211> LENGTH: 140
<212> TYPE: DNA
<213> ORGANISM: Artificial Sequence
<220> FEATURE:
<223> OTHER INFORMATION: Synthetic

<400> SEQUENCE: 44
cataggtgac atggggtttc ccattgactc tataaagccg tatcctttaa gcggagtgca 60
attggtctac gctttgctta acaacaggta tttcctaccg ggtagagagg gctcgctcat 120
agctttaggt agcgtgacgg 140

<210> SEQ ID NO 45
<211> LENGTH: 140
<212> TYPE: DNA
<213> ORGANISM: Artificial Sequence
<220> FEATURE:
<223> OTHER INFORMATION: Synthetic

<400> SEQUENCE: 45
ggtatctcac cgcttgtcac catagtatcc ctcaggtact ccagtattct tgagagaaac 60
gcacctaagc cggatctcag gtttgaatcc ataagaacta tgagtgaagc gggattgaag 120
cccctgctgt ttctaagacc 140

<210> SEQ ID NO 46

<211> LENGTH: 140
<212> TYPE: DNA
<213> ORGANISM: Artificial Sequence
<220> FEATURE:
<223> OTHER INFORMATION: Synthetic

<400> SEQUENCE: 46
taagggagat agagaaacgc atcaaaatac ccttggggaa actgcgtgca ggggttcaat 60
atggagtaga ggtctcagac ataaaggaga agatagctgc ttacgctagg aggaaggggc 120
ttaaatactt cccatcggca 140

<210> SEQ ID NO 47
<211> LENGTH: 140
<212> TYPE: DNA
<213> ORGANISM: Artificial Sequence
<220> FEATURE:
<223> OTHER INFORMATION: Synthetic

<400> SEQUENCE: 47
tgtgaacctc gtgcccggct ctaagtcgtg agggcttgca acataggtgg ggaggaaccc 60
gagcaacggg taagaagaca ggataagcgg tatcgctatg aagagggctg agaaaaggac 120
atatactcct gagcccgtcc 140

<210> SEQ ID NO 48
<211> LENGTH: 140
<212> TYPE: DNA
<213> ORGANISM: Artificial Sequence
<220> FEATURE:
<223> OTHER INFORMATION: Synthetic

<400> SEQUENCE: 48
cgaacatgcc ttccccgtct atatagaccc agtagagttt aaaaacttaa ccagagacgg 60
cttgtgagcc ggatctctcc cccgctaggc cctggattgg gctcgctcct cctgggaccc 120
cggcctccac atgctcggga 140

<210> SEQ ID NO 49
<211> LENGTH: 140
<212> TYPE: DNA
<213> ORGANISM: Artificial Sequence
<220> FEATURE:
<223> OTHER INFORMATION: Synthetic

<400> SEQUENCE: 49
cctgaagggc tcggctaccc tgaagacggg cttctgcgcg accgccgcgt actccgccgt 60
ggagcggtag aagagcgagg ctgtctccgt gagcctgacc attccgtaca gggcgactgc 120
gacgagcact atgactgcga 140

<210> SEQ ID NO 50
<211> LENGTH: 140
<212> TYPE: DNA
<213> ORGANISM: Artificial Sequence
<220> FEATURE:
<223> OTHER INFORMATION: Synthetic

<400> SEQUENCE: 50
gtcaaggtgc tgatgccgaa ggcgactttc gacaccgacg atgccgccga cgccctggcc 60
attgccatct gccacgcgca tcaccggcac agtgttgcct ataggatggc gctggccgga 120
taagtttgtt cttgacctgt 140

<210> SEQ ID NO 51
<211> LENGTH: 140
<212> TYPE: DNA
<213> ORGANISM: Artificial Sequence
<220> FEATURE:
<223> OTHER INFORMATION: Synthetic

<400> SEQUENCE: 51
tctcggttcg gcaataagta ataccaacga ggtattacca tgcgcgtgac cagcaaaggc 60
caagtgacga tcccaaagga gatacgggat catttgggga ttgggccggg ctccgaggtg 120
gagttcgtgc ccacagacga 140

<210> SEQ ID NO 52
<211> LENGTH: 140
<212> TYPE: DNA
<213> ORGANISM: Artificial Sequence
<220> FEATURE:
<223> OTHER INFORMATION: Synthetic

<400> SEQUENCE: 52
ctcgatcata tggccggcac gttggacttg ggaggcatga caacggacga gtatatggag 60
tggctgaggg gtccacgtga agatctcgac attgattgac acaaatgtcc tgatcgatgt 120
ttggggtcct gccggacagg 140

<210> SEQ ID NO 53
<211> LENGTH: 140
<212> TYPE: DNA
<213> ORGANISM: Artificial Sequence
<220> FEATURE:
<223> OTHER INFORMATION: Synthetic

<400> SEQUENCE: 53
caggtgtatt ttacacacct ggacagccag catatgatgc tagcactcgg tgtcccctta 60
tcacggtttc ccgcattgta aagttttcgc gcctgctgcg ccccgtaggg cctggattca 120
tgtctcagaa tccatctccg 140

<210> SEQ ID NO 54
<211> LENGTH: 140
<212> TYPE: DNA
<213> ORGANISM: Artificial Sequence
<220> FEATURE:
<223> OTHER INFORMATION: Synthetic

<400> SEQUENCE: 54
ctggagcctg ttagttgtta caggttcacc ggttgtcgga gtattcagat cattgagcca 60
gcagttgatg gctgcctgta gttcactggt tgtgatgtaa gctgctccat cggaatcaac 120
atcgttccat gggttccagt 140

<210> SEQ ID NO 55
<211> LENGTH: 140
<212> TYPE: DNA
<213> ORGANISM: Artificial Sequence
<220> FEATURE:
<223> OTHER INFORMATION: Synthetic

<400> SEQUENCE: 55
acggtcttgc tttctcctga atccatttca cctgtccaga cccattcata gcggttagct 60
tcactgaggt tctgcttgaa gacaccgtca tcattgttag atgaggttat tgtccagccg 120
gcaggaatga cttcttcgaa 140

<210> SEQ ID NO 56
<211> LENGTH: 140
<212> TYPE: DNA
<213> ORGANISM: Artificial Sequence
<220> FEATURE:
<223> OTHER INFORMATION: Synthetic

<400> SEQUENCE: 56
gtcagcagct cttcatagaa gttctggttt gcaatatccc tctgggcaat gacagggtag 60
tcgacttcgt ttgcagtcag gtggactgca tacagggact tgctgatgtc cggggtatat 120
ccactgtgag gagcatagta 140

<210> SEQ ID NO 57
<211> LENGTH: 140
<212> TYPE: DNA
<213> ORGANISM: Artificial Sequence
<220> FEATURE:
<223> OTHER INFORMATION: Synthetic

<400> SEQUENCE: 57
acccgtcagt cgtgacgtcc tccgctcctc ctatgctatc tccacacacc cactcacgtt 60
cttgcttctt tactacaccc tctttattca gctcttcgag aacattatta atgtgaccct 120
tagagatata ttcattatac 140

<210> SEQ ID NO 58
<211> LENGTH: 140
<212> TYPE: DNA
<213> ORGANISM: Artificial Sequence
<220> FEATURE:
<223> OTHER INFORMATION: Synthetic

<400> SEQUENCE: 58
gtgcctcctc aagcgactgc ttaaacccaa ttacatctga tttatccttt attttagggc 60
ctatagaatc tatgaataat tcggcgattc ttattatttc taaaaccaat tcgtctgttt 120
tgagtggtgt gccttcttca 140

<210> SEQ ID NO 59
<211> LENGTH: 140
<212> TYPE: DNA
<213> ORGANISM: Artificial Sequence
<220> FEATURE:
<223> OTHER INFORMATION: Synthetic

<400> SEQUENCE: 59
catcccatgc attttcataa taatcggaat tcaaatcctc tatattgaat tttatcttaa 60
catttgacat aatcattttc tccttacaga agagatccag ctaagcttac tcataaatgg 120
tagtaccatg ccaatattgg 140

<210> SEQ ID NO 60
<211> LENGTH: 140
<212> TYPE: DNA
<213> ORGANISM: Artificial Sequence
<220> FEATURE:
<223> OTHER INFORMATION: Synthetic

<400> SEQUENCE: 60
cgtagcccgc accttcctct ggtttagcac cagcggtccc cacagagtac ccatcatccc 60
gaaggatatg ctggcaacag tgggcacggg tctcgctcgt tgcctgactt aacaggatgc 120
ttcacagtac gaactgacga 140

<210> SEQ ID NO 61
<211> LENGTH: 140
<212> TYPE: DNA
<213> ORGANISM: Artificial Sequence
<220> FEATURE:
<223> OTHER INFORMATION: Synthetic

<400> SEQUENCE: 61
cctgataggc cgcagattca tcctaaggcg ccggagcttt tgaccacaga acattccagt 60
atctatggta tatctggaat tatcaccagt ttcccggtgt tatgccagac cttagggcag 120
attatccacg tgttactgag 140

<210> SEQ ID NO 62
<211> LENGTH: 140
<212> TYPE: DNA
<213> ORGANISM: Artificial Sequence
<220> FEATURE:
<223> OTHER INFORMATION: Synthetic

<400> SEQUENCE: 62
tgtttggctt gatactaata aaagcacagc taaaatgaaa ataagccgat atttgtgatt 60
catgcaactc accctttct acataaacaa aatactaacc cgaaaaccga aattgaaatt 120
aatgcagaga aaccaggtga 140

<210> SEQ ID NO 63
<211> LENGTH: 140
<212> TYPE: DNA
<213> ORGANISM: Artificial Sequence
<220> FEATURE:
<223> OTHER INFORMATION: Synthetic

<400> SEQUENCE: 63
ttaacggcac caacagttat tatattttta gcagtcccgg gtgaagtaat tatggaatag 60
ttgttagaat tactgttctt attaccagct gatttgaaag caattatacc tgcatcacga 120
attgcagcat cataatattc 140

<210> SEQ ID NO 64
<211> LENGTH: 140
<212> TYPE: DNA
<213> ORGANISM: Artificial Sequence
<220> FEATURE:
<223> OTHER INFORMATION: Synthetic

<400> SEQUENCE: 64
ggctcagacg actgaaaaag caacgattgg aataataggg ggttctgggc tctatgatcc 60
tggtattttg actaacagca gagaaataaa agtatataca ccctatgggg aacctagcga 120
tttgataacg ataggtaaca 140

<210> SEQ ID NO 65
<211> LENGTH: 140
<212> TYPE: DNA
<213> ORGANISM: Artificial Sequence
<220> FEATURE:
<223> OTHER INFORMATION: Synthetic

<400> SEQUENCE: 65
cgcagaacag gttccttcta ttggatattc atcttcggct gcagttgcag gaagagtaag 60
gatatatact acggtcttgc tttctcctga atccatttca cctgtccaga cccattcata 120
gcggttagct tcactgaggt 140

<210> SEQ ID NO 66
<211> LENGTH: 140
<212> TYPE: DNA
<213> ORGANISM: Artificial Sequence
<220> FEATURE:
<223> OTHER INFORMATION: Synthetic

<400> SEQUENCE: 66
cttcctccac gcatttgttg tggtgctgat ggcgtattct ctggaatttg ggatgattct 60
ggaaatccat cctcagacac ttcagatatt ttagtcttac ttccagcgtt taattgaacc 120
ttacctttaa aagcagtagt 140

<210> SEQ ID NO 67
<211> LENGTH: 140
<212> TYPE: DNA
<213> ORGANISM: Artificial Sequence
<220> FEATURE:
<223> OTHER INFORMATION: Synthetic

<400> SEQUENCE: 67
gaaacttacc ttatcagtgt cattaagcat attgcttcca agacccattg aagcacttac 60
atcgttgata cacaggtgcc aggaatagta ttcctcagtc tcactataat cctcgttggt 120
gtagccttca agagagtcaa 140

<210> SEQ ID NO 68
<211> LENGTH: 140
<212> TYPE: DNA
<213> ORGANISM: Artificial Sequence
<220> FEATURE:
<223> OTHER INFORMATION: Synthetic

<400> SEQUENCE: 68
gtttaagcaa ttcttcggat gaaagatggc gctctatagg aatttgttct ggtctagcca 60
taaggcatta tttgtactta attagtaata aatgtttagt taatgactat aaatctgcaa 120
ttggagtctc aaattttcaa 140

<210> SEQ ID NO 69
<211> LENGTH: 140
<212> TYPE: DNA
<213> ORGANISM: Artificial Sequence
<220> FEATURE:
<223> OTHER INFORMATION: Synthetic

<400> SEQUENCE: 69
aacatgaagg atgtgtgtaa gaggaaacgt tattaacaga cgtaatcagg aggatagtta 60
tgccctaaaa acagcagagt taaggtttaa aaataagata agaactcagt tgaggtttat 120
ccattaatcc cattaatcct 140

<210> SEQ ID NO 70
<211> LENGTH: 140
<212> TYPE: DNA
<213> ORGANISM: Artificial Sequence
<220> FEATURE:
<223> OTHER INFORMATION: Synthetic

<400> SEQUENCE: 70
actttctaaa agcgcttgga gcacgtatca ggtcaagtct ttcaacctta aatgctgcca 60
gtgccgtaag tagtgcagtt atgttgctta ttgaaacaaa caacttagcc cacttattac 120
ctcttgtcag tgtttttgat 140

<210> SEQ ID NO 71
<211> LENGTH: 140
<212> TYPE: DNA
<213> ORGANISM: Artificial Sequence
<220> FEATURE:
<223> OTHER INFORMATION: Synthetic

<400> SEQUENCE: 71
gtatccgctg atatatcctg gggatataga tcgctctgaa atggttacat ctatcggttt 60
taaggacagt tccaacacta ttggaccttg cagctatgac aggaataatc tgtttatcga 120
gcacagttga atttgaccta 140

<210> SEQ ID NO 72
<211> LENGTH: 140
<212> TYPE: DNA
<213> ORGANISM: Artificial Sequence
<220> FEATURE:
<223> OTHER INFORMATION: Synthetic

<400> SEQUENCE: 72
tcaataccta attctttcct tagagtgcta ttttgattga attccctcag gaaagattca 60
aaatttaagt agccgagctt acatcttgaa atttccatct ttattatgtt gctcaggctt 120
aatgcttcta agtatgggtt 140

<210> SEQ ID NO 73
<211> LENGTH: 140
<212> TYPE: DNA
<213> ORGANISM: Artificial Sequence
<220> FEATURE:
<223> OTHER INFORMATION: Synthetic

<400> SEQUENCE: 73
agatatcctt tgaaattctc gtaattgctg aaggccacta cttcatcagg tctgatgcaa 60
tctttaatct gaacattgct ttctgaggtc ttaggaataa tcctgtaagg gagtcggata 120
ttgttcgtta agatgctctt 140

<210> SEQ ID NO 74
<211> LENGTH: 140
<212> TYPE: DNA
<213> ORGANISM: Artificial Sequence
<220> FEATURE:
<223> OTHER INFORMATION: Synthetic

<400> SEQUENCE: 74
atagagggac ctagattttc aacgagggca gaaagtagaa tttggaggga agtttataaa 60
gccgatatca tagggatgac tttagttcca gaagtaaatt tagcttgcga aatgcaaatg 120
tgctatgcaa caattgcgat 140

<210> SEQ ID NO 75
<211> LENGTH: 140
<212> TYPE: DNA
<213> ORGANISM: Artificial Sequence
<220> FEATURE:
<223> OTHER INFORMATION: Synthetic

<400> SEQUENCE: 75
gtcttcagca tagtaccagc ttatgttgtc accatcgttc agtacgttac caccaagtcc 60
actgcctgca gctacatcat taatgtacag gaaccaggca tagtaaccgc cagttgatat 120
gtagtcttca ccttcgattc 140

<210> SEQ ID NO 76
<211> LENGTH: 140
<212> TYPE: DNA
<213> ORGANISM: Artificial Sequence
<220> FEATURE:
<223> OTHER INFORMATION: Synthetic

<400> SEQUENCE: 76
actctccatc atgacagcca gatcggtcat agcatcgatt gtgtactctt cgtcgggatt 60
gttgtatgga atgaacttat agttctcacc tgctacctga tccactgtca tttctgcaag 120
agtctgcact gtggtaattc 140

<210> SEQ ID NO 77
<211> LENGTH: 140
<212> TYPE: DNA
<213> ORGANISM: Artificial Sequence
<220> FEATURE:
<223> OTHER INFORMATION: Synthetic

<400> SEQUENCE: 77
atattccgta tttcttatca aaccgatcgt gaagatttga caaaggctta actttagggc 60
tccacttctc attattagcc ttagaatata aagcgtaacc gtaagcctga ggaacgtaaa 120
gcttaggaga ttcaatcccg 140

<210> SEQ ID NO 78
<211> LENGTH: 140
<212> TYPE: DNA
<213> ORGANISM: Artificial Sequence
<220> FEATURE:
<223> OTHER INFORMATION: Synthetic

<400> SEQUENCE: 78
taaaattagc cgaaggcttc ccattaccga aaaagtcgtt tattagctct tcatccttct 60
tctccacgtc cgcccattcc tctccttccc ttggaatttt aagctcgtcc cagctgactc 120
ttatgggcaa ttcaatatcc 140

<210> SEQ ID NO 79
<211> LENGTH: 140
<212> TYPE: DNA
<213> ORGANISM: Artificial Sequence
<220> FEATURE:
<223> OTHER INFORMATION: Synthetic

<400> SEQUENCE: 79
gtataaactt ttgatataac cttgcctaat ttgatatcat agcttatgtt tggcgctatc 60
ccccacttgt agagggtcgc gttatattct ctaatagcaa gagagataca agattcgtta 120
acgttattta tatcactctc 140

<210> SEQ ID NO 80
<211> LENGTH: 140
<212> TYPE: DNA
<213> ORGANISM: Artificial Sequence
<220> FEATURE:
<223> OTHER INFORMATION: Synthetic

<400> SEQUENCE: 80
tccggaggaa tctatcatat taaacctcct caaaatcgcc tcctcttgat tgcttaaagg 60
ctgtgaatta caaagcttat ttaatgcgtc ccaaagcgtt aagtaataat tatttatatt 120
aaacactact atttcagtag 140

<210> SEQ ID NO 81
<211> LENGTH: 140
<212> TYPE: DNA
<213> ORGANISM: Artificial Sequence
<220> FEATURE:
<223> OTHER INFORMATION: Synthetic

<400> SEQUENCE: 81
gttcctcctc aattcaattg gactgaagga gggtacgttc tggaaaacag agcgtaaaag 60
agatatagaa cgtagtatac acatagctgg aaaaagaaca atcattaaga caataaagaa 120
ctttatggaa aagagtagaa 140

<210> SEQ ID NO 82
<211> LENGTH: 140
<212> TYPE: DNA
<213> ORGANISM: Artificial Sequence
<220> FEATURE:
<223> OTHER INFORMATION: Synthetic

<400> SEQUENCE: 82
tcgtgtaaag gttgtataat tcaagcctca gaacatttcg aactccttac aaaatcgttt 60
aaactttcta aggcataaat ttactagaaa ttgtcattta tgagaatgta actatataga 120
tggtaaaatt attaatcctc 140

<210> SEQ ID NO 83
<211> LENGTH: 140
<212> TYPE: DNA
<213> ORGANISM: Artificial Sequence
<220> FEATURE:
<223> OTHER INFORMATION: Synthetic

<400> SEQUENCE: 83
ggctgaaaaa taggttcgat ccgcctcctc acttcttctc cttcttgccc tcggcctcgg 60
aggaggcctc tattcccagc ttcttggcct cctcctcggt cgtcatgaac aggctagtcc 120
tctgccttcc gcccatgctc 140

<210> SEQ ID NO 84
<211> LENGTH: 140
<212> TYPE: DNA
<213> ORGANISM: Artificial Sequence
<220> FEATURE:
<223> OTHER INFORMATION: Synthetic

<400> SEQUENCE: 84
gacctagcct tacgcacagc cctctccaca acctcctcaa gcttatccca gtcaatagag 60
ctcattacaa gttaaccacg cccaccttta atataaacct ttacccctcg tggcaattaa 120
ctttaaccgc tactccggtg 140

<210> SEQ ID NO 85
<211> LENGTH: 140
<212> TYPE: DNA
<213> ORGANISM: Artificial Sequence
<220> FEATURE:
<223> OTHER INFORMATION: Synthetic

<400> SEQUENCE: 85
tggcccttag acctctgccc atgcttaggc gcttacccac acctattagt acggcgccaa 60
tgcccacggc catgaagtac attaaggcac ccatggttgc accgtagagt gccgtgaatg 120
ttccgtagaa tacaccggcc 140

<210> SEQ ID NO 86
<211> LENGTH: 140
<212> TYPE: DNA
<213> ORGANISM: Artificial Sequence
<220> FEATURE:
<223> OTHER INFORMATION: Synthetic

<400> SEQUENCE: 86
tcggcgaatc tgtcgagctc catgacgtcc acagagccgc cgaacttggc cgagaatcta 60
tcggcctggg cggtgcgcct ccctatcagc aaaaccctgg gcgccgtcag tagcgcgacg 120
gccctggcga ttcccctggc 140

<210> SEQ ID NO 87
<211> LENGTH: 140
<212> TYPE: DNA
<213> ORGANISM: Artificial Sequence
<220> FEATURE:
<223> OTHER INFORMATION: Synthetic

<400> SEQUENCE: 87
tccaggtagg atctggccga gagggaggac gccgcgctgt tgtgctccgg gaaccctaga 60
gtcacgaccg ccttgacgcc tatacgttcg gcgtattcag cgacggcggc gccggtgccg 120
cccgtcagcg tgacggcaag 140

<210> SEQ ID NO 88
<211> LENGTH: 140
<212> TYPE: DNA
<213> ORGANISM: Artificial Sequence
<220> FEATURE:
<223> OTHER INFORMATION: Synthetic

<400> SEQUENCE: 88
gcaagagaat acatttttga tgataagaga agcttgtggc atactttctt aggctttatt 60
tcagcattca ctttagcgta ttctatcgtt attttgctat tgttcacatt gtatcaagtg 120
agagaaagag agaagccaac 140

<210> SEQ ID NO 89
<211> LENGTH: 140
<212> TYPE: DNA
<213> ORGANISM: Artificial Sequence
<220> FEATURE:
<223> OTHER INFORMATION: Synthetic

<400> SEQUENCE: 89
agaatcaaag gagtggtgta aagatggaga gaaaaaaagg ttggcatcct atttatgtga 60
gtgaagcggt tttaagtaag ttagataaag agagagaaga aattaaagaa gaattaggta 120
ttccaaagga agagaatttg 140

<210> SEQ ID NO 90
<211> LENGTH: 140
<212> TYPE: DNA
<213> ORGANISM: Artificial Sequence
<220> FEATURE:
<223> OTHER INFORMATION: Synthetic

<400> SEQUENCE: 90
gttcagcata aaagacggtt tcacgggcca aagcctaagc ggcgtaacgg tgaaagaagg 60
agatacggtt ttgggcacga ttgacgacgg cgggacgctg gagctcacga ggggcactca 120
caccttgact ttcgagaagc 140

<210> SEQ ID NO 91
<211> LENGTH: 140
<212> TYPE: DNA
<213> ORGANISM: Artificial Sequence
<220> FEATURE:
<223> OTHER INFORMATION: Synthetic

<400> SEQUENCE: 91
ctgatgttat agaagtccgc aaggacggct ctgtcatctc gcccgagggt gggaaatact 60
atctcggcga cataagcggc ccgacacaaa ttagcatcaa gttcaaggcc ggcgcggtgg 120
gaacccacgg cttcactatc 140

<210> SEQ ID NO 92
<211> LENGTH: 140
<212> TYPE: DNA
<213> ORGANISM: Artificial Sequence
<220> FEATURE:
<223> OTHER INFORMATION: Synthetic

<400> SEQUENCE: 92
tctccctcaa ccttcgcggg gagaacggcg cggagtactg gacgggctac gcggacgcgc 60
tggaagacct gttgaagaaa atccagaggc gggaggtgag ggcatgagaa ggtattgtta 120
catcacgtgg ggatggatca 140

<210> SEQ ID NO 93
<211> LENGTH: 140
<212> TYPE: DNA
<213> ORGANISM: Artificial Sequence
<220> FEATURE:
<223> OTHER INFORMATION: Synthetic

<400> SEQUENCE: 93
gagcgccggg aggtgagggc atgagtgagg aattgatgtt tggtcgtgtc gtggagtatg 60
ttcagcatag tttctacaag aaaccgtttc ctcttggcag tgagctcaag aatgcagtag 120
agaaggttat ggaaacagga 140

<210> SEQ ID NO 94
<211> LENGTH: 140
<212> TYPE: DNA
<213> ORGANISM: Artificial Sequence
<220> FEATURE:
<223> OTHER INFORMATION: Synthetic

<400> SEQUENCE: 94
aggtcagagc ccacgtggca acttttgagg ttctgacaaa agactatgtt cgtgagaaat 60
acaaagacat catagagttc atgagggaga aagggacagt atcgagaaag gaactgcgga 120
agaagttctt cttgcttgct 140

<210> SEQ ID NO 95
<211> LENGTH: 140
<212> TYPE: DNA
<213> ORGANISM: Artificial Sequence
<220> FEATURE:
<223> OTHER INFORMATION: Synthetic

<400> SEQUENCE: 95
gtacctcaaa atacagaatc atattttaca atcgcttgga aatattaata tcaacaatac 60
gcaagtccaa attaacgtcc ctggcaaaca ggtgacaatt tatacccacg aaatactaga 120
taacgccaaa aaggcactcg 140

<210> SEQ ID NO 96
<211> LENGTH: 140
<212> TYPE: DNA
<213> ORGANISM: Artificial Sequence
<220> FEATURE:
<223> OTHER INFORMATION: Synthetic

<400> SEQUENCE: 96
ctttgtatac ttagatcagg aaatggagct aaaaggcact atcaagaaga caaaagattc 60
ctggagagaa acatttaaag agtactccaa gacagacagc gaatatctaa taaattacag 120
actgttttca atactccctc 140

<210> SEQ ID NO 97
<211> LENGTH: 198
<212> TYPE: DNA
<213> ORGANISM: Artificial Sequence
<220> FEATURE:
<223> OTHER INFORMATION: Synthetic

<400> SEQUENCE: 97
acagttctcc ttcttagctt cgtgagaacc aattgctccc tcgtatccct tgtacattat 60
ctcagctccg cttaatgata ttaattttac cttgagtgtt tttgctaaag cctttgccat 120
catcgtttta cctactccag gtggcccgta aagcaacaca gctttggcac acatcatgta 180
gtagacgacc aagacagt 198

<210> SEQ ID NO 98
<211> LENGTH: 198
<212> TYPE: DNA
<213> ORGANISM: Artificial Sequence
<220> FEATURE:
<223> OTHER INFORMATION: Synthetic

<400> SEQUENCE: 98
acagttctcc ttcttagctt cgtgagaact tctccaaaac ctacccagtt ctccgaggaa 60
cctcttagca tctgttaaat cgttattagt attagcttcc accatctcaa gttcctttaa 120
ggcgttactc acactcttct tacctatctt ttagagaacc actcgtcagc acatcatgta 180
gtagacgacc aagacagt 198

<210> SEQ ID NO 99
<211> LENGTH: 198
<212> TYPE: DNA
<213> ORGANISM: Artificial Sequence
<220> FEATURE:
<223> OTHER INFORMATION: Synthetic

<400> SEQUENCE: 99
acagttctcc ttcttagctt cgtgagaacg ttatcaaagc ccttaaagag tggtaggggc 60
aaaagtctga agcgtcctta cttaactgga gtatctgaga tggccttaat ccgcttaggt 120
ctttaatttt atcccttaat gaacattccc tgcactctat gtcttcgggc acatcatgta 180
gtagacgacc aagacagt 198

<210> SEQ ID NO 100
<211> LENGTH: 198
<212> TYPE: DNA
<213> ORGANISM: Artificial Sequence
<220> FEATURE:
<223> OTHER INFORMATION: Synthetic

<400> SEQUENCE: 100
acagttctcc ttcttagctt cgtgagaacg agatgtagca gacgggctaa gagtttcaaa 60
ccctctaagg atcactacaa acaagagaga gagacaatcc tctcttttgt cttgtcattg 120
tgtttcaaac cctctaagga tcactacaaa catctttaac atagataccc acatcatgta 180
gtagacgacc aagacagt 198

<210> SEQ ID NO 101
<211> LENGTH: 198
<212> TYPE: DNA
<213> ORGANISM: Artificial Sequence
<220> FEATURE:
<223> OTHER INFORMATION: Synthetic

<400> SEQUENCE: 101
acagttctcc ttcttagctt cgtgagaacg accggacgtt gtgatcacgg gtaccttgat 60
ctggtactca aaggtttgcc cccgtgaagt ctggtacatg gctagacacg tcactccatt 120
cgagggacat tcgaagttag agaagggcag agcgatacat cagatatatc acatcatgta 180
gtagacgacc aagacagt 198

<210> SEQ ID NO 102
<211> LENGTH: 198
<212> TYPE: DNA
<213> ORGANISM: Artificial Sequence
<220> FEATURE:
<223> OTHER INFORMATION: Synthetic

<400> SEQUENCE: 102
acagttctcc ttcttagctt cgtgagaacg tcttttctct actaattctc ctcacgagat 60
ctctaaacat tcttgctgaa agaggatcca aacctaatgt aggttcgtca agcaataaaa 120
ttggaggatc agttattaat gctcttgcta aggctagttt cctctgcatc acatcatgta 180
gtagacgacc aagacagt 198

<210> SEQ ID NO 103
<211> LENGTH: 198
<212> TYPE: DNA
<213> ORGANISM: Artificial Sequence
<220> FEATURE:
<223> OTHER INFORMATION: Synthetic

<400> SEQUENCE: 103
acagttctcc ttcttagctt cgtgagaacg attttgccat cattaaaaac aacaatttga 60
tcacccatag tcatagcttc taattgatcg tgagttacat aaatacttgt ggtgtttaac 120
atacggtgaa tatttacaat ttctcttcgc atgttttctc ttagtttagc acatcatgta 180
gtagacgacc aagacagt 198

<210> SEQ ID NO 104
<211> LENGTH: 198
<212> TYPE: DNA
<213> ORGANISM: Artificial Sequence
<220> FEATURE:
<223> OTHER INFORMATION: Synthetic

<400> SEQUENCE: 104
acagttctcc ttcttagctt cgtgagaacg tatctttcaa ttctcgaaag aaaaggttac 60
aagtctcata gatttattcc tcttcactgt tgtacgttgg cagctagaga gagtttagat 120
tatgagaaaa ttaagagaat atatgaggat tcgttttctt ggtttaagtc acatcatgta 180
gtagacgacc aagacagt 198

<210> SEQ ID NO 105
<211> LENGTH: 198
<212> TYPE: DNA
<213> ORGANISM: Artificial Sequence
<220> FEATURE:
<223> OTHER INFORMATION: Synthetic

<400> SEQUENCE: 105
acagttctcc ttcttagctt cgtgagaacc taattgattt tcctgtacca tgtggtaaaa 60
caacgctacc tcttaattgt tgatctgctt ttctagtatc aagatttaat ctaaaagcta 120
aatcaactga agcatcaaat tttgtataag aagttttttt cactaattcc acatcatgta 180
gtagacgacc aagacagt 198

<210> SEQ ID NO 106
<211> LENGTH: 198
<212> TYPE: DNA
<213> ORGANISM: Artificial Sequence
<220> FEATURE:
<223> OTHER INFORMATION: Synthetic

<400> SEQUENCE: 106
acagttctcc ttcttagctt cgtgagaact cggttttccc gtgaactaat aaacacctac 60
tggagccaag aacgggtcag aattgatgga ataaacgttg cggagaatga aattaatttg 120
tacatcagag acattgatga caacggtgac cctatacagt caactatacc acatcatgta 180
gtagacgacc aagacagt 198

<210> SEQ ID NO 107
<211> LENGTH: 198
<212> TYPE: DNA
<213> ORGANISM: Artificial Sequence
<220> FEATURE:
<223> OTHER INFORMATION: Synthetic

<400> SEQUENCE: 107
acagttctcc ttcttagctt cgtgagaacc ttaatggaaa gtatgcttta gataccttct 60
ggaacgctat ctcacttggc gggaattcag atatggagag taaattaagg gatctggaag 120
taaagttaat gtcgttaatc tatttaaatg agtcaccatt aaaatcaccc acatcatgta 180
gtagacgacc aagacagt 198

<210> SEQ ID NO 108
<211> LENGTH: 198
<212> TYPE: DNA
<213> ORGANISM: Artificial Sequence
<220> FEATURE:
<223> OTHER INFORMATION: Synthetic

<400> SEQUENCE: 108
acagttctcc ttcttagctt cgtgagaacc ataatatgtt agaggtagaa tttctttgtg 60
atagaatatt attgatgaat gatggaagag aattagcatt aggaaaacct aaggaactgg 120
taaaggatac agaatctaag aatcttgaag aggttttcct taaacttgtc acatcatgta 180
gtagacgacc aagacagt 198

<210> SEQ ID NO 109
<211> LENGTH: 198
<212> TYPE: DNA
<213> ORGANISM: Artificial Sequence
<220> FEATURE:
<223> OTHER INFORMATION: Synthetic

<400> SEQUENCE: 109
acagttctcc ttcttagctt cgtgagaacc cttacttcat ctctcaagat aagggtaata 60
agttcacttc aaatatctgg tcttatcgca agttgattga ggctatagtg tataagctct 120
atgagtatgg tataaacgtg ttcctcgttg tagagtataa cacttcacgc acatcatgta 180
gtagacgacc aagacagt 198

<210> SEQ ID NO 110
<211> LENGTH: 198
<212> TYPE: DNA
<213> ORGANISM: Artificial Sequence
<220> FEATURE:
<223> OTHER INFORMATION: Synthetic

<400> SEQUENCE: 110
acagttctcc ttcttagctt cgtgagaaca gtctaggttt taattcttca actgcttcaa 60
atactagctt actgtagtta tctgccctca tgttaggata tatatctgga atataaggag 120
gttgatgagt tataagaagt ggatgaaatt gttgtcacac actcccctac acatcatgta 180
gtagacgacc aagacagt 198

<210> SEQ ID NO 111
<211> LENGTH: 198
<212> TYPE: DNA
<213> ORGANISM: Artificial Sequence
<220> FEATURE:
<223> OTHER INFORMATION: Synthetic

<400> SEQUENCE: 111
acagttctcc ttcttagctt cgtgagaacc tacctcttcg gccttgtacc aacgtacccc 60
tgatacaagt tccaagcaga gatggaaaac tcgaagatgg tatcacccaa gatgagatac 120
gatatcaatg aaggcgagcc taggtacaag taaagggata ccacgagagc acatcatgta 180
gtagacgacc aagacagt 198

<210> SEQ ID NO 112
<211> LENGTH: 198
<212> TYPE: DNA
<213> ORGANISM: Artificial Sequence
<220> FEATURE:
<223> OTHER INFORMATION: Synthetic

<400> SEQUENCE: 112
acagttctcc ttcttagctt cgtgagaacc tcgtaagcgt ttcctaccct cgagagggcc 60
atcctggtgg tgaggaagtc gtcgaagtgg gctaagtaaa aagcgaagat ctcgacccac 120
aattacctcc tcctgtacac caggaatacc cctatcagga tagagatacc acatcatgta 180
gtagacgacc aagacagt 198

<210> SEQ ID NO 113
<211> LENGTH: 198
<212> TYPE: DNA

<213> ORGANISM: Artificial Sequence
<220> FEATURE:
<223> OTHER INFORMATION: Synthetic

<400> SEQUENCE: 113
acagttctcc ttcttagctt cgtgagaacg cgcgtccggg tcgcggccgg ggacgaccgt 60
cttgacgaag tcggtcgacc cctcgtcggt cgagatggtc gtcacctcgg tgtcgaggcc 120
gtacgtttcg agcgcgtcgc gtaccagttc gccgtccgcg tcgggacggc acatcatgta 180
gtagacgacc aagacagt 198

<210> SEQ ID NO 114
<211> LENGTH: 198
<212> TYPE: DNA
<213> ORGANISM: Artificial Sequence
<220> FEATURE:
<223> OTHER INFORMATION: Synthetic

<400> SEQUENCE: 114
acagttctcc ttcttagctt cgtgagaacc atgtactcgt tccagaaggt gagttcgctc 60
ccctcgattt cgacctcgcc cacgtcgaag ccgccggtcg tttcgagcgc gaacgactcg 120
acgggaccga cgagcgaaac ttcgccgccg agcacgtcgg cgacgcgttc acatcatgta 180
gtagacgacc aagacagt 198

<210> SEQ ID NO 115
<211> LENGTH: 198
<212> TYPE: DNA
<213> ORGANISM: Artificial Sequence
<220> FEATURE:
<223> OTHER INFORMATION: Synthetic

<400> SEQUENCE: 115
acagttctcc ttcttagctt cgtgagaacc tcgatgcgct cgggcttgta ggactccccg 60
agggcgtcct tgttggtgaa gacgttttgt tttcgctcga accggcgcat tagcgtcggt 120
ccgttgtagc gtccccttat ttaaaacccc gatttcatct gattcatgtc acatcatgta 180
gtagacgacc aagacagt 198

<210> SEQ ID NO 116
<211> LENGTH: 198
<212> TYPE: DNA
<213> ORGANISM: Artificial Sequence
<220> FEATURE:
<223> OTHER INFORMATION: Synthetic

<400> SEQUENCE: 116
acagttctcc ttcttagctt cgtgagaact cacggtccgc gacgtgaatc gggcgttcca 60
gtcggcgttc ggctacgacg ccgacgacgt ggtcggaagc gacctcctcg ggcgaatcgt 120
gcccccggtg ccggacccgg acccggtgcc ggaaccgggg gacgacgagc acatcatgta 180
gtagacgacc aagacagt 198

<210> SEQ ID NO 117
<211> LENGTH: 198
<212> TYPE: DNA
<213> ORGANISM: Artificial Sequence
<220> FEATURE:
<223> OTHER INFORMATION: Synthetic

<400> SEQUENCE: 117
acagttctcc ttcttagctt cgtgagaacg cgtccgcgag ttcatcctga acgtcgtccc 60
gctgtcgccc ggcgaggagc gcggggcggg ctacgccatc tacaccgaca tcacggagcg 120
gaagacccgc gaaagcgagc tagagcgaca gaacgagcga ttggaggagc acatcatgta 180
gtagacgacc aagacagt 198

<210> SEQ ID NO 118
<211> LENGTH: 198
<212> TYPE: DNA
<213> ORGANISM: Artificial Sequence
<220> FEATURE:
<223> OTHER INFORMATION: Synthetic

<400> SEQUENCE: 118
acagttctcc ttcttagctt cgtgagaacg cgagaccggc gacgaggtgc gcttcgacac 60
cgccgagcgg gcgctcgaac agatggagga actcatcgac gacctgctgt cgctcgcccg 120
tcgcggccaa ctggtcgacg agacggagcg cgtcgacctc ggggcggtcc acatcatgta 180
gtagacgacc aagacagt 198

<210> SEQ ID NO 119
<211> LENGTH: 198
<212> TYPE: DNA
<213> ORGANISM: Artificial Sequence
<220> FEATURE:
<223> OTHER INFORMATION: Synthetic

<400> SEQUENCE: 119
acagttctcc ttcttagctt cgtgagaaca cgaactcgtc ggtgaacatc tcgtcttccg 60
gggagcccgc cgctcatggc ctgccccccgc cgtaagctgc tgcataaacc cgctccaaaa 120
tatacggatc attcacccct tggaatcgct caatcagatc aatgtacacc acatcatgta 180
gtagacgacc aagacagt 198

<210> SEQ ID NO 120
<211> LENGTH: 198
<212> TYPE: DNA
<213> ORGANISM: Artificial Sequence
<220> FEATURE:
<223> OTHER INFORMATION: Synthetic

<400> SEQUENCE: 120
acagttctcc ttcttagctt cgtgagaact gcgtacattc cccctaagcg gctcccaata 60
tacagacgcc ggttaacgac agctggcgac cctgtgatct cagtaccggt gtcgaatgac 120
cacatcagct tgcctgtccg tgcatggagt tcgtatacgt acccgtcgtc acatcatgta 180
gtagacgacc aagacagt 198

<210> SEQ ID NO 121
<211> LENGTH: 198
<212> TYPE: DNA
<213> ORGANISM: Artificial Sequence
<220> FEATURE:
<223> OTHER INFORMATION: Synthetic

<400> SEQUENCE: 121
acagttctcc ttcttagctt cgtgagaaca gatagatgag ccgatcagag atcgctggtg 60
agttggtaat tgtcccgaca tagacacgcc aacgttctgt tccatctgct gcgtcgtagg 120
tcgcgagata cggccagcca ccaacataca caatcccatc gacgaggacc acatcatgta 180
gtagacgacc aagacagt 198

<210> SEQ ID NO 122
<211> LENGTH: 198
<212> TYPE: DNA
<213> ORGANISM: Artificial Sequence
<220> FEATURE:
<223> OTHER INFORMATION: Synthetic

<400> SEQUENCE: 122
acagttctcc ttcttagctt cgtgagaaca tacaccaccc catcagcaac aactgaatca 60
tgattaagta tcgcaccagc atcgtagcgc cagcgttcac tgccagtggt gctatcgaat 120
gcatagaaga tatgctccta atcgccaata tcagtacttc acaaagccgc acatcatgta 180
gtagacgacc aagacagt 198

<210> SEQ ID NO 123
<211> LENGTH: 198
<212> TYPE: DNA
<213> ORGANISM: Artificial Sequence
<220> FEATURE:
<223> OTHER INFORMATION: Synthetic

<400> SEQUENCE: 123
acagttctcc ttcttagctt cgtgagaact cgacgaggag aggggcgagt acatctgcac 60
gcttacggga gaggtagttg aggagacggt tatagataca gggcccgaat ggagggctta 120
cacacctgag gagaggaccc gcagaagccg cgtgggcagc ccgcttaccc acatcatgta 180
gtagacgacc aagacagt 198

<210> SEQ ID NO 124
<211> LENGTH: 198
<212> TYPE: DNA
<213> ORGANISM: Artificial Sequence
<220> FEATURE:
<223> OTHER INFORMATION: Synthetic

<400> SEQUENCE: 124
acagttctcc ttcttagctt cgtgagaaca gtcgatggct gcggcagctg tctatgctgc 60
ctgccgtata cgcggcatac ccaggagtat agacgacata gcggaggtcg tgaagggtgg 120
ccgtaaggag gttgcccgct gctaccgcct catagtccgc gagctgaagc acatcatgta 180
gtagacgacc aagacagt 198

<210> SEQ ID NO 125
<211> LENGTH: 198
<212> TYPE: DNA
<213> ORGANISM: Artificial Sequence
<220> FEATURE:
<223> OTHER INFORMATION: Synthetic

<400> SEQUENCE: 125
acagttctcc ttcttagctt cgtgagaacg tggagtcttt tgtcacaccg cagaggcgta 60
gcgctgcaga gcaggagccc aagcctactg ccaacataga gaacatagtg gctacagtat 120
ccctcgacca gactctagac ctgaacctca tagagaggag catactgacc acatcatgta 180
gtagacgacc aagacagt 198

<210> SEQ ID NO 126
<211> LENGTH: 198
<212> TYPE: DNA
<213> ORGANISM: Artificial Sequence
<220> FEATURE:
<223> OTHER INFORMATION: Synthetic

<400> SEQUENCE: 126
acagttctcc ttcttagctt cgtgagaacc gtcgcctggg ttaagaggat gttcggcctc 60
tccaaggcgg gtcacggagg cacgctggac ccgaaggtca ccggcgtcct ccccgtagcc 120
ctggaggaag caaccaaggt cataggcctg gtggtgcaca cgagcaaggc acatcatgta 180
gtagacgacc aagacagt 198

<210> SEQ ID NO 127
<211> LENGTH: 198
<212> TYPE: DNA
<213> ORGANISM: Artificial Sequence
<220> FEATURE:
<223> OTHER INFORMATION: Synthetic

<400> SEQUENCE: 127
acagttctcc ttcttagctt cgtgagaacc gtgggcgaga tctaccagag gccgccgctc 60
cgcagcagtg ttaagagaag cctccgcgtc aagaggatat acgagataga gctgctggag 120
tacaacggca ggtacgcgct catgagggtg ctctgcgagg ccggcacatc acatcatgta 180
gtagacgacc aagacagt 198

<210> SEQ ID NO 128
<211> LENGTH: 198
<212> TYPE: DNA
<213> ORGANISM: Artificial Sequence
<220> FEATURE:
<223> OTHER INFORMATION: Synthetic

<400> SEQUENCE: 128
acagttctcc ttcttagctt cgtgagaacc gctggaagaa cgagggcaag gaggacctgc 60
tgcggagcta catcaagccc gtcgagtacg ccgtgagcca cctgcccaag atagttatac 120
gcgataccgc ggtggacgcc atagcccatg gcgcgaacct cgcggtgccc acatcatgta 180
gtagacgacc aagacagt 198

<210> SEQ ID NO 129
<211> LENGTH: 198
<212> TYPE: DNA
<213> ORGANISM: Artificial Sequence
<220> FEATURE:
<223> OTHER INFORMATION: Synthetic

<400> SEQUENCE: 129
acagttctcc ttcttagctt cgtgagaacg ggagacccca aggtgaccgg cgtcctacca 60
gtggggctcg ccaacagcac caaggtcatt ggtaatgtta tacatagtgt taaagaatac 120
gtgatggtta tacagctcca cggcgatgta gccgagcagg atttaagaac acatcatgta 180
gtagacgacc aagacagt 198

<210> SEQ ID NO 130
<211> LENGTH: 198
<212> TYPE: DNA
<213> ORGANISM: Artificial Sequence
<220> FEATURE:
<223> OTHER INFORMATION: Synthetic

<400> SEQUENCE: 130
acagttctcc ttcttagctt cgtgagaact agagggaaag actgtagctt tcattcctag 60
gcacggaaag agacacagaa tacctccaca taagataaat tatagagcta atatatgggc 120
attaaaagaa ctaggagtga aatgggtcat ctcagtttct gccgtaggac acatcatgta 180
gtagacgacc aagacagt 198

<210> SEQ ID NO 131
<211> LENGTH: 198
<212> TYPE: DNA
<213> ORGANISM: Artificial Sequence
<220> FEATURE:
<223> OTHER INFORMATION: Synthetic

<400> SEQUENCE: 131
acagttctcc ttcttagctt cgtgagaact gagggagctc aggaggactc gcacggggcc 60
ctacagggag gatgagacac ttgtaaggct ccaggacgtc agcgaggccc tgctcctgtg 120
gaggagcaac ggggatgaga ggtatcttag acgcatcgtg ctacccgttc acatcatgta 180
gtagacgacc aagacagt 198

<210> SEQ ID NO 132
<211> LENGTH: 198
<212> TYPE: DNA
<213> ORGANISM: Artificial Sequence
<220> FEATURE:
<223> OTHER INFORMATION: Synthetic

<400> SEQUENCE: 132
acagttctcc ttcttagctt cgtgagaacg aaacatctat cgcccacctc ccgaagataa 60
tgatcttgga tacagctgtc gacgccatag cacatggtgc caacctggct gccccaggcg 120
tcgccaggtt aaccaggaac atcgcgaagg gtagtaccgt agcgatcctc acatcatgta 180
gtagacgacc aagacagt 198

<210> SEQ ID NO 133
<211> LENGTH: 198
<212> TYPE: DNA
<213> ORGANISM: Artificial Sequence
<220> FEATURE:
<223> OTHER INFORMATION: Synthetic

<400> SEQUENCE: 133
acagttctcc ttcttagctt cgtgagaact cgctatcccc gtgtacagca tggtgggggt 60
gccgatgccc gggtagaact tggtgacgct ctccagcttc tcgaggacgg tttccttggg 120
gaggctcgcg gtgtccacga gggttatcgc gtcctcggcg ccgtcgccgc acatcatgta 180
gtagacgacc aagacagt 198

<210> SEQ ID NO 134
<211> LENGTH: 198
<212> TYPE: DNA
<213> ORGANISM: Artificial Sequence
<220> FEATURE:
<223> OTHER INFORMATION: Synthetic

<400> SEQUENCE: 134
acagttctcc ttcttagctt cgtgagaacc gaggacgcga agagcgcggt ggatgtggac 60
gcgccgccgc acacgtagcc gtcgaggtag cgcggaacca tcggcgacat cagccccacg 120
acgcgacccg aggcgttgcc gaggatcacg tcgagcgtca cgcgcggcac acatcatgta 180
gtagacgacc aagacagt 198

<210> SEQ ID NO 135
<211> LENGTH: 198

<212> TYPE: DNA
<213> ORGANISM: Artificial Sequence
<220> FEATURE:
<223> OTHER INFORMATION: Synthetic

<400> SEQUENCE: 135
acagttctcc ttcttagctt cgtgagaacc tcgacaccgt gccgttgccc tcctctaagt 60
agtcggaaag cctcatccgc gactccagct tcgccaccgg ctcctcgagc aggaggagga 120
cgcggttgat gcggtaggac gcactgcccg cctccagcac cgcgccgtcc acatcatgta 180
gtagacgacc aagacagt 198

<210> SEQ ID NO 136
<211> LENGTH: 198
<212> TYPE: DNA
<213> ORGANISM: Artificial Sequence
<220> FEATURE:
<223> OTHER INFORMATION: Synthetic

<400> SEQUENCE: 136
acagttctcc ttcttagctt cgtgagaact ctatggtgta gaacgggtcg ttgcggagcc 60
agcctggcgg cacgtaccgg tcgtccgcta tcgccagcga tctctcgaag aggtcgaggt 120
aggcggacgc gttggcgaac gccccgtgta tcacgacgtc tatcccgccc acatcatgta 180
gtagacgacc aagacagt 198

<210> SEQ ID NO 137
<211> LENGTH: 198
<212> TYPE: DNA
<213> ORGANISM: Artificial Sequence
<220> FEATURE:
<223> OTHER INFORMATION: Synthetic

<400> SEQUENCE: 137
acagttctcc ttcttagctt cgtgagaacg tataggtttc aggtattgat aatgcatagg 60
aggtttttaa aaccttgagc cgcatagtct tctggatggg cgagagacat ggttaagtat 120
aagtgcggca ggtgcggata cgtcttcgac gacgaggaga tgaagaggac acatcatgta 180
gtagacgacc aagacagt 198

<210> SEQ ID NO 138
<211> LENGTH: 198
<212> TYPE: DNA
<213> ORGANISM: Artificial Sequence
<220> FEATURE:
<223> OTHER INFORMATION: Synthetic

<400> SEQUENCE: 138
acagttctcc ttcttagctt cgtgagaacc ctacgccggg tgcgtaggag ggctcgagta 60
catccatgtc tatactgatg tatgttttac ccaggtcgcc tagtgccagg ggtcccttta 120
acgcttccag gatagagtac acggtgacgt ctctagtctt cttcaagaac acatcatgta 180
gtagacgacc aagacagt 198

<210> SEQ ID NO 139
<211> LENGTH: 198
<212> TYPE: DNA
<213> ORGANISM: Artificial Sequence
<220> FEATURE:
<223> OTHER INFORMATION: Synthetic

<400> SEQUENCE: 139
acagttctcc ttcttagctt cgtgagaacc tactagcgtg tcaacggagc tcttcaacgc 60
ctttactatt ggataggtta taaggtgctc gcctccgagg aatcccagga gcatgccggg 120
atactcgtct acaacgcctt tcaccacgtc acctatgatt cttaaagagc acatcatgta 180
gtagacgacc aagacagt 198

<210> SEQ ID NO 140
<211> LENGTH: 198
<212> TYPE: DNA
<213> ORGANISM: Artificial Sequence
<220> FEATURE:
<223> OTHER INFORMATION: Synthetic

<400> SEQUENCE: 140
acagttctcc ttcttagctt cgtgagaacc ataggtgaca tggggtttcc cattgactct 60
ataaagccgt atcctttaag cggagtgcaa ttggtctacg ctttgcttaa caacaggtat 120
ttcctaccgg gtagagaggg ctcgctcata gctttaggta gcgtgacggc acatcatgta 180
gtagacgacc aagacagt 198

<210> SEQ ID NO 141
<211> LENGTH: 198
<212> TYPE: DNA
<213> ORGANISM: Artificial Sequence
<220> FEATURE:
<223> OTHER INFORMATION: Synthetic

<400> SEQUENCE: 141
acagttctcc ttcttagctt cgtgagaacg gtatctcacc gcttgtcacc atagtatccc 60
tcaggtactc cagtattctt gagagaaacg cacctaagcc ggatctcagg tttgaatcca 120
taagaactat gagtgaagcg ggattgaagc ccctgctgtt tctaagaccc acatcatgta 180
gtagacgacc aagacagt 198

<210> SEQ ID NO 142
<211> LENGTH: 198
<212> TYPE: DNA
<213> ORGANISM: Artificial Sequence
<220> FEATURE:
<223> OTHER INFORMATION: Synthetic

<400> SEQUENCE: 142
acagttctcc ttcttagctt cgtgagaact aagggagata gagaaacgca tcaaaatacc 60
cttggggaaa ctgcgtgcag ggttcaata tggagtagag gtctcagaca taaaggagaa 120
gatagctgct tacgctagga ggaaggggct taaatacttc ccatcggcac acatcatgta 180
gtagacgacc aagacagt 198

<210> SEQ ID NO 143
<211> LENGTH: 198
<212> TYPE: DNA
<213> ORGANISM: Artificial Sequence
<220> FEATURE:
<223> OTHER INFORMATION: Synthetic

<400> SEQUENCE: 143
acagttctcc ttcttagctt cgtgagaact gtgaacctcg tgcccggctc taagtcgtga 60
gggcttgcaa cataggtggg gaggaacccg agcaacgggt aagaagacag gataagcggt 120
atcgctatga agagggctga gaaaaggaca tatactcctg agcccgtccc acatcatgta 180
gtagacgacc aagacagt 198

<210> SEQ ID NO 144
<211> LENGTH: 198
<212> TYPE: DNA
<213> ORGANISM: Artificial Sequence
<220> FEATURE:
<223> OTHER INFORMATION: Synthetic

<400> SEQUENCE: 144
acagttctcc ttcttagctt cgtgagaacc gaacatgcct tccccgtcta tatagaccca 60
gtagagttta aaaacttaac cagagacggc ttgtgagccg gatctctccc ccgctaggcc 120
ctggattggg ctcgctcctc ctgggacccc ggcctccaca tgctcgggac acatcatgta 180
gtagacgacc aagacagt 198

<210> SEQ ID NO 145
<211> LENGTH: 198
<212> TYPE: DNA
<213> ORGANISM: Artificial Sequence
<220> FEATURE:
<223> OTHER INFORMATION: Synthetic

<400> SEQUENCE: 145
acagttctcc ttcttagctt cgtgagaacc ctgaagggct cggctaccct gaagacgggc 60
ttctgcgcga ccgccgcgta ctccgccgtg gagcggtaga agagcgaggc tgtctccgtg 120
agcctgacca ttccgtacag ggcgactgcg acgagcacta tgactgcgac acatcatgta 180
gtagacgacc aagacagt 198

<210> SEQ ID NO 146
<211> LENGTH: 198
<212> TYPE: DNA
<213> ORGANISM: Artificial Sequence
<220> FEATURE:
<223> OTHER INFORMATION: Synthetic

<400> SEQUENCE: 146
acagttctcc ttcttagctt cgtgagaacg tcaaggtgct gatgccgaag gcgactttcg 60
acaccgacga tgccgccgac gccctggcca ttgccatctg ccacgcgcat caccggcaca 120
gtgttgccta taggatggcg ctggccggat aagtttgttc ttgacctgtc acatcatgta 180
gtagacgacc aagacagt 198

<210> SEQ ID NO 147
<211> LENGTH: 198
<212> TYPE: DNA
<213> ORGANISM: Artificial Sequence
<220> FEATURE:
<223> OTHER INFORMATION: Synthetic

<400> SEQUENCE: 147
acagttctcc ttcttagctt cgtgagaact ctcggttcgg caataagtaa taccaacgag 60
gtattaccat gcgcgtgacc agcaaaggcc aagtgacgat cccaaaggag atacgggatc 120
atttggggat tgggccgggc tccgaggtgg agttcgtgcc cacagacgac acatcatgta 180
gtagacgacc aagacagt 198

<210> SEQ ID NO 148
<211> LENGTH: 198
<212> TYPE: DNA
<213> ORGANISM: Artificial Sequence
<220> FEATURE:

<223> OTHER INFORMATION: Synthetic

<400> SEQUENCE: 148
acagttctcc ttcttagctt cgtgagaacc tcgatcatat ggccggcacg ttggacttgg 60
gaggcatgac aacggacgag tatatggagt ggctgagggg tccacgtgaa gatctcgaca 120
ttgattgaca caaatgtcct gatcgatgtt tggggtcctg ccggacaggc acatcatgta 180
gtagacgacc aagacagt 198

<210> SEQ ID NO 149
<211> LENGTH: 198
<212> TYPE: DNA
<213> ORGANISM: Artificial Sequence
<220> FEATURE:
<223> OTHER INFORMATION: Synthetic

<400> SEQUENCE: 149
acagttctcc ttcttagctt cgtgagaacc aggtgtattt tacacacctg gacagccagc 60
atatgatgct agcactcggt gtccccttat cacggtttcc cgcattgtaa agttttcgcg 120
cctgctgcgc cccgtagggc ctggattcat gtctcagaat ccatctccgc acatcatgta 180
gtagacgacc aagacagt 198

<210> SEQ ID NO 150
<211> LENGTH: 198
<212> TYPE: DNA
<213> ORGANISM: Artificial Sequence
<220> FEATURE:
<223> OTHER INFORMATION: Synthetic

<400> SEQUENCE: 150
acagttctcc ttcttagctt cgtgagaacc tggagcctgt tagttgttac aggttcaccg 60
gttgtcggag tattcagatc attgagccag cagttgatgg ctgcctgtag ttcactggtt 120
gtgatgtaag ctgctccatc ggaatcaaca tcgttccatg ggttccagtc acatcatgta 180
gtagacgacc aagacagt 198

<210> SEQ ID NO 151
<211> LENGTH: 198
<212> TYPE: DNA
<213> ORGANISM: Artificial Sequence
<220> FEATURE:
<223> OTHER INFORMATION: Synthetic

<400> SEQUENCE: 151
acagttctcc ttcttagctt cgtgagaaca cggtcttgct ttctcctgaa tccatttcac 60
ctgtccagac ccattcatag cggttagctt cactgaggtt ctgcttgaag acaccgtcat 120
cattgttaga tgaggttatt gtccagccgg caggaatgac ttcttcgaac acatcatgta 180
gtagacgacc aagacagt 198

<210> SEQ ID NO 152
<211> LENGTH: 198
<212> TYPE: DNA
<213> ORGANISM: Artificial Sequence
<220> FEATURE:
<223> OTHER INFORMATION: Synthetic

<400> SEQUENCE: 152
acagttctcc ttcttagctt cgtgagaacg tcagcagctc ttcatagaag ttctggtttg 60
caatatccct ctgggcaatg acagggtagt cgacttcgtt tgcagtcagg tggactgcat 120
acagggactt gctgatgtcc ggggtatatc cactgtgagg agcatagtac acatcatgta 180
gtagacgacc aagacagt 198

<210> SEQ ID NO 153
<211> LENGTH: 198
<212> TYPE: DNA
<213> ORGANISM: Artificial Sequence
<220> FEATURE:
<223> OTHER INFORMATION: Synthetic

<400> SEQUENCE: 153
acagttctcc ttcttagctt cgtgagaaca cccgtcagtc gtgacgtcct ccgctcctcc 60
tatgctatct ccacacaccc actcacgttc ttgcttcttt actacaccct ctttattcag 120
ctcttcgaga acattattaa tgtgaccctt agagatatat tcattatacc acatcatgta 180
gtagacgacc aagacagt 198

<210> SEQ ID NO 154
<211> LENGTH: 198
<212> TYPE: DNA
<213> ORGANISM: Artificial Sequence
<220> FEATURE:
<223> OTHER INFORMATION: Synthetic

<400> SEQUENCE: 154
acagttctcc ttcttagctt cgtgagaacg tgcctcctca agcgactgct taaacccaat 60
tacatctgat ttatccttta ttttagggcc tatagaatct atgaataatt cggcgattct 120
tattatttct aaaaccaatt cgtctgtttt gagtggtgtg ccttcttcac acatcatgta 180
gtagacgacc aagacagt 198

<210> SEQ ID NO 155
<211> LENGTH: 198
<212> TYPE: DNA
<213> ORGANISM: Artificial Sequence
<220> FEATURE:
<223> OTHER INFORMATION: Synthetic

<400> SEQUENCE: 155
acagttctcc ttcttagctt cgtgagaacc atcccatgca ttttcataat aatcggaatt 60
caaatcctct atattgaatt ttatcttaac atttgacata atcattttct ccttacagaa 120
gagatccagc taagcttact cataaatggt agtaccatgc caatattggc acatcatgta 180
gtagacgacc aagacagt 198

<210> SEQ ID NO 156
<211> LENGTH: 198
<212> TYPE: DNA
<213> ORGANISM: Artificial Sequence
<220> FEATURE:
<223> OTHER INFORMATION: Synthetic

<400> SEQUENCE: 156
acagttctcc ttcttagctt cgtgagaacc gtagcccgca ccttcctctg gtttagcacc 60
agcggtcccc acagagtacc catcatcccg aaggatatgc tggcaacagt gggcacgggt 120
ctcgctcgtt gcctgactta acaggatgct tcacagtacg aactgacgac acatcatgta 180
gtagacgacc aagacagt 198

<210> SEQ ID NO 157

<211> LENGTH: 198
<212> TYPE: DNA
<213> ORGANISM: Artificial Sequence
<220> FEATURE:
<223> OTHER INFORMATION: Synthetic

<400> SEQUENCE: 157
acagttctcc ttcttagctt cgtgagaacc ctgataggcc gcagattcat cctaaggcgc 60
cggagctttt gaccacagaa cattccagta tctatggtat atctggaatt atcaccagtt 120
tcccggtgtt atgccagacc ttagggcaga ttatccacgt gttactgagc acatcatgta 180
gtagacgacc aagacagt 198

<210> SEQ ID NO 158
<211> LENGTH: 198
<212> TYPE: DNA
<213> ORGANISM: Artificial Sequence
<220> FEATURE:
<223> OTHER INFORMATION: Synthetic

<400> SEQUENCE: 158
acagttctcc ttcttagctt cgtgagaact gtttggcttg atactaataa aagcacagct 60
aaaatgaaaa taagccgata tttgtgattc atgcaactca ccctttteta cataaacaaa 120 atactaaccc gaaaaccgaa attgaaatta atgcagagaa accaggtgac acatcatgta 180
gtagacgacc aagacagt 198

<210> SEQ ID NO 159
<211> LENGTH: 198
<212> TYPE: DNA
<213> ORGANISM: Artificial Sequence
<220> FEATURE:
<223> OTHER INFORMATION: Synthetic

<400> SEQUENCE: 159
acagttctcc ttcttagctt cgtgagaact taacggcacc aacagttatt atatttttag 60
cagtcccggg tgaagtaatt atggaatagt tgttagaatt actgttctta ttaccagctg 120
atttgaaagc aattatacct gcatcacgaa ttgcagcatc ataatattcc acatcatgta 180
gtagacgacc aagacagt 198

<210> SEQ ID NO 160
<211> LENGTH: 198
<212> TYPE: DNA
<213> ORGANISM: Artificial Sequence
<220> FEATURE:
<223> OTHER INFORMATION: Synthetic

<400> SEQUENCE: 160
acagttctcc ttcttagctt cgtgagaacg gctcagacga ctgaaaaagc aacgattgga 60
ataatagggg gttctgggct ctatgatcct ggtattttga ctaacagcag agaaataaaa 120
gtatatacac cctatgggga acctagcgat ttgataacga taggtaacac acatcatgta 180
gtagacgacc aagacagt 198

<210> SEQ ID NO 161
<211> LENGTH: 198
<212> TYPE: DNA
<213> ORGANISM: Artificial Sequence
<220> FEATURE:
<223> OTHER INFORMATION: Synthetic

<400> SEQUENCE: 161
acagttctcc ttcttagctt cgtgagaacc gcagaacagg ttccttctat tggatattca 60
tcttcggctg cagttgcagg aagagtaagg atatatacta cggtcttgct ttctcctgaa 120
tccatttcac ctgtccagac ccattcatag cggttagctt cactgaggtc acatcatgta 180
gtagacgacc aagacagt 198

<210> SEQ ID NO 162
<211> LENGTH: 198
<212> TYPE: DNA
<213> ORGANISM: Artificial Sequence
<220> FEATURE:
<223> OTHER INFORMATION: Synthetic

<400> SEQUENCE: 162
acagttctcc ttcttagctt cgtgagaacc ttcctccacg catttgttgt ggtgctgatg 60
gcgtattctc tggaatttgg gatgattctg gaaatccatc ctcagacact tcagatattt 120
tagtcttact tccagcgttt aattgaacct tacctttaaa agcagtagtc acatcatgta 180
gtagacgacc aagacagt 198

<210> SEQ ID NO 163
<211> LENGTH: 198
<212> TYPE: DNA
<213> ORGANISM: Artificial Sequence
<220> FEATURE:
<223> OTHER INFORMATION: Synthetic

<400> SEQUENCE: 163
acagttctcc ttcttagctt cgtgagaacg aaacttacct tatcagtgtc attaagcata 60
ttgcttccaa gacccattga agcacttaca tcgttgatac acaggtgcca ggaatagtat 120
tcctcagtct cactataatc ctcgttggtg tagccttcaa gagagtcaac acatcatgta 180
gtagacgacc aagacagt 198

<210> SEQ ID NO 164
<211> LENGTH: 198
<212> TYPE: DNA
<213> ORGANISM: Artificial Sequence
<220> FEATURE:
<223> OTHER INFORMATION: Synthetic

<400> SEQUENCE: 164
acagttctcc ttcttagctt cgtgagaacg tttaagcaat tcttcggatg aaagatggcg 60
ctctatagga atttgttctg gtctagccat aaggcattat ttgtacttaa ttagtaataa 120
atgtttagtt aatgactata aatctgcaat tggagtctca aattttcaac acatcatgta 180
gtagacgacc aagacagt 198

<210> SEQ ID NO 165
<211> LENGTH: 198
<212> TYPE: DNA
<213> ORGANISM: Artificial Sequence
<220> FEATURE:
<223> OTHER INFORMATION: Synthetic

<400> SEQUENCE: 165
acagttctcc ttcttagctt cgtgagaaca acatgaagga tgtgtgtaag aggaaacgtt 60
attaacagac gtaatcagga ggatagttat gccctaaaaa cagcagagtt aaggtttaaa 120
aataagataa gaactcagtt gaggtttatc cattaatccc attaatcctc acatcatgta 180
gtagacgacc aagacagt 198

<210> SEQ ID NO 166
<211> LENGTH: 198
<212> TYPE: DNA
<213> ORGANISM: Artificial Sequence
<220> FEATURE:
<223> OTHER INFORMATION: Synthetic

<400> SEQUENCE: 166
acagttctcc ttcttagctt cgtgagaaca ctttctaaaa gcgcttggag cacgtatcag 60
gtcaagtctt tcaaccttaa atgctgccag tgccgtaagt agtgcagtta tgttgcttat 120
tgaaacaaac aacttagccc acttattacc tcttgtcagt gtttttgatc acatcatgta 180
gtagacgacc aagacagt 198

<210> SEQ ID NO 167
<211> LENGTH: 198
<212> TYPE: DNA
<213> ORGANISM: Artificial Sequence
<220> FEATURE:
<223> OTHER INFORMATION: Synthetic

<400> SEQUENCE: 167
acagttctcc ttcttagctt cgtgagaacg tatccgctga tatatcctgg ggatatagat 60
cgctctgaaa tggttacatc tatcggtttt aaggacagtt ccaacactat tggaccttgc 120
agctatgaca ggaataatct gtttatcgag cacagttgaa tttgacctac acatcatgta 180
gtagacgacc aagacagt 198

<210> SEQ ID NO 168
<211> LENGTH: 198
<212> TYPE: DNA
<213> ORGANISM: Artificial Sequence
<220> FEATURE:
<223> OTHER INFORMATION: Synthetic

<400> SEQUENCE: 168
acagttctcc ttcttagctt cgtgagaact caatacctaa ttctttcctt agagtgctat 60
tttgattgaa ttccctcagg aaagattcaa aatttaagta gccgagctta catcttgaaa 120
tttccatctt tattatgttg ctcaggctta atgcttctaa gtatgggttc acatcatgta 180
gtagacgacc aagacagt 198

<210> SEQ ID NO 169
<211> LENGTH: 198
<212> TYPE: DNA
<213> ORGANISM: Artificial Sequence
<220> FEATURE:
<223> OTHER INFORMATION: Synthetic

<400> SEQUENCE: 169
acagttctcc ttcttagctt cgtgagaaca gatatccttt gaaattctcg taattgctga 60
aggccactac ttcatcaggt ctgatgcaat ctttaatctg aacattgctt tctgaggtct 120
taggaataat cctgtaaggg agtcggatat tgttcgttaa gatgctcttc acatcatgta 180
gtagacgacc aagacagt 198

<210> SEQ ID NO 170
<211> LENGTH: 198
<212> TYPE: DNA
<213> ORGANISM: Artificial Sequence
<220> FEATURE:
<223> OTHER INFORMATION: Synthetic

<400> SEQUENCE: 170
acagttctcc ttcttagctt cgtgagaaca tagagggacc tagattttca acgagggcag 60
aaagtagaat ttggagggaa gtttataaag ccgatatcat agggatgact ttagttccag 120
aagtaaattt agcttgcgaa atgcaaatgt gctatgcaac aattgcgatc acatcatgta 180
gtagacgacc aagacagt 198

<210> SEQ ID NO 171
<211> LENGTH: 198
<212> TYPE: DNA
<213> ORGANISM: Artificial Sequence
<220> FEATURE:
<223> OTHER INFORMATION: Synthetic

<400> SEQUENCE: 171
acagttctcc ttcttagctt cgtgagaacg tcttcagcat agtaccagct tatgttgtca 60
ccatcgttca gtacgttacc accaagtcca ctgcctgcag ctacatcatt aatgtacagg 120
aaccaggcat agtaaccgcc agttgatatg tagtcttcac cttcgattcc acatcatgta 180
gtagacgacc aagacagt 198

<210> SEQ ID NO 172
<211> LENGTH: 198
<212> TYPE: DNA
<213> ORGANISM: Artificial Sequence
<220> FEATURE:
<223> OTHER INFORMATION: Synthetic

<400> SEQUENCE: 172
acagttctcc ttcttagctt cgtgagaaca ctctccatca tgacagccag atcggtcata 60
gcatcgattg tgtactcttc gtcgggattg ttgtatggaa tgaacttata gttctcacct 120
gctacctgat ccactgtcat ttctgcaaga gtctgcactg tggtaattcc acatcatgta 180
gtagacgacc aagacagt 198

<210> SEQ ID NO 173
<211> LENGTH: 198
<212> TYPE: DNA
<213> ORGANISM: Artificial Sequence
<220> FEATURE:
<223> OTHER INFORMATION: Synthetic

<400> SEQUENCE: 173
acagttctcc ttcttagctt cgtgagaaca tattccgtat ttcttatcaa accgatcgtg 60
aagatttgac aaaggcttaa ctttagggct ccacttctca ttattagcct tagaatataa 120
agcgtaaccg taagcctgag gaacgtaaag cttaggagat tcaatcccgc acatcatgta 180
gtagacgacc aagacagt 198

<210> SEQ ID NO 174
<211> LENGTH: 198
<212> TYPE: DNA
<213> ORGANISM: Artificial Sequence
<220> FEATURE:
<223> OTHER INFORMATION: Synthetic

<400> SEQUENCE: 174
acagttctcc ttcttagctt cgtgagaact aaaattagcc gaaggcttcc cattaccgaa 60

```
aaagtcgttt attagctctt catccttctt ctccacgtcc gcccattcct ctccttccct    120

tggaatttta agctcgtccc agctgactct tatgggcaat tcaatatccc acatcatgta    180

gtagacgacc aagacagt                                                  198


<210> SEQ ID NO 175
<211> LENGTH: 198
<212> TYPE: DNA
<213> ORGANISM: Artificial Sequence
<220> FEATURE:
<223> OTHER INFORMATION: Synthetic

<400> SEQUENCE: 175

acagttctcc ttcttagctt cgtgagaacg tataaacttt tgatataacc ttgcctaatt     60

tgatatcata gcttatgttt ggcgctatcc cccacttgta gagggtcgcg ttatattctc    120

taatagcaag agagatacaa gattcgttaa cgttatttat atcactctcc acatcatgta    180

gtagacgacc aagacagt                                                  198


<210> SEQ ID NO 176
<211> LENGTH: 198
<212> TYPE: DNA
<213> ORGANISM: Artificial Sequence
<220> FEATURE:
<223> OTHER INFORMATION: Synthetic

<400> SEQUENCE: 176

acagttctcc ttcttagctt cgtgagaact ccggaggaat ctatcatatt aaacctcctc     60

aaaatcgcct cctcttgatt gcttaaaggc tgtgaattac aaagcttatt taatgcgtcc    120

caaagcgtta agtaataatt atttatatta aacactacta tttcagtagc acatcatgta    180

gtagacgacc aagacagt                                                  198


<210> SEQ ID NO 177
<211> LENGTH: 198
<212> TYPE: DNA
<213> ORGANISM: Artificial Sequence
<220> FEATURE:
<223> OTHER INFORMATION: Synthetic

<400> SEQUENCE: 177

acagttctcc ttcttagctt cgtgagaacg ttcctcctca attcaattgg actgaaggag     60

ggtacgttct ggaaaacaga gcgtaaaaga gatatagaac gtagtataca catagctgga    120

aaaagaacaa tcattaagac aataaagaac tttatggaaa agagtagaac acatcatgta    180

gtagacgacc aagacagt                                                  198


<210> SEQ ID NO 178
<211> LENGTH: 198
<212> TYPE: DNA
<213> ORGANISM: Artificial Sequence
<220> FEATURE:
<223> OTHER INFORMATION: Synthetic

<400> SEQUENCE: 178

acagttctcc ttcttagctt cgtgagaact cgtgtaaagg ttgtataatt caagcctcag     60

aacatttcga actccttaca aaatcgttta aactttctaa ggcataaatt tactagaaat    120

tgtcatttat gagaatgtaa ctatatagat ggtaaaatta ttaatcctcc acatcatgta    180

gtagacgacc aagacagt                                                  198
```

<210> SEQ ID NO 179
<211> LENGTH: 198
<212> TYPE: DNA
<213> ORGANISM: Artificial Sequence
<220> FEATURE:
<223> OTHER INFORMATION: Synthetic

<400> SEQUENCE: 179
acagttctcc ttcttagctt cgtgagaacg gctgaaaaat aggttcgatc cgcctcctca 60
cttcttctcc ttcttgccct cggcctcgga ggaggcctct attcccagct tcttggcctc 120
ctcctcggtc gtcatgaaca ggctagtcct ctgccttccg cccatgctcc acatcatgta 180
gtagacgacc aagacagt 198

<210> SEQ ID NO 180
<211> LENGTH: 198
<212> TYPE: DNA
<213> ORGANISM: Artificial Sequence
<220> FEATURE:
<223> OTHER INFORMATION: Synthetic

<400> SEQUENCE: 180
acagttctcc ttcttagctt cgtgagaacg acctagcctt acgcacagcc ctctccacaa 60
cctcctcaag cttatcccag tcaatagagc tcattacaag ttaaccacgc ccacctttaa 120
tataaacctt tacccctcgt ggcaattaac tttaaccgct actccggtgc acatcatgta 180
gtagacgacc aagacagt 198

<210> SEQ ID NO 181
<211> LENGTH: 198
<212> TYPE: DNA
<213> ORGANISM: Artificial Sequence
<220> FEATURE:
<223> OTHER INFORMATION: Synthetic

<400> SEQUENCE: 181
acagttctcc ttcttagctt cgtgagaact ggcccttaga cctctgccca tgcttaggcg 60
cttacccaca cctattagta cggcgccaat gcccacggcc atgaagtaca ttaaggcacc 120
catggttgca ccgtagagtg ccgtgaatgt tccgtagaat acaccggccc acatcatgta 180
gtagacgacc aagacagt 198

<210> SEQ ID NO 182
<211> LENGTH: 198
<212> TYPE: DNA
<213> ORGANISM: Artificial Sequence
<220> FEATURE:
<223> OTHER INFORMATION: Synthetic

<400> SEQUENCE: 182
acagttctcc ttcttagctt cgtgagaact cggcgaatct gtcgagctcc atgacgtcca 60
cagagccgcc gaacttggcc gagaatctat cggcctgggc ggtgcgcctc cctatcagca 120
aaaccctggg cgccgtcagt agcgcgacgg ccctggcgat tcccctggcc acatcatgta 180
gtagacgacc aagacagt 198

<210> SEQ ID NO 183
<211> LENGTH: 198
<212> TYPE: DNA
<213> ORGANISM: Artificial Sequence
<220> FEATURE:
<223> OTHER INFORMATION: Synthetic

<400> SEQUENCE: 183
acagttctcc ttcttagctt cgtgagaact ccaggtagga tctggccgag agggaggacg 60
ccgcgctgtt gtgctccggg aaccctagag tcacgaccgc cttgacgcct atacgttcgg 120
cgtattcagc gacggcggcg ccggtgccgc ccgtcagcgt gacggcaagc acatcatgta 180
gtagacgacc aagacagt 198

<210> SEQ ID NO 184
<211> LENGTH: 198
<212> TYPE: DNA
<213> ORGANISM: Artificial Sequence
<220> FEATURE:
<223> OTHER INFORMATION: Synthetic

<400> SEQUENCE: 184
acagttctcc ttcttagctt cgtgagaacg caagagaata catttttgat gataagagaa 60
gcttgtggca tactttctta ggctttattt cagcattcac tttagcgtat tctatcgtta 120
ttttgctatt gttcacattg tatcaagtga gagaaagaga gaagccaacc acatcatgta 180
gtagacgacc aagacagt 198

<210> SEQ ID NO 185
<211> LENGTH: 198
<212> TYPE: DNA
<213> ORGANISM: Artificial Sequence
<220> FEATURE:
<223> OTHER INFORMATION: Synthetic

<400> SEQUENCE: 185
acagttctcc ttcttagctt cgtgagaaca gaatcaaagg agtggtgtaa agatggagag 60
aaaaaaaggt tggcatccta tttatgtgag tgaagcggtt ttaagtaagt tagataaaga 120
gagagaagaa attaaagaag aattaggtat tccaaaggaa gagaatttgc acatcatgta 180
gtagacgacc aagacagt 198

<210> SEQ ID NO 186
<211> LENGTH: 198
<212> TYPE: DNA
<213> ORGANISM: Artificial Sequence
<220> FEATURE:
<223> OTHER INFORMATION: Synthetic

<400> SEQUENCE: 186
acagttctcc ttcttagctt cgtgagaacg ttcagcataa aagacggttt cacgggccaa 60
agcctaagcg gcgtaacggt gaaagaagga gatacggttt tgggcacgat tgacgacggc 120
gggacgctgg agctcacgag gggcactcac accttgactt tcgagaagcc acatcatgta 180
gtagacgacc aagacagt 198

<210> SEQ ID NO 187
<211> LENGTH: 198
<212> TYPE: DNA
<213> ORGANISM: Artificial Sequence
<220> FEATURE:
<223> OTHER INFORMATION: Synthetic

<400> SEQUENCE: 187
acagttctcc ttcttagctt cgtgagaacc tgatgttata gaagtccgca aggacggctc 60
tgtcatctcg cccgagggtg ggaaatacta tctcggcgac ataagcggcc cgacacaaat 120
tagcatcaag ttcaaggccg gcgcggtggg aacccacggc ttcactatcc acatcatgta 180
gtagacgacc aagacagt 198

<210> SEQ ID NO 188
<211> LENGTH: 198
<212> TYPE: DNA
<213> ORGANISM: Artificial Sequence
<220> FEATURE:
<223> OTHER INFORMATION: Synthetic

<400> SEQUENCE: 188
acagttctcc ttcttagctt cgtgagaact ctccctcaac cttcgcgggg agaacggcgc 60
ggagtactgg acgggctacg cggacgcgct ggaagacctg ttgaagaaaa tccagaggcg 120
ggaggtgagg gcatgagaag gtattgttac atcacgtggg gatggatcac acatcatgta 180
gtagacgacc aagacagt 198

<210> SEQ ID NO 189
<211> LENGTH: 198
<212> TYPE: DNA
<213> ORGANISM: Artificial Sequence
<220> FEATURE:
<223> OTHER INFORMATION: Synthetic

<400> SEQUENCE: 189
acagttctcc ttcttagctt cgtgagaacg agcgccggga ggtgagggca tgagtgagga 60
attgatgttt ggtcgtgtcg tggagtatgt tcagcatagt ttctacaaga aaccgtttcc 120
tcttggcagt gagctcaaga atgcagtaga gaaggttatg gaaacaggac acatcatgta 180
gtagacgacc aagacagt 198

<210> SEQ ID NO 190
<211> LENGTH: 198
<212> TYPE: DNA
<213> ORGANISM: Artificial Sequence
<220> FEATURE:
<223> OTHER INFORMATION: Synthetic

<400> SEQUENCE: 190
acagttctcc ttcttagctt cgtgagaaca ggtcagagcc cacgtggcaa cttttgaggt 60
tctgacaaaa gactatgttc gtgagaaata caaagacatc atagagttca tgagggagaa 120
agggacagta tcgagaaagg aactgcggaa gaagttcttc ttgcttgctc acatcatgta 180
gtagacgacc aagacagt 198

<210> SEQ ID NO 191
<211> LENGTH: 198
<212> TYPE: DNA
<213> ORGANISM: Artificial Sequence
<220> FEATURE:
<223> OTHER INFORMATION: Synthetic

<400> SEQUENCE: 191
acagttctcc ttcttagctt cgtgagaacg tacctcaaaa tacagaatca tattttacaa 60
tcgcttggaa atattaatat caacaatacg caagtccaaa ttaacgtccc tggcaaacag 120
gtgacaattt atacccacga aatactagat aacgccaaaa aggcactcgc acatcatgta 180
gtagacgacc aagacagt 198

<210> SEQ ID NO 192
<211> LENGTH: 198
<212> TYPE: DNA

<213> ORGANISM: Artificial Sequence
<220> FEATURE:
<223> OTHER INFORMATION: Synthetic

<400> SEQUENCE: 192
acagttctcc ttcttagctt cgtgagaacc tttgtatact tagatcagga aatggagcta 60
aaaggcacta tcaagaagac aaaagattcc tggagagaaa catttaaaga gtactccaag 120
acagacagcg aatatctaat aaattacaga ctgttttcaa tactccctcc acatcatgta 180
gtagacgacc aagacagt 198

<210> SEQ ID NO 193
<211> LENGTH: 140
<212> TYPE: DNA
<213> ORGANISM: Artificial Sequence
<220> FEATURE:
<223> OTHER INFORMATION: Synthetic

<400> SEQUENCE: 193
caaatgcttt cagtggtttc caatgccctg accagcctgt actcaactaa gggatatgac 60
gtaacattca gtgacctgat cgccgccatt caggcaatga agggctacga tgacagcgca 120
aacgctaaac tcgtcgtgga 140

<210> SEQ ID NO 194
<211> LENGTH: 140
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (74)..(76)
<223> OTHER INFORMATION: n is a, c, g, or t

<400> SEQUENCE: 194
agtcggagct tataaccaca gatcctgaag tattgagaaa gagaagggga tggtgagata 60
aacatgaggt gtgnnnaaag ctgacaatat gtacgcgtgc ttgaaggaca ctgttgtgaa 120
ggaaaggtat cctgtcgcta 140

<210> SEQ ID NO 195
<211> LENGTH: 140
<212> TYPE: DNA
<213> ORGANISM: Artificial Sequence
<220> FEATURE:
<223> OTHER INFORMATION: Synthetic

<400> SEQUENCE: 195
atgcagtata tggcaggtgc gagcaactgc tttaccatgg gtgccatggt gcagaacggg 60
agaagctccc tctactggaa ggttaaggac gcaaatttct ggtccaagac tttcgagagc 120
aagttgcgcg ttctggggct 140

<210> SEQ ID NO 196
<211> LENGTH: 140
<212> TYPE: DNA
<213> ORGANISM: Artificial Sequence
<220> FEATURE:
<223> OTHER INFORMATION: Synthetic

<400> SEQUENCE: 196
ggctgcggaa gccagcaagg aaccttgtct cttcaggaga ggcaggatat acgtcacatt 60
caatgtaagg agggtggcac tgagcggtgc gggacagttg actgccgcca ggacttatgc 120
cataggcaac accgatgcga 140

<210> SEQ ID NO 197
<211> LENGTH: 140
<212> TYPE: DNA
<213> ORGANISM: Artificial Sequence
<220> FEATURE:
<223> OTHER INFORMATION: Synthetic

<400> SEQUENCE: 197
gatgaggtta aggggatatg cgagagattc ggcaaggtcg tggatgccgt gaactctcct 60
gtgcttaccg agagtaatgc ctcgtacagg aatgcggggc tggtgcgtgc caggttcaac 120
tgggactaca tcaggcccga 140

<210> SEQ ID NO 198
<211> LENGTH: 140
<212> TYPE: DNA
<213> ORGANISM: Artificial Sequence
<220> FEATURE:
<223> OTHER INFORMATION: Synthetic

<400> SEQUENCE: 198
tggtctccac ggaaggctac atggacaggg caataggcgt ccaggatatc ggctacctgt 60
tctggcaggc aggtcccacc gcaatgaagg atatgagaat ttacaacggt cccggtggtc 120
tgatcgttct gcctttctat 140

<210> SEQ ID NO 199
<211> LENGTH: 140
<212> TYPE: DNA
<213> ORGANISM: Artificial Sequence
<220> FEATURE:
<223> OTHER INFORMATION: Synthetic

<400> SEQUENCE: 199
ctttctgcgc gcaacaggct ggccaaggga cttccgaaga gcctggacat gtttgccagc 60
gtggaaggtc gtgaccttgg gtacgatccg aggtacataa cagaggaaga ttacaagacc 120
attatgacca aggcccgtct 140

<210> SEQ ID NO 200
<211> LENGTH: 140
<212> TYPE: DNA
<213> ORGANISM: Artificial Sequence
<220> FEATURE:
<223> OTHER INFORMATION: Synthetic

<400> SEQUENCE: 200
ggcatgatag atgaggatgg ctacgaggta ccgaagggtg aagaccccaa cgaccccaga 60
agtgcacaca cctttggttg ggtcgaccaa tcagatggag gcacatccaa tggtggcatg 120
cagtccggtg ggagctctca 140

<210> SEQ ID NO 201
<211> LENGTH: 140
<212> TYPE: DNA
<213> ORGANISM: Artificial Sequence
<220> FEATURE:
<223> OTHER INFORMATION: Synthetic

<400> SEQUENCE: 201
cttaaggacg gggacgtgac aaagctgtat tctcaggacg attacctcag ggtcagcagg 60
ctcaagttca gcgagaatcc gatgcttggc atcgtcaaga atacggatgg cacaggggag 120
gttataggtc cgtcctttgc 140

<210> SEQ ID NO 202
<211> LENGTH: 140
<212> TYPE: DNA
<213> ORGANISM: Artificial Sequence
<220> FEATURE:
<223> OTHER INFORMATION: Synthetic

<400> SEQUENCE: 202
agggaccttc tgtggaacat aatctcgggt gccctgaatg cgggaaggga acagctctac 60
ggggatgcat tcggcggtcc taagatagag cagtacgtga aagcactcac gcaggtgctg 120
tatgacctgt ctgtcaacag 140

<210> SEQ ID NO 203
<211> LENGTH: 140
<212> TYPE: DNA
<213> ORGANISM: Artificial Sequence
<220> FEATURE:
<223> OTHER INFORMATION: Synthetic

<400> SEQUENCE: 203
tgaaggaacg cgtcatcgtc cacaagagca ctacgaggaa cgaagtcctt gaagagttca 60
aggcgtctaa ggagccgaag gtcctatttg cgataaagat ggaagagggt acggatttca 120
gggatgacca ggcaaggtgg 140

<210> SEQ ID NO 204
<211> LENGTH: 140
<212> TYPE: DNA
<213> ORGANISM: Artificial Sequence
<220> FEATURE:
<223> OTHER INFORMATION: Synthetic

<400> SEQUENCE: 204
cagatattgg tcaagactcc ttaccaggat ctgggagacg agtgggtccg cctccatagg 60
gagaagatgg gacggagatg gtacgagata tccgccctcc agcaggtcat ccaggcgagc 120
ggcaggataa tgaggaacga 140

<210> SEQ ID NO 205
<211> LENGTH: 140
<212> TYPE: DNA
<213> ORGANISM: Artificial Sequence
<220> FEATURE:
<223> OTHER INFORMATION: Synthetic

<400> SEQUENCE: 205
cagggactgg ggagacacct acgtccttga catgaacgcc atgaagctca tccgcatgta 60
cgaaaaggaa tgcccccgct ggtttttgaa gaggttgaaa ctatgacgca tcacaatatc 120
accttccccg tccctcccga 140

<210> SEQ ID NO 206
<211> LENGTH: 140
<212> TYPE: DNA
<213> ORGANISM: Artificial Sequence
<220> FEATURE:
<223> OTHER INFORMATION: Synthetic

<400> SEQUENCE: 206
gcaatgtccg caacagttga caacgttgca cgggtcgcgg gatggctcag ggcgactgca 60
gtctccagcg atttcaggcc cgtcaccctg aagaagtacg tccttacccc ccgccatatc 120
atggatgaga aaggggatac 140

<210> SEQ ID NO 207
<211> LENGTH: 140
<212> TYPE: DNA
<213> ORGANISM: Artificial Sequence
<220> FEATURE:
<223> OTHER INFORMATION: Synthetic

<400> SEQUENCE: 207
cgagatacag cagatgctgg ggcgcgccgg gagggcgaaa tacgattcca tgggctacgg 60
ctacatctgc tcatccgacg ttcacctcca ggacgtgtat aagacgtacg ttcatggccg 120
tctggagagc gtaaaatcaa 140

<210> SEQ ID NO 208
<211> LENGTH: 140
<212> TYPE: DNA
<213> ORGANISM: Artificial Sequence
<220> FEATURE:
<223> OTHER INFORMATION: Synthetic

<400> SEQUENCE: 208
ggcactggac gagttcttct ccaccacgct ggcacgccac gagggtgccc gtctggaaga 60
atggatagac aacagccttg tcttcctgca ggacaacgac atgatagtcg ggggacgttc 120
cttcacggct accccccttcg 140

<210> SEQ ID NO 209
<211> LENGTH: 140
<212> TYPE: DNA
<213> ORGANISM: Artificial Sequence
<220> FEATURE:
<223> OTHER INFORMATION: Synthetic

<400> SEQUENCE: 209
ccatccttgc ggactggata gacgagaagc ccgaaagcga catcgtcaat aaatacaaca 60
tctggcctgc cgacctgagg agcagggttg agttggccga atggctctcg cattcccttt 120
acgagatctc gagggtcctg 140

<210> SEQ ID NO 210
<211> LENGTH: 140
<212> TYPE: DNA
<213> ORGANISM: Artificial Sequence
<220> FEATURE:
<223> OTHER INFORMATION: Synthetic

<400> SEQUENCE: 210
ggcgactatt cctacgtcag cgttgcggaa tatttctcca gctcaaggat aatagccact 60
accgcttccc ccggtggcga cagggagaag ataaacgaga tcatgcgcca cctgagaata 120
gagaaccttg aggtgaggga 140

<210> SEQ ID NO 211
<211> LENGTH: 140
<212> TYPE: DNA
<213> ORGANISM: Artificial Sequence
<220> FEATURE:
<223> OTHER INFORMATION: Synthetic

<400> SEQUENCE: 211
atcgacgctc cagctgttca gggacggtgc ggtcaggata ctcgtagcaa cgcaggttgg 60
ggaggaagga ctggacgtac cggctgcaga taccgtcata ttctacgagc cggtggcaag 120
cgaggtccgc tcaatccaga 140

<210> SEQ ID NO 212
<211> LENGTH: 140
<212> TYPE: DNA
<213> ORGANISM: Artificial Sequence
<220> FEATURE:
<223> OTHER INFORMATION: Synthetic

<400> SEQUENCE: 212
cgcggtcctc tttcccagct tcagtccttt ggctttccta tgttctgctg gtactcttcc 60
cattgctctc tctgttgttt ctcctggctt ttcctgaagt tttcgagggc ttcgtccatg 120
ctgtcataag cgttatgcga 140

<210> SEQ ID NO 213
<211> LENGTH: 140
<212> TYPE: DNA
<213> ORGANISM: Artificial Sequence
<220> FEATURE:
<223> OTHER INFORMATION: Synthetic

<400> SEQUENCE: 213
cgaactcctt gacgctcctg gagatgacca gtttctctat ctccaccctc ccgctcttca 60
tgtccgatat tattttcctc gcccttctca gtgcctcgtc cacgttccgg tcgagcacga 120
gattgaacat ttccatgagt 140

<210> SEQ ID NO 214
<211> LENGTH: 140
<212> TYPE: DNA
<213> ORGANISM: Artificial Sequence
<220> FEATURE:
<223> OTHER INFORMATION: Synthetic

<400> SEQUENCE: 214
ccctttcctc gaggtctttg tctattccct tcaccgtttc cctggcccaa gcagtgatgc 60
tggacccgat actgggatcg gtaaacctgt agaagcttga tgcaaacact ccgtagaacg 120
aattcataag caccttcacc 140

<210> SEQ ID NO 215
<211> LENGTH: 140
<212> TYPE: DNA
<213> ORGANISM: Artificial Sequence
<220> FEATURE:
<223> OTHER INFORMATION: Synthetic

<400> SEQUENCE: 215
cagttctcct tccaccccgt ccgcctcttc tatgacggtc gcactttccg tcgagcagac 60
gccctacggc tggatggatc agtatccctc gtcggttgtt gcccatgtca cgggaggcat 120
ccctccctac gcctatcact 140

<210> SEQ ID NO 216
<211> LENGTH: 140
<212> TYPE: DNA
<213> ORGANISM: Artificial Sequence
<220> FEATURE:
<223> OTHER INFORMATION: Synthetic

<400> SEQUENCE: 216
caatctggag gctttcgccg tatccgtcga agtcacggac tcatcggggc attcagtctc 60
aggtgcaatc atgatcaact acggttccat agacctctcc ccgtttggat acatggtaac 120
tttgattttt ccggtgatca 140

<210> SEQ ID NO 217
<211> LENGTH: 140
<212> TYPE: DNA
<213> ORGANISM: Artificial Sequence
<220> FEATURE:
<223> OTHER INFORMATION: Synthetic

<400> SEQUENCE: 217
gaacatccat tgctgaccat cacgatcgat ggctcaaagg acacgttcaa aactggcgat 60
gtcctggaat ggttgaccga aagtgacatc tcaaacatgc acaatgttgc gtccttcaca 120
aaatctctcc tgaggatagt 140

<210> SEQ ID NO 218
<211> LENGTH: 140
<212> TYPE: DNA
<213> ORGANISM: Artificial Sequence
<220> FEATURE:
<223> OTHER INFORMATION: Synthetic

<400> SEQUENCE: 218
gcatgctgcc cgatggccaa tggttcgggg aggtcattgg gaaggacgtg cagggaaatc 60
cctacggcat tgattataca atgtggttgc cgtttaacac ctacgttagg gataagctca 120
gttacaatag ttgggggaag 140

<210> SEQ ID NO 219
<211> LENGTH: 140
<212> TYPE: DNA
<213> ORGANISM: Artificial Sequence
<220> FEATURE:
<223> OTHER INFORMATION: Synthetic

<400> SEQUENCE: 219
ccagcattcc tcctctgagg gagttcggaa ggtaaaatct cctgatgaca tctgagtccc 60
tggcgcccat tgtcttggct gagtagactt ccattttact tgtcgtgctg ccagttgaaa 120
atgcaagtac tgctatcatc 140

<210> SEQ ID NO 220
<211> LENGTH: 140
<212> TYPE: DNA
<213> ORGANISM: Artificial Sequence
<220> FEATURE:
<223> OTHER INFORMATION: Synthetic

<400> SEQUENCE: 220
gttccctgca ggaatgattg ttcaactgca ctcgtcagta catgatagaa caatcttgaa 60
gctgacagat ggagcgcata gaagataagg aatgcaagag gtaccagtac tagtaccact 120
gcatatattc ctgcgtatag 140

<210> SEQ ID NO 221
<211> LENGTH: 140
<212> TYPE: DNA
<213> ORGANISM: Artificial Sequence
<220> FEATURE:
<223> OTHER INFORMATION: Synthetic

<400> SEQUENCE: 221
cgattgcagg aacgtggaaa gtgtgcggtt aatgtatgac tcattgctca catcgaatcg 60
atacagaaga ccgctgtttg ctgccaggta ggaatctatg ttattcaggc caacaaccac 120
atcgtatccc gcccccctttg 140

<210> SEQ ID NO 222
<211> LENGTH: 140
<212> TYPE: DNA
<213> ORGANISM: Artificial Sequence
<220> FEATURE:
<223> OTHER INFORMATION: Synthetic

<400> SEQUENCE: 222
aggattgaac cggttggtgt caacgtagaa tcctcattga cccgccacat aaaactgaac 60
attccaattg tgtcgtctcc tatggatacg gtctctgagg cagatatggc aattgcacta 120
gcaagactcg gtggtattgg 140

<210> SEQ ID NO 223
<211> LENGTH: 140
<212> TYPE: DNA
<213> ORGANISM: Artificial Sequence
<220> FEATURE:
<223> OTHER INFORMATION: Synthetic

<400> SEQUENCE: 223
cttattatac gcgaccttta cactgtaagc ccggaaacac ctgttgacga tgcaatccgt 60
actatgaggg agaagcgaat cgctgggctc ccagtgatat tgaacggcaa acttgtcgga 120
atacttacga acagggacat 140

<210> SEQ ID NO 224
<211> LENGTH: 140
<212> TYPE: DNA
<213> ORGANISM: Artificial Sequence
<220> FEATURE:
<223> OTHER INFORMATION: Synthetic

<400> SEQUENCE: 224
ggtacggcaa gataggctca gggaaatttg taccagaggg agttgaagga gcagttccgt 60
acaaaggtaa agttgcagat gcagtctttc aattgatcgg gggcctgaag tcggggatgg 120
ggtatactgg ctcgcccaca 140

<210> SEQ ID NO 225
<211> LENGTH: 140
<212> TYPE: DNA
<213> ORGANISM: Artificial Sequence
<220> FEATURE:
<223> OTHER INFORMATION: Synthetic

<400> SEQUENCE: 225
ggtggaagcg ttgaggagtt tgtcactcta tcgaggagag tggaggcagc gggattcgac 60
aaggtcgagc tcaatttgtc ctgcccacac gttcagggag ttggatccga ggtaggacag 120
gatgtaggtc ttgtagaaga 140

<210> SEQ ID NO 226
<211> LENGTH: 140
<212> TYPE: DNA
<213> ORGANISM: Artificial Sequence
<220> FEATURE:
<223> OTHER INFORMATION: Synthetic

<400> SEQUENCE: 226
gacacttata gacaggctag acaagaagac gaagacaagg atattcttct cacttgagcg 60
attgatgaag tgcggcatag ggatttgtga cagttgcagc atcaacggca tccgggtatg 120
caaggacgga acaattttcg 140

<210> SEQ ID NO 227
<211> LENGTH: 140
<212> TYPE: DNA
<213> ORGANISM: Artificial Sequence
<220> FEATURE:
<223> OTHER INFORMATION: Synthetic

<400> SEQUENCE: 227
cttcgcaact gcaaagaggt agcttctgga tgcttccctg gaactatccc tacattgctg 60
ttatcttact agtggtactg atttatgcag caatagagga ccttaggaag aggaaaataa 120
caactataac cttccttgca 140

<210> SEQ ID NO 228
<211> LENGTH: 140
<212> TYPE: DNA
<213> ORGANISM: Artificial Sequence
<220> FEATURE:
<223> OTHER INFORMATION: Synthetic

<400> SEQUENCE: 228
gtgacagttg gaactggtct atctccccgg tattttaata agtttatagg cgtagcaaag 60
gcatatacga caagagtagg ggaggggata tttcctactg agatgtttgg ggaagaggca 120
gatagactta gaaccctagg 140

<210> SEQ ID NO 229
<211> LENGTH: 140
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (82)..(82)
<223> OTHER INFORMATION: n is a, c, g, or t

<400> SEQUENCE: 229
gaagaagact taaaggattt aggtagagag cttaaggtac caagaagacc gttcaaaaag 60
ttaacgcata gagaagctgt tnatatattg agatctcatg gcataaaagc aagttatgaa 120
catgagatac cttgggaagc 140

<210> SEQ ID NO 230
<211> LENGTH: 140
<212> TYPE: DNA
<213> ORGANISM: Artificial Sequence
<220> FEATURE:
<223> OTHER INFORMATION: Synthetic

<400> SEQUENCE: 230
acggggaggc tgtctcagga gctgaaagag aatatagagc ggagaaggtt attgagagga 60
tgagagctac tggtgagaac cctgcaaaat acggttggta cattgaaatg ttgaaatatg 120
gtattccgcc gagtgcaggg 140

<210> SEQ ID NO 231

<211> LENGTH: 140
<212> TYPE: DNA
<213> ORGANISM: Artificial Sequence
<220> FEATURE:
<223> OTHER INFORMATION: Synthetic

<400> SEQUENCE: 231
atatgcagat ttagatgaga ttataggggt tgcatctaag gcaggaatag attgcataac 60
tatagatggg tcagaaggtg gaacaggtat gagccctata gctgcgatga gagaactagg 120
atatccaacg ctagtatgtc 140

<210> SEQ ID NO 232
<211> LENGTH: 140
<212> TYPE: DNA
<213> ORGANISM: Artificial Sequence
<220> FEATURE:
<223> OTHER INFORMATION: Synthetic

<400> SEQUENCE: 232
ggacacgaaa ttgctgaagc agctggctca acatggtata tcgacaattt ctgggataaa 60
ctcaaagagg gctgtgtagc atatctaaac atagattcac ctggattaaa agatgcaaca 120
agatatatcg cttacgcgtc 140

<210> SEQ ID NO 233
<211> LENGTH: 140
<212> TYPE: DNA
<213> ORGANISM: Artificial Sequence
<220> FEATURE:
<223> OTHER INFORMATION: Synthetic

<400> SEQUENCE: 233
gtaacttctg gaaacgccca atcaaaacag atcatgacac caaagctaaa attatcttcc 60
ctaatagctt ctataggtgt atctccaggt tgaaatatta gcttctcttt ggcaaataag 120
tgaagtttcc tatactttcc 140

<210> SEQ ID NO 234
<211> LENGTH: 140
<212> TYPE: DNA
<213> ORGANISM: Artificial Sequence
<220> FEATURE:
<223> OTHER INFORMATION: Synthetic

<400> SEQUENCE: 234
ccagatagcc caatagcatc aatttccgtt gcaataatag gtacagtaca caaagaacac 60
gtaattttca gcgacactgc aaatacaggc gacttaataa tttttgccat agatctcgat 120
ggaacatttc accctaagtt 140

<210> SEQ ID NO 235
<211> LENGTH: 140
<212> TYPE: DNA
<213> ORGANISM: Artificial Sequence
<220> FEATURE:
<223> OTHER INFORMATION: Synthetic

<400> SEQUENCE: 235
gttctaattc ctctcttaca gctttaaaag caatcacagc agattccaaa atatcatcca 60
tatcatccag agctataata acacctcttg aagttttccc aatcttatgc ccacttcttc 120
caactctttg aaccaaacga 140

<210> SEQ ID NO 236
<211> LENGTH: 140
<212> TYPE: DNA
<213> ORGANISM: Artificial Sequence
<220> FEATURE:
<223> OTHER INFORMATION: Synthetic

<400> SEQUENCE: 236
gtaacttgtc tgggagacat atattggaca actaaatcaa cggttcctac atcaatccct 60
aactccatag atgatgtaca aataagacct ttcaactcac cgtctttaaa taacctttca 120
acttctatac gaacatctct 140

<210> SEQ ID NO 237
<211> LENGTH: 140
<212> TYPE: DNA
<213> ORGANISM: Artificial Sequence
<220> FEATURE:
<223> OTHER INFORMATION: Synthetic

<400> SEQUENCE: 237
actcaatgaa ccatgatgca catcaatact tagattagga tcgtataagt gaagcctaga 60
agctagtatc tcagctattt cacgagtgtt tacaaaagta agcatagagc ggctcttttc 120
taataactca accaataccc 140

<210> SEQ ID NO 238
<211> LENGTH: 140
<212> TYPE: DNA
<213> ORGANISM: Artificial Sequence
<220> FEATURE:
<223> OTHER INFORMATION: Synthetic

<400> SEQUENCE: 238
cagttaaatc atcttaactc acaaatatta aggctttaat ttctgaggga gtgcaaaatg 60
aaaactgacg tagtaatagt aggtgcaggg cccgcaggca tgtttgctgc acatgaattg 120
gcaactaaat ctaatctgaa 140

<210> SEQ ID NO 239
<211> LENGTH: 140
<212> TYPE: DNA
<213> ORGANISM: Artificial Sequence
<220> FEATURE:
<223> OTHER INFORMATION: Synthetic

<400> SEQUENCE: 239
aaaaatagcc aaggatccaa aattccgtgt atatacaaaa accttcgatg accttacacg 60
tgtattttgc gttaattatc gaggcttcgt cgtccaagaa gtctacggag atatcgttgg 120
tgttaacggc cacactctaa 140

<210> SEQ ID NO 240
<211> LENGTH: 140
<212> TYPE: DNA
<213> ORGANISM: Artificial Sequence
<220> FEATURE:
<223> OTHER INFORMATION: Synthetic

<400> SEQUENCE: 240
tcaaacaaaa atctgaaaat gccaattttg catttctagt tcgagttgaa ctcaccgaac 60
cgcttgaaga cacaaccgcc tacggattct caatagccaa attagcaact accataggtg 120
gaggaaaacc aattcttcaa 140

<210> SEQ ID NO 241
<211> LENGTH: 140
<212> TYPE: DNA
<213> ORGANISM: Artificial Sequence
<220> FEATURE:
<223> OTHER INFORMATION: Synthetic

<400> SEQUENCE: 241
cgagatactg aatttccaaa actcaaagga tatagaattg ttagaatcgc aacacatccg 60
caagttatga gcatgggact aggaagtgaa gggttgtcaa aactttgcca agaagccgaa 120
aagagaggac tagattgggt 140

<210> SEQ ID NO 242
<211> LENGTH: 140
<212> TYPE: DNA
<213> ORGANISM: Artificial Sequence
<220> FEATURE:
<223> OTHER INFORMATION: Synthetic

<400> SEQUENCE: 242
cgaagttttt atcctcctcg gtccaagtca cactggttac ccaggcgttg gaataatgac 60
agaaggcatc tggaaaactt ctttaggaga aatatcaata gatgaaactc tctcgaatac 120
tattttaaat aattgtgacc 140

<210> SEQ ID NO 243
<211> LENGTH: 140
<212> TYPE: DNA
<213> ORGANISM: Artificial Sequence
<220> FEATURE:
<223> OTHER INFORMATION: Synthetic

<400> SEQUENCE: 243
tgacacacta cggcacctac tatggataca caccagctgg tgttgaacca ttaaccaaag 60
ttttagaatg gatataccag acggacaaac aagttattga gagaattaaa agattagatg 120
gagcaggagt aatagaatat 140

<210> SEQ ID NO 244
<211> LENGTH: 140
<212> TYPE: DNA
<213> ORGANISM: Artificial Sequence
<220> FEATURE:
<223> OTHER INFORMATION: Synthetic

<400> SEQUENCE: 244
ctgaaaagtt cattccaatt gttaaatcgc catcttggaa acacggcaca agaaaaggga 60
aaggatttag catcggtgag attaaagcag ccgagataga tattagtatg gcagttaaac 120
tcggtatacc cattgataaa 140

<210> SEQ ID NO 245
<211> LENGTH: 140
<212> TYPE: DNA
<213> ORGANISM: Artificial Sequence
<220> FEATURE:
<223> OTHER INFORMATION: Synthetic

<400> SEQUENCE: 245
gggaataata attaaaataa tgtggcacac cttttagctt cttttcatct catattttca 60
aagaagcctt ccaggtgtgc ctcatcggtg tcccccgctg cggagacacg gtatcatcgt 120
atccgccgaa ggaaactcaa 140

<210> SEQ ID NO 246
<211> LENGTH: 140
<212> TYPE: DNA
<213> ORGANISM: Artificial Sequence
<220> FEATURE:
<223> OTHER INFORMATION: Synthetic

<400> SEQUENCE: 246
gacattgcct atcaattact tcaagccgga atgcaagttc ccggtttcag aaggtcgcca 60
aagataatag aaagaatttt agaaagatat attccaacag tcaccgtact aggcggcatt 120
attgtaggat taatagctgc 140

<210> SEQ ID NO 247
<211> LENGTH: 140
<212> TYPE: DNA
<213> ORGANISM: Artificial Sequence
<220> FEATURE:
<223> OTHER INFORMATION: Synthetic

<400> SEQUENCE: 247
tgtcgttcag ggaggtataa aaatgccaga accacgctac cggtcaaggt ctttaagaag 60
acgatacgta cacacacctg gaggaaaaac cgtcatccat tacaggagaa aaaaacctga 120
cgttgcaaaa tgcgcattat 140

<210> SEQ ID NO 248
<211> LENGTH: 140
<212> TYPE: DNA
<213> ORGANISM: Artificial Sequence
<220> FEATURE:
<223> OTHER INFORMATION: Synthetic

<400> SEQUENCE: 248
gtggtcaacc tctcagagga attcccagac taaggccagg agaattcaga aagttgacaa 60
aaagtcaacg aagaccagag agacctttcg gtggatatct atgccacaaa tgcttagcaa 120
tggaaatcaa gaaagctgtt 140

<210> SEQ ID NO 249
<211> LENGTH: 140
<212> TYPE: DNA
<213> ORGANISM: Artificial Sequence
<220> FEATURE:
<223> OTHER INFORMATION: Synthetic

<400> SEQUENCE: 249
ataggatgaa tctaactggg gcgacccggt agataactga gagtgtagga ggtgaaataa 60
ttgagcgcaa tagaagtagg tagaatatgt gttaaaacta gtggaagaga agcaggaaga 120
aagtgcgtta ttgttgaaat 140

<210> SEQ ID NO 250
<211> LENGTH: 140
<212> TYPE: DNA
<213> ORGANISM: Artificial Sequence
<220> FEATURE:
<223> OTHER INFORMATION: Synthetic

<400> SEQUENCE: 250
acaccatttc ctaatatttt agtaactaga tatgtttgtt atagtattag ggtgaagtat 60
ttgtatgaaa gaaagttgcc atcagacatt aaaagagaga ttctagtaaa aagtgaagca 120
gaaactgacc ctgcttatgg 140

<210> SEQ ID NO 251
<211> LENGTH: 140
<212> TYPE: DNA
<213> ORGANISM: Artificial Sequence
<220> FEATURE:
<223> OTHER INFORMATION: Synthetic

<400> SEQUENCE: 251
cacatgagag aacttagaag aacacgtaca ggaccctta aagaagatga aaccctagta 60
actcttcacg atgtagttga tgcttactat ttttggaagg aagatggaga agaagaattt 120
ctacgaaaag tcatacaacc 140

<210> SEQ ID NO 252
<211> LENGTH: 140
<212> TYPE: DNA
<213> ORGANISM: Artificial Sequence
<220> FEATURE:
<223> OTHER INFORMATION: Synthetic

<400> SEQUENCE: 252
aatggaaaag ggtttagaac acctacctca catttggatt agagattctg ctgtagatgc 60
aatatgccat ggggcaaact tagcagctcc tggtgttgta aaacttcatg acggtatatc 120
acctggagac ttaatagtaa 140

<210> SEQ ID NO 253
<211> LENGTH: 140
<212> TYPE: DNA
<213> ORGANISM: Artificial Sequence
<220> FEATURE:
<223> OTHER INFORMATION: Synthetic

<400> SEQUENCE: 253
cgctgatcat acatgtgcat tgtctttaaa tacactagta acgttaataa tatctagcaa 60
ttttagataa aaataactag cagtgccggg gtagccaagt ggactacagg ccttataccg 120
gttagggcgc gggcctggag 140

<210> SEQ ID NO 254
<211> LENGTH: 140
<212> TYPE: DNA
<213> ORGANISM: Artificial Sequence
<220> FEATURE:
<223> OTHER INFORMATION: Synthetic

<400> SEQUENCE: 254
catgccttaa cgagaggcat gggatggggg agctgtgagc cccccgaacc ggcagatgag 60
gggaagggtg caaagcatcc cttaacgccg gaagctcccg acttcagtcg tggagcagct 120
cactgctttg acgaaaggtt 140

<210> SEQ ID NO 255
<211> LENGTH: 140
<212> TYPE: DNA
<213> ORGANISM: Artificial Sequence
<220> FEATURE:
<223> OTHER INFORMATION: Synthetic

<400> SEQUENCE: 255
gaacttgcaa ggaaggccgg tgttgattat gagacaaagc tgttggtcag gggcaaggaa 60
ccggctgagg acataataga atttgctgac gagatcaggg caagtctcat tgtaataggg 120
gttaggaaga ggagacccgc 140

<210> SEQ ID NO 256
<211> LENGTH: 140
<212> TYPE: DNA
<213> ORGANISM: Artificial Sequence
<220> FEATURE:
<223> OTHER INFORMATION: Synthetic

<400> SEQUENCE: 256
tccagaagag attcaaagct ctcgtattca atgtccccac caaatttctg gtcgcgctca 60
attttgactt taccaaaagc ggggaaaacg tagtgctttg ctaggtctat tatcggattt 120
ccttctacaa cctttggcgg 140

<210> SEQ ID NO 257
<211> LENGTH: 140
<212> TYPE: DNA
<213> ORGANISM: Artificial Sequence
<220> FEATURE:
<223> OTHER INFORMATION: Synthetic

<400> SEQUENCE: 257
gatttgctca ttttctcccc gtcgagtcct gagattatcg gcgtatggat gcagatcggt 60
gccttgtaac cgagggccgg cagattctcc cttgcgagca tgtggatctt tctctgatct 120
attccaccaa ccgccacatc 140

<210> SEQ ID NO 258
<211> LENGTH: 140
<212> TYPE: DNA
<213> ORGANISM: Artificial Sequence
<220> FEATURE:
<223> OTHER INFORMATION: Synthetic

<400> SEQUENCE: 258
tccgggagtt gcagaaccaa gcatggaaat tgctagagat cccgaaaagg tttacgagta 60
cacgaataag tggaacacgg ttgcaattat cactgatggc tcgagggtct tgggactggg 120
caacatcggt gcgatggctt 140

<210> SEQ ID NO 259
<211> LENGTH: 140
<212> TYPE: DNA
<213> ORGANISM: Artificial Sequence
<220> FEATURE:
<223> OTHER INFORMATION: Synthetic

<400> SEQUENCE: 259
gtggtgttat caagagggaa tatattgctc agatggcaga ggatccgata gtctttgcct 60
tatcaaaccc ggtgcctgag atctatccgc aggaggcaaa ggaagccgga gccaggatcg 120
taggaactgg taggagcgac 140

<210> SEQ ID NO 260
<211> LENGTH: 140
<212> TYPE: DNA
<213> ORGANISM: Artificial Sequence
<220> FEATURE:
<223> OTHER INFORMATION: Synthetic

<400> SEQUENCE: 260
gggatctgtt agtatggcat tcagagcctt tatgtcctca tcggtaagct tgtccgatgg 60
cagatcgtat ttcacgatgt ctgaaggagt aactccgaga aacttcgctt ctggtgtcgc 120
aagatactcc gagagatgcg 140

<210> SEQ ID NO 261
<211> LENGTH: 140
<212> TYPE: DNA
<213> ORGANISM: Artificial Sequence
<220> FEATURE:
<223> OTHER INFORMATION: Synthetic

<400> SEQUENCE: 261
tgagtgcggc ttactctgca ctgtgcgaga tcgatgaggt cgttgttgtt gcccccataa 60
cgcagatgag cggagtgggg aggagcatat ccataatgcg gccggttcgt tttttcgagc 120
tcgaaataga tggcatgagg 140

<210> SEQ ID NO 262
<211> LENGTH: 140
<212> TYPE: DNA
<213> ORGANISM: Artificial Sequence
<220> FEATURE:
<223> OTHER INFORMATION: Synthetic

<400> SEQUENCE: 262
aggggaaggg agtactactg gattcatggg gtggaagtcg aaagcgctga gcctggaacg 60
gacatacacg cactcagaaa cgggtatgtc tccattacac cgatatcctt aaatgcaact 120
tcggactgcg aagctttaag 140

<210> SEQ ID NO 263
<211> LENGTH: 140
<212> TYPE: DNA
<213> ORGANISM: Artificial Sequence
<220> FEATURE:
<223> OTHER INFORMATION: Synthetic

<400> SEQUENCE: 263
atagttttat ggagggtggt tggacatgaa tgaaagggca aagaaggtca ttcttattgt 60
ggatgacgat ttggctctgc ttgaagctct tgaactgatg cttcgaggca agtatgaggt 120
tgtgaaggtg acaaatggga 140

<210> SEQ ID NO 264
<211> LENGTH: 140
<212> TYPE: DNA
<213> ORGANISM: Artificial Sequence
<220> FEATURE:
<223> OTHER INFORMATION: Synthetic

<400> SEQUENCE: 264
atgtcgattc cgaaatagca gggagcaatt atcggtgggc ttccgaccct taaatggatt 60
tccttcgctc ccgcctttct tatcatgtcg actattcttt tggatgttgt tgcccgcaca 120
atgctgtcgt caaccagcac 140

<210> SEQ ID NO 265
<211> LENGTH: 140
<212> TYPE: DNA
<213> ORGANISM: Artificial Sequence
<220> FEATURE:
<223> OTHER INFORMATION: Synthetic

<400> SEQUENCE: 265
actttctgag ggaaaaacat tgttgcttat cctaaagagt ttacaagcaa gaagctggaa 60
acaaactctg gatgttatta atttagagcc tgcagcagca tatacaatgt ttagagcggc 120
aataaagaaa ctatacaaag 140

<210> SEQ ID NO 266
<211> LENGTH: 140
<212> TYPE: DNA
<213> ORGANISM: Artificial Sequence
<220> FEATURE:
<223> OTHER INFORMATION: Synthetic

<400> SEQUENCE: 266
gtggttgaga ggctgcttga aggcattgca aagaatgaaa gggtagctta cggattggag 60
gaggttagga gggcaaaaga gtatggagca attgaggttc tgttggtttc agatgacttc 120
ctgctcaccg agcgtgagaa 140

<210> SEQ ID NO 267
<211> LENGTH: 140
<212> TYPE: DNA
<213> ORGANISM: Artificial Sequence
<220> FEATURE:
<223> OTHER INFORMATION: Synthetic

<400> SEQUENCE: 267
tcgcttcgag attcctgata ggagtgggag ttgccggggt ttacgtgcct acgataaaaa 60
taatatccgt ctggttcagg cagaatgagt ttgcaactgc tactgggatt cttttcgcga 120
ttggaaatct aggagcgatt 140

<210> SEQ ID NO 268
<211> LENGTH: 140
<212> TYPE: DNA
<213> ORGANISM: Artificial Sequence
<220> FEATURE:
<223> OTHER INFORMATION: Synthetic

<400> SEQUENCE: 268
gaggtatcgc ctacttagag agttcgtaaa gtcggagata ttggaggaag ttaaatttga 60
aaacgttgtg gacgagtact gggttgcgga accattcata aagatcataa tttttgagga 120
tctcgaaaac cagaaattga 140

<210> SEQ ID NO 269
<211> LENGTH: 140
<212> TYPE: DNA
<213> ORGANISM: Artificial Sequence
<220> FEATURE:
<223> OTHER INFORMATION: Synthetic

<400> SEQUENCE: 269
ctaatccgat tatcgattct acgcttcctg atggtagcag gcttcaggct accctaggaa 60
cagaaattac acctagaggc tcgagcttca cggtgagaaa atttacaacc cagccactga 120
ccccgttaga tctagtgagg 140

<210> SEQ ID NO 270
<211> LENGTH: 140
<212> TYPE: DNA
<213> ORGANISM: Artificial Sequence
<220> FEATURE:
<223> OTHER INFORMATION: Synthetic

<400> SEQUENCE: 270
caaaattata tcgatagagg ataccagaga gataaagctc catcatgaga actggctggc 60
tcaggtgacg agaacgggga taggagagca ggaaattgac atgtatgacc ttctcaaagc 120
cgccttgaga cagagaccgg 140

<210> SEQ ID NO 271
<211> LENGTH: 140
<212> TYPE: DNA
<213> ORGANISM: Artificial Sequence
<220> FEATURE:
<223> OTHER INFORMATION: Synthetic

<400> SEQUENCE: 271
gaatcagttt gttaaatggg atgcgaagaa aaattcgcat gttgaggtag ggattccgaa 60
aaagctagag aaaatcgcga tgtcgagagt ggacgatgct tacgcggagc tggaaagaag 120
aaggaggtat ttggagtgga 140

<210> SEQ ID NO 272
<211> LENGTH: 140
<212> TYPE: DNA
<213> ORGANISM: Artificial Sequence
<220> FEATURE:
<223> OTHER INFORMATION: Synthetic

<400> SEQUENCE: 272
tcagtgaagt tagcacggaa ttcgaaagga tagtggttct cgttgaaatg ggagaggatt 60
tggaaagcgc aatgaggttt gttgcagaaa caactccctc agagaggctc agggtttttc 120
tggagaactt tattgatgtg 140

<210> SEQ ID NO 273
<211> LENGTH: 140
<212> TYPE: DNA
<213> ORGANISM: Artificial Sequence
<220> FEATURE:
<223> OTHER INFORMATION: Synthetic

<400> SEQUENCE: 273
gctggagcgg gaggcgtatc aacgcttgcc ctcaatccgt tacccgaagt tccagaatac 60
tttgagtatt tccagtccga atagaagcag agcacctctc gatcgactag agtctttctg 120
ctagctcttg caccctcatc 140

<210> SEQ ID NO 274
<211> LENGTH: 140
<212> TYPE: DNA
<213> ORGANISM: Artificial Sequence
<220> FEATURE:
<223> OTHER INFORMATION: Synthetic

<400> SEQUENCE: 274
gcggaaatct ctgctgaaaa caccttgact ttttcttcgt atatctccca ttccatcagg 60
caccaccaac tttggtcctg caaagagtca tcggtgcccc atctgctacg ggaacgatct 120
gaaaggcttt accacagaat 140

<210> SEQ ID NO 275
<211> LENGTH: 140
<212> TYPE: DNA
<213> ORGANISM: Artificial Sequence
<220> FEATURE:
<223> OTHER INFORMATION: Synthetic

<400> SEQUENCE: 275
tccggttgca ggattggtct ccccacctct cgagcctatg aggaataccc cattcctgca 60
gagctcgaga agctcttcga attcaagatc cccctctgc aggaatgtgt tgctcattct 120
gacaatcgga aaagcaactc 140

<210> SEQ ID NO 276
<211> LENGTH: 140
<212> TYPE: DNA
<213> ORGANISM: Artificial Sequence
<220> FEATURE:
<223> OTHER INFORMATION: Synthetic

<400> SEQUENCE: 276
aactcctcga ttgttgggtc atcgattatt gtcacgttct ctcctgcaat tctctctcca 60
atctttccag caagaacgct gttttcctgc agaacgtgat ctgcctcgac cgcatgcccg 120
aaagcttcgt gaataaaaac 140

<210> SEQ ID NO 277
<211> LENGTH: 140
<212> TYPE: DNA
<213> ORGANISM: Artificial Sequence
<220> FEATURE:
<223> OTHER INFORMATION: Synthetic

<400> SEQUENCE: 277
ctttcttcaa gaatgctttc tgcggcgata agcccagtaa cagccgctcc aactattccc 60
ctgcttattc cggctccatc gccaattgca tagatgtacg gtatgcttgt cctcatcttc 120
tcgtcaacct taagcttcaa 140

<210> SEQ ID NO 278
<211> LENGTH: 140
<212> TYPE: DNA
<213> ORGANISM: Artificial Sequence
<220> FEATURE:
<223> OTHER INFORMATION: Synthetic

<400> SEQUENCE: 278
tgctggattt ttctttggcc ttgctgtggc cgttgactag acaaaagtcg ccgtactcct 60
ctcttataac ccagcccctc gggcaggtgc agaacgtgcg catgtagtcg tcatgcctct 120
gtgtgattat tctcagcttt 140

<210> SEQ ID NO 279
<211> LENGTH: 140
<212> TYPE: DNA
<213> ORGANISM: Artificial Sequence
<220> FEATURE:
<223> OTHER INFORMATION: Synthetic

<400> SEQUENCE: 279
ttgccttgga attttccgcc acttcgatct tatacttttt tacccatttt tccagccagt 60
cggcaccgct cctcccaact gcaattatga gtttgtcgta gccgaacttg tccccatcgt 120
tcgtcttcac gatcttttct 140

<210> SEQ ID NO 280
<211> LENGTH: 140
<212> TYPE: DNA
<213> ORGANISM: Artificial Sequence
<220> FEATURE:
<223> OTHER INFORMATION: Synthetic

<400> SEQUENCE: 280
aatcaccacc gactgtgaag ctcgaaggat agttggggtt ggcataattc agctttccat 60
ccgaaagtcc tccagcacca cccacaccag aagtaatgtt gcagggatcg catttcttgc 120
aatagctttg cgaaaggtca 140

<210> SEQ ID NO 281
<211> LENGTH: 140
<212> TYPE: DNA
<213> ORGANISM: Artificial Sequence
<220> FEATURE:
<223> OTHER INFORMATION: Synthetic

<400> SEQUENCE: 281
ttaaccaacc tctttcgcat caaaatccca actgcggcat ccgttatcag cgttacatcg 60
attccatctt tcataagctc gtagcaggtg agcctagagc cttggttcag cggcctcgtt 120
tcgcaggcga aaacctttac 140

<210> SEQ ID NO 282
<211> LENGTH: 140
<212> TYPE: DNA
<213> ORGANISM: Artificial Sequence
<220> FEATURE:
<223> OTHER INFORMATION: Synthetic

<400> SEQUENCE: 282
ttatcgagtt aatagctatc agtgttgcta ttacgatcgt tgcgatccca tcaaagatgt 60
tatgaccgaa ggagatagca ataatgccaa atatcgctgc aagcgtcgat aaggagtcgt 120
taaaactctc aaacatcact 140

<210> SEQ ID NO 283
<211> LENGTH: 140
<212> TYPE: DNA
<213> ORGANISM: Artificial Sequence
<220> FEATURE:
<223> OTHER INFORMATION: Synthetic

<400> SEQUENCE: 283
ctcccttcta agcttcgtga tatctgcatt gccaatatca actagaaatt cgattgagat 60
aagcttgtct cttgcggtta agcttgttct ctcgatattt ataccgaaat ttagcaatac 120
acccgtgata tctctcacga 140

<210> SEQ ID NO 284
<211> LENGTH: 140
<212> TYPE: DNA
<213> ORGANISM: Artificial Sequence
<220> FEATURE:
<223> OTHER INFORMATION: Synthetic

<400> SEQUENCE: 284
aagcggggct tttgcctttc caattccgcc gcaaccaacc gttggactta tcaaaccgga 60
acctttcaac tccgagatta aagagcctgg ctccttatcg tgcttaatag caatttctac 120
aatgtcttcc ccgcatacaa 140

<210> SEQ ID NO 285
<211> LENGTH: 140
<212> TYPE: DNA
<213> ORGANISM: Artificial Sequence
<220> FEATURE:
<223> OTHER INFORMATION: Synthetic

<400> SEQUENCE: 285
ctagttcttg gttttcgtcg acgttgacct tgtagaactc tacatctgga aactcctttg 60
aaagcttttc gagcactggg ctgagatacc tgcacggcat gcaccagtcg gcgtagaagt 120
caacaacaac aagcttatcc 140

<210> SEQ ID NO 286
<211> LENGTH: 140
<212> TYPE: DNA
<213> ORGANISM: Artificial Sequence
<220> FEATURE:
<223> OTHER INFORMATION: Synthetic

<400> SEQUENCE: 286
ctccgatcgt ctttaaagct tgcaagtcta aatcctcgcc ccagggaatt tcctgggatt 60
ttctcgcaat ctctatcgcc gaagtatagg ttatcctcgg gaatggtatc tcggggactt 120
cgagctttag ttcgagaata 140

<210> SEQ ID NO 287
<211> LENGTH: 140
<212> TYPE: DNA
<213> ORGANISM: Artificial Sequence
<220> FEATURE:
<223> OTHER INFORMATION: Synthetic

<400> SEQUENCE: 287
gaggttttgt ccctattggg tttctcattg cctgcagcat ttcttctctg ctcagagctc 60
tgcagccatc gcctttcatt cttaaaatgc taacctccca atcatccgga aaatcgagct 120
ctatttccct atcctgccag 140

<210> SEQ ID NO 288
<211> LENGTH: 140
<212> TYPE: DNA
<213> ORGANISM: Artificial Sequence
<220> FEATURE:
<223> OTHER INFORMATION: Synthetic

<400> SEQUENCE: 288
tgtttacagg ctggtgggtg gggaaaggag tgttaagggc aaaaggagtg taagcaagtt 60
cagggttgcg attgcgattc ttctggcatt cattctgata tatcctacat accgcatagc 120
cgagattcaa agcagtgggg 140

<210> SEQ ID NO 289
<211> LENGTH: 140
<212> TYPE: DNA
<213> ORGANISM: Artificial Sequence
<220> FEATURE:
<223> OTHER INFORMATION: Synthetic

<400> SEQUENCE: 289
cagggtcagg aggattcacg agatagaagt cctcgaggtg agaggcaggt tcgcgcttat 60
aagggttctc agcgaccccg gcacgtacat gaggaagctg gcccacgaca tcgggctatt 120
gctcggagta ggtgcacaca 140

<210> SEQ ID NO 290
<211> LENGTH: 140
<212> TYPE: DNA
<213> ORGANISM: Artificial Sequence
<220> FEATURE:

<223> OTHER INFORMATION: Synthetic

<400> SEQUENCE: 290
gaagtcagtc atagaatcaa tggtgtattc ttcatcaggg ttattatacg gaatgaactt 60
atagttctca cctgctacct gatccactgt catttctgca agagtctgca ctgtggtaat 120
tccaccttct tccatccggg 140

<210> SEQ ID NO 291
<211> LENGTH: 140
<212> TYPE: DNA
<213> ORGANISM: Artificial Sequence
<220> FEATURE:
<223> OTHER INFORMATION: Synthetic

<400> SEQUENCE: 291
agtaagggaa tcaatgtctt ccattgctgt aagggttact gttacctttg tagaagtcag 60
accgtaattg gtcagcagct cttcatagaa gttctggttt gcaatatccc tctgggcaat 120
gacagggtag tcgacttcgt 140

<210> SEQ ID NO 292
<211> LENGTH: 198
<212> TYPE: DNA
<213> ORGANISM: Artificial Sequence
<220> FEATURE:
<223> OTHER INFORMATION: Synthetic

<400> SEQUENCE: 292
acagttctcc ttcttagctt cgtgagaacc aaatgctttc agtggtttcc aatgccctga 60
ccagcctgta ctcaactaag ggatatgacg taacattcag tgacctgatc gccgccattc 120
aggcaatgaa gggctacgat gacagcgcaa acgctaaact cgtcgtggac acatcatgta 180
gtagacgacc aagacagt 198

<210> SEQ ID NO 293
<211> LENGTH: 198
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (103)..(105)
<223> OTHER INFORMATION: n is a, c, g, or t

<400> SEQUENCE: 293
acagttctcc ttcttagctt cgtgagaaca gtcggagctt ataaccacag atcctgaagt 60
attgagaaag agaaggggat ggtgagataa acatgaggtg tgnnnaaagc tgacaatatg 120
tacgcgtgct tgaaggacac tgttgtgaag gaaaggtatc ctgtcgctac acatcatgta 180
gtagacgacc aagacagt 198

<210> SEQ ID NO 294
<211> LENGTH: 198
<212> TYPE: DNA
<213> ORGANISM: Artificial Sequence
<220> FEATURE:
<223> OTHER INFORMATION: Synthetic

<400> SEQUENCE: 294
acagttctcc ttcttagctt cgtgagaaca tgcagtatat ggcaggtgcg agcaactgct 60
ttaccatggg tgccatggtg cagaacggga gaagctccct ctactggaag gttaaggacg 120
caaatttctg gtccaagact ttcgagagca agttgcgcgt tctggggctc acatcatgta 180
gtagacgacc aagacagt 198

<210> SEQ ID NO 295
<211> LENGTH: 198
<212> TYPE: DNA
<213> ORGANISM: Artificial Sequence
<220> FEATURE:
<223> OTHER INFORMATION: Synthetic

<400> SEQUENCE: 295
acagttctcc ttcttagctt cgtgagaacg gctgcggaag ccagcaagga accttgtctc 60
ttcaggagag gcaggatata cgtcacattc aatgtaagga gggtggcact gagcggtgcg 120
ggacagttga ctgccgccag gacttatgcc ataggcaaca ccgatgcgac acatcatgta 180
gtagacgacc aagacagt 198

<210> SEQ ID NO 296
<211> LENGTH: 198
<212> TYPE: DNA
<213> ORGANISM: Artificial Sequence
<220> FEATURE:
<223> OTHER INFORMATION: Synthetic

<400> SEQUENCE: 296
acagttctcc ttcttagctt cgtgagaacg atgaggttaa ggggatatgc gagagattcg 60
gcaaggtcgt ggatgccgtg aactctcctg tgcttaccga gagtaatgcc tcgtacagga 120
atgcggggct ggtgcgtgcc aggttcaact gggactacat caggcccgac acatcatgta 180
gtagacgacc aagacagt 198

<210> SEQ ID NO 297
<211> LENGTH: 198
<212> TYPE: DNA
<213> ORGANISM: Artificial Sequence
<220> FEATURE:
<223> OTHER INFORMATION: Synthetic

<400> SEQUENCE: 297
acagttctcc ttcttagctt cgtgagaact ggtctccacg gaaggctaca tggacagggc 60
aataggcgtc caggatatcg gctacctgtt ctggcaggca ggtcccaccg caatgaagga 120
tatgagaatt tacaacggtc ccggtggtct gatcgttctg cctttctatc acatcatgta 180
gtagacgacc aagacagt 198

<210> SEQ ID NO 298
<211> LENGTH: 198
<212> TYPE: DNA
<213> ORGANISM: Artificial Sequence
<220> FEATURE:
<223> OTHER INFORMATION: Synthetic

<400> SEQUENCE: 298
acagttctcc ttcttagctt cgtgagaacc tttctgcgcg caacaggctg gccaagggac 60
ttccgaagag cctggacatg tttgccagcg tggaaggtcg tgaccttggg tacgatccga 120
ggtacataac agaggaagat tacaagacca ttatgaccaa ggcccgtctc acatcatgta 180
gtagacgacc aagacagt 198

<210> SEQ ID NO 299

<211> LENGTH: 198
<212> TYPE: DNA
<213> ORGANISM: Artificial Sequence
<220> FEATURE:
<223> OTHER INFORMATION: Synthetic

<400> SEQUENCE: 299
acagttctcc ttcttagctt cgtgagaacg gcatgataga tgaggatggc tacgaggtac 60
cgaagggtga agaccccaac gaccccagaa gtgcacacac ctttggttgg gtcgaccaat 120
cagatggagg cacatccaat ggtggcatgc agtccggtgg gagctctcac acatcatgta 180
gtagacgacc aagacagt 198

<210> SEQ ID NO 300
<211> LENGTH: 198
<212> TYPE: DNA
<213> ORGANISM: Artificial Sequence
<220> FEATURE:
<223> OTHER INFORMATION: Synthetic

<400> SEQUENCE: 300
acagttctcc ttcttagctt cgtgagaacc ttaaggacgg ggacgtgaca aagctgtatt 60
ctcaggacga ttacctcagg gtcagcaggc tcaagttcag cgagaatccg atgcttggca 120
tcgtcaagaa tacggatggc acaggggagg ttataggtcc gtcctttgcc acatcatgta 180
gtagacgacc aagacagt 198

<210> SEQ ID NO 301
<211> LENGTH: 198
<212> TYPE: DNA
<213> ORGANISM: Artificial Sequence
<220> FEATURE:
<223> OTHER INFORMATION: Synthetic

<400> SEQUENCE: 301
acagttctcc ttcttagctt cgtgagaaca gggaccttct gtggaacata atctcgggtg 60
ccctgaatgc gggaagggaa cagctctacg gggatgcatt cggcggtcct aagatagagc 120
agtacgtgaa agcactcacg caggtgctgt atgacctgtc tgtcaacagc acatcatgta 180
gtagacgacc aagacagt 198

<210> SEQ ID NO 302
<211> LENGTH: 198
<212> TYPE: DNA
<213> ORGANISM: Artificial Sequence
<220> FEATURE:
<223> OTHER INFORMATION: Synthetic

<400> SEQUENCE: 302
acagttctcc ttcttagctt cgtgagaact gaaggaacgc gtcatcgtcc acaagagcac 60
tacgaggaac gaagtccttg aagagttcaa ggcgtctaag gagccgaagg tcctatttgc 120
gataaagatg gaagagggta cggatttcag ggatgaccag gcaaggtggc acatcatgta 180
gtagacgacc aagacagt 198

<210> SEQ ID NO 303
<211> LENGTH: 198
<212> TYPE: DNA
<213> ORGANISM: Artificial Sequence
<220> FEATURE:
<223> OTHER INFORMATION: Synthetic

<400> SEQUENCE: 303
acagttctcc ttcttagctt cgtgagaacc agatattggt caagactcct taccaggatc 60
tgggagacga gtgggtccgc ctccataggg agaagatggg acggagatgg tacgagatat 120
ccgccctcca gcaggtcatc caggcgagcg gcaggataat gaggaacgac acatcatgta 180
gtagacgacc aagacagt 198

<210> SEQ ID NO 304
<211> LENGTH: 198
<212> TYPE: DNA
<213> ORGANISM: Artificial Sequence
<220> FEATURE:
<223> OTHER INFORMATION: Synthetic

<400> SEQUENCE: 304
acagttctcc ttcttagctt cgtgagaacc agggactggg gagacaccta cgtccttgac 60
atgaacgcca tgaagctcat ccgcatgtac gaaaaggaat gcccccgctg gtttttgaag 120
aggttgaaac tatgacgcat cacaatatca ccttccccgt ccctcccgac acatcatgta 180
gtagacgacc aagacagt 198

<210> SEQ ID NO 305
<211> LENGTH: 198
<212> TYPE: DNA
<213> ORGANISM: Artificial Sequence
<220> FEATURE:
<223> OTHER INFORMATION: Synthetic

<400> SEQUENCE: 305
acagttctcc ttcttagctt cgtgagaacg caatgtccgc aacagttgac aacgttgcac 60
gggtcgcggg atggctcagg gcgactgcag tctccagcga tttcaggccc gtcaccctga 120
agaagtacgt ccttaccccc cgccatatca tggatgagaa aggggatacc acatcatgta 180
gtagacgacc aagacagt 198

<210> SEQ ID NO 306
<211> LENGTH: 198
<212> TYPE: DNA
<213> ORGANISM: Artificial Sequence
<220> FEATURE:
<223> OTHER INFORMATION: Synthetic

<400> SEQUENCE: 306
acagttctcc ttcttagctt cgtgagaacc gagatacagc agatgctggg gcgcgccggg 60
agggcgaaat acgattccat gggctacggc tacatctgct catccgacgt tcacctccag 120
gacgtgtata agacgtacgt tcatggccgt ctggagagcg taaaatcaac acatcatgta 180
gtagacgacc aagacagt 198

<210> SEQ ID NO 307
<211> LENGTH: 198
<212> TYPE: DNA
<213> ORGANISM: Artificial Sequence
<220> FEATURE:
<223> OTHER INFORMATION: Synthetic

<400> SEQUENCE: 307
acagttctcc ttcttagctt cgtgagaacg gcactggacg agttcttctc caccacgctg 60
gcacgccacg agggtgcccg tctggaagaa tggatagaca acagccttgt cttcctgcag 120
gacaacgaca tgatagtcgg gggacgttcc ttcacggcta ccccctttcgc acatcatgta 180 gtagacgacc aagacagt 198

<210> SEQ ID NO 308
<211> LENGTH: 198
<212> TYPE: DNA
<213> ORGANISM: Artificial Sequence
<220> FEATURE:
<223> OTHER INFORMATION: Synthetic

<400> SEQUENCE: 308
acagttctcc ttcttagctt cgtgagaacc catccttgcg gactggatag acgagaagcc 60
cgaaagcgac atcgtcaata aatacaacat ctggcctgcc gacctgagga gcagggttga 120
gttggccgaa tggctctcgc attcccttta cgagatctcg agggtcctgc acatcatgta 180
gtagacgacc aagacagt 198

<210> SEQ ID NO 309
<211> LENGTH: 198
<212> TYPE: DNA
<213> ORGANISM: Artificial Sequence
<220> FEATURE:
<223> OTHER INFORMATION: Synthetic

<400> SEQUENCE: 309
acagttctcc ttcttagctt cgtgagaacg gcgactattc ctacgtcagc gttgcggaat 60
atttctccag ctcaaggata atagccacta ccgcttcccc cggtggcgac agggagaaga 120
taaacgagat catgcgccac ctgagaatag agaaccttga ggtgagggac acatcatgta 180
gtagacgacc aagacagt 198

<210> SEQ ID NO 310
<211> LENGTH: 198
<212> TYPE: DNA
<213> ORGANISM: Artificial Sequence
<220> FEATURE:
<223> OTHER INFORMATION: Synthetic

<400> SEQUENCE: 310
acagttctcc ttcttagctt cgtgagaaca tcgacgctcc agctgttcag ggacggtgcg 60
gtcaggatac tcgtagcaac gcaggttggg gaggaaggac tggacgtacc ggctgcagat 120
accgtcatat tctacgagcc ggtggcaagc gaggtccgct caatccagac acatcatgta 180
gtagacgacc aagacagt 198

<210> SEQ ID NO 311
<211> LENGTH: 198
<212> TYPE: DNA
<213> ORGANISM: Artificial Sequence
<220> FEATURE:
<223> OTHER INFORMATION: Synthetic

<400> SEQUENCE: 311
acagttctcc ttcttagctt cgtgagaacc gcggtcctct ttcccagctt cagtcctttg 60
gctttcctat gttctgctgg tactcttccc attgctctct ctgttgtttc tcctggcttt 120
tcctgaagtt ttcgagggct tcgtccatgc tgtcataagc gttatgcgac acatcatgta 180
gtagacgacc aagacagt 198

<210> SEQ ID NO 312
<211> LENGTH: 198
<212> TYPE: DNA
<213> ORGANISM: Artificial Sequence
<220> FEATURE:
<223> OTHER INFORMATION: Synthetic

<400> SEQUENCE: 312
acagttctcc ttcttagctt cgtgagaacc gaactccttg acgctcctgg agatgaccag 60
tttctctatc tccaccctcc cgctcttcat gtccgatatt attttcctcg cccttctcag 120
tgcctcgtcc acgttccggt cgagcacgag attgaacatt tccatgagtc acatcatgta 180
gtagacgacc aagacagt 198

<210> SEQ ID NO 313
<211> LENGTH: 198
<212> TYPE: DNA
<213> ORGANISM: Artificial Sequence
<220> FEATURE:
<223> OTHER INFORMATION: Synthetic

<400> SEQUENCE: 313
acagttctcc ttcttagctt cgtgagaacc cctttcctcg aggtctttgt ctattccctt 60
caccgtttcc ctggcccaag cagtgatgct ggacccgata ctgggatcgg taaacctgta 120
gaagcttgat gcaaacactc cgtagaacga attcataagc accttcaccc acatcatgta 180
gtagacgacc aagacagt 198

<210> SEQ ID NO 314
<211> LENGTH: 198
<212> TYPE: DNA
<213> ORGANISM: Artificial Sequence
<220> FEATURE:
<223> OTHER INFORMATION: Synthetic

<400> SEQUENCE: 314
acagttctcc ttcttagctt cgtgagaacc agttctcctt ccaccccgtc cgcctcttct 60
atgacggtcg cactttccgt cgagcagacg ccctacggct ggatggatca gtatccctcg 120
tcggttgttg cccatgtcac gggaggcatc cctccctacg cctatcactc acatcatgta 180
gtagacgacc aagacagt 198

<210> SEQ ID NO 315
<211> LENGTH: 198
<212> TYPE: DNA
<213> ORGANISM: Artificial Sequence
<220> FEATURE:
<223> OTHER INFORMATION: Synthetic

<400> SEQUENCE: 315
acagttctcc ttcttagctt cgtgagaacc aatctggagg ctttcgccgt atccgtcgaa 60
gtcacggact catcggggca ttcagtctca ggtgcaatca tgatcaacta cggttccata 120
gacctctccc cgtttggata catggtaact ttgatttttc cggtgatcac acatcatgta 180
gtagacgacc aagacagt 198

<210> SEQ ID NO 316
<211> LENGTH: 198
<212> TYPE: DNA
<213> ORGANISM: Artificial Sequence
<220> FEATURE:
<223> OTHER INFORMATION: Synthetic

<400> SEQUENCE: 316
acagttctcc ttcttagctt cgtgagaacg aacatccatt gctgaccatc acgatcgatg 60
gctcaaagga cacgttcaaa actggcgatg tcctggaatg gttgaccgaa agtgacatct 120
caaacatgca caatgttgcg tccttcacaa aatctctcct gaggatagtc acatcatgta 180
gtagacgacc aagacagt 198

<210> SEQ ID NO 317
<211> LENGTH: 198
<212> TYPE: DNA
<213> ORGANISM: Artificial Sequence
<220> FEATURE:
<223> OTHER INFORMATION: Synthetic

<400> SEQUENCE: 317
acagttctcc ttcttagctt cgtgagaacg catgctgccc gatggccaat ggttcgggga 60
ggtcattggg aaggacgtgc agggaaatcc ctacggcatt gattatacaa tgtggttgcc 120
gtttaacacc tacgttaggg ataagctcag ttacaatagt tgggggaagc acatcatgta 180
gtagacgacc aagacagt 198

<210> SEQ ID NO 318
<211> LENGTH: 198
<212> TYPE: DNA
<213> ORGANISM: Artificial Sequence
<220> FEATURE:
<223> OTHER INFORMATION: Synthetic

<400> SEQUENCE: 318
acagttctcc ttcttagctt cgtgagaacc cagcattcct cctctgaggg agttcggaag 60
gtaaaatctc ctgatgacat ctgagtccct ggcgcccatt gtcttggctg agtagacttc 120
cattttactt gtcgtgctgc cagttgaaaa tgcaagtact gctatcatcc acatcatgta 180
gtagacgacc aagacagt 198

<210> SEQ ID NO 319
<211> LENGTH: 198
<212> TYPE: DNA
<213> ORGANISM: Artificial Sequence
<220> FEATURE:
<223> OTHER INFORMATION: Synthetic

<400> SEQUENCE: 319
acagttctcc ttcttagctt cgtgagaacg ttccctgcag gaatgattgt tcaactgcac 60
tcgtcagtac atgatagaac aatcttgaag ctgacagatg gagcgcatag aagataagga 120
atgcaagagg taccagtact agtaccactg catatattcc tgcgtatagc acatcatgta 180
gtagacgacc aagacagt 198

<210> SEQ ID NO 320
<211> LENGTH: 198
<212> TYPE: DNA
<213> ORGANISM: Artificial Sequence
<220> FEATURE:
<223> OTHER INFORMATION: Synthetic

<400> SEQUENCE: 320
acagttctcc ttcttagctt cgtgagaacc gattgcagga acgtggaaag tgtgcggtta 60
atgtatgact cattgctcac atcgaatcga tacagaagac cgctgtttgc tgccaggtag 120
gaatctatgt tattcaggcc aacaaccaca tcgtatcccg ccccctttgc acatcatgta 180
gtagacgacc aagacagt 198

<210> SEQ ID NO 321
<211> LENGTH: 198
<212> TYPE: DNA
<213> ORGANISM: Artificial Sequence
<220> FEATURE:
<223> OTHER INFORMATION: Synthetic

<400> SEQUENCE: 321
acagttctcc ttcttagctt cgtgagaaca ggattgaacc ggttggtgtc aacgtagaat 60
cctcattgac ccgccacata aaactgaaca ttccaattgt gtcgtctcct atggatacgg 120
tctctgaggc agatatggca attgcactag caagactcgg tggtattggc acatcatgta 180
gtagacgacc aagacagt 198

<210> SEQ ID NO 322
<211> LENGTH: 198
<212> TYPE: DNA
<213> ORGANISM: Artificial Sequence
<220> FEATURE:
<223> OTHER INFORMATION: Synthetic

<400> SEQUENCE: 322
acagttctcc ttcttagctt cgtgagaacc ttattatacg cgacctttac actgtaagcc 60
cggaaacacc tgttgacgat gcaatccgta ctatgaggga gaagcgaatc gctgggctcc 120
cagtgatatt gaacggcaaa cttgtcggaa tacttacgaa cagggacatc acatcatgta 180
gtagacgacc aagacagt 198

<210> SEQ ID NO 323
<211> LENGTH: 198
<212> TYPE: DNA
<213> ORGANISM: Artificial Sequence
<220> FEATURE:
<223> OTHER INFORMATION: Synthetic

<400> SEQUENCE: 323
acagttctcc ttcttagctt cgtgagaacg gtacggcaag ataggctcag ggaaatttgt 60
accagaggga gttgaaggag cagttccgta caaaggtaaa gttgcagatg cagtctttca 120
attgatcggg ggcctgaagt cggggatggg gtatactggc tcgcccacac acatcatgta 180
gtagacgacc aagacagt 198

<210> SEQ ID NO 324
<211> LENGTH: 198
<212> TYPE: DNA
<213> ORGANISM: Artificial Sequence
<220> FEATURE:
<223> OTHER INFORMATION: Synthetic

<400> SEQUENCE: 324
acagttctcc ttcttagctt cgtgagaacg gtggaagcgt tgaggagttt gtcactctat 60
cgaggagagt ggaggcagcg ggattcgaca aggtcgagct caatttgtcc tgcccacacg 120
ttcagggagt tggatccgag gtaggacagg atgtaggtct tgtagaagac acatcatgta 180
gtagacgacc aagacagt 198

<210> SEQ ID NO 325
<211> LENGTH: 198
<212> TYPE: DNA
<213> ORGANISM: Artificial Sequence
<220> FEATURE:
<223> OTHER INFORMATION: Synthetic

<400> SEQUENCE: 325
acagttctcc ttcttagctt cgtgagaacg acacttatag acaggctaga caagaagacg 60
aagacaagga tattcttctc acttgagcga ttgatgaagt gcggcatagg gatttgtgac 120
agttgcagca tcaacggcat ccgggtatgc aaggacggaa caattttcgc acatcatgta 180
gtagacgacc aagacagt 198

<210> SEQ ID NO 326
<211> LENGTH: 198
<212> TYPE: DNA
<213> ORGANISM: Artificial Sequence
<220> FEATURE:
<223> OTHER INFORMATION: Synthetic

<400> SEQUENCE: 326
acagttctcc ttcttagctt cgtgagaacc ttcgcaactg caaagaggta gcttctggat 60
gcttccctgg aactatccct acattgctgt tatcttacta gtggtactga tttatgcagc 120
aatagaggac cttaggaaga ggaaaataac aactataacc ttccttgcac acatcatgta 180
gtagacgacc aagacagt 198

<210> SEQ ID NO 327
<211> LENGTH: 198
<212> TYPE: DNA
<213> ORGANISM: Artificial Sequence
<220> FEATURE:
<223> OTHER INFORMATION: Synthetic

<400> SEQUENCE: 327
acagttctcc ttcttagctt cgtgagaacg tgacagttgg aactggtcta tctccccggt 60
attttaataa gtttataggc gtagcaaagg catatacgac aagagtaggg gaggggatat 120
ttcctactga gatgtttggg gaagaggcag atagacttag aaccctaggc acatcatgta 180
gtagacgacc aagacagt 198

<210> SEQ ID NO 328
<211> LENGTH: 198
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (111)..(111)
<223> OTHER INFORMATION: n is a, c, g, or t

<400> SEQUENCE: 328
acagttctcc ttcttagctt cgtgagaacg aagaagactt aaaggattta ggtagagagc 60
ttaaggtacc aagaagaccg ttcaaaaagt taacgcatag agaagctgtt natatattga 120
gatctcatgg cataaaagca agttatgaac atgagatacc ttgggaagcc acatcatgta 180
gtagacgacc aagacagt 198

<210> SEQ ID NO 329
<211> LENGTH: 198
<212> TYPE: DNA
<213> ORGANISM: Artificial Sequence
<220> FEATURE:
<223> OTHER INFORMATION: Synthetic

<400> SEQUENCE: 329
acagttctcc ttcttagctt cgtgagaaca cggggaggct gtctcaggag ctgaaagaga 60
atatagagcg gagaaggtta ttgagaggat gagagctact ggtgagaacc ctgcaaaata 120
cggttggtac attgaaatgt tgaaatatgg tattccgccg agtgcagggc acatcatgta 180
gtagacgacc aagacagt 198

<210> SEQ ID NO 330
<211> LENGTH: 198
<212> TYPE: DNA
<213> ORGANISM: Artificial Sequence
<220> FEATURE:
<223> OTHER INFORMATION: Synthetic

<400> SEQUENCE: 330
acagttctcc ttcttagctt cgtgagaaca tatgcagatt tagatgagat tataggggtt 60
gcatctaagg caggaataga ttgcataact atagatgggt cagaaggtgg aacaggtatg 120
agccctatag ctgcgatgag agaactagga tatccaacgc tagtatgtcc acatcatgta 180
gtagacgacc aagacagt 198

<210> SEQ ID NO 331
<211> LENGTH: 198
<212> TYPE: DNA
<213> ORGANISM: Artificial Sequence
<220> FEATURE:
<223> OTHER INFORMATION: Synthetic

<400> SEQUENCE: 331
acagttctcc ttcttagctt cgtgagaacg gacacgaaat tgctgaagca gctggctcaa 60
catggtatat cgacaatttc tgggataaac tcaaagaggg ctgtgtagca tatctaaaca 120
tagattcacc tggattaaaa gatgcaacaa gatatatcgc ttacgcgtcc acatcatgta 180
gtagacgacc aagacagt 198

<210> SEQ ID NO 332
<211> LENGTH: 198
<212> TYPE: DNA
<213> ORGANISM: Artificial Sequence
<220> FEATURE:
<223> OTHER INFORMATION: Synthetic

<400> SEQUENCE: 332
acagttctcc ttcttagctt cgtgagaacg taacttctgg aaacgcccaa tcaaaacaga 60
tcatgacacc aaagctaaaa ttatcttccc taatagcttc tataggtgta tctccaggtt 120
gaaatattag cttctctttg gcaaataagt gaagtttcct atactttccc acatcatgta 180
gtagacgacc aagacagt 198

<210> SEQ ID NO 333
<211> LENGTH: 198
<212> TYPE: DNA
<213> ORGANISM: Artificial Sequence
<220> FEATURE:
<223> OTHER INFORMATION: Synthetic

<400> SEQUENCE: 333
acagttctcc ttcttagctt cgtgagaacc cagatagccc aatagcatca atttccgttg 60
caataatagg tacagtacac aaagaacacg taattttcag cgacactgca aatacaggcg 120
acttaataat ttttgccata gatctcgatg gaacatttca ccctaagttc acatcatgta 180
gtagacgacc aagacagt 198

<210> SEQ ID NO 334
<211> LENGTH: 198
<212> TYPE: DNA
<213> ORGANISM: Artificial Sequence
<220> FEATURE:
<223> OTHER INFORMATION: Synthetic

<400> SEQUENCE: 334
acagttctcc ttcttagctt cgtgagaacg ttctaattcc tctcttacag ctttaaaagc 60
aatcacagca gattccaaaa tatcatccat atcatccaga gctataataa cacctcttga 120
agttttccca atcttatgcc cacttcttcc aactctttga accaaacgac acatcatgta 180
gtagacgacc aagacagt 198

<210> SEQ ID NO 335
<211> LENGTH: 198
<212> TYPE: DNA
<213> ORGANISM: Artificial Sequence
<220> FEATURE:
<223> OTHER INFORMATION: Synthetic

<400> SEQUENCE: 335
acagttctcc ttcttagctt cgtgagaacg taacttgtct gggagacata tattggacaa 60
ctaaatcaac ggttcctaca tcaatcccta actccataga tgatgtacaa ataagacctt 120
tcaactcacc gtctttaaat aacctttcaa cttctatacg aacatctctc acatcatgta 180
gtagacgacc aagacagt 198

<210> SEQ ID NO 336
<211> LENGTH: 198
<212> TYPE: DNA
<213> ORGANISM: Artificial Sequence
<220> FEATURE:
<223> OTHER INFORMATION: Synthetic

<400> SEQUENCE: 336
acagttctcc ttcttagctt cgtgagaaca ctcaatgaac catgatgcac atcaatactt 60
agattaggat cgtataagtg aagcctagaa gctagtatct cagctatttc acgagtgttt 120
acaaaagtaa gcatagagcg gctcttttct aataactcaa ccaatacccc acatcatgta 180
gtagacgacc aagacagt 198

<210> SEQ ID NO 337
<211> LENGTH: 198
<212> TYPE: DNA
<213> ORGANISM: Artificial Sequence
<220> FEATURE:
<223> OTHER INFORMATION: Synthetic

<400> SEQUENCE: 337
acagttctcc ttcttagctt cgtgagaacc agttaaatca tcttaactca caaatattaa 60
ggctttaatt tctgagggag tgcaaaatga aaactgacgt agtaatagta ggtgcagggc 120
ccgcaggcat gtttgctgca catgaattgg caactaaatc taatctgaac acatcatgta 180
gtagacgacc aagacagt 198

<210> SEQ ID NO 338
<211> LENGTH: 198
<212> TYPE: DNA
<213> ORGANISM: Artificial Sequence
<220> FEATURE:
<223> OTHER INFORMATION: Synthetic

<400> SEQUENCE: 338
acagttctcc ttcttagctt cgtgagaaca aaaatagcca aggatccaaa attccgtgta 60
tatacaaaaa ccttcgatga ccttacacgt gtattttgcg ttaattatcg aggcttcgtc 120
gtccaagaag tctacggaga tatcgttggt gttaacggcc acactctaac acatcatgta 180
gtagacgacc aagacagt 198

<210> SEQ ID NO 339
<211> LENGTH: 198
<212> TYPE: DNA
<213> ORGANISM: Artificial Sequence
<220> FEATURE:
<223> OTHER INFORMATION: Synthetic

<400> SEQUENCE: 339
acagttctcc ttcttagctt cgtgagaact caaacaaaaa tctgaaaatg ccaattttgc 60
atttctagtt cgagttgaac tcaccgaacc gcttgaagac acaaccgcct acggattctc 120
aatagccaaa ttagcaacta ccataggtgg aggaaaacca attcttcaac acatcatgta 180
gtagacgacc aagacagt 198

<210> SEQ ID NO 340
<211> LENGTH: 198
<212> TYPE: DNA
<213> ORGANISM: Artificial Sequence
<220> FEATURE:
<223> OTHER INFORMATION: Synthetic

<400> SEQUENCE: 340
acagttctcc ttcttagctt cgtgagaacc gagatactga atttccaaaa ctcaaaggat 60
atagaattgt tagaatcgca acacatccgc aagttatgag catgggacta ggaagtgaag 120
ggttgtcaaa actttgccaa gaagccgaaa agagaggact agattgggtc acatcatgta 180
gtagacgacc aagacagt 198

<210> SEQ ID NO 341
<211> LENGTH: 198
<212> TYPE: DNA
<213> ORGANISM: Artificial Sequence
<220> FEATURE:
<223> OTHER INFORMATION: Synthetic

<400> SEQUENCE: 341
acagttctcc ttcttagctt cgtgagaacc gaagttttta tcctcctcgg tccaagtcac 60
actggttacc caggcgttgg aataatgaca gaaggcatct ggaaaacttc tttaggagaa 120
atatcaatag atgaaactct ctcgaatact attttaaata attgtgaccc acatcatgta 180
gtagacgacc aagacagt 198

<210> SEQ ID NO 342
<211> LENGTH: 198
<212> TYPE: DNA
<213> ORGANISM: Artificial Sequence
<220> FEATURE:
<223> OTHER INFORMATION: Synthetic

<400> SEQUENCE: 342
acagttctcc ttcttagctt cgtgagaact gacacactac ggcacctact atggatacac 60
accagctggt gttgaaccat taaccaaagt tttagaatgg atataccaga cggacaaaca 120
agttattgag agaattaaaa gattagatgg agcaggagta atagaatatc acatcatgta 180
gtagacgacc aagacagt 198

<210> SEQ ID NO 343
<211> LENGTH: 198
<212> TYPE: DNA
<213> ORGANISM: Artificial Sequence
<220> FEATURE:
<223> OTHER INFORMATION: Synthetic

<400> SEQUENCE: 343
acagttctcc ttcttagctt cgtgagaacc tgaaaagttc attccaattg ttaaatcgcc 60
atcttggaaa cacggcacaa gaaaagggaa aggatttagc atcggtgaga ttaaagcagc 120
cgagatagat attagtatgg cagttaaact cggtataccc attgataaac acatcatgta 180
gtagacgacc aagacagt 198

<210> SEQ ID NO 344
<211> LENGTH: 198
<212> TYPE: DNA
<213> ORGANISM: Artificial Sequence
<220> FEATURE:
<223> OTHER INFORMATION: Synthetic

<400> SEQUENCE: 344
acagttctcc ttcttagctt cgtgagaacg ggaataataa ttaaaataat gtggcacacc 60
ttttagcttc ttttcatctc atattttcaa agaagccttc caggtgtgcc tcatcggtgt 120
cccccgctgc ggagacacgg tatcatcgta tccgccgaag gaaactcaac acatcatgta 180
gtagacgacc aagacagt 198

<210> SEQ ID NO 345
<211> LENGTH: 198
<212> TYPE: DNA
<213> ORGANISM: Artificial Sequence
<220> FEATURE:
<223> OTHER INFORMATION: Synthetic

<400> SEQUENCE: 345
acagttctcc ttcttagctt cgtgagaacg acattgccta tcaattactt caagccggaa 60
tgcaagttcc cggtttcaga aggtcgccaa agataataga aagaatttta gaaagatata 120
ttccaacagt caccgtacta ggcggcatta ttgtaggatt aatagctgcc acatcatgta 180
gtagacgacc aagacagt 198

<210> SEQ ID NO 346
<211> LENGTH: 198
<212> TYPE: DNA
<213> ORGANISM: Artificial Sequence
<220> FEATURE:
<223> OTHER INFORMATION: Synthetic

<400> SEQUENCE: 346
acagttctcc ttcttagctt cgtgagaact gtcgttcagg gaggtataaa aatgccagaa 60
ccacgctacc ggtcaaggtc tttaagaaga cgatacgtac acacacctgg aggaaaaacc 120
gtcatccatt acaggagaaa aaaacctgac gttgcaaaat gcgcattatc acatcatgta 180
gtagacgacc aagacagt 198

<210> SEQ ID NO 347
<211> LENGTH: 198

<212> TYPE: DNA
<213> ORGANISM: Artificial Sequence
<220> FEATURE:
<223> OTHER INFORMATION: Synthetic

<400> SEQUENCE: 347
acagttctcc ttcttagctt cgtgagaacg tggtcaacct ctcagaggaa ttcccagact 60
aaggccagga gaattcagaa agttgacaaa aagtcaacga agaccagaga gacctttcgg 120
tggatatcta tgccacaaat gcttagcaat ggaaatcaag aaagctgttc acatcatgta 180
gtagacgacc aagacagt 198

<210> SEQ ID NO 348
<211> LENGTH: 198
<212> TYPE: DNA
<213> ORGANISM: Artificial Sequence
<220> FEATURE:
<223> OTHER INFORMATION: Synthetic

<400> SEQUENCE: 348
acagttctcc ttcttagctt cgtgagaaca taggatgaat ctaactgggg cgacccggta 60
gataactgag agtgtaggag gtgaaataat tgagcgcaat agaagtaggt agaatatgtg 120
ttaaaactag tggaagagaa gcaggaagaa agtgcgttat tgttgaaatc acatcatgta 180
gtagacgacc aagacagt 198

<210> SEQ ID NO 349
<211> LENGTH: 198
<212> TYPE: DNA
<213> ORGANISM: Artificial Sequence
<220> FEATURE:
<223> OTHER INFORMATION: Synthetic

<400> SEQUENCE: 349
acagttctcc ttcttagctt cgtgagaaca caccatttcc taatatttta gtaactagat 60
atgtttgtta tagtattagg gtgaagtatt tgtatgaaag aaagttgcca tcagacatta 120
aaagagagat tctagtaaaa agtgaagcag aaactgaccc tgcttatggc acatcatgta 180
gtagacgacc aagacagt 198

<210> SEQ ID NO 350
<211> LENGTH: 198
<212> TYPE: DNA
<213> ORGANISM: Artificial Sequence
<220> FEATURE:
<223> OTHER INFORMATION: Synthetic

<400> SEQUENCE: 350
acagttctcc ttcttagctt cgtgagaacc acatgagaga acttagaaga acacgtacag 60
gaccctttaa agaagatgaa accctagtaa ctcttcacga tgtagttgat gcttactatt 120
tttggaagga agatggagaa gaagaatttc tacgaaaagt catacaaccc acatcatgta 180
gtagacgacc aagacagt 198

<210> SEQ ID NO 351
<211> LENGTH: 198
<212> TYPE: DNA
<213> ORGANISM: Artificial Sequence
<220> FEATURE:
<223> OTHER INFORMATION: Synthetic

<400> SEQUENCE: 351
acagttctcc ttcttagctt cgtgagaaca atggaaaagg gtttagaaca cctacctcac 60
atttggatta gagattctgc tgtagatgca atatgccatg gggcaaactt agcagctcct 120
ggtgttgtaa aacttcatga cggtatatca cctggagact taatagtaac acatcatgta 180
gtagacgacc aagacagt 198

<210> SEQ ID NO 352
<211> LENGTH: 198
<212> TYPE: DNA
<213> ORGANISM: Artificial Sequence
<220> FEATURE:
<223> OTHER INFORMATION: Synthetic

<400> SEQUENCE: 352
acagttctcc ttcttagctt cgtgagaacc gctgatcata catgtgcatt gtctttaaat 60
acactagtaa cgttaataat atctagcaat tttagataaa aataactagc agtgccgggg 120
tagccaagtg gactacaggc cttataccgg ttagggcgcg ggcctggagc acatcatgta 180
gtagacgacc aagacagt 198

<210> SEQ ID NO 353
<211> LENGTH: 198
<212> TYPE: DNA
<213> ORGANISM: Artificial Sequence
<220> FEATURE:
<223> OTHER INFORMATION: Synthetic

<400> SEQUENCE: 353
acagttctcc ttcttagctt cgtgagaacc atgccttaac gagaggcatg ggatggggga 60
gctgtgagcc ccccgaaccg gcagatgagg ggaagggtgc aaagcatccc ttaacgccgg 120
aagctcccga cttcagtcgt ggagcagctc actgctttga cgaaaggttc acatcatgta 180
gtagacgacc aagacagt 198

<210> SEQ ID NO 354
<211> LENGTH: 198
<212> TYPE: DNA
<213> ORGANISM: Artificial Sequence
<220> FEATURE:
<223> OTHER INFORMATION: Synthetic

<400> SEQUENCE: 354
acagttctcc ttcttagctt cgtgagaacg aacttgcaag gaaggccggt gttgattatg 60
agacaaagct gttggtcagg ggcaaggaac cggctgagga cataatagaa tttgctgacg 120
agatcagggc aagtctcatt gtaatagggg ttaggaagag gagacccgcc acatcatgta 180
gtagacgacc aagacagt 198

<210> SEQ ID NO 355
<211> LENGTH: 198
<212> TYPE: DNA
<213> ORGANISM: Artificial Sequence
<220> FEATURE:
<223> OTHER INFORMATION: Synthetic

<400> SEQUENCE: 355
acagttctcc ttcttagctt cgtgagaact ccagaagaga ttcaaagctc tcgtattcaa 60
tgtccccacc aaatttctgg tcgcgctcaa ttttgacttt accaaaagcg gggaaaacgt 120
agtgctttgc taggtctatt atcggatttc cttctacaac ctttggcggc acatcatgta 180
gtagacgacc aagacagt 198

<210> SEQ ID NO 356
<211> LENGTH: 198
<212> TYPE: DNA
<213> ORGANISM: Artificial Sequence
<220> FEATURE:
<223> OTHER INFORMATION: Synthetic

<400> SEQUENCE: 356
acagttctcc ttcttagctt cgtgagaacg atttgctcat tttctccccg tcgagtcctg 60
agattatcgg cgtatggatg cagatcggtg ccttgtaacc gagggccggc agattctccc 120
ttgcgagcat gtggatcttt ctctgatcta ttccaccaac cgccacatcc acatcatgta 180
gtagacgacc aagacagt 198

<210> SEQ ID NO 357
<211> LENGTH: 198
<212> TYPE: DNA
<213> ORGANISM: Artificial Sequence
<220> FEATURE:
<223> OTHER INFORMATION: Synthetic

<400> SEQUENCE: 357
acagttctcc ttcttagctt cgtgagaact ccgggagttg cagaaccaag catggaaatt 60
gctagagatc ccgaaaaggt ttacgagtac acgaataagt ggaacacggt tgcaattatc 120
actgatggct cgagggtctt gggactgggc aacatcggtg cgatggcttc acatcatgta 180
gtagacgacc aagacagt 198

<210> SEQ ID NO 358
<211> LENGTH: 198
<212> TYPE: DNA
<213> ORGANISM: Artificial Sequence
<220> FEATURE:
<223> OTHER INFORMATION: Synthetic

<400> SEQUENCE: 358
acagttctcc ttcttagctt cgtgagaacg tggtgttatc aagagggaat atattgctca 60
gatggcagag gatccgatag tctttgcctt atcaaacccg gtgcctgaga tctatccgca 120
ggaggcaaag gaagccggag ccaggatcgt aggaactggt aggagcgacc acatcatgta 180
gtagacgacc aagacagt 198

<210> SEQ ID NO 359
<211> LENGTH: 198
<212> TYPE: DNA
<213> ORGANISM: Artificial Sequence
<220> FEATURE:
<223> OTHER INFORMATION: Synthetic

<400> SEQUENCE: 359
acagttctcc ttcttagctt cgtgagaacg ggatctgtta gtatggcatt cagagccttt 60
atgtcctcat cggtaagctt gtccgatggc agatcgtatt tcacgatgtc tgaaggagta 120
actccgagaa acttcgcttc tggtgtcgca agatactccg agagatgcgc acatcatgta 180
gtagacgacc aagacagt 198

<210> SEQ ID NO 360
<211> LENGTH: 198
<212> TYPE: DNA
<213> ORGANISM: Artificial Sequence
<220> FEATURE:

<223> OTHER INFORMATION: Synthetic

<400> SEQUENCE: 360
acagttctcc ttcttagctt cgtgagaact gagtgcggct tactctgcac tgtgcgagat 60
cgatgaggtc gttgttgttg cccccataac gcagatgagc ggagtgggga ggagcatatc 120
cataatgcgg ccggttcgtt ttttcgagct cgaaatagat ggcatgaggc acatcatgta 180
gtagacgacc aagacagt 198

<210> SEQ ID NO 361
<211> LENGTH: 198
<212> TYPE: DNA
<213> ORGANISM: Artificial Sequence
<220> FEATURE:
<223> OTHER INFORMATION: Synthetic

<400> SEQUENCE: 361
acagttctcc ttcttagctt cgtgagaaca ggggaaggga gtactactgg attcatgggg 60
tggaagtcga aagcgctgag cctggaacgg acatacacgc actcagaaac gggtatgtct 120
ccattacacc gatatcctta aatgcaactt cggactgcga agctttaagc acatcatgta 180
gtagacgacc aagacagt 198

<210> SEQ ID NO 362
<211> LENGTH: 198
<212> TYPE: DNA
<213> ORGANISM: Artificial Sequence
<220> FEATURE:
<223> OTHER INFORMATION: Synthetic

<400> SEQUENCE: 362
acagttctcc ttcttagctt cgtgagaaca tagttttatg gagggtggtt ggacatgaat 60
gaaagggcaa agaaggtcat tcttattgtg gatgacgatt tggctctgct tgaagctctt 120
gaactgatgc ttcgaggcaa gtatgaggtt gtgaaggtga caaatgggac acatcatgta 180
gtagacgacc aagacagt 198

<210> SEQ ID NO 363
<211> LENGTH: 198
<212> TYPE: DNA
<213> ORGANISM: Artificial Sequence
<220> FEATURE:
<223> OTHER INFORMATION: Synthetic

<400> SEQUENCE: 363
acagttctcc ttcttagctt cgtgagaaca tgtcgattcc gaaatagcag ggagcaatta 60
tcggtgggct tccgaccctt aaatggattt ccttcgctcc cgcctttctt atcatgtcga 120
ctattctttt ggatgttgtt gcccgcacaa tgctgtcgtc aaccagcacc acatcatgta 180
gtagacgacc aagacagt 198

<210> SEQ ID NO 364
<211> LENGTH: 198
<212> TYPE: DNA
<213> ORGANISM: Artificial Sequence
<220> FEATURE:
<223> OTHER INFORMATION: Synthetic

<400> SEQUENCE: 364
acagttctcc ttcttagctt cgtgagaaca ctttctgagg gaaaaacatt gttgcttatc 60
ctaaagagtt tacaagcaag aagctggaaa caaactctgg atgttattaa tttagagcct 120
gcagcagcat atacaatgtt tagagcggca ataaagaaac tatacaaagc acatcatgta 180
gtagacgacc aagacagt 198

<210> SEQ ID NO 365
<211> LENGTH: 198
<212> TYPE: DNA
<213> ORGANISM: Artificial Sequence
<220> FEATURE:
<223> OTHER INFORMATION: Synthetic

<400> SEQUENCE: 365
acagttctcc ttcttagctt cgtgagaacg tggttgagag gctgcttgaa ggcattgcaa 60
agaatgaaag ggtagcttac ggattggagg aggttaggag ggcaaaagag tatggagcaa 120
ttgaggttct gttggtttca gatgacttcc tgctcaccga gcgtgagaac acatcatgta 180
gtagacgacc aagacagt 198

<210> SEQ ID NO 366
<211> LENGTH: 198
<212> TYPE: DNA
<213> ORGANISM: Artificial Sequence
<220> FEATURE:
<223> OTHER INFORMATION: Synthetic

<400> SEQUENCE: 366
acagttctcc ttcttagctt cgtgagaact cgcttcgaga ttcctgatag gagtgggagt 60
tgccggggtt tacgtgccta cgataaaaat aatatccgtc tggttcaggc agaatgagtt 120
tgcaactgct actgggattc ttttcgcgat tggaaatcta ggagcgattc acatcatgta 180
gtagacgacc aagacagt 198

<210> SEQ ID NO 367
<211> LENGTH: 198
<212> TYPE: DNA
<213> ORGANISM: Artificial Sequence
<220> FEATURE:
<223> OTHER INFORMATION: Synthetic

<400> SEQUENCE: 367
acagttctcc ttcttagctt cgtgagaacg aggtatcgcc tacttagaga gttcgtaaag 60
tcggagatat tggaggaagt taaatttgaa aacgttgtgg acgagtactg ggttgcggaa 120
ccattcataa agatcataat ttttgaggat ctcgaaaacc agaaattgac acatcatgta 180
gtagacgacc aagacagt 198

<210> SEQ ID NO 368
<211> LENGTH: 198
<212> TYPE: DNA
<213> ORGANISM: Artificial Sequence
<220> FEATURE:
<223> OTHER INFORMATION: Synthetic

<400> SEQUENCE: 368
acagttctcc ttcttagctt cgtgagaacc taatccgatt atcgattcta cgcttcctga 60
tggtagcagg cttcaggcta ccctaggaac agaaattaca cctagaggct cgagcttcac 120
ggtgagaaaa tttacaaccc agccactgac cccgttagat ctagtgaggc acatcatgta 180
gtagacgacc aagacagt 198

<210> SEQ ID NO 369

<211> LENGTH: 198
<212> TYPE: DNA
<213> ORGANISM: Artificial Sequence
<220> FEATURE:
<223> OTHER INFORMATION: Synthetic

<400> SEQUENCE: 369
acagttctcc ttcttagctt cgtgagaacc aaaattatat cgatagagga taccagagag 60
ataaagctcc atcatgagaa ctggctggct caggtgacga gaacggggat aggagagcag 120
gaaattgaca tgtatgacct tctcaaagcc gccttgagac agagaccggc acatcatgta 180
gtagacgacc aagacagt 198

<210> SEQ ID NO 370
<211> LENGTH: 198
<212> TYPE: DNA
<213> ORGANISM: Artificial Sequence
<220> FEATURE:
<223> OTHER INFORMATION: Synthetic

<400> SEQUENCE: 370
acagttctcc ttcttagctt cgtgagaacg aatcagtttg ttaaatggga tgcgaagaaa 60
aattcgcatg ttgaggtagg gattccgaaa aagctagaga aaatcgcgat gtcgagagtg 120
gacgatgctt acgcggagct ggaaagaaga aggaggtatt tggagtggac acatcatgta 180
gtagacgacc aagacagt 198

<210> SEQ ID NO 371
<211> LENGTH: 198
<212> TYPE: DNA
<213> ORGANISM: Artificial Sequence
<220> FEATURE:
<223> OTHER INFORMATION: Synthetic

<400> SEQUENCE: 371
acagttctcc ttcttagctt cgtgagaact cagtgaagtt agcacggaat tcgaaaggat 60
agtggttctc gttgaaatgg gagaggattt ggaaagcgca atgaggtttg ttgcagaaac 120
aactccctca gagaggctca gggtttttct ggagaacttt attgatgtgc acatcatgta 180
gtagacgacc aagacagt 198

<210> SEQ ID NO 372
<211> LENGTH: 198
<212> TYPE: DNA
<213> ORGANISM: Artificial Sequence
<220> FEATURE:
<223> OTHER INFORMATION: Synthetic

<400> SEQUENCE: 372
acagttctcc ttcttagctt cgtgagaacg ctggagcggg aggcgtatca acgcttgccc 60
tcaatccgtt acccgaagtt ccagaatact ttgagtattt ccagtccgaa tagaagcaga 120
gcacctctcg atcgactaga gtctttctgc tagctcttgc accctcatcc acatcatgta 180
gtagacgacc aagacagt 198

<210> SEQ ID NO 373
<211> LENGTH: 198
<212> TYPE: DNA
<213> ORGANISM: Artificial Sequence
<220> FEATURE:
<223> OTHER INFORMATION: Synthetic

<400> SEQUENCE: 373
acagttctcc ttcttagctt cgtgagaacg cggaaatctc tgctgaaaac accttgactt 60
tttcttcgta tatctcccat tccatcaggc accaccaact ttggtcctgc aaagagtcat 120
cggtgcccca tctgctacgg gaacgatctg aaaggcttta ccacagaatc acatcatgta 180
gtagacgacc aagacagt 198

<210> SEQ ID NO 374
<211> LENGTH: 198
<212> TYPE: DNA
<213> ORGANISM: Artificial Sequence
<220> FEATURE:
<223> OTHER INFORMATION: Synthetic

<400> SEQUENCE: 374
acagttctcc ttcttagctt cgtgagaact ccggttgcag gattggtctc cccacctctc 60
gagcctatga ggaatacccc attcctgcag agctcgagaa gctcttcgaa ttcaagatcc 120
cccttctgca ggaatgtgtt gctcattctg acaatcggaa aagcaactcc acatcatgta 180
gtagacgacc aagacagt 198

<210> SEQ ID NO 375
<211> LENGTH: 198
<212> TYPE: DNA
<213> ORGANISM: Artificial Sequence
<220> FEATURE:
<223> OTHER INFORMATION: Synthetic

<400> SEQUENCE: 375
acagttctcc ttcttagctt cgtgagaaca actcctcgat tgttgggtca tcgattattg 60
tcacgttctc tcctgcaatt ctctctccaa tctttccagc aagaacgctg ttttcctgca 120
gaacgtgatc tgcctcgacc gcatgcccga aagcttcgtg aataaaaacc acatcatgta 180
gtagacgacc aagacagt 198

<210> SEQ ID NO 376
<211> LENGTH: 198
<212> TYPE: DNA
<213> ORGANISM: Artificial Sequence
<220> FEATURE:
<223> OTHER INFORMATION: Synthetic

<400> SEQUENCE: 376
acagttctcc ttcttagctt cgtgagaacc tttcttcaag aatgctttct gcggcgataa 60
gcccagtaac agccgctcca actattcccc tgcttattcc ggctccatcg ccaattgcat 120
agatgtacgg tatgcttgtc ctcatcttct cgtcaacctt aagcttcaac acatcatgta 180
gtagacgacc aagacagt 198

<210> SEQ ID NO 377
<211> LENGTH: 198
<212> TYPE: DNA
<213> ORGANISM: Artificial Sequence
<220> FEATURE:
<223> OTHER INFORMATION: Synthetic

<400> SEQUENCE: 377
acagttctcc ttcttagctt cgtgagaact gctggatttt tctttggcct tgctgtggcc 60
gttgactaga caaaagtcgc cgtactcctc tcttataacc cagcccctcg ggcaggtgca 120
gaacgtgcgc atgtagtcgt catgcctctg tgtgattatt ctcagctttc acatcatgta 180
gtagacgacc aagacagt 198

<210> SEQ ID NO 378
<211> LENGTH: 198
<212> TYPE: DNA
<213> ORGANISM: Artificial Sequence
<220> FEATURE:
<223> OTHER INFORMATION: Synthetic

<400> SEQUENCE: 378
acagttctcc ttcttagctt cgtgagaact tgccttggaa ttttccgcca cttcgatctt 60
atactttttt acccattttt ccagccagtc ggcaccgctc ctcccaactg caattatgag 120
tttgtcgtag ccgaacttgt ccccatcgtt cgtcttcacg atcttttctc acatcatgta 180
gtagacgacc aagacagt 198

<210> SEQ ID NO 379
<211> LENGTH: 198
<212> TYPE: DNA
<213> ORGANISM: Artificial Sequence
<220> FEATURE:
<223> OTHER INFORMATION: Synthetic

<400> SEQUENCE: 379
acagttctcc ttcttagctt cgtgagaaca atcaccaccg actgtgaagc tcgaaggata 60
gttggggttg gcataattca gctttccatc cgaaagtcct ccagcaccac ccacaccaga 120
agtaatgttg cagggatcgc atttcttgca atagctttgc gaaaggtcac acatcatgta 180
gtagacgacc aagacagt 198

<210> SEQ ID NO 380
<211> LENGTH: 198
<212> TYPE: DNA
<213> ORGANISM: Artificial Sequence
<220> FEATURE:
<223> OTHER INFORMATION: Synthetic

<400> SEQUENCE: 380
acagttctcc ttcttagctt cgtgagaact taaccaacct ctttcgcatc aaaatcccaa 60
ctgcggcatc cgttatcagc gttacatcga ttccatcttt cataagctcg tagcaggtga 120
gcctagagcc ttggttcagc ggcctcgttt cgcaggcgaa aacctttacc acatcatgta 180
gtagacgacc aagacagt 198

<210> SEQ ID NO 381
<211> LENGTH: 198
<212> TYPE: DNA
<213> ORGANISM: Artificial Sequence
<220> FEATURE:
<223> OTHER INFORMATION: Synthetic

<400> SEQUENCE: 381
acagttctcc ttcttagctt cgtgagaact tatcgagtta atagctatca gtgttgctat 60
tacgatcgtt gcgatcccat caaagatgtt atgaccgaag gagatagcaa taatgccaaa 120
tatcgctgca agcgtcgata aggagtcgtt aaaactctca aacatcactc acatcatgta 180
gtagacgacc aagacagt 198

<210> SEQ ID NO 382
<211> LENGTH: 198
<212> TYPE: DNA
<213> ORGANISM: Artificial Sequence
<220> FEATURE:
<223> OTHER INFORMATION: Synthetic

<400> SEQUENCE: 382
acagttctcc ttcttagctt cgtgagaacc tcccttctaa gcttcgtgat atctgcattg 60
ccaatatcaa ctagaaattc gattgagata agcttgtctc ttgcggttaa gcttgttctc 120
tcgatattta taccgaaatt tagcaataca cccgtgatat ctctcacgac acatcatgta 180
gtagacgacc aagacagt 198

<210> SEQ ID NO 383
<211> LENGTH: 198
<212> TYPE: DNA
<213> ORGANISM: Artificial Sequence
<220> FEATURE:
<223> OTHER INFORMATION: Synthetic

<400> SEQUENCE: 383
acagttctcc ttcttagctt cgtgagaaca agcggggctt ttgcctttcc aattccgccg 60
caaccaaccg ttggacttat caaaccggaa cctttcaact ccgagattaa agagcctggc 120
tccttatcgt gcttaatagc aatttctaca atgtcttccc cgcatacaac acatcatgta 180
gtagacgacc aagacagt 198

<210> SEQ ID NO 384
<211> LENGTH: 198
<212> TYPE: DNA
<213> ORGANISM: Artificial Sequence
<220> FEATURE:
<223> OTHER INFORMATION: Synthetic

<400> SEQUENCE: 384
acagttctcc ttcttagctt cgtgagaacc tagttcttgg ttttcgtcga cgttgacctt 60
gtagaactct acatctggaa actcctttga aagcttttcg agcactgggc tgagatacct 120
gcacggcatg caccagtcgg cgtagaagtc aacaacaaca agcttatccc acatcatgta 180
gtagacgacc aagacagt 198

<210> SEQ ID NO 385
<211> LENGTH: 198
<212> TYPE: DNA
<213> ORGANISM: Artificial Sequence
<220> FEATURE:
<223> OTHER INFORMATION: Synthetic

<400> SEQUENCE: 385
acagttctcc ttcttagctt cgtgagaacc tccgatcgtc tttaaagctt gcaagtctaa 60
atcctcgccc cagggaattt cctgggattt tctcgcaatc tctatcgccg aagtataggt 120
tatcctcggg aatggtatct cggggacttc gagctttagt tcgagaatac acatcatgta 180
gtagacgacc aagacagt 198

<210> SEQ ID NO 386
<211> LENGTH: 198
<212> TYPE: DNA
<213> ORGANISM: Artificial Sequence
<220> FEATURE:
<223> OTHER INFORMATION: Synthetic

<400> SEQUENCE: 386
acagttctcc ttcttagctt cgtgagaacg aggttttgtc cctattgggt ttctcattgc 60
ctgcagcatt tcttctctgc tcagagctct gcagccatcg cctttcattc ttaaaatgct 120
aacctcccaa tcatccggaa aatcgagctc tatttcccta tcctgccagc acatcatgta 180
gtagacgacc aagacagt 198

<210> SEQ ID NO 387
<211> LENGTH: 198
<212> TYPE: DNA
<213> ORGANISM: Artificial Sequence
<220> FEATURE:
<223> OTHER INFORMATION: Synthetic

<400> SEQUENCE: 387
acagttctcc ttcttagctt cgtgagaact gtttacaggc tggtgggtgg ggaaaggagt 60
gttaagggca aaaggagtgt aagcaagttc agggttgcga ttgcgattct tctggcattc 120
attctgatat atcctacata ccgcatagcc gagattcaaa gcagtggggc acatcatgta 180
gtagacgacc aagacagt 198

<210> SEQ ID NO 388
<211> LENGTH: 198
<212> TYPE: DNA
<213> ORGANISM: Artificial Sequence
<220> FEATURE:
<223> OTHER INFORMATION: Synthetic

<400> SEQUENCE: 388
acagttctcc ttcttagctt cgtgagaacc agggtcagga ggattcacga gatagaagtc 60
ctcgaggtga gaggcaggtt cgcgcttata agggttctca gcgaccccgg cacgtacatg 120
aggaagctgg cccacgacat cgggctattg ctcggagtag gtgcacacac acatcatgta 180
gtagacgacc aagacagt 198

<210> SEQ ID NO 389
<211> LENGTH: 198
<212> TYPE: DNA
<213> ORGANISM: Artificial Sequence
<220> FEATURE:
<223> OTHER INFORMATION: Synthetic

<400> SEQUENCE: 389
acagttctcc ttcttagctt cgtgagaacg aagtcagtca tagaatcaat ggtgtattct 60
tcatcagggt tattatacgg aatgaactta tagttctcac ctgctacctg atccactgtc 120
atttctgcaa gagtctgcac tgtggtaatt ccaccttctt ccatccgggc acatcatgta 180
gtagacgacc aagacagt 198

<210> SEQ ID NO 390
<211> LENGTH: 198
<212> TYPE: DNA
<213> ORGANISM: Artificial Sequence
<220> FEATURE:
<223> OTHER INFORMATION: Synthetic

<400> SEQUENCE: 390
acagttctcc ttcttagctt cgtgagaaca gtaagggaat caatgtcttc cattgctgta 60
agggttactg ttacctttgt agaagtcaga ccgtaattgg tcagcagctc ttcatagaag 120
ttctggtttg caatatccct ctgggcaatg acagggtagt cgacttcgtc acatcatgta 180
gtagacgacc aagacagt 198

<210> SEQ ID NO 391
<211> LENGTH: 24
<212> TYPE: DNA
<213> ORGANISM: Artificial Sequence
<220> FEATURE:
<223> OTHER INFORMATION: Synthetic

<400> SEQUENCE: 391
tctccttctt agcttcgtga gaac 24

<210> SEQ ID NO 392
<211> LENGTH: 24
<212> TYPE: DNA
<213> ORGANISM: Artificial Sequence
<220> FEATURE:
<223> OTHER INFORMATION: Synthetic

<400> SEQUENCE: 392
cttggtcgtc tactacatga tgtg 24

<210> SEQ ID NO 393
<211> LENGTH: 198
<212> TYPE: DNA
<213> ORGANISM: Artificial Sequence
<220> FEATURE:
<223> OTHER INFORMATION: Synthetic

<400> SEQUENCE: 393
acagttctcc ttcttagctt cgtgagaacg accggacgtt gtgatcacgg gtaccttgat 60
ctggtactca aaggtttgcc cccgtgaagt ctggtacatg gctagacacg tcactccatt 120
cgagggacat tcgaagttag agaagggcag agcgatacat cagatatatc acatcatgta 180
gtagacgacc aagacagt 198

<210> SEQ ID NO 394
<211> LENGTH: 198
<212> TYPE: DNA
<213> ORGANISM: Artificial Sequence
<220> FEATURE:
<223> OTHER INFORMATION: Synthetic

<400> SEQUENCE: 394
acagttctcc ttcttagctt cgtgagaacc ttaatggaaa gtatgcttta gataccttct 60
ggaacgctat ctcacttggc gggaattcag atatggagag taaattaagg gatctggaag 120
taaagttaat gtcgttaatc tatttaaatg agtcaccatt aaaatcaccc acatcatgta 180
gtagacgacc aagacagt 198

<210> SEQ ID NO 395
<211> LENGTH: 198
<212> TYPE: DNA
<213> ORGANISM: Artificial Sequence
<220> FEATURE:
<223> OTHER INFORMATION: Synthetic

<400> SEQUENCE: 395
acagttctcc ttcttagctt cgtgagaacc ataatatgtt agaggtagaa tttctttgtg 60
atagaatatt attgatgaat gatggaagag aattagcatt aggaaaacct aaggaactgg 120
taaaggatac agaatctaag aatcttgaag aggttttcct taaacttgtc acatcatgta 180
gtagacgacc aagacagt 198

<210> SEQ ID NO 396

<211> LENGTH: 198
<212> TYPE: DNA
<213> ORGANISM: Artificial Sequence
<220> FEATURE:
<223> OTHER INFORMATION: Synthetic

<400> SEQUENCE: 396
acagttctcc ttcttagctt cgtgagaaca gtctaggttt taattcttca actgcttcaa 60
atactagctt actgtagtta tctgccctca tgttaggata tatatctgga atataaggag 120
gttgatgagt tataagaagt ggatgaaatt gttgtcacac actcccctac acatcatgta 180
gtagacgacc aagacagt 198

<210> SEQ ID NO 397
<211> LENGTH: 198
<212> TYPE: DNA
<213> ORGANISM: Artificial Sequence
<220> FEATURE:
<223> OTHER INFORMATION: Synthetic

<400> SEQUENCE: 397
acagttctcc ttcttagctt cgtgagaacc tcgtaagcgt ttcctaccct cgagagggcc 60
atcctggtgg tgaggaagtc gtcgaagtgg gctaagtaaa aagcgaagat ctcgacccac 120
aattacctcc tcctgtacac caggaatacc cctatcagga tagagatacc acatcatgta 180
gtagacgacc aagacagt 198

<210> SEQ ID NO 398
<211> LENGTH: 198
<212> TYPE: DNA
<213> ORGANISM: Artificial Sequence
<220> FEATURE:
<223> OTHER INFORMATION: Synthetic

<400> SEQUENCE: 398
acagttctcc ttcttagctt cgtgagaact cacggtccgc gacgtgaatc gggcgttcca 60
gtcggcgttc ggctacgacg ccgacgacgt ggtcggaagc gacctcctcg ggcgaatcgt 120
gcccccggtg ccggacccgg acccggtgcc ggaaccgggg gacgacgagc acatcatgta 180
gtagacgacc aagacagt 198

<210> SEQ ID NO 399
<211> LENGTH: 198
<212> TYPE: DNA
<213> ORGANISM: Artificial Sequence
<220> FEATURE:
<223> OTHER INFORMATION: Synthetic

<400> SEQUENCE: 399
acagttctcc ttcttagctt cgtgagaacg cgtccgcgag ttcatcctga acgtcgtccc 60
gctgtcgccc ggcgaggagc gcggggcggg ctacgccatc tacaccgaca tcacggagcg 120
gaagacccgc gaaagcgagc tagagcgaca gaacgagcga ttggaggagc acatcatgta 180
gtagacgacc aagacagt 198

<210> SEQ ID NO 400
<211> LENGTH: 198
<212> TYPE: DNA
<213> ORGANISM: Artificial Sequence
<220> FEATURE:
<223> OTHER INFORMATION: Synthetic

<400> SEQUENCE: 400
acagttctcc ttcttagctt cgtgagaaca cgaactcgtc ggtgaacatc tcgtcttccg 60
gggagcccgc cgctcatggc ctgcccccgc cgtaagctgc tgcataaacc cgctccaaaa 120
tatacggatc attcacccct tggaatcgct caatcagatc aatgtacacc acatcatgta 180
gtagacgacc aagacagt 198

<210> SEQ ID NO 401
<211> LENGTH: 198
<212> TYPE: DNA
<213> ORGANISM: Artificial Sequence
<220> FEATURE:
<223> OTHER INFORMATION: Synthetic

<400> SEQUENCE: 401
acagttctcc ttcttagctt cgtgagaact gcgtacattc cccctaagcg gctcccaata 60
tacagacgcc ggttaacgac agctggcgac cctgtgatct cagtaccggt gtcgaatgac 120
cacatcagct tgcctgtccg tgcatggagt tcgtatacgt acccgtcgtc acatcatgta 180
gtagacgacc aagacagt 198

<210> SEQ ID NO 402
<211> LENGTH: 198
<212> TYPE: DNA
<213> ORGANISM: Artificial Sequence
<220> FEATURE:
<223> OTHER INFORMATION: Synthetic

<400> SEQUENCE: 402
acagttctcc ttcttagctt cgtgagaaca tacaccaccc catcagcaac aactgaatca 60
tgattaagta tcgcaccagc atcgtagcgc cagcgttcac tgccagtggt gctatcgaat 120
gcatagaaga tatgctccta atcgccaata tcagtacttc acaaagccgc acatcatgta 180
gtagacgacc aagacagt 198

<210> SEQ ID NO 403
<211> LENGTH: 198
<212> TYPE: DNA
<213> ORGANISM: Artificial Sequence
<220> FEATURE:
<223> OTHER INFORMATION: Synthetic

<400> SEQUENCE: 403
acagttctcc ttcttagctt cgtgagaacg tggagtcttt tgtcacaccg cagaggcgta 60
gcgctgcaga gcaggagccc aagcctactg ccaacataga gaacatagtg gctacagtat 120
ccctcgacca gactctagac ctgaacctca tagagaggag catactgacc acatcatgta 180
gtagacgacc aagacagt 198

<210> SEQ ID NO 404
<211> LENGTH: 198
<212> TYPE: DNA
<213> ORGANISM: Artificial Sequence
<220> FEATURE:
<223> OTHER INFORMATION: Synthetic

<400> SEQUENCE: 404
acagttctcc ttcttagctt cgtgagaacc gtcgcctggg ttaagaggat gttcggcctc 60
tccaaggcgg gtcacggagg cacgctggac ccgaaggtca ccggcgtcct ccccgtagcc 120
ctggaggaag caaccaaggt cataggcctg gtggtgcaca cgagcaaggc acatcatgta 180
gtagacgacc aagacagt 198

<210> SEQ ID NO 405
<211> LENGTH: 198
<212> TYPE: DNA
<213> ORGANISM: Artificial Sequence
<220> FEATURE:
<223> OTHER INFORMATION: Synthetic

<400> SEQUENCE: 405
acagttctcc ttcttagctt cgtgagaacc gtgggcgaga tctaccagag gccgccgctc 60
cgcagcagtg ttaagagaag cctccgcgtc aagaggatat acgagataga gctgctggag 120
tacaacggca ggtacgcgct catgagggtg ctctgcgagg ccggcacatc acatcatgta 180
gtagacgacc aagacagt 198

<210> SEQ ID NO 406
<211> LENGTH: 198
<212> TYPE: DNA
<213> ORGANISM: Artificial Sequence
<220> FEATURE:
<223> OTHER INFORMATION: Synthetic

<400> SEQUENCE: 406
acagttctcc ttcttagctt cgtgagaacc gctggaagaa cgagggcaag gaggacctgc 60
tgcggagcta catcaagccc gtcgagtacg ccgtgagcca cctgcccaag atagttatac 120
gcgataccgc ggtggacgcc atagcccatg gcgcgaacct cgcggtgccc acatcatgta 180
gtagacgacc aagacagt 198

<210> SEQ ID NO 407
<211> LENGTH: 198
<212> TYPE: DNA
<213> ORGANISM: Artificial Sequence
<220> FEATURE:
<223> OTHER INFORMATION: Synthetic

<400> SEQUENCE: 407
acagttctcc ttcttagctt cgtgagaacg ggagacccca aggtgaccgg cgtcctacca 60
gtggggctcg ccaacagcac caaggtcatt ggtaatgtta tacatagtgt taaagaatac 120
gtgatggtta tacagctcca cggcgatgta gccgagcagg atttaagaac acatcatgta 180
gtagacgacc aagacagt 198

<210> SEQ ID NO 408
<211> LENGTH: 198
<212> TYPE: DNA
<213> ORGANISM: Artificial Sequence
<220> FEATURE:
<223> OTHER INFORMATION: Synthetic

<400> SEQUENCE: 408
acagttctcc ttcttagctt cgtgagaact agagggaaag actgtagctt tcattcctag 60
gcacggaaag agacacagaa tacctccaca taagataaat tatagagcta atatatgggc 120
attaaaagaa ctaggagtga aatgggtcat ctcagtttct gccgtaggac acatcatgta 180
gtagacgacc aagacagt 198

<210> SEQ ID NO 409
<211> LENGTH: 198
<212> TYPE: DNA
<213> ORGANISM: Artificial Sequence
<220> FEATURE:
<223> OTHER INFORMATION: Synthetic

<400> SEQUENCE: 409
acagttctcc ttcttagctt cgtgagaact gagggagctc aggaggactc gcacggggcc 60
ctacagggag gatgagacac ttgtaaggct ccaggacgtc agcgaggccc tgctcctgtg 120
gaggagcaac ggggatgaga ggtatcttag acgcatcgtg ctacccgttc acatcatgta 180
gtagacgacc aagacagt 198

<210> SEQ ID NO 410
<211> LENGTH: 198
<212> TYPE: DNA
<213> ORGANISM: Artificial Sequence
<220> FEATURE:
<223> OTHER INFORMATION: Synthetic

<400> SEQUENCE: 410
acagttctcc ttcttagctt cgtgagaacg aaacatctat cgcccacctc ccgaagataa 60
tgatcttgga tacagctgtc gacgccatag cacatggtgc caacctggct gccccaggcg 120
tcgccaggtt aaccaggaac atcgcgaagg gtagtaccgt agcgatcctc acatcatgta 180
gtagacgacc aagacagt 198

<210> SEQ ID NO 411
<211> LENGTH: 198
<212> TYPE: DNA
<213> ORGANISM: Artificial Sequence
<220> FEATURE:
<223> OTHER INFORMATION: Synthetic

<400> SEQUENCE: 411
acagttctcc ttcttagctt cgtgagaact cgctatcccc gtgtacagca tggtgggggt 60
gccgatgccc gggtagaact tggtgacgct ctccagcttc tcgaggacgg tttccttggg 120
gaggctcgcg gtgtccacga gggttatcgc gtcctcggcg ccgtcgccgc acatcatgta 180
gtagacgacc aagacagt 198

<210> SEQ ID NO 412
<211> LENGTH: 198
<212> TYPE: DNA
<213> ORGANISM: Artificial Sequence
<220> FEATURE:
<223> OTHER INFORMATION: Synthetic

<400> SEQUENCE: 412
acagttctcc ttcttagctt cgtgagaacc gaggacgcga agagcgcggt ggatgtggac 60
gcgccgccgc acacgtagcc gtcgaggtag cgcggaacca tcggcgacat cagccccacg 120
acgcgacccg aggcgttgcc gaggatcacg tcgagcgtca cgcgcggcac acatcatgta 180
gtagacgacc aagacagt 198

<210> SEQ ID NO 413
<211> LENGTH: 198
<212> TYPE: DNA
<213> ORGANISM: Artificial Sequence
<220> FEATURE:
<223> OTHER INFORMATION: Synthetic

<400> SEQUENCE: 413
acagttctcc ttcttagctt cgtgagaact ctatggtgta gaacgggtcg ttgcggagcc 60

```
agcctggcgg cacgtaccgg tcgtccgcta tcgccagcga tctctcgaag aggtcgaggt    120

aggcggacgc gttggcgaac gccccgtgta tcacgacgtc tatcccgccc acatcatgta    180

gtagacgacc aagacagt                                                   198
```

<210> SEQ ID NO 414
<211> LENGTH: 198
<212> TYPE: DNA
<213> ORGANISM: Artificial Sequence
<220> FEATURE:
<223> OTHER INFORMATION: Synthetic

<400> SEQUENCE: 414

```
acagttctcc ttcttagctt cgtgagaacc ctacgccggg tgcgtaggag ggctcgagta     60

catccatgtc tatactgatg tatgttttac ccaggtcgcc tagtgccagg ggtcccttta    120

acgcttccag gatagagtac acggtgacgt ctctagtctt cttcaagaac acatcatgta    180

gtagacgacc aagacagt                                                   198
```

<210> SEQ ID NO 415
<211> LENGTH: 198
<212> TYPE: DNA
<213> ORGANISM: Artificial Sequence
<220> FEATURE:
<223> OTHER INFORMATION: Synthetic

<400> SEQUENCE: 415

```
acagttctcc ttcttagctt cgtgagaacc tactagcgtg tcaacggagc tcttcaacgc     60

ctttactatt ggataggtta taaggtgctc gcctccgagg aatcccagga gcatgccggg    120

atactcgtct acaacgcctt tcaccacgtc acctatgatt cttaaagagc acatcatgta    180

gtagacgacc aagacagt                                                   198
```

<210> SEQ ID NO 416
<211> LENGTH: 198
<212> TYPE: DNA
<213> ORGANISM: Artificial Sequence
<220> FEATURE:
<223> OTHER INFORMATION: Synthetic

<400> SEQUENCE: 416

```
acagttctcc ttcttagctt cgtgagaacc ataggtgaca tggggtttcc cattgactct     60

ataaagccgt atcctttaag cggagtgcaa ttggtctacg ctttgcttaa caacaggtat    120

ttcctaccgg gtagagaggg ctcgctcata gctttaggta gcgtgacggc acatcatgta    180

gtagacgacc aagacagt                                                   198
```

<210> SEQ ID NO 417
<211> LENGTH: 198
<212> TYPE: DNA
<213> ORGANISM: Artificial Sequence
<220> FEATURE:
<223> OTHER INFORMATION: Synthetic

<400> SEQUENCE: 417

```
acagttctcc ttcttagctt cgtgagaacg gtatctcacc gcttgtcacc atagtatccc     60

tcaggtactc cagtattctt gagagaaacg cacctaagcc ggatctcagg tttgaatcca    120

taagaactat gagtgaagcg ggattgaagc ccctgctgtt tctaagaccc acatcatgta    180

gtagacgacc aagacagt                                                   198
```

<210> SEQ ID NO 418
<211> LENGTH: 198
<212> TYPE: DNA
<213> ORGANISM: Artificial Sequence
<220> FEATURE:
<223> OTHER INFORMATION: Synthetic

<400> SEQUENCE: 418
acagttctcc ttcttagctt cgtgagaact aagggagata gagaaacgca tcaaaatacc 60
cttggggaaa ctgcgtgcag gggttcaata tggagtagag gtctcagaca taaaggagaa 120
gatagctgct tacgctagga ggaaggggct taaatacttc ccatcggcac acatcatgta 180
gtagacgacc aagacagt 198

<210> SEQ ID NO 419
<211> LENGTH: 198
<212> TYPE: DNA
<213> ORGANISM: Artificial Sequence
<220> FEATURE:
<223> OTHER INFORMATION: Synthetic

<400> SEQUENCE: 419
acagttctcc ttcttagctt cgtgagaact gtgaacctcg tgcccggctc taagtcgtga 60
gggcttgcaa cataggtggg gaggaacccg agcaacgggt aagaagacag gataagcggt 120
atcgctatga agagggctga gaaaaggaca tatactcctg agcccgtccc acatcatgta 180
gtagacgacc aagacagt 198

<210> SEQ ID NO 420
<211> LENGTH: 198
<212> TYPE: DNA
<213> ORGANISM: Artificial Sequence
<220> FEATURE:
<223> OTHER INFORMATION: Synthetic

<400> SEQUENCE: 420
acagttctcc ttcttagctt cgtgagaacc gaacatgcct tccccgtcta tatagaccca 60
gtagagttta aaaacttaac cagagacggc ttgtgagccg gatctctccc ccgctaggcc 120
ctggattggg ctcgctcctc ctgggacccc ggcctccaca tgctcgggac acatcatgta 180
gtagacgacc aagacagt 198

<210> SEQ ID NO 421
<211> LENGTH: 198
<212> TYPE: DNA
<213> ORGANISM: Artificial Sequence
<220> FEATURE:
<223> OTHER INFORMATION: Synthetic

<400> SEQUENCE: 421
acagttctcc ttcttagctt cgtgagaact ctcggttcgg caataagtaa taccaacgag 60
gtattaccat gcgcgtgacc agcaaaggcc aagtgacgat cccaaaggag atacgggatc 120
atttggggat tgggccgggc tccgaggtgg agttcgtgcc cacagacgac acatcatgta 180
gtagacgacc aagacagt 198

<210> SEQ ID NO 422
<211> LENGTH: 198
<212> TYPE: DNA
<213> ORGANISM: Artificial Sequence
<220> FEATURE:
<223> OTHER INFORMATION: Synthetic

<400> SEQUENCE: 422
acagttctcc ttcttagctt cgtgagaacc tcgatcatat ggccggcacg ttggacttgg 60
gaggcatgac aacggacgag tatatggagt ggctgagggg tccacgtgaa gatctcgaca 120
ttgattgaca caaatgtcct gatcgatgtt tggggtcctg ccggacaggc acatcatgta 180
gtagacgacc aagacagt 198

<210> SEQ ID NO 423
<211> LENGTH: 198
<212> TYPE: DNA
<213> ORGANISM: Artificial Sequence
<220> FEATURE:
<223> OTHER INFORMATION: Synthetic

<400> SEQUENCE: 423
acagttctcc ttcttagctt cgtgagaacc aggtgtattt tacacacctg gacagccagc 60
atatgatgct agcactcggt gtccccttat cacggtttcc cgcattgtaa agttttcgcg 120
cctgctgcgc cccgtagggc ctggattcat gtctcagaat ccatctccgc acatcatgta 180
gtagacgacc aagacagt 198

<210> SEQ ID NO 424
<211> LENGTH: 198
<212> TYPE: DNA
<213> ORGANISM: Artificial Sequence
<220> FEATURE:
<223> OTHER INFORMATION: Synthetic

<400> SEQUENCE: 424
acagttctcc ttcttagctt cgtgagaacc gtagcccgca ccttcctctg gtttagcacc 60
agcggtcccc acagagtacc catcatcccg aaggatatgc tggcaacagt gggcacgggt 120
ctcgctcgtt gcctgactta acaggatgct tcacagtacg aactgacgac acatcatgta 180
gtagacgacc aagacagt 198

<210> SEQ ID NO 425
<211> LENGTH: 198
<212> TYPE: DNA
<213> ORGANISM: Artificial Sequence
<220> FEATURE:
<223> OTHER INFORMATION: Synthetic

<400> SEQUENCE: 425
acagttctcc ttcttagctt cgtgagaacg aaacttacct tatcagtgtc attaagcata 60
ttgcttccaa gacccattga agcacttaca tcgttgatac acaggtgcca ggaatagtat 120
tcctcagtct cactataatc ctcgttggtg tagccttcaa gagagtcaac acatcatgta 180
gtagacgacc aagacagt 198

<210> SEQ ID NO 426
<211> LENGTH: 198
<212> TYPE: DNA
<213> ORGANISM: Artificial Sequence
<220> FEATURE:
<223> OTHER INFORMATION: Synthetic

<400> SEQUENCE: 426
acagttctcc ttcttagctt cgtgagaacg tttaagcaat tcttcggatg aaagatggcg 60
ctctatagga atttgttctg gtctagccat aaggcattat ttgtacttaa ttagtaataa 120
atgtttagtt aatgactata aatctgcaat tggagtctca aattttcaac acatcatgta 180
gtagacgacc aagacagt 198

<210> SEQ ID NO 427
<211> LENGTH: 198
<212> TYPE: DNA
<213> ORGANISM: Artificial Sequence
<220> FEATURE:
<223> OTHER INFORMATION: Synthetic

<400> SEQUENCE: 427
acagttctcc ttcttagctt cgtgagaaca acatgaagga tgtgtgtaag aggaaacgtt 60
attaacagac gtaatcagga ggatagttat gccctaaaaa cagcagagtt aaggtttaaa 120
aataagataa gaactcagtt gaggtttatc cattaatccc attaatcctc acatcatgta 180
gtagacgacc aagacagt 198

<210> SEQ ID NO 428
<211> LENGTH: 198
<212> TYPE: DNA
<213> ORGANISM: Artificial Sequence
<220> FEATURE:
<223> OTHER INFORMATION: Synthetic

<400> SEQUENCE: 428
acagttctcc ttcttagctt cgtgagaacg tatccgctga tatatcctgg ggatatagat 60
cgctctgaaa tggttacatc tatcggtttt aaggacagtt ccaacactat tggaccttgc 120
agctatgaca ggaataatct gtttatcgag cacagttgaa tttgacctac acatcatgta 180
gtagacgacc aagacagt 198

<210> SEQ ID NO 429
<211> LENGTH: 198
<212> TYPE: DNA
<213> ORGANISM: Artificial Sequence
<220> FEATURE:
<223> OTHER INFORMATION: Synthetic

<400> SEQUENCE: 429
acagttctcc ttcttagctt cgtgagaaca tattccgtat ttcttatcaa accgatcgtg 60
aagatttgac aaaggcttaa ctttagggct ccacttctca ttattagcct tagaatataa 120
agcgtaaccg taagcctgag gaacgtaaag cttaggagat tcaatcccgc acatcatgta 180
gtagacgacc aagacagt 198

<210> SEQ ID NO 430
<211> LENGTH: 198
<212> TYPE: DNA
<213> ORGANISM: Artificial Sequence
<220> FEATURE:
<223> OTHER INFORMATION: Synthetic

<400> SEQUENCE: 430
acagttctcc ttcttagctt cgtgagaact aaaattagcc gaaggcttcc cattaccgaa 60
aaagtcgttt attagctctt catccttctt ctccacgtcc gcccattcct ctccttccct 120
tggaatttta agctcgtccc agctgactct tatgggcaat tcaatatccc acatcatgta 180
gtagacgacc aagacagt 198

<210> SEQ ID NO 431
<211> LENGTH: 198
<212> TYPE: DNA

<213> ORGANISM: Artificial Sequence
<220> FEATURE:
<223> OTHER INFORMATION: Synthetic

<400> SEQUENCE: 431
acagttctcc ttcttagctt cgtgagaact ccggaggaat ctatcatatt aaacctcctc 60
aaaatcgcct cctcttgatt gcttaaaggc tgtgaattac aaagcttatt taatgcgtcc 120
caaagcgtta agtaataatt atttatatta aacactacta tttcagtagc acatcatgta 180
gtagacgacc aagacagt 198

<210> SEQ ID NO 432
<211> LENGTH: 198
<212> TYPE: DNA
<213> ORGANISM: Artificial Sequence
<220> FEATURE:
<223> OTHER INFORMATION: Synthetic

<400> SEQUENCE: 432
acagttctcc ttcttagctt cgtgagaacg ttcctcctca attcaattgg actgaaggag 60
ggtacgttct ggaaaacaga gcgtaaaaga gatatagaac gtagtataca catagctgga 120
aaaagaacaa tcattaagac aataaagaac tttatggaaa agagtagaac acatcatgta 180
gtagacgacc aagacagt 198

<210> SEQ ID NO 433
<211> LENGTH: 198
<212> TYPE: DNA
<213> ORGANISM: Artificial Sequence
<220> FEATURE:
<223> OTHER INFORMATION: Synthetic

<400> SEQUENCE: 433
acagttctcc ttcttagctt cgtgagaact cgtgtaaagg ttgtataatt caagcctcag 60
aacatttcga actccttaca aaatcgttta aactttctaa ggcataaatt tactagaaat 120
tgtcatttat gagaatgtaa ctatatagat ggtaaaatta ttaatcctcc acatcatgta 180
gtagacgacc aagacagt 198

<210> SEQ ID NO 434
<211> LENGTH: 198
<212> TYPE: DNA
<213> ORGANISM: Artificial Sequence
<220> FEATURE:
<223> OTHER INFORMATION: Synthetic

<400> SEQUENCE: 434
acagttctcc ttcttagctt cgtgagaacg gctgaaaaat aggttcgatc cgcctcctca 60
cttcttctcc ttcttgccct cggcctcgga ggaggcctct attcccagct tcttggcctc 120
ctcctcggtc gtcatgaaca ggctagtcct ctgccttccg cccatgctcc acatcatgta 180
gtagacgacc aagacagt 198

<210> SEQ ID NO 435
<211> LENGTH: 198
<212> TYPE: DNA
<213> ORGANISM: Artificial Sequence
<220> FEATURE:
<223> OTHER INFORMATION: Synthetic

<400> SEQUENCE: 435
acagttctcc ttcttagctt cgtgagaacg ttcagcataa aagacggttt cacgggccaa 60
agcctaagcg gcgtaacggt gaaagaagga gatacggttt tgggcacgat tgacgacggc 120
gggacgctgg agctcacgag gggcactcac accttgactt tcgagaagcc acatcatgta 180
gtagacgacc aagacagt 198

<210> SEQ ID NO 436
<211> LENGTH: 198
<212> TYPE: DNA
<213> ORGANISM: Artificial Sequence
<220> FEATURE:
<223> OTHER INFORMATION: Synthetic

<400> SEQUENCE: 436
acagttctcc ttcttagctt cgtgagaacc tgatgttata gaagtccgca aggacggctc 60
tgtcatctcg cccgagggtg ggaaatacta tctcggcgac ataagcggcc cgacacaaat 120
tagcatcaag ttcaaggccg gcgcggtggg aacccacggc ttcactatcc acatcatgta 180
gtagacgacc aagacagt 198

<210> SEQ ID NO 437
<211> LENGTH: 198
<212> TYPE: DNA
<213> ORGANISM: Artificial Sequence
<220> FEATURE:
<223> OTHER INFORMATION: Synthetic

<400> SEQUENCE: 437
acagttctcc ttcttagctt cgtgagaact ctccctcaac cttcgcgggg agaacggcgc 60
ggagtactgg acgggctacg cggacgcgct ggaagacctg ttgaagaaaa tccagaggcg 120
ggaggtgagg gcatgagaag gtattgttac atcacgtggg gatggatcac acatcatgta 180
gtagacgacc aagacagt 198

<210> SEQ ID NO 438
<211> LENGTH: 198
<212> TYPE: DNA
<213> ORGANISM: Artificial Sequence
<220> FEATURE:
<223> OTHER INFORMATION: Synthetic

<400> SEQUENCE: 438
acagttctcc ttcttagctt cgtgagaacg agcgccggga ggtgagggca tgagtgagga 60
attgatgttt ggtcgtgtcg tggagtatgt tcagcatagt ttctacaaga aaccgtttcc 120
tcttggcagt gagctcaaga atgcagtaga gaaggttatg gaaacaggac acatcatgta 180
gtagacgacc aagacagt 198

<210> SEQ ID NO 439
<211> LENGTH: 198
<212> TYPE: DNA
<213> ORGANISM: Artificial Sequence
<220> FEATURE:
<223> OTHER INFORMATION: Synthetic

<400> SEQUENCE: 439
acagttctcc ttcttagctt cgtgagaaca ggtcagagcc cacgtggcaa cttttgaggt 60
tctgacaaaa gactatgttc gtgagaaata caaagacatc atagagttca tgagggagaa 120
agggacagta tcgagaaagg aactgcggaa gaagttcttc ttgcttgctc acatcatgta 180
gtagacgacc aagacagt 198

<210> SEQ ID NO 440
<211> LENGTH: 198
<212> TYPE: DNA
<213> ORGANISM: Artificial Sequence
<220> FEATURE:
<223> OTHER INFORMATION: Synthetic

<400> SEQUENCE: 440
acagttctcc ttcttagctt cgtgagaacg tacctcaaaa tacagaatca tattttacaa 60
tcgcttggaa atattaatat caacaatacg caagtccaaa ttaacgtccc tggcaaacag 120
gtgacaattt atacccacga aatactagat aacgccaaaa aggcactcgc acatcatgta 180
gtagacgacc aagacagt 198

<210> SEQ ID NO 441
<211> LENGTH: 24
<212> TYPE: DNA
<213> ORGANISM: Artificial Sequence
<220> FEATURE:
<223> OTHER INFORMATION: Synthetic

<400> SEQUENCE: 441
accaaccaac tttcgatctc ttgt 24

<210> SEQ ID NO 442
<211> LENGTH: 25
<212> TYPE: DNA
<213> ORGANISM: Artificial Sequence
<220> FEATURE:
<223> OTHER INFORMATION: Synthetic

<400> SEQUENCE: 442
catctttaag atgttgacgt gcctc 25

<210> SEQ ID NO 443
<211> LENGTH: 22
<212> TYPE: DNA
<213> ORGANISM: Artificial Sequence
<220> FEATURE:
<223> OTHER INFORMATION: Synthetic

<400> SEQUENCE: 443
ctgttttaca ggttcgcgac gt 22

<210> SEQ ID NO 444
<211> LENGTH: 22
<212> TYPE: DNA
<213> ORGANISM: Artificial Sequence
<220> FEATURE:
<223> OTHER INFORMATION: Synthetic

<400> SEQUENCE: 444
taaggatcag tgccaagctc gt 22

<210> SEQ ID NO 445
<211> LENGTH: 22
<212> TYPE: DNA
<213> ORGANISM: Artificial Sequence
<220> FEATURE:
<223> OTHER INFORMATION: Synthetic

<400> SEQUENCE: 445
cggtaataaa ggagctggtg gc 22

<210> SEQ ID NO 446
<211> LENGTH: 24
<212> TYPE: DNA
<213> ORGANISM: Artificial Sequence
<220> FEATURE:
<223> OTHER INFORMATION: Synthetic

<400> SEQUENCE: 446
aaggtgtctg caattcatag ctct 24

<210> SEQ ID NO 447
<211> LENGTH: 22
<212> TYPE: DNA
<213> ORGANISM: Artificial Sequence
<220> FEATURE:
<223> OTHER INFORMATION: Synthetic

<400> SEQUENCE: 447
ggtgtatact gctgccgtga ac 22

<210> SEQ ID NO 448
<211> LENGTH: 25
<212> TYPE: DNA
<213> ORGANISM: Artificial Sequence
<220> FEATURE:
<223> OTHER INFORMATION: Synthetic

<400> SEQUENCE: 448
cacaagtagt ggcaccttct ttagt 25

<210> SEQ ID NO 449
<211> LENGTH: 22
<212> TYPE: DNA
<213> ORGANISM: Artificial Sequence
<220> FEATURE:
<223> OTHER INFORMATION: Synthetic

<400> SEQUENCE: 449
tggtgaaact tcatggcaga cg 22

<210> SEQ ID NO 450
<211> LENGTH: 28
<212> TYPE: DNA
<213> ORGANISM: Artificial Sequence
<220> FEATURE:
<223> OTHER INFORMATION: Synthetic

<400> SEQUENCE: 450
attgatgttg actttctctt tttggagt 28

<210> SEQ ID NO 451
<211> LENGTH: 22
<212> TYPE: DNA
<213> ORGANISM: Artificial Sequence
<220> FEATURE:
<223> OTHER INFORMATION: Synthetic

<400> SEQUENCE: 451
ggtgttgttg gagaaggttc cg 22

<210> SEQ ID NO 452
<211> LENGTH: 22
<212> TYPE: DNA
<213> ORGANISM: Artificial Sequence
<220> FEATURE:
<223> OTHER INFORMATION: Synthetic

<400> SEQUENCE: 452
tagcggcctt ctgtaaaaca cg 22

<210> SEQ ID NO 453
<211> LENGTH: 22
<212> TYPE: DNA
<213> ORGANISM: Artificial Sequence
<220> FEATURE:
<223> OTHER INFORMATION: Synthetic

<400> SEQUENCE: 453
catttgcatc agaggctgct cg 22

<210> SEQ ID NO 454
<211> LENGTH: 22
<212> TYPE: DNA
<213> ORGANISM: Artificial Sequence
<220> FEATURE:
<223> OTHER INFORMATION: Synthetic

<400> SEQUENCE: 454
aggtgacaat ttgtccaccg ac 22

<210> SEQ ID NO 455
<211> LENGTH: 24
<212> TYPE: DNA
<213> ORGANISM: Artificial Sequence
<220> FEATURE:
<223> OTHER INFORMATION: Synthetic

<400> SEQUENCE: 455
agagtttctt agagacggtt ggga 24

<210> SEQ ID NO 456
<211> LENGTH: 24
<212> TYPE: DNA
<213> ORGANISM: Artificial Sequence
<220> FEATURE:
<223> OTHER INFORMATION: Synthetic

<400> SEQUENCE: 456
gcttcaacag cttcactagt aggt 24

<210> SEQ ID NO 457
<211> LENGTH: 24
<212> TYPE: DNA
<213> ORGANISM: Artificial Sequence
<220> FEATURE:
<223> OTHER INFORMATION: Synthetic

<400> SEQUENCE: 457
ttcccacaga agtgttaaca gagg 24

<210> SEQ ID NO 458
<211> LENGTH: 22
<212> TYPE: DNA
<213> ORGANISM: Artificial Sequence
<220> FEATURE:
<223> OTHER INFORMATION: Synthetic

<400> SEQUENCE: 458
gacagcatct gccacaacac ag 22

<210> SEQ ID NO 459
<211> LENGTH: 24

<212> TYPE: DNA
<213> ORGANISM: Artificial Sequence
<220> FEATURE:
<223> OTHER INFORMATION: Synthetic

<400> SEQUENCE: 459
tgagaagtgc tctgcctata cagt 24

<210> SEQ ID NO 460
<211> LENGTH: 27
<212> TYPE: DNA
<213> ORGANISM: Artificial Sequence
<220> FEATURE:
<223> OTHER INFORMATION: Synthetic

<400> SEQUENCE: 460
tcatctaacc aatcttcttc ttgctct 27

<210> SEQ ID NO 461
<211> LENGTH: 22
<212> TYPE: DNA
<213> ORGANISM: Artificial Sequence
<220> FEATURE:
<223> OTHER INFORMATION: Synthetic

<400> SEQUENCE: 461
ggaatttggt gccacttctg ct 22

<210> SEQ ID NO 462
<211> LENGTH: 24
<212> TYPE: DNA
<213> ORGANISM: Artificial Sequence
<220> FEATURE:
<223> OTHER INFORMATION: Synthetic

<400> SEQUENCE: 462
tcatcagatt caacttgcat ggca 24

<210> SEQ ID NO 463
<211> LENGTH: 22
<212> TYPE: DNA
<213> ORGANISM: Artificial Sequence
<220> FEATURE:
<223> OTHER INFORMATION: Synthetic

<400> SEQUENCE: 463
aaacatggag gaggtgttgc ag 22

<210> SEQ ID NO 464
<211> LENGTH: 27
<212> TYPE: DNA
<213> ORGANISM: Artificial Sequence
<220> FEATURE:
<223> OTHER INFORMATION: Synthetic

<400> SEQUENCE: 464
ttcactcttc atttccaaaa agcttga 27

<210> SEQ ID NO 465
<211> LENGTH: 24
<212> TYPE: DNA
<213> ORGANISM: Artificial Sequence
<220> FEATURE:
<223> OTHER INFORMATION: Synthetic

<400> SEQUENCE: 465
tcgcacaaat gtctacttag ctgt 24

<210> SEQ ID NO 466
<211> LENGTH: 22
<212> TYPE: DNA
<213> ORGANISM: Artificial Sequence
<220> FEATURE:
<223> OTHER INFORMATION: Synthetic

<400> SEQUENCE: 466
accacagcag ttaaaacacc ct 22

<210> SEQ ID NO 467
<211> LENGTH: 24
<212> TYPE: DNA
<213> ORGANISM: Artificial Sequence
<220> FEATURE:
<223> OTHER INFORMATION: Synthetic

<400> SEQUENCE: 467
tggcaatctt catccagatt ctgc 24

<210> SEQ ID NO 468
<211> LENGTH: 22
<212> TYPE: DNA
<213> ORGANISM: Artificial Sequence
<220> FEATURE:
<223> OTHER INFORMATION: Synthetic

<400> SEQUENCE: 468
tgcgtgtttc ttctgcatgt gc 22

<210> SEQ ID NO 469
<211> LENGTH: 26
<212> TYPE: DNA
<213> ORGANISM: Artificial Sequence
<220> FEATURE:
<223> OTHER INFORMATION: Synthetic

<400> SEQUENCE: 469
agtgcttaaa aagtgtaaaa gtgcct 26

<210> SEQ ID NO 470
<211> LENGTH: 23
<212> TYPE: DNA
<213> ORGANISM: Artificial Sequence
<220> FEATURE:
<223> OTHER INFORMATION: Synthetic

<400> SEQUENCE: 470
actgtagctg gcactttgag aga 23

<210> SEQ ID NO 471
<211> LENGTH: 22
<212> TYPE: DNA
<213> ORGANISM: Artificial Sequence
<220> FEATURE:
<223> OTHER INFORMATION: Synthetic

<400> SEQUENCE: 471
aatttggaag aagctgctcg gt 22

<210> SEQ ID NO 472
<211> LENGTH: 22
<212> TYPE: DNA
<213> ORGANISM: Artificial Sequence
<220> FEATURE:
<223> OTHER INFORMATION: Synthetic

<400> SEQUENCE: 472
cacaacttgc gtgtggaggt ta 22

<210> SEQ ID NO 473
<211> LENGTH: 27
<212> TYPE: DNA
<213> ORGANISM: Artificial Sequence
<220> FEATURE:
<223> OTHER INFORMATION: Synthetic

<400> SEQUENCE: 473
cttctttctt tgagagaagt gaggact 27

<210> SEQ ID NO 474
<211> LENGTH: 25
<212> TYPE: DNA
<213> ORGANISM: Artificial Sequence
<220> FEATURE:
<223> OTHER INFORMATION: Synthetic

<400> SEQUENCE: 474
tttgttggag tgttaacaat gcagt 25

<210> SEQ ID NO 475
<211> LENGTH: 30
<212> TYPE: DNA
<213> ORGANISM: Artificial Sequence
<220> FEATURE:
<223> OTHER INFORMATION: Synthetic

<400> SEQUENCE: 475
acttctatta aatgggcaga taacaactgt 30

<210> SEQ ID NO 476
<211> LENGTH: 23
<212> TYPE: DNA
<213> ORGANISM: Artificial Sequence
<220> FEATURE:
<223> OTHER INFORMATION: Synthetic

<400> SEQUENCE: 476
gcttgtttac cacacgtaca agg 23

<210> SEQ ID NO 477
<211> LENGTH: 23
<212> TYPE: DNA
<213> ORGANISM: Artificial Sequence
<220> FEATURE:
<223> OTHER INFORMATION: Synthetic

<400> SEQUENCE: 477
gctgttatgt acatgggcac act 23

<210> SEQ ID NO 478
<211> LENGTH: 25
<212> TYPE: DNA
<213> ORGANISM: Artificial Sequence
<220> FEATURE:
<223> OTHER INFORMATION: Synthetic

<400> SEQUENCE: 478
tgtccaactt agggtcaatt tctgt 25

<210> SEQ ID NO 479
<211> LENGTH: 27
<212> TYPE: DNA
<213> ORGANISM: Artificial Sequence
<220> FEATURE:
<223> OTHER INFORMATION: Synthetic

<400> SEQUENCE: 479
acaaagaaaa cagttacaca acaacca 27

<210> SEQ ID NO 480
<211> LENGTH: 25
<212> TYPE: DNA
<213> ORGANISM: Artificial Sequence
<220> FEATURE:
<223> OTHER INFORMATION: Synthetic

<400> SEQUENCE: 480
acgtggcttt attagttgca ttgtt 25

<210> SEQ ID NO 481
<211> LENGTH: 29
<212> TYPE: DNA
<213> ORGANISM: Artificial Sequence
<220> FEATURE:
<223> OTHER INFORMATION: Synthetic

<400> SEQUENCE: 481
ggctattgat tataaacact acacaccct 29

<210> SEQ ID NO 482
<211> LENGTH: 22
<212> TYPE: DNA
<213> ORGANISM: Artificial Sequence
<220> FEATURE:
<223> OTHER INFORMATION: Synthetic

<400> SEQUENCE: 482
gatctgtgtg gccaacctct tc 22

<210> SEQ ID NO 483
<211> LENGTH: 29
<212> TYPE: DNA
<213> ORGANISM: Artificial Sequence
<220> FEATURE:
<223> OTHER INFORMATION: Synthetic

<400> SEQUENCE: 483
actaccgaag ttgtaggaga cattatact 29

<210> SEQ ID NO 484
<211> LENGTH: 27
<212> TYPE: DNA
<213> ORGANISM: Artificial Sequence
<220> FEATURE:
<223> OTHER INFORMATION: Synthetic

<400> SEQUENCE: 484
acagtattct ttgctatagt agtcggc 27

<210> SEQ ID NO 485
<211> LENGTH: 27
<212> TYPE: DNA
<213> ORGANISM: Artificial Sequence
<220> FEATURE:
<223> OTHER INFORMATION: Synthetic

<400> SEQUENCE: 485
acaactacta acatagttac acggtgt 27

<210> SEQ ID NO 486
<211> LENGTH: 25
<212> TYPE: DNA
<213> ORGANISM: Artificial Sequence
<220> FEATURE:
<223> OTHER INFORMATION: Synthetic

<400> SEQUENCE: 486
accagtacag taggttgcaa tagtg 25

<210> SEQ ID NO 487
<211> LENGTH: 23
<212> TYPE: DNA
<213> ORGANISM: Artificial Sequence
<220> FEATURE:
<223> OTHER INFORMATION: Synthetic

<400> SEQUENCE: 487
aggcatgcct tcttactgta ctg 23

<210> SEQ ID NO 488
<211> LENGTH: 26
<212> TYPE: DNA
<213> ORGANISM: Artificial Sequence
<220> FEATURE:
<223> OTHER INFORMATION: Synthetic

<400> SEQUENCE: 488
acattctaac catagctgaa atcggg 26

<210> SEQ ID NO 489
<211> LENGTH: 27
<212> TYPE: DNA
<213> ORGANISM: Artificial Sequence
<220> FEATURE:
<223> OTHER INFORMATION: Synthetic

<400> SEQUENCE: 489
gcaattgttt ttcagctatt ttgcagt 27

<210> SEQ ID NO 490
<211> LENGTH: 23
<212> TYPE: DNA
<213> ORGANISM: Artificial Sequence
<220> FEATURE:
<223> OTHER INFORMATION: Synthetic

<400> SEQUENCE: 490
actgtagtga caagtctctc gca 23

<210> SEQ ID NO 491
<211> LENGTH: 25
<212> TYPE: DNA
<213> ORGANISM: Artificial Sequence
<220> FEATURE:
<223> OTHER INFORMATION: Synthetic

<400> SEQUENCE: 491
ttgtgataca ttctgtgctg gtagt 25

<210> SEQ ID NO 492

<211> LENGTH: 22
<212> TYPE: DNA
<213> ORGANISM: Artificial Sequence
<220> FEATURE:
<223> OTHER INFORMATION: Synthetic

<400> SEQUENCE: 492
tccgcactat caccaacatc ag 22

<210> SEQ ID NO 493
<211> LENGTH: 25
<212> TYPE: DNA
<213> ORGANISM: Artificial Sequence
<220> FEATURE:
<223> OTHER INFORMATION: Synthetic

<400> SEQUENCE: 493
actacagtca gcttatgtgt caacc 25

<210> SEQ ID NO 494
<211> LENGTH: 22
<212> TYPE: DNA
<213> ORGANISM: Artificial Sequence
<220> FEATURE:
<223> OTHER INFORMATION: Synthetic

<400> SEQUENCE: 494
aatacaagca ccaaggtcac gg 22

<210> SEQ ID NO 495
<211> LENGTH: 26
<212> TYPE: DNA
<213> ORGANISM: Artificial Sequence
<220> FEATURE:
<223> OTHER INFORMATION: Synthetic

<400> SEQUENCE: 495
acatagaagt tactggcgat agttgt 26

<210> SEQ ID NO 496
<211> LENGTH: 26
<212> TYPE: DNA
<213> ORGANISM: Artificial Sequence
<220> FEATURE:
<223> OTHER INFORMATION: Synthetic

<400> SEQUENCE: 496
tgtttagaca tgacatgaac aggtgt 26

<210> SEQ ID NO 497
<211> LENGTH: 24
<212> TYPE: DNA
<213> ORGANISM: Artificial Sequence
<220> FEATURE:
<223> OTHER INFORMATION: Synthetic

<400> SEQUENCE: 497
acttgtgttc ctttttgttg ctgc 24

<210> SEQ ID NO 498
<211> LENGTH: 29
<212> TYPE: DNA
<213> ORGANISM: Artificial Sequence
<220> FEATURE:
<223> OTHER INFORMATION: Synthetic

<400> SEQUENCE: 498
agtgtactct ataagttttg atggtgtgt 29

<210> SEQ ID NO 499
<211> LENGTH: 25
<212> TYPE: DNA
<213> ORGANISM: Artificial Sequence
<220> FEATURE:
<223> OTHER INFORMATION: Synthetic

<400> SEQUENCE: 499
gcacaactaa tggtgacttt ttgca 25

<210> SEQ ID NO 500
<211> LENGTH: 26
<212> TYPE: DNA
<213> ORGANISM: Artificial Sequence
<220> FEATURE:
<223> OTHER INFORMATION: Synthetic

<400> SEQUENCE: 500
accactagta gatacacaaa caccag 26

<210> SEQ ID NO 501
<211> LENGTH: 22
<212> TYPE: DNA
<213> ORGANISM: Artificial Sequence
<220> FEATURE:
<223> OTHER INFORMATION: Synthetic

<400> SEQUENCE: 501
ttctgagtac tgtaggcacg gc 22

<210> SEQ ID NO 502
<211> LENGTH: 28
<212> TYPE: DNA
<213> ORGANISM: Artificial Sequence
<220> FEATURE:
<223> OTHER INFORMATION: Synthetic

<400> SEQUENCE: 502
acagaataaa caccaggtaa gaatgagt 28

<210> SEQ ID NO 503
<211> LENGTH: 25
<212> TYPE: DNA
<213> ORGANISM: Artificial Sequence
<220> FEATURE:
<223> OTHER INFORMATION: Synthetic

<400> SEQUENCE: 503
tggtgaatac agtcatgtag ttgcc 25

<210> SEQ ID NO 504
<211> LENGTH: 24
<212> TYPE: DNA
<213> ORGANISM: Artificial Sequence
<220> FEATURE:
<223> OTHER INFORMATION: Synthetic

<400> SEQUENCE: 504
agcacatcac tacgcaactt taga 24

<210> SEQ ID NO 505
<211> LENGTH: 22
<212> TYPE: DNA

<213> ORGANISM: Artificial Sequence
<220> FEATURE:
<223> OTHER INFORMATION: Synthetic

<400> SEQUENCE: 505
acttttgaag aagctgcgct gt 22

<210> SEQ ID NO 506
<211> LENGTH: 25
<212> TYPE: DNA
<213> ORGANISM: Artificial Sequence
<220> FEATURE:
<223> OTHER INFORMATION: Synthetic

<400> SEQUENCE: 506
tggacagtaa actacgtcat caagc 25

<210> SEQ ID NO 507
<211> LENGTH: 23
<212> TYPE: DNA
<213> ORGANISM: Artificial Sequence
<220> FEATURE:
<223> OTHER INFORMATION: Synthetic

<400> SEQUENCE: 507
tcccatctgg taaagttgag ggt 23

<210> SEQ ID NO 508
<211> LENGTH: 22
<212> TYPE: DNA
<213> ORGANISM: Artificial Sequence
<220> FEATURE:
<223> OTHER INFORMATION: Synthetic

<400> SEQUENCE: 508
agtgaaattg ggcctcatag ca 22

<210> SEQ ID NO 509
<211> LENGTH: 22
<212> TYPE: DNA
<213> ORGANISM: Artificial Sequence
<220> FEATURE:
<223> OTHER INFORMATION: Synthetic

<400> SEQUENCE: 509
tgttcgcatt caaccaggac ag 22

<210> SEQ ID NO 510
<211> LENGTH: 26
<212> TYPE: DNA
<213> ORGANISM: Artificial Sequence
<220> FEATURE:
<223> OTHER INFORMATION: Synthetic

<400> SEQUENCE: 510
acttcatagc cacaaggtta aagtca 26

<210> SEQ ID NO 511
<211> LENGTH: 22
<212> TYPE: DNA
<213> ORGANISM: Artificial Sequence
<220> FEATURE:
<223> OTHER INFORMATION: Synthetic

<400> SEQUENCE: 511
ttagcttggt tgtacgctgc tg 22

<210> SEQ ID NO 512
<211> LENGTH: 26
<212> TYPE: DNA
<213> ORGANISM: Artificial Sequence
<220> FEATURE:
<223> OTHER INFORMATION: Synthetic

<400> SEQUENCE: 512
gaacaaagac cattgagtac tctgga 26

<210> SEQ ID NO 513
<211> LENGTH: 23
<212> TYPE: DNA
<213> ORGANISM: Artificial Sequence
<220> FEATURE:
<223> OTHER INFORMATION: Synthetic

<400> SEQUENCE: 513
acacaccact ggttgttact cac 23

<210> SEQ ID NO 514
<211> LENGTH: 22
<212> TYPE: DNA
<213> ORGANISM: Artificial Sequence
<220> FEATURE:
<223> OTHER INFORMATION: Synthetic

<400> SEQUENCE: 514
gtccacactc tcctagcacc at 22

<210> SEQ ID NO 515
<211> LENGTH: 25
<212> TYPE: DNA
<213> ORGANISM: Artificial Sequence
<220> FEATURE:
<223> OTHER INFORMATION: Synthetic

<400> SEQUENCE: 515
actgtgttat gtatgcatca gctgt 25

<210> SEQ ID NO 516
<211> LENGTH: 25
<212> TYPE: DNA
<213> ORGANISM: Artificial Sequence
<220> FEATURE:
<223> OTHER INFORMATION: Synthetic

<400> SEQUENCE: 516
caccaagagt cagtctaaag tagcg 25

<210> SEQ ID NO 517
<211> LENGTH: 29
<212> TYPE: DNA
<213> ORGANISM: Artificial Sequence
<220> FEATURE:
<223> OTHER INFORMATION: Synthetic

<400> SEQUENCE: 517
agtattgccc tattttcttc ataactggt 29

<210> SEQ ID NO 518
<211> LENGTH: 22
<212> TYPE: DNA
<213> ORGANISM: Artificial Sequence
<220> FEATURE:

<223> OTHER INFORMATION: Synthetic

<400> SEQUENCE: 518
tgtaactgga cacattgagc cc 22

<210> SEQ ID NO 519
<211> LENGTH: 26
<212> TYPE: DNA
<213> ORGANISM: Artificial Sequence
<220> FEATURE:
<223> OTHER INFORMATION: Synthetic

<400> SEQUENCE: 519
tgcacatcag tagtcttact ctcagt 26

<210> SEQ ID NO 520
<211> LENGTH: 22
<212> TYPE: DNA
<213> ORGANISM: Artificial Sequence
<220> FEATURE:
<223> OTHER INFORMATION: Synthetic

<400> SEQUENCE: 520
catggctgca tcacggtcaa at 22

<210> SEQ ID NO 521
<211> LENGTH: 23
<212> TYPE: DNA
<213> ORGANISM: Artificial Sequence
<220> FEATURE:
<223> OTHER INFORMATION: Synthetic

<400> SEQUENCE: 521
gttcccttcc atcatatgca gct 23

<210> SEQ ID NO 522
<211> LENGTH: 25
<212> TYPE: DNA
<213> ORGANISM: Artificial Sequence
<220> FEATURE:
<223> OTHER INFORMATION: Synthetic

<400> SEQUENCE: 522
tggtatgaca accattagtt tggct 25

<210> SEQ ID NO 523
<211> LENGTH: 22
<212> TYPE: DNA
<213> ORGANISM: Artificial Sequence
<220> FEATURE:
<223> OTHER INFORMATION: Synthetic

<400> SEQUENCE: 523
tgcaagagat ggttgtgttc cc 22

<210> SEQ ID NO 524
<211> LENGTH: 23
<212> TYPE: DNA
<213> ORGANISM: Artificial Sequence
<220> FEATURE:
<223> OTHER INFORMATION: Synthetic

<400> SEQUENCE: 524
cctacctccc tttgttgtgt tgt 23

<210> SEQ ID NO 525
<211> LENGTH: 22
<212> TYPE: DNA
<213> ORGANISM: Artificial Sequence
<220> FEATURE:
<223> OTHER INFORMATION: Synthetic

<400> SEQUENCE: 525
tacgacagat gtcttgtgct gc 22

<210> SEQ ID NO 526
<211> LENGTH: 22
<212> TYPE: DNA
<213> ORGANISM: Artificial Sequence
<220> FEATURE:
<223> OTHER INFORMATION: Synthetic

<400> SEQUENCE: 526
agcagcatct acagcaaaag ca 22

<210> SEQ ID NO 527
<211> LENGTH: 22
<212> TYPE: DNA
<213> ORGANISM: Artificial Sequence
<220> FEATURE:
<223> OTHER INFORMATION: Synthetic

<400> SEQUENCE: 527
ccacagtacg tctacaagct gg 22

<210> SEQ ID NO 528
<211> LENGTH: 22
<212> TYPE: DNA
<213> ORGANISM: Artificial Sequence
<220> FEATURE:
<223> OTHER INFORMATION: Synthetic

<400> SEQUENCE: 528
cgcagacggt acagactgtg tt 22

<210> SEQ ID NO 529
<211> LENGTH: 29
<212> TYPE: DNA
<213> ORGANISM: Artificial Sequence
<220> FEATURE:
<223> OTHER INFORMATION: Synthetic

<400> SEQUENCE: 529
agtatgtaca aatacctaca acttgtgct 29

<210> SEQ ID NO 530
<211> LENGTH: 29
<212> TYPE: DNA
<213> ORGANISM: Artificial Sequence
<220> FEATURE:
<223> OTHER INFORMATION: Synthetic

<400> SEQUENCE: 530
ttcatgttgg tagttagaga aagtgtgtc 29

<210> SEQ ID NO 531
<211> LENGTH: 23
<212> TYPE: DNA
<213> ORGANISM: Artificial Sequence
<220> FEATURE:
<223> OTHER INFORMATION: Synthetic

<400> SEQUENCE: 531
cgcttccaag aaaaggacga aga 23

<210> SEQ ID NO 532
<211> LENGTH: 23
<212> TYPE: DNA
<213> ORGANISM: Artificial Sequence
<220> FEATURE:
<223> OTHER INFORMATION: Synthetic

<400> SEQUENCE: 532
cacgttcacc taagttggcg tat 23

<210> SEQ ID NO 533
<211> LENGTH: 28
<212> TYPE: DNA
<213> ORGANISM: Artificial Sequence
<220> FEATURE:
<223> OTHER INFORMATION: Synthetic

<400> SEQUENCE: 533
aggactggta tgattttgta gaaaaccc 28

<210> SEQ ID NO 534
<211> LENGTH: 28
<212> TYPE: DNA
<213> ORGANISM: Artificial Sequence
<220> FEATURE:
<223> OTHER INFORMATION: Synthetic

<400> SEQUENCE: 534
aataacggtc aaagagtttt aacctctc 28

<210> SEQ ID NO 535
<211> LENGTH: 25
<212> TYPE: DNA
<213> ORGANISM: Artificial Sequence
<220> FEATURE:
<223> OTHER INFORMATION: Synthetic

<400> SEQUENCE: 535
tgttgacact gacttaacaa agcct 25

<210> SEQ ID NO 536
<211> LENGTH: 22
<212> TYPE: DNA
<213> ORGANISM: Artificial Sequence
<220> FEATURE:
<223> OTHER INFORMATION: Synthetic

<400> SEQUENCE: 536
tagattacca gaagcagcgt gc 22

<210> SEQ ID NO 537
<211> LENGTH: 25
<212> TYPE: DNA
<213> ORGANISM: Artificial Sequence
<220> FEATURE:
<223> OTHER INFORMATION: Synthetic

<400> SEQUENCE: 537
aggaattact tgtgtatgct gctga 25

<210> SEQ ID NO 538
<211> LENGTH: 28

<212> TYPE: DNA
<213> ORGANISM: Artificial Sequence
<220> FEATURE:
<223> OTHER INFORMATION: Synthetic

<400> SEQUENCE: 538
tgacgatgac ttggttagca ttaataca 28

<210> SEQ ID NO 539
<211> LENGTH: 30
<212> TYPE: DNA
<213> ORGANISM: Artificial Sequence
<220> FEATURE:
<223> OTHER INFORMATION: Synthetic

<400> SEQUENCE: 539
gttgataagt actttgattg ttacgatggt 30

<210> SEQ ID NO 540
<211> LENGTH: 22
<212> TYPE: DNA
<213> ORGANISM: Artificial Sequence
<220> FEATURE:
<223> OTHER INFORMATION: Synthetic

<400> SEQUENCE: 540
taacatgttg tgccaaccac ca 22

<210> SEQ ID NO 541
<211> LENGTH: 22
<212> TYPE: DNA
<213> ORGANISM: Artificial Sequence
<220> FEATURE:
<223> OTHER INFORMATION: Synthetic

<400> SEQUENCE: 541
tcaatagccg ccactagagg ag 22

<210> SEQ ID NO 542
<211> LENGTH: 22
<212> TYPE: DNA
<213> ORGANISM: Artificial Sequence
<220> FEATURE:
<223> OTHER INFORMATION: Synthetic

<400> SEQUENCE: 542
agtgcattaa cattggccgt ga 22

<210> SEQ ID NO 543
<211> LENGTH: 22
<212> TYPE: DNA
<213> ORGANISM: Artificial Sequence
<220> FEATURE:
<223> OTHER INFORMATION: Synthetic

<400> SEQUENCE: 543
catcaggaga tgccacaact gc 22

<210> SEQ ID NO 544
<211> LENGTH: 25
<212> TYPE: DNA
<213> ORGANISM: Artificial Sequence
<220> FEATURE:
<223> OTHER INFORMATION: Synthetic

<400> SEQUENCE: 544
gttgagagca aaattcatga ggtcc 25

<210> SEQ ID NO 545
<211> LENGTH: 24
<212> TYPE: DNA
<213> ORGANISM: Artificial Sequence
<220> FEATURE:
<223> OTHER INFORMATION: Synthetic

<400> SEQUENCE: 545
agcaaaatgt tggactgaga ctga 24

<210> SEQ ID NO 546
<211> LENGTH: 23
<212> TYPE: DNA
<213> ORGANISM: Artificial Sequence
<220> FEATURE:
<223> OTHER INFORMATION: Synthetic

<400> SEQUENCE: 546
agcctcataa aactcaggtt ccc 23

<210> SEQ ID NO 547
<211> LENGTH: 26
<212> TYPE: DNA
<213> ORGANISM: Artificial Sequence
<220> FEATURE:
<223> OTHER INFORMATION: Synthetic

<400> SEQUENCE: 547
tgagttaaca ggacacatgt tagaca 26

<210> SEQ ID NO 548
<211> LENGTH: 25
<212> TYPE: DNA
<213> ORGANISM: Artificial Sequence
<220> FEATURE:
<223> OTHER INFORMATION: Synthetic

<400> SEQUENCE: 548
aaccaaaaac ttgtccatta gcaca 25

<210> SEQ ID NO 549
<211> LENGTH: 28
<212> TYPE: DNA
<213> ORGANISM: Artificial Sequence
<220> FEATURE:
<223> OTHER INFORMATION: Synthetic

<400> SEQUENCE: 549
actcaacttt acttaggagg tatgagct 28

<210> SEQ ID NO 550
<211> LENGTH: 29
<212> TYPE: DNA
<213> ORGANISM: Artificial Sequence
<220> FEATURE:
<223> OTHER INFORMATION: Synthetic

<400> SEQUENCE: 550
ggtgtactct cctatttgta ctttactgt 29

<210> SEQ ID NO 551
<211> LENGTH: 22
<212> TYPE: DNA
<213> ORGANISM: Artificial Sequence
<220> FEATURE:
<223> OTHER INFORMATION: Synthetic

<400> SEQUENCE: 551
acctagacca ccacttaacc ga 22

<210> SEQ ID NO 552
<211> LENGTH: 22
<212> TYPE: DNA
<213> ORGANISM: Artificial Sequence
<220> FEATURE:
<223> OTHER INFORMATION: Synthetic

<400> SEQUENCE: 552
acactatgcg agcagaaggg ta 22

<210> SEQ ID NO 553
<211> LENGTH: 22
<212> TYPE: DNA
<213> ORGANISM: Artificial Sequence
<220> FEATURE:
<223> OTHER INFORMATION: Synthetic

<400> SEQUENCE: 553
attctacact ccagggacca cc 22

<210> SEQ ID NO 554
<211> LENGTH: 22
<212> TYPE: DNA
<213> ORGANISM: Artificial Sequence
<220> FEATURE:
<223> OTHER INFORMATION: Synthetic

<400> SEQUENCE: 554
gtaattgagc agggtcgcca at 22

<210> SEQ ID NO 555
<211> LENGTH: 25
<212> TYPE: DNA
<213> ORGANISM: Artificial Sequence
<220> FEATURE:
<223> OTHER INFORMATION: Synthetic

<400> SEQUENCE: 555
tgatttgagt gttgtcaatg ccaga 25

<210> SEQ ID NO 556
<211> LENGTH: 23
<212> TYPE: DNA
<213> ORGANISM: Artificial Sequence
<220> FEATURE:
<223> OTHER INFORMATION: Synthetic

<400> SEQUENCE: 556
cttttctcca agcagggtta cgt 23

<210> SEQ ID NO 557
<211> LENGTH: 23
<212> TYPE: DNA
<213> ORGANISM: Artificial Sequence
<220> FEATURE:
<223> OTHER INFORMATION: Synthetic

<400> SEQUENCE: 557
tcacgcatga tgtttcatct gca 23

<210> SEQ ID NO 558
<211> LENGTH: 26
<212> TYPE: DNA
<213> ORGANISM: Artificial Sequence
<220> FEATURE:
<223> OTHER INFORMATION: Synthetic

<400> SEQUENCE: 558
aagagtcctg ttacattttc agcttg 26

<210> SEQ ID NO 559
<211> LENGTH: 27
<212> TYPE: DNA
<213> ORGANISM: Artificial Sequence
<220> FEATURE:
<223> OTHER INFORMATION: Synthetic

<400> SEQUENCE: 559
tgatagagac ctttatgaca agttgca 27

<210> SEQ ID NO 560
<211> LENGTH: 24
<212> TYPE: DNA
<213> ORGANISM: Artificial Sequence
<220> FEATURE:
<223> OTHER INFORMATION: Synthetic

<400> SEQUENCE: 560
ggtaccaaca gcttctctag tagc 24

<210> SEQ ID NO 561
<211> LENGTH: 22
<212> TYPE: DNA
<213> ORGANISM: Artificial Sequence
<220> FEATURE:
<223> OTHER INFORMATION: Synthetic

<400> SEQUENCE: 561
tgtttatcac ccgcgaagaa gc 22

<210> SEQ ID NO 562
<211> LENGTH: 22
<212> TYPE: DNA
<213> ORGANISM: Artificial Sequence
<220> FEATURE:
<223> OTHER INFORMATION: Synthetic

<400> SEQUENCE: 562
atcacataga caacaggtgc gc 22

<210> SEQ ID NO 563
<211> LENGTH: 22
<212> TYPE: DNA
<213> ORGANISM: Artificial Sequence
<220> FEATURE:
<223> OTHER INFORMATION: Synthetic

<400> SEQUENCE: 563
ggcacatggc tttgagttga ca 22

<210> SEQ ID NO 564
<211> LENGTH: 22
<212> TYPE: DNA
<213> ORGANISM: Artificial Sequence
<220> FEATURE:
<223> OTHER INFORMATION: Synthetic

<400> SEQUENCE: 564
gttgaacctt tctacaagcc gc 22

<210> SEQ ID NO 565
<211> LENGTH: 22
<212> TYPE: DNA
<213> ORGANISM: Artificial Sequence
<220> FEATURE:
<223> OTHER INFORMATION: Synthetic

<400> SEQUENCE: 565
tgttaagcgt gttgactgga ct 22

<210> SEQ ID NO 566
<211> LENGTH: 22
<212> TYPE: DNA
<213> ORGANISM: Artificial Sequence
<220> FEATURE:
<223> OTHER INFORMATION: Synthetic

<400> SEQUENCE: 566
acaaactgcc accatcacaa cc 22

<210> SEQ ID NO 567
<211> LENGTH: 28
<212> TYPE: DNA
<213> ORGANISM: Artificial Sequence
<220> FEATURE:
<223> OTHER INFORMATION: Synthetic

<400> SEQUENCE: 567
tcgatagata tcctgctaat tccattgt 28

<210> SEQ ID NO 568
<211> LENGTH: 25
<212> TYPE: DNA
<213> ORGANISM: Artificial Sequence
<220> FEATURE:
<223> OTHER INFORMATION: Synthetic

<400> SEQUENCE: 568
agtcttgtaa aagtgttcca gaggt 25

<210> SEQ ID NO 569
<211> LENGTH: 22
<212> TYPE: DNA
<213> ORGANISM: Artificial Sequence
<220> FEATURE:
<223> OTHER INFORMATION: Synthetic

<400> SEQUENCE: 569
gctggcttta gcttgtgggt tt 22

<210> SEQ ID NO 570
<211> LENGTH: 28
<212> TYPE: DNA
<213> ORGANISM: Artificial Sequence
<220> FEATURE:
<223> OTHER INFORMATION: Synthetic

<400> SEQUENCE: 570
tgtcagtcat agaacaaaca ccaatagt 28

<210> SEQ ID NO 571

<211> LENGTH: 22
<212> TYPE: DNA
<213> ORGANISM: Artificial Sequence
<220> FEATURE:
<223> OTHER INFORMATION: Synthetic

<400> SEQUENCE: 571
gggtgtggac attgctgcta at 22

<210> SEQ ID NO 572
<211> LENGTH: 24
<212> TYPE: DNA
<213> ORGANISM: Artificial Sequence
<220> FEATURE:
<223> OTHER INFORMATION: Synthetic

<400> SEQUENCE: 572
tcaatttcca tttgactcct gggt 24

<210> SEQ ID NO 573
<211> LENGTH: 28
<212> TYPE: DNA
<213> ORGANISM: Artificial Sequence
<220> FEATURE:
<223> OTHER INFORMATION: Synthetic

<400> SEQUENCE: 573
gttgtccaac aattacctga aacttact 28

<210> SEQ ID NO 574
<211> LENGTH: 30
<212> TYPE: DNA
<213> ORGANISM: Artificial Sequence
<220> FEATURE:
<223> OTHER INFORMATION: Synthetic

<400> SEQUENCE: 574
caaccttaga aactacagat aaatcttggg 30

<210> SEQ ID NO 575
<211> LENGTH: 24
<212> TYPE: DNA
<213> ORGANISM: Artificial Sequence
<220> FEATURE:
<223> OTHER INFORMATION: Synthetic

<400> SEQUENCE: 575
acaggttcat ctaagtgtgt gtgt 24

<210> SEQ ID NO 576
<211> LENGTH: 23
<212> TYPE: DNA
<213> ORGANISM: Artificial Sequence
<220> FEATURE:
<223> OTHER INFORMATION: Synthetic

<400> SEQUENCE: 576
ctcctttatc agaaccagca cca 23

<210> SEQ ID NO 577
<211> LENGTH: 27
<212> TYPE: DNA
<213> ORGANISM: Artificial Sequence
<220> FEATURE:
<223> OTHER INFORMATION: Synthetic

<400> SEQUENCE: 577
tgtcgcaaaa tatactcaac tgtgtca 27

<210> SEQ ID NO 578
<211> LENGTH: 23
<212> TYPE: DNA
<213> ORGANISM: Artificial Sequence
<220> FEATURE:
<223> OTHER INFORMATION: Synthetic

<400> SEQUENCE: 578
tctttatagc cacggaacct cca 23

<210> SEQ ID NO 579
<211> LENGTH: 29
<212> TYPE: DNA
<213> ORGANISM: Artificial Sequence
<220> FEATURE:
<223> OTHER INFORMATION: Synthetic

<400> SEQUENCE: 579
acaaaagaaa atgactctaa agagggttt 29

<210> SEQ ID NO 580
<211> LENGTH: 28
<212> TYPE: DNA
<213> ORGANISM: Artificial Sequence
<220> FEATURE:
<223> OTHER INFORMATION: Synthetic

<400> SEQUENCE: 580
tgaccttctt ttaaagacat aacagcag 28

<210> SEQ ID NO 581
<211> LENGTH: 29
<212> TYPE: DNA
<213> ORGANISM: Artificial Sequence
<220> FEATURE:
<223> OTHER INFORMATION: Synthetic

<400> SEQUENCE: 581
acaaatccaa ttcagttgtc ttcctattc 29

<210> SEQ ID NO 582
<211> LENGTH: 27
<212> TYPE: DNA
<213> ORGANISM: Artificial Sequence
<220> FEATURE:
<223> OTHER INFORMATION: Synthetic

<400> SEQUENCE: 582
tggaaaagaa aggtaagaac aagtcct 27

<210> SEQ ID NO 583
<211> LENGTH: 24
<212> TYPE: DNA
<213> ORGANISM: Artificial Sequence
<220> FEATURE:
<223> OTHER INFORMATION: Synthetic

<400> SEQUENCE: 583
acacgtggtg tttattaccc tgac 24

<210> SEQ ID NO 584
<211> LENGTH: 25
<212> TYPE: DNA

<213> ORGANISM: Artificial Sequence
<220> FEATURE:
<223> OTHER INFORMATION: Synthetic

<400> SEQUENCE: 584
actctgaact cactttccat ccaac 25

<210> SEQ ID NO 585
<211> LENGTH: 29
<212> TYPE: DNA
<213> ORGANISM: Artificial Sequence
<220> FEATURE:
<223> OTHER INFORMATION: Synthetic

<400> SEQUENCE: 585
caattttgta atgatccatt tttgggtgt 29

<210> SEQ ID NO 586
<211> LENGTH: 22
<212> TYPE: DNA
<213> ORGANISM: Artificial Sequence
<220> FEATURE:
<223> OTHER INFORMATION: Synthetic

<400> SEQUENCE: 586
caccagctgt ccaacctgaa ga 22

<210> SEQ ID NO 587
<211> LENGTH: 28
<212> TYPE: DNA
<213> ORGANISM: Artificial Sequence
<220> FEATURE:
<223> OTHER INFORMATION: Synthetic

<400> SEQUENCE: 587
acatcactag gtttcaaact ttacttgc 28

<210> SEQ ID NO 588
<211> LENGTH: 24
<212> TYPE: DNA
<213> ORGANISM: Artificial Sequence
<220> FEATURE:
<223> OTHER INFORMATION: Synthetic

<400> SEQUENCE: 588
gcaacacagt tgctgattct cttc 24

<210> SEQ ID NO 589
<211> LENGTH: 26
<212> TYPE: DNA
<213> ORGANISM: Artificial Sequence
<220> FEATURE:
<223> OTHER INFORMATION: Synthetic

<400> SEQUENCE: 589
agagtccaac caacagaatc tattgt 26

<210> SEQ ID NO 590
<211> LENGTH: 26
<212> TYPE: DNA
<213> ORGANISM: Artificial Sequence
<220> FEATURE:
<223> OTHER INFORMATION: Synthetic

<400> SEQUENCE: 590
accaccaacc ttagaatcaa gattgt 26

<210> SEQ ID NO 591
<211> LENGTH: 23
<212> TYPE: DNA
<213> ORGANISM: Artificial Sequence
<220> FEATURE:
<223> OTHER INFORMATION: Synthetic

<400> SEQUENCE: 591
gggcaaactg gaaagattgc tga 23

<210> SEQ ID NO 592
<211> LENGTH: 23
<212> TYPE: DNA
<213> ORGANISM: Artificial Sequence
<220> FEATURE:
<223> OTHER INFORMATION: Synthetic

<400> SEQUENCE: 592
acctgtgcct gttaaaccat tga 23

<210> SEQ ID NO 593
<211> LENGTH: 22
<212> TYPE: DNA
<213> ORGANISM: Artificial Sequence
<220> FEATURE:
<223> OTHER INFORMATION: Synthetic

<400> SEQUENCE: 593
ccagcaactg tttgtggacc ta 22

<210> SEQ ID NO 594
<211> LENGTH: 22
<212> TYPE: DNA
<213> ORGANISM: Artificial Sequence
<220> FEATURE:
<223> OTHER INFORMATION: Synthetic

<400> SEQUENCE: 594
cagcccctat taaacagcct gc 22

<210> SEQ ID NO 595
<211> LENGTH: 23
<212> TYPE: DNA
<213> ORGANISM: Artificial Sequence
<220> FEATURE:
<223> OTHER INFORMATION: Synthetic

<400> SEQUENCE: 595
caacttactc ctacttggcg tgt 23

<210> SEQ ID NO 596
<211> LENGTH: 25
<212> TYPE: DNA
<213> ORGANISM: Artificial Sequence
<220> FEATURE:
<223> OTHER INFORMATION: Synthetic

<400> SEQUENCE: 596
tgtgtacaaa aactgccata ttgca 25

<210> SEQ ID NO 597
<211> LENGTH: 23
<212> TYPE: DNA
<213> ORGANISM: Artificial Sequence
<220> FEATURE:

<223> OTHER INFORMATION: Synthetic

<400> SEQUENCE: 597
gtggtgattc aactgaatgc agc 23

<210> SEQ ID NO 598
<211> LENGTH: 24
<212> TYPE: DNA
<213> ORGANISM: Artificial Sequence
<220> FEATURE:
<223> OTHER INFORMATION: Synthetic

<400> SEQUENCE: 598
catttcatct gtgagcaaag gtgg 24

<210> SEQ ID NO 599
<211> LENGTH: 22
<212> TYPE: DNA
<213> ORGANISM: Artificial Sequence
<220> FEATURE:
<223> OTHER INFORMATION: Synthetic

<400> SEQUENCE: 599
ttgccttggt gatattgctg ct 22

<210> SEQ ID NO 600
<211> LENGTH: 24
<212> TYPE: DNA
<213> ORGANISM: Artificial Sequence
<220> FEATURE:
<223> OTHER INFORMATION: Synthetic

<400> SEQUENCE: 600
tggagctaag ttgtttaaca agcg 24

<210> SEQ ID NO 601
<211> LENGTH: 25
<212> TYPE: DNA
<213> ORGANISM: Artificial Sequence
<220> FEATURE:
<223> OTHER INFORMATION: Synthetic

<400> SEQUENCE: 601
gcacttggaa aacttcaaga tgtgg 25

<210> SEQ ID NO 602
<211> LENGTH: 24
<212> TYPE: DNA
<213> ORGANISM: Artificial Sequence
<220> FEATURE:
<223> OTHER INFORMATION: Synthetic

<400> SEQUENCE: 602
gtgaagttct tttcttgtgc aggg 24

<210> SEQ ID NO 603
<211> LENGTH: 25
<212> TYPE: DNA
<213> ORGANISM: Artificial Sequence
<220> FEATURE:
<223> OTHER INFORMATION: Synthetic

<400> SEQUENCE: 603
gggctatcat cttatgtcct tccct 25

<210> SEQ ID NO 604
<211> LENGTH: 24
<212> TYPE: DNA
<213> ORGANISM: Artificial Sequence
<220> FEATURE:
<223> OTHER INFORMATION: Synthetic

<400> SEQUENCE: 604
tgccagagat gtcacctaaa tcaa 24

<210> SEQ ID NO 605
<211> LENGTH: 25
<212> TYPE: DNA
<213> ORGANISM: Artificial Sequence
<220> FEATURE:
<223> OTHER INFORMATION: Synthetic

<400> SEQUENCE: 605
tcctttgcaa cctgaattag actca 25

<210> SEQ ID NO 606
<211> LENGTH: 22
<212> TYPE: DNA
<213> ORGANISM: Artificial Sequence
<220> FEATURE:
<223> OTHER INFORMATION: Synthetic

<400> SEQUENCE: 606
tttgactcct ttgagcactg gc 22

<210> SEQ ID NO 607
<211> LENGTH: 22
<212> TYPE: DNA
<213> ORGANISM: Artificial Sequence
<220> FEATURE:
<223> OTHER INFORMATION: Synthetic

<400> SEQUENCE: 607
tgctgtagtt gtctcaaggg ct 22

<210> SEQ ID NO 608
<211> LENGTH: 27
<212> TYPE: DNA
<213> ORGANISM: Artificial Sequence
<220> FEATURE:
<223> OTHER INFORMATION: Synthetic

<400> SEQUENCE: 608
aggtgtgagt aaactgttac aaacaac 27

<210> SEQ ID NO 609
<211> LENGTH: 22
<212> TYPE: DNA
<213> ORGANISM: Artificial Sequence
<220> FEATURE:
<223> OTHER INFORMATION: Synthetic

<400> SEQUENCE: 609
actagcactc tccaagggtg tt 22

<210> SEQ ID NO 610
<211> LENGTH: 25
<212> TYPE: DNA
<213> ORGANISM: Artificial Sequence
<220> FEATURE:
<223> OTHER INFORMATION: Synthetic

<400> SEQUENCE: 610
acacagtctt ttactccaga ttccc 25

<210> SEQ ID NO 611
<211> LENGTH: 22
<212> TYPE: DNA
<213> ORGANISM: Artificial Sequence
<220> FEATURE:
<223> OTHER INFORMATION: Synthetic

<400> SEQUENCE: 611
tcaggtgatg gcacaacaag tc 22

<210> SEQ ID NO 612
<211> LENGTH: 25
<212> TYPE: DNA
<213> ORGANISM: Artificial Sequence
<220> FEATURE:
<223> OTHER INFORMATION: Synthetic

<400> SEQUENCE: 612
acgaaagcaa gaaaaagaag tacgc 25

<210> SEQ ID NO 613
<211> LENGTH: 22
<212> TYPE: DNA
<213> ORGANISM: Artificial Sequence
<220> FEATURE:
<223> OTHER INFORMATION: Synthetic

<400> SEQUENCE: 613
cgactactag cgtgcctttg ta 22

<210> SEQ ID NO 614
<211> LENGTH: 24
<212> TYPE: DNA
<213> ORGANISM: Artificial Sequence
<220> FEATURE:
<223> OTHER INFORMATION: Synthetic

<400> SEQUENCE: 614
actaggttcc attgttcaag gagc 24

<210> SEQ ID NO 615
<211> LENGTH: 22
<212> TYPE: DNA
<213> ORGANISM: Artificial Sequence
<220> FEATURE:
<223> OTHER INFORMATION: Synthetic

<400> SEQUENCE: 615
ccatggcaga ttccaacggt ac 22

<210> SEQ ID NO 616
<211> LENGTH: 23
<212> TYPE: DNA
<213> ORGANISM: Artificial Sequence
<220> FEATURE:
<223> OTHER INFORMATION: Synthetic

<400> SEQUENCE: 616
tggtcagaat agtgccatgg agt 23

<210> SEQ ID NO 617
<211> LENGTH: 22

<212> TYPE: DNA
<213> ORGANISM: Artificial Sequence
<220> FEATURE:
<223> OTHER INFORMATION: Synthetic

<400> SEQUENCE: 617
cgcgttccat gtggtcattc aa 22

<210> SEQ ID NO 618
<211> LENGTH: 25
<212> TYPE: DNA
<213> ORGANISM: Artificial Sequence
<220> FEATURE:
<223> OTHER INFORMATION: Synthetic

<400> SEQUENCE: 618
acgagatgaa acatctgttg tcact 25

<210> SEQ ID NO 619
<211> LENGTH: 23
<212> TYPE: DNA
<213> ORGANISM: Artificial Sequence
<220> FEATURE:
<223> OTHER INFORMATION: Synthetic

<400> SEQUENCE: 619
acacagacca ttccagtagc agt 23

<210> SEQ ID NO 620
<211> LENGTH: 22
<212> TYPE: DNA
<213> ORGANISM: Artificial Sequence
<220> FEATURE:
<223> OTHER INFORMATION: Synthetic

<400> SEQUENCE: 620
tgaaatggtg aattgccctc gt 22

<210> SEQ ID NO 621
<211> LENGTH: 25
<212> TYPE: DNA
<213> ORGANISM: Artificial Sequence
<220> FEATURE:
<223> OTHER INFORMATION: Synthetic

<400> SEQUENCE: 621
tcactaccaa gagtgtgtta gaggt 25

<210> SEQ ID NO 622
<211> LENGTH: 29
<212> TYPE: DNA
<213> ORGANISM: Artificial Sequence
<220> FEATURE:
<223> OTHER INFORMATION: Synthetic

<400> SEQUENCE: 622
ttcaagtgag aaccaaaaga taataagca 29

<210> SEQ ID NO 623
<211> LENGTH: 24
<212> TYPE: DNA
<213> ORGANISM: Artificial Sequence
<220> FEATURE:
<223> OTHER INFORMATION: Synthetic

<400> SEQUENCE: 623
tttgtgcttt ttagcctttc tgct 24

<210> SEQ ID NO 624
<211> LENGTH: 27
<212> TYPE: DNA
<213> ORGANISM: Artificial Sequence
<220> FEATURE:
<223> OTHER INFORMATION: Synthetic

<400> SEQUENCE: 624
aggttcctgg caattaattg taaaagg 27

<210> SEQ ID NO 625
<211> LENGTH: 23
<212> TYPE: DNA
<213> ORGANISM: Artificial Sequence
<220> FEATURE:
<223> OTHER INFORMATION: Synthetic

<400> SEQUENCE: 625
tgaggctggt tctaaatcac cca 23

<210> SEQ ID NO 626
<211> LENGTH: 22
<212> TYPE: DNA
<213> ORGANISM: Artificial Sequence
<220> FEATURE:
<223> OTHER INFORMATION: Synthetic

<400> SEQUENCE: 626
aggtcttcct tgccatgttg ag 22

<210> SEQ ID NO 627
<211> LENGTH: 22
<212> TYPE: DNA
<213> ORGANISM: Artificial Sequence
<220> FEATURE:
<223> OTHER INFORMATION: Synthetic

<400> SEQUENCE: 627
ggccccaagg tttacccaat aa 22

<210> SEQ ID NO 628
<211> LENGTH: 23
<212> TYPE: DNA
<213> ORGANISM: Artificial Sequence
<220> FEATURE:
<223> OTHER INFORMATION: Synthetic

<400> SEQUENCE: 628
tttggcaatg ttgttccttg agg 23

<210> SEQ ID NO 629
<211> LENGTH: 22
<212> TYPE: DNA
<213> ORGANISM: Artificial Sequence
<220> FEATURE:
<223> OTHER INFORMATION: Synthetic

<400> SEQUENCE: 629
tgagggagcc ttgaatacac ca 22

<210> SEQ ID NO 630
<211> LENGTH: 22
<212> TYPE: DNA
<213> ORGANISM: Artificial Sequence
<220> FEATURE:
<223> OTHER INFORMATION: Synthetic

<400> SEQUENCE: 630
cagtacgttt ttgccgaggc tt 22

<210> SEQ ID NO 631
<211> LENGTH: 22
<212> TYPE: DNA
<213> ORGANISM: Artificial Sequence
<220> FEATURE:
<223> OTHER INFORMATION: Synthetic

<400> SEQUENCE: 631
gccaacaaca acaaggccaa ac 22

<210> SEQ ID NO 632
<211> LENGTH: 22
<212> TYPE: DNA
<213> ORGANISM: Artificial Sequence
<220> FEATURE:
<223> OTHER INFORMATION: Synthetic

<400> SEQUENCE: 632
taggctctgt tggtgggaat gt 22

<210> SEQ ID NO 633
<211> LENGTH: 28
<212> TYPE: DNA
<213> ORGANISM: Artificial Sequence
<220> FEATURE:
<223> OTHER INFORMATION: Synthetic

<400> SEQUENCE: 633
tggatgacaa agatccaaat ttcaaaga 28

<210> SEQ ID NO 634
<211> LENGTH: 28
<212> TYPE: DNA
<213> ORGANISM: Artificial Sequence
<220> FEATURE:
<223> OTHER INFORMATION: Synthetic

<400> SEQUENCE: 634
acacactgat taaagattgc tatgtgag 28

<210> SEQ ID NO 635
<211> LENGTH: 24
<212> TYPE: DNA
<213> ORGANISM: Artificial Sequence
<220> FEATURE:
<223> OTHER INFORMATION: Synthetic

<400> SEQUENCE: 635
aacaattgca acaatccatg agca 24

<210> SEQ ID NO 636
<211> LENGTH: 30
<212> TYPE: DNA
<213> ORGANISM: Artificial Sequence
<220> FEATURE:
<223> OTHER INFORMATION: Synthetic

<400> SEQUENCE: 636
ttctcctaag aagctattaa aatcacatgg 30

AMPLICON-BASED SEQUENCING USING DNA SPIKE-INS

CROSS-REFERENCE TO RELATED APPLICATIONS

This application claims the benefit of U.S. Provisional Application Nos. 63/155,258, filed Mar. 1, 2021, and 63/273,117, filed Oct. 10, 2021. The entire contents of the above-identified applications are hereby fully incorporated herein by reference.

STATEMENT REGARDING FEDERALLY SPONSORED RESEARCH

This invention was made with government support under Grant Nos. All 10818, AI1147868, HG010669, and CK000490 awarded by the National Institutes of Health, Grant No. 223-101-8101 awarded by the United States Food and Drug Administration, and Grant No. 75D30120C09605 awarded by the Centers for Diseases Control. The government has certain rights in the invention.

REFERENCE TO AN ELECTRONIC SEQUENCE LISTING

The contents of the electronic sequence listing ("BROD-5360US_ST25.txt"; Size is 205,235 bytes and it was created on Feb. 17, 2022) is herein incorporated by reference in its entirety.

TECHNICAL FIELD

The subject matter disclosed herein is generally directed to synthetic DNA spike-ins and their use for detecting, quantifying, and preventing amplification contamination in genome profiling analysis.

BACKGROUND

The COVID-19 pandemic has demonstrated, once again, the crucial role of genomic sequencing in combatting infectious disease outbreaks globally. Monitoring the emergence of pathogens and the spread of variants of concern has become commonplace in government, academic, and private laboratories[1,2]. Genomics data provides insights into the diversity, evolution and transmission of a virus, a critical guide for public health interventions ranging from contact tracing, identifying cases of reinfection, or documenting resistance to clinical interventions[3-6]. In the year since, genomic data have provided new insights into the diversity, evolution and transmission of the virus, which has increasingly been used to guide impactful public health interventions. In particular, scientists have employed viral genome sequencing to characterize the fine-scale epidemiology of clusters and superspreading events (Lemieux et al., 2021, Phylogenetic analysis of SARS-CoV-2 in Boston highlights the impact of superspreading events, *Science,* 371(6529); Popa et al., 2020, Genomic epidemiology of superspreading events in Austria reveals mutational dynamics and transmission properties of SARS-CoV-2, *Science Translational Medicine,* 12(573); Volz et al., 2021, Transmission of SARS-CoV-2 Lineage B.1.1.7 in England: Insights from linking epidemiological and genetic data, bioRxiv, medRxiv). More recently, genome sequencing to monitor the emergence of new lineages and the spread of variants of concern (VoC) has become paramount (Washington et al., 2021, Genomic epidemiology identifies emergence and rapid transmission of SARS-CoV-2 B.1.1.7 in the United States, medRxiv). As laboratories are now performing viral genomic sequencing on SARS-CoV-2 at an unprecedented scale[7,8], it highlights the need for stringent requirements to ensure the integrity of genomes being produced.

Multiplexed amplicon-based genome sequencing methods have accelerated the massive scale of SARS-CoV-2 genomic surveillance due to their improved sensitivity, cost, and speed over other, lower-amplification RNA sequencing approaches, such as unbiased metagenomic sequencing[9]. Unsurprisingly, amplicon-based approaches that target the SARS-CoV-2 genome for amplification and subsequent sequencing have become the genomic surveillance method of choice during the ongoing pandemic (over 90% of Short Read Archive submissions). In just a year since the first genome sequence enabled the identification of SARS-CoV-2, hundreds of thousands of complete genomes have been sequenced and released by a relatively small group of several hundred laboratories. An open-access tiled primer set developed by the ARTIC network (artic.network/) is the most widely used method for SARS-CoV-2 specific genome amplification followed by sequencing on either Illumina or nanopore instruments (Quick et al., 2017; Tyson et al., 2020). A wide array of protocols and publications are now available that integrate these ARTIC primers with different amplification and library construction indexing strategies (Baker et al., 2020; Gohl et al., 2020). Approaches such as batching samples by viral load to increase sensitivity are impractical to scale to current needs, resulting in incomplete recovery of viral genomes, especially from low titer samples.

However, the risk for contamination during the amplification stage is especially high as the 35 or more cycles of virus-specific PCR produces trillions of SARS-CoV-2 amplicons in a single reaction. Other high-risk modes of contamination, including sample swaps, cross-contamination of samples, or aerosolization, can occur throughout the sample processing pipeline. With many laboratories performing viral sequencing by processing multiple large batches in parallel, the potential for contamination increases[10]. Even small amounts of sample mixing or contaminating amplicons could potentially confound studies where viral detection is sensitive to only tens of molecules[10,11]. Moreover, as SARS-CoV-2 has relatively low genetic diversity and often spreads in local outbreaks or clusters[11,12], many genomes are expected to be identical at the consensus level[11,15-17] a pattern that could also be observed due to contamination. The risk of contamination, and the challenges in detecting it, can confound a wide array of genomic analyses including estimates of the frequencies of variants, lineage dynamics, and transmission events. Additionally, methods to address the critical risk of sample processing errors in clinical sequencing could enable its use more widely in clinical decision making.

To meet the genomic surveillance goals laid out by local and world governments, sequencing efforts will need to be scaled to thousands of centers, many performing viral genomics for the first time. Additional laboratories will enter the SARS-CoV-2 sequencing space with an emphasis to rapidly surveil VoCs for clinical significance, with even higher requirements to ensure the integrity of SARS-CoV-2 genomes being produced. While inclusion of internal standards is commonplace in many experimental approaches[13-15] and some technical assay controls exist for DNA sequencing[16-18], the use of internal controls is currently rare in amplicon-based genomic surveillance. Here Applicants developed and extensively tested a sample identification method using 96 synthetic DNA spike-ins (SDSIs) for amplicon-based sequencing approaches. Using the widely used open-access ARTIC tiled primer design (artic.network/), Applicants implemented these SDSIs for SARS-CoV-2 genomic sequencing from thousands of residual diagnostic (clinical) samples. The resulting user-friendly and highly versatile SDSI+AmpSeq protocol can be easily implemented to improve the quality of genomic data generated for epidemiological and clinical investigations of human pathogens (FIG. 1 and FIG. 13, Table 6).

Citation or identification of any document in this application is not an admission that such a document is available as prior art to the present invention.

SUMMARY

In one aspect, the present invention provides for a method of detecting and preventing contamination in one or more cDNA samples comprising adding a synthetic DNA spike-in (SDSI) to each cDNA sample, wherein each SDSI is capable of amplification simultaneously with the cDNA, and wherein each SDSI comprises a unique sequence capable of differentiating each SDSI; amplifying one or more of the cDNA samples and SDSI; sequencing the amplified sample; and determining the number of reads of the spike-in from the one or more samples. In certain example embodiments, the sample is associated with drug resistance. In certain example embodiments, the sample is for sequencing a pathogen or family of pathogens. In certain example embodiments, the pathogen is a virus. In certain example embodiments, the pathogen is a bacteria and the region sequenced is associated with antibiotic resistance. In certain example embodiments, each sample contains a viral nucleic acid sequence. In certain example embodiments, the samples are for creating one or more sequencing families/clusters.

In certain example embodiments, the SDSI contains a core region and a primer binding region at the 3' end and the 5' end. In certain example embodiments, the core sequence of the SDSI is derived from a rare organism. In certain example embodiments, the rare organism is a thermophilic archaea. In certain example embodiments, the core sequence homology is less than 65%, or less than 60%, or less than 55%, or less than 50%, or less than 45%, or less than 40%, or less than 35%, or less than 30%, or less than 25%, or less than 20%, or less than 15%, or less than 5%, or less than 1% to a sample sequence. In certain example embodiments, the core sequence homology is less than 15, or less than 20, or less than 25, or less than 30, or less than 35, or less than 40, or less than 45, or less than 50 contiguous bases in common with the sample sequence.

In certain example embodiments, the synthetic DNA spike-in sequences are 50-5000 nucleotides in length. In certain example embodiments, the SDSI minimizes self-hybridization and cross-hybridization with nucleic acids in the sample. In certain example embodiments, the primer binding sites of the SDSI have a Tm between 55-65° C. In certain example embodiments, the method further comprises a plurality of SDSIs. In certain example embodiments, the core sequence of the synthetic DNA comprises a sequence as set forth in SEQ ID NOS: 1-96 and 193-291. In certain example embodiments, the primer binding sequences are complementary to the primers having SEQ ID NOS: 391 and 392. In certain example embodiments the SDSIs comprise one or more of SEQ ID NOS: 97-192 and 292-390. In example embodiments, sequences can be used in the alternative. In one example embodiment, sequence SEQ ID NO: 289 can substitute for sequence SEQ ID NO: 16. In one example embodiment, sequence SEQ ID NO: 290 can substitute for sequence SEQ ID NO: 57. In one example embodiment, sequence SEQ ID NO: 291 can substitute for sequence SEQ ID NO: 66. In one example embodiment, sequence SEQ ID NO: 388 can substitute for sequence SEQ ID NO: 112. In one example embodiment, sequence SEQ ID NO: 389 can substitute for sequence SEQ ID NO: 153. In one example embodiment, sequence SEQ ID NO: 390 can substitute for sequence SEQ ID NO: 162. In one example embodiment, one or more of SEQ ID NOS: 16, 57, 66, 112, 153, and 162 can be substituted with their alternative sequence SEQ ID NOS: 289, 290, 291, 388, 389, and 390, respectively.

In certain example embodiments, the concentration of synthetic DNA spike-ins range from 0.1 femtomolar—1.0 femtomolar. In certain example embodiments, the presence of an amplified spike-in corresponding to the spike-in added to a sample indicates a decreased risk of contamination. In certain example embodiments, the presence of an amplified spike-in corresponding to the spike-in not added to a sample indicates an increased risk of contamination.

In another aspect, the present invention is a set of synthetic DNA spike-ins (SDSIs), each SDSI in the set comprising a primer binding sequence at the 3' and 5' end and a unique core sequence between the 3' and 5' primer binding sequences. In certain example embodiments, the set comprises at least 96 spike-ins. In certain example embodiments, the unique core sequence is derived from a rare organism. In certain example embodiments, the rare organism is a thermophilic archaea. In certain example embodiments, the core sequence homology is less than 65%, or less than 60%, or less than 55%, or less than 50%, or less than 45%, or less than 40%, or less than 35%, or less than 30%, or less than 25%, or less than 20%, or less than 15%, or less than 5%, or less than 1% to a sample sequence. In certain example embodiments, the core sequence homology is less than 15, or less than 20, or less than 25, or less than 30, or less than 35, or less than 40, or less than 45, or less than 50 contiguous bases in common with the sample sequence.

In certain example embodiments, the sequence is 50-5000 nucleotides in length. In certain example embodiments, the SDSIs minimizes self-hybridization and cross-hybridization with nucleic acids in the sample. In certain example embodiments, the primer binding sites have a Tm between 55-65° C. In certain example embodiments, the core sequence are the unique sequences as set forth SEQ ID NOS: 1-96 and 193-291. In certain example embodiments, the primer binding sequences are complementary to the primers having SEQ ID NOS: 391 and 392. In certain example embodiments, the SDSIs comprise one or more of SEQ ID NOS: 97-192 and 292-390. In example embodiments, sequences can be used in the alternative. In one example embodiment, sequence SEQ ID NO: 289 can substitute for sequence SEQ ID NO: 16. In one example embodiment, sequence SEQ ID NO: 290 can substitute for sequence SEQ ID NO: 57. In one example embodiment, sequence SEQ ID NO: 291 can substitute for sequence SEQ ID NO: 66. In one example embodiment, sequence SEQ ID NO: 388 can substitute for sequence SEQ ID NO: 112. In one example embodiment, sequence SEQ ID NO: 389 can substitute for sequence SEQ ID NO: 153. In one example embodiment, sequence SEQ ID NO: 390 can substitute for sequence SEQ ID NO: 162. In one example embodiment, one or more of SEQ ID NOS: 16, 57, 66, 112, 153, and 162 can be substituted with their alternative sequence SEQ ID NOS: 289, 290, 291, 388, 389, and 390, respectively.

These and other aspects, objects, features, and advantages of the example embodiments will become apparent to those having ordinary skill in the art upon consideration of the following detailed description of example embodiments.

BRIEF DESCRIPTION OF THE DRAWINGS

An understanding of the features and advantages of the present invention will be obtained by reference to the following detailed description that sets forth illustrative embodiments, in which the principles of the invention may be utilized, and the accompanying drawings of which.

Figure 1:
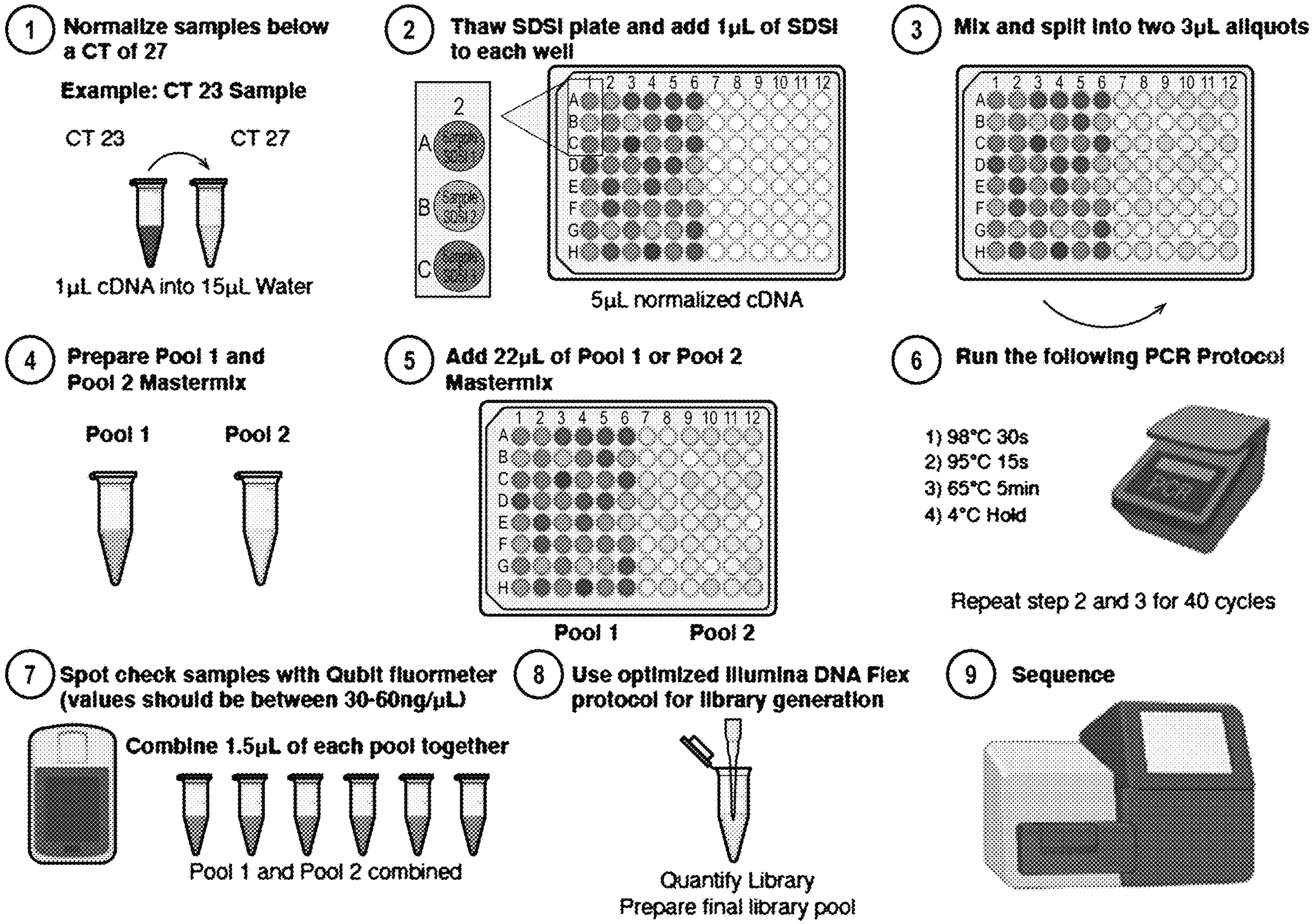
FIG. 1—SDSI-ARTIC Amplicon-Sequencing Protocol—Illustrative workflow for 48 samples through the SDSI+ARTIC amplicon-sequencing pipeline. A synthetic DNA spike-ins (SDSI) will be added to each sample to allow for contamination tracking and accurate sample identification.

The figures herein are for illustrative purposes only and are not necessarily drawn to scale.

DETAILED DESCRIPTION OF THE EXAMPLE EMBODIMENTS

General Definitions

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, $2^{nd}$ edition (1989) (Sambrook, Fritsch, and Maniatis); Molecular Cloning: A Laboratory Manual, $4^{th}$ edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, $2^{nd}$ edition 2013 (E. A. Greenfield ed.); Animal Cell Culture (1987) (R. I. Freshney, ed.); Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, $2^{nd}$ edition (2011).

As used herein, the singular forms "a" "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, +/−5% or less, +/−1% or less, and +/−0.1% or less of and from the specified value, insofar such variations are appropriate to perform in the disclosed invention. It is to be understood that the value to which the modifier "about" or "approximately" refers is itself also specifically, and preferably, disclosed.

As used herein, a "biological sample" may contain whole cells and/or live cells and/or cell debris. The biological sample may contain (or be derived from) a "bodily fluid". The present invention encompasses embodiments wherein the bodily fluid is selected from amniotic fluid, aqueous humour, vitreous humour, bile, blood serum, breast milk, cerebrospinal fluid, cerumen (earwax), chyle, chyme, endolymph, perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), semen, sputum, synovial fluid, sweat, tears, urine, vaginal secretion, vomit and mixtures of one or more thereof. Biological samples include cell cultures, bodily fluids, cell cultures from bodily fluids. Bodily fluids may be obtained from a mammal organism, for example by puncture, or other collecting or sampling procedures.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

All publications, published patent documents, and patent applications cited herein are hereby incorporated by reference to the same extent as though each individual publication, published patent document, or patent application was specifically and individually indicated as being incorporated by reference.

Overview

Embodiments disclosed herein provide a method of detecting and preventing contamination during genome profiling using synthetic DNA spike-ins (SDSIs). Embodiments disclosed herein also provide methods to track sample contamination by implementing synthetic DNA spike-ins (SDSIs) for sample verification. Embodiments disclosed herein also provide synthetic DNA spike-ins (SDSIs) and methods for producing synthetic DNA spike-ins (SDSIs). The global spread and continued evolution of SARS-CoV-2 has driven an unprecedented surge in viral genomic surveillance. Amplicon-based sequencing methods provide a sensitive, low-cost and rapid approach but suffer a high potential for contamination, which can undermine laboratory processes and results. This challenge will only increase with expanding global production of sequences by diverse laboratories for epidemiological and clinical interpretation, as well in genomic surveillance in future outbreaks. Applicants present SDSI+AmpSeq, an approach which uses synthetic DNA spike-ins (SDSIs) to track samples and detect inter-sample contamination through the sequencing workflow. Applying SDSIs to the ARTIC Consortium's amplicon design, Applicants demonstrated their utility and efficiency in a real-time investigation of a suspected hospital cluster of SARS-CoV-2 cases and across thousands of diagnostic samples at multiple laboratories. Applicants established that SDSI+AmpSeq provides increased confidence in genomic data by detecting and in some cases correcting for relatively common, yet previously unobserved modes of error without impacting genome recovery.

The methods described herein add a unique SDSI to each sample (e.g., cDNA) before performing a sequence amplification process during which the samples and SDSIs are amplified in the same reactions. This procedure can be repeated in parallel for each sample undergoing analysis. After the samples have been amplified, the presence of the SDSI is measured. If the SDSI introduced before amplification is the only SDSI present, then the sample is determined to be uncontaminated. However, the presence of any other SDSI immediately reveals contamination of the sample. This method provides a reliable safety measure for pathogen-genome studies and the resulting therapeutic and preventative medicine.

Synthetic DNA Spike-In (SDSI)

In one aspect, the present invention is directed to SDSI's and uses thereof An example SDSI comprises, in a 5' to 3' direction, a 5' primer binding sequence, a core sequence, and a 3' primer binding sequence. In one example embodiment, spike-ins comprise sequences derived from a rare organism. A rare organism is a species that is limited in number or geographic occurrence relative to the distribution and abundance of other species making up the pool of interest. (Raphael, M. et al., Conservation of Rare or Little-Known Species: Biological, Social, and Economic Considerations. Bibliovault OAI Repository (2007) the University of Chicago Press) In some embodiments, the rare organism is an archaea. In some embodiments, the archaea is thermophilic. A thermophilic archaea may exist in environments with temperatures greater than 50° C. In certain embodiments, the present invention includes spike-ins. In certain embodiments, a spike-in comprises a DNA sequence that is not from the target organism. In certain embodiments, a spike in is an RNA molecule that can be added to a sample comprising pathogen RNA. In certain embodiments, the RNA is converted to cDNA concurrently with pathogen RNA. The RNA spike in cDNA can then be amplified with pathogen cDNA using pathogen specific primers and spike-in specific primers.

In certain embodiments, a spike-in sequence is compared to the target organism and the host for the target organism to limit homology. Limited homology can be determined using a BLAST search of all SDSIs. In one example embodiment, a permissive BLAST search is used (e.g., blastn; 5000 max targets; E=10; ws=11; no mask for low-complexity). Results may be filtered by species of interest, e.g. *Homo sapiens*. In one example embodiment, results can be filtered for a pathogen of interest (e.g., SARS-CoV-2). The query coverage and sequence identity may each be set for 35-100%, preferably, 50-100%, and sequences having no significant hits can be selected for use as a spike-in. In certain embodiments, a spike-in set comprises different DNA sequences that can be easily distinguished using sequencing.

In certain embodiments, the GC content of the spike-ins promote similar amplification rates across pathogen targets and the different SDSIs in our set. In one example embodiment, a spike-in comprises a similar GC content as the target organism. In another example embodiment, the GC content of the primer may range from 30%-80%. (Buck, G. A. et al., Design Strategies and Performance of Custom DNA Sequencing Primers, BioTechniques (1999) 27:3, 528-536). In another example embodiment, the GC content of the primer may range from or between 30%-40% nucleotides, or between 40%-50% nucleotides, or between 50%-60% nucleotides, or between 60%-70% nucleotides, or between 70%-80% nucleotides. In general GC content extremes are avoided. For example, sequences may have a median of 50% GC content, preferably, between 35-65%. In another example embodiment, the GC content of the primer may range from or between 40%-70%, or between 30%-50% nucleotides, or between 30%-60% nucleotides, or between 30%-70% nucleotides.

Core Sequence

Each SDSI in the set is differentiated by its core sequences. The SDSI cores are designed to minimize self-hybridization and cross-hybridization with others nucleic acids in a given sample. Accordingly, core sequences are selected based on the type of target sequence to be amplified and the type of sample the target sequence is to be derived from. For example, in the context of detecting a pathogen in a human sample, core sequence should be selected with minimal homology to the target pathogen, other common microbes and non-target pathogens that might be present in the sample, and human sequences as well. In certain example embodiments, the core sequence has a homology of less than about 65%, or less than 64%, or less than 63%, or less than 62%, or less than 61%, or less than 60%, or less than 59%, or less than 58%, or less than 57%, or less than 56%, or less than 55%, or less than 54%, or less than 53%, or less than 52%, or less than 51%, or less than 50%, or less than 49%, or less than 48%, or less than 47%, or less than 46%, or less than 45%, or less than 44%, or less than 43%, or less than 42%, or less than 41%, or less than 40%, or less than 35%, or less than 30%, or less than 25%, or less than 20%, or less than 15%, or less than 10%, or less than 5%, or less than 1%.

The core sequence may vary in length between 50-5,000 nucleotides, or between 50-nucleotides, or between 50-4,500 nucleotides, or between 50-4,000 nucleotides, or between 50-4,000 nucleotides, or between 50-3,500 nucleotides, or between 50-3,000 nucleotides, or between 50-2,500 nucleotides, or between 50-2,000 nucleotides, or between 50-1,500 nucleotides, or between 50-1,000 nucleotides, or between 50-500 nucleotides.

The core sequence may vary in length between 50-60 nucleotides, or between 50-70 nucleotides, or between 50-80 nucleotides, or between 50-90 nucleotides, or between 50-100 nucleotides, or between 50-110 nucleotides, or between 50-120 nucleotides, or between 50-130 nucleotides, or between 50-140 nucleotides, or between 50-150 nucleotides, or between 50-160 nucleotides, or between 50-170 nucleotides, or between 50-180 nucleotides, or between 50-190 nucleotides, or between 50-200 nucleotides, or between 50-210 nucleotides, or between 50-220 nucleotides, or between 50-230 nucleotides, or between 50-240 nucleotides, or between 50-250 nucleotides, or between 50-260 nucleotides, or between 50-270 nucleotides, or between 50-280 nucleotides, or between 50-290 nucleotides, or between 50-300 nucleotides, or between 50-310 nucleotides, or between 50-320 nucleotides, or between 50-330 nucleotides, or between 50-340 nucleotides, or between 50-350 nucleotides, or between 50-360 nucleotides, or between 50-370 nucleotides, or between 50-380 nucleotides, or between 50-390 nucleotides, or between 50-400 nucleotides, or between 50-410 nucleotides, or between 50-420 nucleotides, or between 50-430 nucleotides, or between 50-440 nucleotides, or between 50-450 nucleotides, or between 50-460 nucleotides, or between 50-470 nucleotides, or between 50-480 nucleotides, or between 50-490 nucleotides, or between 50-500 nucleotides, or between 50-510 nucleotides, or between 50-520 nucleotides, or between 50-530 nucleotides, or between 50-540 nucleotides, or between 50-550 nucleotides, or between 50-560 nucleotides, or between 50-570 nucleotides, or between 50-580 nucleotides, or between 50-590 nucleotides, or between 50-600 nucleotides, or between 50-610 nucleotides, or between 50-620 nucleotides, or between 50-630 nucleotides, or between 50-640 nucleotides, or between 50-650 nucleotides, or between 50-660 nucleotides, or between 50-670 nucleotides, or between 50-680 nucleotides, or between 50-690 nucleotides, or between 50-700 nucleotides, or between 50-710 nucleotides, or between 50-720 nucleotides, or between 50-730 nucleotides, or between 50-740 nucleotides, or between 50-750 nucleotides, or between 50-760 nucleotides, or between 50-770 nucleotides, or between 50-780 nucleotides, or between 50-790 nucleotides, or between 50-800 nucleotides, or between 50-810 nucleotides, or between 50-820 nucleotides, or between 50-830 nucleotides, or between 50-840 nucleotides, or between 50-850 nucleotides, or between 50-860 nucleotides, or between 50-870 nucleotides, or between 50-880 nucleotides, or between 50-890 nucleotides, or between 50-900 nucleotides, or between 50-910 nucleotides, or between 50-920 nucleotides, or between 50-930 nucleotides, or between 50-940 nucleotides, or between 50-950 nucleotides, or between 50-960 nucleotides, or between 50-970 nucleotides, or between 50-980 nucleotides, or between 50-990 nucleotides, or between 50-1000 nucleotides, or between 50-1010 nucleotides.

The core sequence may vary in length between 100-5,000 nucleotides, or between 1,000-5,000 nucleotides, or between 2,000-5,000 nucleotides, or between 3,000-5,000 nucleotides, or between 4,000-5,000 nucleotides.

The core sequence may vary in length between 75-150 nucleotides, or between 100-150 nucleotides, or between 100-200 nucleotides, or between 100-300 nucleotides, or between 150-200, or between 150-250 nucleotides.

The homology to a target sequence or non-target sequence in the sample across the size of a given core sequence may be less than 1 nucleotide, or may be less than 2 nucleotides, or may be less than 3 nucleotides, or may be less than 4 nucleotides, or may be less than 5 nucleotides, or may be less than 6 nucleotides, or may be less than 7 nucleotides, or may be less than 8 nucleotides, or may be less than 9 nucleotides, or may be less than 10 nucleotides, or may be less than 11 nucleotides, or may be less than 12 nucleotides, or may be less than 13 nucleotides, or may be less than 14 nucleotides, or may be less than 15 nucleotides, or may be less than 16 nucleotides, or may be less than 17 nucleotides, or may be less than 18 nucleotides, or may be less than 19 nucleotides, or may be less than 20 nucleotides, or may be less than 21 nucleotides, or may be less than 22 nucleotides, or may be less than 23 nucleotides, or may be less than 24 nucleotides, or may be less than 25 nucleotides.

The homology to a target sequence or non-target sequence in the sample across the size of a given core sequence may vary in length between 1-5 nucleotides, or between 1-10 nucleotides, or between 1-15 nucleotides, or between 1-20 nucleotides, or between 1-25 nucleotides, or between 1-5 nucleotides, or between 5-10 nucleotides, or between 10-15 nucleotides, or between 15-20 nucleotides, or between 20-25 nucleotides, or between 1-10 nucleotides, or between 10-20 nucleotides, or between 20-30 nucleotides.

These SDSIs can be implemented in a wide range of genome profiling applications including, but not limited to, investigations of SARS-CoV-2 epidemiology and emerging viral variants. Exemplary SDSIs are provided in Table 1.

Table 1. Sequences of 96 unique SDSIs. The unique core of each SDSIs is 140 bps long (SEQ ID NOS: 1-96 and 193-291). The unique SDSIs including the priming regions (SEQ ID NOS: 97-192 and 292-390). Alternative sequences are also included. SEQ ID NOS: 16, 57, 66, 112, 153, and 162 can be, in the alternative, substituted with 289, 290, 291, 388, 389, and 390 respectively. Sequences for forward and reverse primers for amplifying the SDISs (SEQ ID NOS: 391 and 392 respectively).

TABLE 1

| SEQ ID | |
|---|---|
| | Core Sequences |
| 1 | CAATTGCTCCCTCGTATCCCTTGTACATTATCTCAGCTCCGCTTAATGATATTAATTTTACCTT GAGTGTTTTTGCTAAAGCCTTTGCCATCATCGTTTTACCTACTCCAGGTGGCCCGTAAAGCAAC ACAGCTTTGGCA |
| 2 | TTCTCCAAAACCTACCCAGTTCTCCGAGGAACCTCTTAGCATCTGTTAAATCGTTATTAGTATT AGCTTCCACCATCTCAAGTTCCTTTAAGGCGTTACTCACACTCTTCTTACCTATCTTTTAGAGA ACCACTCGTCAG |
| 3 | GTTATCAAAGCCCTTAAAGAGTGGTAGGGGCAAAAGTCTGAAGCGTCCTTACTTAACTGGAGTA TCTGAGATGGCCTTAATCCGCTTAGGTCTTTAATTTTATCCCTTAATGAACATTCCCTGCACTC TATGTCTTCGGG |
| 4 | GAGATGTAGCAGACGGGCTAAGAGTTTCAAACCCTCTAAGGATCACTACAAACAAGAGAGAGAG ACAATCCTCTCTTTTGTCTTGTCATTGTGTTTCAAACCCTCTAAGGATCACTACAAACATCTTT AACATAGATACC |
| 5 | GACCGGACGTTGTGATCACGGGTACCTTGATCTGGTACTCAAAGGTTTGCCCCCGTGAAGTCTG GTACATGGCTAGACACGTCACTCCATTCGAGGGACATTCGAAGTTAGAGAAGGGCAGAGCGATA CATCAGATATAT |
| 6 | GTCTTTTCTCTACTAATTCTCCTCACGAGATCTCTAAACATTCTTGCTGAAAGAGGATCCAAAC CTAATGTAGGTTCGTCAAGCAATAAAATTGGAGGATCAGTTATTAATGCTCTTGCTAAGGCTAG TTTCCTCTGCAT |
| 7 | GATTTTGCCATCATTAAAAACAACAATTTGATCACCCATAGTCATAGCTTCTAATTGATCGTGA GTTACATAAATACTTGTGGTGTTTAACATACGGTGAATATTTACAATTTCTCTTCGCATGTTTT CTCTTAGTTTAG |
| 8 | GTATCTTTCAATTCTCGAAAGAAAAGGTTACAAGTCTCATAGATTTATTCCTCTTCACTGTTGT ACGTTGGCAGCTAGAGAGAGTTTAGATTATGAGAAAATTAAGAGAATATATGAGGATTCGTTTT CTTGGTTTAAGT |
| 9 | CTAATTGATTTTCCTGTACCATGTGGTAAAACAACGCTACCTCTTAATTGTTGATCTGCTTTTC TAGTATCAAGATTTAATCTAAAAGCTAAATCAACTGAAGCATCAAATTTTGTATAAGAAGTTTT TTTCACTAATTC |
| 10 | TCGGTTTTCCCGTGAACTAATAAACACCTACTGGAGCCAAGAACGGGTCAGAATTGATGGAATA AACGTTGCGGAGAATGAAATTAATTTGTACATCAGAGACATTGATGACAACGGTGACCCTATAC AGTCAACTATAC |
| 11 | CTTAATGGAAAGTATGCTTTAGATACCTTCTGGAACGCTATCTCACTTGGCGGGAATTCAGATA TGGAGAGTAAATTAAGGGATCTGGAAGTAAAGTTAATGTCGTTAATCTATTTAAATGAGTCACC ATTAAAATCACC |
| 12 | CATAATATGTTAGAGGTAGAATTTCTTTGTGATAGAATATTATTGATGAATGATGGAAGAGAAT TAGCATTAGGAAAACCTAAGGAACTGGTAAAGGATACAGAATCTAAGAATCTTGAAGAGGTTTT CCTTAAACTTGT |
| 13 | CCTTACTTCATCTCTCAAGATAAGGGTAATAAGTTCACTTCAAATATCTGGTCTTATCGCAAGT TGATTGAGGCTATAGTGTATAAGCTCTATGAGTATGGTATAAACGTGTTCCTCGTTGTAGAGTA TAACACTTCACG |
| 14 | AGTCTAGGTTTTAATTCTTCAACTGCTTCAAATACTAGCTTACTGTAGTTATCTGCCCTCATGT TAGGATATATATCTGGAATATAAGGAGGTTGATGAGTTATAAGAAGTGGATGAAATTGTTGTCA CACACTCCCCTA |
| 15 | CTACCTCTTCGGCCTTGTACCAACGTACCCCTGATACAAGTTCCAAGCAGAGATGGAAAACTCG AAGATGGTATCACCCAAGATGAGATACGATATCAATGAAGGCGAGCCTAGGTACAAGTAAAGGG ATACCACGAGAG |
| 16 | CTCGTAAGCGTTTCCTACCCTCGAGAGGGCCATCCTGGTGGTGAGGAAGTCGTCGAAGTGGGCT AAGTAAAAAGCGAAGATCTCGACCCACAATTACCTCCTCCTGTACACCAGGAATACCCCTATCA GGATAGAGATAC |
| 17 | GCGCGTCCGGGTCGCGGCCGGGGACGACCGTCTTGACGAAGTCGGTCGACCCCTCGTCGGTCGA GATGGTCGTCACCTCGGTGTCGAGGCCGTACGTTTCGAGCGCGTCGCGTACCAGTTCGCCGTCC GCGTCGGGACGG |

TABLE 1-continued

| SEQ ID | |
|---|---|
| 18 | CATGTACTCGTTCCAGAAGGTGAGTTCGCTCCCCTCGATTTCGACCTCGCCCACGTCGAAGCCG CCGGTCGTTTCGAGCGCGAACGACTCGACGGGACCGACGAGCGAAACTTCGCCGCCGAGCACGT CGGCGACGCGTT |
| 19 | CTCGATGCGCTCGGGCTTGTAGGACTCCCCGAGGGCGTCCTTGTTGGTGAAGACGTTTTGTTTT CGCTCGAACCGGCGCATTAGCGTCGGTCCGTTGTAGCGTCCCCTTATTTAAAACCCCGATTTCA TCTGATTCATGT |
| 20 | TCACGGTCCGCGACGTGAATCGGGCGTTCCAGTCGGCGTTCGGCTACGACGCCGACGACGTGGT CGGAAGCGACCTCCTCGGGCGAATCGTGCCCCCGGTGCCGGACCCGGACCCGGTGCCGGAACCG GGGGACGACGAG |
| 21 | GCGTCCGCGAGTTCATCCTGAACGTCGTCCCGCTGTCGCCCGGCGAGGAGCGCGGGGCGGGCTA CGCCATCTACACCGACATCACGGAGCGGAAGACCCGCGAAAGCGAGCTAGAGCGACAGAACGAG CGATTGGAGGAG |
| 22 | GCGAGACCGGCGACGAGGTGCGCTTCGACACCGCCGAGCGGGCGCTCGAACAGATGGAGGAACT CATCGACGACCTGCTGTCGCTCGCCCGTCGCGGCCAACTGGTCGACGAGACGGAGCGCGTCGAC CTCGGGGCGGTC |
| 23 | ACGAACTCGTCGGTGAACATCTCGTCTTCCGGGGAGCCCGCCGCTCATGGCCTGCCCCCGCCGT AAGCTGCTGCATAAACCCGCTCCAAAATATACGGATCATTCACCCCTTGGAATCGCTCAATCAG ATCAATGTACAC |
| 24 | TGCGTACATTCCCCCTAAGCGGCTCCCAATATACAGACGCCGGTTAACGACAGCTGGCGACCCT GTGATCTCAGTACCGGTGTCGAATGACCACATCAGCTTGCCTGTCCGTGCATGGAGTTCGTATA CGTACCCGTCGT |
| 25 | AGATAGATGAGCCGATCAGAGATCGCTGGTGAGTTGGTAATTGTCCCGACATAGACACGCCAAC GTTCTGTTCCATCTGCTGCGTCGTAGGTCGCGAGATACGGCCAGCCACCAACATACACAATCCC ATCGACGAGGAC |
| 26 | ATACACCACCCCATCAGCAACAACTGAATCATGATTAAGTATCGCACCAGCATCGTAGCGCCAG CGTTCACTGCCAGTGGTGCTATCGAATGCATAGAAGATATGCTCCTAATCGCCAATATCAGTAC TTCACAAAGCCG |
| 27 | TCGACGAGGAGAGGGGCGAGTACATCTGCACGCTTACGGGAGAGGTAGTTGAGGAGACGGTTAT AGATACAGGGCCCGAATGGAGGGCTTACACACCTGAGGAGAGGACCCGCAGAAGCCGCGTGGGC AGCCCGCTTACC |
| 28 | AGTCGATGGCTGCGGCAGCTGTCTATGCTGCCTGCCGTATACGCGGCATACCCAGGAGTATAGA CGACATAGCGGAGGTCGTGAAGGGTGGCCGTAAGGAGGTTGCCCGCTGCTACCGCCTCATAGTC CGCGAGCTGAAG |
| 29 | GTGGAGTCTTTTGTCACACCGCAGAGGCGTAGCGCTGCAGAGCAGGAGCCCAAGCCTACTGCCA ACATAGAGAACATAGTGGCTACAGTATCCCTCGACCAGACTCTAGACCTGAACCTCATAGAGAG GAGCATACTGAC |
| 30 | CGTCGCCTGGGTTAAGAGGATGTTCGGCCTCTCCAAGGCGGGTCACGGAGGCACGCTGGACCCG AAGGTCACCGGCGTCCTCCCCGTAGCCCTGGAGGAAGCAACCAAGGTCATAGGCCTGGTGGTGC ACACGAGCAAGG |
| 31 | CGTGGGCGAGATCTACCAGAGGCCGCCGCTCCGCAGCAGTGTTAAGAGAAGCCTCCGCGTCAAG AGGATATACGAGATAGAGCTGCTGGAGTACAACGGCAGGTACGCGCTCATGAGGGTGCTCTGCG AGGCCGGCACAT |
| 32 | CGCTGGAAGAACGAGGGCAAGGAGGACCTGCTGCGGAGCTACATCAAGCCCGTCGAGTACGCCG TGAGCCACCTGCCCAAGATAGTTATACGCGATACCGCGGTGGACGCCATAGCCCATGGCGCGAA CCTCGCGGTGCC |
| 33 | GGGAGACCCCAAGGTGACCGGCGTCCTACCAGTGGGGCTCGCCAACAGCACCAAGGTCATTGGT AATGTTATACATAGTGTTAAAGAATACGTGATGGTTATACAGCTCCACGGCGATGTAGCCGAGC AGGATTTAAGAA |
| 34 | TAGAGGGAAAGACTGTAGCTTTCATTCCTAGGCACGGAAAGAGACACAGAATACCTCCACATAA GATAAATTATAGAGCTAATATATGGGCATTAAAAGAACTAGGAGTGAAATGGGTCATCTCAGTT TCTGCCGTAGGA |
| 35 | TGAGGGAGCTCAGGAGGACTCGCACGGGGCCCCTACAGGGAGGATGAGACACTTGTAAGGCTCCA GGACGTCAGCGAGGCCCTGCTCCTGTGGAGGAGCAACGGGGATGAGAGGTATCTTAGACGCATC GTGCTACCCGTT |

TABLE 1-continued

| SEQ ID | |
|---|---|
| 36 | GAAACATCTATCGCCCACCTCCCGAAGATAATGATCTTGGATACAGCTGTCGACGCCATAGCAC ATGGTGCCAACCTGGCTGCCCCAGGCGTCGCCAGGTTAACCAGGAACATCGCGAAGGGTAGTAC CGTAGCGATCCT |
| 37 | TCGCTATCCCCGTGTACAGCATGGTGGGGGTGCCGATGCCCGGGTAGAACTTGGTGACGCTCTC CAGCTTCTCGAGGACGGTTTCCTTGGGGAGGCTCGCGGTGTCCACGAGGGTTATCGCGTCCTCG GCGCCGTCGCCG |
| 38 | CGAGGACGCGAAGAGCGCGGTGGATGTGGACGCGCCGCCGCACACGTAGCCGTCGAGGTAGCGC GGAACCATCGGCGACATCAGCCCCACGACGCGACCCGAGGCGTTGCCGAGGATCACGTCGAGCG TCACGCGCGGCA |
| 39 | CTCGACACCGTGCCGTTGCCCTCCTCTAAGTAGTCGGAAAGCCTCATCCGCGACTCCAGCTTCG CCACCGGCTCCTCGAGCAGGAGGAGGACGCGGTTGATGCGGTAGGACGCACTGCCCGCCTCCAG CACCGCGCCGTC |
| 40 | TCTATGGTGTAGAACGGGTCGTTGCGGAGCCAGCCTGGCGGCACGTACCGGTCGTCCGCTATCG CCAGCGATCTCTCGAAGAGGTCGAGGTAGGCGGACGCGTTGGCGAACGCCCCGTGTATCACGAC GTCTATCCCGCC |
| 41 | GTATAGGTTTCAGGTATTGATAATGCATAGGAGGTTTTTAAAACCTTGAGCCGCATAGTCTTCT GGATGGGCGAGAGACATGGTTAAGTATAAGTGCGGCAGGTGCGGATACGTCTTCGACGACGAGG AGATGAAGAGGA |
| 42 | CCTACGCCGGGTGCGTAGGAGGGCTCGAGTACATCCATGTCTATACTGATGTATGTTTTACCCA GGTCGCCTAGTGCCAGGGGTCCCTTTAACGCTTCCAGGATAGAGTACACGGTGACGTCTCTAGT CTTCTTCAAGAA |
| 43 | CTACTAGCGTGTCAACGGAGCTCTTCAACGCCTTTACTATTGGATAGGTTATAAGGTGCTCGCC TCCGAGGAATCCCAGGAGCATGCCGGGATACTCGTCTACAACGCCTTTCACCACGTCACCTATG ATTCTTAAAGAG |
| 44 | CATAGGTGACATGGGGTTTCCCATTGACTCTATAAAGCCGTATCCTTTAAGCGGAGTGCAATTG GTCTACGCTTTGCTTAACAACAGGTATTTCCTACCGGGTAGAGAGGGCTCGCTCATAGCTTTAG GTAGCGTGACGG |
| 45 | GGTATCTCACCGCTTGTCACCATAGTATCCCTCAGGTACTCCAGTATTCTTGAGAGAAACGCAC CTAAGCCGGATCTCAGGTTTGAATCCATAAGAACTATGAGTGAAGCGGGATTGAAGCCCCTGCT GTTTCTAAGACC |
| 46 | TAAGGGAGATAGAGAAACGCATCAAAATACCCTTGGGGAAACTGCGTGCAGGGGTTCAATATGG AGTAGAGGTCTCAGACATAAAGGAGAAGATAGCTGCTTACGCTAGGAGGAAGGGGCTTAAATAC TTCCCATCGGCA |
| 47 | TGTGAACCTCGTGCCCGGCTCTAAGTCGTGAGGGCTTGCAACATAGGTGGGGAGGAACCCGAGC AACGGGTAAGAAGACAGGATAAGCGGTATCGCTATGAAGAGGGCTGAGAAAAGGACATATACTC CTGAGCCCGTCC |
| 48 | CGAACATGCCTTCCCCGTCTATATAGACCCAGTAGAGTTTAAAAACTTAACCAGAGACGGCTTG TGAGCCGGATCTCTCCCCCGCTAGGCCCTGGATTGGGCTCGCTCCTCCTGGGACCCCGGCCTCC ACATGCTCGGGA |
| 49 | CCTGAAGGGCTCGGCTACCCTGAAGACGGGCTTCTGCGCGACCGCCGCGTACTCCGCCGTGGAG CGGTAGAAGAGCGAGGCTGTCTCCGTGAGCCTGACCATTCCGTACAGGGCGACTGCGACGAGCA CTATGACTGCGA |
| 50 | GTCAAGGTGCTGATGCCGAAGGCGACTTTCGACACCGACGATGCCGCCGACGCCCTGGCCATTG CCATCTGCCACGCGCATCACCGGCACAGTGTTGCCTATAGGATGGCGCTGGCCGGATAAGTTTG TTCTTGACCTGT |
| 51 | TCTCGGTTCGGCAATAAGTAATACCAACGAGGTATTACCATGCGCGTGACCAGCAAAGGCCAAG TGACGATCCCAAAGGAGATACGGGATCATTTGGGGATTGGGCCGGGCTCCGAGGTGGAGTTCGT GCCCACAGACGA |
| 52 | CTCGATCATATGGCCGGCACGTTGGACTTGGGAGGCATGACAACGGACGAGTATATGGAGTGGC TGAGGGGTCCACGTGAAGATCTCGACATTGATTGACACAAATGTCCTGATCGATGTTTGGGGTC CTGCCGGACAGG |
| 53 | CAGGTGTATTTTACACACCTGGACAGCCAGCATATGATGCTAGCACTCGGTGTCCCCTTATCAC GGTTTCCCGCATTGTAAAGTTTTCGCGCCTGCTGCGCCCCGTAGGGCCTGGATTCATGTCTCAG AATCCATCTCCG |

TABLE 1-continued

| SEQ ID | |
|---|---|
| 54 | CTGGAGCCTGTTAGTTGTTACAGGTTCACCGGTTGTCGGAGTATTCAGATCATTGAGCCAGCAG TTGATGGCTGCCTGTAGTTCACTGGTTGTGATGTAAGCTGCTCCATCGGAATCAACATCGTTCC ATGGGTTCCAGT |
| 55 | ACGGTCTTGCTTTCTCCTGAATCCATTTCACCTGTCCAGACCCATTCATAGCGGTTAGCTTCAC TGAGGTTCTGCTTGAAGACACCGTCATCATTGTTAGATGAGGTTATTGTCCAGCCGGCAGGAAT GACTTCTTCGAA |
| 56 | GTCAGCAGCTCTTCATAGAAGTTCTGGTTTGCAATATCCCTCTGGGCAATGACAGGGTAGTCGA CTTCGTTTGCAGTCAGGTGGACTGCATACAGGGACTTGCTGATGTCCGGGGTATATCCACTGTG AGGAGCATAGTA |
| 57 | ACCCGTCAGTCGTGACGTCCTCCGCTCCTCCTATGCTATCTCCACACACCCACTCACGTTCTTG CTTCTTTACTACACCCTCTTTATTCAGCTCTTCGAGAACATTATTAATGTGACCCTTAGAGATA TATTCATTATAC |
| 58 | GTGCCTCCTCAAGCGACTGCTTAAACCCAATTACATCTGATTTATCCTTTATTTTAGGGCCTAT AGAATCTATGAATAATTCGGCGATTCTTATTATTTCTAAAACCAATTCGTCTGTTTTGAGTGGT GTGCCTTCTTCA |
| 59 | CATCCCATGCATTTTCATAATAATCGGAATTCAAATCCTCTATATTGAATTTTATCTTAACATT TGACATAATCATTTTCTCCTTACAGAAGAGATCCAGCTAAGCTTACTCATAAATGGTAGTACCA TGCCAATATTGG |
| 60 | CGTAGCCCGCACCTTCCTCTGGTTTAGCACCAGCGGTCCCCACAGAGTACCCATCATCCCGAAG GATATGCTGGCAACAGTGGGCACGGGTCTCGCTCGTTGCCTGACTTAACAGGATGCTTCACAGT ACGAACTGACGA |
| 61 | CCTGATAGGCCGCAGATTCATCCTAAGGCGCCGGAGCTTTTGACCACAGAACATTCCAGTATCT ATGGTATATCTGGAATTATCACCAGTTTCCCGGTGTTATGCCAGACCTTAGGGCAGATTATCCA CGTGTTACTGAG |
| 62 | TGTTTGGCTTGATACTAATAAAAGCACAGCTAAAATGAAAATAAGCCGATATTTGTGATTCATG CAACTCACCCTTTTCTACATAAACAAAATACTAACCCGAAAACCGAAATTGAAATTAATGCAGA GAAACCAGGTGA |
| 63 | TTAACGGCACCAACAGTTATTATATTTTTAGCAGTCCCGGGTGAAGTAATTATGGAATAGTTGT TAGAATTACTGTTCTTATTACCAGCTGATTTGAAAGCAATTATACCTGCATCACGAATTGCAGC ATCATAATATTC |
| 64 | GGCTCAGACGACTGAAAAAGCAACGATTGGAATAATAGGGGGTTCTGGGCTCTATGATCCTGGT ATTTTGACTAACAGCAGAGAAATAAAAGTATATACACCCTATGGGGAACCTAGCGATTTGATAA CGATAGGTAACA |
| 65 | CGCAGAACAGGTTCCTTCTATTGGATATTCATCTTCGGCTGCAGTTGCAGGAAGAGTAAGGATA TATACTACGGTCTTGCTTTCTCCTGAATCCATTTCACCTGTCCAGACCCATTCATAGCGGTTAG CTTCACTGAGGT |
| 66 | CTTCCTCCACGCATTTGTTGTGGTGCTGATGGCGTATTCTCTGGAATTTGGGATGATTCTGGAA ATCCATCCTCAGACACTTCAGATATTTTAGTCTTACTTCCAGCGTTTAATTGAACCTTACCTTT AAAAGCAGTAGT |
| 67 | GAAACTTACCTTATCAGTGTCATTAAGCATATTGCTTCCAAGACCCATTGAAGCACTTACATCG TTGATACACAGGTGCCAGGAATAGTATTCCTCAGTCTCACTATAATCCTCGTTGGTGTAGCCTT CAAGAGAGTCAA |
| 68 | GTTTAAGCAATTCTTCGGATGAAAGATGGCGCTCTATAGGAATTTGTTCTGGTCTAGCCATAAG GCATTATTTGTACTTAATTAGTAATAAATGTTTAGTTAATGACTATAAATCTGCAATTGGAGTC TCAAATTTTCAA |
| 69 | AACATGAAGGATGTGTGTAAGAGGAAACGTTATTAACAGACGTAATCAGGAGGATAGTTATGCC CTAAAAACAGCAGAGTTAAGGTTTAAAAATAAGATAAGAACTCAGTTGAGGTTTATCCATTAAT CCCATTAATCCT |
| 70 | ACTTTCTAAAAGCGCTTGGAGCACGTATCAGGTCAAGTCTTTCAACCTTAAATGCTGCCAGTGC CGTAAGTAGTGCAGTTATGTTGCTTATTGAAACAAACAACTTAGCCCACTTATTACCTCTTGTC AGTGTTTTTGAT |
| 71 | GTATCCGCTGATATATCCTGGGGATATAGATCGCTCTGAAATGGTTACATCTATCGGTTTTAAG GACAGTTCCAACACTATTGGACCTTGCAGCTATGACAGGAATAATCTGTTTATCGAGCACAGTT GAATTTGACCTA |

TABLE 1-continued

| SEQ ID | |
|---|---|
| 72 | TCAATACCTAATTCTTTCCTTAGAGTGCTATTTTGATTGAATTCCCTCAGGAAAGATTCAAAATTTAAGTAGCCGAGCTTACATCTTGAAATTTCCATCTTTATTATGTTGCTCAGGCTTAATGCTTCTAAGTATGGGTT |
| 73 | AGATATCCTTTGAAATTCTCGTAATTGCTGAAGGCCACTACTTCATCAGGTCTGATGCAATCTTTAATCTGAACATTGCTTTCTGAGGTCTTAGGAATAATCCTGTAAGGGAGTCGGATATTGTTCGTTAAGATGCTCTT |
| 74 | ATAGAGGGACCTAGATTTTCAACGAGGGCAGAAAGTAGAATTTGGAGGGAAGTTTATAAAGCCGATATCATAGGGATGACTTTAGTTCCAGAAGTAAATTTAGCTTGCGAAATGCAAATGTGCTATGCAACAATTGCGAT |
| 75 | GTCTTCAGCATAGTACCAGCTTATGTTGTCACCATCGTTCAGTACGTTACCACCAAGTCCACTGCCTGCAGCTACATCATTAATGTACAGGAACCAGGCATAGTAACCGCCAGTTGATATGTAGTCTTCACCTTCGATTC |
| 76 | ACTCTCCATCATGACAGCCAGATCGGTCATAGCATCGATTGTGTACTCTTCGTCGGGATTGTTGTATGGAATGAACTTATAGTTCTCACCTGCTACCTGATCCACTGTCATTTCTGCAAGAGTCTGCACTGTGGTAATTC |
| 77 | ATATTCCGTATTTCTTATCAAACCGATCGTGAAGATTTGACAAAGGCTTAACTTTAGGGCTCCACTTCTCATTATTAGCCTTAGAATATAAAGCGTAACCGTAAGCCTGAGGAACGTAAAGCTTAGGAGATTCAATCCCG |
| 78 | TAAAATTAGCCGAAGGCTTCCCATTACCGAAAAAGTCGTTTATTAGCTCTTCATCCTTCTTCTCCACGTCCGCCCATTCCTCTCCTTCCCTTGGAATTTTAAGCTCGTCCCAGCTGACTCTTATGGGCAATTCAATATCC |
| 79 | GTATAAACTTTTGATATAACCTTGCCTAATTTGATATCATAGCTTATGTTTGGCGCTATCCCCCACTTGTAGAGGGTCGCGTTATATTCTCTAATAGCAAGAGAGATACAAGATTCGTTAACGTTATTTATATCACTCTC |
| 80 | TCCGGAGGAATCTATCATATTAAACCTCCTCAAAATCGCCTCCTCTTGATTGCTTAAAGGCTGTGAATTACAAAGCTTATTTAATGCGTCCCAAAGCGTTAAGTAATAATTATTTATATTAAACACTACTATTTCAGTAG |
| 81 | GTTCCTCCTCAATTCAATTGGACTGAAGGAGGGTACGTTCTGGAAAACAGAGCGTAAAAGAGATATAGAACGTAGTATACACATAGCTGGAAAAAGAACAATCATTAAGACAATAAAGAACTTTATGGAAAAGAGTAGAA |
| 82 | TCGTGTAAAGGTTGTATAATTCAAGCCTCAGAACATTTCGAACTCCTTACAAAATCGTTTAAACTTTCTAAGGCATAAATTTACTAGAAATTGTCATTTATGAGAATGTAACTATATAGATGGTAAAATTATTAATCCTC |
| 83 | GGCTGAAAAATAGGTTCGATCCGCCTCCTCACTTCTTCTCCTTCTTGCCCTCGGCCTCGGAGGAGGCCTCTATTCCCAGCTTCTTGGCCTCCTCCTCGGTCGTCATGAACAGGCTAGTCCTCTGCCTTCCGCCCATGCTC |
| 84 | GACCTAGCCTTACGCACAGCCCTCTCCACAACCTCCTCAAGCTTATCCCAGTCAATAGAGCTCATTACAAGTTAACCACGCCCACCTTTAATATAAACCTTTACCCCTCGTGGCAATTAACTTTAACCGCTACTCCGGTG |
| 85 | TGGCCCTTAGACCTCTGCCCATGCTTAGGCGCTTACCCACACCTATTAGTACGGCGCCAATGCCCACGGCCATGAAGTACATTAAGGCACCCATGGTTGCACCGTAGAGTGCCGTGAATGTTCCGTAGAATACACCGGCC |
| 86 | TCGGCGAATCTGTCGAGCTCCATGACGTCCACAGAGCCGCCGAACTTGGCCGAGAATCTATCGGCCTGGGCGGTGCGCCTCCCTATCAGCAAAACCCTGGGCGCCGTCAGTAGCGCGACGGCCCTGGCGATTCCCCTGGC |
| 87 | TCCAGGTAGGATCTGGCCGAGAGGGAGGACGCCGCGCTGTTGTGCTCCGGGAACCCTAGAGTCACGACCGCCTTGACGCCTATACGTTCGGCGTATTCAGCGACGGCGGCGCCGGTGCCGCCCGTCAGCGTGACGGCAAG |
| 88 | GCAAGAGAATACATTTTTGATGATAAGAGAAGCTTGTGGCATACTTTCTTAGGCTTTATTTCAGCATTCACTTTAGCGTATTCTATCGTTATTTTGCTATTGTTCACATTGTATCAAGTGAGAGAAAGAGAGAAGCCAAC |
| 89 | AGAATCAAAGGAGTGGTGTAAAGATGGAGAGAAAAAAAGGTTGGCATCCTATTTATGTGAGTGAAGCGGTTTTAAGTAAGTTAGATAAAGAGAGAGAAGAAATTAAAGAAGAATTAGGTATTCCAAAGGAAGAGAATTTG |

TABLE 1-continued

| SEQ ID | |
|---|---|
| 90 | GTTCAGCATAAAAGACGGTTTCACGGGCCAAAGCCTAAGCGGCGTAACGGTGAAAGAAGGAGAT<br>ACGGTTTTGGGCACGATTGACGACGGCGGGACGCTGGAGCTCACGAGGGGCACTCACACCTTGA<br>CTTTCGAGAAGC |
| 91 | CTGATGTTATAGAAGTCCGCAAGGACGGCTCTGTCATCTCGCCCGAGGGTGGGAAATACTATCT<br>CGGCGACATAAGCGGCCCGACACAAATTAGCATCAAGTTCAAGGCCGGCGCGGTGGGAACCCAC<br>GGCTTCACTATC |
| 92 | TCTCCCTCAACCTTCGCGGGGAGAACGGCGCGGAGTACTGGACGGGCTACGCGGACGCGCTGGA<br>AGACCTGTTGAAGAAAATCCAGAGGCGGGAGGTGAGGGCATGAGAAGGTATTGTTACATCACGT<br>GGGGATGGATCA |
| 93 | GAGCGCCGGGAGGTGAGGGCATGAGTGAGGAATTGATGTTTGGTCGTGTCGTGGAGTATGTTCA<br>GCATAGTTTCTACAAGAAACCGTTTCCTCTTGGCAGTGAGCTCAAGAATGCAGTAGAGAAGGTT<br>ATGGAAACAGGA |
| 94 | AGGTCAGAGCCCACGTGGCAACTTTTGAGGTTCTGACAAAAGACTATGTTCGTGAGAAATACAA<br>AGACATCATAGAGTTCATGAGGGAGAAAGGGACAGTATCGAGAAAGGAACTGCGGAAGAAGTTC<br>TTCTTGCTTGCT |
| 95 | GTACCTCAAAATACAGAATCATATTTTACAATCGCTTGGAAATATTAATATCAACAATACGCAA<br>GTCCAAATTAACGTCCCTGGCAAACAGGTGACAATTTATACCCACGAAATACTAGATAACGCCA<br>AAAAGGCACTCG |
| 96 | CTTTGTATACTTAGATCAGGAAATGGAGCTAAAAGGCACTATCAAGAAGACAAAAGATTCCTGG<br>AGAGAAACATTTAAAGAGTACTCCAAGACAGACAGCGAATATCTAATAAATTACAGACTGTTTT<br>CAATACTCCCTC |
| | Primer and Core Sequence |
| 97 | ACAGTTCTCCTTCTTAGCTTCGTGAGAACCAATTGCTCCCTCGTATCCCTTGTACATTATCTCA<br>GCTCCGCTTAATGATATTAATTTTACCTTGAGTGTTTTTGCTAAAGCCTTTGCCATCATCGTTT<br>TACCTACTCCAGGTGGCCCGTAAAGCAACACAGCTTTGGCACACATCATGTAGTAGACGACCAA<br>GACAGT |
| 98 | ACAGTTCTCCTTCTTAGCTTCGTGAGAACTTCTCCAAAACCTACCCAGTTCTCCGAGGAACCTC<br>TTAGCATCTGTTAAATCGTTATTAGTATTAGCTTCCACCATCTCAAGTTCCTTTAAGGCGTTAC<br>TCACACTCTTCTTACCTATCTTTTAGAGAACCACTCGTCAGCACATCATGTAGTAGACGACCAA<br>GACAGT |
| 99 | ACAGTTCTCCTTCTTAGCTTCGTGAGAACGTTATCAAAGCCCTTAAAGAGTGGTAGGGGCAAAA<br>GTCTGAAGCGTCCTTACTTAACTGGAGTATCTGAGATGGCCTTAATCCGCTTAGGTCTTTAATT<br>TTATCCCTTAATGAACATTCCCTGCACTCTATGTCTTCGGGCACATCATGTAGTAGACGACCAA<br>GACAGT |
| 100 | ACAGTTCTCCTTCTTAGCTTCGTGAGAACGAGATGTAGCAGACGGGCTAAGAGTTTCAAACCCT<br>CTAAGGATCACTACAAACAAGAGAGAGAGACAATCCTCTCTTTTGTCTTGTCATTGTGTTTCAA<br>ACCCTCTAAGGATCACTACAAACATCTTTAACATAGATACCCACATCATGTAGTAGACGACCAA<br>GACAGT |
| 101 | ACAGTTCTCCTTCTTAGCTTCGTGAGAACGACCGGACGTTGTGATCACGGGTACCTTGATCTGG<br>TACTCAAAGGTTTGCCCCCGTGAAGTCTGGTACATGGCTAGACACGTCACTCCATTCGAGGGAC<br>ATTCGAAGTTAGAGAAGGGCAGAGCGATACATCAGATATATCACATCATGTAGTAGACGACCAA<br>GACAGT |
| 102 | ACAGTTCTCCTTCTTAGCTTCGTGAGAACGTCTTTTCTCTACTAATTCTCCTCACGAGATCTCT<br>AAACATTCTTGCTGAAAGAGGATCCAAACCTAATGTAGGTTCGTCAAGCAATAAAATTGGAGGA<br>TCAGTTATTAATGCTCTTGCTAAGGCTAGTTTCCTCTGCATCACATCATGTAGTAGACGACCAA<br>GACAGT |
| 103 | ACAGTTCTCCTTCTTAGCTTCGTGAGAACGATTTTGCCATCATTAAAAACAACAATTTGATCAC<br>CCATAGTCATAGCTTCTAATTGATCGTGAGTTACATAAATACTTGTGGTGTTTAACATACGGTG<br>AATATTTACAATTTCTCTTCGCATGTTTTCTCTTAGTTTAGCACATCATGTAGTAGACGACCAA<br>GACAGT |
| 104 | ACAGTTCTCCTTCTTAGCTTCGTGAGAACGTATCTTTCAATTCTCGAAAGAAAAGGTTACAAGT<br>CTCATAGATTTATTCCTCTTCACTGTTGTACGTTGGCAGCTAGAGAGAGTTTAGATTATGAGAA<br>AATTAAGAGAATATATGAGGATTCGTTTTCTTGGTTTAAGTCACATCATGTAGTAGACGACCAA<br>GACAGT |

TABLE 1-continued

| SEQ ID | |
|---|---|
| 105 | ACAGTTCTCCTTCTTAGCTTCGTGAGAACCTAATTGATTTTCCTGTACCATGTGGTAAAACAAC GCTACCTCTTAATTGTTGATCTGCTTTTCTAGTATCAAGATTTAATCTAAAAGCTAAATCAACT GAAGCATCAAATTTTGTATAAGAAGTTTTTTTCACTAATTCCACATCATGTAGTAGACGACCAA GACAGT |
| 106 | ACAGTTCTCCTTCTTAGCTTCGTGAGAACTCGGTTTTCCCGTGAACTAATAAACACCTACTGGA GCCAAGAACGGGTCAGAATTGATGGAATAAACGTTGCGGAGAATGAAATTAATTTGTACATCAG AGACATTGATGACAACGGTGACCCTATACAGTCAACTATACCACATCATGTAGTAGACGACCAA GACAGT |
| 107 | ACAGTTCTCCTTCTTAGCTTCGTGAGAACCTTAATGGAAAGTATGCTTTAGATACCTTCTGGAA CGCTATCTCACTTGGCGGGAATTCAGATATGGAGAGTAAATTAAGGGATCTGGAAGTAAAGTTA ATGTCGTTAATCTATTTAAATGAGTCACCATTAAAATCACCCACATCATGTAGTAGACGACCAA GACAGT |
| 108 | ACAGTTCTCCTTCTTAGCTTCGTGAGAACCATAATATGTTAGAGGTAGAATTTCTTTGTGATAG AATATTATTGATGAATGATGGAAGAGAATTAGCATTAGGAAAACCTAAGGAACTGGTAAAGGAT ACAGAATCTAAGAATCTTGAAGAGGTTTTCCTTAAACTTGTCACATCATGTAGTAGACGACCAA GACAGT |
| 109 | ACAGTTCTCCTTCTTAGCTTCGTGAGAACCCTTACTTCATCTCTCAAGATAAGGGTAATAAGTT CACTTCAAATATCTGGTCTTATCGCAAGTTGATTGAGGCTATAGTGTATAAGCTCTATGAGTAT GGTATAAACGTGTTCCTCGTTGTAGAGTATAACACTTCACGCACATCATGTAGTAGACGACCAA GACAGT |
| 110 | ACAGTTCTCCTTCTTAGCTTCGTGAGAACAGTCTAGGTTTTAATTCTTCAACTGCTTCAAATAC TAGCTTACTGTAGTTATCTGCCCTCATGTTAGGATATATATCTGGAATATAAGGAGGTTGATGA GTTATAAGAAGTGGATGAAATTGTTGTCACACACTCCCCTACACATCATGTAGTAGACGACCAA GACAGT |
| 111 | ACAGTTCTCCTTCTTAGCTTCGTGAGAACCTACCTCTTCGGCCTTGTACCAACGTACCCCTGAT ACAAGTTCCAAGCAGAGATGGAAAACTCGAAGATGGTATCACCCAAGATGAGATACGATATCAA TGAAGGCGAGCCTAGGTACAAGTAAAGGGATACCACGAGAGCACATCATGTAGTAGACGACCAA GACAGT |
| 112 | ACAGTTCTCCTTCTTAGCTTCGTGAGAACCTCGTAAGCGTTTCCTACCCTCGAGAGGGCCATCC TGGTGGTGAGGAAGTCGTCGAAGTGGGCTAAGTAAAAAGCGAAGATCTCGACCCACAATTACCT CCTCCTGTACACCAGGAATACCCCTATCAGGATAGAGATACCACATCATGTAGTAGACGACCAA GACAGT |
| 113 | ACAGTTCTCCTTCTTAGCTTCGTGAGAACGCGCGTCCGGGTCGCGGCCGGGGACGACCGTCTTG ACGAAGTCGGTCGACCCCTCGTCGGTCGAGATGGTCGTCACCTCGGTGTCGAGGCCGTACGTTT CGAGCGCGTCGCGTACCAGTTCGCCGTCCGCGTCGGGACGGCACATCATGTAGTAGACGACCAA GACAGT |
| 114 | ACAGTTCTCCTTCTTAGCTTCGTGAGAACCATGTACTCGTTCCAGAAGGTGAGTTCGCTCCCCT CGATTTCGACCTCGCCCACGTCGAAGCCGCCGGTCGTTTCGAGCGCGAACGACTCGACGGGACC GACGAGCGAAACTTCGCCGCCGAGCACGTCGGCGACGCGTTCACATCATGTAGTAGACGACCAA GACAGT |
| 115 | ACAGTTCTCCTTCTTAGCTTCGTGAGAACCTCGATGCGCTCGGGCTTGTAGGACTCCCCGAGGG CGTCCTTGTTGGTGAAGACGTTTTGTTTTCGCTCGAACCGGCGCATTAGCGTCGGTCCGTTGTA GCGTCCCCTTATTTAAAACCCCGATTTCATCTGATTCATGTCACATCATGTAGTAGACGACCAA GACAGT |
| 116 | ACAGTTCTCCTTCTTAGCTTCGTGAGAACTCACGGTCCGCGACGTGAATCGGGCGTTCCAGTCG GCGTTCGGCTACGACGCCGACGACGTGGTCGGAAGCGACCTCCTCGGGCGAATCGTGCCCCCGG TGCCGGACCCGGACCCGGTGCCGGAACCGGGGGACGACGAGCACATCATGTAGTAGACGACCAA GACAGT |
| 117 | ACAGTTCTCCTTCTTAGCTTCGTGAGAACGCGTCCGCGAGTTCATCCTGAACGTCGTCCCGCTG TCGCCCGGCGAGGAGCGCGGGGCGGGCTACGCCATCTACACCGACATCACGGAGCGGAAGACCC GCGAAAGCGAGCTAGAGCGACAGAACGAGCGATTGGAGGAGCACATCATGTAGTAGACGACCAA GACAGT |
| 118 | ACAGTTCTCCTTCTTAGCTTCGTGAGAACGCGAGACCGGCGACGAGGTGCGCTTCGACACCGCC GAGCGGGCGCTCGAACAGATGGAGGAACTCATCGACGACCTGCTGTCGCTCGCCCGTCGCGGCC AACTGGTCGACGAGACGGAGCGCGTCGACCTCGGGGCGGTCCACATCATGTAGTAGACGACCAA GACAGT |
| 119 | ACAGTTCTCCTTCTTAGCTTCGTGAGAACACGAACTCGTCGGTGAACATCTCGTCTTCCGGGGA GCCCGCCGCTCATGGCCTGCCCCCGCCGTAAGCTGCTGCATAAACCCGCTCCAAAATATACGGA TCATTCACCCCTTGGAATCGCTCAATCAGATCAATGTACACCACATCATGTAGTAGACGACCAA GACAGT |
| 120 | ACAGTTCTCCTTCTTAGCTTCGTGAGAACTGCGTACATTCCCCCTAAGCGGCTCCCAATATACA GACGCCGGTTAACGACAGCTGGCGACCCTGTGATCTCAGTACCGGTGTCGAATGACCACATCAG |

TABLE 1-continued

| SEQ ID | |
|---|---|
| | CTTGCCTGTCCGTGCATGGAGTTCGTATACGTACCCGTCGTCACATCATGTAGTAGACGACCAA GACAGT |
| 121 | ACAGTTCTCCTTCTTAGCTTCGTGAGAACAGATAGATGAGCCGATCAGAGATCGCTGGTGAGTT GGTAATTGTCCCGACATAGACACGCCAACGTTCTGTTCCATCTGCTGCGTCGTAGGTCGCGAGA TACGGCCAGCCACCAACATACACAATCCCATCGACGAGGACCACATCATGTAGTAGACGACCAA GACAGT |
| 122 | ACAGTTCTCCTTCTTAGCTTCGTGAGAACATACACCACCCCATCAGCAACAACTGAATCATGAT TAAGTATCGCACCAGCATCGTAGCGCCAGCGTTCACTGCCAGTGGTGCTATCGAATGCATAGAA GATATGCTCCTAATCGCCAATATCAGTACTTCACAAAGCCGCACATCATGTAGTAGACGACCAA GACAGT |
| 123 | ACAGTTCTCCTTCTTAGCTTCGTGAGAACTCGACGAGGAGAGGGGCGAGTACATCTGCACGCTT ACGGGAGAGGTAGTTGAGGAGACGGTTATAGATACAGGGCCCGAATGGAGGGCTTACACACCTG AGGAGAGGACCCGCAGAAGCCGCGTGGGCAGCCCGCTTACCCACATCATGTAGTAGACGACCAA GACAGT |
| 124 | ACAGTTCTCCTTCTTAGCTTCGTGAGAACAGTCGATGGCTGCGGCAGCTGTCTATGCTGCCTGC CGTATACGCGGCATACCCAGGAGTATAGACGACATAGCGGAGGTCGTGAAGGGTGGCCGTAAGG AGGTTGCCCGCTGCTACCGCCTCATAGTCCGCGAGCTGAAGCACATCATGTAGTAGACGACCAA GACAGT |
| 125 | ACAGTTCTCCTTCTTAGCTTCGTGAGAACGTGGAGTCTTTTGTCACACCGCAGAGGCGTAGCGC TGCAGAGCAGGAGCCCAAGCCTACTGCCAACATAGAGAACATAGTGGCTACAGTATCCCTCGAC CAGACTCTAGACCTGAACCTCATAGAGAGGAGCATACTGACCACATCATGTAGTAGACGACCAA GACAGT |
| 126 | ACAGTTCTCCTTCTTAGCTTCGTGAGAACCGTCGCCTGGGTTAAGAGGATGTTCGGCCTCTCCA AGGCGGGTCACGGAGGCACGCTGGACCCGAAGGTCACCGGCGTCCTCCCCGTAGCCCTGGAGGA AGCAACCAAGGTCATAGGCCTGGTGGTGCACACGAGCAAGGCACATCATGTAGTAGACGACCAA GACAGT |
| 127 | ACAGTTCTCCTTCTTAGCTTCGTGAGAACCGTGGGCGAGATCTACCAGAGGCCGCCGCTCCGCA GCAGTGTTAAGAGAAGCCTCCGCGTCAAGAGGATATACGAGATAGAGCTGCTGGAGTACAACGG CAGGTACGCGCTCATGAGGGTGCTCTGCGAGGCCGGCACATCACATCATGTAGTAGACGACCAA GACAGT |
| 128 | ACAGTTCTCCTTCTTAGCTTCGTGAGAACCGCTGGAAGAACGAGGGCAAGGAGGACCTGCTGCG GAGCTACATCAAGCCCGTCGAGTACGCCGTGAGCCACCTGCCCAAGATAGTTATACGCGATACC GCGGTGGACGCCATAGCCCATGGCGCGAACCTCGCGGTGCCCACATCATGTAGTAGACGACCAA GACAGT |
| 129 | ACAGTTCTCCTTCTTAGCTTCGTGAGAACGGGAGACCCCAAGGTGACCGGCGTCCTACCAGTGG GGCTCGCCAACAGCACCAAGGTCATTGGTAATGTTATACATAGTGTTAAAGAATACGTGATGGT TATACAGCTCCACGGCGATGTAGCCGAGCAGGATTTAAGAACACATCATGTAGTAGACGACCAA GACAGT |
| 130 | ACAGTTCTCCTTCTTAGCTTCGTGAGAACTAGAGGGAAAGACTGTAGCTTTCATTCCTAGGCAC GGAAAGAGACACAGAATACCTCCACATAAGATAAATTATAGAGCTAATATATGGGCATTAAAAG AACTAGGAGTGAAATGGGTCATCTCAGTTTCTGCCGTAGGACACATCATGTAGTAGACGACCAA GACAGT |
| 131 | ACAGTTCTCCTTCTTAGCTTCGTGAGAACTGAGGGAGCTCAGGAGGACTCGCACGGGGCCCTAC AGGGAGGATGAGACACTTGTAAGGCTCCAGGACGTCAGCGAGGCCCTGCTCCTGTGGAGGAGCA ACGGGGATGAGAGGTATCTTAGACGCATCGTGCTACCCGTTCACATCATGTAGTAGACGACCAA GACAGT |
| 132 | ACAGTTCTCCTTCTTAGCTTCGTGAGAACGAAACATCTATCGCCCACCTCCCGAAGATAATGAT CTTGGATACAGCTGTCGACGCCATAGCACATGGTGCCAACCTGGCTGCCCCAGGCGTCGCCAGG TTAACCAGGAACATCGCGAAGGGTAGTACCGTAGCGATCCTCACATCATGTAGTAGACGACCAA GACAGT |
| 133 | ACAGTTCTCCTTCTTAGCTTCGTGAGAACTCGCTATCCCCGTGTACAGCATGGTGGGGGTGCCG ATGCCCGGGTAGAACTTGGTGACGCTCTCCAGCTTCTCGAGGACGGTTTCCTTGGGGAGGCTCG CGGTGTCCACGAGGGTTATCGCGTCCTCGGCGCCGTCGCCGCACATCATGTAGTAGACGACCAA GACAGT |
| 134 | ACAGTTCTCCTTCTTAGCTTCGTGAGAACCGAGGACGCGAAGAGCGCGGTGGATGTGGACGCGC CGCCGCACACGTAGCCGTCGAGGTAGCGCGGAACCATCGGCGACATCAGCCCCACGACGCGACC CGAGGCGTTGCCGAGGATCACGTCGAGCGTCACGCGCGGCACACATCATGTAGTAGACGACCAA GACAGT |
| 135 | ACAGTTCTCCTTCTTAGCTTCGTGAGAACCTCGACACCGTGCCGTTGCCCTCCTCTAAGTAGTC GGAAAGCCTCATCCGCGACTCCAGCTTCGCCACCGGCTCCTCGAGCAGGAGGAGGACGCGGTTG ATGCGGTAGGACGCACTGCCCGCCTCCAGCACCGCGCCGTCCACATCATGTAGTAGACGACCAA GACAGT |

TABLE 1-continued

| SEQ ID | |
|---|---|
| 136 | ACAGTTCTCCTTCTTAGCTTCGTGAGAACTCTATGGTGTAGAACGGGTCGTTGCGGAGCCAGCC TGGCGGCACGTACCGGTCGTCCGCTATCGCCAGCGATCTCTCGAAGAGGTCGAGGTAGGCGGAC GCGTTGGCGAACGCCCCGTGTATCACGACGTCTATCCCGCCCACATCATGTAGTAGACGACCAA GACAGT |
| 137 | ACAGTTCTCCTTCTTAGCTTCGTGAGAACGTATAGGTTTCAGGTATTGATAATGCATAGGAGGT TTTTAAAACCTTGAGCCGCATAGTCTTCTGGATGGGCGAGAGACATGGTTAAGTATAAGTGCGG CAGGTGCGGATACGTCTTCGACGACGAGGAGATGAAGAGGACACATCATGTAGTAGACGACCAA GACAGT |
| 138 | ACAGTTCTCCTTCTTAGCTTCGTGAGAACCCTACGCCGGGTGCGTAGGAGGGCTCGAGTACATC CATGTCTATACTGATGTATGTTTTACCCAGGTCGCCTAGTGCCAGGGGTCCCTTTAACGCTTCC AGGATAGAGTACACGGTGACGTCTCTAGTCTTCTTCAAGAACACATCATGTAGTAGACGACCAA GACAGT |
| 139 | ACAGTTCTCCTTCTTAGCTTCGTGAGAACCTACTAGCGTGTCAACGGAGCTCTTCAACGCCTTT ACTATTGGATAGGTTATAAGGTGCTCGCCTCCGAGGAATCCCAGGAGCATGCCGGGATACTCGT CTACAACGCCTTTCACCACGTCACCTATGATTCTTAAAGAGCACATCATGTAGTAGACGACCAA GACAGT |
| 140 | ACAGTTCTCCTTCTTAGCTTCGTGAGAACCATAGGTGACATGGGGTTTCCCATTGACTCTATAA AGCCGTATCCTTTAAGCGGAGTGCAATTGGTCTACGCTTTGCTTAACAACAGGTATTTCCTACC GGGTAGAGAGGGCTCGCTCATAGCTTTAGGTAGCGTGACGGCACATCATGTAGTAGACGACCAA GACAGT |
| 141 | ACAGTTCTCCTTCTTAGCTTCGTGAGAACGGTATCTCACCGCTTGTCACCATAGTATCCCTCAG GTACTCCAGTATTCTTGAGAGAAACGCACCTAAGCCGGATCTCAGGTTTGAATCCATAAGAACT ATGAGTGAAGCGGGATTGAAGCCCCTGCTGTTTCTAAGACCCACATCATGTAGTAGACGACCAA GACAGT |
| 142 | ACAGTTCTCCTTCTTAGCTTCGTGAGAACTAAGGGAGATAGAGAAACGCATCAAAATACCCTTG GGGAAACTGCGTGCAGGGGTTCAATATGGAGTAGAGGTCTCAGACATAAAGGAGAAGATAGCTG CTTACGCTAGGAGGAAGGGGCTTAAATACTTCCCATCGGCACACATCATGTAGTAGACGACCAA GACAGT |
| 143 | ACAGTTCTCCTTCTTAGCTTCGTGAGAACTGTGAACCTCGTGCCCGGCTCTAAGTCGTGAGGGC TTGCAACATAGGTGGGGAGGAACCCGAGCAACGGGTAAGAAGACAGGATAAGCGGTATCGCTAT GAAGAGGGCTGAGAAAAGGACATATACTCCTGAGCCCGTCCCACATCATGTAGTAGACGACCAA GACAGT |
| 144 | ACAGTTCTCCTTCTTAGCTTCGTGAGAACCGAACATGCCTTCCCCGTCTATATAGACCCAGTAG AGTTTAAAAACTTAACCAGAGACGGCTTGTGAGCCGGATCTCTCCCCCGCTAGGCCCTGGATTG GGCTCGCTCCTCCTGGGACCCCGGCCTCCACATGCTCGGGACACATCATGTAGTAGACGACCAA GACAGT |
| 145 | ACAGTTCTCCTTCTTAGCTTCGTGAGAACCCTGAAGGGCTCGGCTACCCTGAAGACGGGCTTCT GCGCGACCGCCGCGTACTCCGCCGTGGAGCGGTAGAAGAGCGAGGCTGTCTCCGTGAGCCTGAC CATTCCGTACAGGGCGACTGCGACGAGCACTATGACTGCGACACATCATGTAGTAGACGACCAA GACAGT |
| 146 | ACAGTTCTCCTTCTTAGCTTCGTGAGAACGTCAAGGTGCTGATGCCGAAGGCGACTTTCGACAC CGACGATGCCGCCGACGCCCTGGCCATTGCCATCTGCCACGCGCATCACCGGCACAGTGTTGCC TATAGGATGGCGCTGGCCGGATAAGTTTGTTCTTGACCTGTCACATCATGTAGTAGACGACCAA GACAGT |
| 147 | ACAGTTCTCCTTCTTAGCTTCGTGAGAACTCTCGGTTCGGCAATAAGTAATACCAACGAGGTAT TACCATGCGCGTGACCAGCAAAGGCCAAGTGACGATCCCAAAGGAGATACGGGATCATTTGGGG ATTGGGCCGGGCTCCGAGGTGGAGTTCGTGCCCACAGACGACACATCATGTAGTAGACGACCAA GACAGT |
| 148 | ACAGTTCTCCTTCTTAGCTTCGTGAGAACCTCGATCATATGGCCGGCACGTTGGACTTGGGAGG CATGACAACGGACGAGTATATGGAGTGGCTGAGGGGTCCACGTGAAGATCTCGACATTGATTGA CACAAATGTCCTGATCGATGTTTGGGGTCCTGCCGGACAGGCACATCATGTAGTAGACGACCAA GACAGT |
| 149 | ACAGTTCTCCTTCTTAGCTTCGTGAGAACCAGGTGTATTTTACACACCTGGACAGCCAGCATAT GATGCTAGCACTCGGTGTCCCCTTATCACGGTTTCCCGCATTGTAAAGTTTTCGCGCCTGCTGC GCCCCGTAGGGCCTGGATTCATGTCTCAGAATCCATCTCCGCACATCATGTAGTAGACGACCAA GACAGT |
| 150 | ACAGTTCTCCTTCTTAGCTTCGTGAGAACCTGGAGCCTGTTAGTTGTTACAGGTTCACCGGTTG TCGGAGTATTCAGATCATTGAGCCAGCAGTTGATGGCTGCCTGTAGTTCACTGGTTGTGATGTA AGCTGCTCCATCGGAATCAACATCGTTCCATGGGTTCCAGTCACATCATGTAGTAGACGACCAA GACAGT |

TABLE 1-continued

| SEQ ID | |
|---|---|
| 151 | ACAGTTCTCCTTCTTAGCTTCGTGAGAACACGGTCTTGCTTTCTCCTGAATCCATTTCACCTGT CCAGACCCATTCATAGCGGTTAGCTTCACTGAGGTTCTGCTTGAAGACACCGTCATCATTGTTA GATGAGGTTATTGTCCAGCCGGCAGGAATGACTTCTTCGAACACATCATGTAGTAGACGACCAA GACAGT |
| 152 | ACAGTTCTCCTTCTTAGCTTCGTGAGAACGTCAGCAGCTCTTCATAGAAGTTCTGGTTTGCAAT ATCCCTCTGGGCAATGACAGGGTAGTCGACTTCGTTTGCAGTCAGGTGGACTGCATACAGGGAC TTGCTGATGTCCGGGGTATATCCACTGTGAGGAGCATAGTACACATCATGTAGTAGACGACCAA GACAGT |
| 153 | ACAGTTCTCCTTCTTAGCTTCGTGAGAACACCCGTCAGTCGTGACGTCCTCCGCTCCTCCTATG CTATCTCCACACACCCACTCACGTTCTTGCTTCTTTACTACACCCTCTTTATTCAGCTCTTCGA GAACATTATTAATGTGACCCTTAGAGATATATTCATTATACCACATCATGTAGTAGACGACCAA GACAGT |
| 154 | ACAGTTCTCCTTCTTAGCTTCGTGAGAACGTGCCTCCTCAAGCGACTGCTTAAACCCAATTACA TCTGATTTATCCTTTATTTAGGGCCTATAGAATCTATGAATAATTCGGCGATTCTTATTATTT CTAAAACCAATTCGTCTGTTTTGAGTGGTGTGCCTTCTTCACACATCATGTAGTAGACGACCAA GACAGT |
| 155 | ACAGTTCTCCTTCTTAGCTTCGTGAGAACCATCCCATGCATTTTCATAATAATCGGAATTCAAA TCCTCTATATTGAATTTTATCTTAACATTTGACATAATCATTTTCTCCTTACAGAAGAGATCCA GCTAAGCTTACTCATAAATGGTAGTACCATGCCAATATTGGCACATCATGTAGTAGACGACCAA GACAGT |
| 156 | ACAGTTCTCCTTCTTAGCTTCGTGAGAACCGTAGCCCGCACCTTCCTCTGGTTTAGCACCAGCG GTCCCCACAGAGTACCCATCATCCCGAAGGATATGCTGGCAACAGTGGGCACGGGTCTCGCTCG TTGCCTGACTTAACAGGATGCTTCACAGTACGAACTGACGACACATCATGTAGTAGACGACCAA GACAGT |
| 157 | ACAGTTCTCCTTCTTAGCTTCGTGAGAACCCTGATAGGCCGCAGATTCATCCTAAGGCGCCGGA GCTTTTGACCACAGAACATTCCAGTATCTATGGTATATCTGGAATTATCACCAGTTTCCCGGTG TTATGCCAGACCTTAGGGCAGATTATCCACGTGTTACTGAGCACATCATGTAGTAGACGACCAA GACAGT |
| 158 | ACAGTTCTCCTTCTTAGCTTCGTGAGAACTGTTTGGCTTGATACTAATAAAAGCACAGCTAAAA TGAAAATAAGCCGATATTTGTGATTCATGCAACTCACCCTTTTCTACATAAACAAAATACTAAC CCGAAAACCGAAATTGAAATTAATGCAGAGAAACCAGGTGACACATCATGTAGTAGACGACCAA GACAGT |
| 159 | ACAGTTCTCCTTCTTAGCTTCGTGAGAACTTAACGGCACCAACAGTTATTATATTTTTAGCAGT CCCGGGTGAAGTAATTATGGAATAGTTGTTAGAATTACTGTTCTTATTACCAGCTGATTTGAAA GCAATTATACCTGCATCACGAATTGCAGCATCATAATATTCCACATCATGTAGTAGACGACCAA GACAGT |
| 160 | ACAGTTCTCCTTCTTAGCTTCGTGAGAACGGCTCAGACGACTGAAAAAGCAACGATTGGAATAA TAGGGGGTTCTGGGCTCTATGATCCTGGTATTTTGACTAACAGCAGAGAAATAAAAGTATATAC ACCCTATGGGGAACCTAGCGATTTGATAACGATAGGTAACACACATCATGTAGTAGACGACCAA GACAGT |
| 161 | ACAGTTCTCCTTCTTAGCTTCGTGAGAACCGCAGAACAGGTTCCTTCTATTGGATATTCATCTT CGGCTGCAGTTGCAGGAAGAGTAAGGATATATACTACGGTCTTGCTTTCTCCTGAATCCATTTC ACCTGTCCAGACCCATTCATAGCGGTTAGCTTCACTGAGGTCACATCATGTAGTAGACGACCAA GACAGT |
| 162 | ACAGTTCTCCTTCTTAGCTTCGTGAGAACCTTCCTCCACGCATTTGTTGTGGTGCTGATGGCGT ATTCTCTGGAATTTGGGATGATTCTGGAAATCCATCCTCAGACACTTCAGATATTTTAGTCTTA CTTCCAGCGTTTAATTGAACCTTACCTTTAAAAGCAGTAGTCACATCATGTAGTAGACGACCAA GACAGT |
| 163 | ACAGTTCTCCTTCTTAGCTTCGTGAGAACGAAACTTACCTTATCAGTGTCATTAAGCATATTGC TTCCAAGACCCATTGAAGCACTTACATCGTTGATACACAGGTGCCAGGAATAGTATTCCTCAGT CTCACTATAATCCTCGTTGGTGTAGCCTTCAAGAGAGTCAACACATCATGTAGTAGACGACCAA GACAGT |
| 164 | ACAGTTCTCCTTCTTAGCTTCGTGAGAACGTTTAAGCAATTCTTCGGATGAAAGATGGCGCTCT ATAGGAATTTGTTCTGGTCTAGCCATAAGGCATTATTTGTACTTAATTAGTAATAAATGTTTAG TTAATGACTATAAATCTGCAATTGGAGTCTCAAATTTTCAACACATCATGTAGTAGACGACCAA GACAGT |
| 165 | ACAGTTCTCCTTCTTAGCTTCGTGAGAACAACATGAAGGATGTGTGTAAGAGGAAACGTTATTA ACAGACGTAATCAGGAGGATAGTTATGCCCTAAAAACAGCAGAGTTAAGGTTTAAAAATAAGAT AAGAACTCAGTTGAGGTTTATCCATTAATCCCATTAATCCTCACATCATGTAGTAGACGACCAA GACAGT |
| 166 | ACAGTTCTCCTTCTTAGCTTCGTGAGAACACTTTCTAAAAGCGCTTGGAGCACGTATCAGGTCA AGTCTTTCAACCTTAAATGCTGCCAGTGCCGTAAGTAGTGCAGTTATGTTGCTTATTGAAACAA |

TABLE 1-continued

| SEQ ID | |
|---|---|
| | ACAACTTAGCCCACTTATTACCTCTTGTCAGTGTTTTTGATCACATCATGTAGTAGACGACCAA GACAGT |
| 167 | ACAGTTCTCCTTCTTAGCTTCGTGAGAACGTATCCGCTGATATATCCTGGGGATATAGATCGCT CTGAAATGGTTACATCTATCGGTTTTAAGGACAGTTCCAACACTATTGGACCTTGCAGCTATGA CAGGAATAATCTGTTTATCGAGCACAGTTGAATTTGACCTACACATCATGTAGTAGACGACCAA GACAGT |
| 168 | ACAGTTCTCCTTCTTAGCTTCGTGAGAACTCAATACCTAATTCTTTCCTTAGAGTGCTATTTTG ATTGAATTCCCTCAGGAAAGATTCAAAATTTAAGTAGCCGAGCTTACATCTTGAAATTTCCATC TTTATTATGTTGCTCAGGCTTAATGCTTCTAAGTATGGGTTCACATCATGTAGTAGACGACCAA GACAGT |
| 169 | ACAGTTCTCCTTCTTAGCTTCGTGAGAACAGATATCCTTTGAAATTCTCGTAATTGCTGAAGGC CACTACTTCATCAGGTCTGATGCAATCTTTAATCTGAACATTGCTTTCTGAGGTCTTAGGAATA ATCCTGTAAGGGAGTCGGATATTGTTCGTTAAGATGCTCTTCACATCATGTAGTAGACGACCAA GACAGT |
| 170 | ACAGTTCTCCTTCTTAGCTTCGTGAGAACATAGAGGGACCTAGATTTTCAACGAGGGCAGAAAG TAGAATTTGGAGGGAAGTTTATAAAGCCGATATCATAGGGATGACTTTAGTTCCAGAAGTAAAT TTAGCTTGCGAAATGCAAATGTGCTATGCAACAATTGCGATCACATCATGTAGTAGACGACCAA GACAGT |
| 171 | ACAGTTCTCCTTCTTAGCTTCGTGAGAACGTCTTCAGCATAGTACCAGCTTATGTTGTCACCAT CGTTCAGTACGTTACCACCAAGTCCACTGCCTGCAGCTACATCATTAATGTACAGGAACCAGGC ATAGTAACCGCCAGTTGATATGTAGTCTTCACCTTCGATTCCACATCATGTAGTAGACGACCAA GACAGT |
| 172 | ACAGTTCTCCTTCTTAGCTTCGTGAGAACACTCTCCATCATGACAGCCAGATCGGTCATAGCAT CGATTGTGTACTCTTCGTCGGGATTGTTGTATGGAATGAACTTATAGTTCTCACCTGCTACCTG ATCCACTGTCATTTCTGCAAGAGTCTGCACTGTGGTAATTCCACATCATGTAGTAGACGACCAA GACAGT |
| 173 | ACAGTTCTCCTTCTTAGCTTCGTGAGAACATATTCCGTATTTCTTATCAAACCGATCGTGAAGA TTTGACAAAGGCTTAACTTTAGGGCTCCACTTCTCATTATTAGCCTTAGAATATAAAGCGTAAC CGTAAGCCTGAGGAACGTAAAGCTTAGGAGATTCAATCCCGCACATCATGTAGTAGACGACCAA GACAGT |
| 174 | ACAGTTCTCCTTCTTAGCTTCGTGAGAACTAAAATTAGCCGAAGGCTTCCCATTACCGAAAAAG TCGTTTATTAGCTCTTCATCCTTCTTCTCCACGTCCGCCCATTCCTCTCCTTCCCTTGGAATTT TAAGCTCGTCCCAGCTGACTCTTATGGGCAATTCAATATCCCACATCATGTAGTAGACGACCAA GACAGT |
| 175 | ACAGTTCTCCTTCTTAGCTTCGTGAGAACGTATAAACTTTTGATATAACCTTGCCTAATTTGAT ATCATAGCTTATGTTTGGCGCTATCCCCCACTTGTAGAGGGTCGCGTTATATTCTCTAATAGCA AGAGAGATACAAGATTCGTTAACGTTATTTATATCACTCTCCACATCATGTAGTAGACGACCAA GACAGT |
| 176 | ACAGTTCTCCTTCTTAGCTTCGTGAGAACTCCGGAGGAATCTATCATATTAAACCTCCTCAAAA TCGCCTCCTCTTGATTGCTTAAAGGCTGTGAATTACAAAGCTTATTTAATGCGTCCCAAAGCGT TAAGTAATAATTATTTATATTAAACACTACTATTTCAGTAGCACATCATGTAGTAGACGACCAA GACAGT |
| 177 | ACAGTTCTCCTTCTTAGCTTCGTGAGAACGTTCCTCCTCAATTCAATTGGACTGAAGGAGGGTA CGTTCTGGAAAACAGAGCGTAAAAGAGATATAGAACGTAGTATACACATAGCTGGAAAAAGAAC AATCATTAAGACAATAAAGAACTTTATGGAAAAGAGTAGAACACATCATGTAGTAGACGACCAA GACAGT |
| 178 | ACAGTTCTCCTTCTTAGCTTCGTGAGAACTCGTGTAAAGGTTGTATAATTCAAGCCTCAGAACA TTTCGAACTCCTTACAAAATCGTTTAAACTTTCTAAGGCATAAATTTACTAGAAATTGTCATTT ATGAGAATGTAACTATATAGATGGTAAAATTATTAATCCTCCACATCATGTAGTAGACGACCAA GACAGT |
| 179 | ACAGTTCTCCTTCTTAGCTTCGTGAGAACGGCTGAAAAATAGGTTCGATCCGCCTCCTCACTTC TTCTCCTTCTTGCCCTCGGCCTCGGAGGAGGCCTCTATTCCCAGCTTCTTGGCCTCCTCCTCGG TCGTCATGAACAGGCTAGTCCTCTGCCTTCCGCCCATGCTCCACATCATGTAGTAGACGACCAA GACAGT |
| 180 | ACAGTTCTCCTTCTTAGCTTCGTGAGAACGACCTAGCCTTACGCACAGCCCTCTCCACAACCTC CTCAAGCTTATCCCAGTCAATAGAGCTCATTACAAGTTAACCACGCCCACCTTTAATATAAACC TTTACCCCTCGTGGCAATTAACTTTAACCGCTACTCCGGTGCACATCATGTAGTAGACGACCAA GACAGT |
| 181 | ACAGTTCTCCTTCTTAGCTTCGTGAGAACTGGCCCTTAGACCTCTGCCCATGCTTAGGCGCTTA CCCACACCTATTAGTACGGCGCCAATGCCCACGGCCATGAAGTACATTAAGGCACCCATGGTTG CACCGTAGAGTGCCGTGAATGTTCCGTAGAATACACCGGCCCACATCATGTAGTAGACGACCAA GACAGT |

TABLE 1-continued

| SEQ ID | |
|---|---|
| 182 | ACAGTTCTCCTTCTTAGCTTCGTGAGAACTCGGCGAATCTGTCGAGCTCCATGACGTCCACAGA<br>GCCGCCGAACTTGGCCGAGAATCTATCGGCCTGGGCGGTGCGCCTCCCTATCAGCAAAACCCTG<br>GGCGCCGTCAGTAGCGCGACGGCCCTGGCGATTCCCCTGGCCACATCATGTAGTAGACGACCAA<br>GACAGT |
| 183 | ACAGTTCTCCTTCTTAGCTTCGTGAGAACTCCAGGTAGGATCTGGCCGAGAGGGAGGACGCCGC<br>GCTGTTGTGCTCCGGGAACCCTAGAGTCACGACCGCCTTGACGCCTATACGTTCGGCGTATTCA<br>GCGACGGCGGCGCCGGTGCCGCCCGTCAGCGTGACGGCAAGCACATCATGTAGTAGACGACCAA<br>GACAGT |
| 184 | ACAGTTCTCCTTCTTAGCTTCGTGAGAACGCAAGAGAATACATTTTTGATGATAAGAGAAGCTT<br>GTGGCATACTTTCTTAGGCTTTATTTCAGCATTCACTTTAGCGTATTCTATCGTTATTTTGCTA<br>TTGTTCACATTGTATCAAGTGAGAGAAAGAGAGAAGCCAACCACATCATGTAGTAGACGACCAA<br>GACAGT |
| 185 | ACAGTTCTCCTTCTTAGCTTCGTGAGAACAGAATCAAAGGAGTGGTGTAAAGATGGAGAGAAAA<br>AAAGGTTGGCATCCTATTTATGTGAGTGAAGCGGTTTTAAGTAAGTTAGATAAAGAGAGAGAAG<br>AAATTAAAGAAGAATTAGGTATTCCAAAGGAAGAGAATTTGCACATCATGTAGTAGACGACCAA<br>GACAGT |
| 186 | ACAGTTCTCCTTCTTAGCTTCGTGAGAACGTTCAGCATAAAAGACGGTTTCACGGGCCAAAGCC<br>TAAGCGGCGTAACGGTGAAAGAAGGAGATACGGTTTTGGGCACGATTGACGACGGCGGGACGCT<br>GGAGCTCACGAGGGGCACTCACACCTTGACTTTCGAGAAGCCACATCATGTAGTAGACGACCAA<br>GACAGT |
| 187 | ACAGTTCTCCTTCTTAGCTTCGTGAGAACCTGATGTTATAGAAGTCCGCAAGGACGGCTCTGTC<br>ATCTCGCCCGAGGGTGGGAAATACTATCTCGGCGACATAAGCGGCCCGACACAAATTAGCATCA<br>AGTTCAAGGCCGGCGCGGTGGGAACCCACGGCTTCACTATCCACATCATGTAGTAGACGACCAA<br>GACAGT |
| 188 | ACAGTTCTCCTTCTTAGCTTCGTGAGAACTCTCCCTCAACCTTCGCGGGGAGAACGGCGCGGAG<br>TACTGGACGGGCTACGCGGACGCGCTGGAAGACCTGTTGAAGAAAATCCAGAGGCGGGAGGTGA<br>GGGCATGAGAAGGTATTGTTACATCACGTGGGGATGGATCACACATCATGTAGTAGACGACCAA<br>GACAGT |
| 189 | ACAGTTCTCCTTCTTAGCTTCGTGAGAACGAGCGCCGGGAGGTGAGGGCATGAGTGAGGAATTG<br>ATGTTTGGTCGTGTCGTGGAGTATGTTCAGCATAGTTTCTACAAGAAACCGTTTCCTCTTGGCA<br>GTGAGCTCAAGAATGCAGTAGAGAAGGTTATGGAAACAGGACACATCATGTAGTAGACGACCAA<br>GACAGT |
| 190 | ACAGTTCTCCTTCTTAGCTTCGTGAGAACAGGTCAGAGCCCACGTGGCAACTTTTGAGGTTCTG<br>ACAAAAGACTATGTTCGTGAGAAATACAAAGACATCATAGAGTTCATGAGGGAGAAAGGGACAG<br>TATCGAGAAAGGAACTGCGGAAGAAGTTCTTCTTGCTTGCTCACATCATGTAGTAGACGACCAA<br>GACAGT |
| 191 | ACAGTTCTCCTTCTTAGCTTCGTGAGAACGTACCTCAAAATACAGAATCATATTTTACAATCGC<br>TTGGAAATATTAATATCAACAATACGCAAGTCCAAATTAACGTCCCTGGCAAACAGGTGACAAT<br>TTATACCCACGAAATACTAGATAACGCCAAAAAGGCACTCGCACATCATGTAGTAGACGACCAA<br>GACAGT |
| 192 | ACAGTTCTCCTTCTTAGCTTCGTGAGAACCTTTGTATACTTAGATCAGGAAATGGAGCTAAAAG<br>GCACTATCAAGAAGACAAAAGATTCCTGGAGAGAAACATTTAAAGAGTACTCCAAGACAGACAG<br>CGAATATCTAATAAATTACAGACTGTTTTCAATACTCCCTCCACATCATGTAGTAGACGACCAA<br>GACAGT |
| | Core Sequence |
| 193 | CAAATGCTTTCAGTGGTTTCCAATGCCCTGACCAGCCTGTACTCAACTAAGGGATATGACGTAA<br>CATTCAGTGACCTGATCGCCGCCATTCAGGCAATGAAGGGCTACGATGACAGCGCAAACGCTAA<br>ACTCGTCGTGGA |
| 194 | AGTCGGAGCTTATAACCACAGATCCTGAAGTATTGAGAAAGAGAAGGGGATGGTGAGATAAACA<br>TGAGGTGTGNNNAAAGCTGACAATATGTACGCGTGCTTGAAGGACACTGTTGTGAAGGAAAGGT<br>ATCCTGTCGCTA |
| 195 | ATGCAGTATATGGCAGGTGCGAGCAACTGCTTTACCATGGGTGCCATGGTGCAGAACGGGAGAA<br>GCTCCCTCTACTGGAAGGTTAAGGACGCAAATTTCTGGTCCAAGACTTTCGAGAGCAAGTTGCG<br>CGTTCTGGGGCT |
| 196 | GGCTGCGGAAGCCAGCAAGGAACCTTGTCTCTTCAGGAGAGGCAGGATATACGTCACATTCAAT<br>GTAAGGAGGGTGGCACTGAGCGGTGCGGGACAGTTGACTGCCGCCAGGACTTATGCCATAGGCA<br>ACACCGATGCGA |
| 197 | GATGAGGTTAAGGGGATATGCGAGAGATTCGGCAAGGTCGTGGATGCCGTGAACTCTCCTGTGC<br>TTACCGAGAGTAATGCCTCGTACAGGAATGCGGGGCTGGTGCGTGCCAGGTTCAACTGGGACTA<br>CATCAGGCCCGA |

TABLE 1-continued

| SEQ ID | |
|---|---|
| 198 | TGGTCTCCACGGAAGGCTACATGGACAGGGCAATAGGCGTCCAGGATATCGGCTACCTGTTCTG GCAGGCAGGTCCCACCGCAATGAAGGATATGAGAATTTACAACGGTCCCGGTGGTCTGATCGTT CTGCCTTTCTAT |
| 199 | CTTTCTGCGCGCAACAGGCTGGCCAAGGGACTTCCGAAGAGCCTGGACATGTTTGCCAGCGTGG AAGGTCGTGACCTTGGGTACGATCCGAGGTACATAACAGAGGAAGATTACAAGACCATTATGAC CAAGGCCCGTCT |
| 200 | GGCATGATAGATGAGGATGGCTACGAGGTACCGAAGGGTGAAGACCCCAACGACCCCAGAAGTG CACACACCTTTGGTTGGGTCGACCAATCAGATGGAGGCACATCCAATGGTGGCATGCAGTCCGG TGGGAGCTCTCA |
| 201 | CTTAAGGACGGGGACGTGACAAAGCTGTATTCTCAGGACGATTACCTCAGGGTCAGCAGGCTCA AGTTCAGCGAGAATCCGATGCTTGGCATCGTCAAGAATACGGATGGCACAGGGGAGGTTATAGG TCCGTCCTTTGC |
| 202 | AGGGACCTTCTGTGGAACATAATCTCGGGTGCCCTGAATGCGGGAAGGGAACAGCTCTACGGGG ATGCATTCGGCGGTCCTAAGATAGAGCAGTACGTGAAAGCACTCACGCAGGTGCTGTATGACCT GTCTGTCAACAG |
| 203 | TGAAGGAACGCGTCATCGTCCACAAGAGCACTACGAGGAACGAAGTCCTTGAAGAGTTCAAGGC GTCTAAGGAGCCGAAGGTCCTATTTGCGATAAAGATGGAAGAGGGTACGGATTTCAGGGATGAC CAGGCAAGGTGG |
| 204 | CAGATATTGGTCAAGACTCCTTACCAGGATCTGGGAGACGAGTGGGTCCGCCTCCATAGGGAGA AGATGGGACGGAGATGGTACGAGATATCCGCCCTCCAGCAGGTCATCCAGGCGAGCGGCAGGAT AATGAGGAACGA |
| 205 | CAGGGACTGGGGAGACACCTACGTCCTTGACATGAACGCCATGAAGCTCATCCGCATGTACGAA AAGGAATGCCCCCGCTGGTTTTTGAAGAGGTTGAAACTATGACGCATCACAATATCACCTTCCC CGTCCCTCCCGA |
| 206 | GCAATGTCCGCAACAGTTGACAACGTTGCACGGGTCGCGGGATGGCTCAGGGCGACTGCAGTCT CCAGCGATTTCAGGCCCGTCACCCTGAAGAAGTACGTCCTTACCCCCCGCCATATCATGGATGA GAAAGGGGATAC |
| 207 | CGAGATACAGCAGATGCTGGGGCGCGCCGGGAGGGCGAAATACGATTCCATGGGCTACGGCTAC ATCTGCTCATCCGACGTTCACCTCCAGGACGTGTATAAGACGTACGTTCATGGCCGTCTGGAGA GCGTAAAATCAA |
| 208 | GGCACTGGACGAGTTCTTCTCCACCACGCTGGCACGCCACGAGGGTGCCCGTCTGGAAGAATGG ATAGACAACAGCCTTGTCTTCCTGCAGGACAACGACATGATAGTCGGGGGACGTTCCTTCACGG CTACCCCCTTCG |
| 209 | CCATCCTTGCGGACTGGATAGACGAGAAGCCCGAAAGCGACATCGTCAATAAATACAACATCTG GCCTGCCGACCTGAGGAGCAGGGTTGAGTTGGCCGAATGGCTCTCGCATTCCCTTTACGAGATC TCGAGGGTCCTG |
| 210 | GGCGACTATTCCTACGTCAGCGTTGCGGAATATTTCTCCAGCTCAAGGATAATAGCCACTACCG CTTCCCCCGGTGGCGACAGGGAGAAGATAAACGAGATCATGCGCCACCTGAGAATAGAGAACCT TGAGGTGAGGGA |
| 211 | ATCGACGCTCCAGCTGTTCAGGGACGGTGCGGTCAGGATACTCGTAGCAACGCAGGTTGGGGAG GAAGGACTGGACGTACCGGCTGCAGATACCGTCATATTCTACGAGCCGGTGGCAAGCGAGGTCC GCTCAATCCAGA |
| 212 | CGCGGTCCTCTTTCCCAGCTTCAGTCCTTTGGCTTTCCTATGTTCTGCTGGTACTCTTCCCATT GCTCTCTCTGTTGTTTCTCCTGGCTTTTCCTGAAGTTTTCGAGGGCTTCGTCCATGCTGTCATA AGCGTTATGCGA |
| 213 | CGAACTCCTTGACGCTCCTGGAGATGACCAGTTTCTCTATCTCCACCCTCCCGCTCTTCATGTC CGATATTATTTTCCTCGCCCTTCTCAGTGCCTCGTCCACGTTCCGGTCGAGCACGAGATTGAAC ATTTCCATGAGT |
| 214 | CCCTTTCCTCGAGGTCTTTGTCTATTCCCTTCACCGTTTCCCTGGCCCAAGCAGTGATGCTGGA CCCGATACTGGGATCGGTAAACCTGTAGAAGCTTGATGCAAACACTCCGTAGAACGAATTCATA AGCACCTTCACC |
| 215 | CAGTTCTCCTTCCACCCCGTCCGCCTCTTCTATGACGGTCGCACTTTCCGTCGAGCAGACGCCC TACGGCTGGATGGATCAGTATCCCTCGTCGGTTGTTGCCCATGTCACGGGAGGCATCCCTCCCT ACGCCTATCACT |
| 216 | CAATCTGGAGGCTTTCGCCGTATCCGTCGAAGTCACGGACTCATCGGGGCATTCAGTCTCAGGT GCAATCATGATCAACTACGGTTCCATAGACCTCTCCCCGTTTGGATACATGGTAACTTTGATTT TTCCGGTGATCA |

TABLE 1-continued

| SEQ ID | |
|---|---|
| 217 | GAACATCCATTGCTGACCATCACGATCGATGGCTCAAAGGACACGTTCAAAACTGGCGATGTCC TGGAATGGTTGACCGAAAGTGACATCTCAAACATGCACAATGTTGCGTCCTTCACAAAATCTCT CCTGAGGATAGT |
| 218 | GCATGCTGCCCGATGGCCAATGGTTCGGGGAGGTCATTGGGAAGGACGTGCAGGGAAATCCCTA CGGCATTGATTATACAATGTGGTTGCCGTTTAACACCTACGTTAGGGATAAGCTCAGTTACAAT AGTTGGGGGAAG |
| 219 | CCAGCATTCCTCCTCTGAGGGAGTTCGGAAGGTAAAATCTCCTGATGACATCTGAGTCCCTGGC GCCCATTGTCTTGGCTGAGTAGACTTCCATTTTACTTGTCGTGCTGCCAGTTGAAAATGCAAGT ACTGCTATCATC |
| 220 | GTTCCCTGCAGGAATGATTGTTCAACTGCACTCGTCAGTACATGATAGAACAATCTTGAAGCTG ACAGATGGAGCGCATAGAAGATAAGGAATGCAAGAGGTACCAGTACTAGTACCACTGCATATAT TCCTGCGTATAG |
| 221 | CGATTGCAGGAACGTGGAAAGTGTGCGGTTAATGTATGACTCATTGCTCACATCGAATCGATAC AGAAGACCGCTGTTTGCTGCCAGGTAGGAATCTATGTTATTCAGGCCAACAACCACATCGTATC CCGCCCCCTTTG |
| 222 | AGGATTGAACCGGTTGGTGTCAACGTAGAATCCTCATTGACCCGCCACATAAAACTGAACATTC CAATTGTGTCGTCTCCTATGGATACGGTCTCTGAGGCAGATATGGCAATTGCACTAGCAAGACT CGGTGGTATTGG |
| 223 | CTTATTATACGCGACCTTTACACTGTAAGCCCGGAAACACCTGTTGACGATGCAATCCGTACTA TGAGGGAGAAGCGAATCGCTGGGCTCCCAGTGATATTGAACGGCAAACTTGTCGGAATACTTAC GAACAGGGACAT |
| 224 | GGTACGGCAAGATAGGCTCAGGGAAATTTGTACCAGAGGGAGTTGAAGGAGCAGTTCCGTACAA AGGTAAAGTTGCAGATGCAGTCTTTCAATTGATCGGGGGCCTGAAGTCGGGGATGGGGTATACT GGCTCGCCCACA |
| 225 | GGTGGAAGCGTTGAGGAGTTTGTCACTCTATCGAGGAGAGTGGAGGCAGCGGGATTCGACAAGG TCGAGCTCAATTTGTCCTGCCCACACGTTCAGGGAGTTGGATCCGAGGTAGGACAGGATGTAGG TCTTGTAGAAGA |
| 226 | GACACTTATAGACAGGCTAGACAAGAAGACGAAGACAAGGATATTCTTCTCACTTGAGCGATTG ATGAAGTGCGGCATAGGGATTTGTGACAGTTGCAGCATCAACGGCATCCGGGTATGCAAGGACG GAACAATTTTCG |
| 227 | CTTCGCAACTGCAAAGAGGTAGCTTCTGGATGCTTCCCTGGAACTATCCCTACATTGCTGTTAT CTTACTAGTGGTACTGATTTATGCAGCAATAGAGGACCTTAGGAAGAGGAAAATAACAACTATA ACCTTCCTTGCA |
| 228 | GTGACAGTTGGAACTGGTCTATCTCCCCGGTATTTTAATAAGTTTATAGGCGTAGCAAAGGCAT ATACGACAAGAGTAGGGGAGGGGATATTTCCTACTGAGATGTTTGGGGAAGAGGCAGATAGACT TAGAACCCTAGG |
| 229 | GAAGAAGACTTAAAGGATTTAGGTAGAGAGCTTAAGGTACCAAGAAGACCGTTCAAAAAGTTAA CGCATAGAGAAGCTGTTNATATATTGAGATCTCATGGCATAAAAGCAAGTTATGAACATGAGAT ACCTTGGGAAGC |
| 230 | ACGGGGAGGCTGTCTCAGGAGCTGAAAGAGAATATAGAGCGGAGAAGGTTATTGAGAGGATGAG AGCTACTGGTGAGAACCCTGCAAAATACGGTTGGTACATTGAAATGTTGAAATATGGTATTCCG CCGAGTGCAGGG |
| 231 | ATATGCAGATTTAGATGAGATTATAGGGGTTGCATCTAAGGCAGGAATAGATTGCATAACTATA GATGGGTCAGAAGGTGGAACAGGTATGAGCCCTATAGCTGCGATGAGAGAACTAGGATATCCAA CGCTAGTATGTC |
| 232 | GGACACGAAATTGCTGAAGCAGCTGGCTCAACATGGTATATCGACAATTTCTGGGATAAACTCA AAGAGGGCTGTGTAGCATATCTAAACATAGATTCACCTGGATTAAAAGATGCAACAAGATATAT CGCTTACGCGTC |
| 233 | GTAACTTCTGGAAACGCCCAATCAAAACAGATCATGACACCAAAGCTAAAATTATCTTCCCTAA TAGCTTCTATAGGTGTATCTCCAGGTTGAAATATTAGCTTCTCTTTGGCAAATAAGTGAAGTTT CCTATACTTTCC |
| 234 | CCAGATAGCCCAATAGCATCAATTTCCGTTGCAATAATAGGTACAGTACACAAAGAACACGTAA TTTTCAGCGACACTGCAAATACAGGCGACTTAATAATTTTTGCCATAGATCTCGATGGAACATT TCACCCTAAGTT |
| 235 | GTTCTAATTCCTCTCTTACAGCTTTAAAAGCAATCACAGCAGATTCCAAAATATCATCCATATC ATCCAGAGCTATAATAACACCTCTTGAAGTTTTCCCAATCTTATGCCCACTTCTTCCAACTCTT TGAACCAAACGA |

TABLE 1-continued

| SEQ ID | |
|---|---|
| 236 | GTAACTTGTCTGGGAGACATATATTGGACAACTAAATCAACGGTTCCTACATCAATCCCTAACTCCATAGATGATGTACAAATAAGACCTTTCAACTCACCGTCTTTAAATAACCTTTCAACTTCTATACGAACATCTCT |
| 237 | ACTCAATGAACCATGATGCACATCAATACTTAGATTAGGATCGTATAAGTGAAGCCTAGAAGCTAGTATCTCAGCTATTTCACGAGTGTTTACAAAAGTAAGCATAGAGCGGCTCTTTTCTAATAACTCAACCAATACCC |
| 238 | CAGTTAAATCATCTTAACTCACAAATATTAAGGCTTTAATTTCTGAGGGAGTGCAAAATGAAAACTGACGTAGTAATAGTAGGTGCAGGGCCCGCAGGCATGTTTGCTGCACATGAATTGGCAACTAAATCTAATCTGAA |
| 239 | AAAAATAGCCAAGGATCCAAAATTCCGTGTATATACAAAAACCTTCGATGACCTTACACGTGTATTTTGCGTTAATTATCGAGGCTTCGTCGTCCAAGAAGTCTACGGAGATATCGTTGGTGTTAACGGCCACACTCTAA |
| 240 | TCAAACAAAAATCTGAAAATGCCAATTTTGCATTTCTAGTTCGAGTTGAACTCACCGAACCGCTTGAAGACACAACCGCCTACGGATTCTCAATAGCCAAATTAGCAACTACCATAGGTGGAGGAAAACCAATTCTTCAA |
| 241 | CGAGATACTGAATTTCCAAAACTCAAAGGATATAGAATTGTTAGAATCGCAACACATCCGCAAGTTATGAGCATGGGACTAGGAAGTGAAGGGTTGTCAAAACTTTGCCAAGAAGCCGAAAAGAGAGGACTAGATTGGGT |
| 242 | CGAAGTTTTTATCCTCCTCGGTCCAAGTCACACTGGTTACCCAGGCGTTGGAATAATGACAGAAGGCATCTGGAAAACTTCTTTAGGAGAAATATCAATAGATGAAACTCTCTCGAATACTATTTTAAATAATTGTGACC |
| 243 | TGACACACTACGGCACCTACTATGGATACACACCAGCTGGTGTTGAACCATTAACCAAAGTTTTAGAATGGATATACCAGACGGACAAACAAGTTATTGAGAGAATTAAAAGATTAGATGGAGCAGGAGTAATAGAATAT |
| 244 | CTGAAAAGTTCATTCCAATTGTTAAATCGCCATCTTGGAAACACGGCACAAGAAAAGGGAAAGGATTTAGCATCGGTGAGATTAAAGCAGCCGAGATAGATATTAGTATGGCAGTTAAACTCGGTATACCCATTGATAAA |
| 245 | GGGAATAATAATTAAAATAATGTGGCACACCTTTTAGCTTCTTTTCATCTCATATTTTCAAAGAAGCCTTCCAGGTGTGCCTCATCGGTGTCCCCCGCTGCGGAGACACGGTATCATCGTATCCGCCGAAGGAAACTCAA |
| 246 | GACATTGCCTATCAATTACTTCAAGCCGGAATGCAAGTTCCCGGTTTCAGAAGGTCGCCAAAGATAATAGAAAGAATTTTAGAAAGATATATTCCAACAGTCACCGTACTAGGCGGCATTATTGTAGGATTAATAGCTGC |
| 247 | TGTCGTTCAGGGAGGTATAAAAATGCCAGAACCACGCTACCGGTCAAGGTCTTTAAGAAGACGATACGTACACACACCTGGAGGAAAAACCGTCATCCATTACAGGAGAAAAAAACCTGACGTTGCAAAATGCGCATTAT |
| 248 | GTGGTCAACCTCTCAGAGGAATTCCCAGACTAAGGCCAGGAGAATTCAGAAAGTTGACAAAAAGTCAACGAAGACCAGAGAGACCTTTCGGTGGATATCTATGCCACAAATGCTTAGCAATGGAAATCAAGAAAGCTGTT |
| 249 | ATAGGATGAATCTAACTGGGGCGACCCGGTAGATAACTGAGAGTGTAGGAGGTGAAATAATTGAGCGCAATAGAAGTAGGTAGAATATGTGTTAAAACTAGTGGAAGAGAAGCAGGAAGAAAGTGCGTTATTGTTGAAAT |
| 250 | ACACCATTTCCTAATATTTTAGTAACTAGATATGTTTGTTATAGTATTAGGGTGAAGTATTTGTATGAAAGAAAGTTGCCATCAGACATTAAAAGAGAGATTCTAGTAAAAAGTGAAGCAGAAACTGACCCTGCTTATGG |
| 251 | CACATGAGAGAACTTAGAAGAACACGTACAGGACCCTTTAAAGAAGATGAAACCCTAGTAACTCTTCACGATGTAGTTGATGCTTACTATTTTTGGAAGGAAGATGGAGAAGAAGAATTTCTACGAAAAGTCATACAACC |
| 252 | AATGGAAAAGGGTTTAGAACACCTACCTCACATTTGGATTAGAGATTCTGCTGTAGATGCAATATGCCATGGGGCAAACTTAGCAGCTCCTGGTGTTGTAAAACTTCATGACGGTATATCACCTGGAGACTTAATAGTAA |
| 253 | CGCTGATCATACATGTGCATTGTCTTTAAATACACTAGTAACGTTAATAATATCTAGCAATTTTAGATAAAAATAACTAGCAGTGCCGGGGTAGCCAAGTGGACTACAGGCCTTATACCGGTTAGGGCGCGGGCCTGGAG |

TABLE 1-continued

| SEQ ID | |
|---|---|
| 254 | CATGCCTTAACGAGAGGCATGGGATGGGGGAGCTGTGAGCCCCCCGAACCGGCAGATGAGGGGAAGGGTGCAAAGCATCCCTTAACGCCGGAAGCTCCCGACTTCAGTCGTGGAGCAGCTCACTGCTTTGACGAAAGGTT |
| 255 | GAACTTGCAAGGAAGGCCGGTGTTGATTATGAGACAAAGCTGTTGGTCAGGGGCAAGGAACCGGCTGAGGACATAATAGAATTTGCTGACGAGATCAGGGCAAGTCTCATTGTAATAGGGGTTAGGAAGAGGAGACCCGC |
| 256 | TCCAGAAGAGATTCAAAGCTCTCGTATTCAATGTCCCCACCAAATTTCTGGTCGCGCTCAATTTTGACTTTACCAAAAGCGGGGAAAACGTAGTGCTTTGCTAGGTCTATTATCGGATTTCCTTCTACAACCTTTGGCGG |
| 257 | GATTTGCTCATTTTCTCCCCGTCGAGTCCTGAGATTATCGGCGTATGGATGCAGATCGGTGCCTTGTAACCGAGGGCCGGCAGATTCTCCCTTGCGAGCATGTGGATCTTTCTCTGATCTATTCCACCAACCGCCACATC |
| 258 | TCCGGGAGTTGCAGAACCAAGCATGGAAATTGCTAGAGATCCCGAAAAGGTTTACGAGTACACGAATAAGTGGAACACGGTTGCAATTATCACTGATGGCTCGAGGGTCTTGGGACTGGGCAACATCGGTGCGATGGCTT |
| 259 | GTGGTGTTATCAAGAGGGAATATATTGCTCAGATGGCAGAGGATCCGATAGTCTTTGCCTTATCAAACCCGGTGCCTGAGATCTATCCGCAGGAGGCAAAGGAAGCCGGAGCCAGGATCGTAGGAACTGGTAGGAGCGAC |
| 260 | GGGATCTGTTAGTATGGCATTCAGAGCCTTTATGTCCTCATCGGTAAGCTTGTCCGATGGCAGATCGTATTTCACGATGTCTGAAGGAGTAACTCCGAGAAACTTCGCTTCTGGTGTCGCAAGATACTCCGAGAGATGCG |
| 261 | TGAGTGCGGCTTACTCTGCACTGTGCGAGATCGATGAGGTCGTTGTTGTTGCCCCCATAACGCAGATGAGCGGAGTGGGGAGGAGCATATCCATAATGCGGCCGGTTCGTTTTTTCGAGCTCGAAATAGATGGCATGAGG |
| 262 | AGGGGAAGGGAGTACTACTGGATTCATGGGGTGGAAGTCGAAAGCGCTGAGCCTGGAACGGACATACACGCACTCAGAAACGGGTATGTCTCCATTACACCGATATCCTTAAATGCAACTTCGGACTGCGAAGCTTTAAG |
| 263 | ATAGTTTTATGGAGGGTGGTTGGACATGAATGAAAGGGCAAAGAAGGTCATTCTTATTGTGGATGACGATTTGGCTCTGCTTGAAGCTCTTGAACTGATGCTTCGAGGCAAGTATGAGGTTGTGAAGGTGACAAATGGGA |
| 264 | ATGTCGATTCCGAAATAGCAGGGAGCAATTATCGGTGGGCTTCCGACCCTTAAATGGATTTCCTTCGCTCCCGCCTTTCTTATCATGTCGACTATTCTTTTGGATGTTGTTGCCCGCACAATGCTGTCGTCAACCAGCAC |
| 265 | ACTTTCTGAGGGAAAAACATTGTTGCTTATCCTAAAGAGTTTACAAGCAAGAAGCTGGAAACAAACTCTGGATGTTATTAATTTAGAGCCTGCAGCAGCATATACAATGTTTAGAGCGGCAATAAAGAAACTATACAAAG |
| 266 | GTGGTTGAGAGGCTGCTTGAAGGCATTGCAAAGAATGAAAGGGTAGCTTACGGATTGGAGGAGGTTAGGAGGGCAAAAGAGTATGGAGCAATTGAGGTTCTGTTGGTTTCAGATGACTTCCTGCTCACCGAGCGTGAGAA |
| 267 | TCGCTTCGAGATTCCTGATAGGAGTGGGAGTTGCCGGGGTTTACGTGCCTACGATAAAAATAATATCCGTCTGGTTCAGGCAGAATGAGTTTGCAACTGCTACTGGGATTCTTTTCGCGATTGGAAATCTAGGAGCGATT |
| 268 | GAGGTATCGCCTACTTAGAGAGTTCGTAAAGTCGGAGATATTGGAGGAAGTTAAATTTGAAAACGTTGTGGACGAGTACTGGGTTGCGGAACCATTCATAAAGATCATAATTTTTGAGGATCTCGAAAACCAGAAATTGA |
| 269 | CTAATCCGATTATCGATTCTACGCTTCCTGATGGTAGCAGGCTTCAGGCTACCCTAGGAACAGAAATTACACCTAGAGGCTCGAGCTTCACGGTGAGAAAATTTACAACCCAGCCACTGACCCCGTTAGATCTAGTGAGG |
| 270 | CAAAATTATATCGATAGAGGATACCAGAGAGATAAAGCTCCATCATGAGAACTGGCTGGCTCAGGTGACGAGAACGGGGATAGGAGAGCAGGAAATTGACATGTATGACCTTCTCAAAGCCGCCTTGAGACAGAGACCGG |
| 271 | GAATCAGTTTGTTAAATGGGATGCGAAGAAAAATTCGCATGTTGAGGTAGGGATTCCGAAAAAGCTAGAGAAAATCGCGATGTCGAGAGTGGACGATGCTTACGCGGAGCTGGAAAGAAGAAGGAGGTATTTGGAGTGGA |

TABLE 1-continued

| SEQ ID | |
|---|---|
| 272 | TCAGTGAAGTTAGCACGGAATTCGAAAGGATAGTGGTTCTCGTTGAAATGGGAGAGGATTTGGAAAGCGCAATGAGGTTTGTTGCAGAAACAACTCCCTCAGAGAGGCTCAGGGTTTTTCTGGAGAACTTTATTGATGTG |
| 273 | GCTGGAGCGGGAGGCGTATCAACGCTTGCCCTCAATCCGTTACCCGAAGTTCCAGAATACTTTGAGTATTTCCAGTCCGAATAGAAGCAGAGCACCTCTCGATCGACTAGAGTCTTTCTGCTAGCTCTTGCACCCTCATC |
| 274 | GCGGAAATCTCTGCTGAAAACACCTTGACTTTTTCTTCGTATATCTCCCATTCCATCAGGCACCACCAACTTTGGTCCTGCAAAGAGTCATCGGTGCCCCATCTGCTACGGGAACGATCTGAAAGGCTTTACCACAGAAT |
| 275 | TCCGGTTGCAGGATTGGTCTCCCCACCTCTCGAGCCTATGAGGAATACCCCATTCCTGCAGAGCTCGAGAAGCTCTTCGAATTCAAGATCCCCCTTCTGCAGGAATGTGTTGCTCATTCTGACAATCGGAAAAGCAACTC |
| 276 | AACTCCTCGATTGTTGGGTCATCGATTATTGTCACGTTCTCTCCTGCAATTCTCTCTCCAATCTTTCCAGCAAGAACGCTGTTTTCCTGCAGAACGTGATCTGCCTCGACCGCATGCCCGAAAGCTTCGTGAATAAAAAC |
| 277 | CTTTCTTCAAGAATGCTTTCTGCGGCGATAAGCCCAGTAACAGCCGCTCCAACTATTCCCCTGCTTATTCCGGCTCCATCGCCAATTGCATAGATGTACGGTATGCTTGTCCTCATCTTCTCGTCAACCTTAAGCTTCAA |
| 278 | TGCTGGATTTTTCTTTGGCCTTGCTGTGGCCGTTGACTAGACAAAAGTCGCCGTACTCCTCTCTTATAACCCAGCCCCTCGGGCAGGTGCAGAACGTGCGCATGTAGTCGTCATGCCTCTGTGTGATTATTCTCAGCTTT |
| 279 | TTGCCTTGGAATTTTCCGCCACTTCGATCTTATACTTTTTTACCCATTTTTCCAGCCAGTCGGCACCGCTCCTCCCAACTGCAATTATGAGTTTGTCGTAGCCGAACTTGTCCCCATCGTTCGTCTTCACGATCTTTTCT |
| 280 | AATCACCACCGACTGTGAAGCTCGAAGGATAGTTGGGGTTGGCATAATTCAGCTTTCCATCCGAAAGTCCTCCAGCACCACCCACACCAGAAGTAATGTTGCAGGGATCGCATTTCTTGCAATAGCTTTGCGAAAGGTCA |
| 281 | TTAACCAACCTCTTTCGCATCAAAATCCCAACTGCGGCATCCGTTATCAGCGTTACATCGATTCCATCTTTCATAAGCTCGTAGCAGGTGAGCCTAGAGCCTTGGTTCAGCGGCCTCGTTTCGCAGGCGAAAACCTTTAC |
| 282 | TTATCGAGTTAATAGCTATCAGTGTTGCTATTACGATCGTTGCGATCCCATCAAAGATGTTATGACCGAAGGAGATAGCAATAATGCCAAATATCGCTGCAAGCGTCGATAAGGAGTCGTTAAAACTCTCAAACATCACT |
| 283 | CTCCCTTCTAAGCTTCGTGATATCTGCATTGCCAATATCAACTAGAAATTCGATTGAGATAAGCTTGTCTCTTGCGGTTAAGCTTGTTCTCTCGATATTTATACCGAAATTTAGCAATACACCCGTGATATCTCTCACGA |
| 284 | AAGCGGGGCTTTGCCTTTCCAATTCCGCCGCAACCAACCGTTGGACTTATCAAACCGGAACCTTTCAACTCCGAGATTAAAGAGCCTGGCTCCTTATCGTGCTTAATAGCAATTTCTACAATGTCTTCCCCGCATACAA |
| 285 | CTAGTTCTTGGTTTTCGTCGACGTTGACCTTGTAGAACTCTACATCTGGAAACTCCTTTGAAAGCTTTTCGAGCACTGGGCTGAGATACCTGCACGGCATGCACCAGTCGGCGTAGAAGTCAACAACAACAAGCTTATCC |
| 286 | CTCCGATCGTCTTTAAAGCTTGCAAGTCTAAATCCTCGCCCCAGGGAATTTCCTGGGATTTTCTCGCAATCTCTATCGCCGAAGTATAGGTTATCCTCGGGAATGGTATCTCGGGGACTTCGAGCTTTAGTTCGAGAATA |
| 287 | GAGGTTTTGTCCCTATTGGGTTTCTCATTGCCTGCAGCATTTCTTCTCTGCTCAGAGCTCTGCAGCCATCGCCTTTCATTCTTAAAATGCTAACCTCCCAATCATCCGGAAAATCGAGCTCTATTTCCCTATCCTGCCAG |
| 288 | TGTTTACAGGCTGGTGGGTGGGGAAAGGAGTGTTAAGGGCAAAAGGAGTGTAAGCAAGTTCAGGGTTGCGATTGCGATTCTTCTGGCATTCATTCTGATATATCCTACATACCGCATAGCCGAGATTCAAAGCAGTGGGG |
| 289 | CAGGGTCAGGAGGATTCACGAGATAGAAGTCCTCGAGGTGAGAGGCAGGTTCGCGCTTATAAGGGTTCTCAGCGACCCCGGCACGTACATGAGGAAGCTGGCCCACGACATCGGGCTATTGCTCGGAGTAGGTGCACACA |
| 290 | GAAGTCAGTCATAGAATCAATGGTGTATTCTTCATCAGGGTTATTATACGGAATGAACTTATAGTTCTCACCTGCTACCTGATCCACTGTCATTTCTGCAAGAGTCTGCACTGTGGTAATTCCACCTTCTTCCATCCGGG |

TABLE 1-continued

| SEQ ID | |
|---|---|
| 291 | AGTAAGGGAATCAATGTCTTCCATTGCTGTAAGGGTTACTGTTACCTTTGTAGAAGTCAGACCG<br>TAATTGGTCAGCAGCTCTTCATAGAAGTTCTGGTTTGCAATATCCCTCTGGGCAATGACAGGGT<br>AGTCGACTTCGT |
| | Primer and Core Sequence |
| 292 | ACAGTTCTCCTTCTTAGCTTCGTGAGAACCAAATGCTTTCAGTGGTTTCCAATGCCCTGACCAG<br>CCTGTACTCAACTAAGGGATATGACGTAACATTCAGTGACCTGATCGCCGCCATTCAGGCAATG<br>AAGGGCTACGATGACAGCGCAAACGCTAAACTCGTCGTGGACACATCATGTAGTAGACGACCAA<br>GACAGT |
| 293 | ACAGTTCTCCTTCTTAGCTTCGTGAGAACAGTCGGAGCTTATAACCACAGATCCTGAAGTATTG<br>AGAAAGAGAAGGGGATGGTGAGATAAACATGAGGTGTGNNNAAAGCTGACAATATGTACGCGTG<br>CTTGAAGGACACTGTTGTGAAGGAAAGGTATCCTGTCGCTACACATCATGTAGTAGACGACCAA<br>GACAGT |
| 294 | ACAGTTCTCCTTCTTAGCTTCGTGAGAACATGCAGTATATGGCAGGTGCGAGCAACTGCTTTAC<br>CATGGGTGCCATGGTGCAGAACGGGAGAAGCTCCCTCTACTGGAAGGTTAAGGACGCAAATTTC<br>TGGTCCAAGACTTTCGAGAGCAAGTTGCGCGTTCTGGGGCTCACATCATGTAGTAGACGACCAA<br>GACAGT |
| 295 | ACAGTTCTCCTTCTTAGCTTCGTGAGAACGGCTGCGGAAGCCAGCAAGGAACCTTGTCTCTTCA<br>GGAGAGGCAGGATATACGTCACATTCAATGTAAGGAGGGTGGCACTGAGCGGTGCGGGACAGTT<br>GACTGCCGCCAGGACTTATGCCATAGGCAACACCGATGCGACACATCATGTAGTAGACGACCAA<br>GACAGT |
| 296 | ACAGTTCTCCTTCTTAGCTTCGTGAGAACGATGAGGTTAAGGGGATATGCGAGAGATTCGGCAA<br>GGTCGTGGATGCCGTGAACTCTCCTGTGCTTACCGAGAGTAATGCCTCGTACAGGAATGCGGGG<br>CTGGTGCGTGCCAGGTTCAACTGGGACTACATCAGGCCCGACACATCATGTAGTAGACGACCAA<br>GACAGT |
| 297 | ACAGTTCTCCTTCTTAGCTTCGTGAGAACTGGTCTCCACGGAAGGCTACATGGACAGGGCAATA<br>GGCGTCCAGGATATCGGCTACCTGTTCTGGCAGGCAGGTCCCACCGCAATGAAGGATATGAGAA<br>TTTACAACGGTCCCGGTGGTCTGATCGTTCTGCCTTTCTATCACATCATGTAGTAGACGACCAA<br>GACAGT |
| 298 | ACAGTTCTCCTTCTTAGCTTCGTGAGAACCTTTCTGCGCGCAACAGGCTGGCCAAGGGACTTCC<br>GAAGAGCCTGGACATGTTTGCCAGCGTGGAAGGTCGTGACCTTGGGTACGATCCGAGGTACATA<br>ACAGAGGAAGATTACAAGACCATTATGACCAAGGCCCGTCTCACATCATGTAGTAGACGACCAA<br>GACAGT |
| 299 | ACAGTTCTCCTTCTTAGCTTCGTGAGAACGGCATGATAGATGAGGATGGCTACGAGGTACCGAA<br>GGGTGAAGACCCCAACGACCCCAGAAGTGCACACACCTTTGGTTGGGTCGACCAATCAGATGGA<br>GGCACATCCAATGGTGGCATGCAGTCCGGTGGGAGCTCTCACACATCATGTAGTAGACGACCAA<br>GACAGT |
| 300 | ACAGTTCTCCTTCTTAGCTTCGTGAGAACCTTAAGGACGGGGACGTGACAAAGCTGTATTCTCA<br>GGACGATTACCTCAGGGTCAGCAGGCTCAAGTTCAGCGAGAATCCGATGCTTGGCATCGTCAAG<br>AATACGGATGGCACAGGGGAGGTTATAGGTCCGTCCTTTGCCACATCATGTAGTAGACGACCAA<br>GACAGT |
| 301 | ACAGTTCTCCTTCTTAGCTTCGTGAGAACAGGGACCTTCTGTGGAACATAATCTCGGGTGCCCT<br>GAATGCGGGAAGGGAACAGCTCTACGGGGATGCATTCGGCGGTCCTAAGATAGAGCAGTACGTG<br>AAAGCACTCACGCAGGTGCTGTATGACCTGTCTGTCAACAGCACATCATGTAGTAGACGACCAA<br>GACAGT |
| 302 | ACAGTTCTCCTTCTTAGCTTCGTGAGAACTGAAGGAACGCGTCATCGTCCACAAGAGCACTACG<br>AGGAACGAAGTCCTTGAAGAGTTCAAGGCGTCTAAGGAGCCGAAGGTCCTATTTGCGATAAAGA<br>TGGAAGAGGGTACGGATTTCAGGGATGACCAGGCAAGGTGGCACATCATGTAGTAGACGACCAA<br>GACAGT |
| 303 | ACAGTTCTCCTTCTTAGCTTCGTGAGAACCAGATATTGGTCAAGACTCCTTACCAGGATCTGGG<br>AGACGAGTGGGTCCGCCTCCATAGGGAGAAGATGGGACGGAGATGGTACGAGATATCCGCCCTC<br>CAGCAGGTCATCCAGGCGAGCGGCAGGATAATGAGGAACGACACATCATGTAGTAGACGACCAA<br>GACAGT |
| 304 | ACAGTTCTCCTTCTTAGCTTCGTGAGAACCAGGGACTGGGGAGACACCTACGTCCTTGACATGA<br>ACGCCATGAAGCTCATCCGCATGTACGAAAAGGAATGCCCCCGCTGGTTTTTGAAGAGGTTGAA<br>ACTATGACGCATCACAATATCACCTTCCCCGTCCCTCCCGACACATCATGTAGTAGACGACCAA<br>GACAGT |
| 305 | ACAGTTCTCCTTCTTAGCTTCGTGAGAACGCAATGTCCGCAACAGTTGACAACGTTGCACGGGT<br>CGCGGGATGGCTCAGGGCGACTGCAGTCTCCAGCGATTTCAGGCCCGTCACCCTGAAGAAGTAC<br>GTCCTTACCCCCCGCCATATCATGGATGAGAAAGGGGATACCACATCATGTAGTAGACGACCAA<br>GACAGT |

TABLE 1-continued

| SEQ ID | |
|---|---|
| 306 | ACAGTTCTCCTTCTTAGCTTCGTGAGAACCGAGATACAGCAGATGCTGGGGCGCGCCGGGAGGGCGAAATACGATTCCATGGGCTACGGCTACATCTGCTCATCCGACGTTCACCTCCAGGACGTGTATAAGACGTACGTTCATGGCCGTCTGGAGAGCGTAAAATCAACACATCATGTAGTAGACGACCAAGACAGT |
| 307 | ACAGTTCTCCTTCTTAGCTTCGTGAGAACGGCACTGGACGAGTTCTTCTCCACCACGCTGGCACGCCACGAGGGTGCCCGTCTGGAAGAATGGATAGACAACAGCCTTGTCTTCCTGCAGGACAACGACATGATAGTCGGGGGACGTTCCTTCACGGCTACCCCCTTCGCACATCATGTAGTAGACGACCAAGACAGT |
| 308 | ACAGTTCTCCTTCTTAGCTTCGTGAGAACCCATCCTTGCGGACTGGATAGACGAGAAGCCCGAAAGCGACATCGTCAATAAATACAACATCTGGCCTGCCGACCTGAGGAGCAGGGTTGAGTTGGCCGAATGGCTCTCGCATTCCCTTTACGAGATCTCGAGGGTCCTGCACATCATGTAGTAGACGACCAAGACAGT |
| 309 | ACAGTTCTCCTTCTTAGCTTCGTGAGAACGGCGACTATTCCTACGTCAGCGTTGCGGAATATTTCTCCAGCTCAAGGATAATAGCCACTACCGCTTCCCCCGGTGGCGACAGGGAGAAGATAAACGAGATCATGCGCCACCTGAGAATAGAGAACCTTGAGGTGAGGGACACATCATGTAGTAGACGACCAAGACAGT |
| 310 | ACAGTTCTCCTTCTTAGCTTCGTGAGAACATCGACGCTCCAGCTGTTCAGGGACGGTGCGGTCAGGATACTCGTAGCAACGCAGGTTGGGGAGGAAGGACTGGACGTACCGGCTGCAGATACCGTCATATTCTACGAGCCGGTGGCAAGCGAGGTCCGCTCAATCCAGACACATCATGTAGTAGACGACCAAGACAGT |
| 311 | ACAGTTCTCCTTCTTAGCTTCGTGAGAACCGCGGTCCTCTTTCCCAGCTTCAGTCCTTTGGCTTTCCTATGTTCTGCTGGTACTCTTCCCATTGCTCTCTCTGTTGTTTCTCCTGGCTTTTCCTGAAGTTTTCGAGGGCTTCGTCCATGCTGTCATAAGCGTTATGCGACACATCATGTAGTAGACGACCAAGACAGT |
| 312 | ACAGTTCTCCTTCTTAGCTTCGTGAGAACCGAACTCCTTGACGCTCCTGGAGATGACCAGTTTCTCTATCTCCACCCTCCCGCTCTTCATGTCCGATATTATTTTCCTCGCCCTTCTCAGTGCCTCGTCCACGTTCCGGTCGAGCACGAGATTGAACATTTCCATGAGTCACATCATGTAGTAGACGACCAAGACAGT |
| 313 | ACAGTTCTCCTTCTTAGCTTCGTGAGAACCCCTTTCCTCGAGGTCTTTGTCTATTCCCTTCACCGTTTCCCTGGCCCAAGCAGTGATGCTGGACCCGATACTGGGATCGGTAAACCTGTAGAAGCTTGATGCAAACACTCCGTAGAACGAATTCATAAGCACCTTCACCCACATCATGTAGTAGACGACCAAGACAGT |
| 314 | ACAGTTCTCCTTCTTAGCTTCGTGAGAACCAGTTCTCCTTCCACCCCGTCCGCCTCTTCTATGACGGTCGCACTTTCCGTCGAGCAGACGCCCTACGGCTGGATGGATCAGTATCCCTCGTCGGTTGTTGCCCATGTCACGGGAGGCATCCCTCCCTACGCCTATCACTCACATCATGTAGTAGACGACCAAGACAGT |
| 315 | ACAGTTCTCCTTCTTAGCTTCGTGAGAACCAATCTGGAGGCTTTCGCCGTATCCGTCGAAGTCACGGACTCATCGGGGCATTCAGTCTCAGGTGCAATCATGATCAACTACGGTTCCATAGACCTCTCCCCGTTTGGATACATGGTAACTTTGATTTTTCCGGTGATCACACATCATGTAGTAGACGACCAAGACAGT |
| 316 | ACAGTTCTCCTTCTTAGCTTCGTGAGAACGAACATCCATTGCTGACCATCACGATCGATGGCTCAAAGGACACGTTCAAAACTGGCGATGTCCTGGAATGGTTGACCGAAAGTGACATCTCAAACATGCACAATGTTGCGTCCTTCACAAAATCTCTCCTGAGGATAGTCACATCATGTAGTAGACGACCAAGACAGT |
| 317 | ACAGTTCTCCTTCTTAGCTTCGTGAGAACGCATGCTGCCCGATGGCCAATGGTTCGGGGAGGTCATTGGGAAGGACGTGCAGGGAAATCCCTACGGCATTGATTATACAATGTGGTTGCCGTTTAACACCTACGTTAGGGATAAGCTCAGTTACAATAGTTGGGGGAAGCACATCATGTAGTAGACGACCAAGACAGT |
| 318 | ACAGTTCTCCTTCTTAGCTTCGTGAGAACCCAGCATTCCTCCTCTGAGGGAGTTCGGAAGGTAAAATCTCCTGATGACATCTGAGTCCCTGGCGCCCATTGTCTTGGCTGAGTAGACTTCCATTTTACTTGTCGTGCTGCCAGTTGAAAATGCAAGTACTGCTATCATCCACATCATGTAGTAGACGACCAAGACAGT |
| 319 | ACAGTTCTCCTTCTTAGCTTCGTGAGAACGTTCCCTGCAGGAATGATTGTTCAACTGCACTCGTCAGTACATGATAGAACAATCTTGAAGCTGACAGATGGAGCGCATAGAAGATAAGGAATGCAAGAGGTACCAGTACTAGTACCACTGCATATATTCCTGCGTATAGCACATCATGTAGTAGACGACCAAGACAGT |
| 320 | ACAGTTCTCCTTCTTAGCTTCGTGAGAACCGATTGCAGGAACGTGGAAAGTGTGCGGTTAATGTATGACTCATTGCTCACATCGAATCGATACAGAAGACCGCTGTTTGCTGCCAGGTAGGAATCTATGTTATTCAGGCCAACAACCACATCGTATCCCGCCCCCTTTGCACATCATGTAGTAGACGACCAAGACAGT |
| 321 | ACAGTTCTCCTTCTTAGCTTCGTGAGAACAGGATTGAACCGGTTGGTGTCAACGTAGAATCCTCATTGACCCGCCACATAAAACTGAACATTCCAATTGTGTCGTCTCCTATGGATACGGTCTCTGAG |

TABLE 1-continued

| SEQ ID | |
|---|---|
| | GCAGATATGGCAATTGCACTAGCAAGACTCGGTGGTATTGGCACATCATGTAGTAGACGACCAAGACAGT |
| 322 | ACAGTTCTCCTTCTTAGCTTCGTGAGAACCTTATTATACGCGACCTTTACACTGTAAGCCCGGAAACACCTGTTGACGATGCAATCCGTACTATGAGGGAGAAGCGAATCGCTGGGCTCCCAGTGATATTGAACGGCAAACTTGTCGGAATACTTACGAACAGGGACATCACATCATGTAGTAGACGACCAAGACAGT |
| 323 | ACAGTTCTCCTTCTTAGCTTCGTGAGAACGGTACGGCAAGATAGGCTCAGGGAAATTTGTACCAGAGGGAGTTGAAGGAGCAGTTCCGTACAAAGGTAAAGTTGCAGATGCAGTCTTTCAATTGATCGGGGGCCTGAAGTCGGGGATGGGGTATACTGGCTCGCCCACACACATCATGTAGTAGACGACCAAGACAGT |
| 324 | ACAGTTCTCCTTCTTAGCTTCGTGAGAACGGTGGAAGCGTTGAGGAGTTTGTCACTCTATCGAGGAGAGTGGAGGCAGCGGGATTCGACAAGGTCGAGCTCAATTTGTCCTGCCCACACGTTCAGGGAGTTGGATCCGAGGTAGGACAGGATGTAGGTCTTGTAGAAGACACATCATGTAGTAGACGACCAAGACAGT |
| 325 | ACAGTTCTCCTTCTTAGCTTCGTGAGAACGACACTTATAGACAGGCTAGACAAGAAGACGAAGACAAGGATATTCTTCTCACTTGAGCGATTGATGAAGTGCGGCATAGGGATTTGTGACAGTTGCAGCATCAACGGCATCCGGGTATGCAAGGACGGAACAATTTTCGCACATCATGTAGTAGACGACCAAGACAGT |
| 326 | ACAGTTCTCCTTCTTAGCTTCGTGAGAACCTTCGCAACTGCAAAGAGGTAGCTTCTGGATGCTTCCCTGGAACTATCCCTACATTGCTGTTATCTTACTAGTGGTACTGATTTATGCAGCAATAGAGGACCTTAGGAAGAGGAAAATAACAACTATAACCTTCCTTGCACACATCATGTAGTAGACGACCAAGACAGT |
| 327 | ACAGTTCTCCTTCTTAGCTTCGTGAGAACGTGACAGTTGGAACTGGTCTATCTCCCCGGTATTTTAATAAGTTTATAGGCGTAGCAAAGGCATATACGACAAGAGTAGGGGAGGGGATATTTCCTACTGAGATGTTTGGGGAAGAGGCAGATAGACTTAGAACCCTAGGCACATCATGTAGTAGACGACCAAGACAGT |
| 328 | ACAGTTCTCCTTCTTAGCTTCGTGAGAACGAAGAAGACTTAAAGGATTTAGGTAGAGAGCTTAAGGTACCAAGAAGACCGTTCAAAAAGTTAACGCATAGAGAAGCTGTTNATATATTGAGATCTCATGGCATAAAAGCAAGTTATGAACATGAGATACCTTGGGAAGCCACATCATGTAGTAGACGACCAAGACAGT |
| 329 | ACAGTTCTCCTTCTTAGCTTCGTGAGAACACGGGGAGGCTGTCTCAGGAGCTGAAAGAGAATATAGAGCGGAGAAGGTTATTGAGAGGATGAGAGCTACTGGTGAGAACCCTGCAAAATACGGTTGGTACATTGAAATGTTGAAATATGGTATTCCGCCGAGTGCAGGGCACATCATGTAGTAGACGACCAAGACAGT |
| 330 | ACAGTTCTCCTTCTTAGCTTCGTGAGAACATATGCAGATTTAGATGAGATTATAGGGGTTGCATCTAAGGCAGGAATAGATTGCATAACTATAGATGGGTCAGAAGGTGGAACAGGTATGAGCCCTATAGCTGCGATGAGAGAACTAGGATATCCAACGCTAGTATGTCCACATCATGTAGTAGACGACCAAGACAGT |
| 331 | ACAGTTCTCCTTCTTAGCTTCGTGAGAACGGACACGAAATTGCTGAAGCAGCTGGCTCAACATGGTATATCGACAATTTCTGGGATAAACTCAAAGAGGGCTGTGTAGCATATCTAAACATAGATTCACCTGGATTAAAAGATGCAACAAGATATATCGCTTACGCGTCCACATCATGTAGTAGACGACCAAGACAGT |
| 332 | ACAGTTCTCCTTCTTAGCTTCGTGAGAACGTAACTTCTGGAAACGCCCAATCAAAACAGATCATGACACCAAAGCTAAAATTATCTTCCCTAATAGCTTCTATAGGTGTATCTCCAGGTTGAAATATTAGCTTCTCTTTGGCAAATAAGTGAAGTTTCCTATACTTTCCCACATCATGTAGTAGACGACCAAGACAGT |
| 333 | ACAGTTCTCCTTCTTAGCTTCGTGAGAACCCAGATAGCCCAATAGCATCAATTTCCGTTGCAATAATAGGTACAGTACACAAAGAACACGTAATTTTCAGCGACACTGCAAATACAGGCGACTTAATAATTTTTGCCATAGATCTCGATGGAACATTTCACCCTAAGTTCACATCATGTAGTAGACGACCAAGACAGT |
| 334 | ACAGTTCTCCTTCTTAGCTTCGTGAGAACGTTCTAATTCCTCTCTTACAGCTTTAAAAGCAATCACAGCAGATTCCAAAATATCATCCATATCATCCAGAGCTATAATAACACCTCTTGAAGTTTTCCCAATCTTATGCCCACTTCTTCCAACTCTTTGAACCAAACGACACATCATGTAGTAGACGACCAAGACAGT |
| 335 | ACAGTTCTCCTTCTTAGCTTCGTGAGAACGTAACTTGTCTGGGAGACATATATTGGACAACTAAATCAACGGTTCCTACATCAATCCCTAACTCCATAGATGATGTACAAATAAGACCTTTCAACTCACCGTCTTTAAATAACCTTTCAACTTCTATACGAACATCTCTCACATCATGTAGTAGACGACCAAGACAGT |
| 336 | ACAGTTCTCCTTCTTAGCTTCGTGAGAACACTCAATGAACCATGATGCACATCAATACTTAGATTAGGATCGTATAAGTGAAGCCTAGAAGCTAGTATCTCAGCTATTTCACGAGTGTTTACAAAAGTAAGCATAGAGCGGCTCTTTTCTAATAACTCAACCAATACCCCACATCATGTAGTAGACGACCAAGACAGT |

TABLE 1-continued

| SEQ ID | |
|---|---|
| 337 | ACAGTTCTCCTTCTTAGCTTCGTGAGAACCAGTTAAATCATCTTAACTCACAAATATTAAGGCT<br>TTAATTTCTGAGGGAGTGCAAAATGAAAACTGACGTAGTAATAGTAGGTGCAGGGCCCGCAGGC<br>ATGTTTGCTGCACATGAATTGGCAACTAAATCTAATCTGAACACATCATGTAGTAGACGACCAA<br>GACAGT |
| 338 | ACAGTTCTCCTTCTTAGCTTCGTGAGAACAAAAATAGCCAAGGATCCAAAATTCCGTGTATATA<br>CAAAAACCTTCGATGACCTTACACGTGTATTTTGCGTTAATTATCGAGGCTTCGTCGTCCAAGA<br>AGTCTACGGAGATATCGTTGGTGTTAACGGCCACACTCTAACACATCATGTAGTAGACGACCAA<br>GACAGT |
| 339 | ACAGTTCTCCTTCTTAGCTTCGTGAGAACTCAAACAAAAATCTGAAAATGCCAATTTTGCATTT<br>CTAGTTCGAGTTGAACTCACCGAACCGCTTGAAGACACAACCGCCTACGGATTCTCAATAGCCA<br>AATTAGCAACTACCATAGGTGGAGGAAAACCAATTCTTCAACACATCATGTAGTAGACGACCAA<br>GACAGT |
| 340 | ACAGTTCTCCTTCTTAGCTTCGTGAGAACCGAGATACTGAATTTCCAAAACTCAAAGGATATAG<br>AATTGTTAGAATCGCAACACATCCGCAAGTTATGAGCATGGGACTAGGAAGTGAAGGGTTGTCA<br>AAACTTTGCCAAGAAGCCGAAAAGAGAGGACTAGATTGGGTCACATCATGTAGTAGACGACCAA<br>GACAGT |
| 341 | ACAGTTCTCCTTCTTAGCTTCGTGAGAACCGAAGTTTTTATCCTCCTCGGTCCAAGTCACACTG<br>GTTACCCAGGCGTTGGAATAATGACAGAAGGCATCTGGAAAACTTCTTTAGGAGAAATATCAAT<br>AGATGAAACTCTCTCGAATACTATTTTAAATAATTGTGACCCACATCATGTAGTAGACGACCAA<br>GACAGT |
| 342 | ACAGTTCTCCTTCTTAGCTTCGTGAGAACTGACACACTACGGCACCTACTATGGATACACACCA<br>GCTGGTGTTGAACCATTAACCAAAGTTTTAGAATGGATATACCAGACGGACAAACAAGTTATTG<br>AGAGAATTAAAAGATTAGATGGAGCAGGAGTAATAGAATATCACATCATGTAGTAGACGACCAA<br>GACAGT |
| 343 | ACAGTTCTCCTTCTTAGCTTCGTGAGAACCTGAAAAGTTCATTCCAATTGTTAAATCGCCATCT<br>TGGAAACACGGCACAAGAAAAGGGAAAGGATTTAGCATCGGTGAGATTAAAGCAGCCGAGATAG<br>ATATTAGTATGGCAGTTAAACTCGGTATACCCATTGATAAACACATCATGTAGTAGACGACCAA<br>GACAGT |
| 344 | ACAGTTCTCCTTCTTAGCTTCGTGAGAACGGGAATAATAATTAAAATAATGTGGCACACCTTTT<br>AGCTTCTTTTCATCTCATATTTCAAAGAAGCCTTCCAGGTGTGCCTCATCGGTGTCCCCCGCT<br>GCGGAGACACGGTATCATCGTATCCGCCGAAGGAAACTCAACACATCATGTAGTAGACGACCAA<br>GACAGT |
| 345 | ACAGTTCTCCTTCTTAGCTTCGTGAGAACGACATTGCCTATCAATTACTTCAAGCCGGAATGCA<br>AGTTCCCGGTTTCAGAAGGTCGCCAAAGATAATAGAAAGAATTTTAGAAAGATATATTCCAACA<br>GTCACCGTACTAGGCGGCATTATTGTAGGATTAATAGCTGCCACATCATGTAGTAGACGACCAA<br>GACAGT |
| 346 | ACAGTTCTCCTTCTTAGCTTCGTGAGAACTGTCGTTCAGGGAGGTATAAAAATGCCAGAACCAC<br>GCTACCGGTCAAGGTCTTTAAGAAGACGATACGTACACACACCTGGAGGAAAAACCGTCATCCA<br>TTACAGGAGAAAAAAACCTGACGTTGCAAAATGCGCATTATCACATCATGTAGTAGACGACCAA<br>GACAGT |
| 347 | ACAGTTCTCCTTCTTAGCTTCGTGAGAACGTGGTCAACCTCTCAGAGGAATTCCCAGACTAAGG<br>CCAGGAGAATTCAGAAAGTTGACAAAAAGTCAACGAAGACCAGAGAGACCTTTCGGTGGATATC<br>TATGCCACAAATGCTTAGCAATGGAAATCAAGAAAGCTGTTCACATCATGTAGTAGACGACCAA<br>GACAGT |
| 348 | ACAGTTCTCCTTCTTAGCTTCGTGAGAACATAGGATGAATCTAACTGGGGCGACCCGGTAGATA<br>ACTGAGAGTGTAGGAGGTGAAATAATTGAGCGCAATAGAAGTAGGTAGAATATGTGTTAAAACT<br>AGTGGAAGAGAAGCAGGAAGAAAGTGCGTTATTGTTGAAATCACATCATGTAGTAGACGACCAA<br>GACAGT |
| 349 | ACAGTTCTCCTTCTTAGCTTCGTGAGAACACACCATTTCCTAATATTTTAGTAACTAGATATGT<br>TTGTTATAGTATTAGGGTGAAGTATTTGTATGAAAGAAAGTTGCCATCAGACATTAAAAGAGAG<br>ATTCTAGTAAAAAGTGAAGCAGAAACTGACCCTGCTTATGGCACATCATGTAGTAGACGACCAA<br>GACAGT |
| 350 | ACAGTTCTCCTTCTTAGCTTCGTGAGAACCACATGAGAGAACTTAGAAGAACACGTACAGGACC<br>CTTTAAAGAAGATGAAACCCTAGTAACTCTTCACGATGTAGTTGATGCTTACTATTTTTGGAAG<br>GAAGATGGAGAAGAAGAATTTCTACGAAAAGTCATACAACCCACATCATGTAGTAGACGACCAA<br>GACAGT |
| 351 | ACAGTTCTCCTTCTTAGCTTCGTGAGAACAATGGAAAAGGGTTTAGAACACCTACCTCACATTT<br>GGATTAGAGATTCTGCTGTAGATGCAATATGCCATGGGGCAAACTTAGCAGCTCCTGGTGTTGT<br>AAAACTTCATGACGGTATATCACCTGGAGACTTAATAGTAACACATCATGTAGTAGACGACCAA<br>GACAGT |

TABLE 1-continued

| SEQ ID | |
|---|---|
| 352 | ACAGTTCTCCTTCTTAGCTTCGTGAGAACCGCTGATCATACATGTGCATTGTCTTTAAATACAC TAGTAACGTTAATAATATCTAGCAATTTTAGATAAAAATAACTAGCAGTGCCGGGGTAGCCAAG TGGACTACAGGCCTTATACCGGTTAGGGCGCGGCCTGGAGCACATCATGTAGTAGACGACCAA GACAGT |
| 353 | ACAGTTCTCCTTCTTAGCTTCGTGAGAACCATGCCTTAACGAGAGGCATGGGATGGGGGAGCTG TGAGCCCCCCGAACCGGCAGATGAGGGGAAGGGTGCAAAGCATCCCTTAACGCCGGAAGCTCCC GACTTCAGTCGTGGAGCAGCTCACTGCTTTGACGAAAGGTTCACATCATGTAGTAGACGACCAA GACAGT |
| 354 | ACAGTTCTCCTTCTTAGCTTCGTGAGAACGAACTTGCAAGGAAGGCCGGTGTTGATTATGAGAC AAAGCTGTTGGTCAGGGGCAAGGAACCGGCTGAGGACATAATAGAATTTGCTGACGAGATCAGG GCAAGTCTCATTGTAATAGGGGTTAGGAAGAGGAGACCCGCCACATCATGTAGTAGACGACCAA GACAGT |
| 355 | ACAGTTCTCCTTCTTAGCTTCGTGAGAACTCCAGAAGAGATTCAAAGCTCTCGTATTCAATGTC CCCACCAAATTTCTGGTCGCGCTCAATTTTGACTTTACCAAAAGCGGGGAAAACGTAGTGCTTT GCTAGGTCTATTATCGGATTTCCTTCTACAACCTTTGGCGGCACATCATGTAGTAGACGACCAA GACAGT |
| 356 | ACAGTTCTCCTTCTTAGCTTCGTGAGAACGATTTGCTCATTTTCTCCCCGTCGAGTCCTGAGAT TATCGGCGTATGGATGCAGATCGGTGCCTTGTAACCGAGGGCCGGCAGATTCTCCCTTGCGAGC ATGTGGATCTTTCTCTGATCTATTCCACCAACCGCCACATCCACATCATGTAGTAGACGACCAA GACAGT |
| 357 | ACAGTTCTCCTTCTTAGCTTCGTGAGAACTCCGGGAGTTGCAGAACCAAGCATGGAAATTGCTA GAGATCCCGAAAAGGTTTACGAGTACACGAATAAGTGGAACACGGTTGCAATTATCACTGATGG CTCGAGGGTCTTGGGACTGGGCAACATCGGTGCGATGGCTTCACATCATGTAGTAGACGACCAA GACAGT |
| 358 | ACAGTTCTCCTTCTTAGCTTCGTGAGAACGTGGTGTTATCAAGAGGGAATATATTGCTCAGATG GCAGAGGATCCGATAGTCTTTGCCTTATCAAACCCGGTGCCTGAGATCTATCCGCAGGAGGCAA AGGAAGCCGGAGCCAGGATCGTAGGAACTGGTAGGAGCGACCACATCATGTAGTAGACGACCAA GACAGT |
| 359 | ACAGTTCTCCTTCTTAGCTTCGTGAGAACGGGATCTGTTAGTATGGCATTCAGAGCCTTTATGT CCTCATCGGTAAGCTTGTCCGATGGCAGATCGTATTTCACGATGTCTGAAGGAGTAACTCCGAG AAACTTCGCTTCTGGTGTCGCAAGATACTCCGAGAGATGCGCACATCATGTAGTAGACGACCAA GACAGT |
| 360 | ACAGTTCTCCTTCTTAGCTTCGTGAGAACTGAGTGCGGCTTACTCTGCACTGTGCGAGATCGAT GAGGTCGTTGTTGTTGCCCCCATAACGCAGATGAGCGGAGTGGGGAGGAGCATATCCATAATGC GGCCGGTTCGTTTTTTCGAGCTCGAAATAGATGGCATGAGGCACATCATGTAGTAGACGACCAA GACAGT |
| 361 | ACAGTTCTCCTTCTTAGCTTCGTGAGAACAGGGGAAGGGAGTACTACTGGATTCATGGGGTGGA AGTCGAAAGCGCTGAGCCTGGAACGGACATACACGCACTCAGAAACGGGTATGTCTCCATTACA CCGATATCCTTAAATGCAACTTCGGACTGCGAAGCTTTAAGCACATCATGTAGTAGACGACCAA GACAGT |
| 362 | ACAGTTCTCCTTCTTAGCTTCGTGAGAACATAGTTTTATGGAGGGTGGTTGGACATGAATGAAA GGGCAAAGAAGGTCATTCTTATTGTGGATGACGATTTGGCTCTGCTTGAAGCTCTTGAACTGAT GCTTCGAGGCAAGTATGAGGTTGTGAAGGTGACAAATGGGACACATCATGTAGTAGACGACCAA GACAGT |
| 363 | ACAGTTCTCCTTCTTAGCTTCGTGAGAACATGTCGATTCCGAAATAGCAGGGAGCAATTATCGG TGGGCTTCCGACCCTTAAATGGATTTCCTTCGCTCCCGCCTTTCTTATCATGTCGACTATTCTT TTGGATGTTGTTGCCCGCACAATGCTGTCGTCAACCAGCACCACATCATGTAGTAGACGACCAA GACAGT |
| 364 | ACAGTTCTCCTTCTTAGCTTCGTGAGAACACTTTCTGAGGGAAAAACATTGTTGCTTATCCTAA AGAGTTTACAAGCAAGAAGCTGGAAACAAACTCTGGATGTTATTAATTTAGAGCCTGCAGCAGC ATATACAATGTTTAGAGCGGCAATAAAGAAACTATACAAAGCACATCATGTAGTAGACGACCAA GACAGT |
| 365 | ACAGTTCTCCTTCTTAGCTTCGTGAGAACGTGGTTGAGAGGCTGCTTGAAGGCATTGCAAAGAA TGAAAGGGTAGCTTACGGATTGGAGGAGGTTAGGAGGGCAAAAGAGTATGGAGCAATTGAGGTT CTGTTGGTTTCAGATGACTTCCTGCTCACCGAGCGTGAGAACACATCATGTAGTAGACGACCAA GACAGT |
| 366 | ACAGTTCTCCTTCTTAGCTTCGTGAGAACTCGCTTCGAGATTCCTGATAGGAGTGGGAGTTGCC GGGGTTTACGTGCCTACGATAAAAATAATATCCGTCTGGTTCAGGCAGAATGAGTTTGCAACTG CTACTGGGATTCTTTTCGCGATTGGAAATCTAGGAGCGATTCACATCATGTAGTAGACGACCAA GACAGT |
| 367 | ACAGTTCTCCTTCTTAGCTTCGTGAGAACGAGGTATCGCCTACTTAGAGAGTTCGTAAAGTCGG AGATATTGGAGGAAGTTAAATTTGAAAACGTTGTGGACGAGTACTGGGTTGCGGAACCATTCAT |

TABLE 1-continued

| SEQ ID | |
|---|---|
| | AAAGATCATAATTTTTGAGGATCTCGAAAACCAGAAATTGACACATCATGTAGTAGACGACCAAGACAGT |
| 368 | ACAGTTCTCCTTCTTAGCTTCGTGAGAACCTAATCCGATTATCGATTCTACGCTTCCTGATGGTAGCAGGCTTCAGGCTACCCTAGGAACAGAAATTACACCTAGAGGCTCGAGCTTCACGGTGAGAAAATTTACAACCCAGCCACTGACCCCGTTAGATCTAGTGAGGCACATCATGTAGTAGACGACCAAGACAGT |
| 369 | ACAGTTCTCCTTCTTAGCTTCGTGAGAACCAAAATTATATCGATAGAGGATACCAGAGAGATAAAGCTCCATCATGAGAACTGGCTGGCTCAGGTGACGAGAACGGGGATAGGAGAGCAGGAAATTGACATGTATGACCTTCTCAAAGCCGCCTTGAGACAGAGACCGGCACATCATGTAGTAGACGACCAAGACAGT |
| 370 | ACAGTTCTCCTTCTTAGCTTCGTGAGAACGAATCAGTTTGTTAAATGGGATGCGAAGAAAAATTCGCATGTTGAGGTAGGATTCCGAAAAAGCTAGAGAAAATCGCGATGTCGAGAGTGGACGATGCTTACGCGGAGCTGGAAAGAAGAAGGAGGTATTTGGAGTGGACACATCATGTAGTAGACGACCAAGACAGT |
| 371 | ACAGTTCTCCTTCTTAGCTTCGTGAGAACTCAGTGAAGTTAGCACGGAATTCGAAAGGATAGTGGTTCTCGTTGAAATGGGAGAGGATTTGGAAAGCGCAATGAGGTTTGTTGCAGAAACAACTCCCTCAGAGAGGCTCAGGGTTTTTCTGGAGAACTTTATTGATGTGCACATCATGTAGTAGACGACCAAGACAGT |
| 372 | ACAGTTCTCCTTCTTAGCTTCGTGAGAACGCTGGAGCGGGAGGCGTATCAACGCTTGCCCTCAATCCGTTACCCGAAGTTCCAGAATACTTTGAGTATTTCCAGTCCGAATAGAAGCAGAGCACCTCTCGATCGACTAGAGTCTTTCTGCTAGCTCTTGCACCCTCATCCACATCATGTAGTAGACGACCAAGACAGT |
| 373 | ACAGTTCTCCTTCTTAGCTTCGTGAGAACGCGGAAATCTCTGCTGAAAACACCTTGACTTTTTCTTCGTATATCTCCCATTCCATCAGGCACCACCAACTTTGGTCCTGCAAAGAGTCATCGGTGCCCCATCTGCTACGGGAACGATCTGAAAGGCTTTACCACAGAATCACATCATGTAGTAGACGACCAAGACAGT |
| 374 | ACAGTTCTCCTTCTTAGCTTCGTGAGAACTCCGGTTGCAGGATTGGTCTCCCCACCTCTCGAGCCTATGAGGAATACCCCATTCCTGCAGAGCTCGAGAAGCTCTTCGAATTCAAGATCCCCCTTCTGCAGGAATGTGTTGCTCATTCTGACAATCGGAAAAGCAACTCCACATCATGTAGTAGACGACCAAGACAGT |
| 375 | ACAGTTCTCCTTCTTAGCTTCGTGAGAACAACTCCTCGATTGTTGGGTCATCGATTATTGTCACGTTCTCTCCTGCAATTCTCTCTCCAATCTTTCCAGCAAGAACGCTGTTTTCCTGCAGAACGTGATCTGCCTCGACCGCATGCCCGAAAGCTTCGTGAATAAAAACCACATCATGTAGTAGACGACCAAGACAGT |
| 376 | ACAGTTCTCCTTCTTAGCTTCGTGAGAACCTTTCTTCAAGAATGCTTTCTGCGGCGATAAGCCCAGTAACAGCCGCTCCAACTATTCCCCTGCTTATTCCGGCTCCATCGCCAATTGCATAGATGTACGGTATGCTTGTCCTCATCTTCTCGTCAACCTTAAGCTTCAACACATCATGTAGTAGACGACCAAGACAGT |
| 377 | ACAGTTCTCCTTCTTAGCTTCGTGAGAACTGCTGGATTTTTCTTTGGCCTTGCTGTGGCCGTTGACTAGACAAAAGTCGCCGTACTCCTCTCTTATAACCCAGCCCCTCGGGCAGGTGCAGAACGTGCGCATGTAGTCGTCATGCCTCTGTGTGATTATTCTCAGCTTTCACATCATGTAGTAGACGACCAAGACAGT |
| 378 | ACAGTTCTCCTTCTTAGCTTCGTGAGAACTTGCCTTGGAATTTTCCGCCACTTCGATCTTATACTTTTTTACCCATTTTTCCAGCCAGTCGGCACCGCTCCTCCCAACTGCAATTATGAGTTTGTCGTAGCCGAACTTGTCCCCATCGTTCGTCTTCACGATCTTTTCTCACATCATGTAGTAGACGACCAAGACAGT |
| 379 | ACAGTTCTCCTTCTTAGCTTCGTGAGAACAATCACCACCGACTGTGAAGCTCGAAGGATAGTTGGGGTTGGCATAATTCAGCTTTCCATCCGAAAGTCCTCCAGCACCACCCACACCAGAAGTAATGTTGCAGGGATCGCATTTCTTGCAATAGCTTTGCGAAAGGTCACACATCATGTAGTAGACGACCAAGACAGT |
| 380 | ACAGTTCTCCTTCTTAGCTTCGTGAGAACTTAACCAACCTCTTTCGCATCAAAATCCCAACTGCGGCATCCGTTATCAGCGTTACATCGATTCCATCTTTCATAAGCTCGTAGCAGGTGAGCCTAGAGCCTTGGTTCAGCGGCCTCGTTTCGCAGGCGAAAACCTTTACCACATCATGTAGTAGACGACCAAGACAGT |
| 381 | ACAGTTCTCCTTCTTAGCTTCGTGAGAACTTATCGAGTTAATAGCTATCAGTGTTGCTATTACGATCGTTGCGATCCCATCAAAGATGTTATGACCGAAGGAGATAGCAATAATGCCAAATATCGCTGCAAGCGTCGATAAGGAGTCGTTAAAACTCTCAAACATCACTCACATCATGTAGTAGACGACCAAGACAGT |
| 382 | ACAGTTCTCCTTCTTAGCTTCGTGAGAACCTCCCTTCTAAGCTTCGTGATATCTGCATTGCCAATATCAACTAGAAATTCGATTGAGATAAGCTTGTCTCTTGCGGTTAAGCTTGTTCTCTCGATATTTATACCGAAATTTAGCAATACACCCGTGATATCTCTCACGACACATCATGTAGTAGACGACCAAGACAGT |

TABLE 1-continued

| SEQ ID | |
|---|---|
| 383 | ACAGTTCTCCTTCTTAGCTTCGTGAGAACAAGCGGGGCTTTTGCCTTTCCAATTCCGCCGCAACCAACCGTTGGACTTATCAAACCGGAACCTTTCAACTCCGAGATTAAAGAGCCTGGCTCCTTATCGTGCTTAATAGCAATTTCTACAATGTCTTCCCCGCATACAACACATCATGTAGTAGACGACCAAGACAGT |
| 384 | ACAGTTCTCCTTCTTAGCTTCGTGAGAACCTAGTTCTTGGTTTTCGTCGACGTTGACCTTGTAGAACTCTACATCTGGAAACTCCTTTGAAAGCTTTTCGAGCACTGGGCTGAGATACCTGCACGGCATGCACCAGTCGGCGTAGAAGTCAACAACAACAAGCTTATCCCACATCATGTAGTAGACGACCAAGACAGT |
| 385 | ACAGTTCTCCTTCTTAGCTTCGTGAGAACCTCCGATCGTCTTTAAAGCTTGCAAGTCTAAATCCTCGCCCCAGGGAATTTCCTGGGATTTTCTCGCAATCTCTATCGCCGAAGTATAGGTTATCCTCGGGAATGGTATCTCGGGGACTTCGAGCTTTAGTTCGAGAATACACATCATGTAGTAGACGACCAAGACAGT |
| 386 | ACAGTTCTCCTTCTTAGCTTCGTGAGAACGAGGTTTTGTCCCTATTGGGTTTCTCATTGCCTGCAGCATTTCTTCTCTGCTCAGAGCTCTGCAGCCATCGCCTTTCATTCTTAAAATGCTAACCTCCCAATCATCCGGAAAATCGAGCTCTATTTCCCTATCCTGCCAGCACATCATGTAGTAGACGACCAAGACAGT |
| 387 | ACAGTTCTCCTTCTTAGCTTCGTGAGAACTGTTTACAGGCTGGTGGGTGGGGAAAGGAGTGTTAAGGGCAAAAGGAGTGTAAGCAAGTTCAGGGTTGCGATTGCGATTCTTCTGGCATTCATTCTGATATATCCTACATACCGCATAGCCGAGATTCAAAGCAGTGGGGCACATCATGTAGTAGACGACCAAGACAGT |
| 388 | ACAGTTCTCCTTCTTAGCTTCGTGAGAACCAGGGTCAGGAGGATTCACGAGATAGAAGTCCTCGAGGTGAGAGGCAGGTTCGCGCTTATAAGGGTTCTCAGCGACCCCGGCACGTACATGAGGAAGCTGGCCCACGACATCGGGCTATTGCTCGGAGTAGGTGCACACACACATCATGTAGTAGACGACCAAGACAGT |
| 389 | ACAGTTCTCCTTCTTAGCTTCGTGAGAACGAAGTCAGTCATAGAATCAATGGTGTATTCTTCATCAGGGTTATTATACGGAATGAACTTATAGTTCTCACCTGCTACCTGATCCACTGTCATTTCTGCAAGAGTCTGCACTGTGGTAATTCCACCTTCTTCCATCCGGGCACATCATGTAGTAGACGACCAAGACAGT |
| 390 | ACAGTTCTCCTTCTTAGCTTCGTGAGAACAGTAAGGGAATCAATGTCTTCCATTGCTGTAAGGGTTACTGTTACCTTTGTAGAAGTCAGACCGTAATTGGTCAGCAGCTCTTCATAGAAGTTCTGGTTTGCAATATCCCTCTGGGCAATGACAGGGTAGTCGACTTCGTCACATCATGTAGTAGACGACCAAGACAGT |
| | Forward and Reverse Primers |
| 391 | TCTCCTTCTTAGCTTCGTGAGAAC |
| 392 | CTTGGTCGTCTACTACATGATGTG |

Primer Binding Sequences

The 5' and 3' primer binding sequences are selected to be complementary to a SDSI 5' and 3' primer which is included in an amplification reaction and used to amplify SDSIs present in a given sample. The primer binding sites may be optimized for multiplex amplification with a set of primers used to amplify a genome for sequencing. In one example embodiments, the 5' and 3' primer binding sites have a Tm of between 55-65° C. In one example embodiment, the 5' and 3' primer binding site are complementary to primers having SEQ ID NOS: 391 and 392.

Methods of Detecting and Preventing Sample Contamination

In one example embodiment, a method of detecting and preventing contamination in one or more amplification reactions comprises adding a SDSI according to the example embodiments disclosed above to a one or more samples to be assayed. An amplification reaction is then used to amplify a target sequence in the samples. The amplification reaction will include probes and primers needed to amplify the target sequence and to amplify the SDSI. The amplicons generated from the amplification step are then used the one or more samples, sequencing the amplified samples and determining the number of reads of the SDSI from the one or more samples, wherein detection of only a single SDSI in the sample indicates contamination free amplification of the same, and wherein detection of multiple SDSI's indicates possible contamination of the sample. Samples identified as potentially contaminated may then be discarded or marked for repeat to confirm accuracy of results.

Amplification

The present invention solves this problem by providing for the sequencing of spike-DNA sequences at concentrations that can be amplified concurrently with the nucleic acids of interest. In one example embodiment, sequencing includes extracting total RNA or DNA from a biological sample, such as a sample collected with a swab (e.g., nasal, rectal, vaginal). Methods of extracting total RNA or DNA are known in the art and commercial kits are available. The presence of a pathogen may be confirmed in a sample. Exemplary methods for confirming include PCR, RT-PCR and RT-qPCR. In certain embodiments, sequencing includes DNase treatment to remove residual DNA. In certain example embodiments, sequencing may include depletion of ribosomal RNA (rRNA). In certain example embodiments, cDNA may be prepared from total RNA using RT-PCR. In certain example embodiments, RT-PCR may be performed using random hexamer priming. In one example embodiments, a SDSI is added to each cDNA sample. The SDSI can be added to the total cDNA sample. In certain example embodiments, cDNA samples may be normalized to a constant amplification level. In certain example embodiments, real time PCR may be performed on the cDNA using one or more standard primers and a Ct value is used to normalize cDNA samples. As used herein, standard primers refer to a primer set that is used for every sample. In certain embodiments, the standard primers are directed to a region of the pathogen to be sequenced. The samples can be diluted such that all of the samples for amplification have the same Ct value in the amplification reaction. In certain embodiments, each sample is normalized to a Ct value less than 35, 34, 33, 32, 30, 29, 28, 27, 26, 25, or 24. In preferred embodiments, the samples are normalized to a Ct value of 26 to 28, preferably 27. In one example embodiment, a SDSI is added to the normalized sample used for PCR amplification of the pathogen. The cDNA may be amplified in the same reaction with pathogen specific primers and primers specific to the SDSI. Amplification may be performed in a multi-well plate (e.g., a standard PCR plate).

In certain example embodiments, the primer concentration is 100 μM. In certain example embodiments, the primer concentration is between 50 μM-150 μM, or between 50 μM-200 μM, or between 50 μM-250 μM, or between 50 μm-250 μM or between 50 μm-300 μM or between 50 μm-350 μM or between 50 μm-400 μM or between 50 μm-450 μM or between 50 μm-500 μM. In certain example embodiments, the primer concentrations is between 50 μm-70 μM or between 70 μm-90 μM or between 90 μm-110 μM or between 110 μm-130 μM or between 130 μm-150 μM or between 150 μm-170 μM or between 170 μm-190 μM or between 190 μm-210 μM or between 210 μm-230 μM or between 230 μm-250 μM or between 250 μm-270 μM or between 270 μm-290 μM or between 290 μm-310 μM or between 310 μm-330 μM or between 330 μm-350 μM or between 350 μm-370 μM or between 370 μm-390 μM or between 390 μm-410 μM or between 410 μm-430 μM or between 430 μm-450 μM or between 450 μm-470 μM or between 470 μm-490 μM. In certain example embodiments, the primer concentration is between 50 μm-100 μM or between 100 μm-150 μM or between 150 μm-200 μM or between 200 μm-250 μM or between 250 μm-300 μM or between 300 μm-350 μM or between 350 μm-400 μM or between 400 μm-450 μM or between 450 μm-500 μM.

In certain example embodiments, a spike-in may be relatively the same length as the amplicons generated for the target organism. In one example embodiment, spike-ins are the same size and share the same priming region to ensure similar amplification performance. In certain embodiments, a spike-in for MNase-seq, ChIP-seq, and genomic DNA are around 150 nucleotides in length. In one example embodiment, a spike-in accounts for 0.1%—3.5% reads. A spike-in to total sample ratio may be from 1,000:1 to 50:1. In one example embodiment, a spike-in includes primer binding sites on the 3' end and/or the 5' end. (Chen K., et al., The overlooked fact: fundamental need for spike-in control for virtually all genome-wide analyses. Mol Cell Biol (2016) 36:662-667) The primers and primer binding sites on the SDSI may range between 15-40 nucleotides in length. The primer's melting temperature (Tm) may range from 40° C.-95° C., preferably between 55-65° C.

Sequencing

After amplification of cDNA, standard sequence library generation can be performed. In certain embodiments, sequencing comprises high-throughput (formerly "next-generation") technologies to generate sequencing reads. In DNA sequencing, a read is an inferred sequence of base pairs (or base pair probabilities) corresponding to all or part of a single DNA fragment. A typical sequencing experiment involves fragmentation of the genome into millions of molecules or generating complementary DNA (cDNA) fragments, which are size-selected and ligated to adapters. The set of fragments is referred to as a sequencing library, which is sequenced to produce a set of reads. Methods for constructing sequencing libraries are known in the art (see, e.g., Head et al., Library construction for next-generation sequencing: Overviews and challenges. Biotechniques. 2014; 56(2): 61-77). A "library" or "fragment library" may be a collection of nucleic acid molecules derived from one or more nucleic acid samples, in which fragments of nucleic acid have been modified, generally by incorporating terminal adapter sequences comprising one or more primer binding sites and identifiable sequence tags. In certain embodiments, the library members (e.g., genomic DNA, cDNA) may include sequencing adaptors that are compatible with use in, e.g., Illumina's reversible terminator method, long read nanopore sequencing, Roche's pyrosequencing method (454), Life Technologies' sequencing by ligation (the SOLiD platform) or Life Technologies' Ion Torrent platform. Examples of such methods are described in the following references: Margulies et al (Nature 2005 437: 376-80); Schneider and Dekker (Nat Biotechnol. 2012 Apr. 10; 30(4):326-8); Ronaghi et al. (Analytical Biochemistry 1996 242: 84-9); Shendure et al. (Science 2005 309: 1728-32); Imelfort et al. (Brief Bioinform. 2009 10:609-18); Fox et al. (Methods Mol. Biol. 2009; 553:79-108); Appleby et al. (Methods Mol. Biol. 2009; 513:19-39); and Morozova et al. (Genomics. 2008 92:255-64), which are incorporated by reference for the general descriptions of the methods and the particular steps of the methods, including all starting products, reagents, and final products for each of the steps.

In one example embodiment, any suitable RNA or DNA amplification technique may be used to amplify a sample and SDSI. In one example embodiment, the RNA or DNA amplification is an isothermal amplification. The isothermal amplification may be nucleic-acid sequenced-based amplification (NASBA), recombinase polymerase amplification (RPA), loop-mediated isothermal amplification (LAMP), strand displacement amplification (SDA), helicase-dependent amplification (HDA), or nicking enzyme amplification reaction (NEAR). In certain example embodiments, non-isothermal amplification methods may be used which include, but are not limited to, PCR, multiple displacement amplification (MDA), rolling circle amplification (RCA), ligase chain reaction (LCR), or ramification amplification method (RAM).

Example Applications

In one example embodiment, the present invention is used to improve any method of sequencing wherein the nucleic acids to be sequenced are amplified (i.e., amplicon-based methods). In certain example embodiments, the amplification method preferentially amplifies a contaminant nucleic acid if it is present in a sample. In preferred embodiments, samples comprising a pathogen of interest are sequenced. In more preferred embodiments, the pathogen of interest includes variants that can be clustered into families or a lineage. As used herein, the term "variant" refers to any virus having one or more mutations as compared to a known virus. A strain is a genetic variant or subtype of a virus. The terms 'strain', 'variant', and 'isolate' may be used interchangeably. In certain embodiments, a variant has developed a "specific group of mutations" that causes the variant to behave differently than that of the strain it originated from. In certain example embodiments, the families of variants are important for tracking and responding to epidemics and pandemics. For example, sequencing can be used to determine variants that are emerging as the dominant variants causing disease or are spreading more quickly. In another example, sequencing variants can be used to track community transmission and superspreading events (see e.g., Lemieux et al., 2020). Variants may also include those that are resistant to a specific treatment, such as drug resistance. In certain embodiments, variants are associated with more severe disease. As used herein, the term "epidemic" refers to the rapid spread of disease to a large number of people in a given population within a short period of time or the occurrence of more cases of disease, injury, or other health condition than expected in a given area or among a specific group of persons during a particular period. For example, in meningococcal infections, an attack rate in excess of 15 cases per 100,000 people for two consecutive weeks is considered an epidemic. Epidemics of infectious disease are generally caused by several factors including a change in the ecology of the host population (e.g., increased stress or increase in the density of a vector species), a genetic change in the pathogen reservoir or the introduction of an emerging pathogen to a host population (by movement of pathogen or host). Generally, an epidemic occurs when host immunity to either an established pathogen or newly emerging novel pathogen is suddenly reduced below that found in the endemic equilibrium and the transmission threshold is exceeded. An epidemic may be restricted to one location; however, if it spreads to other countries or continents and affects a substantial number of people, it may be termed a pandemic. Effective preparations for a response to a pandemic are multi-layered. The first layer is a disease surveillance system, which includes sequencing of all variants in a population. In certain embodiments, sequencing contaminants that were amplified from a sample would provide an incorrect identification and clustering of the variants.

Any method of sequencing variants in pathogens, such as viral pathogens, is applicable to the present invention (see e.g., Lemieux et al., 2020). Current sequencing methods all suffer from the risk of contamination and the user would be blind to whether the results were accurate.

In certain example embodiments, a pathogen with a DNA genome is sequenced. Sequencing may include whole genome sequencing. Whole genome sequencing (also known as WGS, full genome sequencing, complete genome sequencing, or entire genome sequencing) is the process of determining the complete DNA sequence of an organism's genome at a single time. This entails sequencing all of an organism's chromosomal DNA as well as DNA contained in the mitochondria and, for plants, in the chloroplast. "Whole genome amplification" ("WGA") refers to any amplification method that aims to produce an amplification product that is representative of the genome from which it was amplified. In certain embodiments, the SDSIs of the present invention are added at the amplification step. Non-limiting WGA methods include Primer extension PCR (PEP) and improved PEP (I-PEP), Degenerated oligonucleotide primed PCR (DOP-PCR), Ligation-mediated PCR (LMP), T7-based linear amplification of DNA (TLAD), and Multiple displacement amplification (MDA).

In certain example embodiments, the present invention includes whole exome sequencing. Exome sequencing, also known as whole exome sequencing (WES), is a genomic technique for sequencing all of the protein-coding genes in a genome (known as the exome) (see, e.g., Ng et al., 2009, Nature volume 461, pages 272-276). It consists of two steps: the first step is to select only the subset of DNA that encodes proteins. These regions are known as exons—humans have about 180,000 exons, constituting about 1% of the human genome, or approximately 30 million base pairs. The second step is to sequence the exonic DNA using any high-throughput DNA sequencing technology. In certain embodiments, whole exome sequencing is used to determine germline mutations in genes associated with disease.

In certain example embodiments, targeted sequencing is used in the present invention (see, e.g., Mantere et al., PLoS Genet 12 e1005816 2016; and Carneiro et al. BMC Genomics, 2012 13:375). Targeted gene sequencing panels are useful tools for analyzing specific mutations in a given sample. Focused panels contain a select set of genes or gene regions that have known or suspected associations with the disease or phenotype under study. In certain embodiments, targeted sequencing is used to detect mutations associated with a disease in a subject in need thereof. Targeted sequencing can increase the cost-effectiveness of variant discovery and detection. In certain embodiments, targeted sequencing includes amplification and the SDSIs of the present invention are added at the amplification step.

In one example embodiment, the mitochondrial genome from more than one sample is sequenced. In certain embodiments, mitochondrial genome sequencing includes amplification and the SDSIs of the present invention are added at or before the amplification step. An exemplary method includes MitoRCA-seq (see e.g., Ni et al., MitoRCA-seq reveals unbalanced cytosin to thymine transition in Polg mutant mice. Sci Rep. 2015 Jul. 27; 5:12049. doi: 10.1038/srep12049). The method employs rolling circle amplification, which enriches the full-length circular mtDNA by either custom mtDNA-specific primers or a commercial kit and minimizes the contamination of nuclear encoded mitochondrial DNA (Numts). In certain embodiments, RCA-seq is used to detect low-frequency mtDNA point mutations starting with as little as 1 ng of total DNA.

In another example embodiment, multiple displacement amplification (MDA) is used to generate a sequencing library. Multiple displacement amplification (MDA, is a non-PCR-based isothermal method based on the annealing of random hexamers to denatured DNA, followed by strand-displacement synthesis at constant temperature (Blanco et al. J. Biol. Chem. 1989, 264, 8935-8940). It has been applied to samples with small quantities of genomic DNA, leading to the synthesis of high molecular weight DNA with limited sequence representation bias (Lizardi et al. Nature Genetics 1998, 19, 225-232; Dean et al., Proc. Natl. Acad. Sci. U.S.A 2002, 99, 5261-5266). As DNA is synthesized by strand displacement, a gradually increasing number of priming events occur, forming a network of hyper-branched DNA structures. The reaction can be catalyzed by enzymes such as the Phi29 DNA polymerase or the large fragment of the Bst DNA polymerase. The Phi29 DNA polymerase possesses a proofreading activity resulting in error rates 100 times lower than Taq polymerase (Lasken et al. Trends Biotech. 2003, 21, 531-535). In certain embodiments, the SDSIs of the present invention are added to samples and amplified during MDA or in a subsequent amplification step.

In one example embodiment, is sequencing comprises sequencing of SARS-CoV-2 variants. The scale of the SARS-CoV-2 pandemic has led to a particular focus on reducing the cost and time of amplicon-based methods, often at the cost of slightly reduced sensitivity. However, viral loads of SARS-CoV-2 can vary widely between individuals, in particular when samples are caught early in infection or follow-up sampling is needed. An open-access tiled primer set developed by the ARTIC network is the most widely used method for SARS-CoV-2 specific genome amplification followed by sequencing on either Illumina or nanopore instruments (Quick et al., 2017; Tyson et al., 2020). A wide array of protocols and publications are now available that integrate these ARTIC primers with different amplification and library construction indexing strategies (Baker et al., 2020; Gohl et al., 2020). Approaches such as batching samples by viral load to increase sensitivity are impractical to scale to current needs, resulting in incomplete recovery of viral genomes, especially from low titer samples.

In certain embodiments, the methods described herein can be used to sequence viral samples with low viral loads. A viral load may also be interchangeably referred to as viral burden or viral titer. A viral load may be expressed in viral particles per mL, infectious particles per mL, copies per mL, or virus per mL. A low viral load may be a cycle threshold (CT) >30 or copies per mL<$10^4$. A high viral load may be a CT<30 or par or copies per mL >$10^5$. For example, viral loads lower than 10,000, 1,000, 500, 400, 300, 200, 100, 50, 40, 30, 20, 10 viral particles. In certain embodiments, a single viral particle is sequenced.

In certain embodiments, the SDSI is used to detect and prevent contamination in genomic analysis samples of pathogens. A pathogen may include viruses, bacteria, fungi, and protozoa. In certain embodiments, a virus may belong to any morphological category including helical, envelope, or icosahedral. In certain embodiments, a virus me comprise of DNA or RNA, may be single stranded or double stranded, and may be linear or circular. In certain embodiments, the genome of the virus may be one nucleic acid molecule or several nucleic acid segments. In certain embodiments a virus may belong to the family: Adenoviridae, Papovaviridae, Parvoviridae, Herpesviridae, Poxviridae, Anelloviridae, Pleolipoviridae, Reoviridae, Picornaviridae, Caliciviridae, Togaviridae, Arenaviridae, Flaviviridae, Orthomyxoviridae, Paramyxoviridae, Bunyaviridae, Rhabdoviridae, Filoviridae, Astroviridae, Bornaviridae, Arteriviridae, Hepeviridae, Retroviridae, Caulimoviridae, Hepadnaviridae, Coronaviridae. In certain embodiment, the virus is SARS-CoV-2. (Gelderblom HR. Structure and Classification of Viruses. In: Baron S, editor. Medical Microbiology. 4th edition. Galveston (TX): University of Texas Medical Branch at Galveston; 1996. Chapter 41).

In an exemplary embodiment, the pathogen sequenced is a coronavirus. As used herein, "coronavirus" refers to enveloped viruses with a positive-sense single-stranded RNA genome and a nucleocapsid of helical symmetry that constitute the subfamily Orthocoronavirinae, in the family Coronaviridae (see, e.g., Woo P C, Huang Y, Lau S K, Yuen K Y. Coronavirus genomics and bioinformatics analysis. Viruses. 2010; 2(8):1804-1820). Severe acute respiratory syndrome coronavirus 2 (SARS-CoV-2) is the virus causing the ongoing Coronavirus Disease 19 (COVID19) pandemic (see, e.g., Zhou, et al. (2020). A pneumonia outbreak associated with a new coronavirus of probable bat origin. Nature 579, 270-273). In preferred embodiments, the virus is SARS-CoV-2 or variants thereof. In preferred embodiments, the disease treated is COVID-19. SARS-CoV-2 is the third zoonotic betacoronavirus to cause a human outbreak after SARS-CoV in 2002 and Middle East respiratory syndrome coronavirus (MERS-CoV) in 2012 (de Wit et al., 2016, SARS and MERS: recent insights into emerging coronaviruses. Nat Rev Microbiol 14, 523-534). While there are many thousands of variants of SARS-CoV-2, (Koyama, Takahiko Koyama; Platt, Daniela; Parida, Laxmi (June 2020). "Variant analysis of SARS-CoV-2 genomes". Bulletin of the World Health Organization. 98: 495-504) there are also much larger groupings called clades. Several different clade nomenclatures for SARS-CoV-2 have been proposed. As of December 2020, GISAID, referring to SARS-CoV-2 as hCoV-19 identified seven clades (0, S, L, V, G, GH, and GR) (Alm E, Broberg E K, Connor T, et al. Geographical and temporal distribution of SARS-CoV-2 clades in the WHO European Region, January to June 2020 [published correction appears in Euro Surveill. 2020 August; 25(33):]. Euro Surveill. 2020; 25(32):2001410). Also as of December 2020, Nextstrain identified five (19A, 19B, 20A, 20B, and 20C) (Cited in Alm et al. 2020). Guan et al. identified five global clades (G614, S84, V251, 1378 and D392) (Guan Q, Sadykov M, Mfarrej S, et al. A genetic barcode of SARS-CoV-2 for monitoring global distribution of different clades during the COVID-19 pandemic. Int J Infect Dis. 2020; 100:216-223). Rambaut et al. proposed the term "lineage" in a 2020 article in Nature Microbiology; as of December 2020, there have been five major lineages (A, B, B.1, B.1.1, and B.1.777) identified (Rambaut, A.; Holmes, E. C.; O'Toole, A.; et al. "A dynamic nomenclature proposal for SARS-*CoV*-2 *lineages to assist genomic epidemiology*". 5: 1403-1407).

Exemplary, non-limiting variants applicable to the present invention are described below. Genetic variants of SARS-CoV-2 have been emerging and circulating around the world throughout the COVID-19 pandemic (see, e.g., The US Centers for Disease Control and Prevention; www.cdc.gov/coronavirus/2019-ncov/variants/variant-info.html). Exemplary, non-limiting variants applicable to the present disclosure include variants of SARS-CoV-2, particularly those having substitutions of therapeutic concern. Table A shows exemplary, non-limiting genetic substitutions in SARS-CoV-2 variants.

TABLE A

| Spike Protein Substitution | Common Pango Lineages with Spike Protein Substitutions |
|---|---|
| L452R | A.2.5, B.1, B.1.429, B.1.427, B.1.617.1, B.1.526.1, B.1.617.2, C.36.3 |
| E484K | B.1.1.318, B.1.1.7, B.1.351, B.1.525, B.1.526, B.1.621, B.1.623, P.1, P.1.1, P.1.2, R.1 |
| K417N, E484K, N501Y | B.1.351, B.1.351.3 |
| K417T, E484K, N501Y | P.1, P.1.1, P.1.2 |
| A67V, del69-70, T95I, del142-144, Y145D, del211, L212I, ins214EPE, G339D, S371L, S373P, S375F, | B.1.1.529 and BA lineages |

TABLE A-continued

| Spike Protein Substitution | Common Pango Lineages with Spike Protein Substitutions |
| --- | --- |
| K417N, N440K, G446S, S477N, T478K, E484A, Q493R, G496S, Q498R, N501Y, Y505H, T547K, D614G, H655Y, N679K, P681H, N764K, D796Y, N856K, Q954H, N969K, L981F | |

Phylogenetic Assignment of Named Global Outbreak (PANGO) Lineages is software tool developed by members of the Rambaut Lab. The associated web application was developed by the Centre for Genomic Pathogen Surveillance in South Cambridgeshire and is intended to implement the dynamic nomenclature of SARS-CoV-2 lineages, known as the PANGO nomenclature. It is available at cov-lineages.org.

In some embodiments, the SARS-CoV-2 variant is and/or includes: B.1.1.7, also known as Alpha (WHO) or UK variant, having the following spike protein substitutions: 69del, 70del, 144del, (E484K*), (S494P*), N501Y, A570D, D614G, P681H, T7161, S982A, and D1118H (K1191N*); B.1.351, also known as Beta (WHO) or South Africa variant, having the following spike protein substitutions: D80A, D215G, 241del, 242del, 243del, K417N, E484K, N501Y, D614G, and A701V; B.1.427, also known as Epsilon (WHO) or US California variant, having the following spike protein substitutions: L452R, and D614G; B.1.429, also known as Epsilon (WHO) or US California variant, having the following spike protein substitutions: S13I, W152C, L452R, and D614G; B.1.617.2, also known as Delta (WHO) or India variant, having the following spike protein substitutions: T19R, (G142D), 156del, 157del, R158G, L452R, T478K, D614G, P681R, and D950N; P.1, also known as Gamma (WHO) or Japan/Brazil variant, having the following spike protein substitutions: L18F, T20N, P26S, D138Y, R190S, K417T, E484K, N501Y, D614G, H655Y, and T1027I; and B.1.1.529 also known as Omicron (WHO), having the following spike protein substitutions: A67V, del69-70, T95I, del142-144, Y145D, del211, L212I, ins214EPE, G339D, S371L, S373P, S375F, K417N, N440K, G446S, S477N, T478K, E484A, Q493R, G496S, Q498R, N501Y, Y505H, T547K, D614G, H655Y, N679K, P681H, N764K, D796Y, N856K, Q954H, N969K, L981F, or any combination thereof.

In some embodiments, the SARS-CoV-2 variant is classified and/or otherwise identified as a Variant of Concern (VOC) by the World Health Organization and/or the U.S. Centers for Disease Control. A VOC is a variant for which there is evidence of an increase in transmissibility, more severe disease (e.g., increased hospitalizations or deaths), significant reduction in neutralization by antibodies generated during previous infection or vaccination, reduced effectiveness of treatments or vaccines, or diagnostic detection failures.

In some embodiments, the SARS-Cov-2 variant is classified and/or otherwise identified as a Variant of High Consequence (VHC) by the World Health Organization and/or the U.S. Centers for Disease Control. A variant of high consequence has clear evidence that prevention measures or medical countermeasures (MCMs) have significantly reduced effectiveness relative to previously circulating variants.

In some embodiments, the SARS-Cov-2 variant is classified and/or otherwise identified as a Variant of Interest (VOI) by the World Health Organization and/or the U.S. Centers for Disease Control. A VOI is a variant with specific genetic markers that have been associated with changes to receptor binding, reduced neutralization by antibodies generated against previous infection or vaccination, reduced efficacy of treatments, potential diagnostic impact, or predicted increase in transmissibility or disease severity.

In some embodiments, the SARS-Cov-2 variant is classified and/or is otherwise identified as a Variant of Note (VON). As used herein, VON refers to both "variants of concern" and "variants of note" as the two phrases are used and defined by Pangolin (cov-lineages.org) and provided in their available "VOC reports" available at cov-lineages.org.

In some embodiments the SARS-Cov-2 variant is a VOC. In some embodiments, the SARS-CoV-2 variant is or includes an Alpha variant (e.g., Pango lineage B.1.1.7), a Beta variant (e.g., Pango lineage B.1.351, B.1.351.1, B.1.351.2, and/or B.1.351.3), a Delta variant (e.g., Pango lineage B.1.617.2, AY.1, AY.2, AY.3 and/or AY.3.1); a Gamma variant (e.g., Pango lineage P.1, P.1.1, P.1.2, P.1.4, P.1.6, and/or P.1.7), a Omicon variant (B.1.1.529) or any combination thereof.

In some embodiments the SARS-Cov-2 variant is a VOL. In some embodiments, the SARS-CoV-2 variant is or includes an Eta variant (e.g., Pango lineage B.1.525 (Spike protein substitutions A67V, 69del, 70del, 144 del, E484K, D614G, Q677H, F888L)); an Iota variant (e.g., Pango lineage B.1.526 (Spike protein substitutions L5F, (D80G*), T95I, (Y144-*), (F157S*), D253G, (L452R*), (S477N*), E484K, D614G, A701V, (T859N*), (D950H*), (Q957R*))); a Kappa variant (e.g., Pango lineage B.1.617.1 (Spike protein substitutions (T95I), G142D, E154K, L452R, E484Q, D614G, P681R, Q1071H)); Pango lineage variant B.1.617.2 (Spike protein substitutions T19R, G142D, L452R, E484Q, D614G, P681R, D950N)), Lambda (e.g., Pango lineage C.37); or any combination thereof.

In some embodiments SARS-Cov-2 variant is a VON. In some embodiments, the SARS-Cov-2 variant is or includes Pango lineage variant P.1 (alias, B.1.1.28.1.) as described in Rambaut et al. 2020. Nat. Microbiol. 5:1403-1407) (spike protein substitutions: T20N, P26S, D138Y, R190S, K417T, E484K, N501Y, H655Y, TI027I)); an Alpha variant (e.g., Pango lineage B.1.1.7); a Beta variant (e.g., Pango lineage B.1.351, B.1.351.1, B.1.351.2, and/or B.1.351.3); Pango lineage variant B.1.617.2 (Spike protein substitutions T19R, G142D, L452R, E484Q, D614G, P681R, D950N)); an Eta variant (e.g., Pango lineage B.1.525); Pango lineage variant A.23.1 (as described in Bugembe et al. medRxiv. 2021. doi: doi.org/10.1101/2021.02.08.21251393) (spike protein substitutions: F157L, V367F, Q613H, P681R); or any combination thereof.

In certain embodiments, the pathogen sequenced is a pathogenic bacteria and may include: spirochetes; spirilla; vibrios; gram-negative aerobic rods and cocci; enterics; pyogenic cocci; and endospore-forming bacteria; actinomycetes and related bacteria; rickettsias and chlamydiae; mycoplasmas, which are groups defined by some bacteriological criteria. A pathogenic bacteria may include: *Escherichia*

*coli, Salmonella enterica, Salmonella typhi, Shigella dysenteriae, Yersinia pestis, Pseudomonas aeruginosa, Vibrio cholerae, Bordetella pertussis, Haemophilus influenza, Helicobacter pylori, Campylobacter jejuni, Neisseria gonorrhoeae, Neisseria meningitidis, Brucella abortus, Bacteroides fragilis, Staphylococcus aureus, Streptococcus pyogenes, Streptococcus pneumoniae, Bacillus anthracis, Bacillus cereus, Clostridium tetani, Clostridium perfringens, Clostridium botulinum, Clostridium difficile, Corynebacterium diphtheriae, Listeria monocytogenes, Mycobacterium tuberculosis, Mycobacterium leprae, Chlamydia trachomatis, Chlamydia pneumoniae, Mycoplasma pneumoniae, Rickettsias, Treponema pallidum, Borrelia burgdorferi*, or a variant thereof. (Todar, K. Textbook of Bacteriology (2020) Online).

In an exemplary embodiment, the pathogen sequenced is a pathogenic fungi and may include: *Aspergillus; Blastomyces; Candida; Coccidioides; Cryptococcus; Fusarium; Microsporum; Epidermophyton; Trichophyton; Histoplasma; Rhizopus; Mucor; Rhizomucor; Syncephalastrum; Cunninghamella; Apophysomyces; Lichtheimia* (formerly *Absidia*); *Eumycetoma; Pneumocystis; Trichophyton; Microsporum; Epidermophyton; Sporothrix; Paracoccidioides; Talaromyces* or a variant or species thereof. (CDC)

In an exemplary embodiment, the pathogen sequenced is a pathogenic protozoa belonging to the group: Sarcodina; Mastigophora; Ciliophora; or Sporozoa defined by their mode of movement. (CDC) In certain embodiments, the pathogenic protozoa may include: Entamoeba; Trichomonas; Leishmania; Chilomonas; Giardia; Isopora; Sarcocystis; Nosema; Balantidium; Eimeria; Histomonas; Trypanosoma; Plasmodium; Babesia; or Haemoproteus or a variant or species thereof.

Further embodiments are illustrated in the following Examples which are given for illustrative purposes only and are not intended to limit the scope of the invention.

EXAMPLES

Here Applicants designed, optimized, and implemented a novel sample identification method using synthetic DNA spike-ins (SDSIs) that is broadly compatible with SARS-CoV-2 sequencing approaches and settings. Applicants implemented these SDSIs for Illumina sequencing with SARS-CoV-2 specific amplification using the ARTIC consortium's amplicon designs. To maximize epidemiological utility by increasing the number of genomes recovered from samples with low viral loads, Applicants benchmarked key amplification and library construction steps. Applicants propose a modified protocol, hereafter termed SDSI+ARTIC, that provides increased confidence in the veracity of genomes with minimal extra cost and time that can be applied to investigations of SARS-CoV-2 epidemiology and emerging viral variants (FIG. 1).

Example 1—Design and in Silico Validation of Novel Amplicon Spike-Ins

Figure 2A:
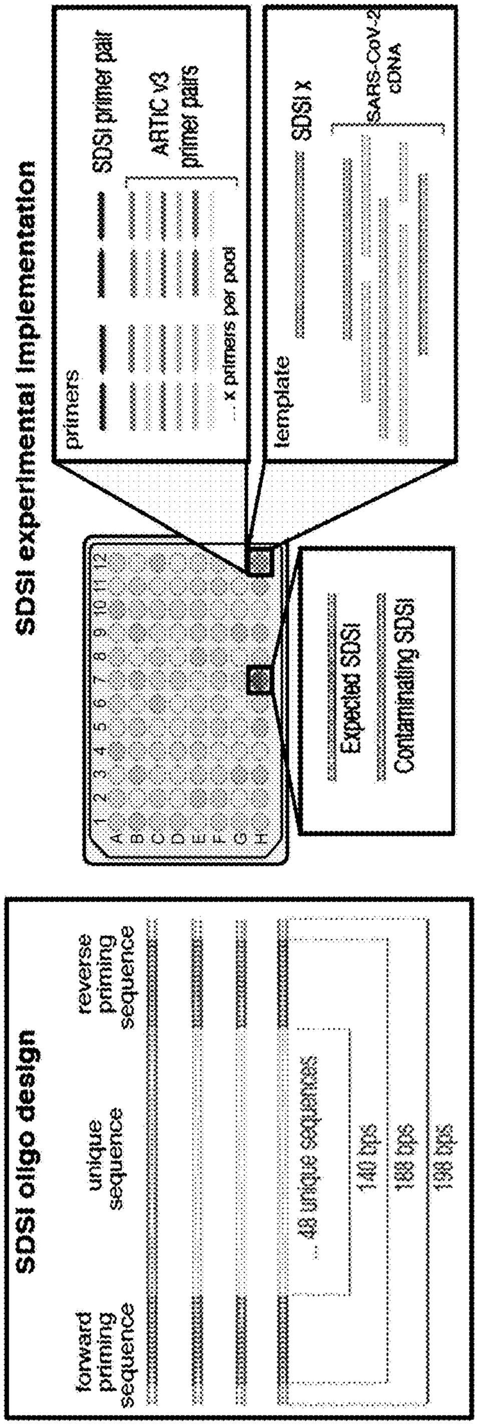
FIG. 2A-2C—Synthetic DNA oligos spiked into amp-seq reactions flag contamination and sample swaps—A. Schematic detailing SDSI design. Each oligo contains 140 bp of sui generis sequence flanked by unique primer binding sites. Primers designed to amplify SDSIs are added to ARTIC primer pools, and a unique SDSI is added to each clinical sample. Identification of multiple SDSIs in the same sample indicates contamination. B. In a titration of SDSIs across clinical samples with variable CTs, the number of reads mapping to both SARS-CoV-2 and the SDSI were quantified, and the percentage of each was calculated. C. For each of 48 unique clinical samples (on the horizontal axis), reads mapping to each of 48 unique SDSIs (on the vertical axis) were quantified; the log of this read count is represented by the intensity of color displayed. Samples and SDSIs were ordered such that the intended match is on the diagonal of this matrix, thus any off-diagonal signal would reveal non-specific identification of SDSIs or contamination of SDSIs across samples.

Applicants sought to design a robust system for contamination tracing and sample tracking applicable to a wide-variety of viral sequencing strategies via known synthetic DNA sequences. Applicants envisioned that these novel synthetic DNA spike-ins (SDSIs) would consist of a uniquely identifiable sequence such that each sample in a sequencing batch could be paired with a different SDSI, enabling in-sample labeling. SDSIs should be sufficiently distinct from one another as well as common laboratory or human pathogens to ensure reliable identification. Each unique sequence is then flanked by constant priming regions so that a single additional primer set can be integrated into a multiplexed PCR to co-amplify the SDSI with the sample (FIG. 2A). In labeling all amplified viral genomic material in a laboratory setting, Applicants could track sample swaps and viral contamination with exquisite resolution and accuracy.

Figure 6A:
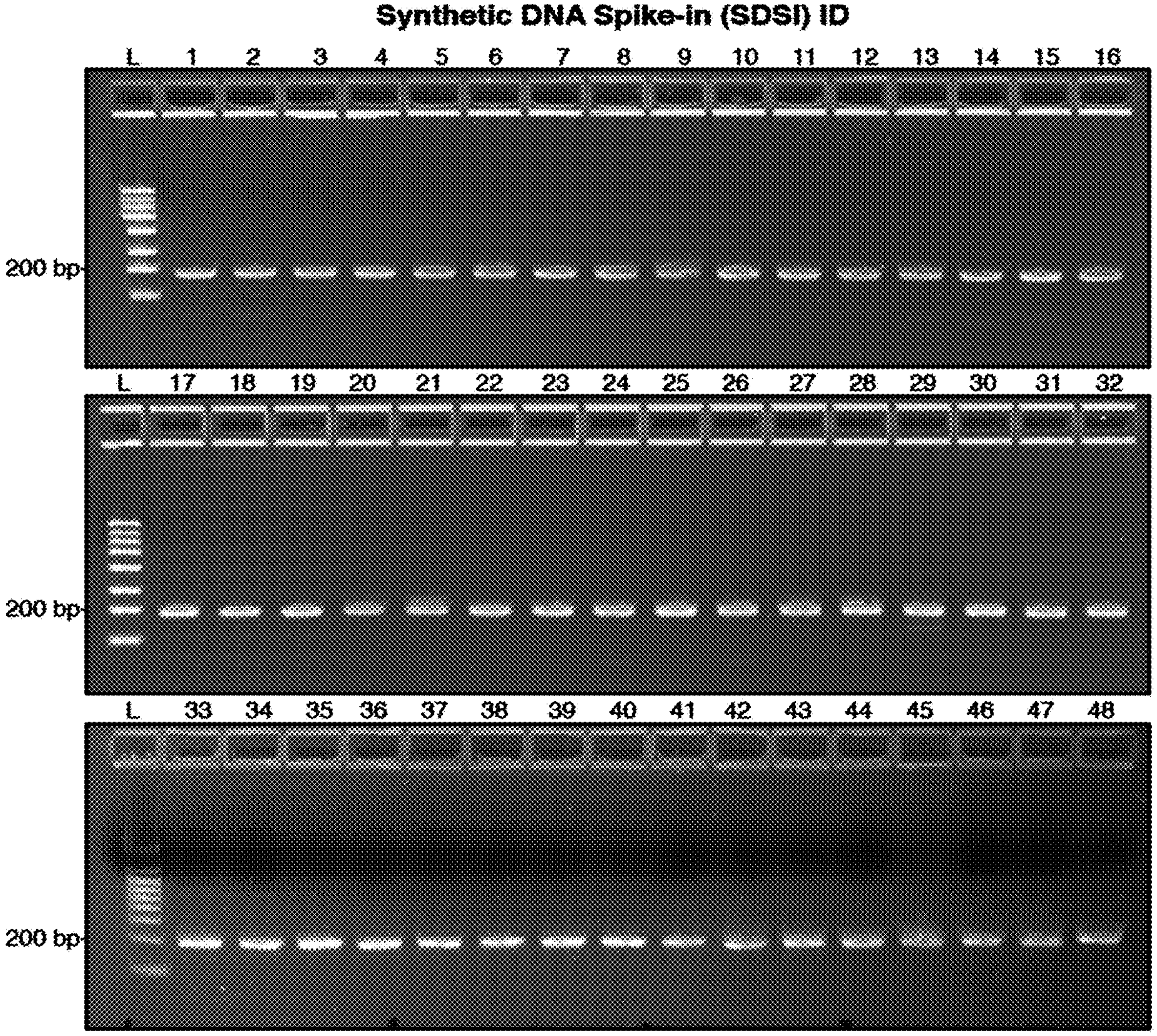
FIG. 6A-6C—Spike-in validation—A. 100 fmol DNA spike-in amplified under standard ARTIC PCR conditions for 40 cycles run on 2.2% agarose gel image with 188 bp amplified spike-in (SDSI 1-48) B. RT-PCR for Spike-in and spike-in specific primers, Spike-in specific primers water control, Spike-in with COVID positive cDNA and spike-in specific primers, COVID positive cDNA and spike-in specific primers. C. Both SDSIs and ARTIC amplicons avoid extremes of GC content, and the two have generally overlapping distributions. SDSI primers also have a length and GC content similar to the average ARTIC v3 primer, resulting in a compatible TM.
Figure 6B:
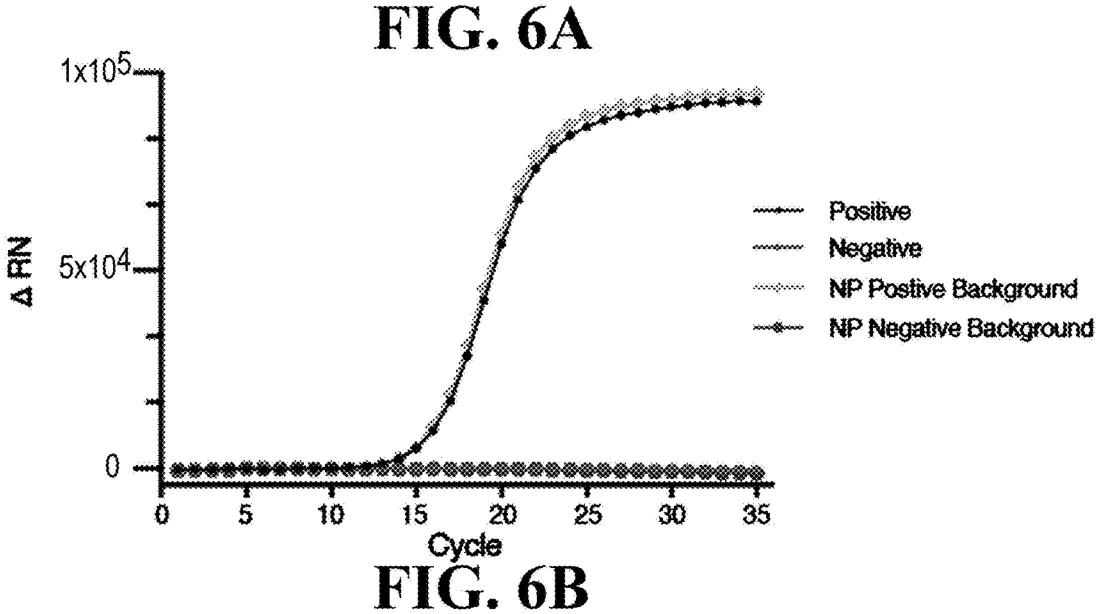
Figure 6C:
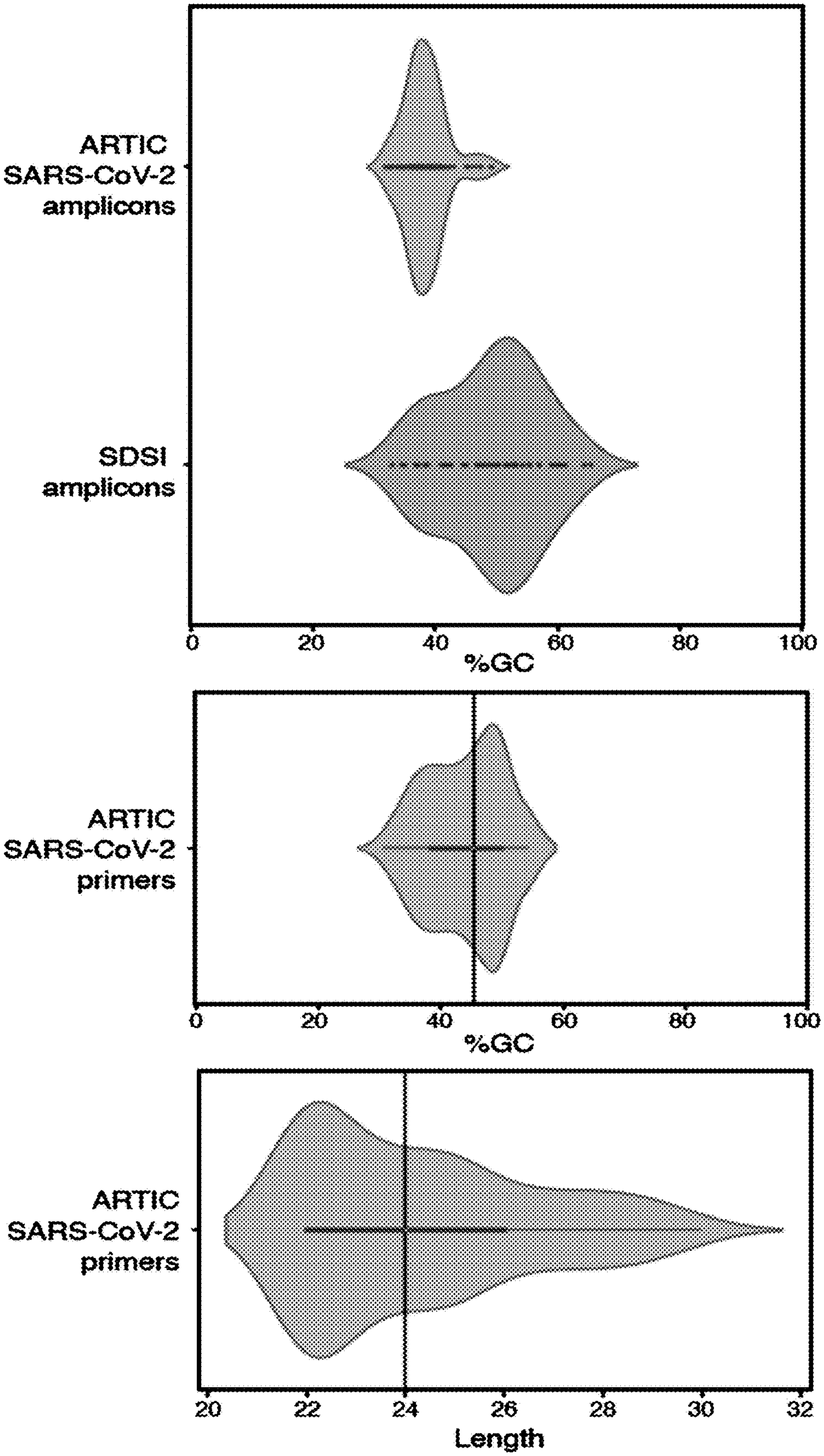

Excerpting DNA sequences from diverse, exotic archaea genomes to serve as the unique portion of the SDSI precludes false detection and cross-identification. To balance common sequencing library construction constraints, DNA synthesis costs, and providing enough sequence to be uniquely identifiable, Applicants generated SDSIs with a 140 bp stretch of variable sequence. Applicants confirmed that the various SDSIs were significantly different from each other to mitigate cross-identification; among all SDSIs, the minimum pairwise Hamming distances of the 140 bp stretch of unique sequence was 84 (mean=105; max=121). Since false detection of SDSI would occur if its sequence shared significant homology with other genetic material in a sample, Applicants based these sequences on archaea, which are divergent from organisms found in typical laboratory or clinical settings (Table 2). A permissive search performed against the entire NCBI database confirmed that 44/48 SDSI sequences had significant homology (>75% sequence identity over >75% query cover) exclusively within the domain archaea; the remaining SDSIs had homology to a handful of bacterial genuses unlikely to be found in laboratories (Table 2). In considering the application of these SDSIs to ARTIC SARS-CoV-2 amplicon sequencing, Applicants also specifically verified that each unique SDSI sequences were unlikely to be confused with expected COVID-19 clinical sample content, confirming that each sequence had very limited homology (nothing >50% sequence identity over >50% query cover) to both *Homo sapiens* and SARS-CoV-2. In designing these amplicon sequences Applicants also avoided extremes of GC content (range: 35-65%) in order to promote similar amplification rates across different SDSIs, as well as other potential targets of the multiplexed reaction, such as viral amplicons. Applicants specifically ensured that the SDSIs had similar GC content to ARTIC SARS-CoV-2 amplicons (FIG. 6).

Similarly, the design of common primers for SDSI amplicons enabled compatibility with a broad spectrum of amplicon-based sequencing reactions, including in clinical settings. To preclude off-target priming in the PCR reaction that could outcompete amplification of a primary target, Applicants limited SDSI primer homology to common organisms, particularly on the 3' end of the primer. Applicants specifically confirmed that primers were unlikely to amplify human or SARS-CoV-2 to promote SDSI primer integration into the ARTIC SARS-CoV-2 amplicon sequencing PCR reaction. Primers were compatible with ARTIC v3 primer sets, with a similar length (24 bps each) and GC content (45.8% each) (FIG. 6).

Example 2—Application of Spike-Ins to ARTIC SARS-CoV-2 Sequencing

Figure 2B:
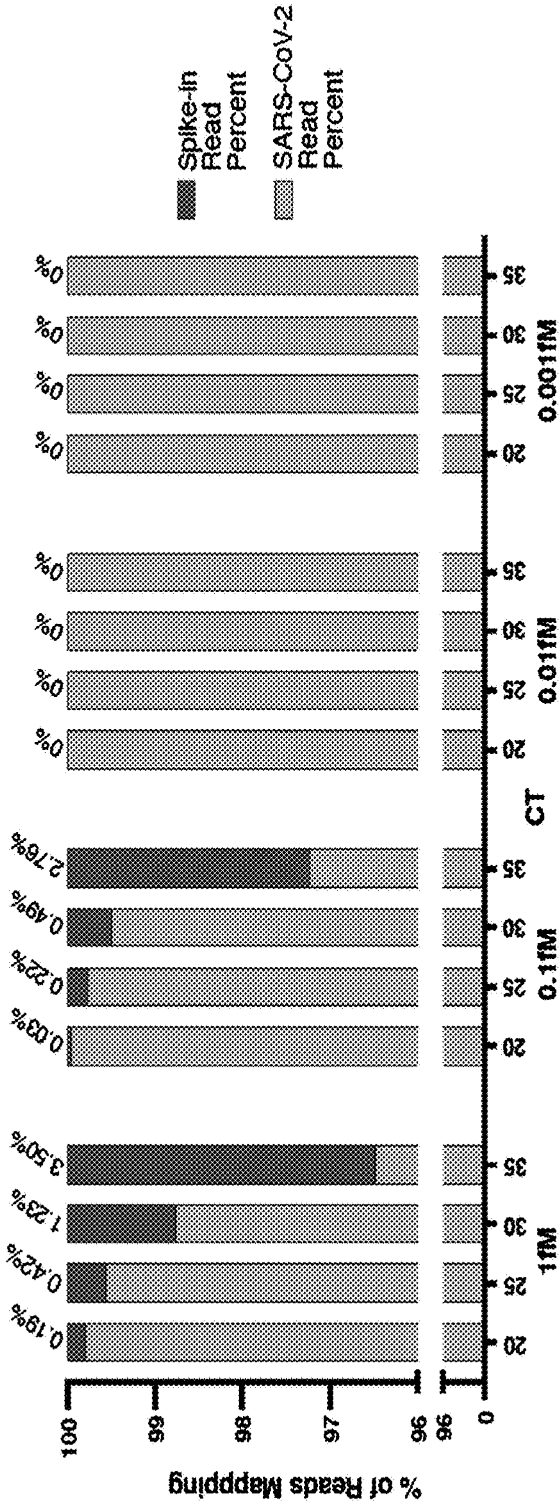
Figure 7:
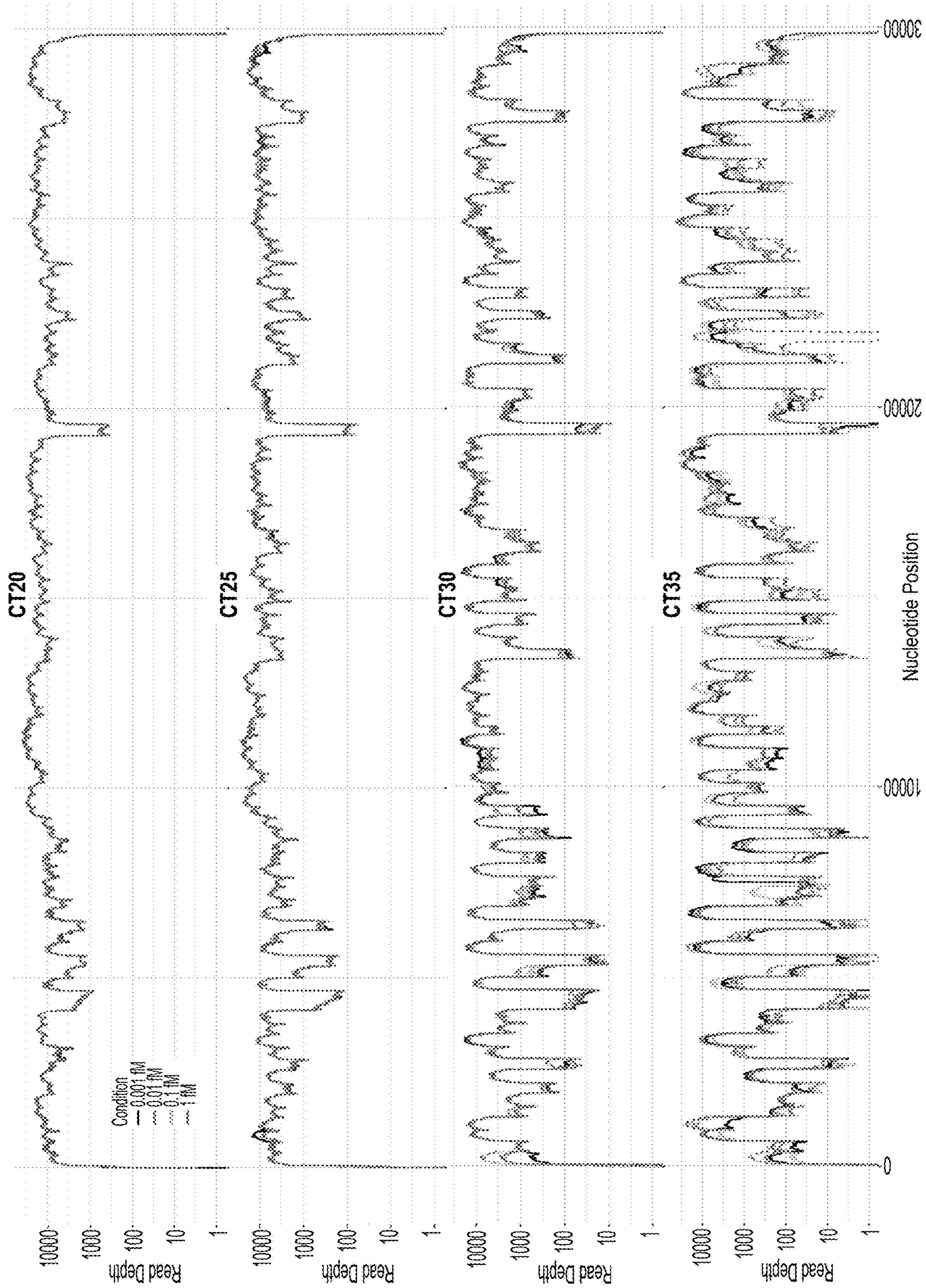
FIG. 7—SDSI Titration—Coverage plots for four different SDSI concentrations (1 fM, 0.1 fM, 0.01 fM, 0.001 fM) at four different CT dilutions (CT=20,25,30,35).

Applicants demonstrated that the addition of SDSIs into the ARTIC multiplexed PCR provided a sample-specific internal control and did not detrimentally affect the amplification of SARS-CoV-2 RNA. SDSI primers did not produce any nonspecific amplification, including in the presence of NP swab RNA, supporting the expectation that primers shared limited homology with genomic material from clinical samples (FIG. 6). All SDSIs amplified in an ARTIC SARS-CoV-2 PCR reaction with SDSI primers included, in each case yielding a single clean product of the expected size (FIG. 6). Applicants next sought to ensure that inclusion of the SDSI oligo and SDSI primers did not limit amplification of SARS-CoV-2 RNA. To prevent SDSIs overtaking the amplification and sequencing of SARS-CoV-2 amplicons, Applicants optimized the amount of SDSI added to each reaction through limited titration (FIG. 7). Applicants found that 1 μl of a 1 fM SDSI resulted in the reliable detection of the SDSI across a range of CT values (CT 20, 25, 30, 35) while the majority of reads (>96%) still mapped to SARS-CoV-2 (Table 3; FIG. 2B).

Figure 2C:
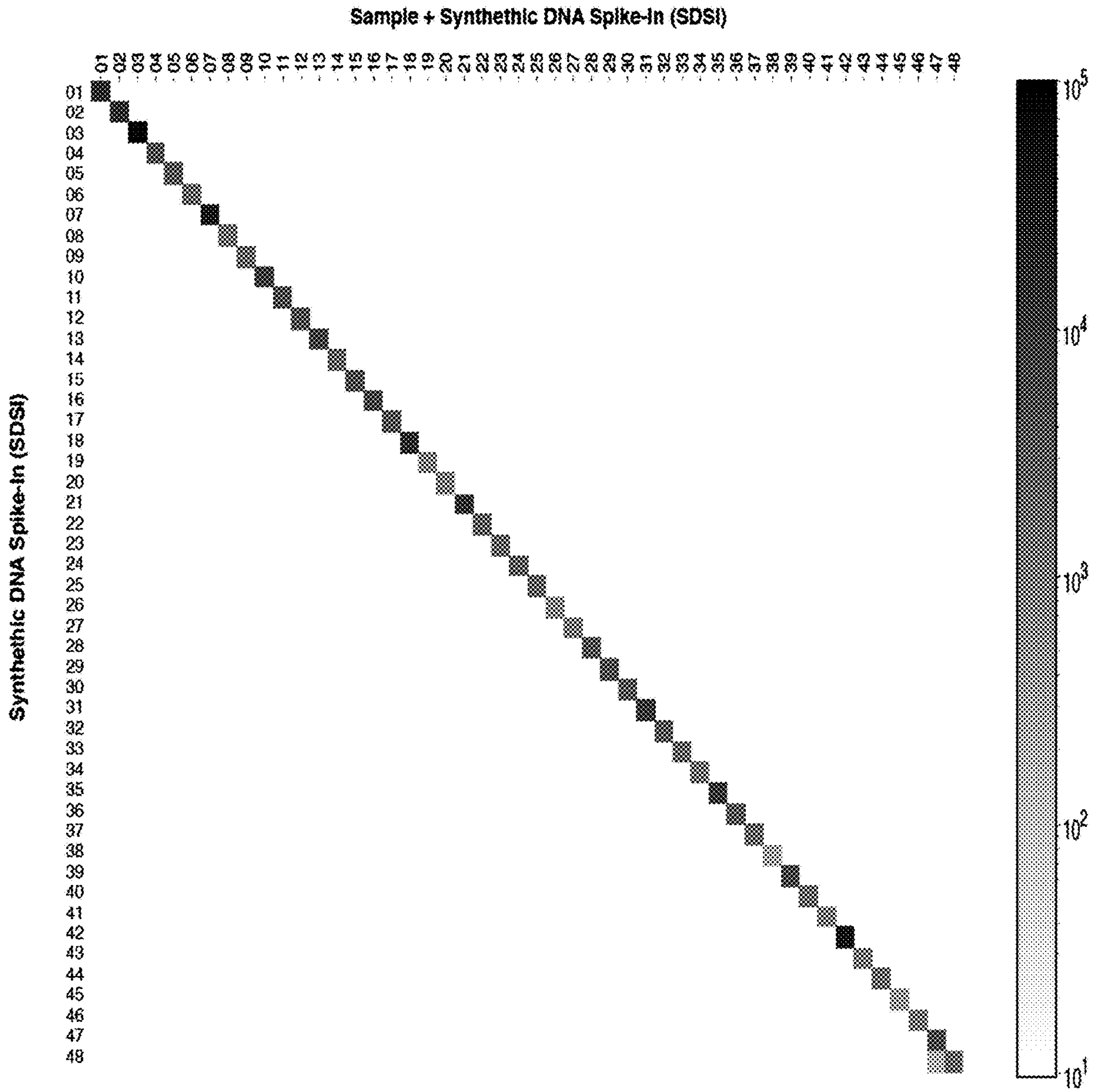

Applicants performed SDSI+ARTIC sequencing on a batch of 48 SARS-CoV-2+clinical samples to demonstrate its feasibility and utility in tracking samples and identifying contamination. After adding a different SDSI to each sample, Applicants found that 47/48 SDSIs were identified exclusively in the anticipated sample, validating the use of SDSIs as an internal control for sample tracking. One SDSI (SDSI_48) was detected in the sample that it was added to as well as a neighboring sample in the batch (FIG. 2C). Applicants suspect that this represents unintentional within-batch contamination that was likely a consequence of spill-over between neighboring wells. This case reveals the insidious nature of commonplace contamination and underscores the importance of this novel method for identifying it.

Figure 8A:
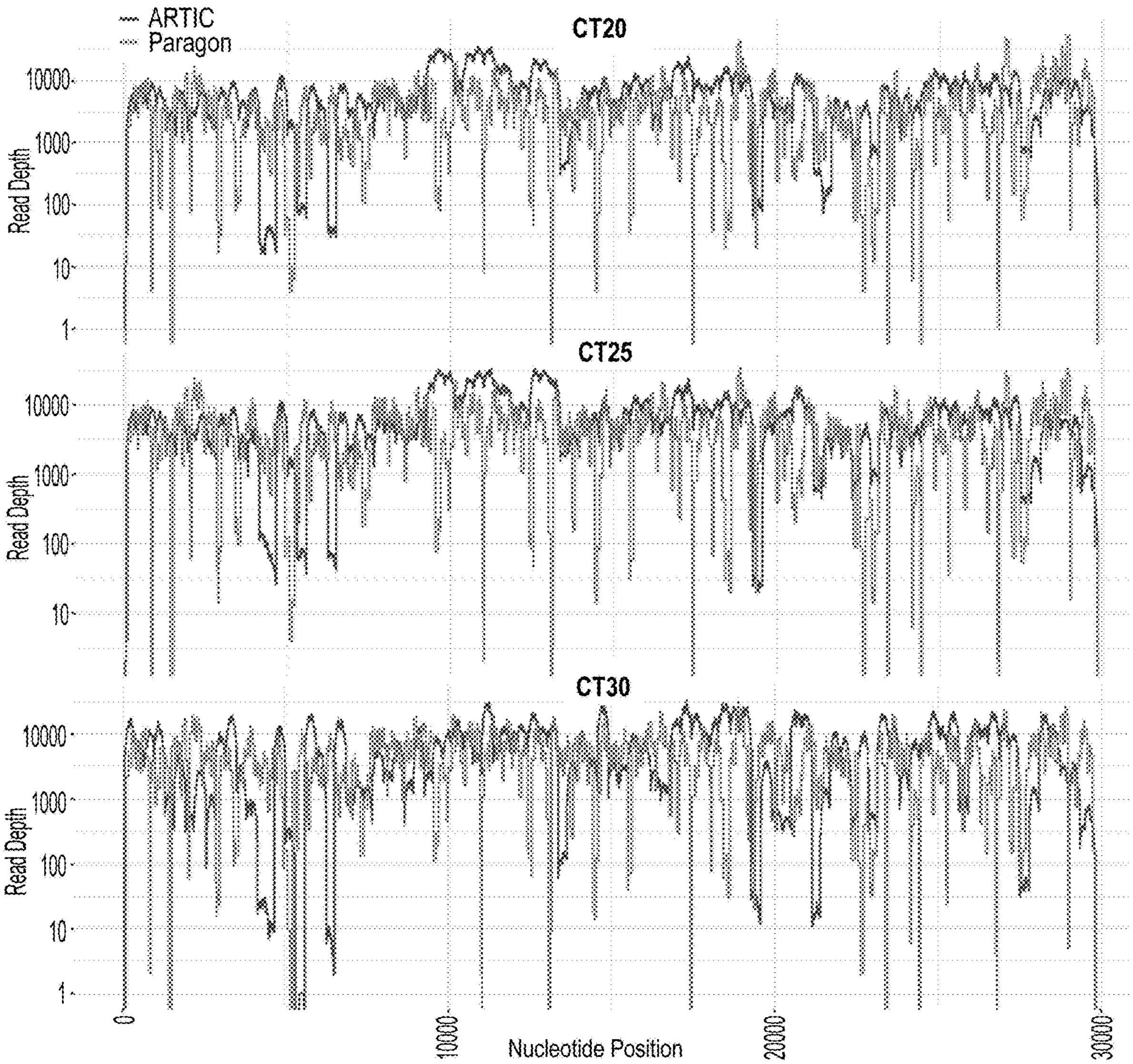
FIG. 8A-8C—Comparison to alternate amp-seq strategies—A. Three representative coverage plots for CT 20, CT 25, and CT 30 samples. B. SNP detection for the CT 20 and CT 25 sample. ARTIC and Paragon consensus sequences were compared to the metagenomic consensus sequences. The SNP that was not called in Paragon was due to low coverage at that position. Analysis was performed with assemblies generated with a minimum coverage of both 3 and 20, yielding identical results. C. Base pairs of the SARS-CoV-2 genome covered for the modified ARTIC pipeline versus Paragon CleanPlex Panel at different depths of coverage. Five samples at varying CTs were compared.
Figure 8B:
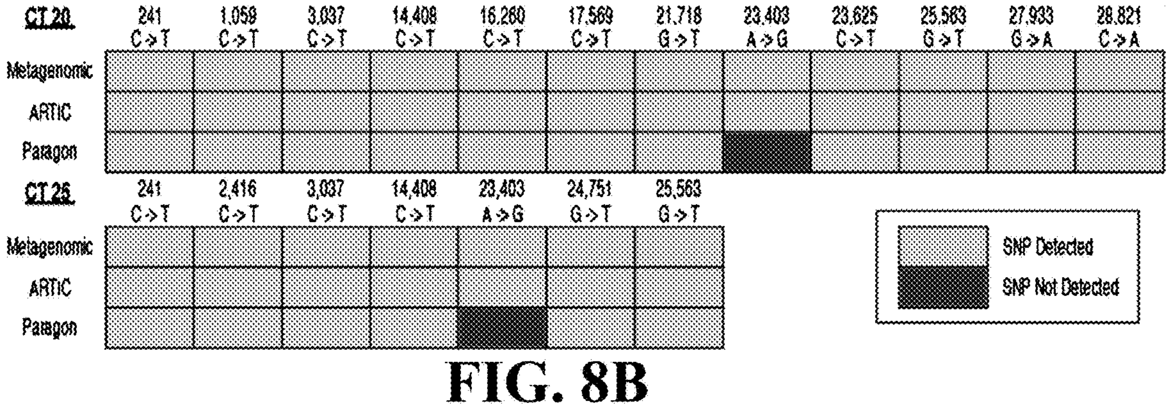
Figure 8C:
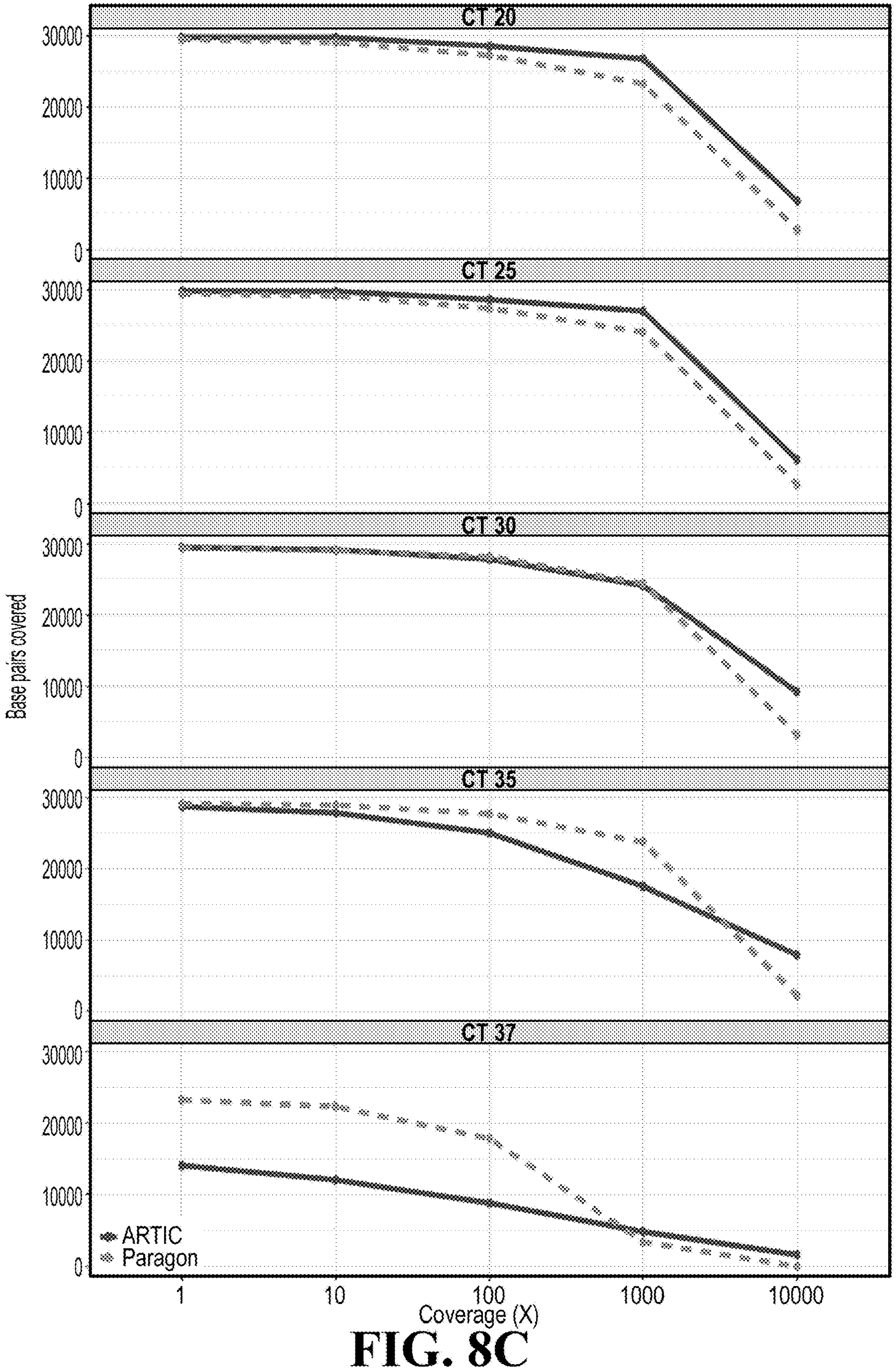

As shorter amplicons have been purported to yield superior recovery for low viral load samples (Antonov et al., 2005; No et al., 2019)), Applicants explored extending SDSIs to the Paragon Genomics' CleanPlex SARS-CoV-2 panel, but identified fatal shortcomings. Paragon amplicons are on average half the size of ARTIC (149 bp vs 343 bp), and compatible with the SDSI length 140 bp. (Antonov et al., 2005; No et al., 2019) (*SARS-CoV-*2 *COVID-*19 *Coronavirus Research and Surveillance*, n.d.)(Antonov et al., 2005; No et al., 2019). However, the Paragon panel had dropout regions even in low CT samples which resulted in missed SNP calls compared to ARTIC across 5 samples (CTs=20-37), consistent with other reports (FIG. 8A, 8B) (Klempt et al., 2020). Although this panel did recover more of the genome in very high CT samples (>35), Applicants did not proceed with SDSI integration as the uneven and unreliable genome coverage across most clinical CTs limited Paragon's epidemiological utility (FIG. 8C).

Figure 3A:
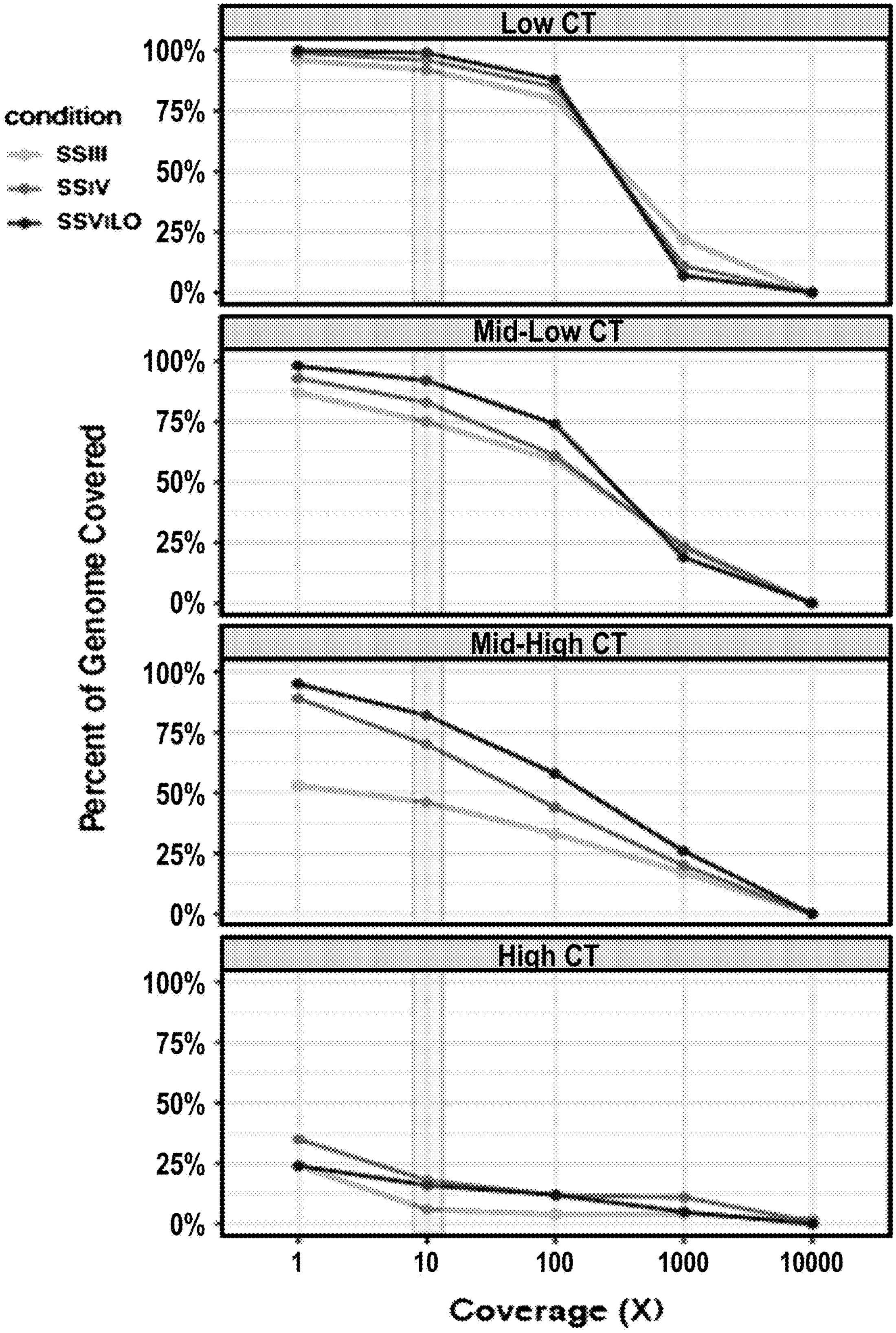
FIG. 3A-3D—Maximizing Genome Recovery and Coverage with SDSI-ARTIC—A. The percent of the target genome covered at various depths of coverage when three reverse transcriptases, Superscript III, Superscript IV, and Superscript VILO were used for cDNA synthesis. Data represents four individual samples. B. Amplicons with at least 0.2× of the mean amplicon coverage with the normal ARTIC v3 primer pools or with a modified primer pool with a 2× concentration of 20 different ARTIC primer pairs. Four samples with low, mid-low, mid-high, and high CTs were used. C. Gini coefficients for two mid-high CT samples and four high CT when using either 35, 40, or 45 cycles for the ARTIC PCR. Error bars represent standard deviation. D. Comparison of Nextera DNA Flex and Nextera XT on the number of SARS-CoV-2 base pairs covered at various depths of coverage for three samples at different CTs.
Figure 9A:
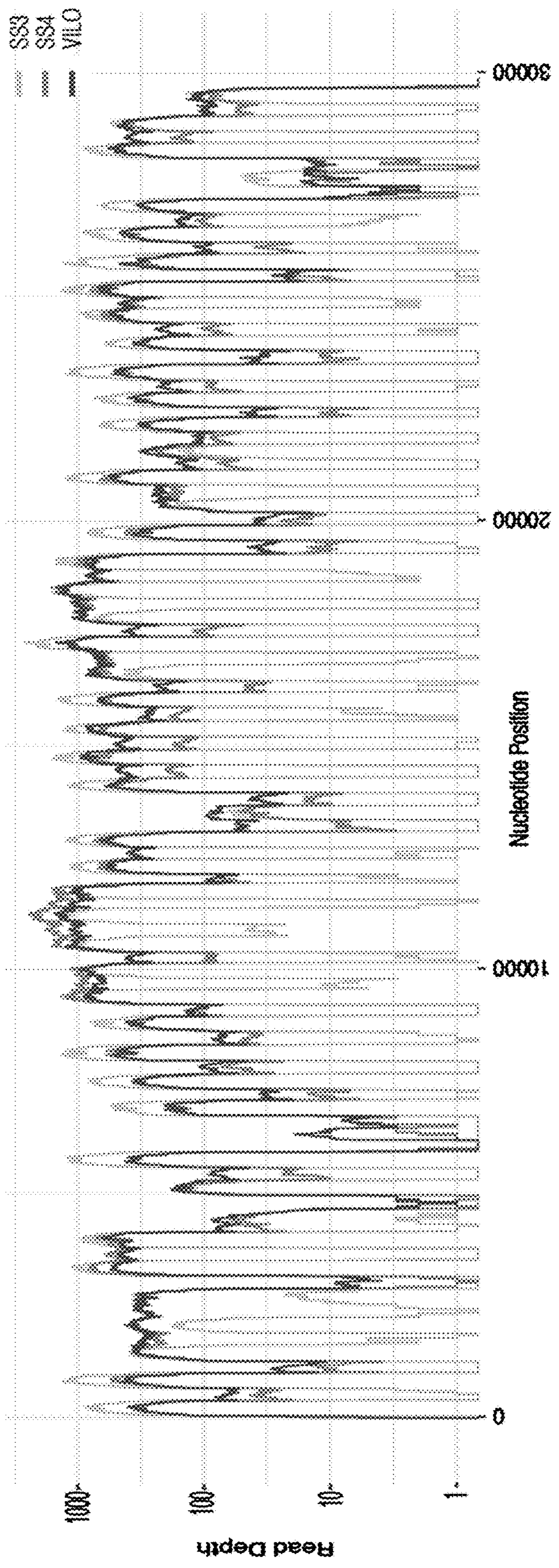
FIG. 9A-9D—RT comparisons for cDNA length—A. Read depth across each nucleotides position for the same sample (CT=13.89) when using three different reverse transcriptases (SSIII, SSIV, or SSVILO) for cDNA synthesis. B. Base pairs of the SARS-CoV-2 genome covered at various depths when using different enzymes for the ARTIC PCR. C. Base pairs of the SARS-CoV-2 genome covered at various depths when using either normal ramping speed (3° C./s) for the ARTIC PCR or reduce the ramping (1.5° C./s). D. Read depth across each nucleotides position for normal ARTIC PCR vs an alternate hybridization PCR.
Figure 9B:
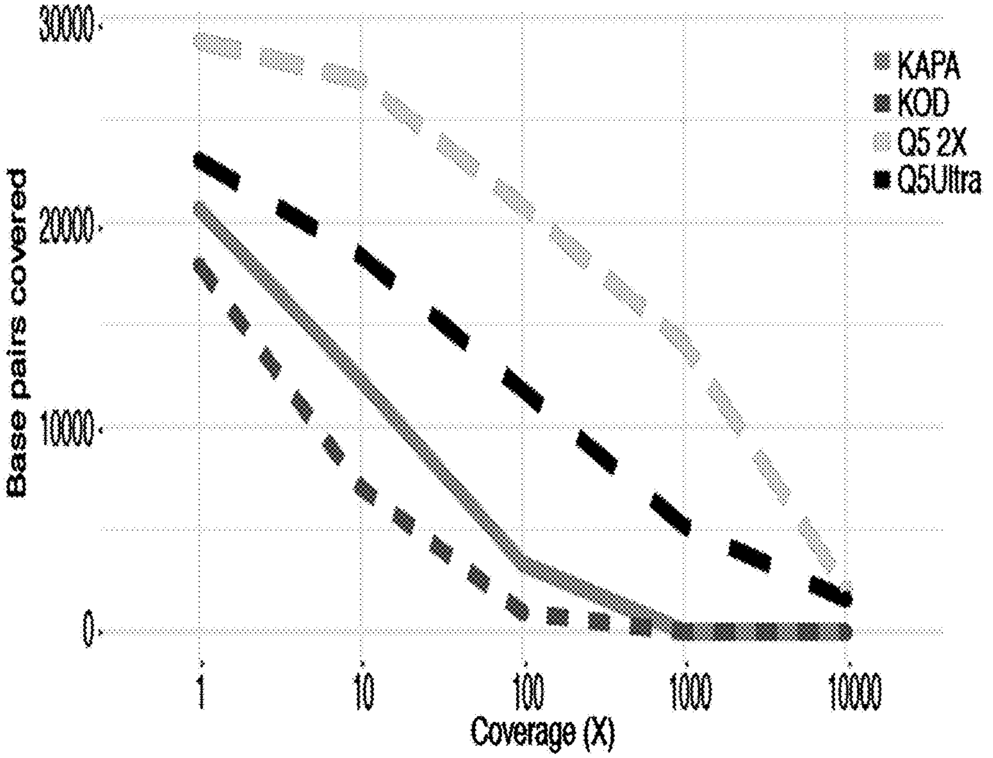

Example 3—Improving Genome Recovery and Coverage for Illumina-Based ARTIC SARS-CoV-2 Sequencing Applicants benchmarked various alterations to Illumina-based SDSI+ARTIC sequencing in order to maximize the number of complete, high-quality genomes recovered from clinically diverse samples. Higher CT samples prove especially challenging to sequence but their recovery is still of critical importance to epidemiological and clinical applications of viral genomics. Applicants found that substituting a more processive reverse transcriptase provided the single biggest benefit. Comparing cDNA produced with Superscripts III, IV, or IV-VILO across a range of clinical CTs (low CT: <20, mid-low CT: 20-25, mid-high CT: 25-30, and high CT: >30), SSIV-VILO and SSIV produced the highest number of amplicons with at least 10× coverage across 13 samples (SSIII: 72.64%, SSIV: 81.93%, SSIV-VILO: 86.97%) (FIG. 3A). These processive reverse transcriptases also displayed lower variability as measured by the percent of amplicons with <20% mean coverage (SSIII: 36.89% SSIV: 31.24% SSIV-VILO: 22.45%) (FIG. 9A). Applicants also tested five DNA polymerase and conditions in the SDSI+ARTIC PCR reaction (Methods) and found that Q5 Hot Start High-Fidelity 2× Master Mix and KAPA reactions yielded the highest amplification (average 85.3 nM and 56 nM respectively) (FIG. 9B).

Figure 3B:
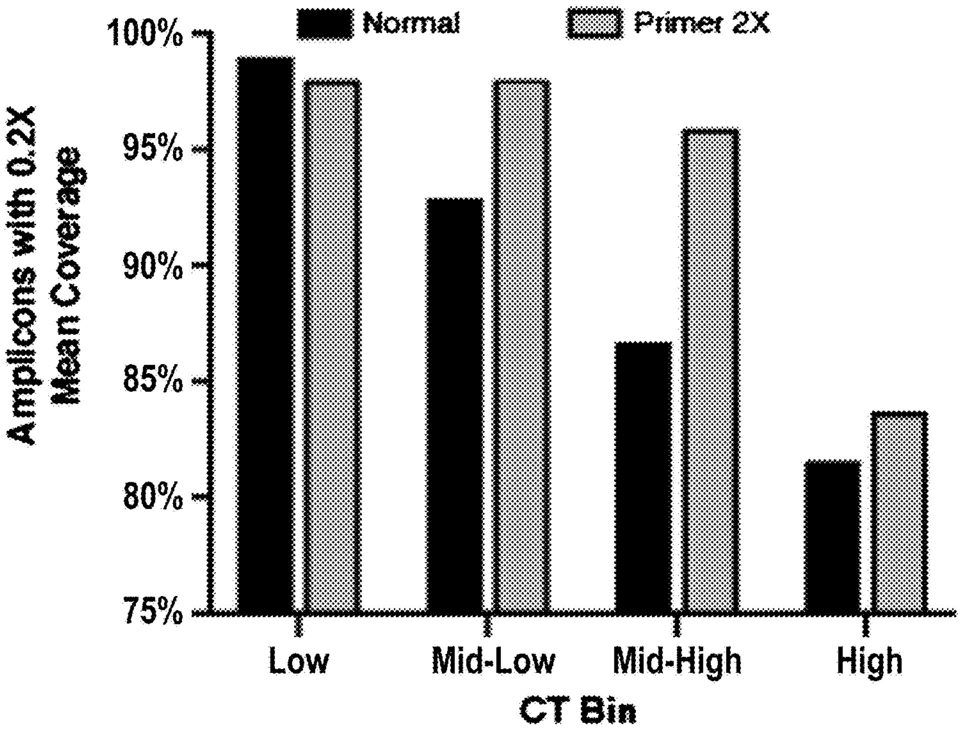
Figure 3C:
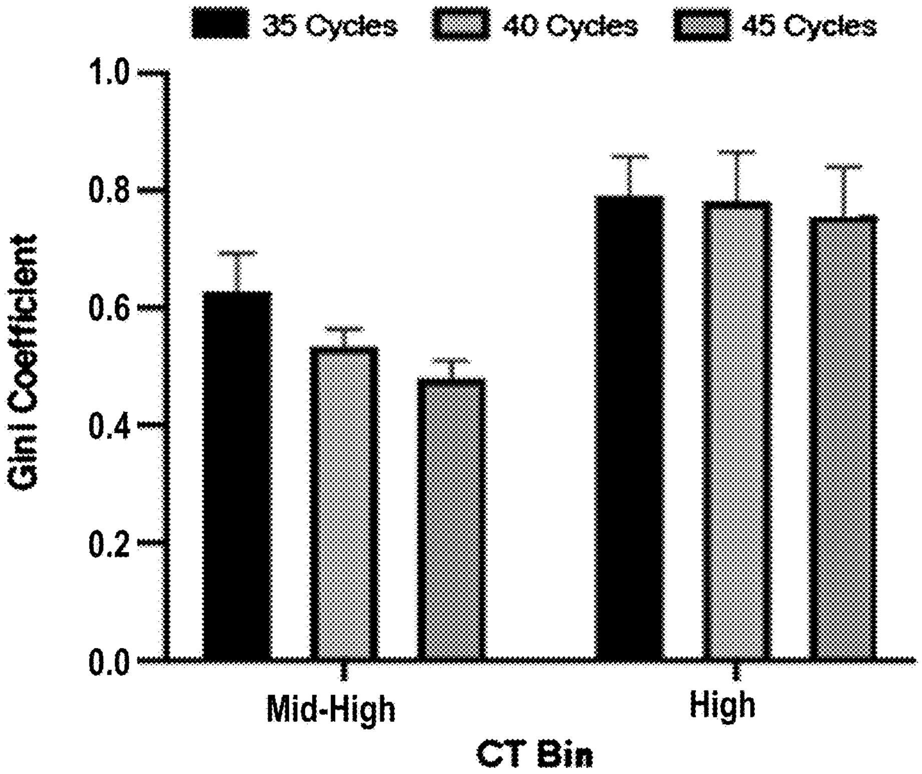
Figure 3D:
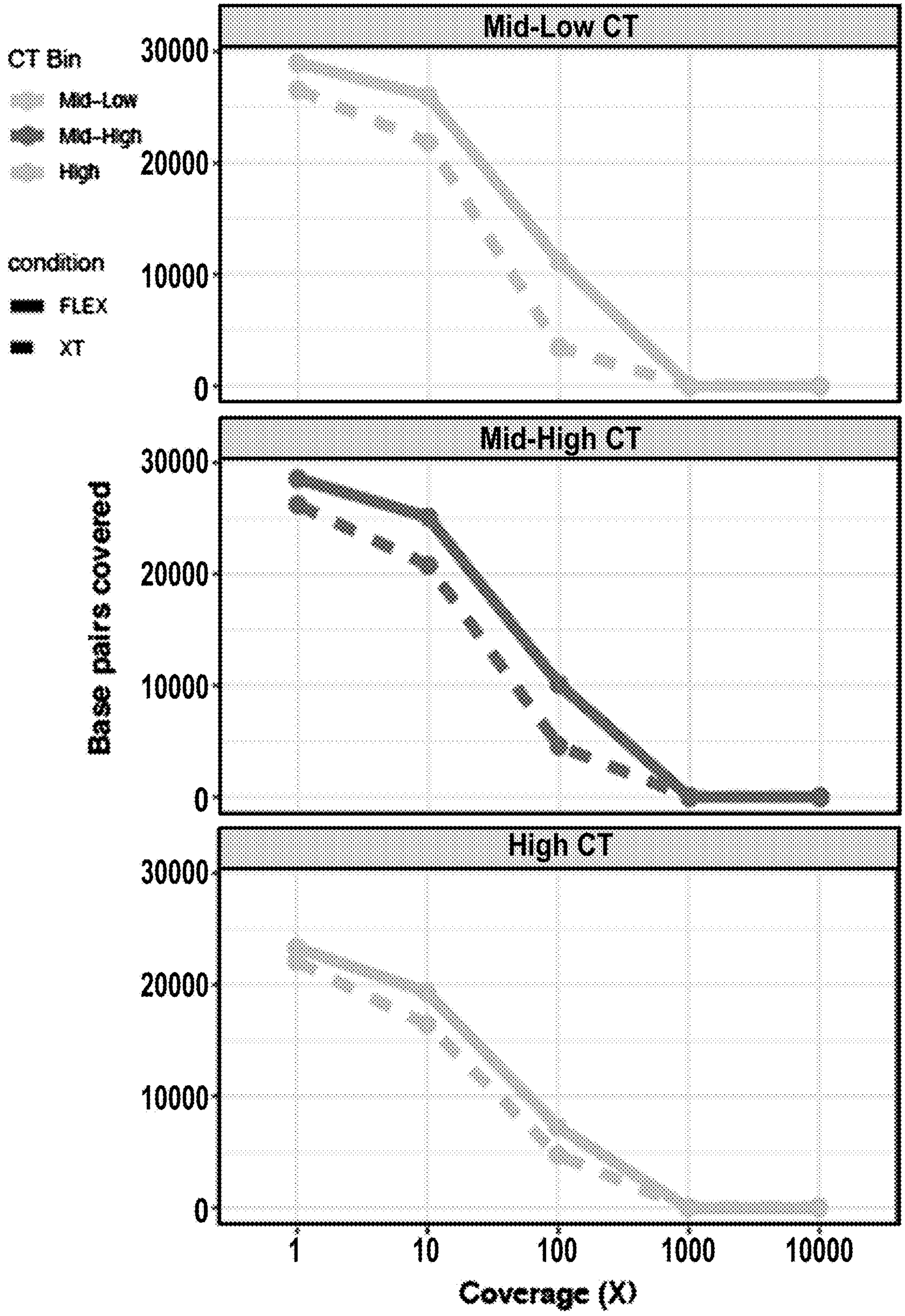
Figure 9C:
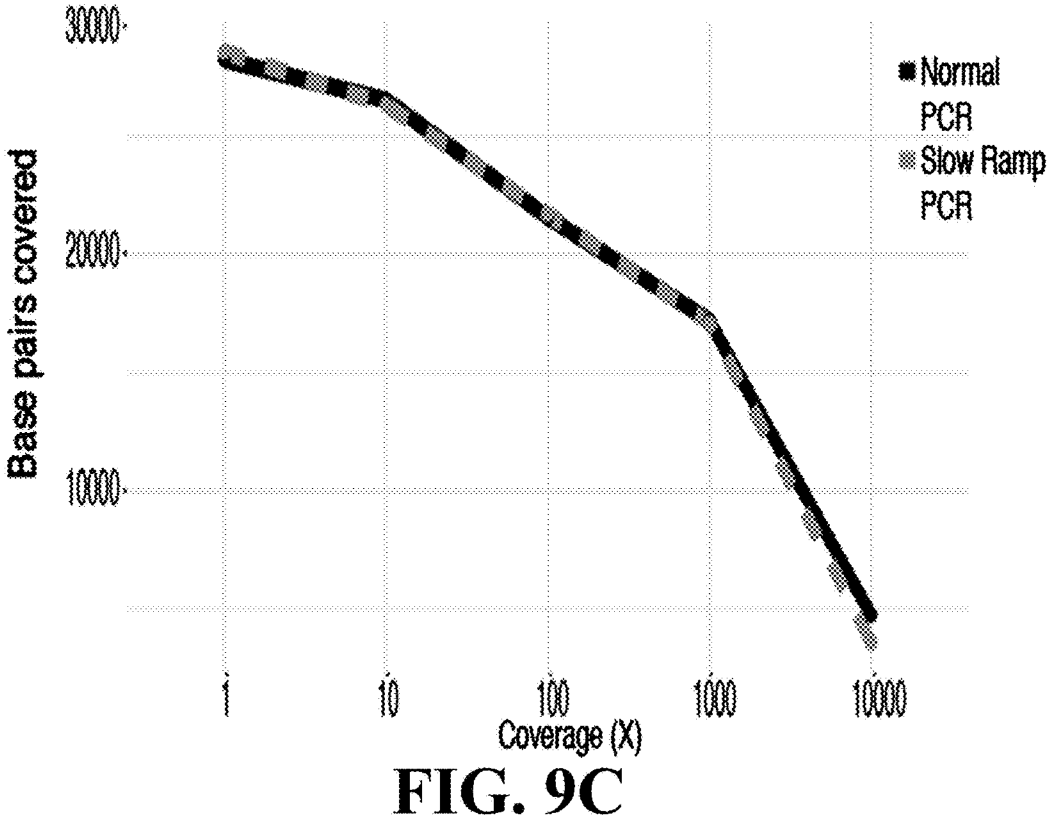
Figure 9D:
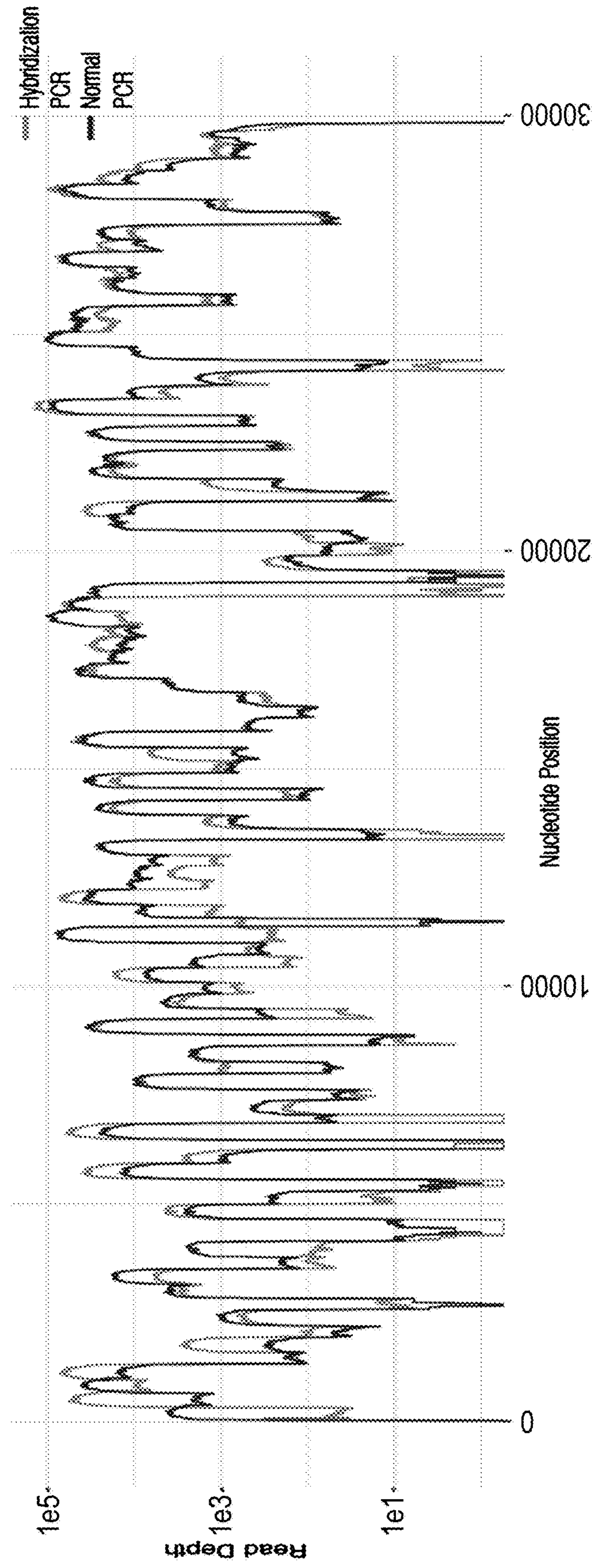
Figure 10:
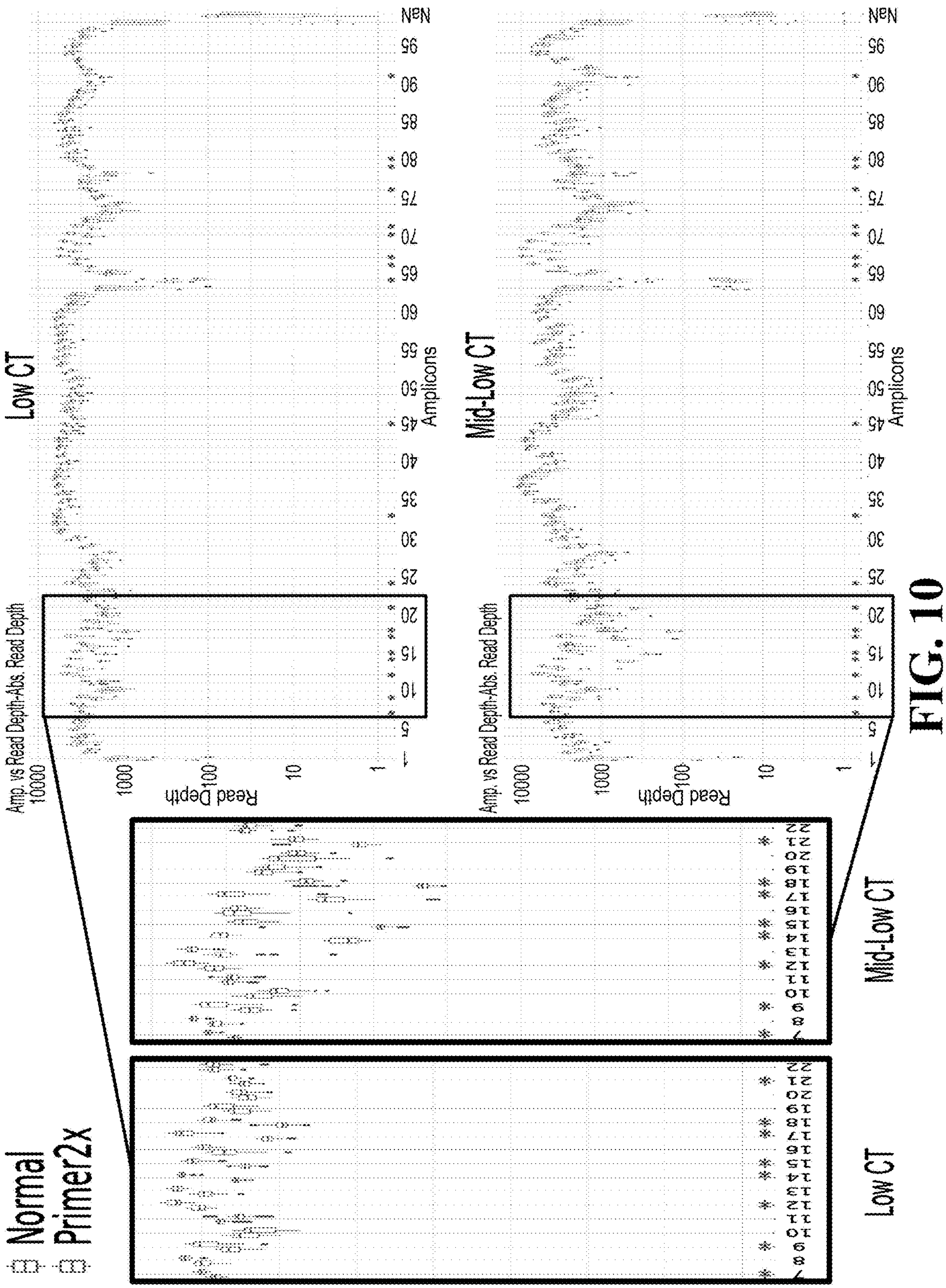
FIG. 10—Increasing primer concentration 2-fold in regions of low amplicon coverage—Red asterisk indicates amplicons in which the primer pairs were spiked in at 2× the concentration of the others in the pool. Box plots showing the distribution of absolute sequencing coverage (log 10) per amplicon for ARTIC PCR conditions (Normal) and Primer 2× concentrations for 4 representative samples. The boxes are plotted by the Q1, median, and Q3, the whiskers by Q1/Q4, and the outliers by the dots.
Figure 10:
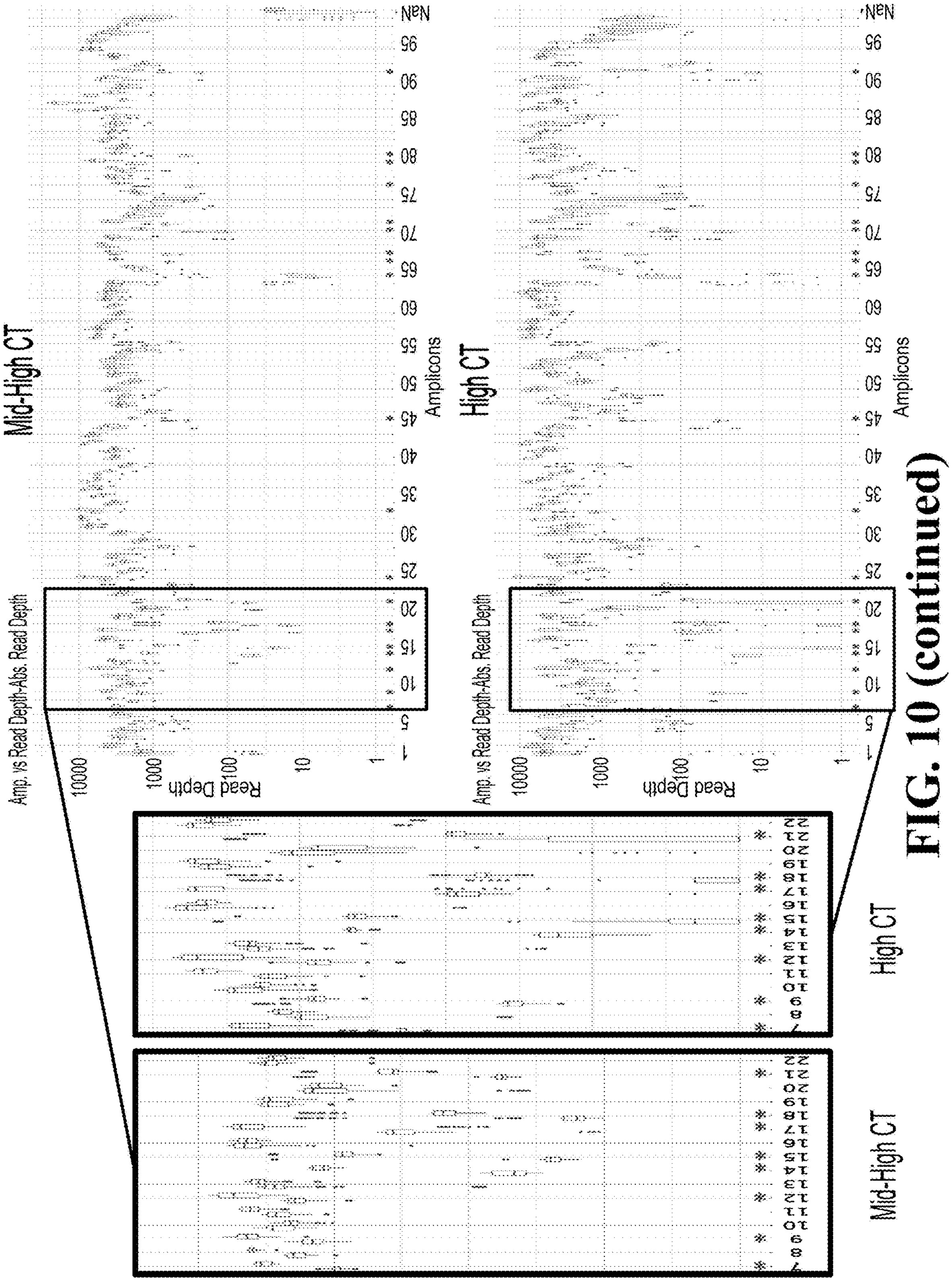
Figure 11:
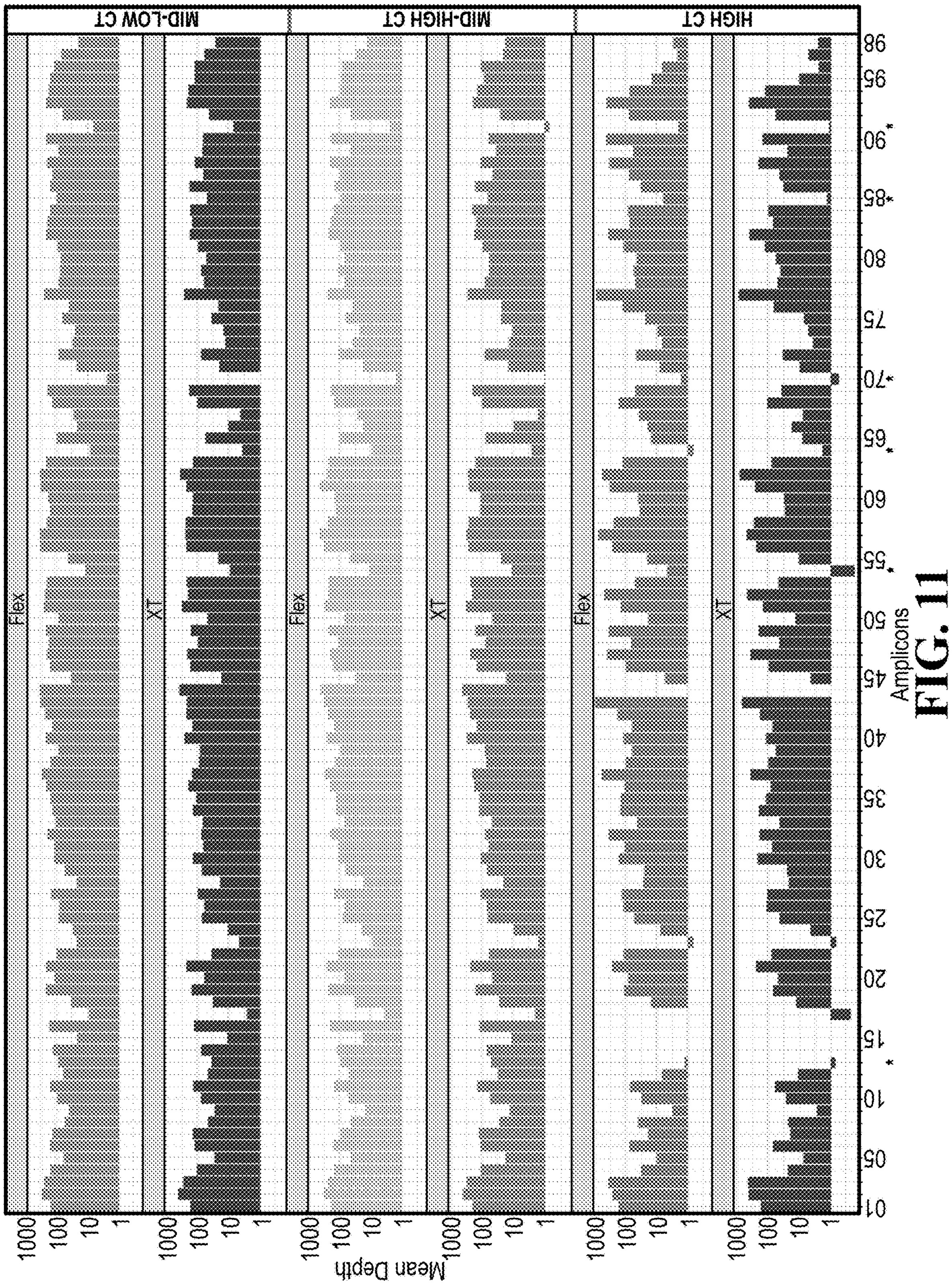
FIG. 11—Modified Flex outperforms XT in coverage depth and evenness at lower cost—Illumina Nextera XT and modified Illumina Nextera Flex library construction on three samples with varying CTs. Asterisks indicate amplicons with large levels of drop out that were improved with the Nextera Flex. Plotted is the mean sequencing depth (log 10) per amplicon.

Applicants also attempted protocol modifications to increase sequence depth uniformity in SDSI+ARTIC, which is crucial for recovering complete genomes in the fewest number of reads. When Applicants increased (2×) primer concentrations (20.8 nM final) for low efficiency amplicons, Applicants observed increased coverage in these amplicons that enabled whole genome recovery for multiple samples, especially those with higher CTs (FIG. 3B; FIG. 10; Table 4). Other groups have also noted that alternative primers or changes in annealing temperature can reduce the formation of certain primer interactions, and Applicants suspect exploration of these avenues would further optimize SDSI+ARTIC (Itokawa et al., 2020). Applicants also attempted to recover high CT samples by increasing the number of PCR cycles and observed greater coverage uniformity with increasing cycles (FIG. 3C). However, at 45 cycles Applicants observed 3 SNPs that were not present in lower-amplified samples. To avoid erroneous SNP calls, Applicants decided to implement and optimize the SDSI's for a 40 cycle PCR. Additional modifications such as DNA-rehybridization steps (Mathieu-Daude et al., 1996) or slower temperature ramp speeds had no significant effects (FIG. 9C, 9D).

Applicants reduced the potential for highly amplified library contamination within the laboratory or clinical setting by scaling down (0.5×) the Illumina DNA Flex library construction kit, which also reduced per sample cost without impacting performance (Table 5; Table 6). In benchmarking library construction methods, Applicants confirmed Nextera DNA Flex generated greater coverage depth than DNA XT (FIG. 10). In combination, the final suggested modifications to Illumina ARTIC sequencing include using more processive reverse transcriptases, 40 cycles of PCR, and 2× primer concentration to recover higher CT samples, as well as a 0.5× scale down of Illumina DNA Flex to produce less concentrated, and thus less likely to contaminate libraries at a halved cost. Integrating these modifications into the SDSI approach may enable greater genomic surveillance in a limited number of samples.

Figure 4A:
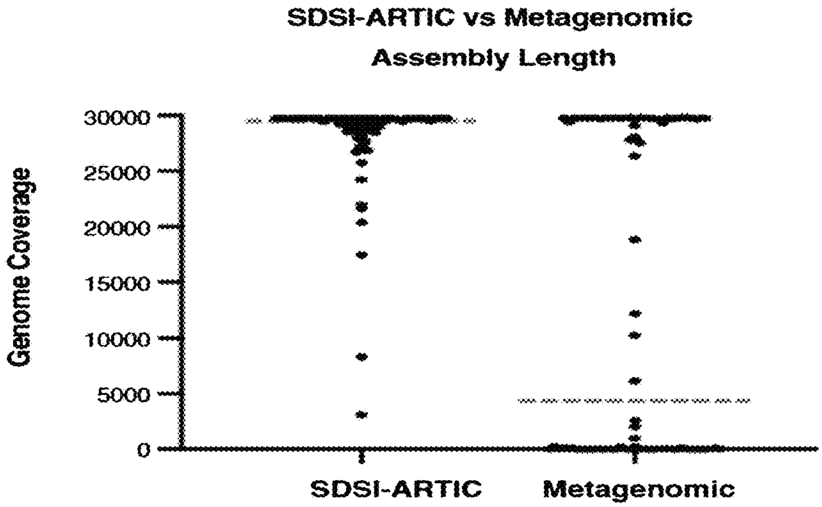
FIG. 4A-4C—Improved amp-seq assembles more complete genomes than metagenomic sequencing with few errors across a wide range of samples—A. SDSI+ARTIC (N=81) and metagenomic (N=81) assembly lengths. All samples were downsampled to 975,000 reads. Dotted line indicates median assembly length (SDSI+ARTIC=29,577; Metagenomic=4,389) B. Percent of assemblies with greater than 98% or 80% coverage in different CT bins (SDSI+ARTIC N=81, Metagenomic N=81) (downsampled to 975,000 reads). C. SNP concordance plot between SDSI+ARTIC and metagenomic consensus sequences. Two discordant SNPs, outlined in a red box, were found.
Figure 4B:
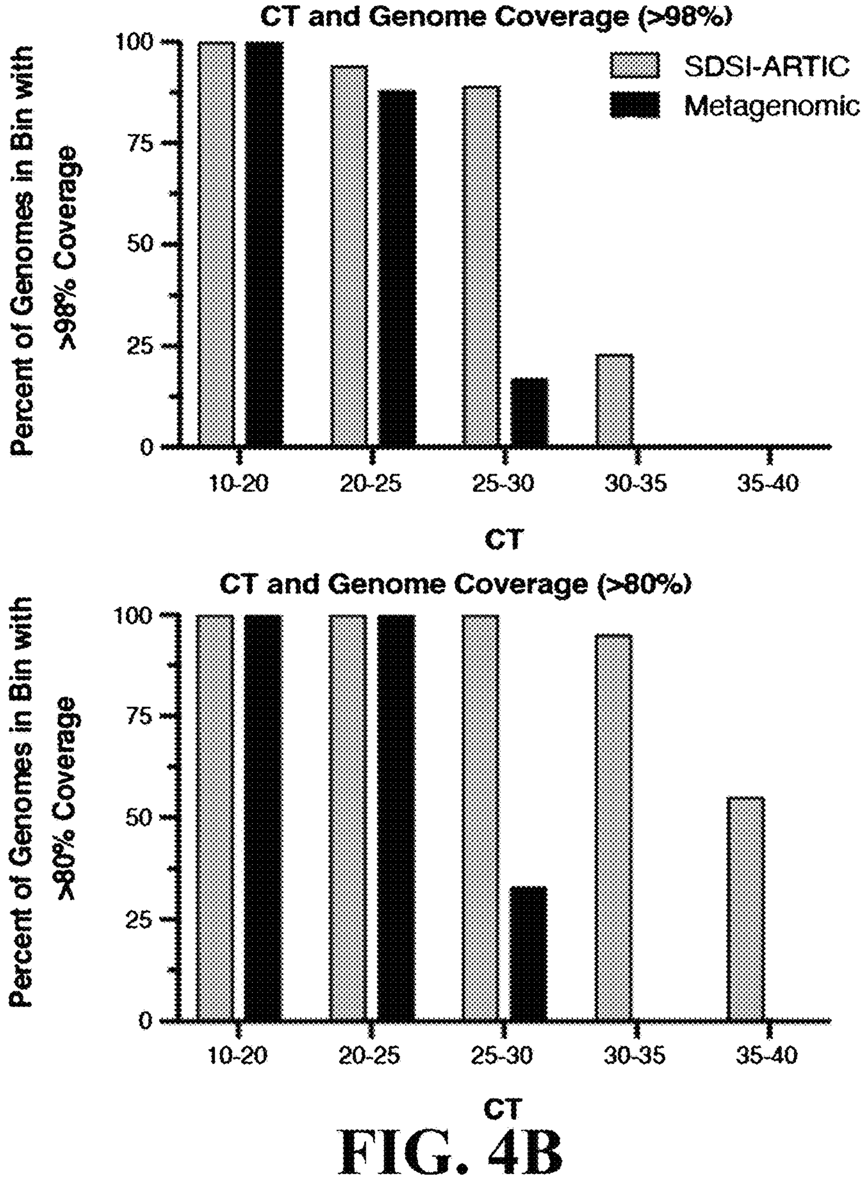
Figure 12A:
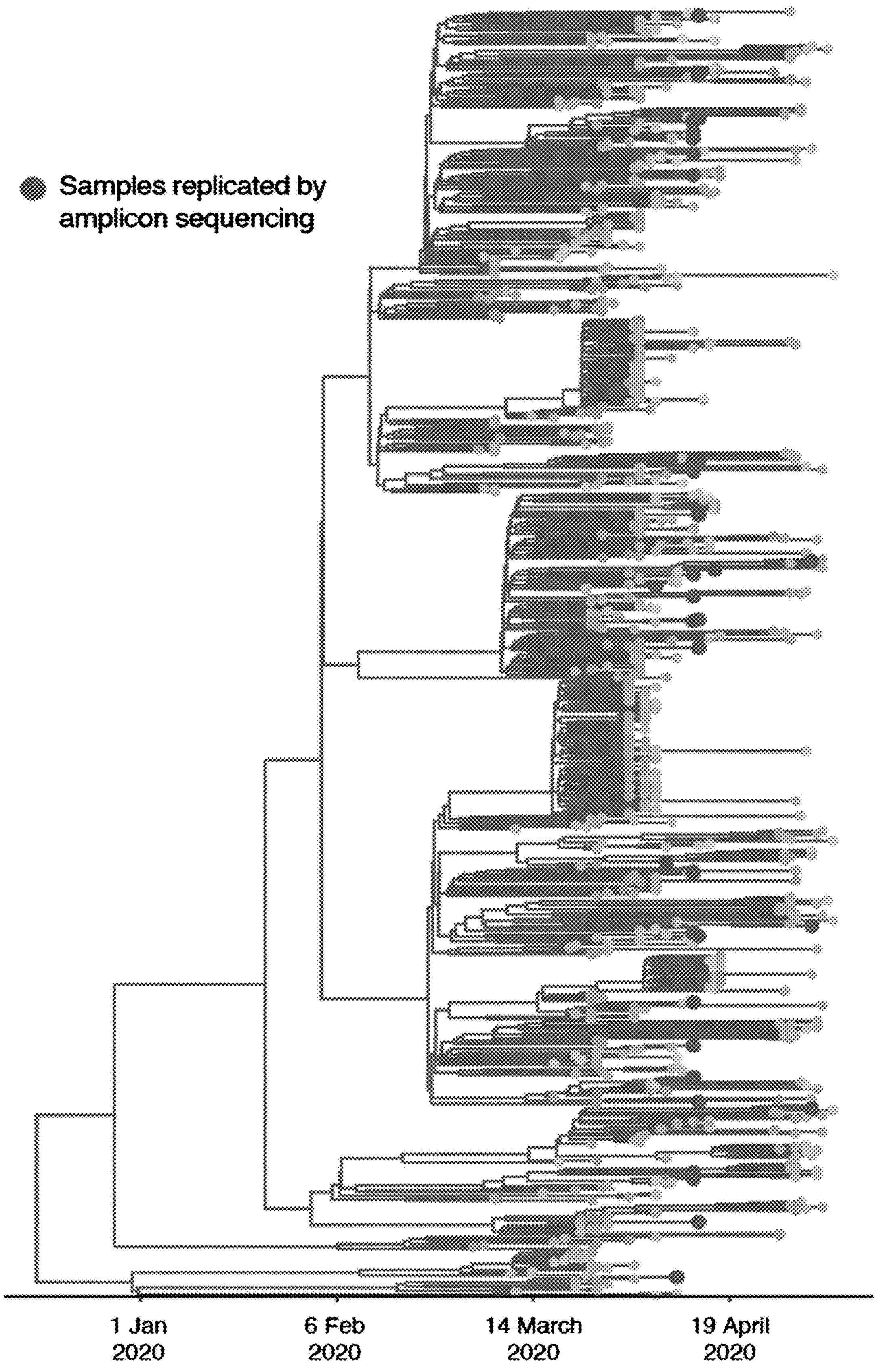
FIG. 12A-12C—SDSI+ARTIC over a diverse set of samples is advantageous when compared to metagenomics—A. Time-measured maximum clade credibility tree of 772 genomes from Massachusetts, reported in Lemieux et al., 2020. The 89 samples compared for metagenomic and amplicon sequencing are shown with red dots. B. Genome coverage for metagenomics versus SDSI+ARTIC amplicon sequencing pipeline (N=81, excluded samples had no detectable CT). All samples downsampled to 975,000 reads. C. Gini coefficients grouped by CT (N=70, excluded samples that did not generate assemblies in either one or both methods). Dashed red line represents the median.
Figure 12B:
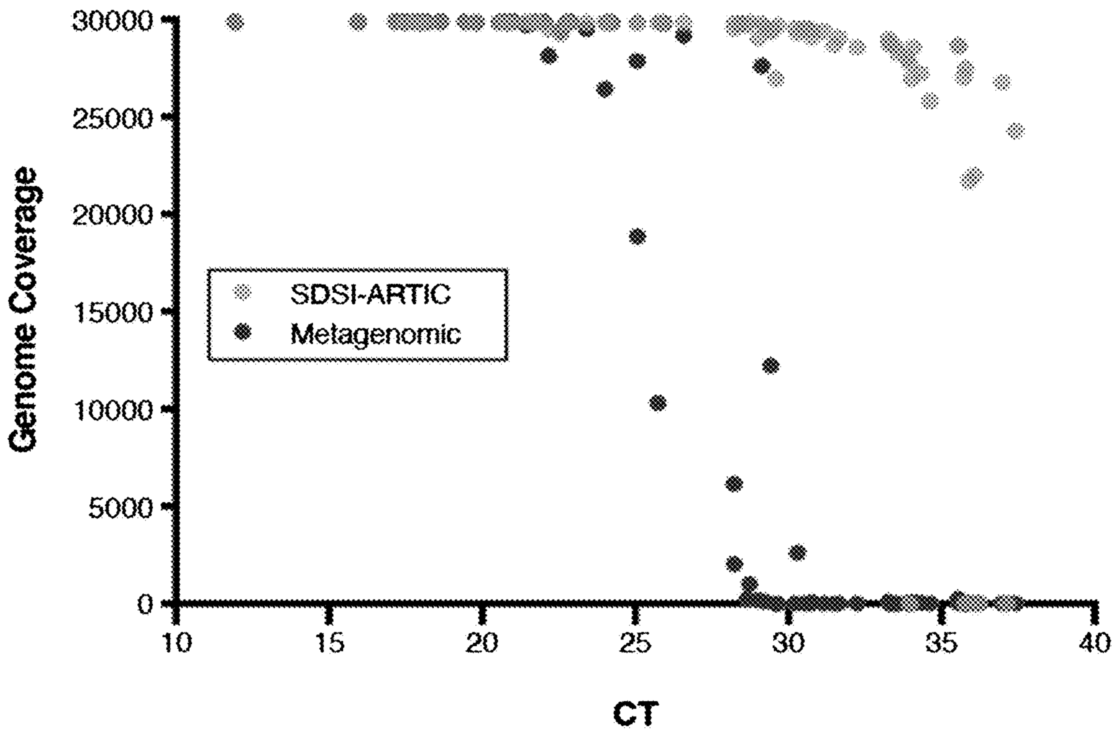
Figure 12C:
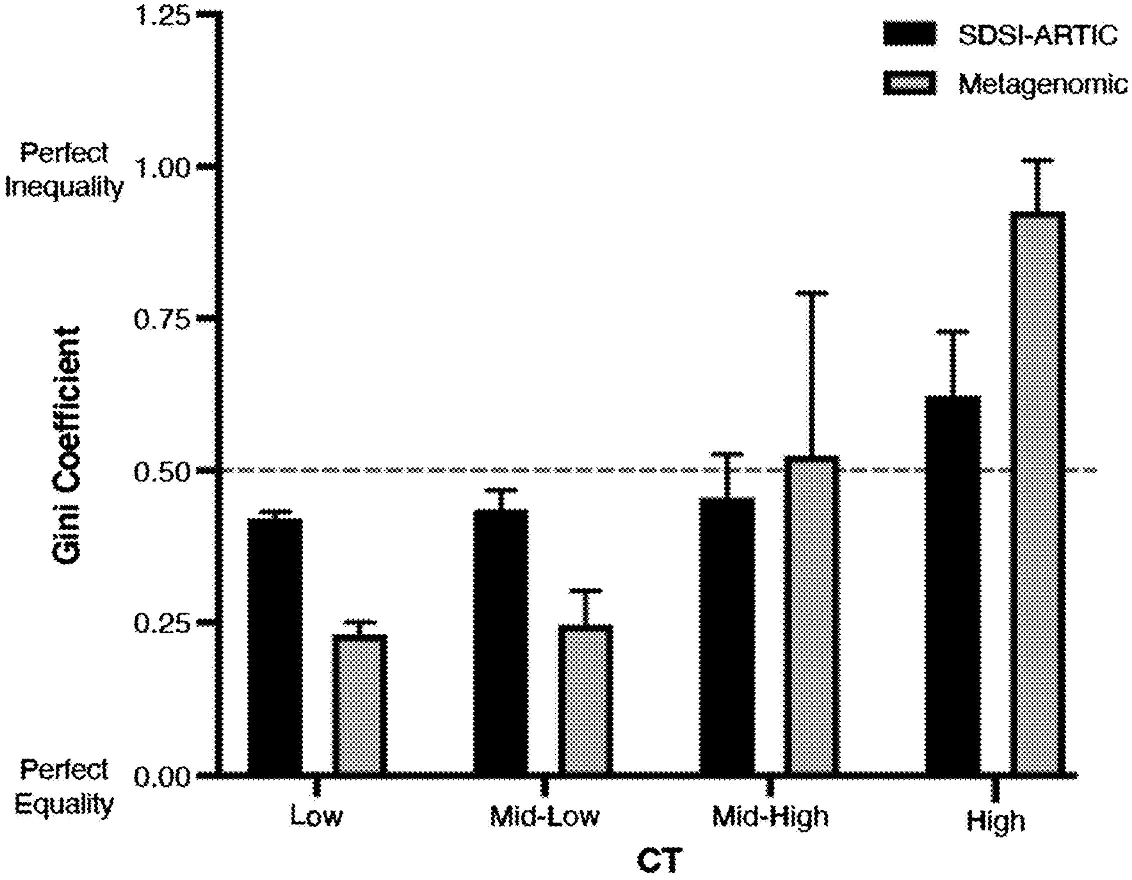

Example 4—SDSI-ARTIC Sequencing Benchmarks Well Against Metagenomic Sequencing Highlighting the reliability and robustness of this approach, Applicants observed high sequence correlation and superior genome recovery with SDSI+ARTIC compared to an unbiased metagenomics approach, the gold standard in generating error-free viral genomes. Applicants sequenced a small batch of six samples (CTs=16-31) using ARTIC without SDSIs, and generated full length genomes with 100% concordance to those generated with metagenomic sequencing, indicating the accuracy of ARTIC-based sequencing methods (Lemieux et al., 2021). Applicants then resequenced 89 unique patient samples with SDSI+ARTIC that were previously sequenced using the same standard metagenomics approach (Lemieux et al., 2021) to serve as a direct comparison. The 89 samples in the validation batch consisted of diverse viral lineages and a broad range of CTs (range=11.9-37.4; mean=27.4) (FIG. 12A). SDSI+ARTIC outperformed metagenomic sequencing in terms of genome recovery, with increased median assembly lengths (29,577 bp and 4,389 bp respectively) (FIG. 4A), and a higher number of complete (>98%) genomes assembled (50 and 31 respectively). Applicants recovered even more partial (>80%) genomes with SDSI+ARTIC when compared to metagenomic sequencing (75 vs 36 respectively). Notably, 5 complete genomes recovered for SDSI+ARTIC had a CT above 30 (FIG. 4B; FIG. 12B). Applicants also assessed coverage uniformity in both methods, as increasing uniformity reduces the sequencing depth required to generate reliable genomes, thus improving throughput and efficiency. (So et al., 2018). As measured by a gini coefficient for each sample that generated an assembly, uniformity decreased in both methods above a CT of 25 but was markedly worse for metagenomics (FIG. 12C).

Figure 4C:
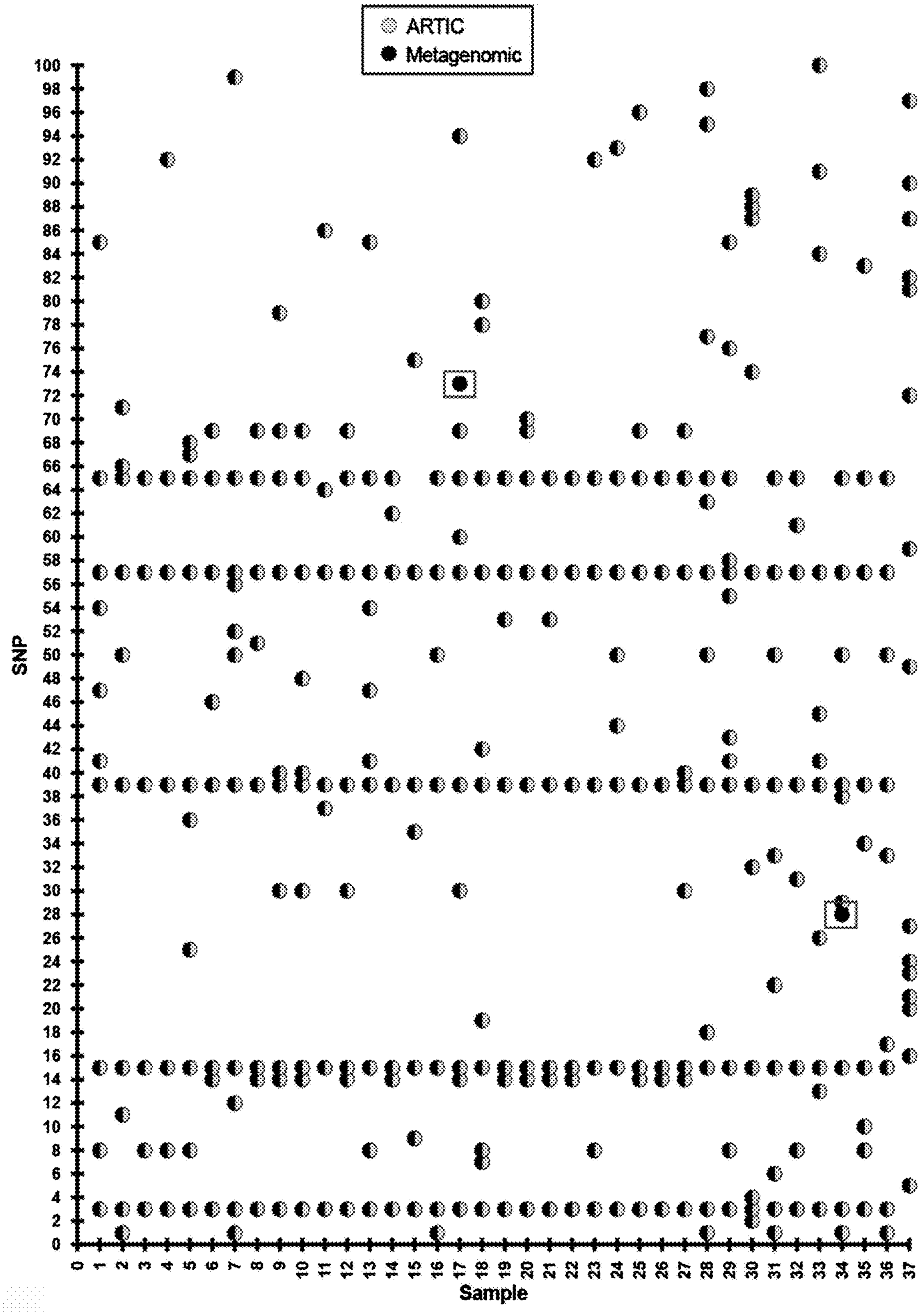

SDSI+ARTIC displayed high concordance in sequence variant identification to metagenomics, producing only two divergent SNP calls out of 331 total SNPs across 38 genomes (FIG. 4C). Notably, this discordance was present with both relaxed (n=3) and conservative (n=20) minimum coverage thresholds. The discordant SNPs, observed in two samples, were present in different regions. However, both were located in ARTIC primer regions and matched the primer sequence even though primer trimming was performed and confirmed by manual inspection. Additionally, the coverage depth in the regions of the SNPs was greater than 1000× for both platforms in both samples. Applicants believe these errors likely arose during the ARTIC PCR, suggesting a discordance rate of 0.6% between amplicon-based and metagenomic sequencing. Notably these few mismatches did not result in lineage misassignment for either sample. To evaluate concordance, Applicants compared consensus sequences without down sampling using only samples that produced a full genome to make the most equivalent comparison (Methods).

Example 5—Rapid Deployment of SDSI-ARTIC Sequencing Confirms a Suspected Nosocomial Transmission Cluster SDSI+ARTIC is a powerful method for public health interventions, especially as superspreading events—and clusters of cases linked to close contact settings more broadly—have become a defining feature of the SARS-CoV-2 pandemic ((Adam et al., 2020; Dearlove et al., 2020; Lemieux et al., 2021; Wong & Collins, 2020)). Viral genomes can reveal whether these clusters are linked through transmission, based on shared viral sequences, providing useful information for public health interventions. Such outbreak investigations of single cases leading to many are distinguishable due to low viral sequence variation but requires higher levels of confidence to ensure such a pattern has not occurred due to laboratory contamination. To demonstrate the utility of the novel SDSIs and modified protocol, Applicants applied the method to investigate a putative cluster of 14 SARS-CoV-2 cases from Massachusetts General Hospital (MGH), for which the infection control unit had suspicion of a nosocomial outbreak. Applicants sequenced 24 samples; 14 samples believed to be part of the cluster based on traditional contact-tracing, 8 unlinked samples and 2 negative controls.

Figure 5A:
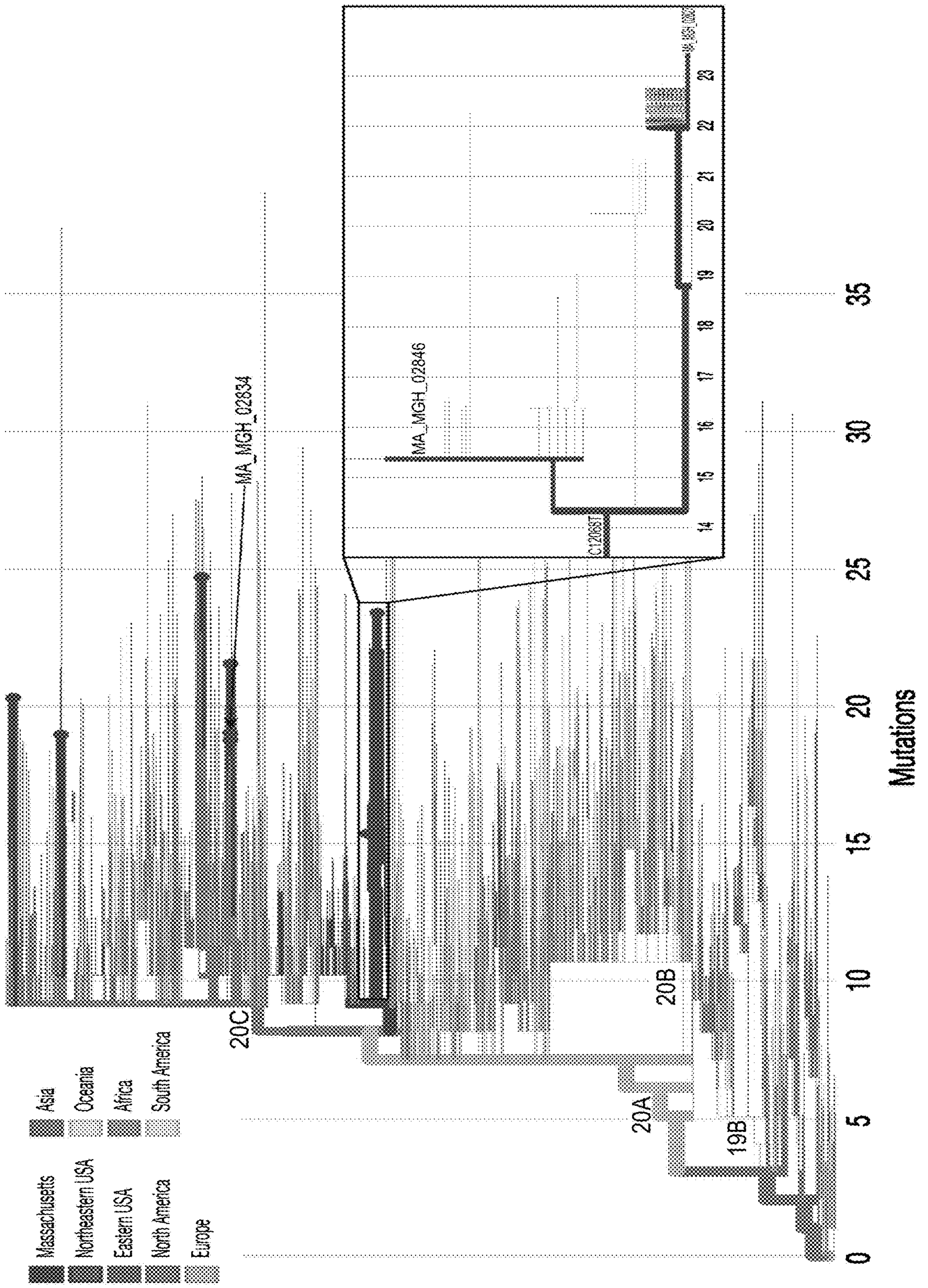
FIG. 5A-5C—Rapid deployment of optimized amp-seq to determine a nosocomial transmission cluster—A. Phylogenetic tree showing the location of the putative cluster sequences in the context of a global subset of circulating SARS-CoV-2 diversity. Zoom box shows the 10 highly similar cluster genomes. Sample named on the main tree is the one putative cluster sample that was excluded from the cluster based on genome sequence. B. Distance matrix showing pairwise differences between the 17 complete genomes assembled from this sample set. Putative cluster samples are bolded. C. Spike-in counts for each of the 24 samples and water controls in this sequencing batch.
Figure 5C:
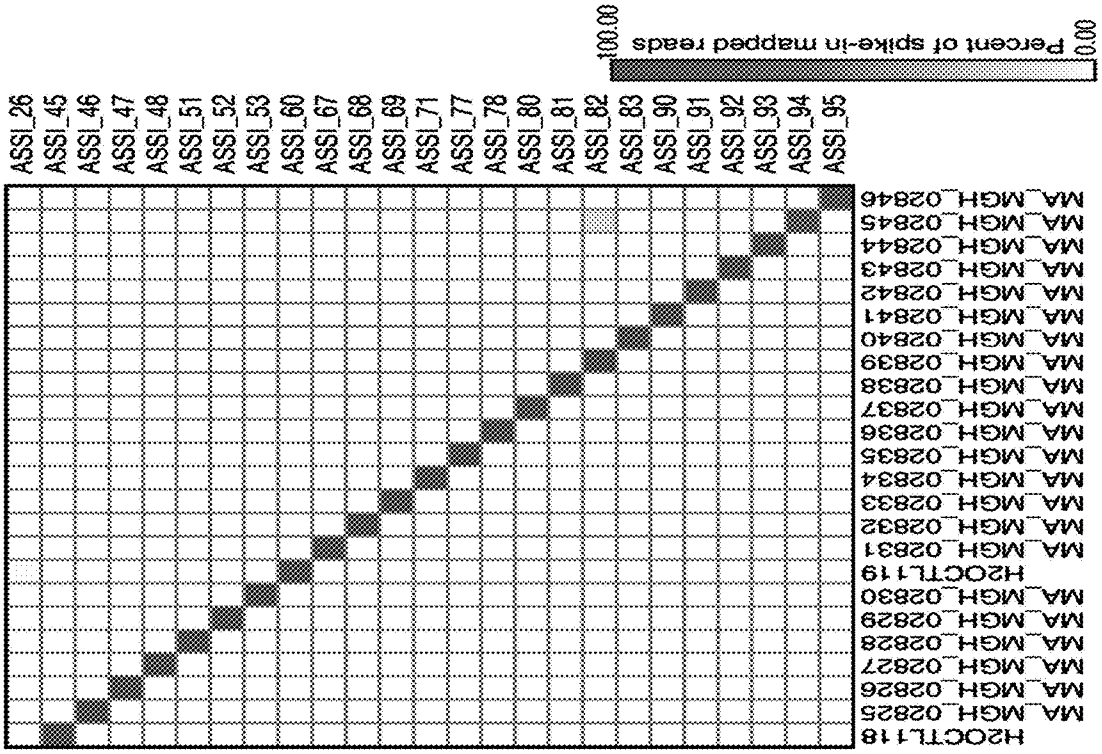
Figure 5B:
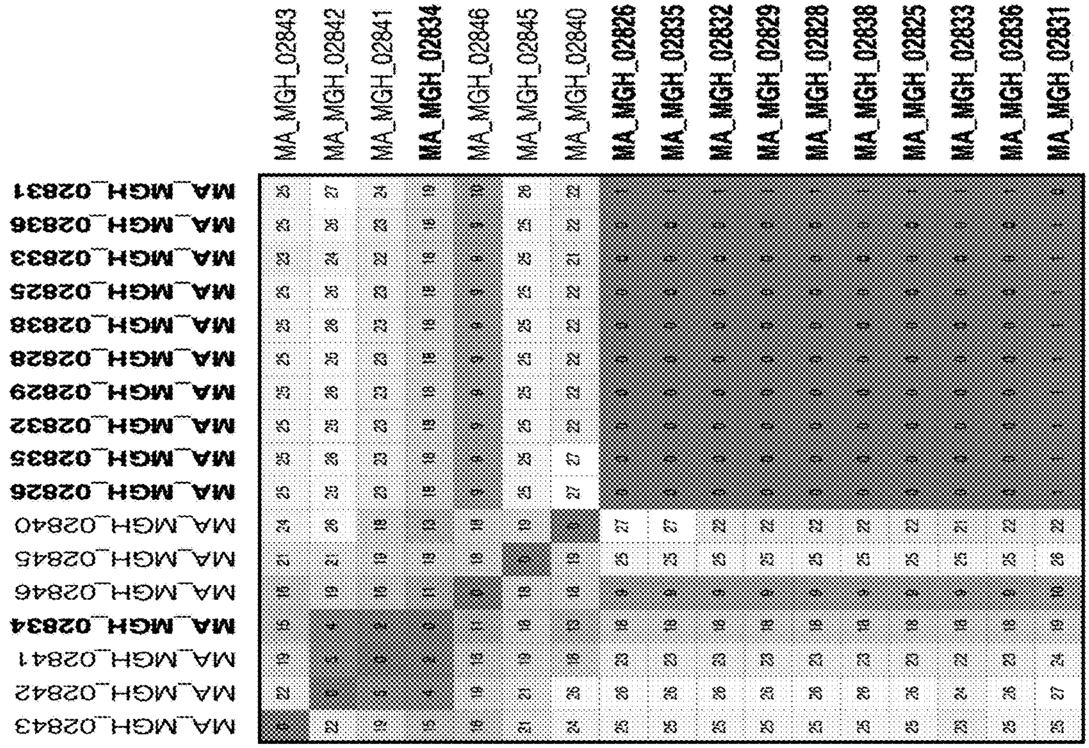

The SDSI+ARTIC method enabled fast and confident identification of a nosocomial cluster, with samples processed within 24 hours and final genomes assembled within 52 hours of bio-sample receipt. Applicants assembled 14 complete genomes (>98% complete) of which 9 were from cluster-associated samples. Those samples that did not yield a full genome were those with lower viral loads (CT >30). Phylogenetic analysis showed that samples from the cluster were genetically highly similar and clustered together (FIG. 5A, 5B) to the exclusion of other samples from Boston around the same time, strongly suggesting that this cluster did reflect transmission within the hospital. One sample, MA-MGH-02834, differed from other cluster-associated samples by 18-19 consensus-level variants suggesting that this infection was likely acquired separately and not as part of the same nosocomial transmission. Analysis of the SDSIs confirmed that genome sequence similarity was not the result of cross-contamination from highly amplified final libraries (FIG. 5C).

Example 6—Discussion on Novel Amplicon Spike-Ins

As the SARS-CoV-2 pandemic intensifies and new genomic variants continue to emerge, it is imperative to build robust experimental confidence into genomic surveillance data interpretation. Here, Applicants report a novel design and implementation of Synthetic DNA Spike-ins (SDSI) as an essential component for tracking and tracing contamination, a potential confounder in amplicon-based sequencing methods of SARS-CoV-2. The in-silico design generated robust synthetic targets at low costs while mitigating inter-spike-in sequence homology as well as homology with human, SARS-CoV-2, and common laboratory reagents. While broadly applicable to most amplicon-based approaches, as a proof-of-principle Applicants coupled the SDSIs to an improved ARTIC amplicon sequencing protocol yielding faster throughput with an overall reduced cost compared to existing Illumina DNA Flex-based protocols.

SDSIs can readily be adopted by laboratories and platforms of all sizes with only minor changes to existing methodologies, little additional cost per sample ($0.006), and no interruption to standard workflow methodologies. Additional synthetic targets could be designed using the same principles to expand into 384 well formats and beyond. Primer sites could also be modulated for integration with new advancements in amplicon sequencing, like tailed primer approaches (Gohl et al., 2020). More broadly, standardizing controls across the viral surveillance community will increase accuracy and integrity of SARS-CoV-2 genomic data worldwide. These SDSIs not only enable profiling of in-batch contamination, but also laboratory-wide detection as their presence in other data (amplicon, metagenomic, qPCR, or otherwise) would indicate a tagged amplification and thus contamination. Moreover the approach is applicable to both Illumina and Nanopore sequencing platforms as well as any other existing or future tiled amplicon panel, such as those previously used for Zika, Ebola, and other recent outbreaks (Quick et al., 2016) (Metsky et al., 2017). SDSIs could serve as a broad tool for tracing potential contamination across a plethora of fields that employ amplicon based genomic sequencing, such as food safety, species identification or environmental sampling.

In optimizing the SDSI+ARTIC protocol Applicants tested and incorporated a number of cost and time saving adjustments. Modifications that can be used include implementing liquid handlers in high volume settings such as public health laboratories. Additional methodological improvements could allow for direct PCR amplification of SARS-CoV-2 using primers with indexing adapter compatible ends (Baker et al., 2020; Gohl et al., 2020) or the inclusion of unique molecular identifiers to understand intra-host variation. The SDSIs were designed to be compatible with such potential future approaches. Applicants note that there is still considerable non-uniformity in per-amplicon coverage for samples with low viral loads highlighting the need for methods that can confidently capture this information. A recent update to the ARTIC protocol for nanopore suggests that a change in the annealing temperature from 65° C. to 63° C. can reduce dropout of amplicon 64 (Tyson et al., 2020), a particularly poorly performing amplicon. The results show that 2× primer concentration for a subset of underperforming amplicons improved performance, and matching primer concentrations with amplicon efficiency would likely yield more uniform coverage (Table 4). Alternative approaches for the recovery of genomes from samples with low viral load include the use of targeted enrichment approaches (Houldcroft et al., 2017; Metsky et al., 2019) are more costly and time-consuming.

Amplicon based sequencing methods fill a critical need for rapid turn around and full genome recovery for epidemiological surveillance where SNP identification is crucial. While benchmarking the modified protocol against the gold standard approach of metagenomics Applicants observed discordant SNPs were rare (2/331). This emphasizes the need for caution and replication of libraries for highly important samples. Other commercial amplicon-based designs such as those by Paragon Genomics are significantly faster workflows and use smaller size amplicons, but the ARTIC primer set results in better overall coverage for the majority of samples (up to CT=35) and genome accuracy. Applicants believe subsequent generations of amplicon-based sequencing will address this pressing need pushing cost down while increasing genomic surveillance accuracy, which is sorely needed in the public health setting. The rapid deployment of SDSI+ARTIC confirming a nosocomial infection cluster further emphasizes the utility of the SDSIs to confidently identify samples of high genetic similarity.

The potential emergence of SARS-CoV-2 immune and vaccine escape variants underscores the ongoing necessity of accurate, reliable, and accessible genome sequencing. The modifications and suggestions build upon a remarkable global genomic surveillance response that has developed new tools for the rapid sequencing of viral genomes at an unprecedented rate. In light of the latest surges in SARS-CoV-2 cases globally and the emergence of more transmissible lineages and variants of concern that are rising in frequency in multiple continents, continual innovation in these protocols to improve their efficiency, cost-effectiveness and reliability are essential to meet the growing need for genomic surveillance of SARS-CoV-2. Moreover, stringent sample tracking and contamination detection strategies must become a standard practice, maximizing the utility of genomic data and its increasing importance for shaping public health interventions.

Example 7—Design and Characterization of Synthetic DNA Spike-Ins for AmpSeq

Figure 13:
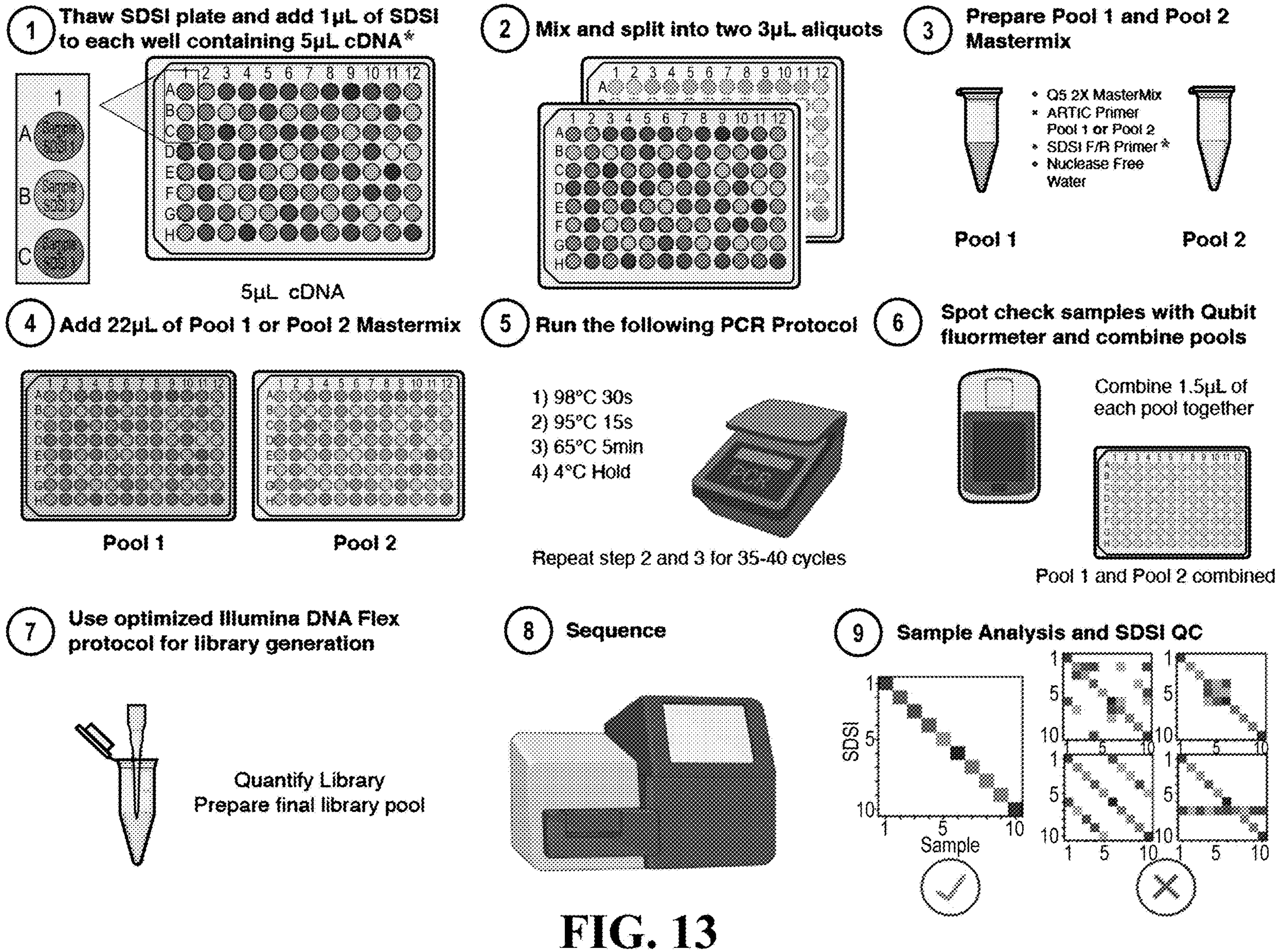
FIG. 13—SDSI+AmpSeq Protocol. Illustrative workflow for 96 samples through the SDSI+AmpSeq amplicon-sequencing pipeline. A unique, synthetic DNA spike-in (SDSI) will be added to each cDNA sample to allow for contamination tracking and accurate sample identification in analysis. Asterisks indicate additional steps to the standard ARTIC pipeline.
Figure 14A:
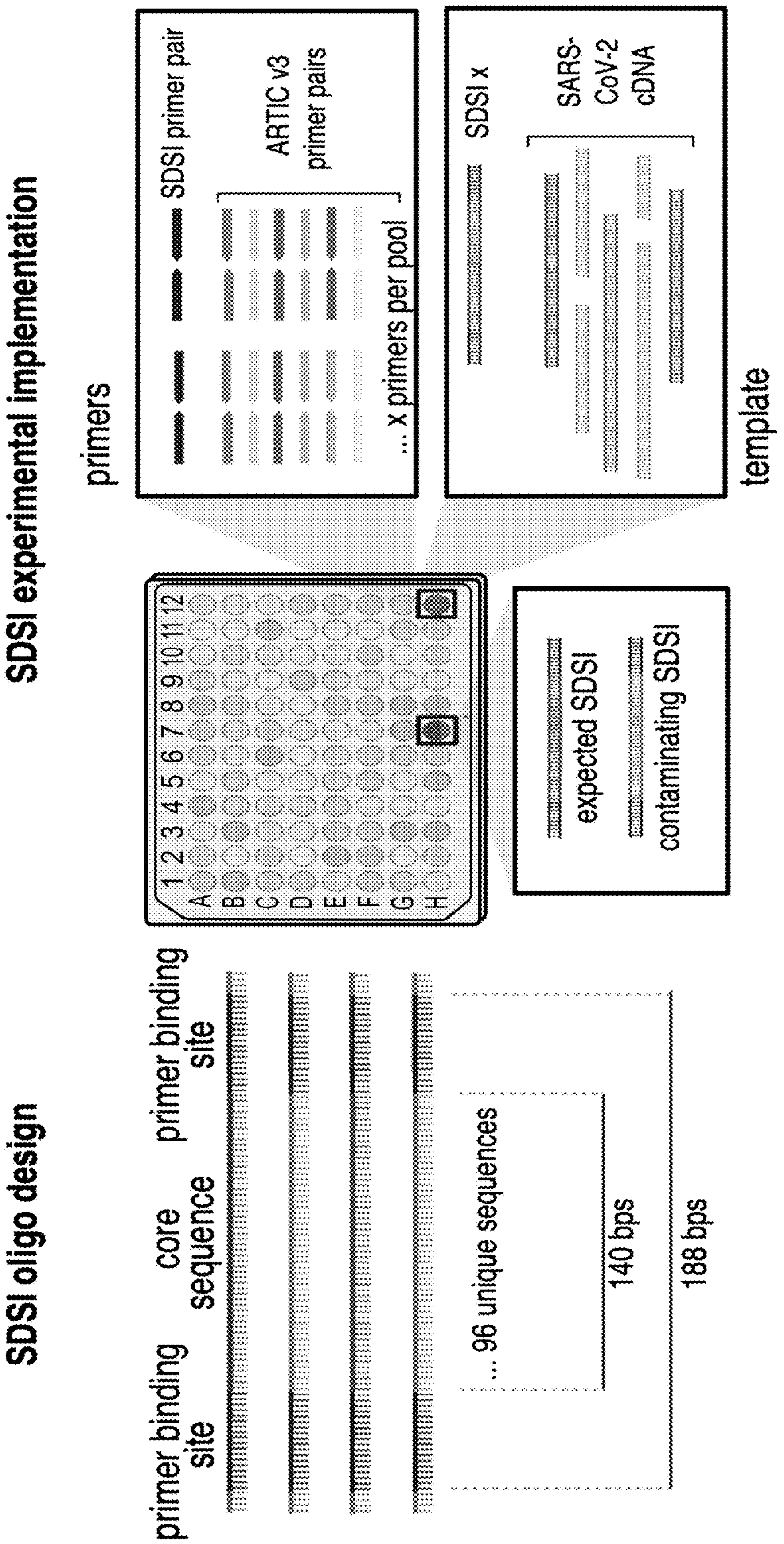
FIG. 14A-14B—Synthetic DNA oligos spiked into ampseq reactions designed to flag contamination and sample swaps. A. Schematic of SDSI design. Each oligo contains 140 bp of unique sequence flanked by common primer binding sites. Primers designed to amplify all SDSIs are added to ARTIC primer pools, and a unique SDSI is added to each clinical sample. Identification of multiple SDSIs in the same sample indicates contamination. B. Percent of SDSI reads mapping for each of the 96 SDSIs (horizontal axis) were quantified for each of the 96 SDSIs (vertical axis). Any off-diagonal signal would indicate non-specific identification of SDSIs.
Figure 14B:
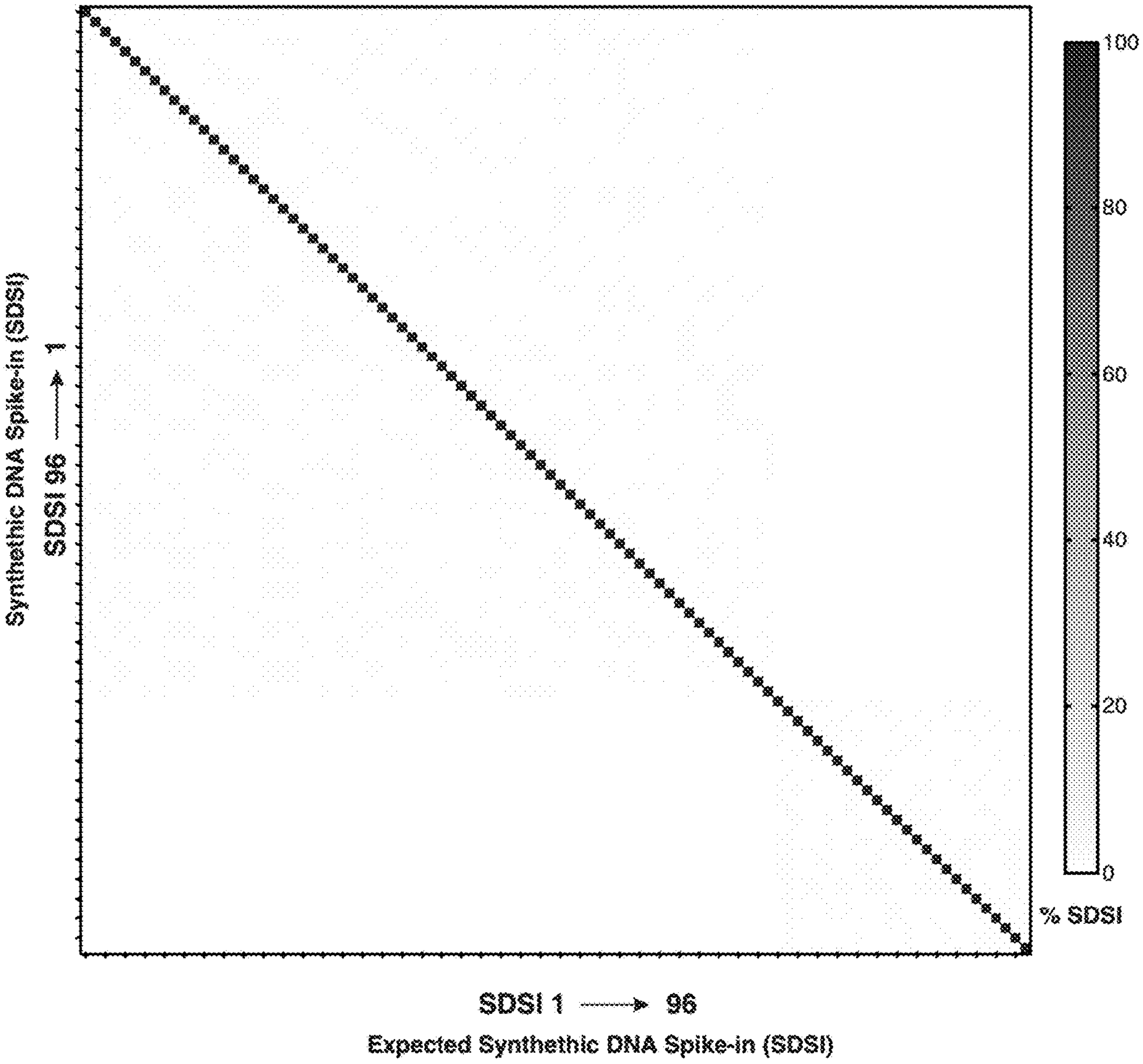
Figure 18A:
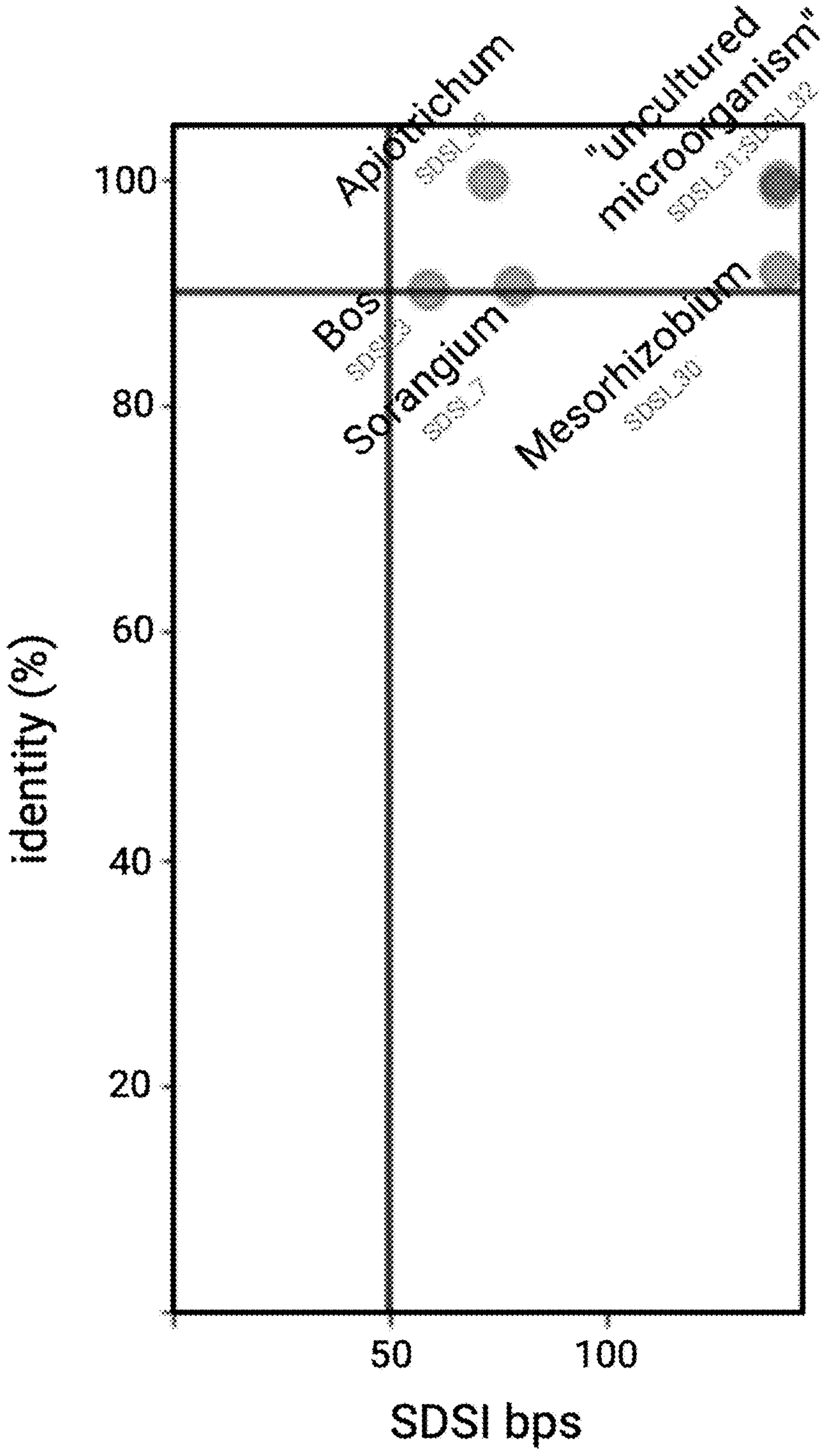
FIG. 18A-18B—SDSI core sequence in silico validation. Applicants surveyed the core SDSI sequences by BLASTn to identify significant homology. A. Significant homology between SDSIs and anything in the NCBI database outside the domain archaea was identified and the SDSI and genus were plotted if identity (y-axis) was greater than 90% and query cover (x-axis) was greater than 50 bps. B. For each SDSI, Applicants identified and plotted (see color scale) the maximum alignment score for a significant homology to human (taxid:9606) and viral (taxid:10239) sequences in the NCBI database. Applicants also identified and plotted the alignment score for each pairwise combination of SDSIs.
Figure 18B:
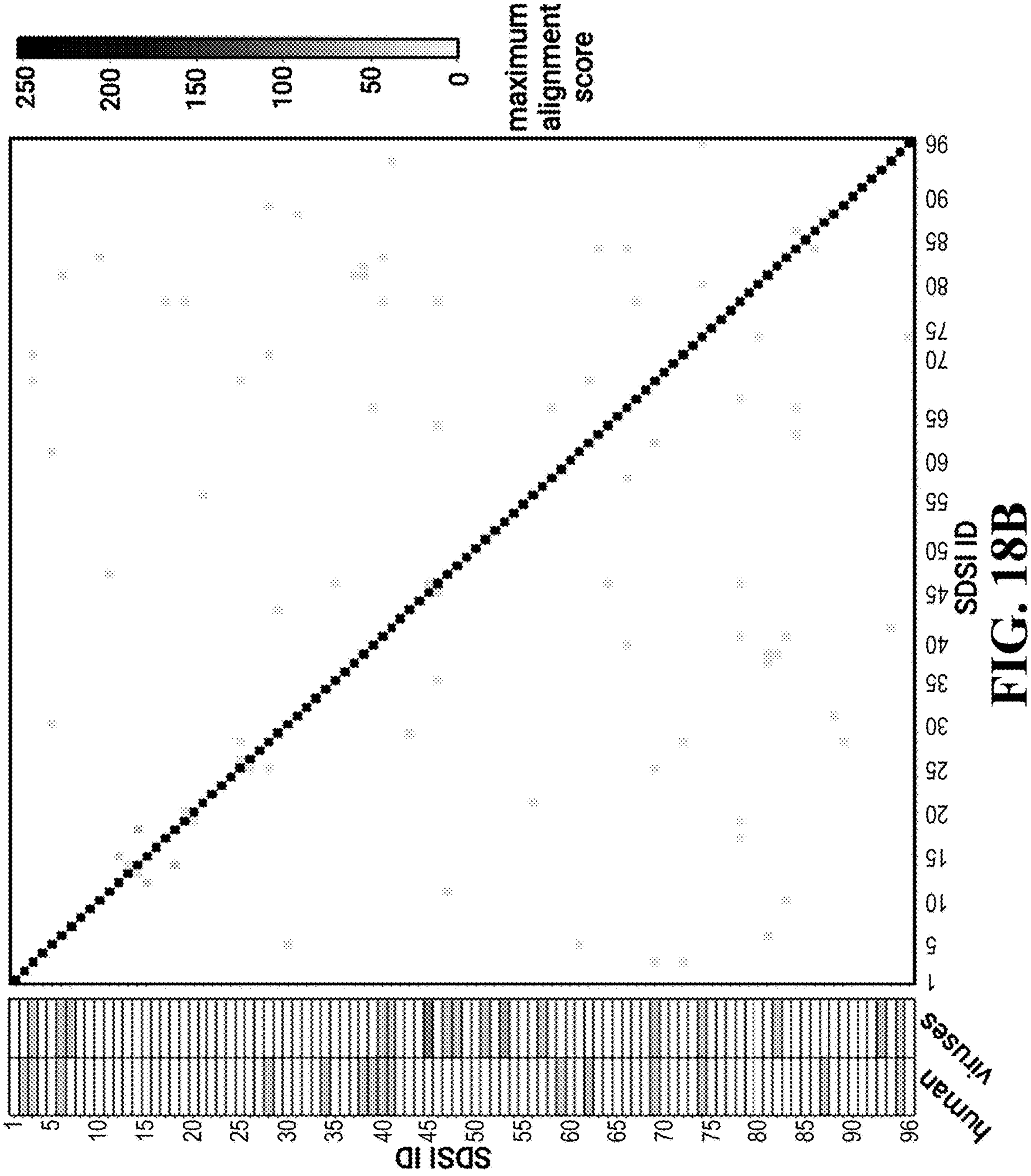

Applicants designed a simple and flexible system for sample tracking and contamination tracing using a core uniquely identifiable DNA sequence flanked by constant priming regions that satisfy several design requirements. This design allows in-sample tracking through the addition of a different SDSI to each sample during sample processing. Following sequencing, the data can be analyzed for both the presence of the expected SDSI and any other SDSI, illuminating both sample misassignment and contamination with high resolution and accuracy (FIG. 13). Applicants focused the initial design on highly stable DNA oligos that would be added to sample cDNA and could capture contamination at or after the critical viral amplification step, including contamination generated during amplification and in handling amplified material. By using a longer unique core sequence, as compared to a short barcode system, these SDSIs are compatible with both tagmentation- and ligation-based sequencing approaches. The constant priming regions mean that only a single primer pair needs to be added into the existing multiplexed PCR step to co-amplify all SDSIs with the primary reaction target(s) (FIG. 14A). In particular, Applicants sought to design a system that could be integrated into diverse amplicon-based viral sequencing approaches. 96 distinct DNA sequences from the genomes of diverse, uncommon archaea serve as the core portion of each SDSI, precluding false detection and cross-identification (Table 1, Methods). By using extremophilic archaea, the designs maximized evolutionary distance from common human pathogens. To avoid false positive results the core SDSI sequences should be sufficiently distinct from one another, as well as sequences commonly found in laboratories and clinical samples. A permissive BLASTn search performed against the entire NCBI database confirmed that the unique SDSI core sequences had limited homology outside the domain archaea, specifically to genera unlikely to be found in laboratories (FIG. 18A). While this limited homology outside of the domain archaea maximized the potential for broad applications, Applicants also confirmed that none of the core sequences shared significant homology with *Homo sapiens* or known viral genomes (Methods). Applicants considered significant homology as >90% sequence identity over 50 bps, as library construction can result in the generation of small fragments. Similarly, Applicants confirmed that all SDSIs were significantly different from each other to prevent misidentification; among all pairwise combinations of SDSIs, the greatest homology occurred between SDSI 14 and 18, which had 15 mismatches over 66 bps (FIG. 18B). Sequencing of the SDSIs confirmed that each of the 96 constructs resulted in a robust and specific signal of mapped reads (FIG. 14B).

Figure 19A:
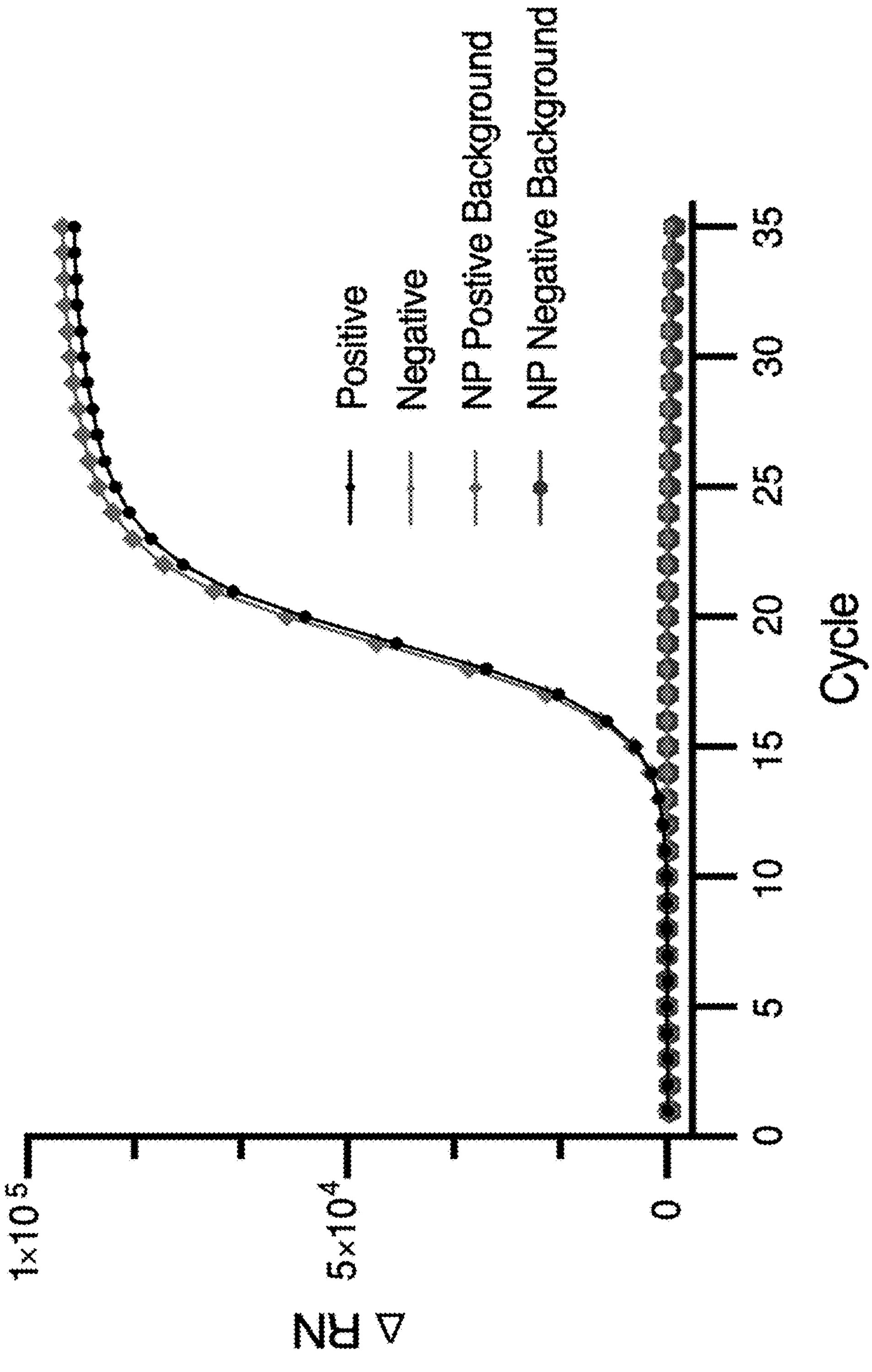
FIG. 19A-19E—Spike-in validation. A. RT-PCR for an SDSI in water and a SARS-CoV-2 positive clinical sample background. Mastermix and SDSI specific primers were added to all samples. SARS-CoV-2 positive clinical sample is cDNA generated from a nasopharyngeal (NP) swab. B. The distribution of GC content and length for ARTIC v3 primers. C. The distribution of GC content of SDSI amplicons. D. 100 fmol DNA spike-in amplified under standard ARTIC PCR conditions for 40 cycles run on 2.2% agarose gel image with 188 bp amplified spike-in (SDSI 1-48). E. % SDSI reads over total reads for SDSI (2-48) over a range of SDSI GC % (33%-65.4%) showed no significant read depth bias. Error bars represent 95% CI. Linear regression p-value=0.8160 (Broad, N=2,903).
Figure 19B:
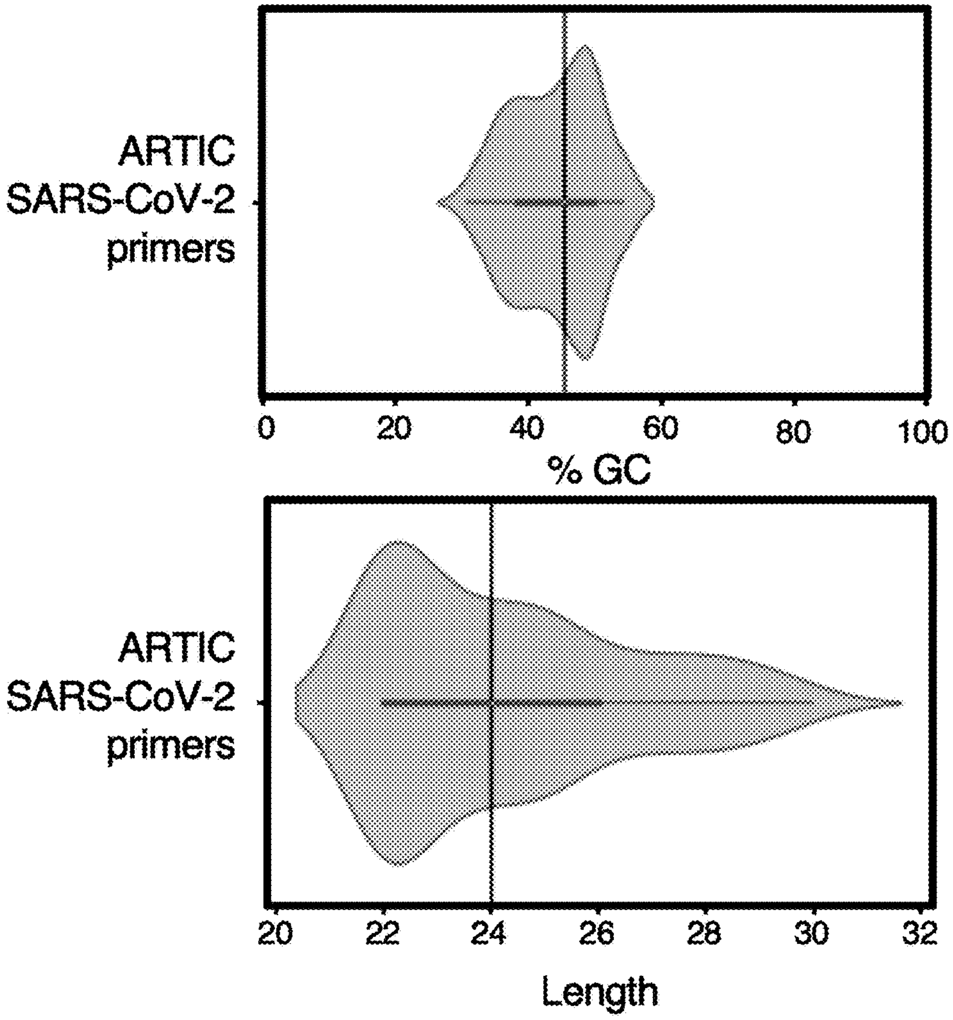
Figure 19C:
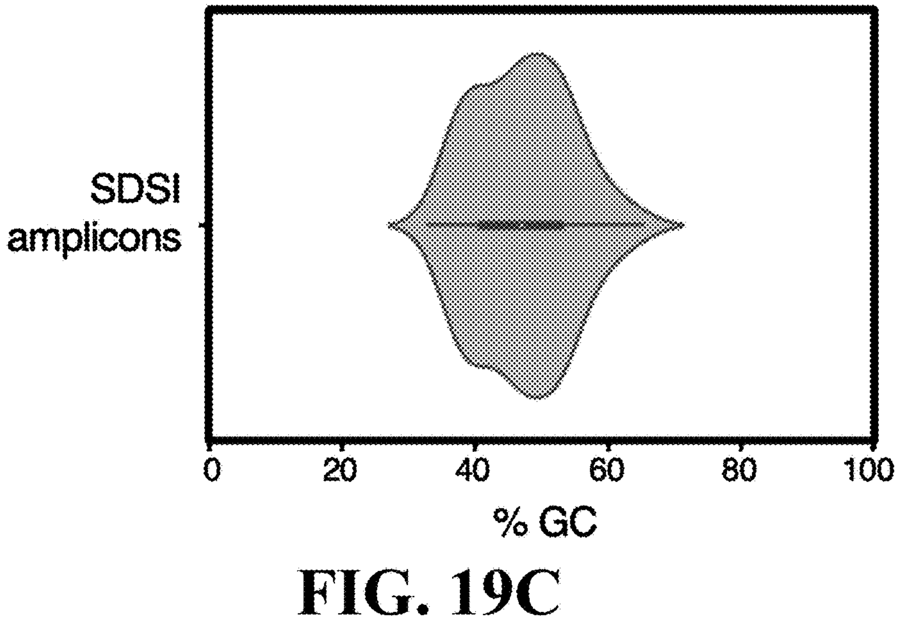
Figure 19D:
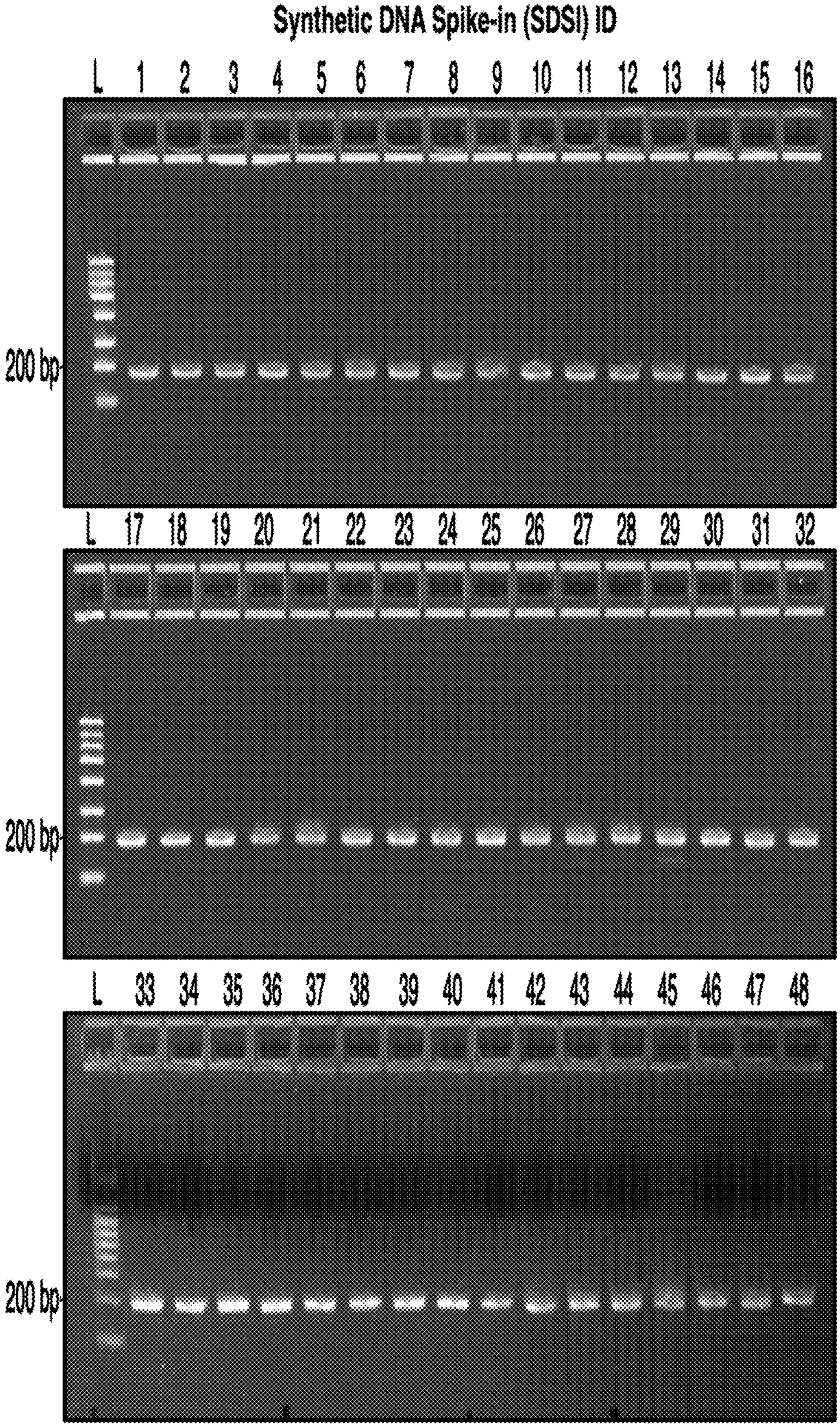
Figure 19E:
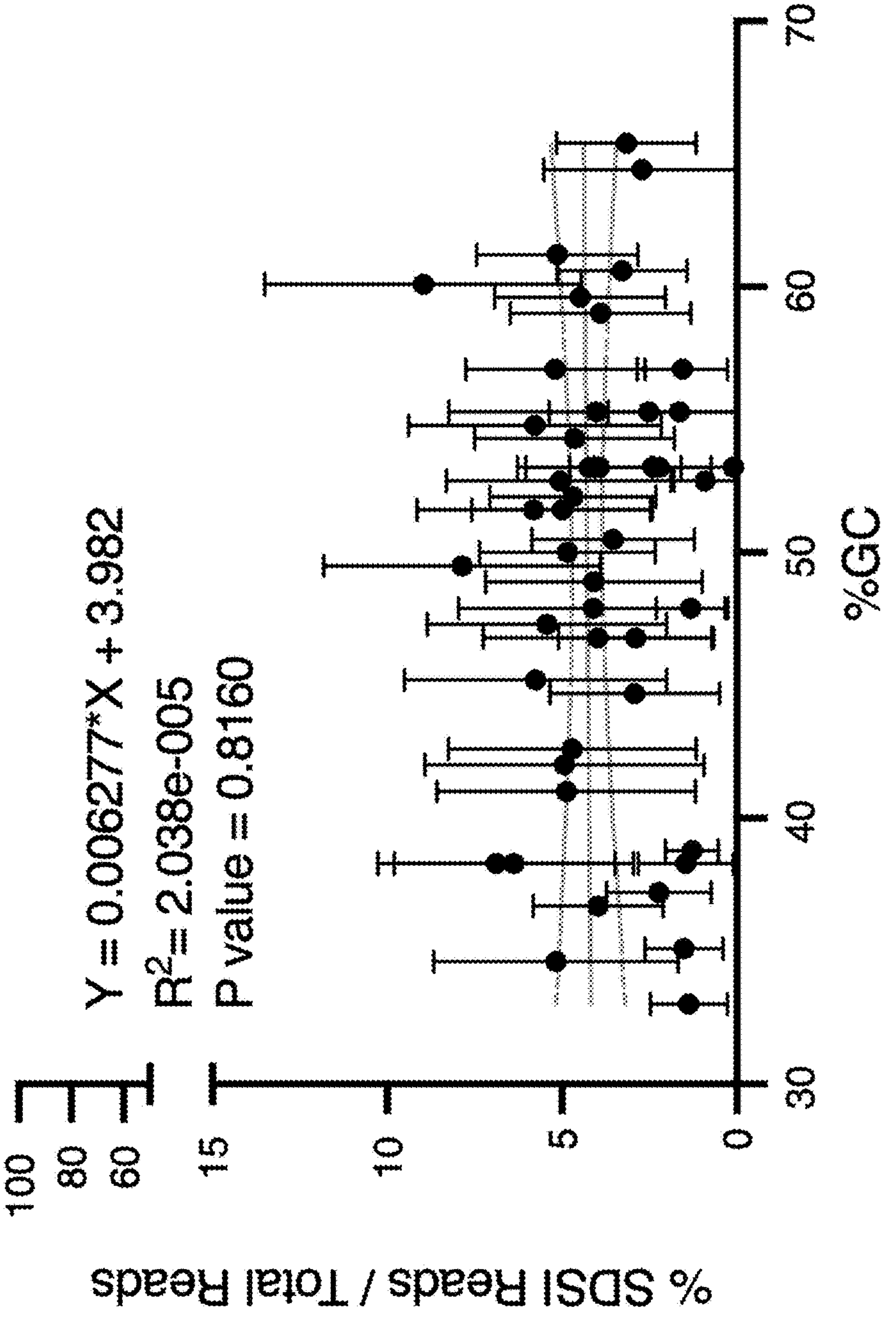

Applicants selected a pair of primers and corresponding priming regions on each SDSI that are highly specific and show reliable amplification across SDSIs and under standard PCR conditions. Using Primer-BLAST, Applicants predicted that these sequences had limited homology to common organisms and thus were unlikely to amplify nonspecific templates that could outcompete amplification of a primary target. Experimentally Applicants confirmed that the SDSI primers did not produce any nonspecific amplification, including in the presence of cDNA from a nasopharyngeal (NP) swab sample (FIG. 19A). The primer pair also had a common length (24 bps), GC content (45.8%), and melting temperature (62° C. and 63° C., respectively in the SDSI+AmpSeq protocol), ensuring their compatibility with many multiplexed PCR reactions, including the most widely used SARS-CoV-2 amplicon sequencing strategy (artic.network/) (FIG. 19B). Since each SDSI was identically sized and shared a priming region, a similar amplification rate was expected across all SDSIs. Applicants avoided extremes of GC content in SDSI amplicons (range: 33-65%) in order to promote similar amplification rates across different SDSIs and to viral amplicons (e.g., the GC content of the SARS-CoV-2 genome is roughly 37±5%)[19] (FIG. 19C). Applicants confirmed experimentally that all SDSIs amplified in an ARTIC SARS-CoV-2 PCR reaction with SDSI primers included, in each case yielding a single clean product of the expected size (FIG. 19D). Furthermore, Applicants observed that GC content did not significantly bias the number of SDSI reads detected in clinical samples (FIG. 19E).

Example 8—Validation of an SDSI+AmpSeq SARS-CoV-2 Sequencing Approach

Figure 15A:
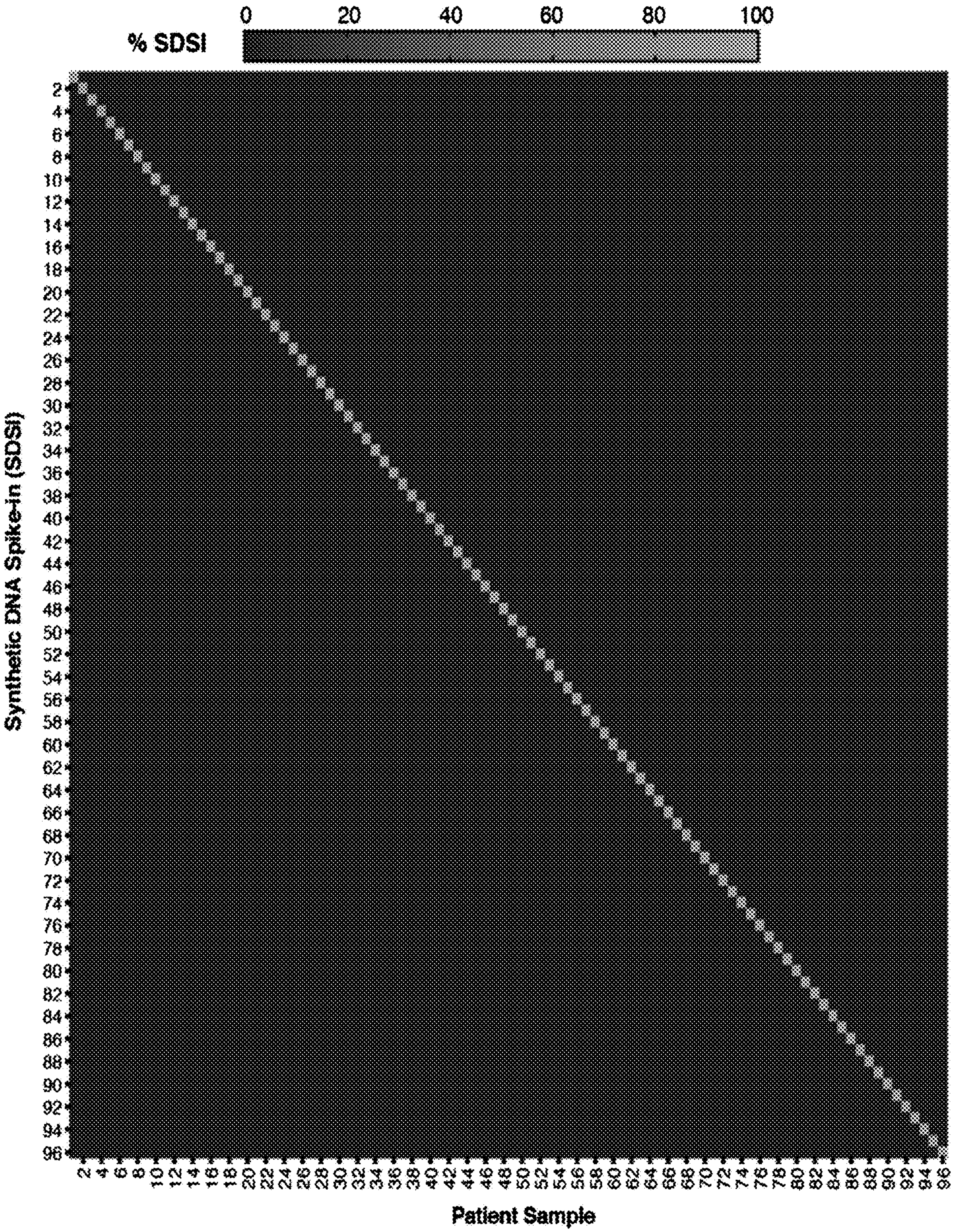
FIG. 15A-15C—SDSI+AmpSeq amplicon coverage and genome concordance. A. Percent of SDSI for SDSI 1-96 in patient samples. B. Log of the mean amplicon coverage for the same clinical samples run with and without an SDSI (n=14). A unique SDSI was used in each sample. The solid blue line represents SDSI+AmpSeq and the solid black line is ARTIC only with no SDSI. Blue and black shading around the solid lines represents the confidence interval. There were no statistical differences (p-value >0.05) in the mean amplicon coverage for each amplicon between the groups (two-tailed Mann Whitney t-test and multiple comparison two-stage step-up Benjamini, Krieger, and Yekutieli test with FDR set to 5%). C. SNV concordance plot between SDSI+AmpSeq and unbiased consensus sequences. Two discordant SNVs, outlined in a red box, were found. Blue dots represent SNVs found in both the unbiased and SDSI+AmpSeq method, whereas black dots indicate the SNV was only present in unbiased.
Figure 15B:
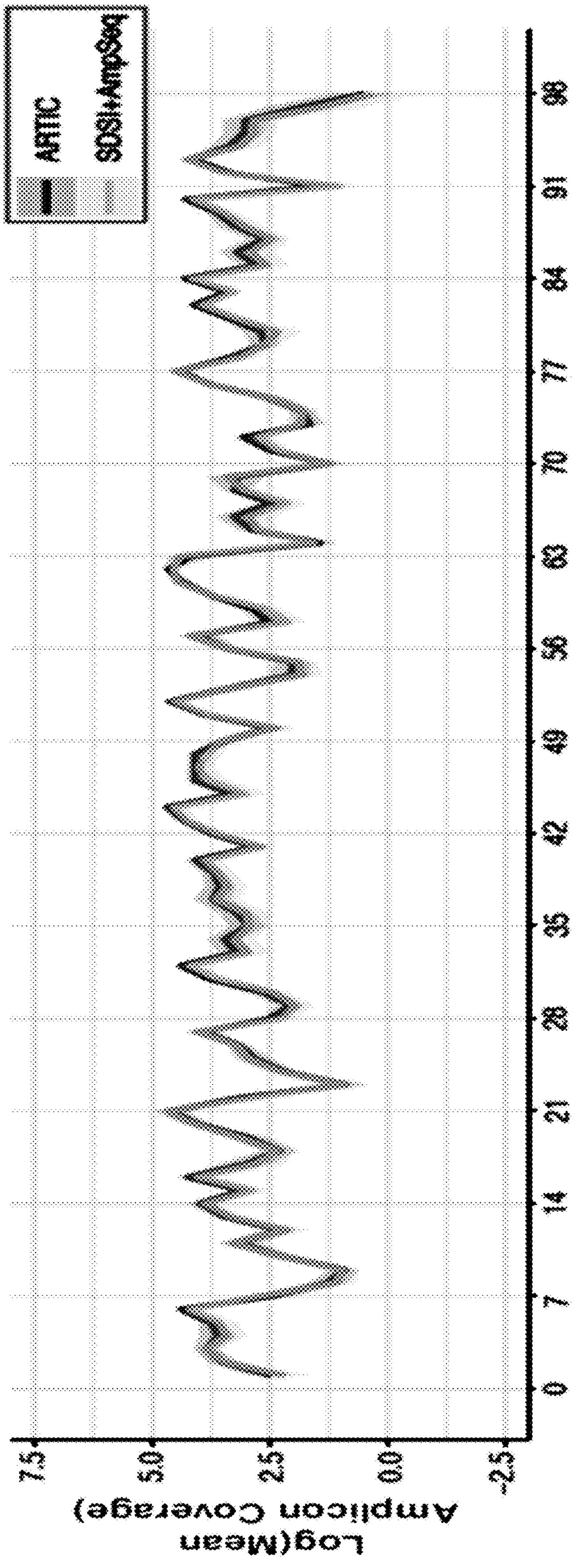
Figure 20A:
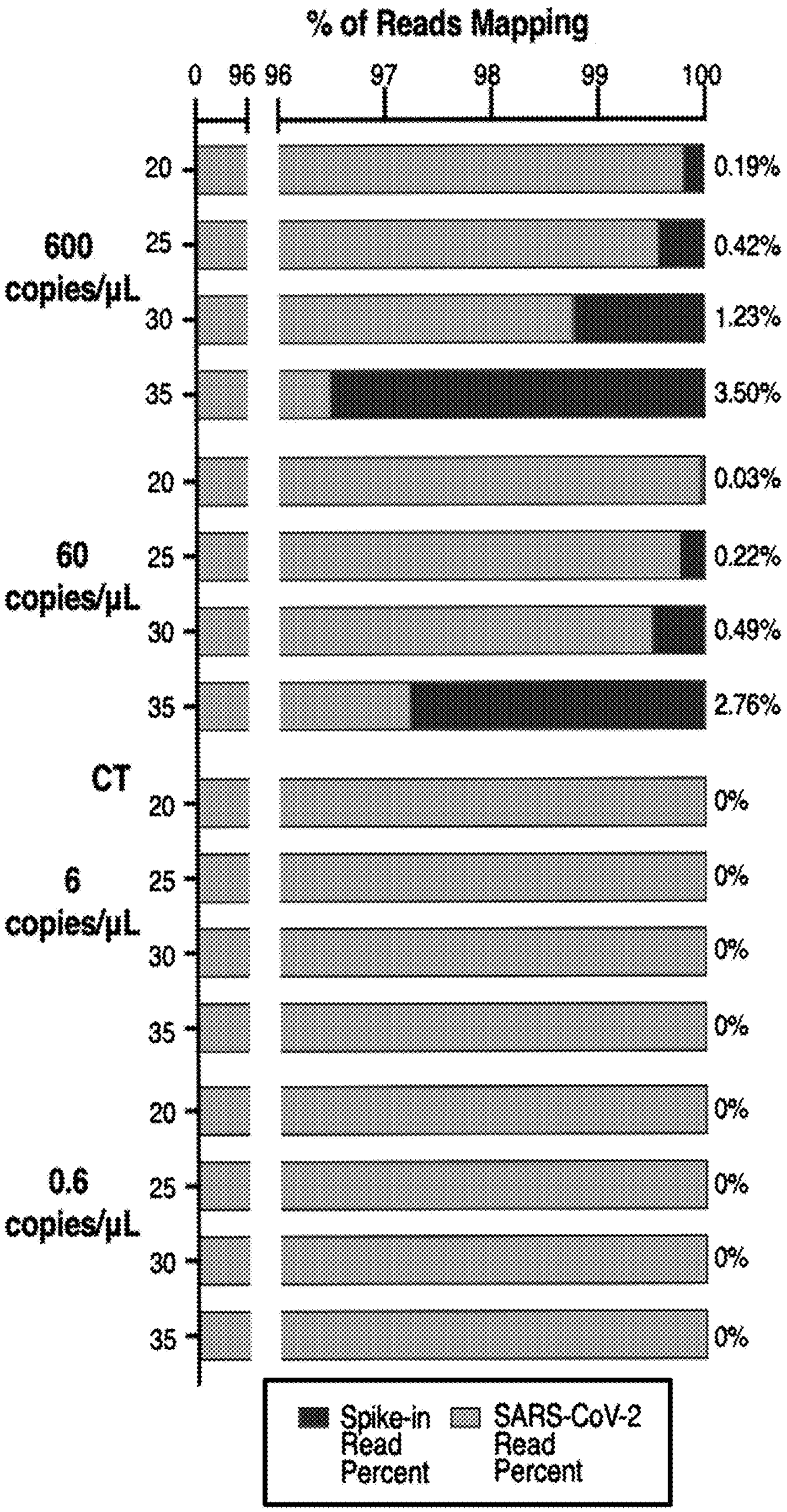
FIG. 20A-20B—SDSI Titration. A. In a titration of SDSI 49 across one clinical sample (CT=16) mock diluted to various CTs (CT=20,25,30,35), the number of reads mapping to both SARS-CoV-2 and the SDSI were quantified, and the percentage of each was calculated. SDSI 49 was tested at 600,60,6, and 0.6 copies/uL in each mock diluted sample. B. Coverage plots for the SDSI 49 titration experiment.
Figure 21A:
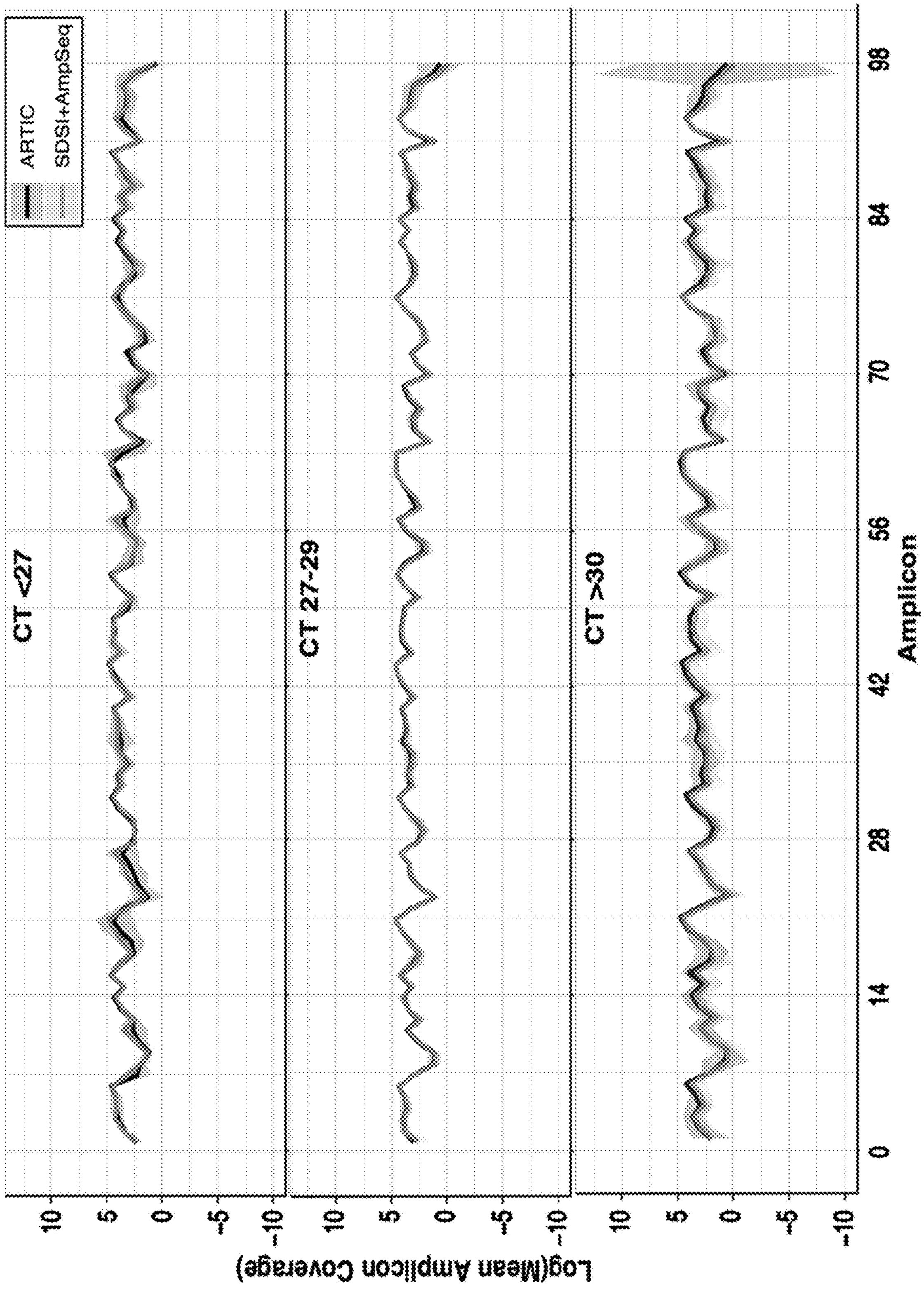
FIG. 21A-21B—ARTIC SARS-CoV-2 amplicon sequencing with and without SDSI and normalization. A. In three different CT bins, Applicants showed coverage plots with confidence intervals for multiple samples sequenced with and without SDSIs (CT<27, n=4; CT 27-29, n=6; CT>30, n=4). The solid blue line represents SDSI+AmpSeq and the solid black line is ARTIC only with no SDSI. Blue and black shading around the solid lines represents the confidence interval. There were no significant differences (p-value >0.05) between the with and without SDSI group for the mean coverage at any of the amplicons (two-tailed Mann Whitney t-test and multiple comparison two-stage step-up Benjamini, Krieger, and Yekutieli test with FDR set to 5%). B. The percentage of SDSI reads for 4 different SDSIs was assessed within 4 clinical samples that were run with and without CT normalization of the cDNA prior to the ARTIC PCR.

Applicants determined that the addition of SDSIs into the ARTIC multiplexed PCR did not detrimentally affect or otherwise alter the amplification of SARS-CoV-2 cDNA from clinical samples. First, to prevent SDSIs from overtaking the amplification and sequencing of SARS-CoV-2 amplicons, Applicants optimized the amount of SDSI added to each reaction through limited titration. Using a randomly selected SDSI (SDSI 49), Applicants found that the highest concentration tested, 600 copies/μL, resulted in reliable SDSI detection with >96% of reads still mapping to SARS-CoV-2 and no apparent alteration in coverage across the genome (FIG. 20A,B). Applicants then validated the specificity of the 96 selected SDSIs in a batch of clinical samples to confirm that there was no unpredicted cross-mapping, misidentification, or significant differences in amplification rate (FIG. 15A). To assess more precisely how the addition of SDSIs would affect SARS-CoV-2 genome sequencing in clinical samples, Applicants processed 14 samples, spanning a range of CT values (CT range=25-33), with both the standard ARTIC and SDSI+AmpSeq methods. For each amplicon, across all samples, there was no significant difference in coverage between the ARTIC and SDSI+AmpSeq conditions (FIG. 15B). Even in samples with low viral loads (CT>30), Applicants found that there were no significant differences in amplicon coverage (FIG. 21A). Additionally, within the 14 samples processed with and without an SDSI, Applicants see a 100% genome concordance rate illustrating the addition of the SDSIs does not impact recovery of accurate genomes.

Figure 15C:
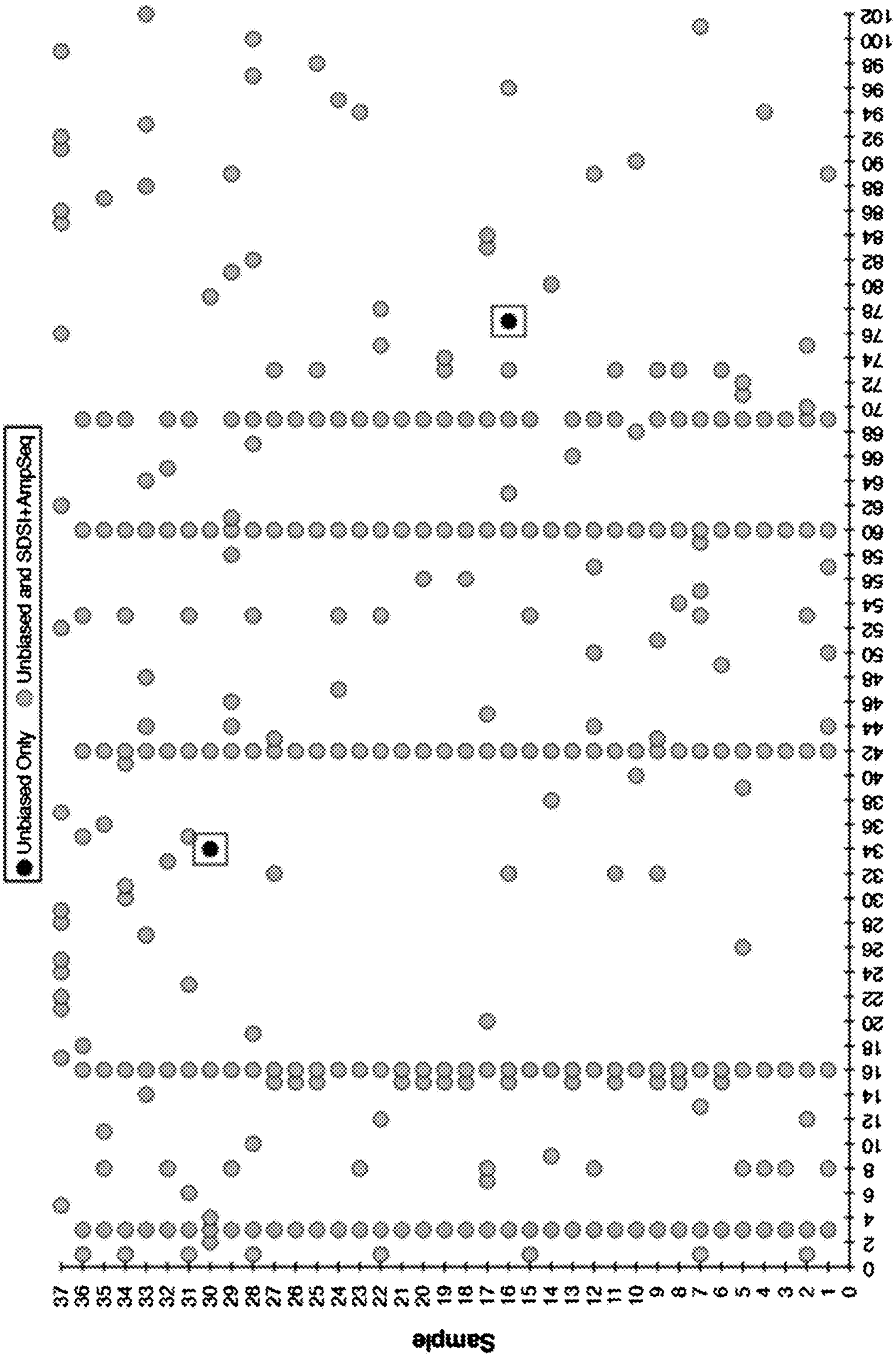
Figure 22A:
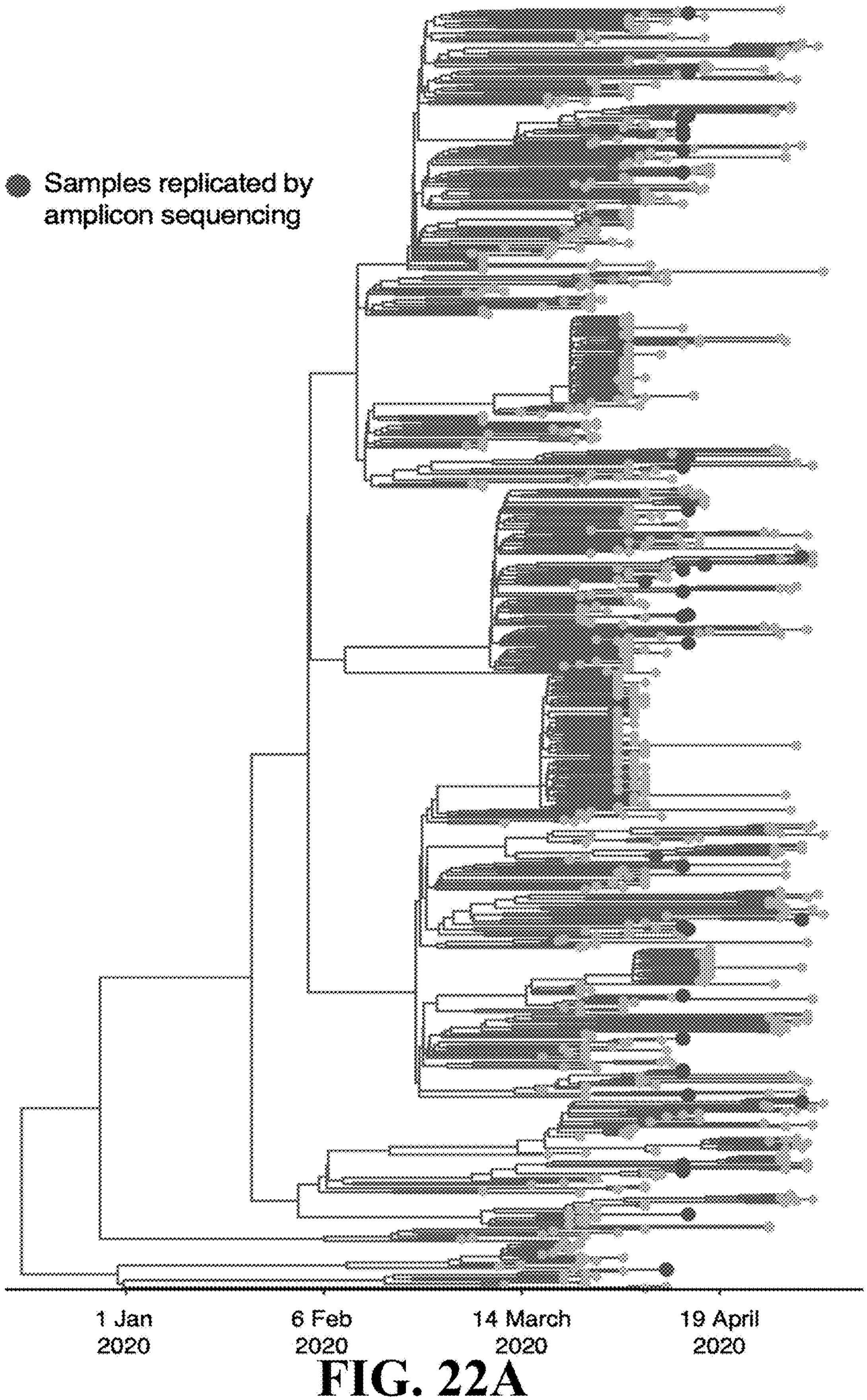
FIG. 22A-22E—SDSI+AmpSeq over a diverse set of samples has superior genome recovery and more coverage uniformity at higher CTs. A. Time-measured maximum clade credibility tree of 772 genomes from Massachusetts, reported in Lemieux et al., 2021. The 89 samples compared for metagenomic and amplicon sequencing are shown with red dots. B. Percent of assemblies with greater than 98% or C. 80% coverage in different CT bins (SDSI+AmpSeq N=81; Unbiased N=81) (downsampled to 975,000 reads). D. Genome coverage for unbiased metagenomic sequencing versus SDSI+AmpSeq amplicon sequencing pipeline (N=81, excluded samples had no detectable CT). All samples downsampled to 975,000 reads. E. Gini coefficients grouped by CT (N=70, excluded samples that did not generate assemblies in either one or both methods). Dashed red line represents the median. Error bars represent standard deviation.
Figure 22B:
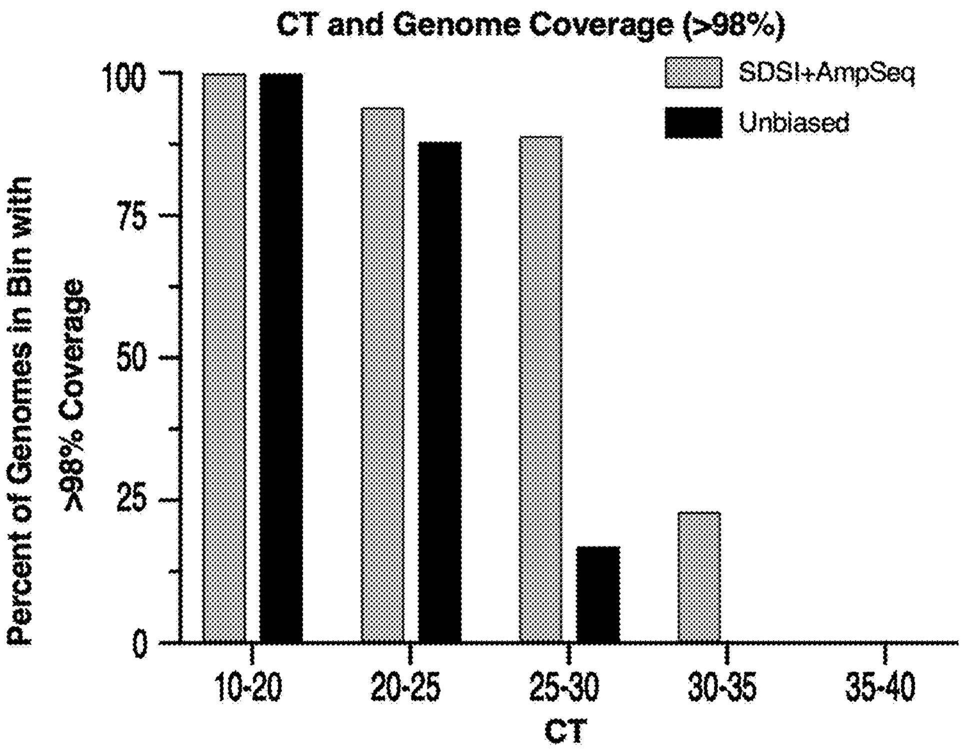
Figure 22C:
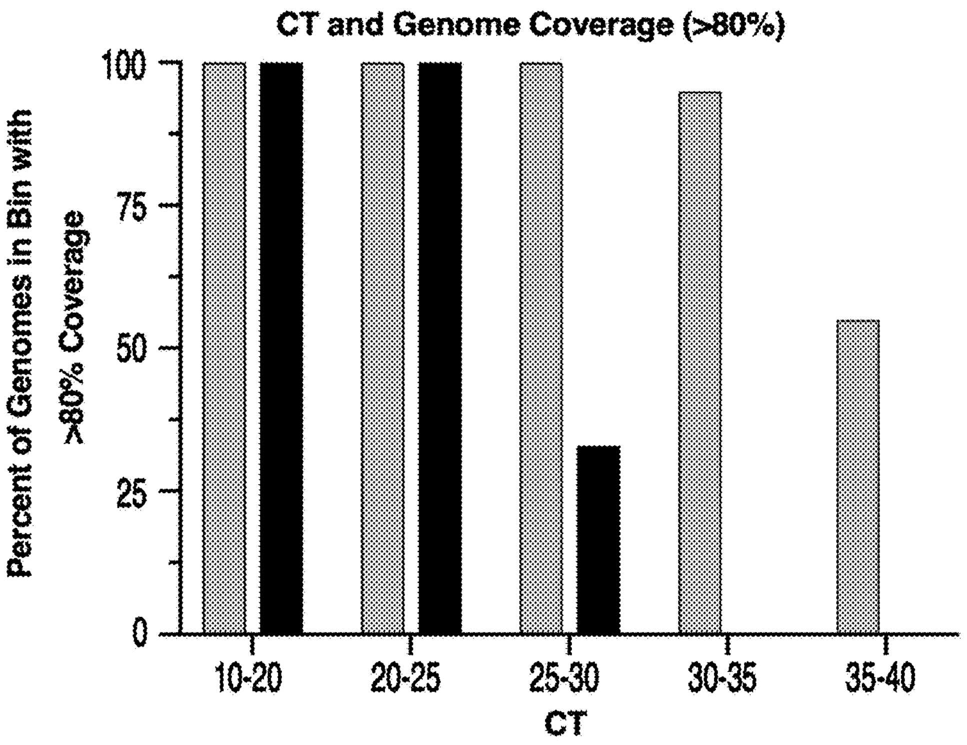
Figure 22D:
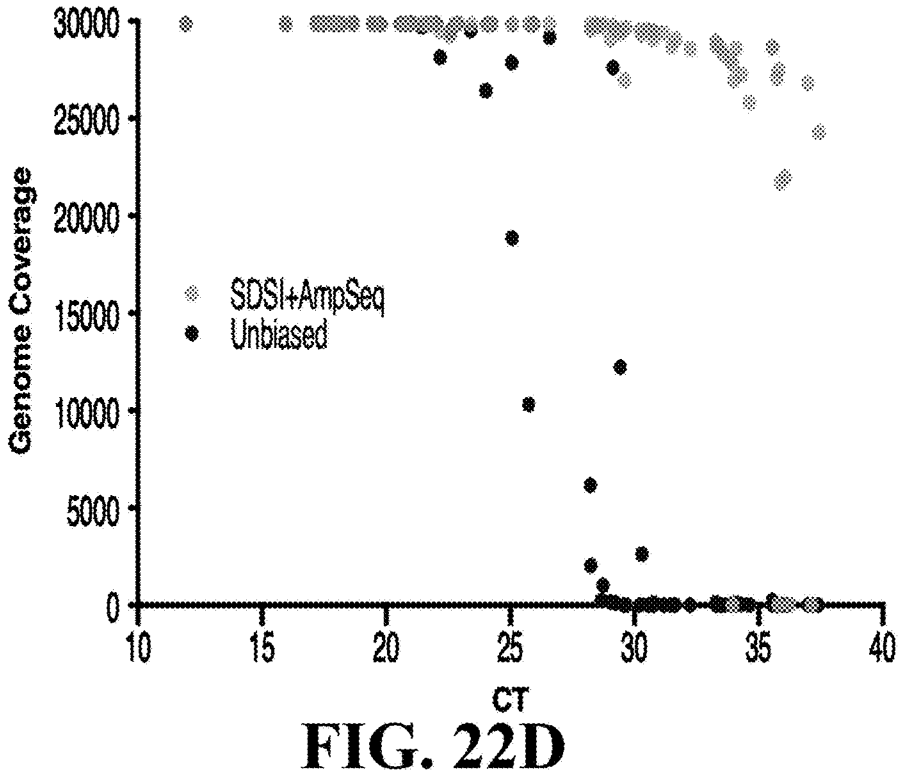
Figure 22E:
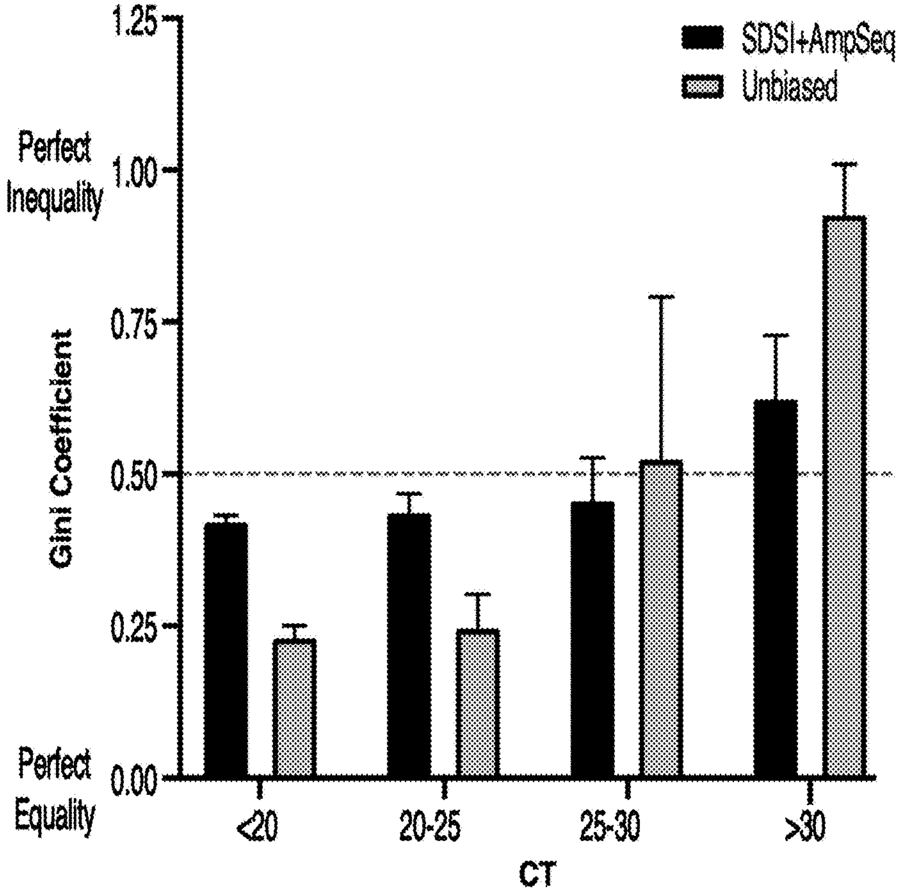

As extensive PCR can result in the propagation of numerous types of errors, such as DNA polymerase base substitution errors, PCR recombination events, template switching, and thermocycling induced DNA damage, Applicants further compared SARS-CoV-2 genome concordance between the SDSI+AmpSeq method and unbiased, metagenomic sequencing[9,10,20]. Applicants performed SDSI+AmpSeq on a batch of 89 unique patient samples previously sequenced with unbiased metagenomics[21]. The samples consisted of diverse viral lineages and a broad range of viral loads (CT range=11.9-37.4; mean=27.4) with the more sensitive amplicon sequencing method generating more complete genomes at higher CTs (FIG. 22A-D). Applicants assessed the coverage uniformity between the methods, as increasing uniformity reduces the sequencing depth required to generate reliable genomes[22]. Applicants found that unbiased sequencing had more uniform coverage up to a CT of 25 (N=31, Gini Coefficient=0.240±0.046 (unbiased) vs 0.428±0.026 (SDSI+AmpSeq)), while SDSI+AmpSeq generated more uniform coverage for samples above a CT of 25 (N=39, Gini Coeff=0.766±0.265 (unbiased) vs 0.554±0.124 (SDSI+AmpSeq)) (FIG. 22E). For the 37 samples that assembled a full genome in both methods, only two out of 332 total single nucleotide variants (SNVs) identified compared to the reference (Wuhan-Hu-1) were divergently identified by SDSI+AmpSeq (FIG. 15C). Each SNVs was observed in only one sample, and both fell within an ARTIC primer region, despite primer trimming during analysis; this suggests that PCR error from the ARTIC protocol may have contributed to the discrepancy[23]. Manual inspection of one SNV, (a C9565T mutation in unbiased sequencing) indicated the presence of intra-host variation in both methods with a variant allele frequency of 39.4% (SDSI+AmpSeq) and 59.2% (unbiased sequencing). Overall, the discordance rate between SNV calling for SDSI+AmpSeq and unbiased sequencing was 0.6%, a percentage that is reasonable with SNV rates and sequencing based errors. Consistent with previous reports from other groups, ARTIC amplicon sequencing maintains a high level of concordance at the consensus genome level[10], even with the addition of SDSIs.

Figure 23A:
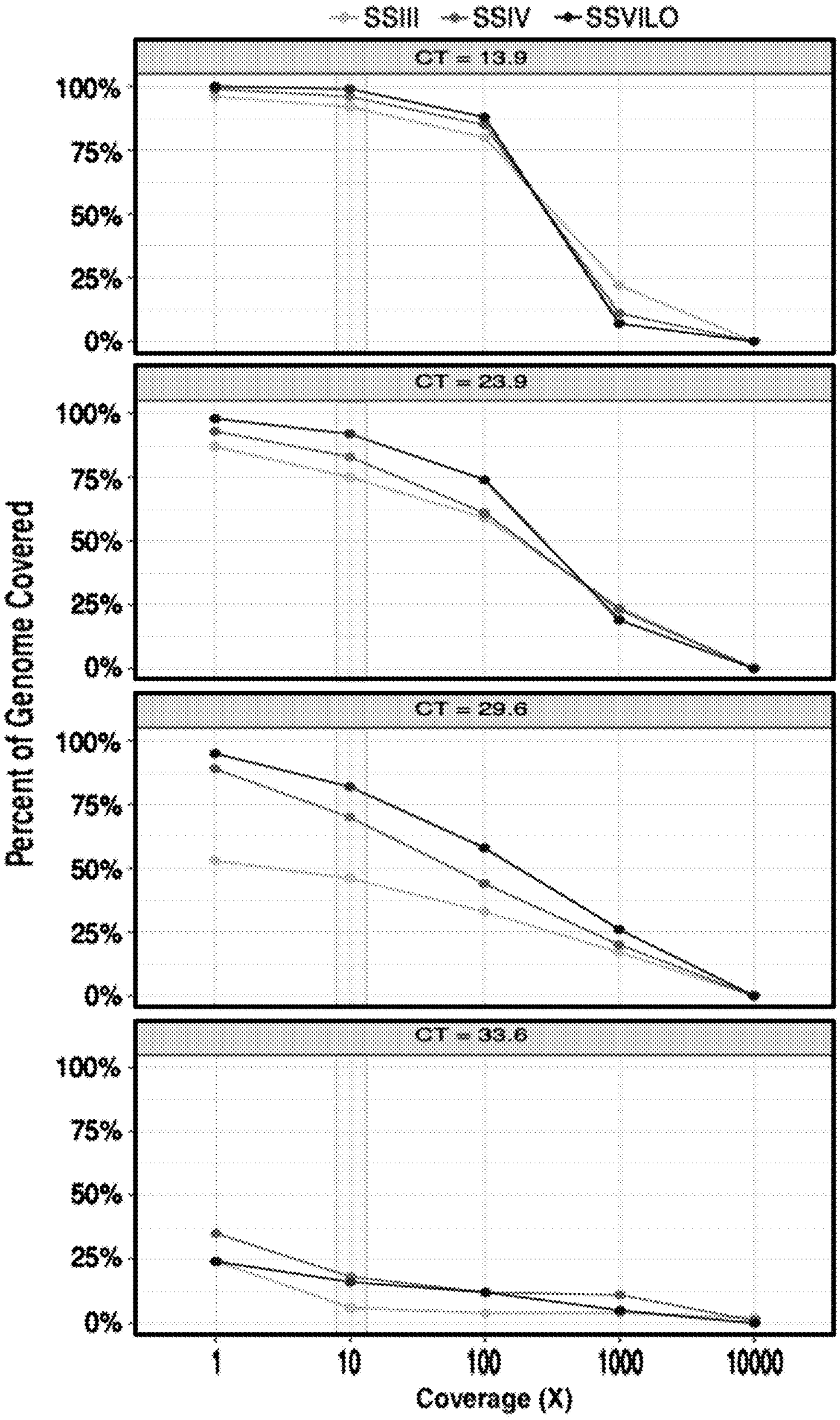
FIG. 23A-23H—Maximizing Genome Recovery and Coverage with SDSI+AmpSeq. A. The percent of the target genome covered at various depths of coverage for four individual samples (CT=13.9, 23.9, 29.6, 33.6), with each undergoing cDNA with three different reverse transcriptases (SSIII, SSIV, or SSVILO). Yellow bar highlights comparison between the reverse transcriptases at a coverage depth of 10×. B. Read depth across each nucleotide position for the same sample (CT=13.9) when using these reverse transcriptases. C. Base pairs of the SARS-CoV-2 genome covered at various depths when using different enzymes for the ARTIC PCR (n=1). D. Amplicons with at least 0.2× of the mean amplicon coverage with the normal ARTIC v3 primer pools or with a modified primer pool with a 2× concentration of 20 poor-performing ARTIC primer pairs. Six individual samples with different CTs were used. E. Read depth across each nucleotide position for normal ARTIC PCR vs an alternate hybridization PCR (n=1). F. Base pairs of the SARS-CoV-2 genome covered at various depths when using either normal ramping (3° C./s) or reduced ramping (1.5° C./s) speed for the ARTIC PCR (n=1). G. Gini coefficients for two mid-high CT samples and four high CT samples when using either 35, 40, or 45 cycles for the ARTIC PCR. Error bars represent standard deviation. H. Comparison of Nextera DNA Flex and Nextera XT on the number of SARS-CoV-2 base pairs covered at various depths of coverage for three samples with different CTs.
Figure 23B:
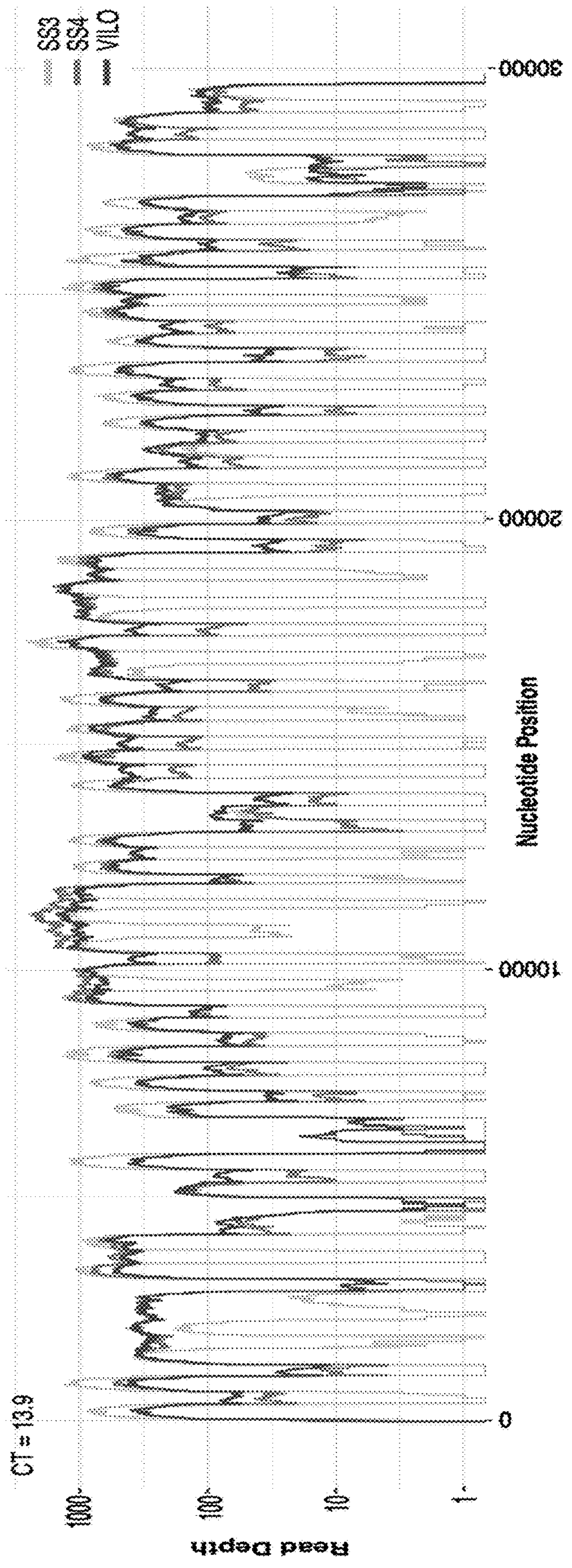
Figure 23C:
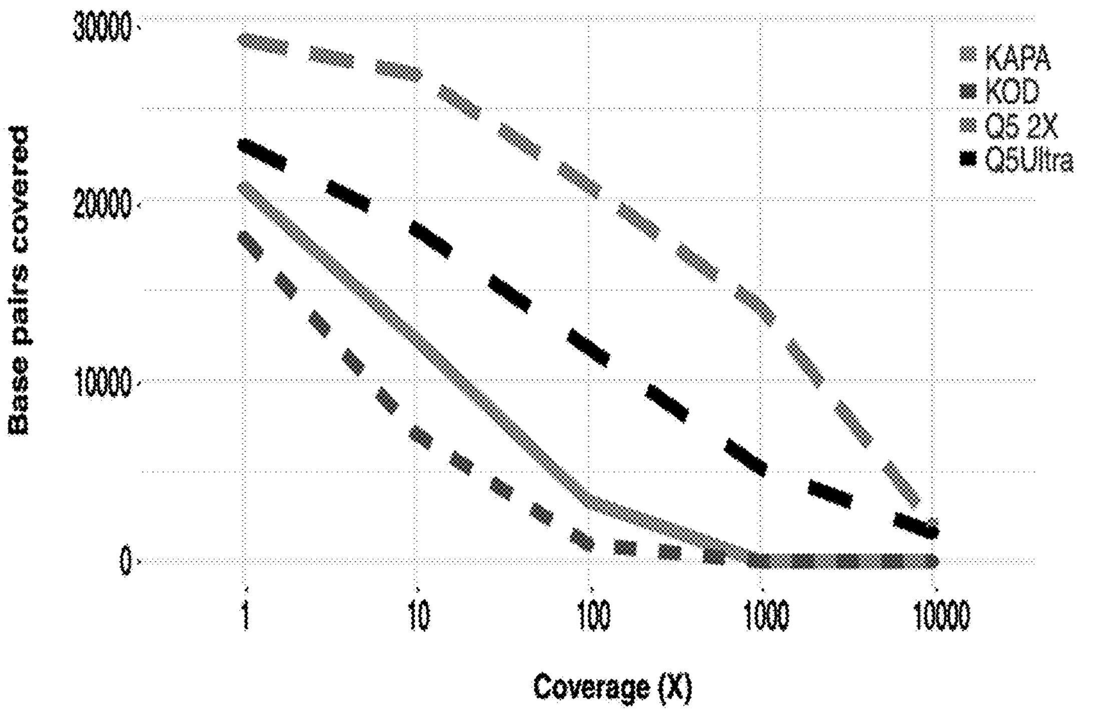
Figure 23D:
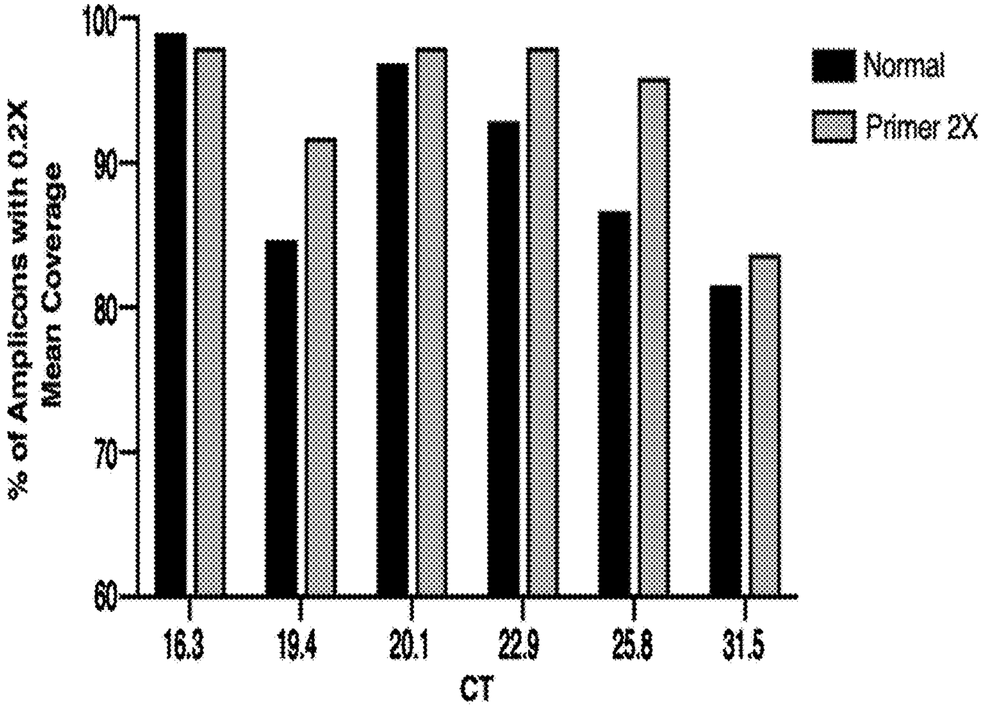
Figure 23E:
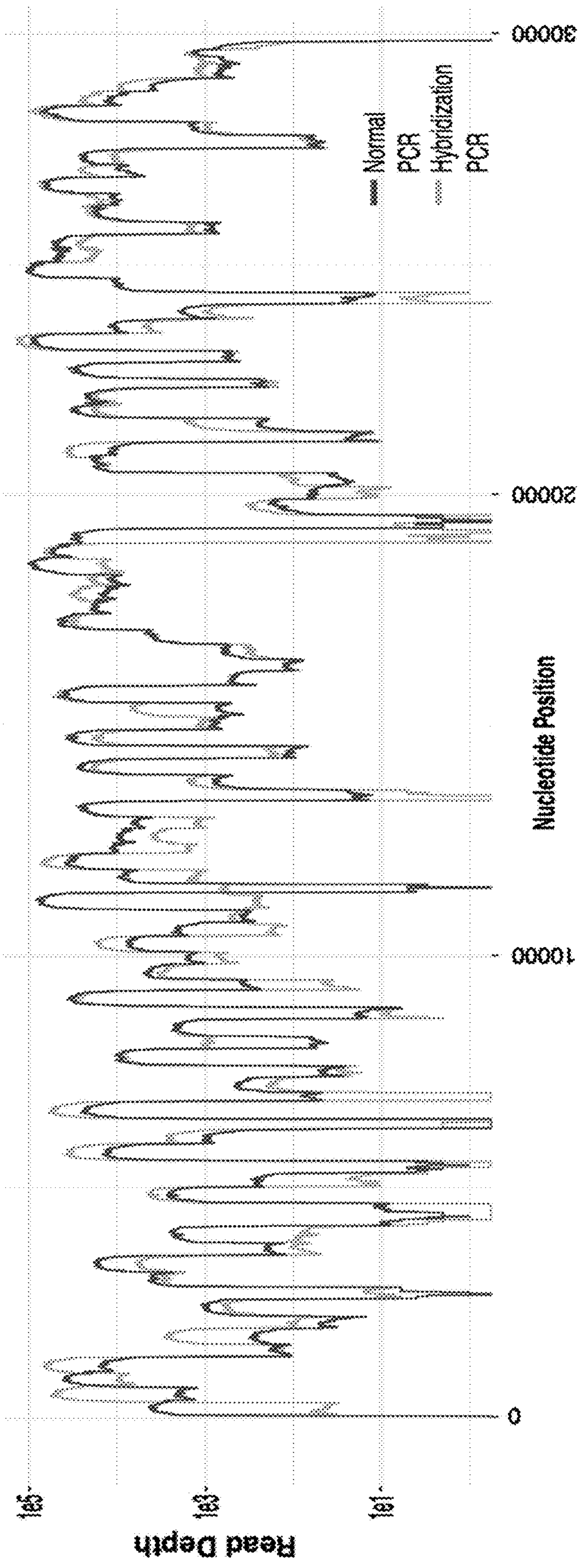
Figure 23F:
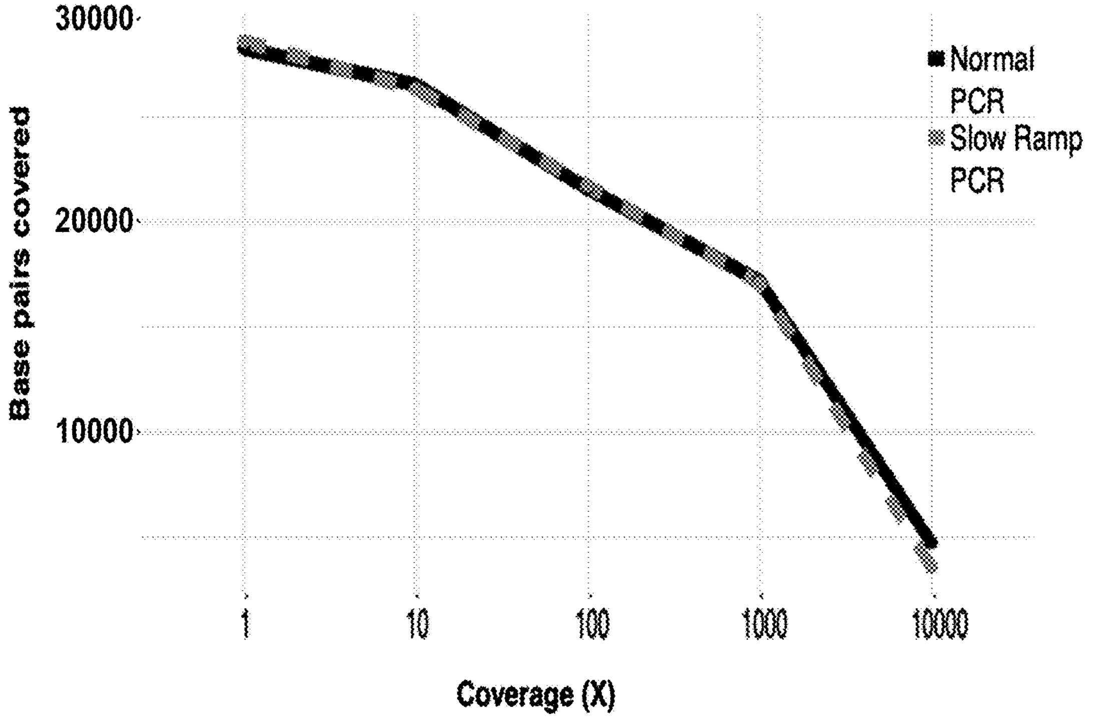
Figure 23G:
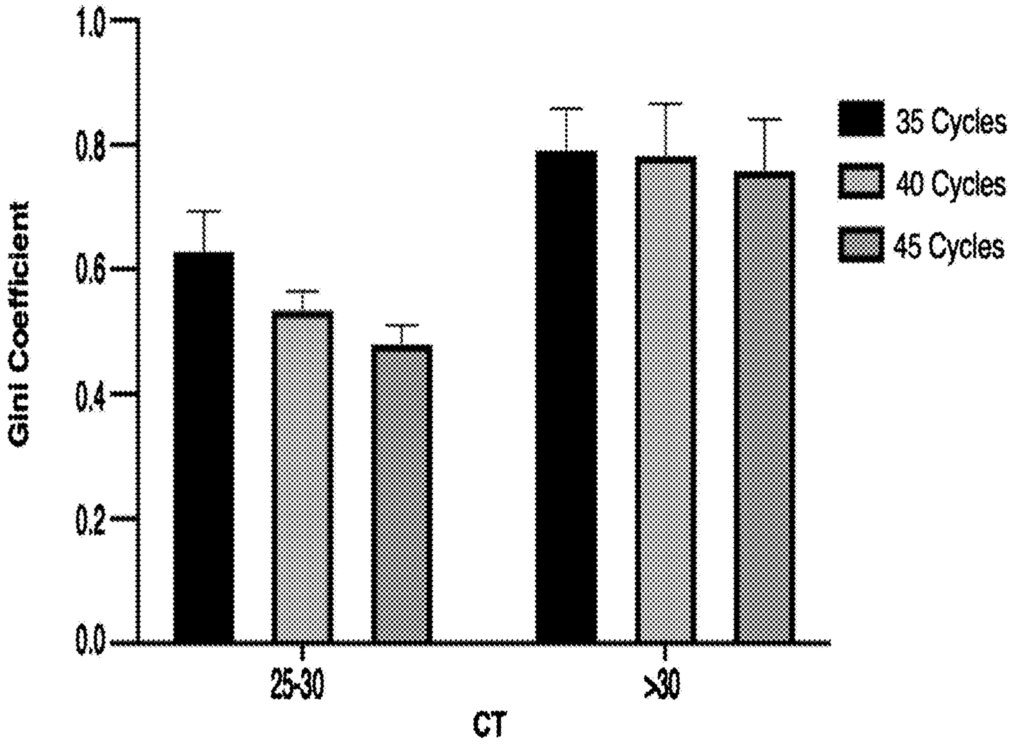
Figure 24:
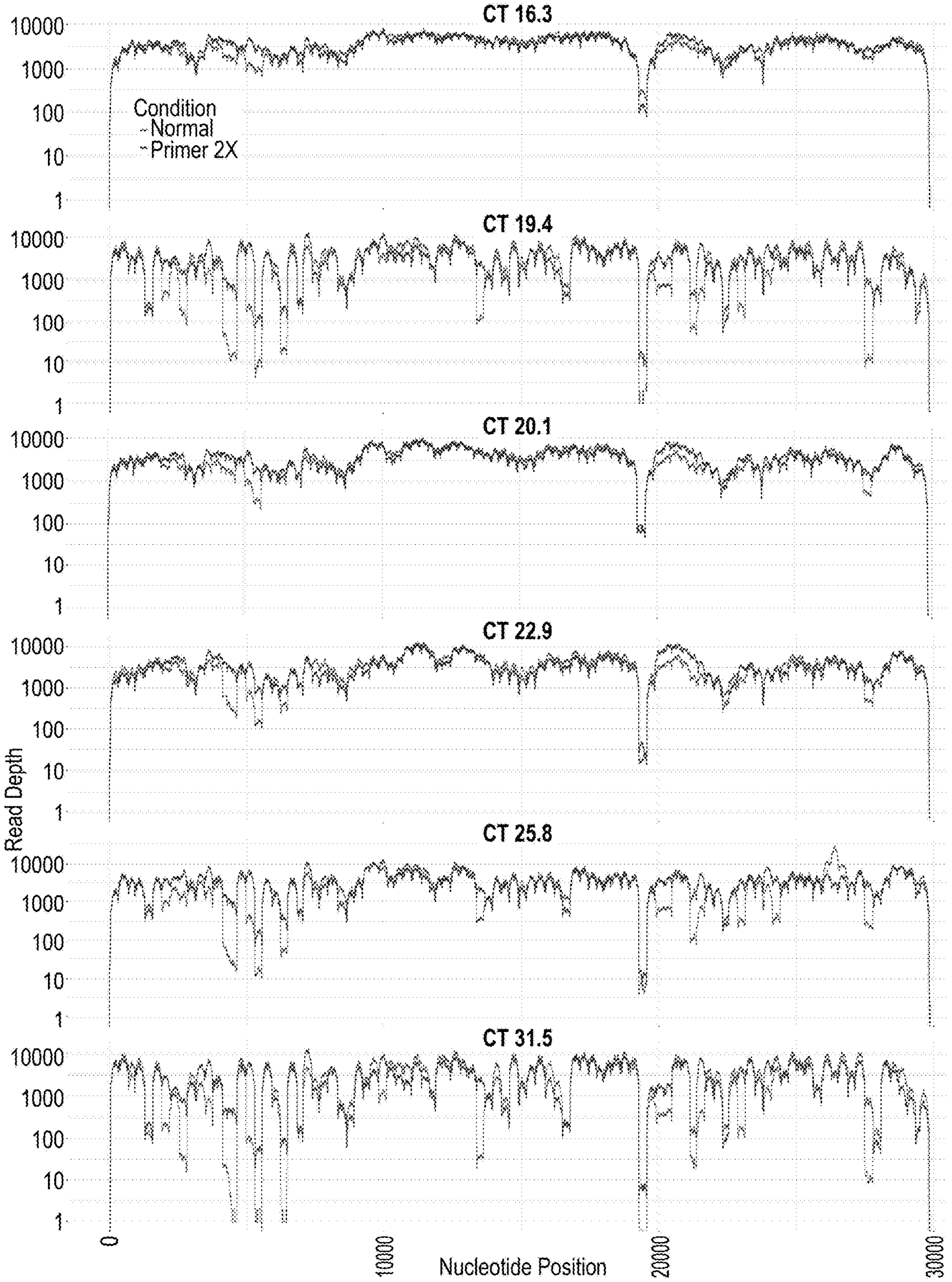
FIG. 24—Increasing primer concentration 2-fold in regions of low amplicon coverage. Data represents 6 individual samples at different CTs.

Applicants explored a number of other technical modifications to the ARTIC amplicon sequencing protocol in order to improve genome recovery, limit contamination points, and enhance reproducibility of the SDSI approach. Foremost, increasing cDNA length by use of more processive reverse transcriptases improves amplicon coverage (FIG. 23A,B). Amplification of ARTIC amplicons and SDSIs by Q5 Hot Start High-Fidelity 2× Master Mix results in higher amplification (FIG. 23C, Table 7). Applicants found that increasing (2×) primer concentrations (20.8 nM final) for poor performing amplicons increased coverage in these amplicons, even enabling whole genome recovery for multiple samples supporting that primer rebalancing can enable greater coverage[24,25] (FIG. 23D, FIG. 24, Table 4). Applicants then explored the effects of different numbers of PCR cycles, DNA-hybridization steps, and temperature ramp speeds. Both DNA-hybridization steps and temperature ramping provided no significant changes in amplification (FIG. 23E,F). Although it may lead to a potential increase in erroneous SNV calls[23], additional cycles of PCR can be beneficial for low viral load samples by increasing genome coverage uniformity (FIG. 23G). Using a standardized cDNA input, Applicants found that the DNA Flex library preparation kit resulted in an increased depth of coverage for the SARS-CoV-2 genome across all CT values tested, compared to Nextera XT (FIG. 2311). To further mitigate the risk of contamination from such highly amplified libraries, Applicants took advantage of the self-normalizing feature of the DNA flex kit and found that limiting the tagmentation beads by scaling down (0.5×) all components of the DNA Flex library construction reagents restricted library overamplification. Notably, this limitation did not impact final library size distributions or SDSI amplification, while having the desired effect of generating final sequencing libraries at half their original concentrations (Table 8). This approach also had the added benefit of nearly halving the library construction cost per sample (Methods). Applicants have summarized the results of the optimizations within the full SDSI+AmpSeq protocol (benchling.com/s/prt-R95gOtCxKOeCAgn8lAk3); additionally, Applicants have found that the SDSIs can be easily integrated with numerous protocol alterations.

Example 9—Implementation of SDSIs to SARS-CoV-2 Clinical Samples at Scale

Figure 16A:
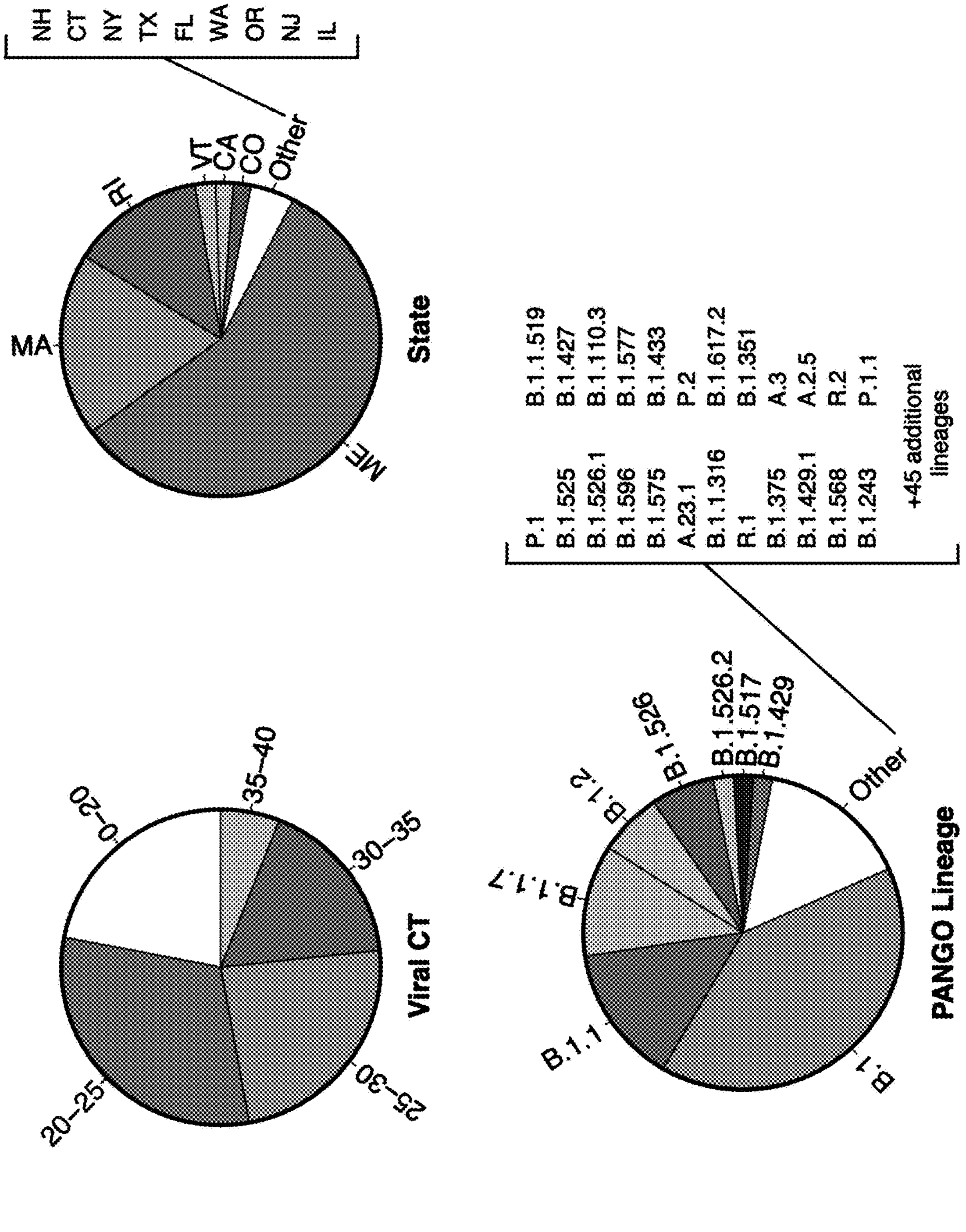
FIG. 16A-16C—SDSI+AmpSeq performs well across thousands of samples. A. Sample diversity from two different institutions representing a range of CTs, viral lineages, and states of sample collection from samples where the data was available. B. The percent of SDSI reads out of the sum of all SDSI reads that map to the correct spike-in (Left: JAX, N=3,838, Right: Broad, N=2,903). Error bars represent SEM. C. The percent of SDSI reads over the total of all sequenced reads for all SARS-CoV-2 positive samples (Left: JAX, N=3,093, Right: Broad, N=2,670). Error bars represent SEM.

The SDSI+AmpSeq method is compatible with a range of viral CTs, SARS-CoV-2 lineages, origin of the patient sample, and laboratory in which the pipeline is implemented demonstrating that this is a robust and flexible approach that can be readily implemented for surveillance. A half plate of SDSIs were used at two large-scale sequencing facilities, the Broad Institute and Jackson Laboratories (JAX), for SDSI+AmpSeq SARS-CoV-2 surveillance across a total of 6,741 clinical samples and controls (JAX: N=3,838; Broad: N=2,903). Individual batches typically consisted of 92 clinical samples with 4 designated water controls. Clinical samples were largely from Maine, Massachusetts, and Rhode Island from December 2020 to July 2021 and covered a wide range of viral CT values (CT 8.4-39.9) and pango lineages (77 total lineages) (FIG. 16A). The SDSI+AmpSeq method worked robustly despite minor implementation differences in protocols between the two laboratories including alterations in the cDNA synthesis enzymes (SSIV vs Lunascript), CT normalization implementation, and library construction approaches (0.5× Illumina DNA Flex vs Illumina COVIDSeq) (Methods).

Figure 16B:
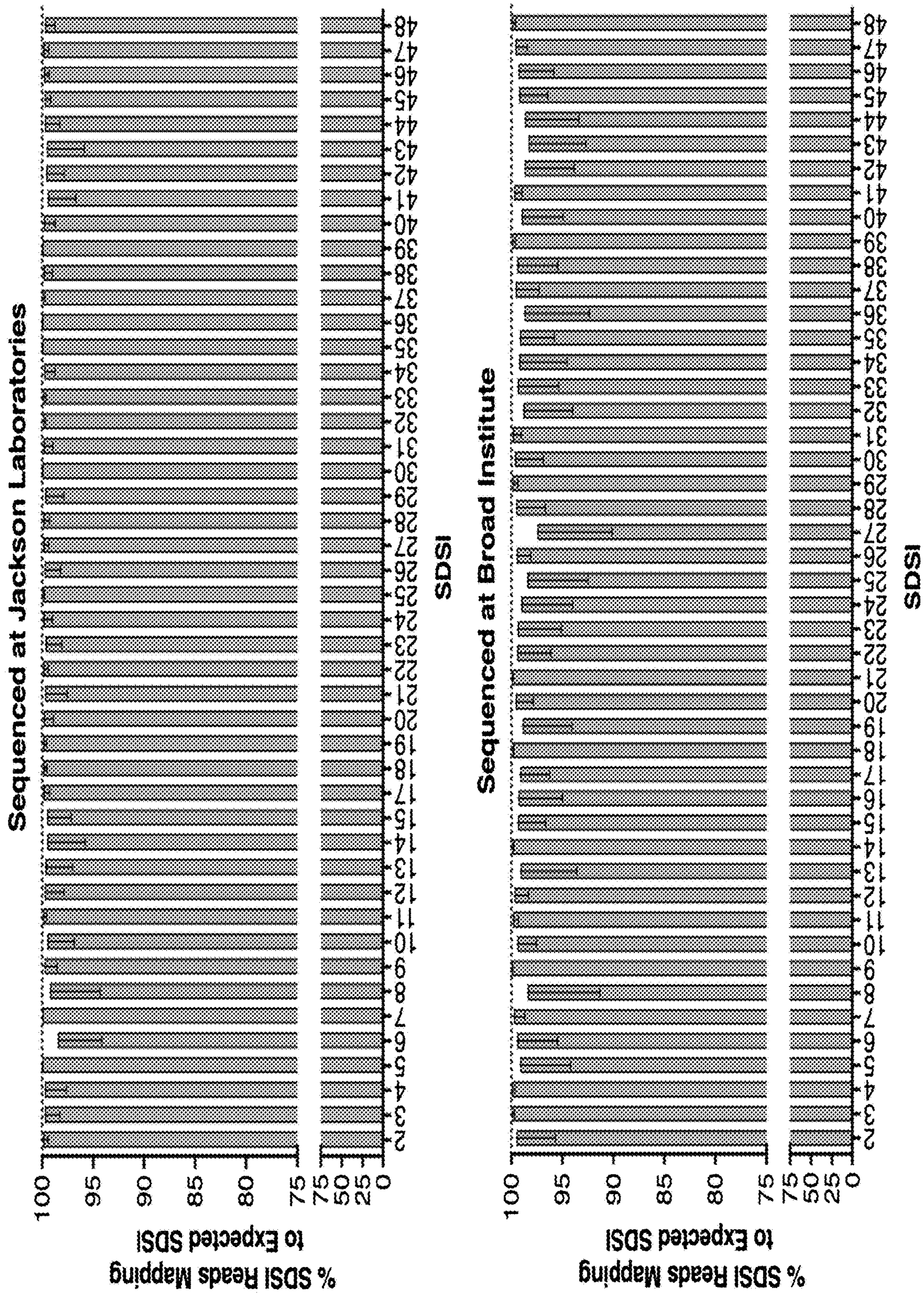
Figure 16C:
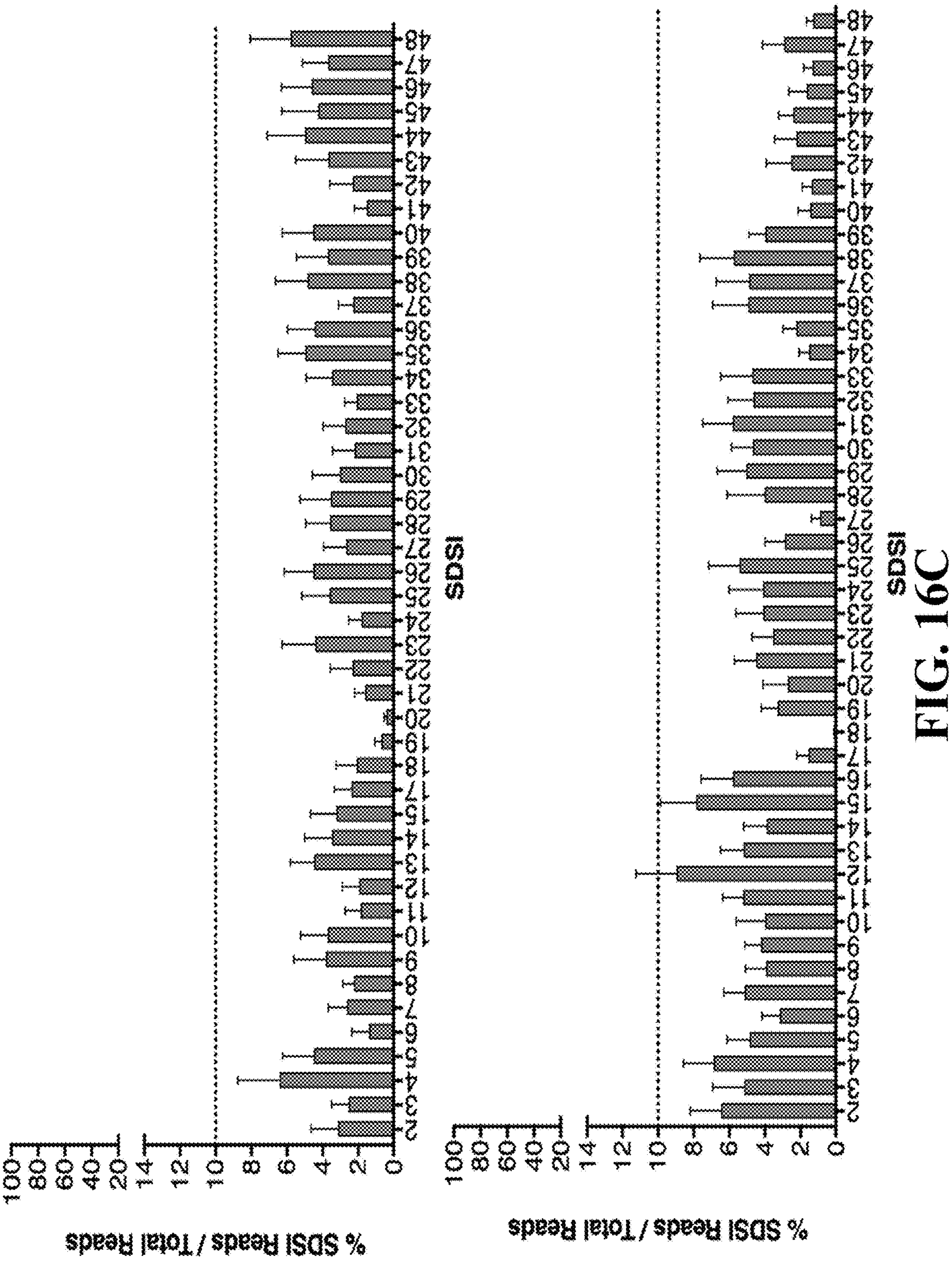
Figure 21B:
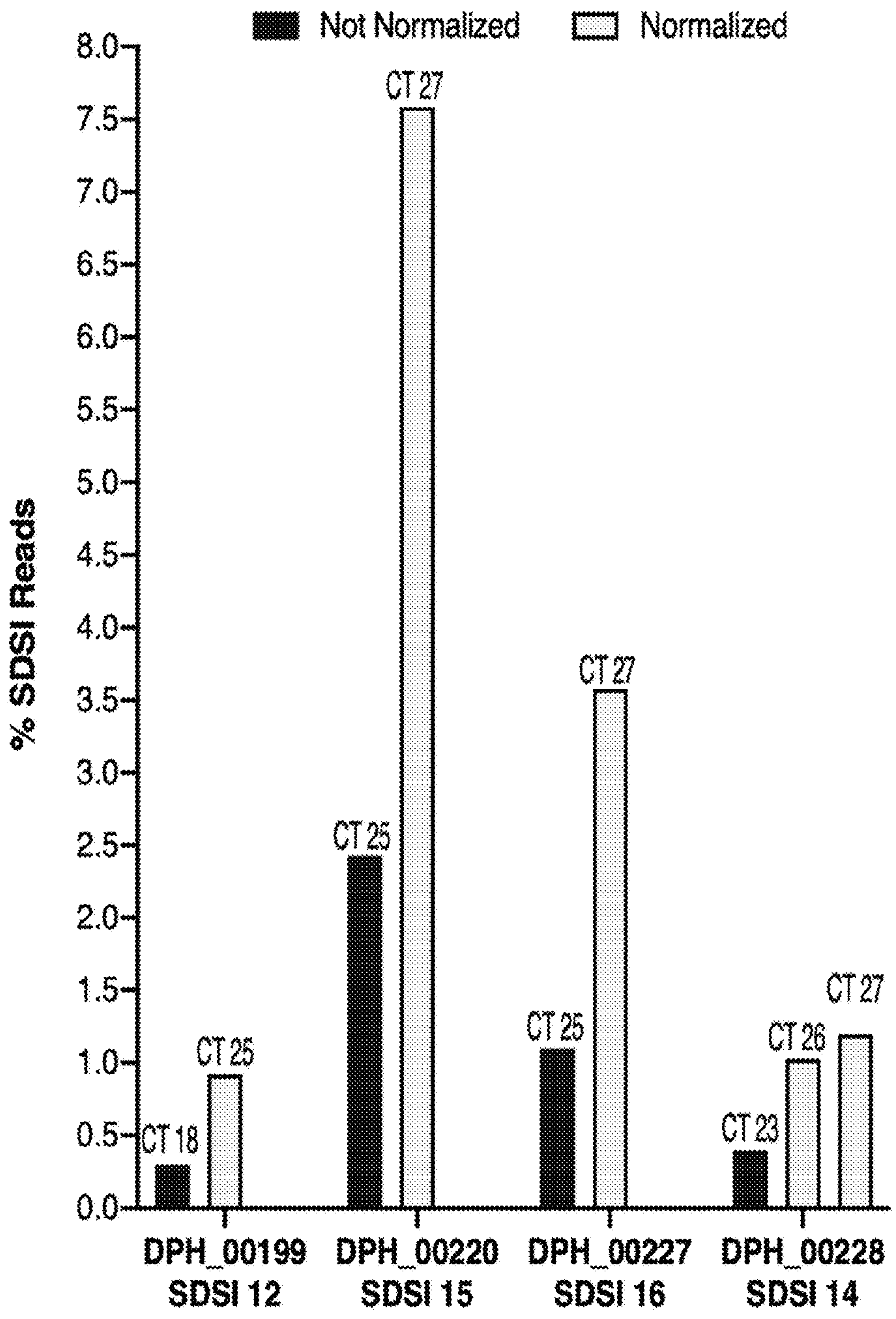

The SDSI+AmpSeq is a tractable and easily-implemented method for genome quality control when applied to high-throughput processing of clinical samples. Across thousands of clinical samples, the SDSIs performed consistently and reliably (FIG. 16B,C). The mean percentage of SDSI reads that mapped to the expected SDSI was above 95% for all SDSIs in both laboratories (FIG. 16B). This demonstrated that across a large set of highly variable clinical samples, there were no systemic issues of misidentification for specific SDSIs. Additionally, across all samples from both institutions, the percentage of all SDSI reads in SARS-CoV-2 positive samples averaged 3.71% (90% of samples fell between 0.002-9.989%) (FIG. 16C). Each SDSI consumed roughly the same read percentage, with no SDSI consistently absent or regularly taking up more than 10% of the sample reads, supporting the prediction that the unique constructs amplified at similar rates. Importantly, this low, but consistent percentage of reads mapping to SDSIs allows for their implementation without needing to greatly increase sequencing depth. Across batches, SDSIs also take up roughly similar shares of the reads, indicating that the SDSI+AmpSeq method is consistent over time. Notably, the SDSIs performed well with and without prior normalization of cDNA based on CT, however normalizing did increase the percentage of SDSI reads (FIG. 21B, FIG. 16B left, Methods). Normalization of viral CT may provide an additional level of quality control that is especially important for labs with limited sequencing capacities.

Example 10—SDSI+AmpSeq Provides Highly Confident Genome Sequencing and Analysis

Figure 17A:
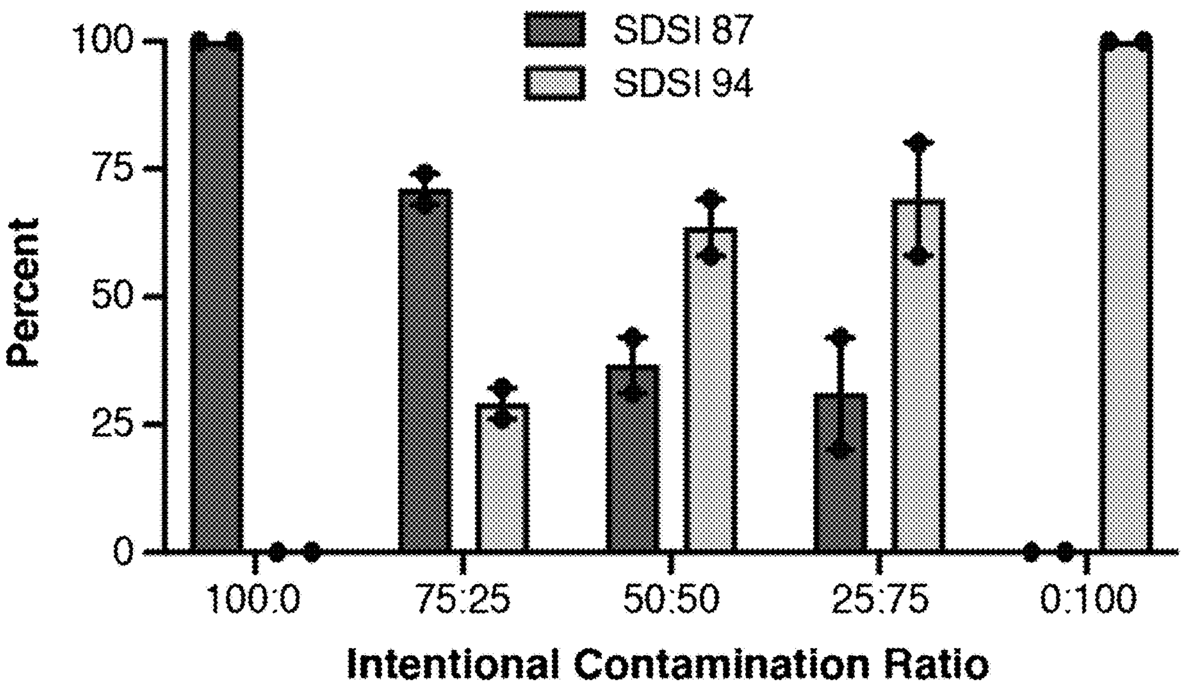
FIG. 17A-17C—SDSI+AmpSeq is used to identify sample swaps and contamination. A. Intentional SDSI contamination experiment (run in duplicate) assessing if different ratios of contamination between SDSI 87 and SDSI 94 (SDSI 87:SDSI 94) were detectable with the SDSI+AmpSeq method. B. Examples of experimental errors that were caught using the SDSI+AmpSeq method. C. Top: Distance matrix showing pairwise differences between the 17 complete genomes assembled from this sample set. Putative cluster samples are bolded. Bottom: Spike-in counts for each of the 24 samples and water controls in this sequencing batch.
Figure 17B:
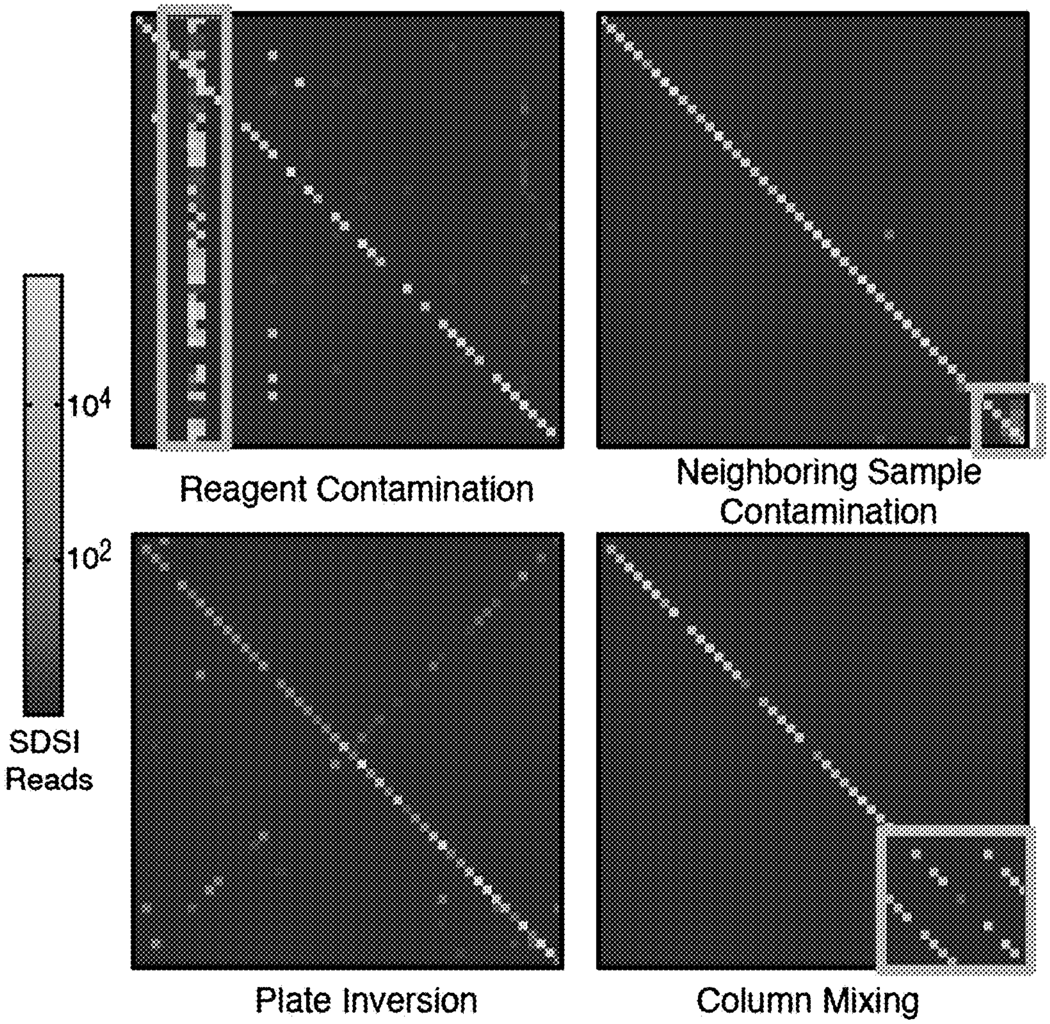

SDSIs enable detection of sample swaps and contamination events that occur in large scale batch processing which may otherwise go undetected. In a controlled experiment, Applicants demonstrated that the SDSI+AmpSeq approach provides a feasible method to accurately detect contamination. Applicants mixed two SDSIs at various ratios prior to the ARTIC PCR and found that those SDSI ratios were reflected in the sequencing output (FIG. 17A). With evidence of SDSI's robust detection, uniqueness, and ability to detect intentional contamination, Applicants proceeded to use them to identify sample swaps and contamination in large batch processing. Across thousands of SARS-CoV-2 samples processed, SDSIs detected in samples to which they were not intentionally added allowed for identification of multiple key modes of error (FIG. 17B). As plotted, a plate without contaminating events or sample swaps should display a simple diagonal pattern with 1-1 matching of expected and observed SDSIs. In some cases, off-diagonal events occur in clear patterns, enabling speculation on the nature of the contamination, clearly demonstrating the utility of SDSIs as an internal control and in-sample label. Applicants observed cases where a plate was likely inverted when SDSI+AmpSeq pool 1 was mixed with pool 2 (FIG. 15B). The SDSI+AmpSeq approach allows researchers to detect entire flawed batches that may not have been flagged with standard controls (as in the case with the plate inversion where water controls in plate corners would not have been affected). In another example, SDSIs were detected unexpectedly throughout a batch, indicating that SDSI (and possibly SARS-CoV-2 and other genetic material) contaminated a common reagent.

SDSI+AmpSeq also enables fine-resolution insight into sample processing errors with high specificity. In one example, SDSI counts indicated columns were unintentionally mixed together (FIG. 17B). Here, in-sample labeling in all wells allowed researchers to confidently move forward with analyses on unaffected samples. In other cases, samples are associated with both the expected SDSI and SDSIs that were expected in neighboring samples. This indicates a potential spillover event or pipetting errors. Again, genomes generated from samples with suspicious SDSI profiles can be investigated further, and potentially removed from analyses and/or reprocessed. Applicants recommend manual curation of genomes assembled from any samples with <95% of SDSI reads mapping to the expected SDSI. This level of impurity is likely attributable to sample processing contamination, given minimal baseline crosstalk from sources like indexing primer or oligo synthesis observed (Methods, FIG. 25). Moreover, these patterns of contamination events identified via use of SDSI+AmpSeq illuminated key sources of error in processing pipelines and provided an opportunity to improve processing fidelity in subsequent batches.

Figure 17C:
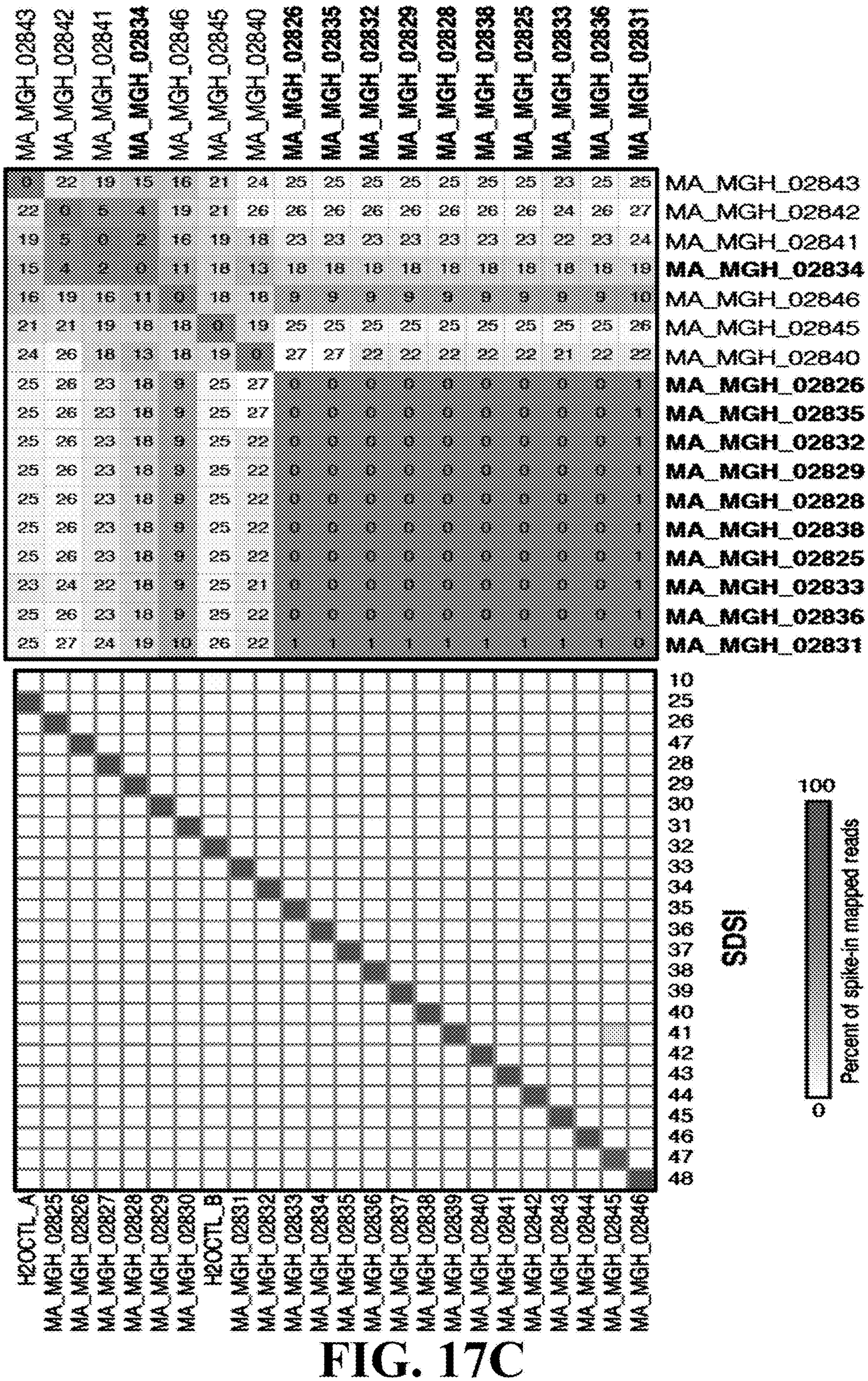

To demonstrate the application of the SDSIs for confident interpretation of sequencing data Applicants used SDSI+AmpSeq to investigate a putative SARS-CoV-2 cluster from Massachusetts General Hospital (MGH) for which the Infection Control Unit suspected nosocomial transmission, a context in which both sample swaps and contamination could easily undermine findings. Applicants sequenced 22 samples with SDSI+AmpSeq (14 samples suspected to be part of the cluster based on epidemiological contact-tracing and 8 unlinked samples as controls), within 24 hours and final genomes were assembled within 52 hours of biosample receipt. Of the 11 samples that Applicants assembled genomes from that were suspected to be part of the cluster, 10 were genetically highly similar (0-1 consensus nucleotide difference) (FIG. 17C) and distinct from other samples from Massachusetts around the same time (FIG. 26), strongly suggesting that this cluster did arise from nosocomial transmission. Analysis of the SDSIs confirmed that genome sequence similarity among cluster-associated samples was not the result of cross-contamination (FIG. 17C). Indeed, 23/24 libraries (22 patient samples and 2 water controls) contained >95% SDSI-mapped reads corresponding to the expected SDSI. One sample that was not part of the cluster (MA_MGH_02845) showed 18% of reads from a second SDSI, which was added to a different sample in the batch (MA_MGH_02839). Applicants re-sequenced both samples implicated in the contamination event. Applicants confirmed that the two genome sequences for MA_MGH_02845 were 100% concordant, and no genome was assembled for MA_MGH_02839 in either attempt, likely due to its very low viral load (CT=37). This example illustrates how SDSIs can be used to isolate and validate only those samples implicated in contamination events and altogether increase confidence in cluster investigations.

Figure 27A:
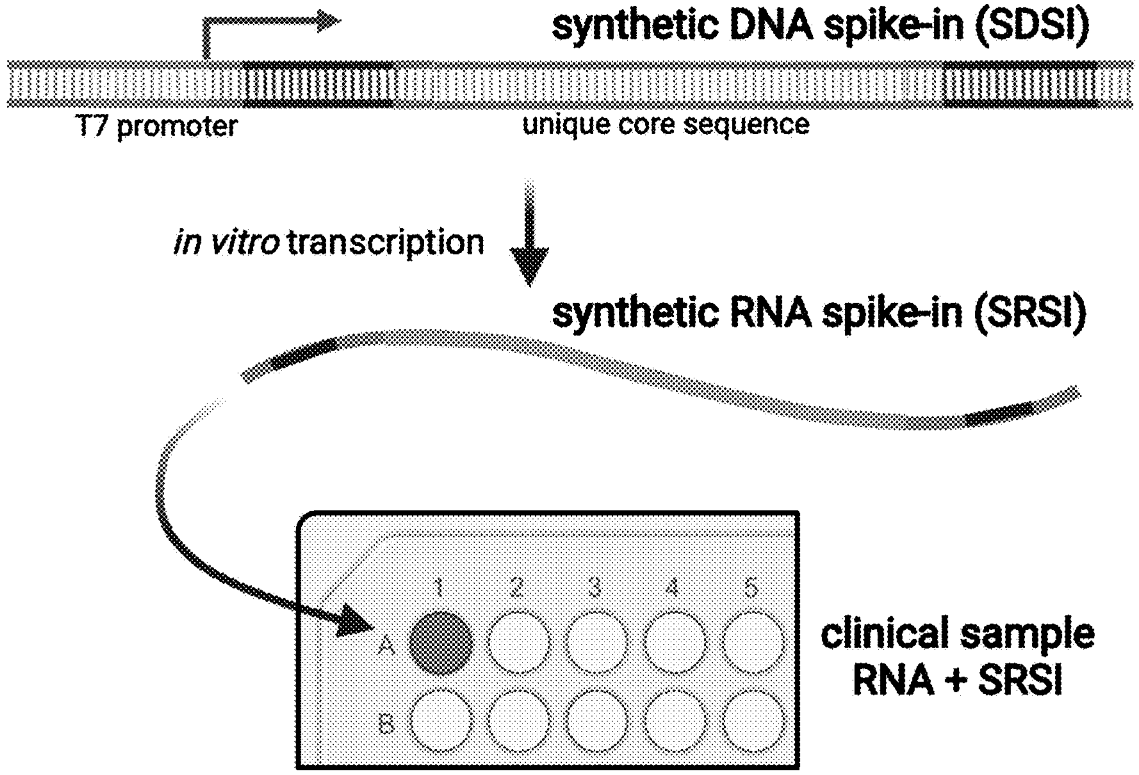
FIG. 27A-27B—Modification enables addition of spike-ins to RNA. A. A schematic of how to design, produce, and apply synthetic RNA spike-ins (SRSIs). B. A limited titration experiment where SRSIs of varying concentrations were added to two clinical samples with low and intermediate SARS-CoV-2 Cts. SRSIs were added to the sample at the RNA stage; the sample with a low CT (20) was then normalized to CT 25 at the cDNA stage, whereas the sample with mid CT (26) was not normalized.
Figure 27B:
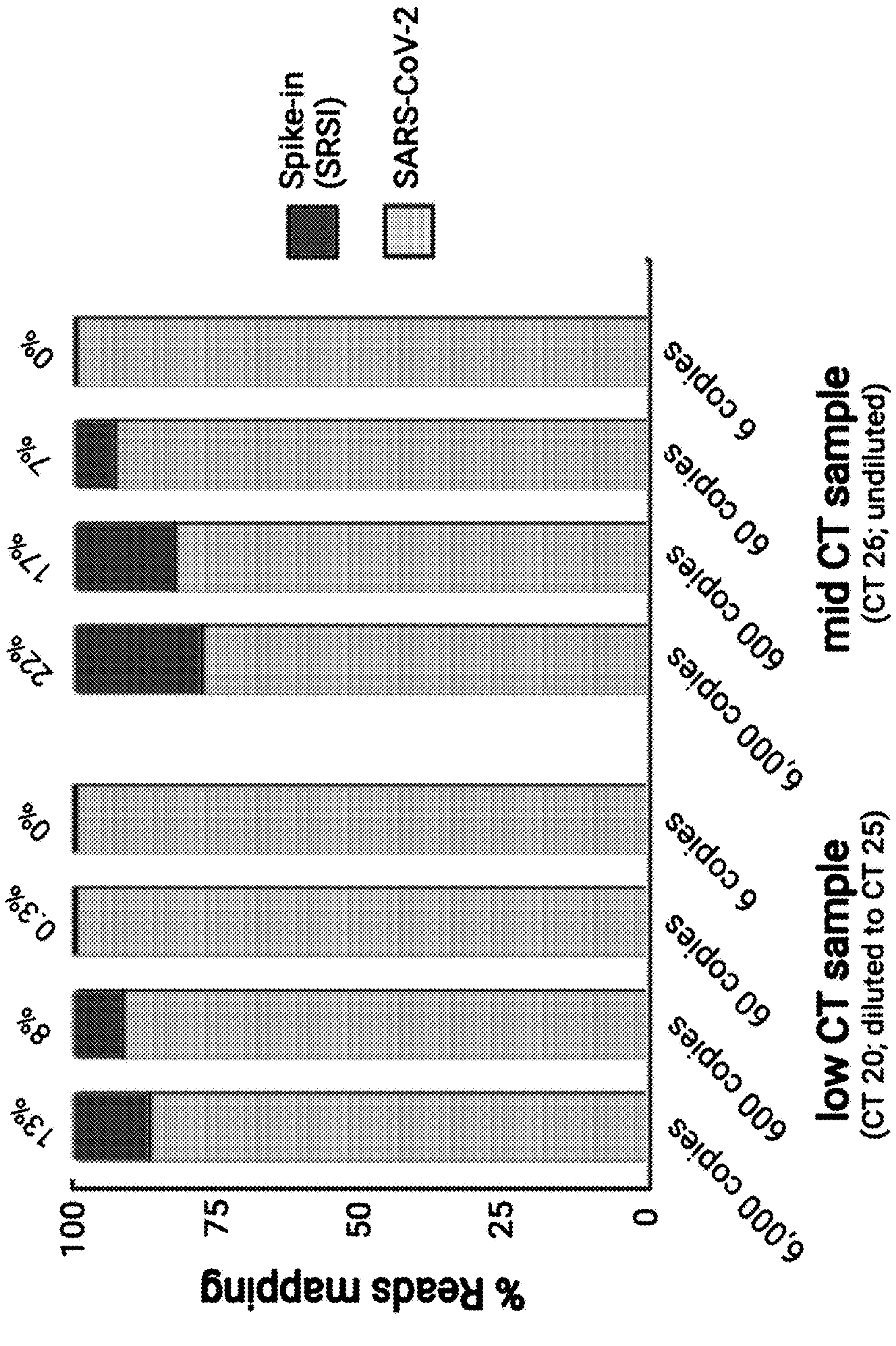

To further increase the confidence in AmpSeq methods for viral genomics, Applicants sought to capture contamination and sample swaps that might occur before the cDNA stage. Applicants explored the feasibility of modifying the SDSI approach to enable synthetic RNA spike-ins (SRSI) from the same constructs, which could be added to clinical sample RNA to provide end-to-end quality control. For a subset of SDSIs, Applicants included a T7 promoter site to enable in-vitro production of these constructs as RNAs. For two clinical samples representing low (20) and mid (26) CTs, Applicants detected reads from the RNA spike-ins added directly to extracted viral RNA as a proof of principle (FIG. 27). Notably, this approach did not require any additional protocol modifications, and Applicants therefore expect it to be a highly versatile and user-friendly method when deployed at scale for complete end-to-end sample tracking.

Example 11—Discussion on SDSI+AmpSeq

Amplicon-based sequencing methods crucially empower rapid, full genome recovery for emerging SARS-CoV-2 variant surveillance; however, robust tools are needed to ensure accuracy in genomic data. SDSI+AmpSeq is a reliable technique for detecting key modes of contamination, addressing this critical gap in standard controls and practices. SDSIs do not compromise genome quality, have been successfully deployed in thousands of clinical samples, and are in use across multiple laboratories with differing protocols. These SDSIs revealed numerous instances of sample swaps and contamination, many of which would go unnoticed with standard batch-level controls. SDSIs further provide critical confidence in the interpretation of clusters of identical genomes, a renewed challenge in the surveillance of more transmissible variants. The common primer design of the SDSI approach enables them to be readily applied to multiple short amplicon designs and sequencing strategies, adding only minor changes to existing protocols and minimal additional cost.

SDSIs overcome multiple modes of error in the production of amplicon-based genomic sequencing data and are a critical component of quality control measures. The approach is most effective when adopted fully within a laboratory setting and thus Applicants propose routine use of the SDSI+AmpSeq method to flag laboratory-wide contamination. Applicants have implemented SDSI's across diverse approaches and provide an extensively tested protocol with ARTIC v3 and Illumina-based tagmentation. It can also be applied to other sequencing pipelines, though this potentially requires further optimization. The pathogen-exclusion design criteria allows the 96 validated SDSIs to be immediately incorporated into other tiled amplicon panels, such as existing ones for Zika, Ebola, and other viruses of epidemic potential[26,27].

The SDSI-labeling paradigm is broadly applicable to many amplicon-based needs: amenable to a variety of technical enhancements, flexible to remaining error modes, and expandable to additional targets. One could apply the same design parameters to expand the set of SDSIs, such as to 384 well formats. Additionally, uniquely permuted sets of any size could be created for specific sample batches. To design larger panels of SDSIs, Applicants could use artificial core sequences, rather than excerpting from archaea. Primer sites could also be easily adapted for integration with new advancements in amplicon sequencing, like tailed primer approaches or new primer schemes[28-32]. In its current implementation, the SDSIs detect contamination or workflow errors that occur during and after amplification, but not issues arising at the RNA or cDNA generation stage, and act qualitatively, rather than quantitatively. Further refinement of the RNA spike-in approach could address other modes of contamination, enabling end-to-end sample tracking at scale. Future work improving quantification and SDSI analysis pipelines may enable them to serve as within sample controls, since samples or batches with outlier SDSI read counts may reveal missing or defective PCR components, incomplete mixing, thermocycling issues, or other types of experimental error.

The integration of SDSIs can mitigate a critical vulnerability of amplicon-based sequencing while preserving the many advantages, increasing the robustness of its use across laboratory and clinical settings. Adoption of controls across the viral surveillance community would increase accuracy and integrity of genomic data worldwide. Looking forward, SDSIs could serve as a crucial component in improving data integrity in amplicon based genomic sequencing beyond infectious disease surveillance, such as food safety, species identification and environmental sampling.

Example 12—Methods

SDSI Design and in Silico Validation

Applicants designed synthetic DNA fragments that each contained a 140 bp unique sequence and constant priming regions. Core SDSI sequence homology to sequences from various organisms was predicted by a permissive BLAST search (blastn; 5000 max targets; E=10; word size=11; no mask for low complexity). Applicants considered homologies identified with this BLASTn search described above that were additionally >50 bps (>35% query cover) and >90% sequence identity to be significant homologies. For all 96 selected SDSIs, there were no such significant homologies when results were filtered to all *Homo sapiens* (taxid: 9606) or viral (taxid:10239) sequences in the NCBI database. For significant homologies to bacterial or eukaryotic sequences in the NCBI database (excluding archaea: taxid: 2157), Applicants report both the SDSI and the genus it mapped to in each case (FIG. 18A). Using the same BLASTn parameters, Applicants also mapped SDSIs against a custom database including SDSI core sequences and found no significant homologies between SDSIs. As there were no significant homologies between SDSIs and human, virus, or other SDSI sequences, Applicants noted the maximum alignment scores for any non-significant homology identified and reported these (FIG. 18B).

Applicants confirmed that SDSI primers and amplicons were predicted to amplify specifically and consistently with ARTIC v3 amplicons. Applicants used Primer-BLAST to predict 50-5000 bp amplicons produced on templates in the entire nr database; no amplicons were identified. Applicants calculated the length and GC content of SDSI primers and full SDSI amplicon sequences and ARTIC v3 primers and amplicons using Geneious Prime (2019.2.1) and compared their distributions (FIG. 19B-C). ARTIC and SDSI primer melting temperatures were matched and calculated using the New England Biolabs online calculator (tmcalculator.neb-.com).

SDSI Experimental Validation

Applicants sought to validate in silico predictions for the performance of the SDSI primers and amplicons. Applicants ordered primers (IDT) (oligo sequences in Supplementary Data File 1) and performed qPCR using the Q5 Hotstart 2× Mastermix, with 500 nM SDSI primers and 0.17×SYBR Gold (ThermoFisher #S11494), and without ARTIC primer pools. Applicants performed this assay in triplicate in 10 μL reactions on a QuantStudio 6 with the following cycling conditions: 95° C. for 30 seconds, followed by 35 cycles of 95° C. for 15 seconds and 65° C. for 5 minutes. Applicants tested 4 conditions: (1) 0.5 μL of an SDSI gene block (IDT) (1 μM), (2) 0.5 μL of an SDSI gene block+0.5 μL of cDNA from an NP swab, (3) 0.5 μL of cDNA from an NP swab, and (4) no template to detect any nonspecific amplification of the primers (FIG. 19A). Applicants performed PCR on each SDSI oligo, using the standard SDSI+AmpSeq PCR conditions (benchling.com/s/prt-R95g0tCxKOeCAgn8lAk3), then ran the PCR products on a 2.2% agarose gel to confirm that these primers amplified the SDSIs and that the product was clean and of the expected size (FIG. 19D).

Figure 25:
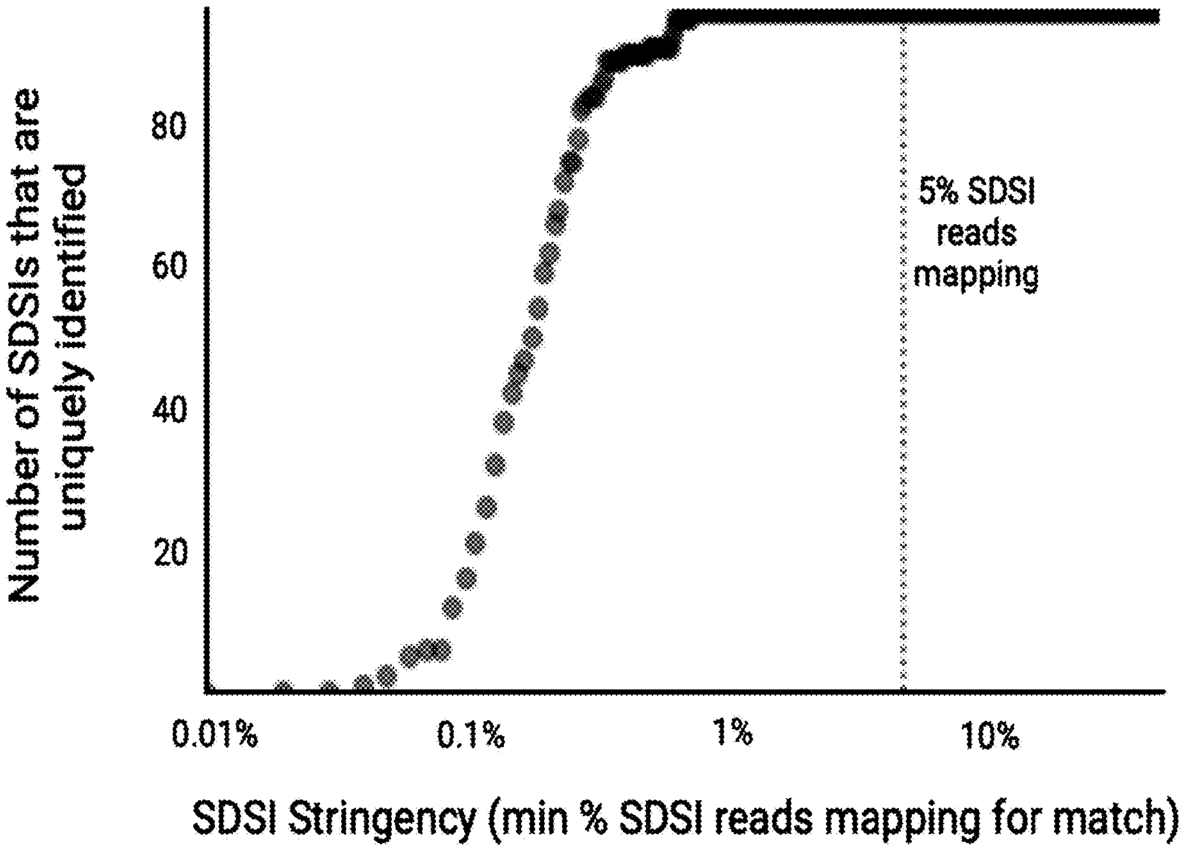
FIG. 25—Unique identification of SDSIs given varying thresholds of SDSI mapping stringency. Applicants considered a range of cutoffs of the percentage of all SDSI-mapped reads mapping to a given SDSI (0.01%-50%, with a step size of 0.01). For an experiment where Applicants sequenced SDSIs without any clinical sample, Applicants calculated, at each cutoff, the number of SDSIs (y-axis) in the set Applicants present (96 total) for which only the expected SDSI had a proportion of mapped reads that exceeded the cutoff (x-axis). Assuming no contamination, all 96 SDSIs should be identified uniquely, i.e. no other SDSI should have a proportion of mapped reads that exceeds the cutoff. The dotted line at x=5% represents the stringency cutoff that Applicants recommend in practice to detect contamination events.

Applicants ordered unique oligos as TruGrade ultramers (IDT), then resuspended and stored them at 10 M in water (oligo sequences in Table 1). Further characterization for identification of 96 SDSIs was achieved by direct PCR amplification with primers containing the constant SDSI handle and an Illumina P5/P7 adapter followed by sequencing with a MiSeq Nano 2×150 bp kit (Illumina #MS-102-2002). SDSI reads were quantified by mapping each SDSI against other SDSIs with the align_and_count_multiple_report wdl implemented in Terra, as described below, and purity and sequence fidelity of SDSIs was achieved by calculating the percentage of reads mapping to each SDSI out of total SDSI reads (FIG. 14B). Given these same data, Applicants explored the SDSI mapping stringency threshold. Applicants determined whether each SDSI was uniquely identified over a range of SDSI stringency thresholds (0.01%-50% of SDSI reads mapping, with a step size of 0.01%) (FIG. 25). Applicants tested 142 total unique SDSIs; all SDSIs amplified successfully with high sequence fidelity and purity (>95% of reads mapped to the expected SDSI in the experiment described above). The final set of 96 SDSIs were chosen after first pass validation in a combination of clinical sample amplification tests, GC cutoffs, and sequence homology cutoffs. SDSIs excluded because of poor amplification or impurity in clinical sample processing were not retested to determine whether error was technical or biological.

Sample Collection and Study Design

Research was conducted at the Broad Institute with an exempt determination from the Broad Office of Research Subjects Protections and with approval from the MIT Institutional Review Board under protocol #1612793224. Samples were obtained from Massachusetts General Hospital (MGH), Massachusetts Department of Public Health, the Rhode Island Department of Public Health and the Broad Institute Clinical Research Sequencing Platform. Samples from Massachusetts General Hospital (MGH) fall under Partners Institutional Review Board under protocol #2019P003305. Samples were secondary-use or residual clinical and diagnostic specimens (referred to collectively throughout as clinical samples), obtained by researchers under a waiver of consent. All samples were nasopharyngeal or anterior nares swabs in a stabilizing medium (e.g., MTM or VTM). These unique biological materials are not available to other researchers as they are human patient samples from clinical excess material and thus are of limited volume. Samples sequenced at Jackson Laboratories (JAX) were approved under protocol 2020-NHSR-019-BH.

Viral CT Determination

Viral cycle threshold (CT) for all samples sequenced at the Broad Institute were obtained using the CDC RT-qPCR assay with the N1 probe as previously described[21]. Viral CTs for samples sequenced at JAX were obtained from various providers and thus the RT-qPCR assays used are variable.

CT Normalization

CT normalization was performed by first setting a desired mock viral CT and calculating the difference between this desired mock viral CT and the measured viral CT of a given sample, rounding to the nearest whole number. Applicants next calculated the number of doublings required for the mock viral CT (assuming 100% PCR efficiency) and multiplied this by the volume of cDNA input to be used for the normalization. The final volume of water used to dilute the cDNA was the doubling factor minus the volume of cDNA input. An example calculation is illustrated below:

Example of CT Normalization:

N = Difference between actual and mock
X = Volume (μL) of cDNA to use for normalization
DF = Doubling factor is $X(2^N)$
Volume water for dilution (μL) = DF-X
Actual viral CT = 23
Desired mock viral CT = 27
N = 27-23 = 4
X = 1 μL
DF = $1(2^4)$
Volume water for dilution (μL) = 16-1 = 15 μL
Add 1 μL of cDNA to 15 μL nuclease free water.

This CT normalization was done for certain method development samples which are described throughout the manuscript as being "mock diluted" or "normalized to CT X". The nosocomial cluster was normalized to CT 27. The majority of batch data generated at the Broad Institute underwent CT normalization to CT 25. Batch data from JAX did not undergo CT normalization. CT normalization of the cDNA prior to the ARTIC PCR should reduce the potential for generating excessively large libraries from very high viral load samples, keep the percentage of SDSI reads in a detectable range (FIG. 21B), and further reduce the need for additional normalization steps later in the pipeline.

cDNA Generation and ARTIC Amplification Optimization

Reverse Transcriptase

Applicants tested reverse transcriptase enzymes using extracted RNA from four SARS-CoV-2 positive clinical samples (CTs=13.9, 23.9, 29.6, 33.6) (FIG. 23A,B). Applicants added 2 μL of purified DNase treated RNA as input into SuperScript III (Thermo #18080093), SuperScript IV (Thermo #18091050), or SuperScript IV VILO (Thermo #11756500). Superscript IV (SSIV) reactions incubated at room temperature for 10 minutes, followed by 50° C. for 60 minutes and an inactivation step at 80° C. for 10 min. Superscript IV VILO shared the same protocol, but with a temperature of 85° C. for the inactivation step. Applicants input 2.5 L of cDNA for ARTIC pool #1 PCR under standard conditions for 40 cycles. Applicants then tested the resulting pool #1 using the scaled down Illumina DNA Flex library construction (as described in Methods below) and sequenced on Illumina Miseq (V2 reagent kit) with 2×150 bp paired end sequencing.

ARTIC PCR Enzyme

Applicants tested PCR enzyme efficiency using extracted RNA from SARS-CoV-2 positive clinical samples followed by cDNA generation using SuperScript IV and diluted the resulting cDNA to a mock CT value of 35 for standardization across all PCR enzyme tests. Applicants set up the standard ARTIC PCR pool #1 and pool #2 using an input of 2.5 μL, altering only the PCR enzyme and corresponding buffer. Applicants tested NEB Q5 Hot Start High-fidelity 2× Master Mix (Q5 2× MM) (NEB #M0494L), NEB Q5 Hot Start High-fidelity 2× Master Mix plus 0.01% SDS, NEB Q5 Ultra II Master Mix (NEB #M0544L), KAPA HiFi HotStart (Roche #KK2601), and KOD Hot Start DNA polymerase (Sigma-Aldrich #71842) (FIG. 23C). Applicants quantified the resulting ARTIC PCR amplicons using a High Sensitivity DNA Qubit kit, then input 25 ng from each pool (50 ng total) into scaled down Illumina DNA Flex library construction. The resulting libraries (except Q5 plus 0.01% SDS, which had no visible product using the Tapestation D1000 High Sensitivity Kit) were quantified and pooled on Illumina Miseq (V2 reagent kit) with 2×150 paired end sequencing.

Rehybridization PCR

Applicants optimized PCR cycling conditions on mock CT 35 cDNA (generated as described above) using standard ARTIC PCR primer conditions. Applicants performed a catch-up/rehybridization PCR under the following conditions: 98° C. for 30s, 95° C. for 15s then 65° C. for 5 min (10 cycles), 95° C. for 15s then 80° C. for 30s then 65° C. for 5 min (2 cycles), 95° C. for 15s then 65° C. for 5 min (8 cycles), 4° C. hold (FIG. 23E). Applicants quantified the resulting ARTIC PCR amplicons using a High Sensitivity DNA Qubit kit, then input 25 ng from each pool (50 ng total) into scaled down Illumina DNA Flex library construction. Applicants then quantified these libraries and pooled on Illumina Miseq (V2 reagent kit) with 2×150 paired end sequencing.

Cycle Test

Applicants further optimized ARTIC PCR by modifying PCR cycle numbers. Extracted RNA from six SARS-CoV-2 positive clinical samples ranging from CT 27-37 were converted to cDNA with Superscript IV and amplified under standard ARTIC PCR reaction components (with Q5 2× MM) modifying the final number of cycles of PCR from 35, 40 and 45 (FIG. 23G). Applicants quantified cDNA and used at a standard 50 ng of input for scaled down Illumina DNA Flex Library Construction, then quantified the resulting libraries and pooled on Illumina Miseq (V2 reagent kit) with 2×150 paired end sequencing.

Ramp Test

Applicants used mock CT 35 cDNA to test the effect of decreased ramp speed on genome recovery and coverage. ARTIC PCR conditions for this experiment were 98° C. for 30 seconds, followed by 40 cycles of 95° C. for 15 seconds and 65° C. for 5 minutes with a cooling and heating ramping speed of 3C/s. Applicants tested a slow ramp PCR protocol with the ramp speed reduced to 1.5° C./s (FIG. 23F). Libraries were constructed with Illumina DNA Flex and were sequenced on Illumina Miseq (V2 reagent kit) with 2×150 paired end sequencing.

Primer Concentration Optimization

Under standard ARTIC protocol conditions, Applicants ordered lyophilized ARTIC v3 primers from IDT and resuspended in water at 100 M each. Pool #1 primers consisted of all odd numbered amplicons whereas pool #2 primers consisted of all even numbered amplicons. To generate the 100 M pool #1 primer stock, Applicants combined 5 μL of each 100 M pool #1 primer, and repeated this protocol for the even numbered primers to give a 100 M pool #2 primer stock. Applicants selected a total of 20 amplicons as regions of low coverage from previous sequencing data (Table 4). Low coverage amplicons were present in both pools, with 11 coming from pool #1 and 9 coming from pool #2. For the primer 2× pools, Applicants spiked in primers for the corresponding amplicons at 2× the concentration (20.8 nM final) of the other primers in the pool. For these low coverage primers, Applicants used 10 μL of the 100 M stock rather than 5 μL. Applicants diluted both the original and 2× primer pools 1:10 in nuclease free water to generate a 10 M working stock. Applicants then selected 8 samples with varying CT values to determine if selectively increasing primer concentrations reduced amplicon dropout (FIG. 23D). Applicants used the SDSI+AmpSeq protocol (without the SDSI or SDSI primers) and processed each sample with both the original primer pool, as well as the 2× primer pool, then sequenced these 16 samples on an Illumina Miseq (V2 reagent kit) with 2×150 paired end sequencing. Only 6 of the 8 samples generated complete genomes (>98%) in both conditions and were used for further analysis.

CT Normalization Experiment

The CT normalization experiment was performed by taking four individual clinical samples (CT=18-25) with four randomly selected SDSIs and either not normalizing the cDNA or normalizing to CT 25, 26, or 27 prior to the ARTIC PCR (FIG. 21B). Samples were processed with the standard SDSI+AmpSeq protocol described below and were sequenced on a NextSeq 500 Mid Output Kit v2.5 (300 Cycles).

Illumina DNA Flex

Figure 23H:
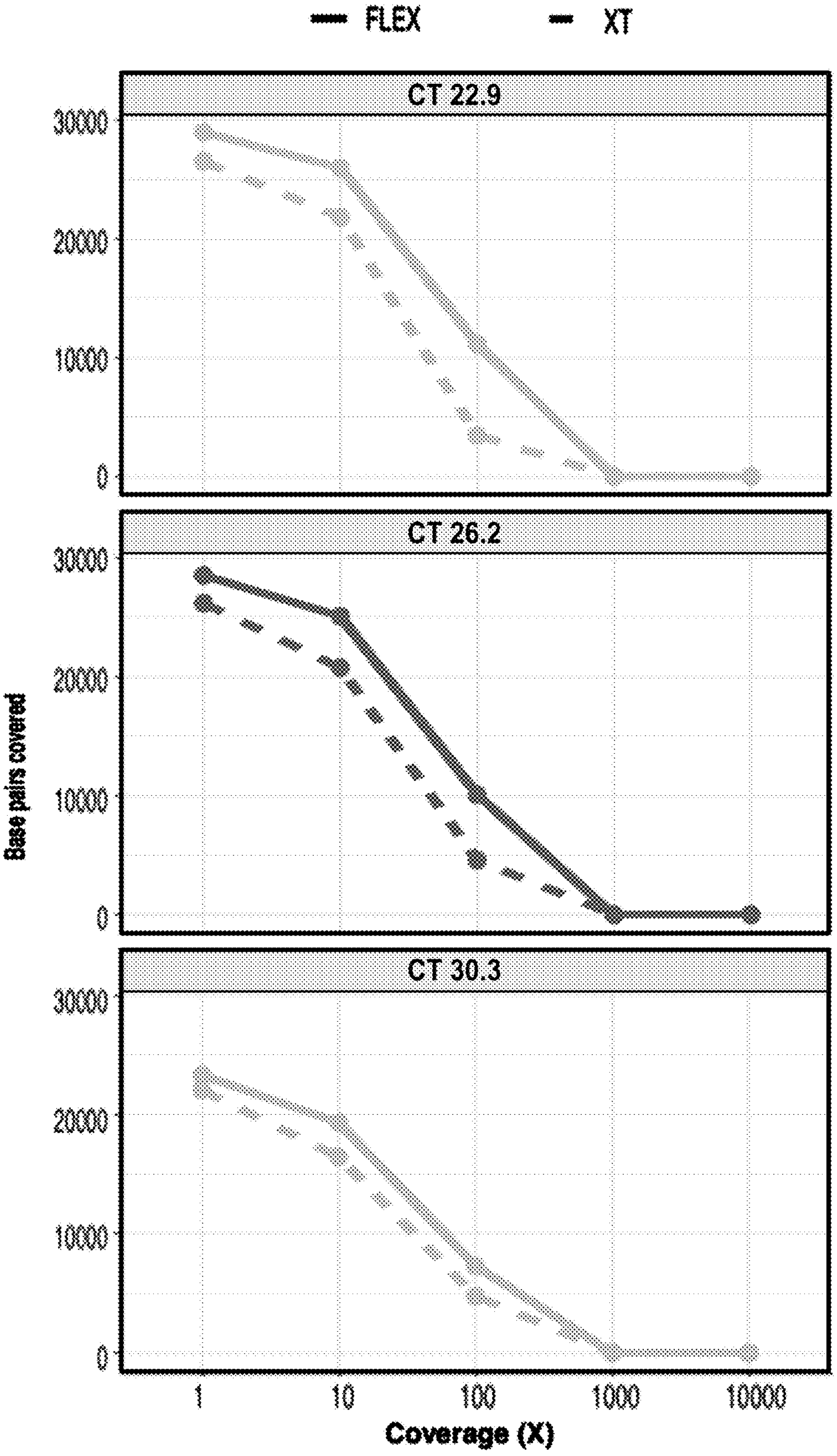

Applicants performed a head-to-head comparison of standard Illumina Nextera DNA Flex and Nextera XT (Illumina #FC-131-1096) library construction kits (FIG. 23H). The Nextera XT protocol was performed as previously described[21,33]. Both library construction methods were compared on post ARTIC v1 PCR amplicons from clinical samples. In short, applicants amplified samples with a range of SARS-CoV-2 viral CT values (CTs=22.9, 26.2, 30.3) with ARTIC v1 primers, producing 400 bp size fragments. Applicants then quantified amplicons from each ARTIC primer pool and pooled in equal molar concentrations. Standard Nextera DNA Flex input was 100 ng (50 ng from each pool) and 1 ng (0.5 ng from each pool) for Nextera XT. Applicants quantified and pooled the resulting libraries before sequencing on an Illumina Miseq (V2 reagent kit) with 2 ×150 paired end sequencing.

Applicants optimized Illumina DNA Flex library construction (Illumina #20018705) construction with the goal of reducing normalization steps, cost and increasing throughput. Applicants scaled down (0.5×) Illumina DNA Flex throughout the standard Illumina sequencing protocol, also scaling down sample input for a total of 50 ng (25 ng from each primer pool). Due to the CT normalization step, applicants removed the pre-DNA Flex DNA concentration and pooling step. Applicants used 1-2 μL of post ARTIC PCR amplicon as input into the scaled down DNA Flex library construction and performed post library construction quantification and pooling with more uniform library size and concentration, further reducing time and cost of pooling libraries for sequencing. This protocol was used for all method development experiments, the cluster investigation, and a portion of the batch data generated from both the Broad Institute and JAX.

SDSI+AmpSeq SDSI Titration in ARTIC SARS-CoV-2 Sequencing

Figure 20B:
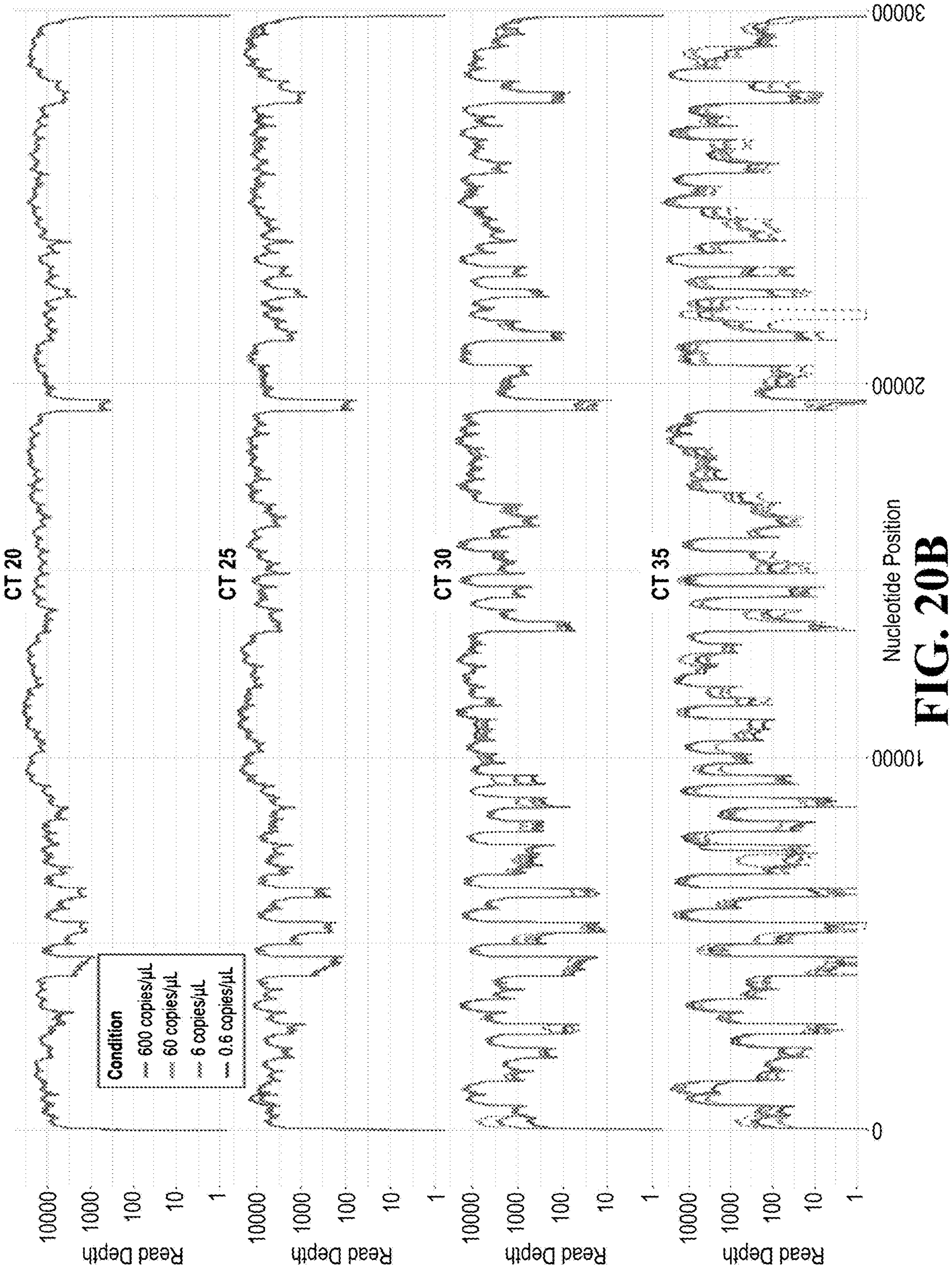

To determine an optimal concentration for SDSIs in ARTIC SARS-CoV-2 sequencing, applicants diluted SDSI 49 to 0.6, 6, 60, and 600 copies/μL (1, 0.1, 0.01, and 0.001 fM); 1 μL of SDSI 49 was added to 5 μL of cDNA, to be split to 2×3 μL for each ARTIC pool (FIG. 20, Table 1). SDSI primers were added to each ARTIC pool with a final concentration of 40 nM. The cDNA from one clinical sample (MA_MGH_00195; CT=16) was mock diluted to CT 20,25, 30, and 35 for this experiment using the protocol described within the CT normalization section. Based on the results of this experiment, SDSIs were used at 6e2 copies/μL (1 fM) for all method development data. Batch processing modifications to this approach from the Broad Institute and Jackson Laboratories are detailed below.

SDSI+AmpSeq Protocol

Full protocol details can be found here: benchling.com/s/prt-R95gOtCxKOeCAgn8lAk3 (FIG. 13). In short, cDNA synthesis is performed on 2.5 μL of DNAse-treated viral RNA with SSIV following the manufacturer's protocol with an extension of the 50° C. incubation from 10 minutes to 60 minutes. An additional cDNA normalization step can be performed (see above) or one can move directly into the ARTIC PCR by taking 5 μL of cDNA and mixing this with 1 uL of a 1 fM SDSI (equal to 600 copies/μL). After mixing, split into 2×3 μL aliquots and add ARTIC primer pool 1 or pool 2, as well as 1 M of the spike-in forward and reverse primers (40 nM final concentration in the ARTIC pool). The ARTIC PCR conditions were 98° C. for 30 seconds, followed by 40 cycles of 95° C. for 15 seconds and 65° C. for 5 minutes. Pool 1 and pool 2 PCR reactions were combined and taken through library construction with scaled down Illumina DNA Flex.

Broad Institute Sample Processing

The batch data from the Broad Institute was generated using SDSI+AmpSeq with minor modifications (FIG. 16). In short, SSIV was used for cDNA synthesis. Q5 2× MM was used for the ARTIC PCR which was run for 35 cycles. The SDSIs were spiked in at 6e3 copies/μL and the SDSI specific primers were added to each ARTIC pool at a final concentration of 40 nM. Library construction was performed either with the scaled down Illumina DNA Flex (previously described) or COVID-seq (Illumina #20043675). Samples were sequenced on a NovaSeq 6000 SP Reagent Kit v1 (300 cycles) or v1.5 kits (300 cycles), or NextSeq 500 v2 kit (300 cycles).

The GC percent for each SDSIs and percent SDSI reads over total reads correlation for SDSI (2-48) was performed with the samples sequenced at the Broad Institute (N=2,903) (FIG. 19E). A linear regression was used to evaluate significance (p-value=0.8160).

Jackson Laboratory Sample Processing

Data generated at Jackson Laboratory (JAX) used two different protocols publicly available here: github.com/tewhey-lab/SARS-CoV-2-Consensus (FIG. 16). All samples included 6e2 copies/μL of SDSIs and the SDSI specific primers were added to each ARTIC pool at a final concentration of 4 nM. Samples processed from December 2020 to April 2021 used Lunascript (NEB #E3010) for cDNA synthesis and Q5 2× MM for the ARTIC PCR which was run for 35 cycles. These samples used scaled down Illumina DNA Flex for library construction. Samples sequenced after April 2021 used the standard COVID-seq protocol. All samples were sequenced on a NextSeq500 using paired 75 bp reads by the Genome Technology group on Jackson Laboratory's Bar Harbor campus. The validation of all SDSIs in clinical samples (FIG. 15A) was performed with this protocol and is presented as the percent of SDSI reads over the total of all reads for each sample.

Of note, the SDSIs (used at the lowest recommended concentration of 6e2 copies/uL) were reliably detected in the samples sequenced at JAX. This reliable detection however is also dependent on the sequencing depth used by the institution.

SDSI Impact on Genome Recovery

For +/−SDSI experiments testing impact on recovery of viral genomes, fourteen clinical samples spanning a range of CTs (CT=17.6-30) were selected (FIG. 15B, FIG. 21A). Samples were CT normalized and split after cDNA synthesis into 2×5 μL aliquots. Samples below CT 20 were normalized to CT 25 and samples between CT 20-25 were normalized to CT 26. Fourteen randomly selected SDSIs were used with each sample receiving either an SDSI (600 copies/μL) and the SDSI specific primers (40 nM final concentration in the ARTIC pool) or just the ARTIC pool 1 and pool 2 mastermix with additional nuclease free water and no SDSI primers. Samples were processed according to the SDSI+AmpSeq protocol using scaled down Illumina DNA Flex for library construction, sequenced on a NextSeq 500 Mid Output Kit v2.5 (300 Cycles) and analyzed as described below.

Statistical analysis for the plus/minus SDSI experiment involved analysis of the mean coverage for all 98 amplicons for the full sample set with a two-tailed Mann Whitney t-test and multiple comparison two-stage step-up Benjamini, Krieger, and Yekutieli test with FDR set to 5%. All 98 amplicons were found to be not significantly different (p-value >0.05) between the plus and minus SDSI group. Samples were also separated into three CT bins (CT<27 (n=4), 27-29 (n=6), CT>30 (n=4)) and this test repeated for each CT bin. This analysis also revealed that there was no significant difference (p-value >0.05) in the mean coverage across any amplicon for any CT bin.

Intentional SDSI Contamination Experiment

The intentional contamination experiment used SDSI 87 and SDSI 94 (SDSI 87: SDSI 94). The SDSIs were mixed at five different proportions (100:0, 75:25, 50:50, 25:75, and 0:100) (FIG. 17A). Each condition was performed in duplicate. All validation experiment samples were processed according to the SDSI+AmpSeq protocol using scaled down Illumina DNA Flex for library construction. Samples were processed with the standard SDSI+AmpSeq protocol and sequenced on a NextSeq 500 Mid Output Kit v2.5 (300 Cycles).

Production and Application of Synthetic RNA Spike-Ins (SRSI)

Applicants ordered SDSI oligos with minor modifications to enable in-vitro transcription of RNAs (including a T7 promoter upstream of the SDSI amplicon, as well as 17 bps of constant sequence within the primer region) (Twist Bioscience) (sequences in attached Sup Data File 1). For two SDSIs (SDSI 1 and SDSI 4) applicants in-vitro transcribed RNA using a T7 transcription kit (NEB E2050), quantified by RNA screen tape (Agilent 5067-5579 and 5067-5580), then diluted in water to 10 fM (6,000 copies/μL), 1 fM (600 copies/μL), 100 μM (60 copies/μL), and 10 μM (6 copies/μL). Applicants added 1 μL of SRSI at each concentration directly to 5 μL of RNA from two patient samples with high and intermediate viral loads, respectively, and prepared sequencing libraries using the SDSI+AmpSeq protocol (without the SDSI addition step at the cDNA stage). For the sample with a high viral load, applicants performed a dilution at the cDNA stage (diluting 32-fold for a mock Ct of 25 rather than 20). Reads mapping to unique SDSI sequences and SARS-CoV-2 were quantified using the align_and_count_multiple_report and assemble_refbased wdls respectively, and % SDSI/total reads was reported (FIG. 27).

Computational Analysis Workflow

Applicants analyzed sequencing data on the Terra platform (app.terra.bio) using viral-ngs 2.1.28 with workflows that are publicly available on the Dockstore Tool Repository Service (dockstore.org/organizations/BroadInstitute/collections/pgs). Samples were demultiplexed using the demux_plus workflow with a spike in database file for the SDSIs. Applicants performed any separate analyses to quantify read counts, including those for SDSIs, with the align_and_count multiple_report workflow with the relevant database. For most analyses involving direct comparisons between samples, applicants performed downsampling to the lowest number of reads passing filter with the downsample workflow. Applicants performed assembly using the assemble_refbased workflow to the following reference fasta: www.ncbi.nim.nih.gov/nuccore/NC_045512.2?report=fasta. Applicants used iVar version 1.2.1 for primer trimming on all samples followed by assembly with minimap2 set to a minimum coverage of either 3, 10, or 20, skipping deduplication procedures. The computational pipeline for all samples sequenced at JAX is publicly available at the following: github.com/tewhey-lab/SARS-CoV-2-Consensus.

Samples from the batch data were subset in the following way for analysis. All samples with a present SDSI were used for the percent of SDSI reads out of the sum of all SDSI reads analysis (JAX: N=3,838, Broad: N=2,903). Samples with known experimental contamination errors or where the dominant (>50%) SDSI was not the correct SDSI were removed. For the percent of SDSI reads over the total of all sequenced reads analysis (JAX: N=3,093, Broad: N=2,670), non-template controls (waters) and clinical samples with no detectable viral load (CT>40 or not detected via qPCR as described above) were removed from analysis.

Metagenomic Sequencing and Comparison

Metagenomic sequencing data and genome assemblies used for the comparison of amplicon-based sequencing were prepared, sequenced, analyzed as described previously,[21] and the data are publicly available at NCBI's GenBank and SRA databases under BioProject PRJNA622837. Applicants prepared amplicon sequencing libraries from the sample RNA extract following the SDSI+AmpSeq protocol (FIG. 13). In order to increase sample throughput and bypass an additional more laborious quantification step post the ARTIC PCR, applicants normalized cDNA samples that had a high viral load (CT<27) to a CT of 27. To prepare for the ARTIC PCR, applicants transferred 5 μL of the normalized cDNA to a new plate and added 1 μL of a SDSI (600 copies/μL). After mixing, applicants transferred 3 μL to a new plate, added ARTIC PCR pool #1 mastermix and pool #2 mastermix to the respective plates, and on a thermal cycler incubated at 98° C. for 30s, followed by 40 cycles of 95° C. for 15s and 65° C. for 5 min. Applicants then combined in equal molar amounts of amplified samples for a total of 50 ng and processed through 0.5× Illumina Flex library construction pipeline. Applicants sequenced the concordance data set on a NovaSeq 6000 SP Reagent Kit vi (300 cycles) and analyzed as detailed in the methods below. For SNV analysis, the coverage depth over each divergent SNV was greater than 1000× for both platforms, and both SNV calls persisted at relaxed (n=3) and conservative (n=20) minimum coverage thresholds. Primer trimming using iVar version 1.2.1 was manually confirmed.

Suspected Nosocomial Cluster Investigation

Applicants received NP swab samples in UTM and extracted RNA from 200 μL of biosample as previously described[21]. Applicants prepared amplicon sequencing libraries as described above and analyzed them as detailed in the methods below. A pairwise distance was calculated between all partial genomes (>80% complete), excluding gaps, to determine whether samples were likely to be the result of nosocomial transmission (FIG. 17C). Applicants calculated the proportion of reads that mapped to a given SDSI out of all reads that mapped to any SDSI. Data has been made available in both the Short Read Archive and NCBI GenBank under Bioproject PRJNA622837. GenBank accessions for SARS-CoV-2 genomes from this set of samples are MW454553-MW454562.

Figure 26:
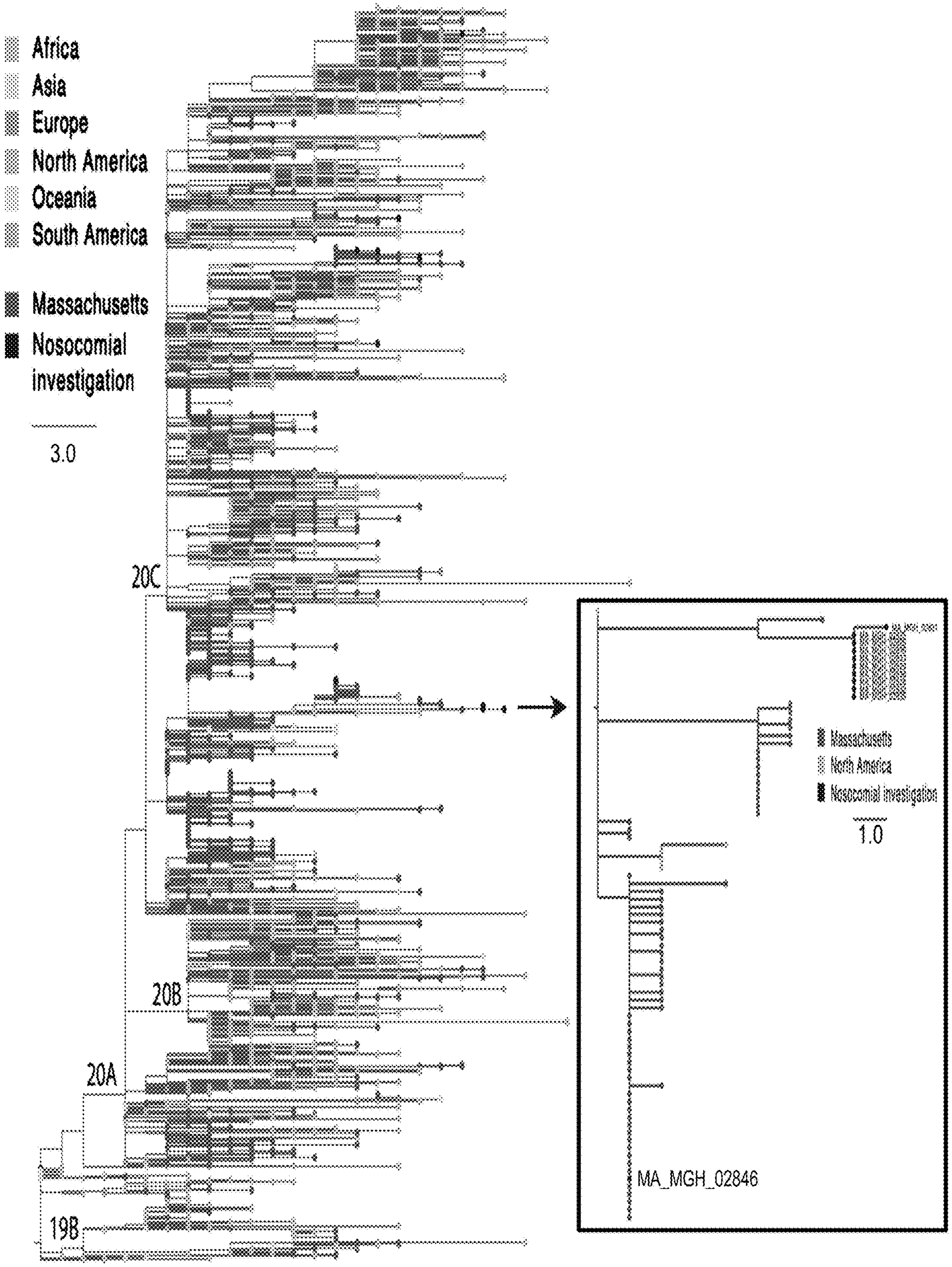
FIG. 26—Deployment of SDSI+AmpSeq to assess for possible nosocomial transmission. Phylogenetic tree showing the location of the putative cluster sequences in the context of a global subset of circulating SARS-CoV-2 diversity. Zoom box shows the 10 highly similar cluster genomes. Sample named on the main tree is the one putative cluster sample that was excluded from the cluster based on genome sequence.

For phylogenetic tree reconstruction applicants placed the suspected nosocomial cluster in a broader genomic context by performing a subsampling of the genome sequences available in GISAID (as of Jan. 26 2021) (FIG. 26). Applicants used the sarscov2_nextstrain workflow to perform a Massachusetts-weighted subsampling of samples from 1 Jan. 2020-1 Nov. 2020. Applicants' subsampled dataset included 3146 sequences; 1449 samples from Massachusetts, 1425 samples from elsewhere in the United States and 283 from other countries. Applicants constructed a maximum likelihood tree using iqtree with a GTR substitution model and edited and interpreted the tree in Figtree v1.4.4.

Data Presentation

Data analysis and graphing was performed using R Statistical Software (version 1.3.959; R Foundation for Statistical Computing, Vienna, Austria), GraphPad PRISM (version 9.0.2; GraphPad Software, La Jolla California USA, www.graphpad.com) and Python (version 3.7). Applicants created original figures using BioRender (BioRender.com).

Code Availability

Viral genomes were processed using the Terra platform (app.terra.bio) using viral-ngs 2.1.1 with workflows that are publicly available on the Dockstore Tool Repository Service (dockstore.org/organizations/BroadInstitute/collections/pgs). Downstream analyses were performed using Geneious or standard R packages. Custom scripts used to generate figures are available upon request.

Methods

Data Availability

Sequences and genome assembly data are publicly available on NCBI's Genbank and SRA databases under BioProject PRJNA622837. GenBank accessions for SARS-CoV-2 genomes newly reported in this study are MW454553—MW454562.

REFERENCES

1. Washington, N. L. et al. Genomic epidemiology identifies emergence and rapid transmission of SARS CoV-2 B.1.1.7 in the United States. medRxiv (2021) doi: 10.1101/2021.02.06.21251159.
2. Walensky, R. P., Walke, H. T. & Fauci, A. S. SARS-CoV-2 Variants of Concern in the United States—Challenges and Opportunities. JAMA vol. 325 1037 (2021).
3. Wang, P. et al. Antibody resistance of SARS-CoV-2 variants B.1.351 and B.1.1.7. Nature 593, 130-135 (2021).
4. Focosi, D., Tuccori, M., Baj, A. & Maggi, F. SARS-CoV-2 Variants: A Synopsis of In Vitro Efficacy Data of Convalescent Plasma, Currently Marketed Vaccines, and Monoclonal Antibodies. Viruses 13, (2021).
5. Wang, P. et al. Increased resistance of SARS-CoV-2 variant P.1 to antibody neutralization. Cell Host Microbe 29, 747-751.e4 (2021).
6. Naveca, F. et al. SARS-CoV-2 reinfection by the new Variant of Concern (VOC) P. 1 in Amazonas, Brazil. virological. org (2021).
7. Organization, W. H. & Others. Genomic sequencing of SARS-CoV-2: a guide to implementation for maximum impact on public health, 8 Jan. 2021. (2021).
8. COVID-19 Genomics UK (COG-UK) consortiumcontact@cogconsortium.uk. An integrated national scale SARS-CoV-2 genomic surveillance network. Lancet Microbe 1, e99-e100 (2020).
9. Chiara, M. et al. Next generation sequencing of SARS-CoV-2 genomes: challenges, applications and opportunities. Brief Bioinform. (2020) doi:10.1093/bib/bbaa297.
10. Charre, C. et al. Evaluation of NGS-based approaches for SARS-CoV-2 whole genome characterisation. Virus Evol 6, veaa075 (2020).
11. Rausch, J. W., Capoferri, A. A., Katusiime, M. G., Patro, S. C. & Kearney, M. F. Low genetic diversity may be an Achilles heel of SARS-CoV-2. Proceedings of the National Academy of Sciences of the United States of America vol. 117 24614-24616 (2020).
12. Endo, A., Centre for the Mathematical Modelling of Infectious Diseases COVID-19 Working Group, Abbott, S., Kucharski, A. J. & Funk, S. Estimating the overdispersion in COVID-19 transmission using outbreak sizes outside China. Wellcome Open Res 5, 67 (2020).
13. Lagerborg, K. A., Watrous, J. D., Cheng, S. & Jain, M. High-Throughput Measure of Bioactive Lipids Using Non-targeted Mass Spectrometry. Methods Mol. Biol. 1862, 17-35 (2019).
14. Boja, E. S. & Rodriguez, H. Mass spectrometry-based targeted quantitative proteomics: achieving sensitive and reproducible detection of proteins. Proteomics 12, 1093-1110 (2012).
15. Chen, K. et al. The Overlooked Fact: Fundamental Need for Spike-In Control for Virtually All Genome-Wide Analyses. Molecular and Cellular Biology vol. 36 662-667 (2016).
16. Illumina COVIDSeq Test. emea.illumina.com/products/by-type/ivd-products/covidseq.html.
17. Jiang, L. et al. Synthetic spike-in standards for RNA-seq experiments. Genome Res. 21, 1543-1551 (2011).
18. Quail, M. A. et al. SASI-Seq: sample assurance Spike-Ins, and highly differentiating 384 barcoding for Illumina sequencing. BMC Genomics 15, 110 (2014).
19. Dilucca, M., Forcelloni, S., Pavlopoulou, A., Georgakilas, A. G. & Giansanti, A. Codon usage and evolutionary rates of the 2019-nCoV genes. Cold Spring Harbor Laboratory 2020.03.25.006569 (2020) doi:10.1101/2020.03.25.006569.
20. Potapov, V. & Ong, J. L. Examining Sources of Error in PCR by Single-Molecule Sequencing. PLOS ONE vol. 12 e0169774 (2017).
21. Lemieux, J. E. et al. Phylogenetic analysis of SARS-CoV-2 in Boston highlights the impact of superspreading events. Science 371, (2021).
22. So, A. P. et al. A robust targeted sequencing approach for low input and variable quality DNA from clinical samples. NPJ Genom Med 3, 2 (2018).
23. Grubaugh, N. D. et al. An amplicon-based sequencing framework for accurately measuring intrahost virus diversity using PrimalSeq and iVar. Genome Biol. 20, 8 (2019).
24. Pipelines R&D, D. N. A. et al. COVID-19 ARTIC v3 Illumina library construction and sequencing protocol v5. protocols.io (2020) doi:10.17504/protocols.io.bibtkann.
25. Lam, C. et al. Sars-CoV-2 Genome Sequencing Methods Differ In Their Ability To Detect Variants From Low Viral Load Samples. J. Clin. Microbiol. JCM0104621 (2021).
26. Quick, J. et al. Real-time, portable genome sequencing for Ebola surveillance. Nature 530, 228-232 (2016).
27. Metsky, H. C. et al. Zika virus evolution and spread in the Americas. Nature 546, 411-415 (2017).
28. Gohl, D. M. et al. A rapid, cost-effective tailed amplicon method for sequencing SARS-CoV-2. BMC Genomics 21, 863 (2020).
29. Itokawa, K., Sekizuka, T., Hashino, M., Tanaka, R. & Kuroda, M. Disentangling primer interactions improves SARS-CoV-2 genome sequencing by multiplex tiling PCR. PLoS One 15, e0239403 (2020).
30. Tyson, J. R. et al. Improvements to the ARTIC multiplex PCR method for SARS-CoV-2 genome sequencing using nanopore. bioRxiv (2020) doi:10.1101/2020.09.04.283077.
31. VarSkip: VarSkip multiplex PCR designs for SARS-CoV-2 sequencing. (Github).
32. primer_schemes/nCoV-2019 at master artic-network/artic-ncov2019. github.com/artic-network/artic-ncov2019.
33. Wong, F., & Collins, J. J. (2020). Evidence that coronavirus superspreading is fat-tailed. In *Proceedings of the National Academy of Sciences* (Vol. 117, Issue 47, pp. 29416-29418). doi.org/10.1073/pnas.2018490117.
34. Adam, D. C., Wu, P., Wong, J. Y., Lau, E. H. Y., Tsang, T. K., Cauchemez, S., Leung, G. M., & Cowling, B. J. (2020). Clustering and superspreading potential of SARS-CoV-2 infections in Hong Kong. In *Nature Medicine* (Vol. 26, Issue 11, pp. 1714-1719). doi.org/10.1038/s41591-020-1092-0.
35. Aird, D., Ross, M. G., Chen, W.-S., Danielsson, M., Fennell, T., Russ, C., Jaffe, D. B., Nusbaum, C., & Gnirke, A. (2011). Analyzing and minimizing PCR amplification bias in Illumina sequencing libraries. *Genome Biology,* 12(2), R18.
36. Antonov, J., Goldstein, D. R., Oberli, A., Baltzer, A., Pirotta, M., Fleischmann, A., Altermatt, H. J., & Jaggi, R. (2005). Reliable gene expression measurements from degraded RNA by quantitative real-time PCR depend on short amplicons and a proper normalization. *Laboratory Investigation; a Journal of Technical Methods and Pathology,* 85(8), 1040-1050.
37. *Artic Network.* (n.d.). Retrieved Feb. 2, 2021, from artic.network/
38. Baker, D. J., Kay, G. L., Aydin, A., Le-Viet, T., Rudder, S., Tedim, A. P., Kolyva, A., Diaz, M., de Oliveira Martins, L., Alikhan, N.-F., Meadows, L., Bell, A., Gutierrez, A. V., Trotter, A. J., Thomson, N. M., Gilroy, R., Griffith, L., Adriaenssens, E. M., Stanley, R., . . . O'Grady, J. (2020). CoronaHiT: large scale multiplexing of SARS-CoV-2 genomes using Nanopore sequencing. In *Cold Spring Harbor Laboratory* (p. 2020.06.24.162156). doi.org/10. 1101/2020.06.24.162156.
39. Dearlove, B., Lewitus, E., Bai, H., Li, Y., Reeves, D. B., Gordon Joyce, M., Scott, P. T., Amare, M. F., Vasan, S., Michael, N. L., Modjarrad, K., & Rolland, M. (2020). A SARS-CoV-2 vaccine candidate would likely match all currently circulating variants. In *Proceedings of the National Academy of Sciences* (Vol. 117, Issue 38, pp. 23652-23662) doi.org/10.1073/pnas.2008281117.
40. Houldcroft, C. J., Beale, M. A., & Breuer, J. (2017). Clinical and biological insights from viral genome sequencing. *Nature Reviews. Microbiology,* 15(3), 183-192.
41. Klempt, P., Brož, P., Kašný, M., Novotny, A., Kvapilová, K., & Kvapil, P. (2020). Performance of Targeted Library Preparation Solutions for SARS-CoV-2 Whole Genome Analysis. Diagnostics (Basel, Switzerland), 10(10). doi.org/10.3390/diagnostics10100769.
42. Mathieu-Daudé, F., Welsh, J., Vogt, T., & McClelland, M. (1996). DNA Rehybridization During PCR: The "C o t Effect" and Its Consequences. *Nucleic Acids Research,* 24(11), 2080-2086.
43. Metsky, H. C., Siddle, K. J., Gladden-Young, A., Qu, J., Yang, D. K., Brehio, P., Goldfarb, A., Piantadosi, A., Wohl, S., Carter, A., Lin, A. E., Barnes, K. G., Tully, D. C., Corleis, B., Hennigan, S., Barbosa-Lima, G., Vieira, Y. R., Paul, L. M., Tan, A. L., . . . Matranga, C. B. (2019). Capturing sequence diversity in metagenomes with comprehensive and scalable probe design. *Nature Biotechnology,* 37(2), 160-168.
44. No, J. S., Kim, W.-K., Cho, S., Lee, S.-H., Kim, J.-A., Lee, D., Song, D. H., Gu, S. H., Jeong, S. T., Wiley, M. R., Palacios, G., & Song, J.-W. (2019). Comparison of targeted next-generation sequencing for whole-genome sequencing of Hantaan orthohantavirus in *Apodemus agrarius* lung tissues. *Scientific Reports,* 9(1), 16631.

45. Popa, A., Genger, J.-W., Nicholson, M. D., Penz, T., Schmid, D., Aberle, S. W., Agerer, B., Lercher, A., Endler, L., Colago, H., Smyth, M., Schuster, M., Grau, M. L., Martinez-Jimenez, F., Pich, O., Borena, W., Pawelka, E., Keszei, Z., Senekowitsch, M., . . . Bergthaler, A. (2020). Genomic epidemiology of superspreading events in Austria reveals mutational dynamics and transmission properties of SARS-CoV-2. *Science Translational Medicine,* 12(573). doi.org/10.1126/scitranslmed.abe2555.

46. Quick, J., Grubaugh, N. D., Pullan, S. T., Claro, I. M., Smith, A. D., Gangavarapu, K., Oliveira, G., Robles-Sikisaka, R., Rogers, T. F., Beutler, N. A., Burton, D. R., Lewis-Ximenez, L. L., de Jesus, J. G., Giovanetti, M., Hill, S. C., Black, A., Bedford, T., Carroll, M. W., Nunes, M., . . . Loman, N. J. (2017). Multiplex PCR method for MinION and Illumina sequencing of Zika and other virus genomes directly from clinical samples. *Nature Protocols,* 12(6), 1261-1276.

47. *SARS-CoV*-2 *COVID*-19 *Coronavirus research and surveillance.* (n.d.). Retrieved Feb. 12, 2021, from www-.paragongenomics.com/product/cleanplex-sars-cov-2-panel/Sethuraman, N., Jeremiah, S. S., & Ryo, A. (2020). Interpreting Diagnostic Tests for SARS-CoV-2. *JAMA: The Journal of the American Medical Association,* 323 (22), 2249-2251.

48. Volz, E., Mishra, S., Chand, M., Barrett, J. C., Johnson, R., Geidelberg, L., Hinsley, W. R., Laydon, D. J., Dabrera, G., O'Toole, A., Amato, R., Ragonnet-Cronin, M., Harrison, I., Jackson, B., Ariani, C. V., Boyd, O., Loman, N. J., McCrone, J. T., Gongalves, S., . . . The COVID-19 Genomics UK (COG-UK) consortium. (2021). Transmission of SARS-CoV-2 Lineage B.1.1.7 in England: Insights from linking epidemiological and genetic data. In bioRxiv. medRxiv. doi.org/10.1101/2020.12.30.20249034.

Tables

TABLE 2

Non-limiting set of designed spike-ins.

| Oligo ID | Sequence to order (5' to 3') | Nonarchaeal genuses with significant homology* |
|---|---|---|
| SDSI forward primer | TCTCCTTCTTAGCTTCGTGAGAAC (SEQ ID NO: 391) | n/a |
| SDSI reverse primer | CTTGGTCGTCTACTACATGATGTG (SEQ ID NO: 392) | n/a |
| SDSI 1 | ACAGTTCTCCTTCTTAGCTTCGTGAGAACGACCGGACGTTGTGATCACGGGTACCTTGATCTGGTACTCAAAGGTTTGCCCCCGTGAAGTCTGGTACATGGCTAGACACGTCACTCCATTCGAGGGACATTCGAAGTTAGAGAAGGGCAGAGCGATACATCAGATATATCACATCATGTAGTAGACGACCAAGACAGT (SEQ ID NO: 393) | none |
| SDSI 2 | ACAGTTCTCCTTCTTAGCTTCGTGAGAACCTTAATGGAAAGTATGCTTTAGATACCTTCTGGAACGCTATCTCACTTGGCGGAATTCAGATATGGAGAGTAAATTAAGGGATCTGGAAGTAAAGTTAATGTCGTTAATCTATTTAAATGAGTCACCATTAAAATCACCCACATCATGTAGTAGACGACCAAGACAGT (SEQ ID NO: 394) | none |
| SDSI 3 | ACAGTTCTCCTTCTTAGCTTCGTGAGAACCATAATATGTTAGAGGTAGAATTTCTTTGTGATAGAATATTATTGATGAATGATGGAAGAGAATTAGCATTAGGAAAACCTAAGGAACTGGTAAAGGATACAGAATCTAAGAATCTTGAAGAGGTTTTCCTTAAACTTGTCACATCATGTAGTAGACGACCAAGACAGT (SEQ ID NO: 395) | none |
| SDSI 4 | ACAGTTCTCCTTCTTAGCTTCGTGAGAACAGTCTAGGTTTTAATTCTTCAACTGCTTCAAATACTAGCTTACTGTAGTTATCTGCCCTCATGTTAGGATATATATCTGGAATATAAGGAGGTTGATGAGTTATAAGAAGTGGATGAAATTGTTGTCACACACTCCCCTACACATCATGTAGTAGACGACCAAGACAGT (SEQ ID NO: 396) | none |
| SDSI 5 | ACAGTTCTCCTTCTTAGCTTCGTGAGAACCTCGTAAGCGTTTCCTACCCTCGAGAGGGCCATCCTGGTGGTGAGGAAGTCGTCGAAGTGGGCTAAGTAAAAAGCGAAGATCTCGACCCACAATTACCTCCTCCTGTACACCAGGAATACCCCTATCAGGATAGAGATACCACATCATGTAGTAGACGACCAAGACAGT (SEQ ID NO: 397) | none |
| SDSI 6 | ACAGTTCTCCTTCTTAGCTTCGTGAGAACTCACGGTCCGCGACGTGAATCGGGCGTTCCAGTCGGCGTTCGGCTACGACGCCGACGACGTGGTCGGAAGCGACCTCCTCGGGCGAATCGTGCCCCCGGTGCCGGACCCGGACCCGGTGCCGGAACCGGGGGACGACGAGCACATCATGTAGTAGACGACCAAGACAGT (SEQ ID NO: 398) | none |
| SDSI 7 | ACAGTTCTCCTTCTTAGCTTCGTGAGAACGCGTCCGCGAGTTCATCCTGAACGTCGTCCCGCTGTCGCCCGGCGAGGAGCGCGGGGCGGGCTACGCCATCTACACCGACATCACGGAGCGGAAGACCCGCGAAAGCGAGCTAGAGCGACAGAACGAGCGATTGGAGGAGCACATCATGTAGTAGACGACCAAGACAGT (SEQ ID NO: 399) | none |

TABLE 2-continued

Non-limiting set of designed spike-ins.

| Oligo ID | Sequence to order (5' to 3') | Nonarchaeal genuses with significant homology* |
| --- | --- | --- |
| SDSI 8 | ACAGTTCTCCTTCTTAGCTTCGTGAGAACACGAACTCGTCGGTGAACATCTCGTCTTCCGGGGAGCCCGCCGCTCATGGCCTGCCCCCGCCGTAAGCTGCTGCATAAACCCGCTCCAAAATATACGGATCATTCACCCCTTGGAATCGCTCAATCAGATCAATGTACACCACATCATGTAGTAGACGACCAAGACAGT (SEQ ID NO: 400) | none |
| SDSI 9 | ACAGTTCTCCTTCTTAGCTTCGTGAGAACTGCGTACATTCCCCCTAAGCGGCTCCCAATATACAGACGCCGGTTAACGACAGCTGGCGACCCTGTGATCTCAGTACCGGTGTCGAATGACCACATCAGCTTGCCTGTCCGTGCATGGAGTTCGTATACGTACCCGTCGTCACATCATGTAGTAGACGACCAAGACAGT (SEQ ID NO: 401) | none |
| SDSI 10 | ACAGTTCTCCTTCTTAGCTTCGTGAGAACATACACCACCCCATCAGCAACAACTGAATCATGATTAAGTATCGCACCAGCATCGTAGCGCCAGCGTTCACTGCCAGTGGTGCTATCGAATGCATAGAAGATATGCTCCTAATCGCCAATATCAGTACTTCACAAAGCCGCACATCATGTAGTAGACGACCAAGACAGT (SEQ ID NO: 402) | none |
| SDSI 11 | ACAGTTCTCCTTCTTAGCTTCGTGAGAACGTGGAGTCTTTTGTCACACCGCAGAGGCGTAGCGCTGCAGAGCAGGAGCCCAAGCCTACTGCCAACATAGAGAACATAGTGGCTACAGTATCCCTCGACCAGACTCTAGACCTGAACCTCATAGAGAGGAGCATACTGACCACATCATGTAGTAGACGACCAAGACAGT (SEQ ID NO: 403) | none |
| SDSI 12 | ACAGTTCTCCTTCTTAGCTTCGTGAGAACCGTCGCCTGGGTTAAGAGGATGTTCGGCCTCTCCAAGGCGGGTCACGGAGGCACGCTGGACCCGAAGGTCACCGGCGTCCTCCCCGTAGCCCTGGAGGAAGCAACCAAGGTCATAGGCCTGGTGGTGCACACGAGCAAGGCACATCATGTAGTAGACGACCAAGACAGT (SEQ ID NO: 404) | none |
| SDSI 13 | ACAGTTCTCCTTCTTAGCTTCGTGAGAACCGTGGGCGAGATCTACCAGAGGCCGCCGCTCCGCAGCAGTGTTAAGAGAAGCCTCCGCGTCAAGAGGATATACGAGATAGAGCTGCTGGAGTACAACGGCAGGTACGCGCTCATGAGGGTGCTCTGCGAGGCCGGCACATCACATCATGTAGTAGACGACCAAGACAGT (SEQ ID NO: 405) | none |
| SDSI 14 | ACAGTTCTCCTTCTTAGCTTCGTGAGAACCGCTGGAAGAACGAGGGCAAGGAGGACCTGCTGCGGAGCTACATCAAGCCCGTCGAGTACGCCGTGAGCCACCTGCCCAAGATAGTTATACGCGATACCGCGGTGGACGCCATAGCCCATGGCGCGAACCTCGCGGTGCCCACATCATGTAGTAGACGACCAAGACAGT (SEQ ID NO: 406) | none |
| SDSI 15 | ACAGTTCTCCTTCTTAGCTTCGTGAGAACGGGAGACCCCAAGGTGACCGGCGTCCTACCAGTGGGGCTCGCCAACAGCACCAAGGTCATTGGTAATGTTATACATAGTGTTAAAGAATACGTGATGGTTATACAGCTCCACGGCGATGTAGCCGAGCAGGATTTAAGAACACATCATGTAGTAGACGACCAAGACAGT (SEQ ID NO: 407) | none |
| SDSI 16 | ACAGTTCTCCTTCTTAGCTTCGTGAGAACTAGAGGGAAAGACTGTAGCTTTCATTCCTAGGCACGGAAAGAGACACAGAATACCTCCACATAAGATAAATTATAGAGCTAATATATGGGCATTAAAAGAACTAGGAGTGAAATGGGTCATCTCAGTTTCTGCCGTAGGACACATCATGTAGTAGACGACCAAGACAGT (SEQ ID NO: 408) | none |
| SDSI 17 | ACAGTTCTCCTTCTTAGCTTCGTGAGAACTGAGGGAGCTCAGGAGGACTCGCACGGGGCCCTACAGGGAGGATGAGACACTTGTAAGGCTCCAGGACGTCAGCGAGGCCCTGCTCCTGTGGAGGAGCAACGGGGATGAGAGGTATCTTAGACGCATCGTGCTACCCGTTCACATCATGTAGTAGACGACCAAGACAGT (SEQ ID NO: 409) | none |
| SDSI 18 | ACAGTTCTCCTTCTTAGCTTCGTGAGAACGAAACATCTATCGCCCACCTCCCGAAGATAATGATCTTGGATACAGCTGTCGACGCCATAGCACATGGTGCCAACCTGGCTGCCCCAGGCGTCGCCAGGTTAACCAGGAACATCGCGAAGGGTAGTACCGTAGCGATCCTCACATCATGTAGTAGACGACCAAGACAGT (SEQ ID NO: 410) | none |
| SDSI 19 | ACAGTTCTCCTTCTTAGCTTCGTGAGAACTCGCTATCCCCGTGTACAGCATGGTGGGGGTGCCGATGCCCGGGTAGAACTTGGTGACGCTCTCCAGCTTCTCGAGGACGGTTTCCTTGGGGAGGCTCGCGGTGTCCACGAGGGTTATCGCGTCCTCGGCGCCGTCGCCGCACATCATGTAGTAGACGACCAAGACAGT (SEQ ID NO: 411) | none |

TABLE 2-continued

Non-limiting set of designed spike-ins.

| Oligo ID | Sequence to order (5' to 3') | Nonarchaeal genuses with significant homology* |
|---|---|---|
| SDSI 20 | ACAGTTCTCCTTCTTAGCTTCGTGAGAACCGAGGACGCGAAGAGCGCGGTGGATGTGGACGCGCCGCCGCACACGTAGCCGTCGAGGTAGCGCGGAACCATCGGCGACATCAGCCCCACGACGCGACCCGAGGCGTTGCCGAGGATCACGTCGAGCGTCACGCGCGGCACACATCATGTAGTAGACGACCAAGACAGT (SEQ ID NO: 412) | none |
| SDSI 21 | ACAGTTCTCCTTCTTAGCTTCGTGAGAACTCTATGGTGTAGAACGGGTCGTTGCGGAGCCAGCCTGGCGGCACGTACCGGTCGTCCGCTATCGCCAGCGATCTCTCGAAGAGGTCGAGGTAGGCGGACGCGTTGGCGAACGCCCCGTGTATCACGACGTCTATCCCGCCCACATCATGTAGTAGACGACCAAGACAGT (SEQ ID NO: 413) | none |
| SDSI 22 | ACAGTTCTCCTTCTTAGCTTCGTGAGAACCCTACGCCGGGTGCGTAGGAGGGCTCGAGTACATCCATGTCTATACTGATGTATGTTTTACCCAGGTCGCCTAGTGCCAGGGGTCCCTTTAACGCTTCCAGGATAGAGTACACGGTGACGTCTCTAGTCTTCTTCAAGAACACATCATGTAGTAGACGACCAAGACAGT (SEQ ID NO: 414) | none |
| SDSI 23 | ACAGTTCTCCTTCTTAGCTTCGTGAGAACCTACTAGCGTGTCAACGGAGCTCTTCAACGCCTTTACTATTGGATAGGTTATAAGGTGCTCGCCTCCGAGGAATCCCAGGAGCATGCCGGGATACTCGTCTACAACGCCTTTCACCACGTCACCTATGATTCTTAAAGAGCACATCATGTAGTAGACGACCAAGACAGT (SEQ ID NO: 415) | none |
| SDSI 24 | ACAGTTCTCCTTCTTAGCTTCGTGAGAACCATAGGTGACATGGGGTTTCCCATTGACTCTATAAAGCCGTATCCTTTAAGCGGAGTGCAATTGGTCTACGCTTTGCTTAACAACAGGTATTTCCTACCGGGTAGAGAGGGCTCGCTCATAGCTTTAGGTAGCGTGACGGCACATCATGTAGTAGACGACCAAGACAGT (SEQ ID NO: 416) | none |
| SDSI 25 | ACAGTTCTCCTTCTTAGCTTCGTGAGAACGGTATCTCACCGCTTGTCACCATAGTATCCCTCAGGTACTCCAGTATTCTTGAGAGAAACGCACCTAAGCCGGATCTCAGGTTTGAATCCATAAGAACTATGAGTGAAGCGGGATTGAAGCCCCTGCTGTTTCTAAGACCCACATCATGTAGTAGACGACCAAGACAGT (SEQ ID NO: 417) | none |
| SDSI 26 | ACAGTTCTCCTTCTTAGCTTCGTGAGAACTAAGGGAGATAGAGAAACGCATCAAAATACCCTTGGGGAAACTGCGTGCAGGGGTTCAATATGGAGTAGAGGTCTCAGACATAAAGGAGAAGATAGCTGCTTACGCTAGGAGGAAGGGGCTTAAATACTTCCCATCGGCACACATCATGTAGTAGACGACCAAGACAGT (SEQ ID NO: 418) | none |
| SDSI 27 | ACAGTTCTCCTTCTTAGCTTCGTGAGAACTGTGAACCTCGTGCCCGGCTCTAAGTCGTGAGGGCTTGCAACATAGGTGGGGAGGAACCCGAGCAACGGGTAAGAAGACAGGATAAGCGGTATCGCTATGAAGAGGGCTGAGAAAAGGACATATACTCCTGAGCCCGTCCCACATCATGTAGTAGACGACCAAGACAGT (SEQ ID NO: 419) | none |
| SDSI 28 | ACAGTTCTCCTTCTTAGCTTCGTGAGAACCGAACATGCCTTCCCCGTCTATATAGACCCAGTAGAGTTTAAAAACTTAACCAGAGACGGCTTGTGAGCCGGATCTCTCCCCCGCTAGGCCCTGGATTGGGCTCGCTCCTCCTGGGACCCCGGCCTCCACATGCTCGGGACACATCATGTAGTAGACGACCAAGACAGT (SEQ ID NO: 420) | none |
| SDSI 29 | ACAGTTCTCCTTCTTAGCTTCGTGAGAACTCTCGGTTCGGCAATAAGTAATACCAACGAGGTATTACCATGCGCGTGACCAGCAAAGGCCAAGTGACGATCCCAAAGGAGATACGGGATCATTTGGGGATTGGGCCGGGCTCCGAGGTGGAGTTCGTGCCCACAGACGACACATCATGTAGTAGACGACCAAGACAGT (SEQ ID NO: 421) | *mesorhizobium*; *neorhizobium* |
| SDSI 30 | ACAGTTCTCCTTCTTAGCTTCGTGAGAACCTCGATCATATGGCCGGCACGTTGGACTTGGGAGGCATGACAACGGACGAGTATATGGAGTGGCTGAGGGGTCCACGTGAAGATCTCGACATTGATTGACACAAATGTCCTGATCGATGTTTGGGGTCCTGCCGGACAGGCACATCATGTAGTAGACGACCAAGACAGT (SEQ ID NO: 422) | *mesorhizobium*; *neorhizobium*; *rhizobium*; *neorhizobium*; *aminobacter*; *sinorhizobium*; *shinella*; |
| SDSI 31 | ACAGTTCTCCTTCTTAGCTTCGTGAGAACCAGGTGTATTTTACACACCTGGACAGCCAGCATATGATGCTAGCACTCGGTGTCCCCTTATCACGGTTTCCCGCATTGTAAAGTTTTCGCGCCTGCTGCGCCCCGTAGGGCCTGGATTCATGTCTCAGAATCCATCTCCGCACATCATGTAGTAGACGACCAAGACAGT (SEQ ID NO: 423) | 'uncultured bacteria' |

TABLE 2-continued

Non-limiting set of designed spike-ins.

| Oligo ID | Sequence to order (5' to 3') | Nonarchaeal genuses with significant homology* |
|---|---|---|
| SDSI 32 | ACAGTTCTCCTTCTTAGCTTCGTGAGAACCGTAGCCCGCACCTTCCTCTGGTTTAGCACCAGCGGTCCCCACAGAGTACCCATCATCCCGAAGGATATGCTGGCAACAGTGGGCACGGGTCTCGCTCGTTGCCTGACTTAACAGGATGCTTCACAGTACGAACTGACGACACATCATGTAGTAGACGACCAAGACAGT (SEQ ID NO: 424) | 'uncultured bacteria' |
| SDSI 33 | ACAGTTCTCCTTCTTAGCTTCGTGAGAACGAAACTTACCTTATCAGTGTCATTAAGCATATTGCTTCCAAGACCCATTGAAGCACTTACATCGTTGATACACAGGTGCCAGGAATAGTATTCCTCAGTCTCACTATAATCCTCGTTGGTGTAGCCTTCAAGAGAGTCAACACATCATGTAGTAGACGACCAAGACAGT (SEQ ID NO: 425) | none |
| SDSI 34 | ACAGTTCTCCTTCTTAGCTTCGTGAGAACGTTTAAGCAATTCTTCGGATGAAAGATGGCGCTCTATAGGAATTTGTTCTGGTCTAGCCATAAGGCATTATTTGTACTTAATTAGTAATAAATGTTTAGTTAATGACTATAAATCTGCAATTGGAGTCTCAAATTTTCAACACATCATGTAGTAGACGACCAAGACAGT (SEQ ID NO: 426) | none |
| SDSI 35 | ACAGTTCTCCTTCTTAGCTTCGTGAGAACAACATGAAGGATGTGTGTAAGAGGAAACGTTATTAACAGACGTAATCAGGAGGATAGTTATGCCCTAAAAACAGCAGAGTTAAGGTTTAAAAATAAGATAAGAACTCAGTTGAGGTTTATCCATTAATCCCATTAATCCTCACATCATGTAGTAGACGACCAAGACAGT (SEQ ID NO: 427) | none |
| SDSI 36 | ACAGTTCTCCTTCTTAGCTTCGTGAGAACGTATCCGCTGATATATCCTGGGGATATAGATCGCTCTGAAATGGTTACATCTATCGGTTTTAAGGACAGTTCCAACACTATTGGACCTTGCAGCTATGACAGGAATAATCTGTTTATCGAGCACAGTTGAATTTGACCTACACATCATGTAGTAGACGACCAAGACAGT (SEQ ID NO: 428) | none |
| SDSI 37 | ACAGTTCTCCTTCTTAGCTTCGTGAGAACATATTCCGTATTTCTTATCAAACCGATCGTGAAGATTTGACAAAGGCTTAACTTTAGGGCTCCACTTCTCATTATTAGCCTTAGAATATAAAGCGTAACCGTAAGCCTGAGGAACGTAAAGCTTAGGAGATTCAATCCCGCACATCATGTAGTAGACGACCAAGACAGT (SEQ ID NO: 429) | none |
| SDSI 38 | ACAGTTCTCCTTCTTAGCTTCGTGAGAACTAAAATTAGCCGAAGGCTTCCCATTACCGAAAAAGTCGTTTATTAGCTCTTCATCCTTCTTCTCCACGTCCGCCCATTCCTCTCCTTCCCTTGGAATTTTAAGCTCGTCCCAGCTGACTCTTATGGGCAATTCAATATCCCACATCATGTAGTAGACGACCAAGACAGT (SEQ ID NO: 430) | none |
| SDSI 39 | ACAGTTCTCCTTCTTAGCTTCGTGAGAACTCCGGAGGAATCTATCATATTAAACCTCCTCAAAATCGCCTCCTCTTGATTGCTTAAAGGCTGTGAATTACAAAGCTTATTTAATGCGTCCCAAAGCGTTAAGTAATAATTATTTATATTAAACACTACTATTTCAGTAGCACATCATGTAGTAGACGACCAAGACAGT (SEQ ID NO: 431) | none |
| SDSI 40 | ACAGTTCTCCTTCTTAGCTTCGTGAGAACGTTCCTCCTCAATTCAATTGGACTGAAGGAGGGTACGTTCTGGAAAACAGAGCGTAAAAGAGATATAGAACGTAGTATACACATAGCTGGAAAAAGAACAATCATTAAGACAATAAAGAACTTTATGGAAAAGAGTAGAACACATCATGTAGTAGACGACCAAGACAGT (SEQ ID NO: 432) | none |
| SDSI 41 | ACAGTTCTCCTTCTTAGCTTCGTGAGAACTCGTGTAAAGGTTGTATAATTCAAGCCTCAGAACATTTCGAACTCCTTACAAAATCGTTTAAACTTTCTAAGGCATAAATTTACTAGAAATTGTCATTTATGAGAATGTAACTATATAGATGGTAAAATTATTAATCCTCCACATCATGTAGTAGACGACCAAGACAGT (SEQ ID NO: 433) | none |
| SDSI 42 | ACAGTTCTCCTTCTTAGCTTCGTGAGAACGGCTGAAAAATAGGTTCGATCCGCCTCCTCACTTCTTCTCCTTCTTGCCCTCGGCCTCGGAGGAGGCCTCTATTCCCAGCTTCTTGGCCTCCTCCTCGGTCGTCATGAACAGGCTAGTCCTCTGCCTTCCGCCCATGCTCCACATCATGTAGTAGACGACCAAGACAGT (SEQ ID NO: 434) | none |
| SDSI 43 | ACAGTTCTCCTTCTTAGCTTCGTGAGAACGTTCAGCATAAAAGACGGTTTCACGGGCCAAAGCCTAAGCGGCGTAACGGTGAAAGAAGGAGATACGGTTTTGGGCACGATTGACGACGGCGGGACGCTGGAGCTCACGAGGGGCACTCACACCTTGACTTTCGAGAAGCCACATCATGTAGTAGACGACCAAGACAGT (SEQ ID NO: 435) | none |
| SDSI 44 | ACAGTTCTCCTTCTTAGCTTCGTGAGAACCTGATGTTATAGAAGTCCGCAAGGACGGCTCTGTCATCTCGCCCGAGGGTGGGAAATACTATCTCGGCGACAT | none |

TABLE 2-continued

Non-limiting set of designed spike-ins.

| Oligo ID | Sequence to order (5' to 3') | Nonarchaeal genuses with significant homology* |
|---|---|---|
| | AAGCGGCCCGACACAAATTAGCATCAAGTTCAAGGCCGGCGCGGTGGGAACCCACGGCTTCACTATCCACATCATGTAGTAGACGACCAAGACAGT (SEQ ID NO: 436) | |
| SDSI 45 | ACAGTTCTCCTTCTTAGCTTCGTGAGAACTCTCCCTCAACCTTCGCGGGGAGAACGGCGCGGAGTACTGGACGGGCTACGCGGACGCGCTGGAAGACCTGTTGAAGAAAATCCAGAGGCGGGAGGTGAGGGCATGAGAAGGTATTGTTACATCACGTGGGGATGGATCACACATCATGTAGTAGACGACCAAGACAGT (SEQ ID NO: 437) | none |
| SDSI 46 | ACAGTTCTCCTTCTTAGCTTCGTGAGAACGAGCGCCGGGAGGTGAGGGCATGAGTGAGGAATTGATGTTTGGTCGTGTCGTGGAGTATGTTCAGCATAGTTTCTACAAGAAACCGTTTCCTCTTGGCAGTGAGCTCAAGAATGCAGTAGAGAAGGTTATGGAAACAGGACACATCATGTAGTAGACGACCAAGACAGT (SEQ ID NO: 438) | none |
| SDSI 47 | ACAGTTCTCCTTCTTAGCTTCGTGAGAACAGGTCAGAGCCCACGTGGCAACTTTTGAGGTTCTGACAAAAGACTATGTTCGTGAGAAATACAAAGACATCATAGAGTTCATGAGGGAGAAAGGGACAGTATCGAGAAAGGAACTGCGGAAGAAGTTCTTCTTGCTTGCTCACATCATGTAGTAGACGACCAAGACAGT (SEQ ID NO: 439) | none |
| SDSI 48 | ACAGTTCTCCTTCTTAGCTTCGTGAGAACGTACCTCAAAATACAGAATCATATTTTACAATCGCTTGGAAATATTAATATCAACAATACGCAAGTCCAAATTAACGTCCCTGGCAAACAGGTGACAATTTATACCCACGAAATACTAGATAACGCCAAAAAGGCACTCGCACATCATGTAGTAGACGACCAAGACAGT (SEQ ID NO: 440) | none |

TABLE 3

SDSI and Viral Read Percentages

| Mock CT | Viral reads % | Spike-in reads % |
|---|---|---|
| 20 | 99.56 | 0.18 |
| 25 | 99.19 | 0.38 |

TABLE 3-continued

SDSI and Viral Read Percentages

| Mock CT | Viral reads % | Spike-in reads % |
|---|---|---|
| 30 | 98.47 | 1.11 |
| 35 | 99.65 | 3.17 |

TABLE 4

Exemplary ARTIC v3 Primers and Primers Spiked in at 2X

| Name | Pool | Sequence | Length | % GC | Spiked in at 2X |
|---|---|---|---|---|---|
| nCoV-2019_1_LEFT | nCoV-2019_1 | ACCAACCAACTTTCGATCTCTTGT (SEQ ID NO: 441) | 24 | 41.7 | |
| nCoV-2019_1_RIGHT | nCoV-2019_1 | CATCTTTAAGATGTTGACGTGCCTC (SEQ ID NO: 442) | 25 | 44.0 | |
| nCoV-2019_2_LEFT | nCoV-2019_2 | CTGTTTTACAGGTTCGCGACGT (SEQ ID NO: 443) | 22 | 50.0 | |
| nCoV-2019_2_RIGHT | nCoV-2019_2 | TAAGGATCAGTGCCAAGCTCGT (SEQ ID NO: 444) | 22 | 50.0 | |
| nCoV-20193_LEFT | nCoV-2019_1 | CGGTAATAAAGGAGCTGGTGGC (SEQ ID NO: 445) | 22 | 54.6 | |
| nCoV-2019_3_RIGHT | nCoV-2019_1 | AAGGTGTCTGCAATTCATAGCTCT (SEQ ID NO: 446) | 24 | 41.7 | |
| nCoV-2019_4_LEFT | nCoV-2019_2 | GGTGTATACTGCTGCCGTGAAC (SEQ ID NO: 447) | 22 | 54.6 | |
| nCoV-2019_4_RIGHT | nCoV-2019_2 | CACAAGTAGTGGCACCTTCTTTAGT (SEQ ID NO: 448) | 25 | 44.0 | |

TABLE 4-continued

Exemplary ARTIC v3 Primers and Primers Spiked in at 2X

| Name | Pool | Sequence | Length | % GC | Spiked in at 2X |
|---|---|---|---|---|---|
| nCoV-2019_5_LEFT | nCoV-2019_1 | TGGTGAAACTTCATGGCAGACG (SEQ ID NO: 449) | 22 | 50.0 | |
| nCoV-2019_5_RIGHT | nCoV-2019_1 | ATTGATGTTGACTTTCTCTTTTTGGAGT (SEQ ID NO: 450) | 28 | 32.1 | |
| nCoV-2019_6_LEFT | nCoV-2019_2 | GGTGTTGTTGGAGAAGGTTCCG (SEQ ID NO: 451) | 22 | 54.6 | |
| nCoV-2019_6_RIGHT | nCoV-2019_2 | TAGCGGCCTTCTGTAAAACACG (SEQ ID NO: 452) | 22 | 50.0 | |
| nCoV-2019_7_LEFT_alt0 | nCoV-2019_1 | CATTTGCATCAGAGGCTGCTCG (SEQ ID NO: 453) | 22 | 54.6 | X |
| nCoV-2019_7_RIGHT_alt5 | nCoV-2019_1 | AGGTGACAATTTGTCCACCGAC (SEQ ID NO: 454) | 22 | 50.0 | X |
| nCoV-2019_8_LEFT | nCoV-2019_2 | AGAGTTTCTTAGAGACGGTTGGGA (SEQ ID NO: 455) | 24 | 45.8 | |
| nCoV-2019_8_RIGHT | nCoV-2019_2 | GCTTCAACAGCTTCACTAGTAGGT (SEQ ID NO: 456) | 24 | 45.8 | |
| nCoV-2019_9_LEFT_alt4 | nCoV-2019_1 | TTCCCACAGAAGTGTTAACAGAGG (SEQ ID NO: 457) | 24 | 45.8 | X |
| nCoV-2019_9_RIGHT_alt2 | nCoV-2019_1 | GACAGCATCTGCCACAACACAG (SEQ ID NO: 458) | 22 | 54.6 | X |
| nCoV-2019_10_LEFT | nCoV-2019_2 | TGAGAAGTGCTCTGCCTATACAGT (SEQ ID NO: 459) | 24 | 45.8 | |
| nCoV-2019_10_RIGHT | nCoV-2019_2 | TCATCTAACCAATCTTCTTCTTGCTCT (SEQ ID NO: 460 | 27 | 37.0 | |
| nCoV-2019_11_LEFT | nCoV-2019_1 | GGAATTTGGTGCCACTTCTGCT (SEQ ID NO: 461) | 22 | 50.0 | |
| nCoV-2019_11_RIGHT | nCoV-2019_1 | TCATCAGATTCAACTTGCATGGCA (SEQ ID NO: 462) | 24 | 41.7 | |
| nCoV-2019_12_LEFT | nCoV-2019_2 | AAACATGGAGGAGGTGTTGCAG (SEQ ID NO: 463) | 22 | 50.0 | X |
| nCoV-2019_12_RIGHT | nCoV-2019_2 | TTCACTCTTCATTTCCAAAAAGCTTGA (SEQ ID NO: 464) | 27 | 33.3 | X |
| nCoV-2019_13_LEFT | nCoV-2019_1 | TCGCACAAATGTCTACTTAGCTGT (SEQ ID NO: 465) | 24 | 41.7 | |
| nCoV-2019_13_RIGHT | nCoV-2019_1 | ACCACAGCAGTTAAAACACCCT (SEQ ID NO: 466) | 22 | 45.5 | |
| nCoV-2019_14_LEFT_alt4 | nCoV-2019_2 | TGGCAATCTTCATCCAGATTCTGC (SEQ ID NO: 467) | 24 | 45.8 | X |
| nCoV-2019_14_RIGHT_alt2 | nCoV-2019_2 | TGCGTGTTTCTTCTGCATGTGC (SEQ ID NO: 468) | 22 | 50.0 | X |
| nCoV-2019_15_LEFT_alt1 | nCoV-2019_1 | AGTGCTTAAAAAGTGTAAAAGTGCCT (SEQ ID NO: 469) | 26 | 34.6 | X |
| nCoV-2019_15_RIGHT_alt3 | nCoV-2019_1 | ACTGTAGCTGGCACTTTGAGAGA (SEQ ID NO: 470) | 23 | 47.8 | X |
| nCoV-2019_16_LEFT | nCoV-2019_2 | AATTTGGAAGAAGCTGCTCGGT (SEQ ID NO: 471) | 22 | 45.5 | |
| nCoV-2019_16_RIGHT | nCoV-2019_2 | CACAACTTGCGTGTGGAGGTTA (SEQ ID NO: 472) | 22 | 50.0 | |
| nCoV-2019_17_LEFT | nCoV-2019_1 | CTTCTTTCTTTGAGAGAAGTGAGGACT (SEQ ID NO: 473) | 27 | 40.7 | X |

TABLE 4-continued

Exemplary ARTIC v3 Primers and Primers Spiked in at 2X

| Name | Pool | Sequence | Length | % GC | Spiked in at 2X |
|---|---|---|---|---|---|
| nCoV-2019_17_RIGHT | nCoV-2019_1 | TTTGTTGGAGTGTTAACAATGCAGT (SEQ ID NO: 474) | 25 | 36.0 | X |
| nCoV-2019_18_LEFT_alt2 | nCoV-2019_2 | ACTTCTATTAAATGGGCAGATAACAACT GT (SEQ ID NO: 475) | 30 | 33.3 | X |
| nCoV-2019_18_RIGHT_alt1 | nCoV-2019_2 | GCTTGTTTACCACACGTACAAGG (SEQ ID NO: 476) | 23 | 47.8 | X |
| nCoV-2019_19_LEFT | nCoV-2019_1 | GCTGTTATGTACATGGGCACACT (SEQ ID NO: 477) | 23 | 47.8 | |
| nCoV-2019_19_RIGHT | nCoV-2019_1 | TGTCCAACTTAGGGTCAATTTCTGT (SEQ ID NO: 478) | 25 | 40.0 | |
| nCoV-2019_20_LEFT | nCoV-2019_2 | ACAAAGAAAACAGTTACACAACAACCA (SEQ ID NO: 479) | 27 | 33.3 | |
| nCoV-2019_20_RIGHT | nCoV-2019_2 | ACGTGGCTTTATTAGTTGCATTGTT (SEQ ID NO: 480) | 25 | 36.0 | |
| nCoV-2019_21_LEFT_alt2 | nCoV-2019_1 | GGCTATTGATTATAAACACTACACACCC T (SEQ ID NO: 481 | 29 | 37.9 | X |
| nCoV-2019_21_RIGHT_alt0 | nCoV-2019_1 | GATCTGTGTGGCCAACCTCTTC (SEQ ID NO: 482) | 22 | 54.6 | X |
| nCoV-2019_22_LEFT | nCoV-2019_2 | ACTACCGAAGTTGTAGGAGACATTATAC T (SEQ ID NO: 483) | 29 | 37.9 | |
| nCoV-2019_22_RIGHT | nCoV-2019_2 | ACAGTATTCTTTGCTATAGTAGTCGGC (SEQ ID NO: 484) | 27 | 40.7 | |
| nCoV-201923_LEFT | nCoV-2019_1 | ACAACTACTAACATAGTTACACGGTGT (SEQ ID NO: 485) | 27 | 37.0 | |
| nCoV-201923_RIGHT | nCoV-2019_1 | ACCAGTACAGTAGGTTGCAATAGTG (SEQ ID NO: 486) | 25 | 44.0 | |
| nCoV-2019_24_LEFT | nCoV-2019_2 | AGGCATGCCTTCTTACTGTACTG (SEQ ID NO: 487) | 23 | 47.8 | X |
| nCoV-2019_24_RIGHT | nCoV-2019_2 | ACATTCTAACCATAGCTGAAATCGGG (SEQ ID NO: 488) | 26 | 42.3 | X |
| nCoV-2019_25_LEFT | nCoV-2019_1 | GCAATTGTTTTTCAGCTATTTTGCAGT (SEQ ID NO: 489) | 27 | 33.3 | |
| nCoV-2019_25_RIGHT | nCoV-2019_1 | ACTGTAGTGACAAGTCTCTCGCA (SEQ ID NO: 490) | 23 | 47.8 | |
| nCoV-2019_26_LEFT | nCoV-2019_2 | TTGTGATACATTCTGTGCTGGTAGT (SEQ ID NO: 491) | 25 | 40.0 | |
| nCoV-2019_26_RIGHT | nCoV-2019_2 | TCCGCACTATCACCAACATCAG (SEQ ID NO: 492) | 22 | 50.0 | |
| nCoV-2019_27_LEFT | nCoV-2019_1 | ACTACAGTCAGCTTATGTGTCAACC (SEQ ID NO: 493) | 25 | 44.0 | |
| nCoV-2019_27_RIGHT | nCoV-2019_1 | AATACAAGCACCAAGGTCACGG (SEQ ID NO: 494) | 22 | 50.0 | |
| nCoV-2019_28_LEFT | nCoV-2019_2 | ACATAGAAGTTACTGGCGATAGTTGT (SEQ ID NO: 495) | 26 | 38.5 | |
| nCoV-2019_28_RIGHT | nCoV-2019_2 | TGTTTAGACATGACATGAACAGGTGT (SEQ ID NO: 496) | 26 | 38.5 | |
| nCoV-2019_29_LEFT | nCoV-2019_1 | ACTTGTGTTCCTTTTTGTTGCTGC (SEQ ID NO: 497) | 24 | 41.7 | |
| nCoV-2019_29_RIGHT | nCoV-2019_1 | AGTGTACTCTATAAGTTTTGATGGTGTGT (SEQ ID NO: 498) | 29 | 34.5 | |

TABLE 4-continued

Exemplary ARTIC v3 Primers and Primers Spiked in at 2X

| Name | Pool | Sequence | Length | % GC | Spiked in at 2X |
|---|---|---|---|---|---|
| nCoV-2019_30_LEFT | nCoV-2019_2 | GCACAACTAATGGTGACTTTTTGCA (SEQ ID NO: 499) | 25 | 40.0 | |
| nCoV-2019_30_RIGHT | nCoV-2019_2 | ACCACTAGTAGATACACAAACACCAG (SEQ ID NO: 500) | 26 | 42.3 | |
| nCoV-201931_LEFT | nCoV-2019_1 | TTCTGAGTACTGTAGGCACGGC (SEQ ID NO: 501) | 22 | 54.6 | |
| nCoV-2019_31_RIGHT | nCoV-2019_1 | ACAGAATAAACACCAGGTAAGAATGAG T (SEQ ID NO: 502) | 28 | 35.7 | |
| nCoV-2019_32_LEFT | nCoV-2019_2 | TGGTGAATACAGTCATGTAGTTGCC (SEQ ID NO: 503) | 25 | 44.0 | |
| nCoV-2019_32_RIGHT | nCoV-2019_2 | AGCACATCACTACGCAACTTTAGA (SEQ ID NO: 504) | 24 | 41.7 | |
| nCoV-2019_33_LEFT | nCoV-2019_1 | ACTTTTGAAGAAGCTGCGCTGT (SEQ ID NO: 505) | 22 | 45.5 | X |
| nCoV-2019_33_RIGHT | nCoV-2019_1 | TGGACAGTAAACTACGTCATCAAGC (SEQ ID NO: 506) | 25 | 44.0 | X |
| nCoV-2019_34_LEFT | nCoV-2019_2 | TCCCATCTGGTAAAGTTGAGGGT (SEQ ID NO: 507) | 23 | 47.8 | |
| nCoV-2019_34_RIGHT | nCoV-2019_2 | AGTGAAATTGGGCCTCATAGCA (SEQ ID NO: 508) | 22 | 45.5 | |
| nCoV-2019_35_LEFT | nCoV-2019_1 | TGTTCGCATTCAACCAGGACAG (SEQ ID NO: 509) | 22 | 50.0 | |
| nCoV-2019_35_RIGHT | nCoV-2019_1 | ACTTCATAGCCACAAGGTTAAAGTCA (SEQ ID NO: 510) | 26 | 38.5 | |
| nCoV-2019_36_LEFT | nCoV-2019_2 | TTAGCTTGGTTGTACGCTGCTG (SEQ ID NO: 511) | 22 | 50.0 | |
| nCoV-2019_36_RIGHT | nCoV-2019_2 | GAACAAAGACCATTGAGTACTCTGGA (SEQ ID NO: 512) | 26 | 42.3 | |
| nCoV-2019_37_LEFT | nCoV-2019_1 | ACACACCACTGGTTGTTACTCAC (SEQ ID NO: 513) | 23 | 47.8 | |
| nCoV-2019_37_RIGHT | nCoV-2019_1 | GTCCACACTCTCCTAGCACCAT (SEQ ID NO: 514) | 22 | 54.6 | |
| nCoV-2019_38_LEFT | nCoV-2019_2 | ACTGTGTTATGTATGCATCAGCTGT (SEQ ID NO: 515) | 25 | 40.0 | |
| nCoV-2019_38_RIGHT | nCoV-2019_2 | CACCAAGAGTCAGTCTAAAGTAGCG (SEQ ID NO: 516) | 25 | 48.0 | |
| nCoV-2019_39_LEFT | nCoV-2019_1 | AGTATTGCCCTATTTTCTTCATAACTGGT (SEQ ID NO: 517) | 29 | 34.5 | |
| nCoV-2019_39_RIGHT | nCoV-2019_1 | TGTAACTGGACACATTGAGCCC (SEQ ID NO: 518) | 22 | 50.0 | |
| nCoV-2019_40_LEFT | nCoV-2019_2 | TGCACATCAGTAGTCTTACTCTCAGT (SEQ ID NO: 519) | 26 | 42.3 | |
| nCoV-2019_40_RIGHT | nCoV-2019_2 | CATGGCTGCATCACGGTCAAAT (SEQ ID NO: 520) | 22 | 50.0 | |
| nCoV-2019_41_LEFT | nCoV-2019_1 | GTTCCCTTCCATCATATGCAGCT (SEQ ID NO: 521) | 23 | 47.8 | |
| nCoV-2019_41_RIGHT | nCoV-2019_1 | TGGTATGACAACCATTAGTTTGGCT (SEQ ID NO: 522) | 25 | 40.0 | |
| nCoV-2019_42_LEFT | nCoV-2019_2 | TGCAAGAGATGGTTGTGTTCCC (SEQ ID NO: 523) | 22 | 50.0 | |

TABLE 4-continued

Exemplary ARTIC v3 Primers and Primers Spiked in at 2X

| Name | Pool | Sequence | Length | % GC | Spiked in at 2X |
|---|---|---|---|---|---|
| nCoV-2019_42_RIGHT | nCoV-2019_2 | CCTACCTCCCTTTGTTGTGTTGT (SEQ ID NO: 524) | 23 | 47.8 | |
| nCoV-2019_43_LEFT | nCoV-2019_1 | TACGACAGATGTCTTGTGCTGC (SEQ ID NO: 525) | 22 | 50.0 | |
| nCoV-2019_43_RIGHT | nCoV-2019_1 | AGCAGCATCTACAGCAAAAGCA (SEQ ID NO: 526) | 22 | 45.5 | |
| nCoV-2019_44_LEFT_alt3 | nCoV-2019_2 | CCACAGTACGTCTACAAGCTGG (SEQ ID NO: 527) | 22 | 54.6 | |
| nCoV-2019_44_RIGHT_alt0 | nCoV-2019_2 | CGCAGACGGTACAGACTGTGTT (SEQ ID NO: 528) | 22 | 54.6 | |
| nCoV-2019_45_LEFT_alt2 | nCoV-2019_1 | AGTATGTACAAATACCTACAACTTGTGCT (SEQ ID NO: 529) | 29 | 34.5 | X |
| nCoV-2019_45_RIGHT_alt7 | nCoV-2019_1 | TTCATGTTGGTAGTTAGAGAAAGTGTGTC (SEQ ID NO: 530) | 29 | 37.9 | X |
| nCoV-2019_46_LEFT_alt1 | nCoV-2019_2 | CGCTTCCAAGAAAAGGACGAAGA (SEQ ID NO: 531) | 23 | 47.8 | |
| nCoV-2019_46_RIGHT_alt2 | nCoV-2019_2 | CACGTTCACCTAAGTTGGCGTAT (SEQ ID NO: 532) | 23 | 47.8 | |
| nCoV-2019_47_LEFT | nCoV-2019_1 | AGGACTGGTATGATTTTGTAGAAAACCC (SEQ ID NO: 533) | 28 | 39.3 | |
| nCoV-2019_47_RIGHT | nCoV-2019_1 | AATAACGGTCAAAGAGTTTTAACCTCTC (SEQ ID NO: 534) | 28 | 35.7 | |
| nCoV-2019_48_LEFT | nCoV-2019_2 | TGTTGACACTGACTTAACAAAGCCT (SEQ ID NO: 535) | 25 | 40.0 | |
| nCoV-2019_48_RIGHT | nCoV-2019_2 | TAGATTACCAGAAGCAGCGTGC (SEQ ID NO: 536) | 22 | 50.0 | |
| nCoV-2019_49_LEFT | nCoV-2019_1 | AGGAATTACTTGTGTATGCTGCTGA (SEQ ID NO: 537) | 25 | 40.0 | |
| nCoV-2019_49_RIGHT | nCoV-2019_1 | TGACGATGACTTGGTTAGCATTAATACA (SEQ ID NO: 538) | 28 | 35.7 | |
| nCoV-2019_50_LEFT | nCoV-2019_2 | GTTGATAAGTACTTTGATTGTTACGATGGT (SEQ ID NO: 539) | 30 | 33.3 | |
| nCoV-2019_50_RIGHT | nCoV-2019_2 | TAACATGTTGTGCCAACCACCA (SEQ ID NO: 540) | 22 | 45.5 | |
| nCoV-2019_51_LEFT | nCoV-2019_1 | TCAATAGCCGCCACTAGAGGAG (SEQ ID NO: 541) | 22 | 54.6 | |
| nCoV-2019_51_RIGHT | nCoV-2019_1 | AGTGCATTAACATTGGCCGTGA (SEQ ID NO: 542) | 22 | 45.5 | |
| nCoV-2019_52_LEFT | nCoV-2019_2 | CATCAGGAGATGCCACAACTGC (SEQ ID NO: 543) | 22 | 54.6 | |
| nCoV-2019_52_RIGHT | nCoV-2019_2 | GTTGAGAGCAAAATTCATGAGGTCC (SEQ ID NO: 544) | 25 | 44.0 | |
| nCoV-2019_53_LEFT | nCoV-2019_1 | AGCAAAATGTTGGACTGAGACTGA (SEQ ID NO: 545) | 24 | 41.7 | |
| nCoV-2019_53_RIGHT | nCoV-2019_1 | AGCCTCATAAAACTCAGGTTCCC (SEQ ID NO: 546) | 23 | 47.8 | |
| nCoV-2019_54_LEFT | nCoV-2019_2 | TGAGTTAACAGGACACATGTTAGACA (SEQ ID NO: 547) | 26 | 38.5 | |
| nCoV-2019_54_RIGHT | nCoV-2019_2 | AACCAAAAACTTGTCCATTAGCACA (SEQ ID NO: 548) | 25 | 36.0 | |

TABLE 4-continued

Exemplary ARTIC v3 Primers and Primers Spiked in at 2X

| Name | Pool | Sequence | Length | % GC | Spiked in at 2X |
|---|---|---|---|---|---|
| nCoV-2019_55_LEFT | nCoV-2019_1 | ACTCAACTTTACTTAGGAGGTATGAGCT (SEQ ID NO: 549) | 28 | 39.3 | |
| nCoV-2019_55_RIGHT | nCoV-2019_1 | GGTGTACTCTCCTATTTGTACTTTACTGT (SEQ ID NO: 550) | 29 | 37.9 | |
| nCoV-2019_56_LEFT | nCoV-2019_2 | ACCTAGACCACCACTTAACCGA (SEQ ID NO: 551) | 22 | 50.0 | |
| nCoV-2019_56_RIGHT | nCoV-2019_2 | ACACTATGCGAGCAGAAGGGTA (SEQ ID NO: 552) | 22 | 50.0 | |
| nCoV-2019_57_LEFT | nCoV-2019_1 | ATTCTACACTCCAGGGACCACC (SEQ ID NO: 553) | 22 | 54.6 | |
| nCoV-2019_57_RIGHT | nCoV-2019_1 | GTAATTGAGCAGGGTCGCCAAT (SEQ ID NO: 554) | 22 | 50.0 | |
| nCoV-2019_58_LEFT | nCoV-2019_2 | TGATTTGAGTGTTGTCAATGCCAGA (SEQ ID NO: 555) | 25 | 40.0 | |
| nCoV-2019_58_RIGHT | nCoV-2019_2 | CTTTTCTCCAAGCAGGGTTACGT (SEQ ID NO: 556) | 23 | 47.8 | |
| nCoV-2019_59_LEFT | nCoV-2019_1 | TCACGCATGATGTTTCATCTGCA (SEQ ID NO: 557) | 23 | 43.5 | |
| nCoV-2019_59_RIGHT | nCoV-2019_1 | AAGAGTCCTGTTACATTTTCAGCTTG (SEQ ID NO: 558) | 26 | 38.5 | |
| nCoV-2019_60_LEFT | nCoV-2019_2 | TGATAGAGACCTTTATGACAAGTTGCA (SEQ ID NO: 559) | 27 | 37.0 | |
| nCoV-2019_60_RIGHT | nCoV-2019_2 | GGTACCAACAGCTTCTCTAGTAGC (SEQ ID NO: 560) | 24 | 50.0 | |
| nCoV-2019_61_LEFT | nCoV-2019_1 | TGTTTATCACCCGCGAAGAAGC (SEQ ID NO: 561) | 22 | 50.0 | |
| nCoV-2019_61_RIGHT | nCoV-2019_1 | ATCACATAGACAACAGGTGCGC (SEQ ID NO: 562) | 22 | 50.0 | |
| nCoV-2019_62_LEFT | nCoV-2019_2 | GGCACATGGCTTTGAGTTGACA (SEQ ID NO: 563) | 22 | 50.0 | |
| nCoV-2019_62_RIGHT | nCoV-2019_2 | GTTGAACCTTTCTACAAGCCGC (SEQ ID NO: 564) | 22 | 50.0 | |
| nCoV-2019_63_LEFT | nCoV-2019_1 | TGTTAAGCGTGTTGACTGGACT (SEQ ID NO: 565) | 22 | 45.5 | |
| nCoV-2019_63_RIGHT | nCoV-2019_1 | ACAAACTGCCACCATCACAACC (SEQ ID NO: 566) | 22 | 50.0 | |
| nCoV-2019_64_LEFT | nCoV-2019_2 | TCGATAGATATCCTGCTAATTCCATTGT (SEQ ID NO: 567) | 28 | 35.7 | X |
| nCoV-2019_64_RIGHT | nCoV-2019_2 | AGTCTTGTAAAAGTGTTCCAGAGGT (SEQ ID NO: 568) | 25 | 40.0 | X |
| nCoV-2019_65_LEFT | nCoV-2019_1 | GCTGGCTTTAGCTTGTGGGTTT (SEQ ID NO: 569) | 22 | 50.0 | |
| nCoV-2019_65_RIGHT | nCoV-2019_1 | TGTCAGTCATAGAACAAACACCAATAGT (SEQ ID NO: 570) | 28 | 35.7 | |
| nCoV-2019_66_LEFT | nCoV-2019_2 | GGGTGTGGACATTGCTGCTAAT (SEQ ID NO: 571) | 22 | 50.0 | X |
| nCoV-2019_66_RIGHT | nCoV-2019_2 | TCAATTTCCATTTGACTCCTGGGT (SEQ ID NO: 572) | 24 | 41.7 | X |
| nCoV-2019_67_LEFT | nCoV-2019_1 | GTTGTCCAACAATTACCTGAAACTTACT (SEQ ID NO: 573) | 28 | 35.7 | X |

TABLE 4-continued

Exemplary ARTIC v3 Primers and Primers Spiked in at 2X

| Name | Pool | Sequence | Length | % GC | Spiked in at 2X |
|---|---|---|---|---|---|
| nCoV-2019_67_RIGHT | nCoV-2019_1 | CAACCTTAGAAACTACAGATAAATCTTG GG (SEQ ID NO: 574) | 30 | 36.7 | X |
| nCoV-2019_68_LEFT | nCoV-2019_2 | ACAGGTTCATCTAAGTGTGTGTGT (SEQ ID NO: 575) | 24 | 41.7 | |
| nCoV-2019_68_RIGHT | nCoV-2019_2 | CTCCTTTATCAGAACCAGCACCA (SEQ ID NO: 576) | 23 | 47.8 | |
| nCoV-2019_69_LEFT | nCoV-2019_1 | TGTCGCAAAATATACTCAACTGTGTCA (SEQ ID NO: 577) | 27 | 37.0 | |
| nCoV-2019_69_RIGHT | nCoV-2019_1 | TCTTTATAGCCACGGAACCTCCA (SEQ ID NO: 578) | 23 | 47.8 | |
| nCoV-2019_70_LEFT | nCoV-2019_2 | ACAAAAGAAAATGACTCTAAAGAGGGT TT (SEQ ID NO: 579) | 29 | 31.0 | X |
| nCoV-2019_70_RIGHT | nCoV-2019_2 | TGACCTTCTTTTAAAGACATAACAGCAG (SEQ ID NO: 580) | 28 | 35.7 | X |
| nCoV-2019_71_LEFT | nCoV-2019_1 | ACAAATCCAATTCAGTTGTCTTCCTATTC (SEQ ID NO: 581) | 29 | 34.5 | X |
| nCoV-2019_71_RIGHT | nCoV-2019_1 | TGGAAAAGAAAGGTAAGAACAAGTCCT (SEQ ID NO: 582) | 27 | 37.0 | X |
| nCoV-2019_72_LEFT | nCoV-2019_2 | ACACGTGGTGTTTATTACCCTGAC (SEQ ID NO: 583) | 24 | 45.8 | |
| nCoV-2019_72_RIGHT | nCoV-2019_2 | ACTCTGAACTCACTTTCCATCCAAC (SEQ ID NO: 584) | 25 | 44.0 | |
| nCoV-2019_73_LEFT | nCoV-2019_1 | CAATTTTGTAATGATCCATTTTTGGGTGT (SEQ ID NO: 585) | 29 | 31.0 | |
| nCoV-2019_73_RIGHT | nCoV-2019_1 | CACCAGCTGTCCAACCTGAAGA (SEQ ID NO: 586) | 22 | 54.6 | |
| nCoV-2019_74_LEFT | nCoV-2019_2 | ACATCACTAGGTTTCAAACTTTACTTGC (SEQ ID NO: 587) | 28 | 35.7 | |
| nCoV-2019_74_RIGHT | nCoV-2019_2 | GCAACACAGTTGCTGATTCTCTTC (SEQ ID NO: 588) | 24 | 45.8 | |
| nCoV-2019_75_LEFT | nCoV-2019_1 | AGAGTCCAACCAACAGAATCTATTGT (SEQ ID NO: 589) | 26 | 38.5 | |
| nCoV-2019_75_RIGHT | nCoV-2019_1 | ACCACCAACCTTAGAATCAAGATTGT (SEQ ID NO: 590) | 26 | 38.5 | |
| nCoV-2019_76_LEFT_alt3 | nCoV-2019_2 | GGGCAAACTGGAAAGATTGCTGA (SEQ ID NO: 591) | 23 | 47.8 | X |
| nCoV-2019_76_RIGHT_alt0 | nCoV-2019_2 | ACCTGTGCCTGTTAAACCATTGA (SEQ ID NO: 592) | 23 | 43.5 | X |
| nCoV-2019_77_LEFT | nCoV-2019_1 | CCAGCAACTGTTTGTGGACCTA (SEQ ID NO: 593) | 22 | 50.0 | |
| nCoV-2019_77_RIGHT | nCoV-2019_1 | CAGCCCCTATTAAACAGCCTGC (SEQ ID NO: 594) | 22 | 54.6 | |
| nCoV-2019_78_LEFT | nCoV-2019_2 | CAACTTACTCCTACTTGGCGTGT (SEQ ID NO: 595) | 23 | 47.8 | |
| nCoV-2019_78_RIGHT | nCoV-2019_2 | TGTGTACAAAAACTGCCATATTGCA (SEQ ID NO: 596) | 25 | 36.0 | |
| nCoV-2019_79_LEFT | nCoV-2019_1 | GTGGTGATTCAACTGAATGCAGC (SEQ ID NO: 597) | 23 | 47.8 | X |
| nCoV-2019_79_RIGHT | nCoV-2019_1 | CATTTCATCTGTGAGCAAAGGTGG (SEQ ID NO: 598) | 24 | 45.8 | X |

TABLE 4-continued

Exemplary ARTIC v3 Primers and Primers Spiked in at 2X

| Name | Pool | Sequence | Length | % GC | Spiked in at 2X |
|---|---|---|---|---|---|
| nCoV-2019_80_LEFT | nCoV-2019_2 | TTGCCTTGGTGATATTGCTGCT (SEQ ID NO: 599) | 22 | 45.5 | X |
| nCoV-2019_80_RIGHT | nCoV-2019_2 | TGGAGCTAAGTTGTTTAACAAGCG (SEQ ID NO: 600) | 24 | 41.7 | X |
| nCoV-2019_81_LEFT | nCoV-2019_1 | GCACTTGGAAAACTTCAAGATGTGG (SEQ ID NO: 601) | 25 | 44.0 | |
| nCoV-2019_81_RIGHT | nCoV-2019_1 | GTGAAGTTCTTTTCTTGTGCAGGG (SEQ ID NO: 602) | 24 | 45.8 | |
| nCoV-2019_82_LEFT | nCoV-2019_2 | GGGCTATCATCTTATGTCCTTCCCT (SEQ ID NO: 603) | 25 | 48.0 | |
| nCoV-2019_82_RIGHT | nCoV-2019_2 | TGCCAGAGATGTCACCTAAATCAA (SEQ ID NO: 604) | 24 | 41.7 | |
| nCoV-2019_83_LEFT | nCoV-2019_1 | TCCTTTGCAACCTGAATTAGACTCA (SEQ ID NO: 605) | 25 | 40.0 | |
| nCoV-2019_83_RIGHT | nCoV-2019_1 | TTTGACTCCTTTGAGCACTGGC (SEQ ID NO: 606) | 22 | 50.0 | |
| nCoV-2019_84_LEFT | nCoV-2019_2 | TGCTGTAGTTGTCTCAAGGGCT (SEQ ID NO: 607) | 22 | 50.0 | |
| nCoV-2019_84_RIGHT | nCoV-2019_2 | AGGTGTGAGTAAACTGTTACAAACAAC (SEQ ID NO: 608) | 27 | 37.0 | |
| nCoV-2019_85_LEFT | nCoV-2019_1 | ACTAGCACTCTCCAAGGGTGTT (SEQ ID NO: 609) | 22 | 50.0 | |
| nCoV-2019_85_RIGHT | nCoV-2019_1 | ACACAGTCTTTTACTCCAGATTCCC (SEQ ID NO: 610) | 25 | 44.0 | |
| nCoV-2019_86_LEFT | nCoV-2019_2 | TCAGGTGATGGCACAACAAGTC (SEQ ID NO: 611) | 22 | 50.0 | |
| nCoV-2019_86_RIGHT | nCoV-2019_2 | ACGAAAGCAAGAAAAAGAAGTACGC (SEQ ID NO: 612) | 25 | 40.0 | |
| nCoV-2019_87_LEFT | nCoV-2019_1 | CGACTACTAGCGTGCCTTTGTA (SEQ ID NO: 613) | 22 | 50.0 | |
| nCoV-2019_87_RIGHT | nCoV-2019_1 | ACTAGGTTCCATTGTTCAAGGAGC (SEQ ID NO: 614) | 24 | 45.8 | |
| nCoV-2019_88_LEFT | nCoV-2019_2 | CCATGGCAGATTCCAACGGTAC (SEQ ID NO: 615) | 22 | 54.6 | |
| nCoV-2019_88_RIGHT | nCoV-2019_2 | TGGTCAGAATAGTGCCATGGAGT (SEQ ID NO: 616) | 23 | 47.8 | |
| nCoV-2019_89_LEFT_alt2 | nCoV-2019_1 | CGCGTTCCATGTGGTCATTCAA (SEQ ID NO: 617) | 22 | 50.0 | |
| nCoV-2019_89_RIGHT_alt4 | nCoV-2019_1 | ACGAGATGAAACATCTGTTGTCACT (SEQ ID NO: 618) | 25 | 40.0 | |
| nCoV-2019_90_LEFT | nCoV-2019_2 | ACACAGACCATTCCAGTAGCAGT (SEQ ID NO: 619) | 23 | 47.8 | |
| nCoV-2019_90_RIGHT | nCoV-2019_2 | TGAAATGGTGAATTGCCCTCGT (SEQ ID NO: 620) | 22 | 45.5 | |
| nCoV-2019_91_LEFT | nCoV-2019_1 | TCACTACCAAGAGTGTGTTAGAGGT (SEQ ID NO: 621) | 25 | 44.0 | X |
| nCoV-2019_91_RIGHT | nCoV-2019_1 | TTCAAGTGAGAACCAAAAGATAATAAGCA (SEQ ID NO: 622) | 29 | 31.0 | X |
| nCoV-2019_92_LEFT | nCoV-2019_2 | TTTGTGCTTTTTAGCCTTTCTGCT (SEQ ID NO: 623) | 24 | 37.5 | |

TABLE 4-continued

| Name | Pool | Sequence | Length | % GC | Spiked in at 2X |
|---|---|---|---|---|---|
| nCoV-2019_92_RIGHT | nCoV-2019_2 | AGGTTCCTGGCAATTAATTGTAAAAGG (SEQ ID NO: 624) | 27 | 37.0 | |
| nCoV-2019_93_LEFT | nCoV-2019_1 | TGAGGCTGGTTCTAAATCACCCA (SEQ ID NO: 625) | 23 | 47.8 | |
| nCoV-2019_93_RIGHT | nCoV-2019_1 | AGGTCTTCCTTGCCATGTTGAG (SEQ ID NO: 626) | 22 | 50.0 | |
| nCoV-2019_94_LEFT | nCoV-2019_2 | GGCCCCAAGGTTTACCCAATAA (SEQ ID NO: 627) | 22 | 50.0 | |
| nCoV-2019_94_RIGHT | nCoV-2019_2 | TTTGGCAATGTTGTTCCTTGAGG (SEQ ID NO: 628) | 23 | 43.5 | |
| nCoV-2019_95_LEFT | nCoV-2019_1 | TGAGGGAGCCTTGAATACACCA (SEQ ID NO: 629) | 22 | 50.0 | |
| nCoV-2019_95_RIGHT | nCoV-2019_1 | CAGTACGTTTTTGCCGAGGCTT (SEQ ID NO: 630) | 22 | 50.0 | |
| nCoV-2019_96_LEFT | nCoV-2019_2 | GCCAACAACAACAAGGCCAAAC (SEQ ID NO: 631) | 22 | 50.0 | |
| nCoV-2019_96_RIGHT | nCoV-2019_2 | TAGGCTCTGTTGGTGGGAATGT (SEQ ID NO: 632) | 22 | 50.0 | |
| nCoV-2019_97_LEFT | nCoV-2019_1 | TGGATGACAAAGATCCAAATTTCAAAGA (SEQ ID NO: 633) | 28 | 32.1 | |
| nCoV-2019_97_RIGHT | nCoV-2019_1 | ACACACTGATTAAAGATTGCTATGTGAG (SEQ ID NO: 634) | 28 | 35.7 | |
| nCoV-2019_98_LEFT | nCoV-2019_2 | AACAATTGCAACAATCCATGAGCA (SEQ ID NO: 635) | 24 | 37.5 | |
| nCoV-2019_98_RIGHT | nCoV-2019_2 | TTCTCCTAAGAAGCTATTAAAATCACATGG (SEQ ID NO: 636) | 30 | 33.3 | |

Exemplary ARTIC v3 Primers and Primers Spiked in at 2X

TABLE 5

Time and Cost Comparison of FLEX vs XT

| Library Prep Kit | Cost Per Sample ($) | Time (hrs) |
|---|---|---|
| Illumina DNA Flex | 45.96 | 10 |
| Illumina Nextera XT | 64.43 | 13.5 |

TABLE 6

Cost of SDSI + AmpSeq

| Processing Step | Reagent | Vendor | Item Number | Cost (dollars) | Number of Reactions | Cost per Reaction |
|---|---|---|---|---|---|---|
| Biosample Extraction | MagMAX ™ mirVana ™ Total RNA Isolation Kit | Thermo Fisher Scientific | A27828 | 495 | 96 | 5.16 |
| | SSIV RT master mix | Thermo Fisher Scientific | 18090050 | 383 | 50 | 7.66 |
| cDNA Synthesis | Random hexamers (50 ng/ul) | Thermo Fisher Scientific | N808127 | 91 | 100 | 0.91 |
| | dNTPs (10 nM) | Thermo Fisher Scientific | 18427-013 | 99 | 100 | 0.99 |
| | 5x RT buffer | Thermo Fisher Scientific | 18090050 | x | x | x |
| | DTT (100 mM) | Thermo Fisher Scientific | 18090050 | x | x | x |
| | Superase rnase inhibitor | Thermo Fisher Scientific | 10777-019 | 188 | 125 | 1.50 |

TABLE 6-continued

Cost of SDSI + AmpSeq

| Processing Step | Reagent | Vendor | Item Number | Cost (dollars) | Number of Reactions | Cost per Reaction |
|---|---|---|---|---|---|---|
| ARTIC PCR | Q5 Hot Start High-Fidelity 2X Master Mix | New England BioLabs | M0494L | 845 | 500 | 1.69 |
| | Artic Primers Pool#1 and Pool#2 | IDT | | 30 | 500 | 0.06 |
| Spike-ins | Spike in Primers (Forward/Reverse) | IDT | | 500 | 1000000 | 0.00 |
| | Spike-in targets n = 96 | IDT | | 5821 | 1000000 | 0.01 |
| Post Artic Pooling Quantification | Qubit ™ dsDNA HS Assay Kit | Thermo Fisher Scientific | Q32854 | 308 | 500 | 0.62 |
| Library Construction | Nextera DNA flex Library Prep (n = 96) | Illumina | 20018705 | 4153 | 190 | 21.86 |
| | Nextera index UD Set A (n = 96) | Illumina | 20027213 | 672 | 384 | 1.75 |
| Library Quantification | High Sensitivity D1000 ScreenTape | Agilent | 5067-5584 | 362 | 112 | 3.23 |
| | High Sensitivity D1000 Sample Buffer | Agilent | 5067-5603 | 59.14 | 112 | 0.53 |
| TOTAL: | | | | | | 45.96 |

TABLE 7

Final Library Quantification for Enzyme Optimization Experiment

| PCR Enzyme | Quant (nM) |
|---|---|
| Q5 2X MM | 85.3 |
| Q5 2X MM + 0.01% SDS | 0.258 |
| Q5 Ultra | 34.5 |
| KAPA | 56 |
| KOD | 8.1 |

TABLE 8

Library Size DNA Flex

| Sample | CT Dilution | Standard DNA Flex Standard DNA Flex .5X DNA Flex Library Concentration Library Size (bp) Library Size (bp) (nM) | .5X DNA Flex Library Concentration (nM) |
|---|---|---|---|
| MA_MGH_00109 | 15.39 | 340 332 92 | 54.3 |
| MA_MGH_00110 | 26.39 | 293 271 13.4 | 6.84 |
| MA_MGH_00113 | 31.93 | 211 207 3.05 | 1.84 |

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

What is claimed is:

1. A method for detecting contamination in amplicon sequencing, said method consisting of:

(a) providing one or more cDNA samples, each of which contains a target sequence;

(b) adding a synthetic DNA spike-in (SDSI) to each cDNA sample of the one or more cDNA samples, wherein each SDSI is capable of being amplified simultaneously with the target sequence present in the cDNA sample to which the SDSI is added, wherein each SDSI comprises a unique core nucleotide sequence capable of differentiating each SDSI, covalently linked to an upstream 5' primer binding region, and a downstream 3' primer binding region, wherein the nucleotide sequence of the 5' and 3' primer binding regions is the same in each SDSI;

(c) amplifying each target sequence present in the one or more cDNA samples together with the unique core sequence present in each added SDSI;

(d) sequencing the amplified target and SDSI sequences, and (e) determining the presence of the amplified SDSI sequence(s) in the one or more cDNA samples, wherein detection of a single SDSI unique core sequence in each cDNA sample indicates contamination-free amplification of each cDNA sample, and wherein detection of more than one SDSI unique core sequence in a cDNA sample indicates possible contamination of that cDNA sample with cDNA(s) from a different cDNA sample.

2. The method of claim 1, wherein each SDSI unique core sequence is selected to minimize self-hybridization and cross-hybridization with other nucleic acid molecules present in the one or more cDNA samples.

3. The method of claim 2, wherein the sequence homology between each SDSI's unique core sequence and the sequence of the nucleic acid molecules in each cDNA sample is less than 65%, or less than 60%, or less than 55%, or less than 50%, or less than 45%, or less than 40%, or less than 35%, or less than 30%, or less than 25%, or less than 20%, or less than 15%, or less than 5%, or less than 1%, and/or wherein the length of the sequence homology between each SDSI's unique core sequence and the sequence of the nucleic acid molecules in each cDNA sample is less than 15, or less than 20, or less than 25, or less than 30, or less than 35, or less than 40, or less than 45, or less than 50 contiguous bases, and/or wherein each SDSI is from 50 to 5000 nucleotides in length.

4. The method of claim 2, wherein each SDSI's unique core sequence is derived from a rare organism, optionally wherein the rare organism is a thermophilic archaeon.

5. The method of claim 2, wherein the unique core sequence of each SDSI comprises a nucleotide sequence chosen from any one of SEQ ID NOs: 1-96 and 193-291, optionally, wherein the unique core sequences comprising the nucleotide sequences of SEQ ID NOs: 16, 57, and 66 are substituted for the nucleotide sequences of SEQ ID NOs: 289, 290, and 291, respectively.

6. The method of claim 2, wherein each SDSI comprises the nucleotide sequences chosen from any one of SEQ ID NOs: 97-192 and 292-390, optionally, wherein the unique core sequences comprising the nucleotide sequences of SEQ ID NOs: 112, 153, and 162 are substituted for the nucleotide sequences of SEQ ID NOs: 388, 389, 390, respectively.

7. The method of claim 2, wherein the primer binding regions have a Tm between 55-65° C.

8. The method of claim 2, wherein the amplification is conducted using SEQ ID NO: 391 as a forward primer and SEQ ID NO: 392 as a reverse primer.

9. The method of claim 1, wherein the concentration of each SDSI ranges from 0.1 femtomolar-1.0 femtomolar.

10. The method of claim 1, wherein the one or more cDNA samples are for sequencing a pathogen or family of pathogens, optionally, wherein the pathogen is a virus or a bacteria, and the region of the bacterial genome sequenced is associated with antibiotic resistance.

11. The method of claim 1, wherein the one or more cDNA samples contain viral nucleic acid sequences.

12. The method of claim 1, wherein the one or more cDNA samples are for creating one or more sequencing families/clusters.

13. The method of claim 1, wherein the one or more cDNA samples are obtained by reverse transcription of their respective RNA(s).

14. A method for detecting contamination in amplicon sequencing comprising:

(a) providing one or more cDNA samples, each of which contains a target sequence;

(b) adding a synthetic DNA spike-in (SDSI) to each cDNA sample of the one or more cDNA samples, wherein each SDSI is capable of being amplified simultaneously with the target sequence present in the cDNA sample to which the SDSI is added, wherein each SDSI comprises a unique core nucleotide sequence capable of differentiating each SDSI, covalently linked to an upstream 5' primer binding region and a downstream 3' primer binding region, wherein the nucleotide sequence of the 5' and 3' primer binding regions is the same in each SDSI, and wherein each SDSI's unique core sequence is chosen from the nucleotide sequences of SEQ ID NOs: 1-96 and 193-291, (c) amplifying each target sequence present in the one or more cDNA samples together with the unique core sequence present in each added SDSI;

(d) sequencing the amplified target and SDSI sequences, and (e) determining the presence of the amplified SDSI sequence(s) in the one or more cDNA samples, wherein detection of a single SDSI unique core sequence in each cDNA sample indicates contamination-free amplification of each cDNA sample, and wherein detection of more than one SDSI unique core sequence in a cDNA sample indicates possible contamination of that cDNA sample with cDNA(s) from a different cDNA sample.

* * * * *